(12) United States Patent
Colletti et al.

(10) Patent No.: US 10,532,068 B2
(45) Date of Patent: *Jan. 14, 2020

(54) DUAL MOLECULAR DELIVERY OF OLIGONUCLEOTIDES AND PEPTIDE CONTAINING CONJUGATES

(71) Applicant: Merck Sharp & Dohme Corp., Rahway, NJ (US)

(72) Inventors: Steven L. Colletti, Princeton Junction, NJ (US); Thomas J. Tucker, North Wales, PA (US); David M. Tellers, Lansdale, PA (US); Boyoung Kim, Natick, MA (US); Rob Burke, Encinitas, CA (US); Kathleen B. Calati, Saline, MI (US); Matthew G. Stanton, Needham, MA (US); Rubina G. Parmar, Acton, MA (US); Jeffrey G. Aaronson, San Francisco, CA (US); Weimin Wang, Churchville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/974,135

(22) Filed: May 8, 2018

(65) Prior Publication Data

US 2019/0015442 A1    Jan. 17, 2019

Related U.S. Application Data

(63) Continuation of application No. 15/033,715, filed as application No. PCT/US2014/063621 on Nov. 3, 2014, now Pat. No. 10,010,562.

(60) Provisional application No. 61/900,542, filed on Nov. 6, 2013.

(51) Int. Cl.
| | |
|---|---|
| *C12N 15/87* | (2006.01) |
| *A61K 31/713* | (2006.01) |
| *A61K 38/10* | (2006.01) |
| *A61K 38/16* | (2006.01) |
| *C12N 15/11* | (2006.01) |
| *C12N 15/113* | (2010.01) |
| *A61K 31/7125* | (2006.01) |

(52) U.S. Cl.
CPC ........ *A61K 31/7125* (2013.01); *A61K 31/713* (2013.01); *A61K 38/10* (2013.01); *A61K 38/16* (2013.01); *C12N 15/111* (2013.01); *C12N 15/113* (2013.01); *C12N 15/87* (2013.01); *C07K 2319/10* (2013.01); *C12N 2310/14* (2013.01); *C12N 2310/351* (2013.01); *C12N 2320/31* (2013.01)

(58) Field of Classification Search
None
See application file for complete search history.

(56) References Cited

U.S. PATENT DOCUMENTS

2012/0165393 A1    6/2012    Rozema et al.

FOREIGN PATENT DOCUMENTS

| WO | WO2005041859 | 5/2005 |
|---|---|---|
| WO | WO2008036825 | 3/2008 |
| WO | WO2009005793 A2 | 5/2009 |
| WO | WO2009126933 | 10/2009 |
| WO | WO2010039088 A1 | 4/2010 |
| WO | WO2012030683 A2 | 3/2012 |

OTHER PUBLICATIONS

Cheng, Enhanced siRNA delivery into cells by exploiting the synergy between targeting ligands and cell-penetrating peptides, Biomaterials, 2011, 6194-3203, 32-26.
Jiang, Qi-Yang, et al., Gene delivery to tumor cells by cationic polymeric nanovectors coupled to folic acid and the cell-penetrating peptide octaarginine, Biomaterials, 2011, pp. 7253-7262, vol. 32.
Wong, Co-injection of a targeted, reversibly masked endosomolytic polymer dramatically improves the efficacy of cholesterol-conjugated small interfering RNAs in vivo nucleic acid therapeutics, Nucleic acid Therapeutics, 2012, 380-390, 22-6.
Wooddell, Hepatocyte-targeted RNAi Therapeutics for the Treatment of Chronic Hepatitis B Virus Infection, Molecular Therapy, 2013, 973-985, 21-5.

*Primary Examiner* — Richard A Schnizer
(74) *Attorney, Agent, or Firm* — Yong Zhao; Anna L. Cocuzzo

(57) ABSTRACT

Disclosed herein is a method for inhibiting expression of a gene of a subject comprising administering (1) a composition comprising $R\text{-}(L)_a\text{-}(G)_b$; wherein R is an oligonucleotide selected from the group consisting of DNA, RNA, siRNA, and microRNA; L is a linker and each occurrence of L is independently selected from Table 3; G is a targeting ligand and each occurrence of G is independently selected from Table 4; each of a and b is independently 0, 1, 2, 3 or 4; and (2) a composition comprising $(P)_c\text{-}(L)_d\text{-}(G)_e$; wherein P is a peptide and each occurrence of P is independently selected from Table 2; L is a linker and each occurrence of L is independently selected from Table 3; G is a targeting ligand and each occurrence of G is independently selected from Table 4; d is 0, 1, 2, 3, 4, 5 or 6; and each of c and e is independently 1, 2, 3, 4, 5 or 6. Compositions in (1) and (2) can be co-administered or sequentially administered.

18 Claims, 7 Drawing Sheets
Specification includes a Sequence Listing.

DUAL MOLECULAR DELIVERY OF OLIGONUCLEOTIDES AND PEPTIDE CONTAINING CONJUGATES

CROSS REFERENCE TO RELATED APPLICATIONS

This application is a continuation of U.S. application Ser. No. 15/033,715, filed May 2, 2016, which is a U.S. National Phase application under 35 U.S.C. § 371 of PCT Application No. PCT/US2014/063621, filed Nov. 3, 2014, which claims priority from U.S. Provisional Application Ser. No. 61/900,542, filed Nov. 6, 2013.

REFERENCE TO SEQUENCE LISTING SUBMITTED ELECTRONICALLY

The sequence listing of the present application is submitted electronically via EFS-Web as an ASCII formatted sequence listing with a file name "23648USCNT-SEQLIST-23JUL2018.TXT," creation date of Jul. 23, 2018, and a size of 503 KB. This sequence listing submitted EFS-Web is part of the specification and is herein incorporated by reference in its entirety.

BACKGROUND OF THE INVENTION

The delivery of oligonucleotides and other cell membrane impermeable compounds into a living cell is highly restricted by the complex membrane system of the cell. Drugs used in antisense, RNAi, and gene therapies are relatively large hydrophilic polymers and are frequently highly negatively charged. These physical characteristics severely restrict their direct diffusion across the cell membrane. For this reason, the major barrier to polynucleotide therapeutic efficacy is the delivery of the polynucleotide across a cell membrane to the cell cytoplasm or nucleus.

One approach that has been used to deliver small nucleic acid in vivo has been to attach the nucleic acid to either a small targeting molecule or a lipid or sterol. While some delivery and activity has been observed with these conjugates, the very large nucleic acid dose required with these methods is impractical.

Considerable amount of literature evidence supports the hypothesis that the major hurdles for oligonucleotide delivery are cell uptake and endosomal escape. Small interfering RNAs (siRNA) can achieve selective knock-down of therapeutic targets by degradation of specific messenger RNA, provided the siRNA reaches the RNA Induced Silencing Complex (RISC) in the cell cytosol. Receptor-targeted siRNA constructs can be taken up by cell surface receptors and accumulate in subcellular vesicles termed endosomes. A small fraction of the siRNA traverses the endosomal membrane to reach the cytosol. The process, termed endosomal escape, is a major barrier to cytosolic delivery and higher potency of siRNA therapeutics.

There remains a need for additional compositions or or delivery methods that can provide effective in vivo delivery, cell uptake and/or endosomal escape of oligonucleotides.

SUMMARY OF THE INVENTION

The compositions and administration methods disclosed herein provide unexpected effective in vivo delivery of an oligonucleotide through dual molecular delivery of the oligonucleotide and a peptide containing conjugate which are not covalently linked to each other.

One embodiment includes a method for inhibiting expression of a gene of a subject comprising administering (1) a composition comprising R-$(L)_a$-$(G)_b$ to the subject; wherein R is an oligonucleotide with the ability to inhibit expression of a gene; L is a linker and each occurrence of L is independently selected from Table 3; G is a targeting ligand and each occurrence of G is independently selected from Table 4; each of a and b is independently 0, 1, 2, 3 or 4; and (2) a composition comprising $(P)_c$-$(L)_d$-$(G)_e$ to the subject; wherein P is a peptide and each occurrence of P is independently selected from Table 2; L is a linker and each occurrence of L is independently selected from Table 3; G is a targeting ligand and each occurrence of G is independently selected from Table 4; d is 0, 1, 2, 3, 4, 5 or 6; and each of c and e is independently 1, 2, 3, 4, 5 or 6. In one embodiment, R is an oligonucleotide selected from the group consisting of DNA, RNA, siRNA, and microRNA.

In one embodiment, a method for expressing a protein or polypeptide in a subject comprises administering: (1) a composition comprising R-$(L)_a$-$(G)_b$ to the subject; wherein R is an oligonucleotide with the ability to encode a protein or polypeptide; L is a linker and each occurrence of L is independently selected from Table 3; G is a targeting ligand and each occurrence of G is independently selected from Table 4; each of a and b is independently 0, 1, 2, 3 or 4; and (2) a composition comprising $(P)_c$-$(L)_d$-$(G)_e$ to the subject; wherein P is a peptide and each occurrence of P is independently selected from Table 2; L is a linker and each occurrence of L is independently selected from Table 3; G is a targeting ligand and each occurrence of G is independently selected from Table 4; d is 0, 1, 2, 3, 4, 5 or 6; and each of c and e is independently 1, 2, 3, 4, 5 or 6. In one embodiment, R is an oligonucleotide selected from the group consisting of DNA, RNA, and mRNA.

In one embodiment, a composition for dual molecular delivery of an oligonucleotide and a peptide conjugate comprises (1) R-$(L)_a$-$(G)_b$; and (2) $(P)_c$-$(L)_d$-$(G)_e$; wherein R is an oligonucleotide with the ability to inhibit expression of a gene; P is a peptide and each occurrence of P is independently selected from Table 2; L is a linker and each occurrence of L is independently selected from Table 3; G is a targeting ligand and each occurrence of G is independently selected from Table 4; each of a and b is independently 0, 1, 2, 3 or 4; d is 0, 1, 2, 3, 4, 5 or 6; and each of c and e is independently 1, 2, 3, 4, 5 or 6. In one embodiment, R is an oligonucleotide selected from the group consisting of DNA, RNA, siRNA, and microRNA In one embodiment, a composition for dual molecular delivery of an oligonucleotide and a peptide conjugate comprises (1) R-$(L)_a$-$(G)_b$; and (2) $(P)_c$-$(L)_d$-$(G)_e$; wherein R is an oligonucleotide with the ability to encode a protein or polypeptide; P is a peptide and each occurrence of P is independently selected from Table 2; L is a linker and each occurrence of L is independently selected from Table 3; G is a targeting ligand and each occurrence of G is independently selected from Table 4; each of a and b is independently 0, 1, 2, 3 or 4; d is 0, 1, 2, 3, 4, 5 or 6; and each of c and e is independently 1, 2, 3, 4, 5 or 6. In one embodiment, R is an oligonucleotide selected from the group consisting of DNA, RNA, and mRNA.

In one embodiment, the composition comprises R-$(L)_a$-$(G)_b$ and the composition comprising $(P)_c$-$(L)_d$-$(G)_e$ are co-administered to the subject at the same time. In one embodiment, the composition comprising R-$(L)_a$-$(G)_b$ and the composition comprising $(P)_c\text{-}(L)_d\text{-}(G)_e$ are sequentially administered to the subject about 5 to 60 minutes apart.

BRIEF DESCRIPTION OF THE DRAWINGS

FIG. 1 shows both peptides generated faster mRNA knockdown (KD) compared to siRNA alone (dose matched by i.v. or standard SCE format by s.c.).

DETAILED DESCRIPTION OF THE INVENTION

Figure 1:
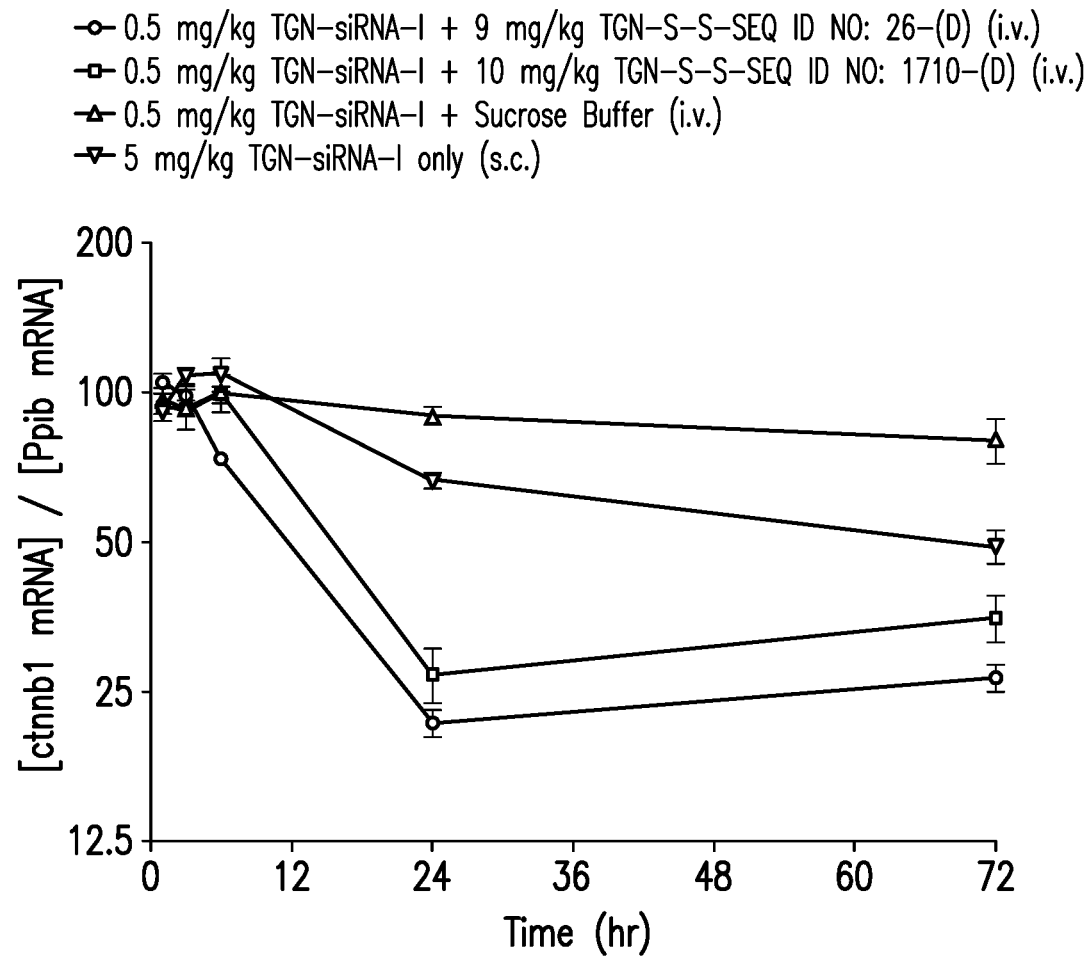
FIG. 1 shows a time course of mRNA KD following different treatments. Sequential dosing with peptide (or sucrose buffer) was dosed 15 min after siRNA. The 5 mg/kg siRNA only group had no peptide or sucrose buffer and was dosed s.c. compared to all other groups dosed via i.v. route.
Figure 2:
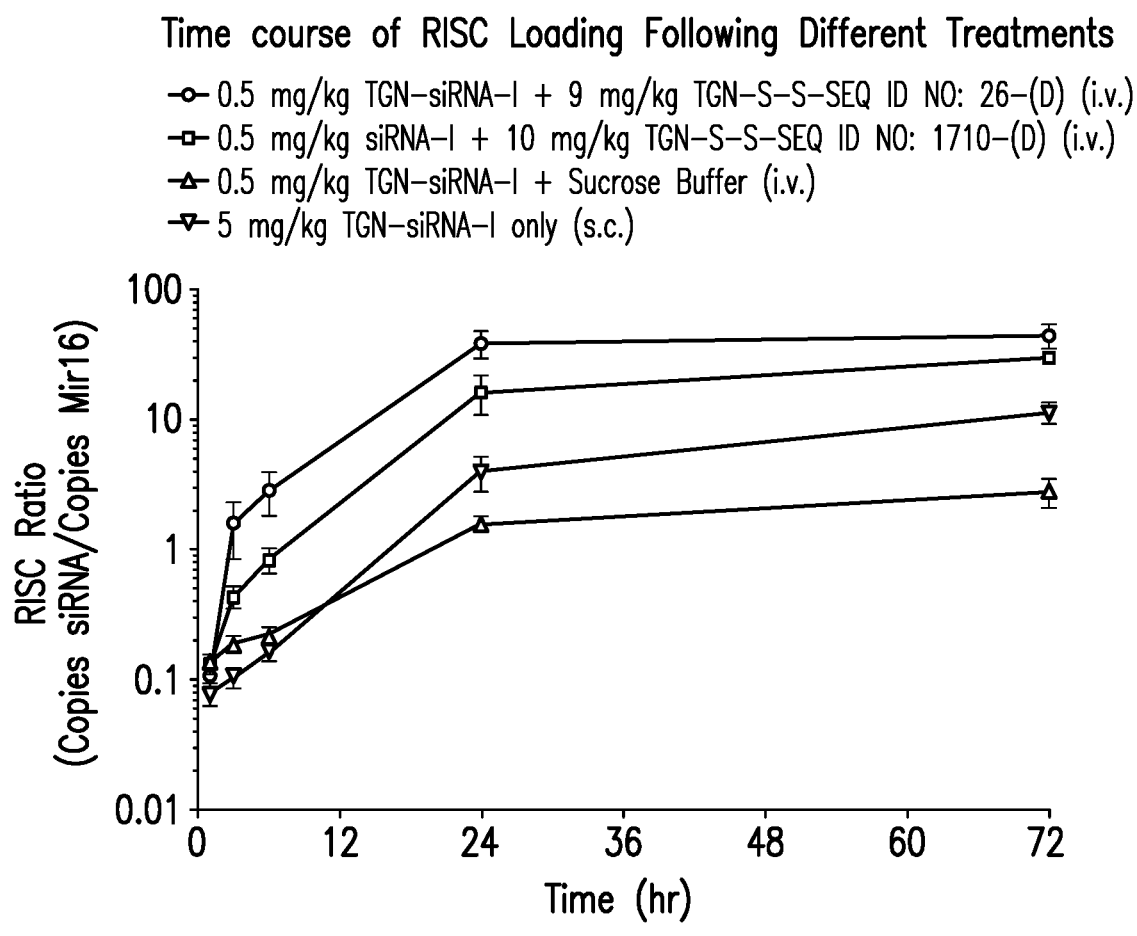
FIG. 2 shows a time course of RISC loading following different treatments. RISC data which shows faster RISC loading for both peptides matches the mRNA KD data. At 72 hr, there is 10 to 20-fold higher RISC loading with DMD compared to 0.5 mg/kg dose of siRNA with buffer (no peptide). With DMD format, there is 3 to 4-fold higher RISC loading compared to a 10× higher dose with standard subQ siRNA format.
Figure 3:
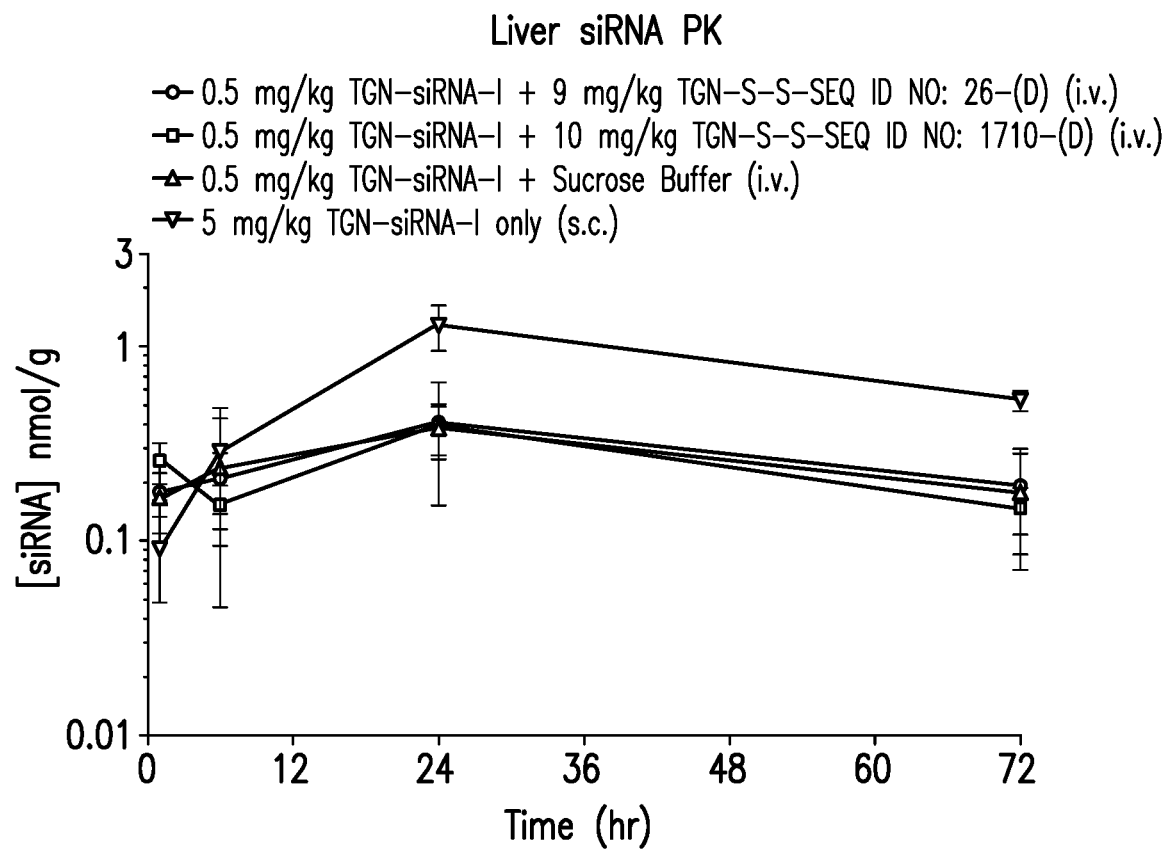
FIG. 3 shows liver siRNA PK. This figure indicates peptide does not influence amount of siRNA in liver over time. It also shows that s.c. injection of 10-fold higher siRNA dose gets more siRNA into liver. DMD can achieve greater RISC loading and mRNA KD with less siRNA in liver.
Figure 4:
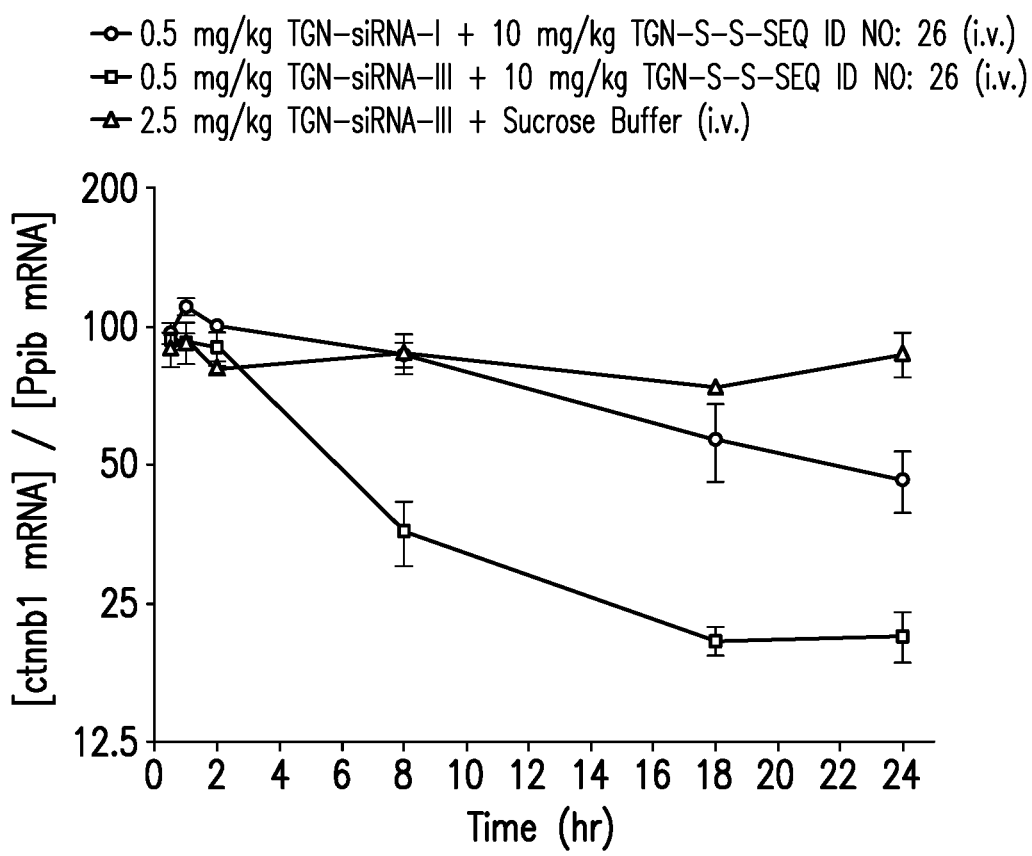
FIG. 4 shows a time course of mRNA KD following different treatments. Sequential dosing with peptide (or sucrose buffer) dosed 15 min after siRNA. This figure shows that addition of vinylPmoeT to GS (siRNA-III) generates faster KD compared to siRNA-I. Both siRNAs show faster and greater KD in DMD format compared to 5-fold higher dose of siRNA-III alone.
Figure 5:
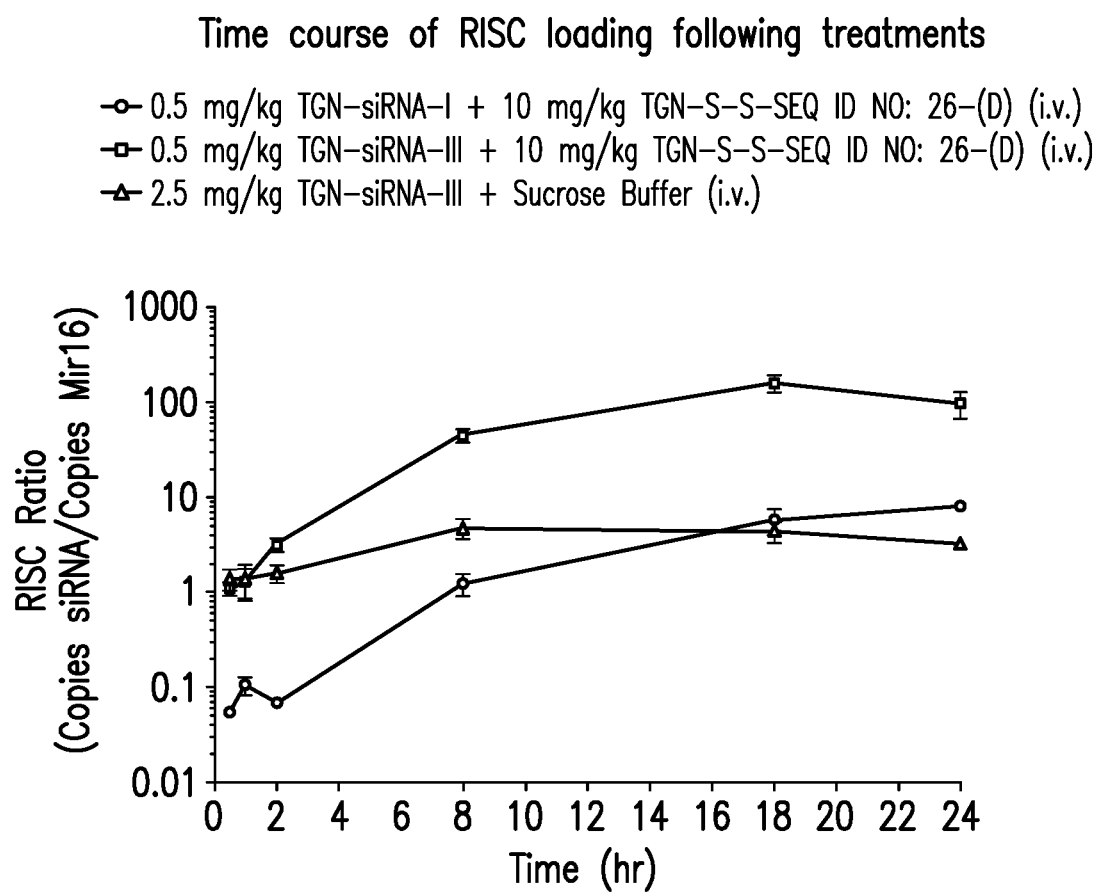
FIG. 5 shows a time course of RISC loading following different treatments. This data matches the mRNA KD data, showing the siRNA-III generates faster RISC loading due to addition of vinyl phosphonate. It also shows the rate of RISC loading is much faster when using peptides in DMD format compared to siRNA alone.
Figure 6:
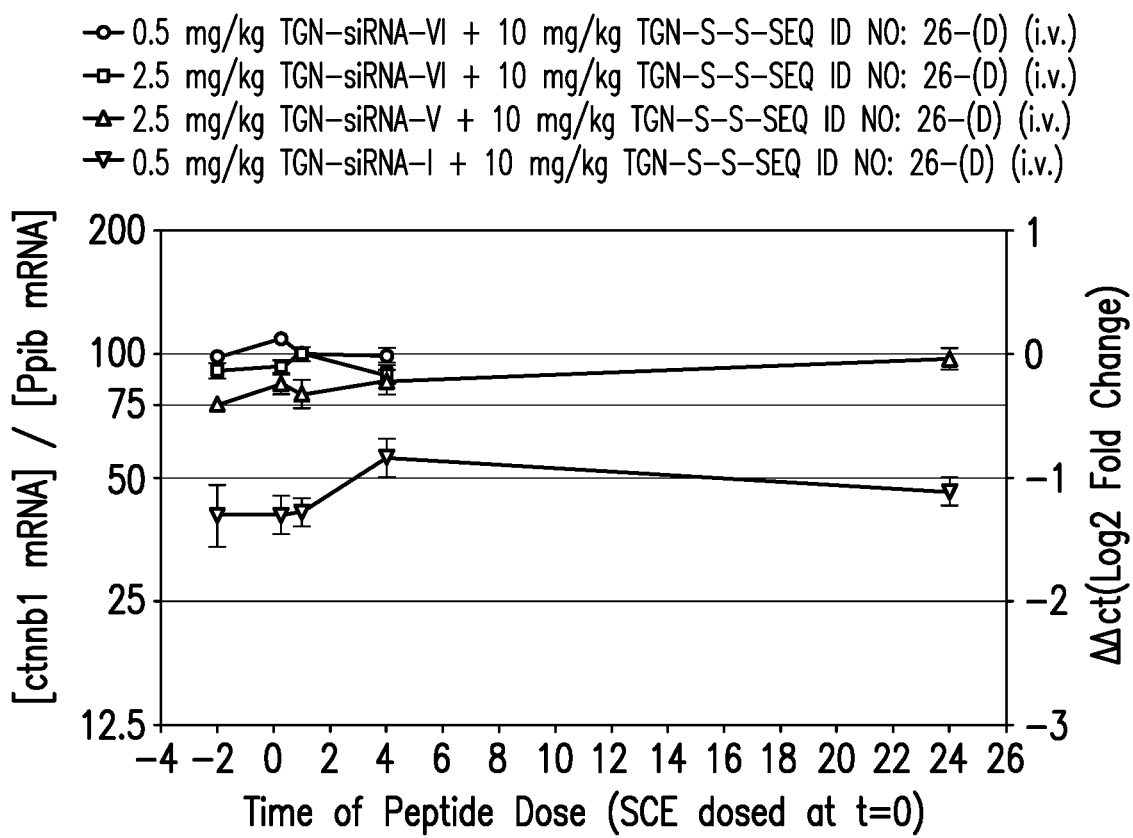
FIG. 6 shows a time course of RISC loading following different treatments. The order of siRNA stability is siRNA-I>siRNA-V>siRNA-VI and the data shows that metabolic stability is critical to siRNA activity. With a highly stable siRNA-I, the timing of peptide dose does not significantly change the activity (within 2 hr before up to 24 hr after siRNA dose). With the moderately stable siRNA-V, peptide dose times within 2 hr (before or after) the siRNA generate a low level of activity (~25% KD). Longer separation times (4-24 hr post-siRNA dose) or more unstable siRNAs (siRNA-VI) both reduced the activity to background levels.
Figure 7:
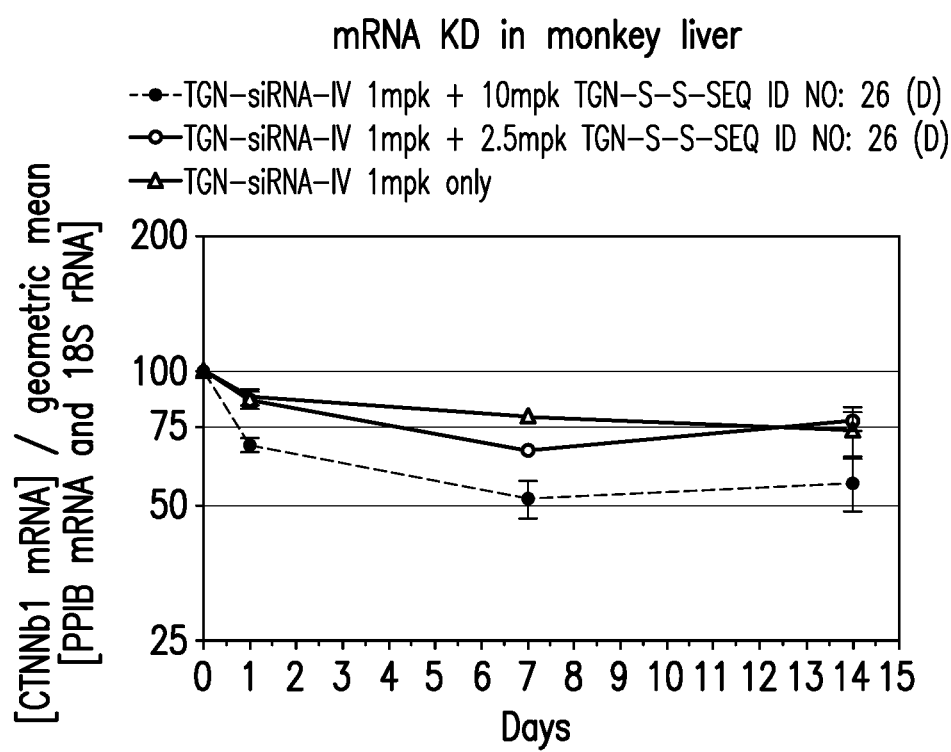
FIG. 7 shows mRNA KD in monkey liver. The mRNA expression relative to each animal's pre-dose biopsy. Achieved ~50% KD in non-human primates at 10 mpk of peptide dose.

The compositions and administration methods disclosed herein provide effective in vivo delivery of an oligonucleotide through dual molecular delivery of the oligonucleotide and a peptide containing conjugate. The oligonucleotide and the peptide containing conjugate are not covalently linked to each other and can be co-administered or sequentially administered to a subject.

The use of dual molecular delivery disclosed herein provides the unexpected benefits of effective in vivo cytosolic delivery of the oligonucleotide by directing the oligonucleotide to the site of action of a particular cell. The peptides may function as endosomolytic, cell penetrating and/or fusogenic agents. For example, the co-administered or sequentially administered peptide-containing conjugate helps with membrane translocation of the oligonucleotide and/or targeting of intended cells.

The oligonucleotide may be used directly as one component of the dual molecular delivery system. Alternatively, it can be attached to a targeting ligand, and optionally through a linker, to form a conjugate before administration. When present, the targeting ligands and/or linkers are attached to the oligonucleotide at different 2'-positions of the ribose rings and/or the terminal 3' and/or 5'-positions of the oligonucleotide.

For peptide conjugates used herein, an optional linker may be present between each peptide and a targeting ligand. Multiple peptides and/or multiple linkers and ligands may be used in the conjugates.

In one embodiment, a method for inhibiting expression of a gene of a subject comprises administering:
(1) a composition comprising

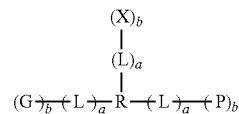

to the subject; wherein:
R is an oligonucleotide with the ability to inhibit expression of a gene;
L is a linker and each occurrence of L is independently selected from Table 3;
G is a targeting ligand and each occurrence of G is independently selected from Table 4;
X is a lipid;
P is a peptide selected from Table 2; and
each of a and b is independently 0, 1, 2, 3 or 4; and
(2) a composition comprising $(P)_c\text{-}(L)_d\text{-}(G)_e$ to the subject; wherein:
P is a peptide and each occurrence of P is independently selected from Table 2;
L is a linker and each occurrence of L is independently selected from Table 3;
G is a targeting ligand and each occurrence of G is independently selected from Table 4;
d is 0, 1, 2, 3, 4, 5 or 6; and
each of c and e is independently 1, 2, 3, 4, 5 or 6.

In one embodiment, a method for inhibiting expression of a gene of a subject comprises administering:
(1) a composition comprising $R\text{-}(L)_a\text{-}(G)_b$ to the subject; wherein:
R is an oligonucleotide with the ability to inhibit expression of a gene;
L is a linker and each occurrence of L is independently selected from Table 3;
G is a targeting ligand and each occurrence of G is independently selected from Table 4; and
each of a and b is independently 0, 1, 2, 3 or 4; and
(2) a composition comprising $(P)_c\text{-}(L)_d\text{-}(G)_e$ to the subject; wherein:
P is a peptide and each occurrence of P is independently selected from Table 2;

L is a linker and each occurrence of L is independently selected from Table 3;
G is a targeting ligand and each occurrence of G is independently selected from Table 4;
d is 0, 1, 2, 3, 4, 5 or 6; and
each of c and e is independently 1, 2, 3, 4, 5 or 6.

In one embodiment, a method for inhibiting expression of a gene of a subject comprises administering to the subject a composition comprising:

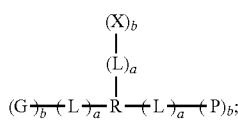

wherein:
R is an oligonucleotide with the ability to inhibit expression of a gene;
L is a linker and each occurrence of L is independently selected from Table 3;
G is a targeting ligand and each occurrence of G is independently selected from Table 4;
X is a lipid;
P is a peptide selected from Table 2; and
each of a and b is independently 0, 1, 2, 3 or 4; and
(2) $(P)_c\text{-}(L)_d\text{-}(G)_e$; wherein:
P is a peptide and each occurrence of P is independently selected from Table 2;
L is a linker and each occurrence of L is independently selected from Table 3;
G is a targeting ligand and each occurrence of G is independently selected from Table 4;
d is 0, 1, 2, 3, 4, 5 or 6; and
each of c and e is independently 1, 2, 3, 4, 5 or 6.

In one embodiment, a method for inhibiting expression of a gene of a subject comprises administering to the subject a composition comprising:
(1) $R\text{-}(L)_a\text{-}(G)_b$; wherein:
R is an oligonucleotide selected from the group consisting of DNA, RNA, siRNA, and microRNA;
L is a linker and each occurrence of L is independently selected from Table 3;
G is a targeting ligand and each occurrence of G is independently selected from Table 4; and
each of a and b is independently 0, 1, 2, 3 or 4; and
(2) $(P)_c\text{-}(L)_d\text{-}(G)_e$; wherein:
P is a peptide and each occurrence of P is independently selected from Table 2;
L is a linker and each occurrence of L is independently selected from Table 3;
G is a targeting ligand and each occurrence of G is independently selected from Table 4;
d is 0, 1, 2, 3, 4, 5 or 6; and
each of c and e is independently 1, 2, 3, 4, 5 or 6.

In one embodiment of the above inhibition methods, R is an oligonucleotide selected from the group consisting of DNA, RNA, siRNA, and microRNA.

In one embodiment, a method for expressing a protein or polypeptide in a subject comprises administering:
(1) a composition comprising

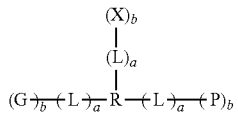

to the subject; wherein:
R is an oligonucleotide with the ability to encode a protein or polypeptide;
L is a linker and each occurrence of L is independently selected from Table 3;
G is a targeting ligand and each occurrence of G is independently selected from Table 4;
X is a lipid;
P is a peptide selected from Table 2; and
each of a and b is independently 0, 1, 2, 3 or 4; and
(2) a composition comprising $(P)_c\text{-}(L)_d\text{-}(G)_e$ to the subject; wherein:
P is a peptide and each occurrence of P is independently selected from Table 2;
L is a linker and each occurrence of L is independently selected from Table 3;
G is a targeting ligand and each occurrence of G is independently selected from Table 4;
d is 0, 1, 2, 3, 4, 5 or 6; and
each of c and e is independently 1, 2, 3, 4, 5 or 6.

In one embodiment, a method for expressing a protein or polypeptide in a subject comprises administering:
(1) a composition comprising $R\text{-}(L)_a\text{-}(G)_b$ to the subject; wherein:
R is an oligonucleotide with the ability to encode a protein or polypeptide;
L is a linker and each occurrence of L is independently selected from Table 3;
G is a targeting ligand and each occurrence of G is independently selected from Table 4; and
each of a and b is independently 0, 1, 2, 3 or 4; and
(2) a composition comprising $(P)_c\text{-}(L)_d\text{-}(G)_e$ to the subject; wherein:
P is a peptide and each occurrence of P is independently selected from Table 2;
L is a linker and each occurrence of L is independently selected from Table 3;
G is a targeting ligand and each occurrence of G is independently selected from Table 4;
d is 0, 1, 2, 3, 4, 5 or 6; and
each of c and e is independently 1, 2, 3, 4, 5 or 6.

In one embodiment, a method for expressing a protein or polypeptide in a subject comprises administering to the subject a composition comprising:

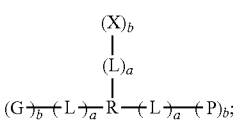

wherein:
R is an oligonucleotide with the ability to encode a protein or polypeptide;
L is a linker and each occurrence of L is independently selected from Table 3;
G is a targeting ligand and each occurrence of G is independently selected from Table 4;
X is a lipid;
P is a peptide selected from Table 2; and
each of a and b is independently 0, 1, 2, 3 or 4; and
(2) $(P)_c\text{-}(L)_d\text{-}(G)_e$; wherein:
P is a peptide and each occurrence of P is independently selected from Table 2;

L is a linker and each occurrence of L is independently selected from Table 3;
G is a targeting ligand and each occurrence of G is independently selected from Table 4;
d is 0, 1, 2, 3, 4, 5 or 6; and
each of c and e is independently 1, 2, 3, 4, 5 or 6.

In one embodiment, a method for expressing a protein or polypeptide in a subject comprises administering to the subject a composition comprising:
(1) $R\text{-}(L)_a\text{-}(G)_b$; wherein:
R is an oligonucleotide with the ability to encode a protein or polypeptide;
L is a linker and each occurrence of L is independently selected from Table 3;
G is a targeting ligand and each occurrence of G is independently selected from Table 4; and
each of a and b is independently 0, 1, 2, 3 or 4; and
(2) $(P)_c\text{-}(L)_d\text{-}(G)_e$ to the subject; wherein:
P is a peptide and each occurrence of P is independently selected from Table 2;
L is a linker and each occurrence of L is independently selected from Table 3;
G is a targeting ligand and each occurrence of G is independently selected from Table 4;
d is 0, 1, 2, 3, 4, 5 or 6; and
each of c and e is independently 1, 2, 3, 4, 5 or 6.

In one embodiment of the above expression methods, R is an oligonucleotide selected from the group consisting of DNA, RNA, and mRNA.

In one embodiment of the above methods, R is a ds siRNA or ss siRNA.

In one embodiment of the above methods, occurrence of P is independently selected from Table 2a.

In one embodiment of the above methods, occurrence of P is independently selected from Table 2b.

In one embodiment of the above methods, each occurrence of L is independently selected from Table 3a.

In one embodiment of the above methods, each occurrence of G is independently selected from Table 4a.

In one embodiment of the above methods, G comprises:

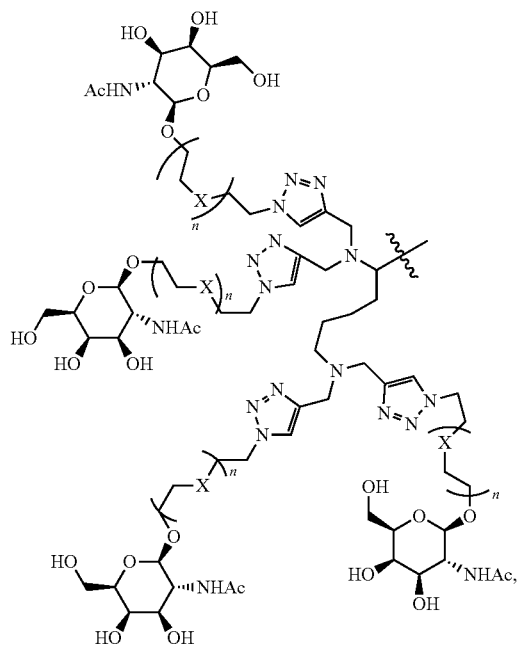

wherein Ac is acetyl;
wherein each X is independently —O—, —S—, —CH$_2$— or —NH—; each n is independently 1, 2, 3, or 4; and the bond with "⌇⌇" indicates the point of attachment.

In one embodiment of the above methods, G comprises:

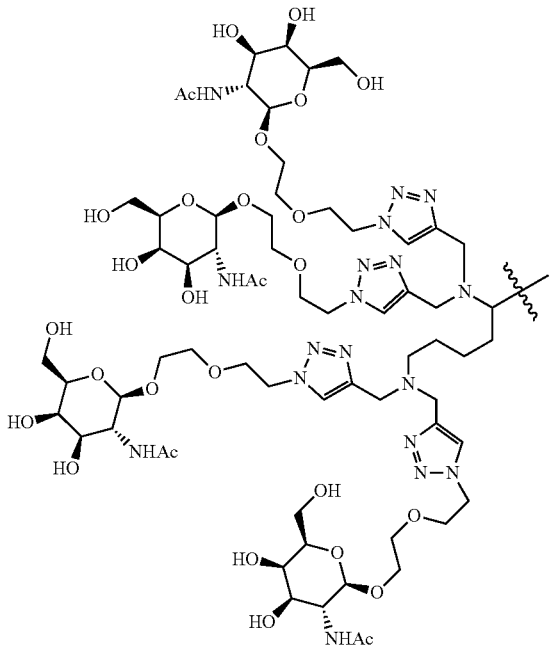

In one embodiment of the above methods, each of a and b is independently 0, 1 or 2; c is 1 or 2; and each of d and e is independently 1, 2 or 3.

In one embodiment of the above methods, each of a and b is independently 0 or 1; c is 1; and each of d and e is independently 1 or 2.

In one embodiment of the above methods, each of a and b is 1; c is 1; and each of d and e is 1.

In one embodiment, a method comprises:
(1) administering a composition comprising $R\text{-}(L)_a\text{-}(G)_b$ to the subject; wherein:
R is an siRNA;
L is a linker and each occurrence of L is independently selected from Table 3a;
G is a targeting ligand and each occurrence of G is independently selected from Table 4a; and
each of a and b is independently 0, 1 or 2; and
(2) administering a composition comprising $(P)_c\text{-}(L)_d\text{-}(G)_e$ to the subject; wherein:
P is a peptide and each occurrence of P is independently selected from Table 2b;
L is a linker and each occurrence of L is independently selected from Table 3a;
G is a targeting ligand and each occurrence of G is independently selected from Table 4a; and
each of c, d and e is independently 1, 2 or 3.

In one embodiment of the above methods:
L of $R\text{-}(L)_a\text{-}(G)_b$ is

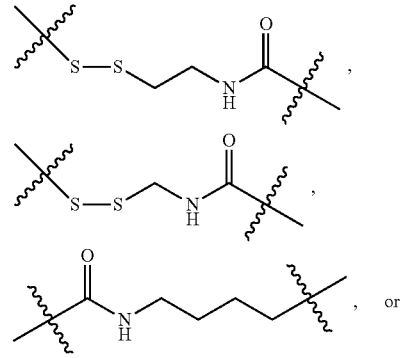

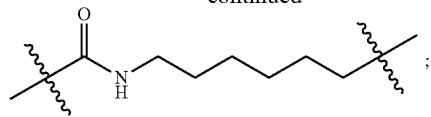
G of R-(L)$_a$-(G)$_b$ is:
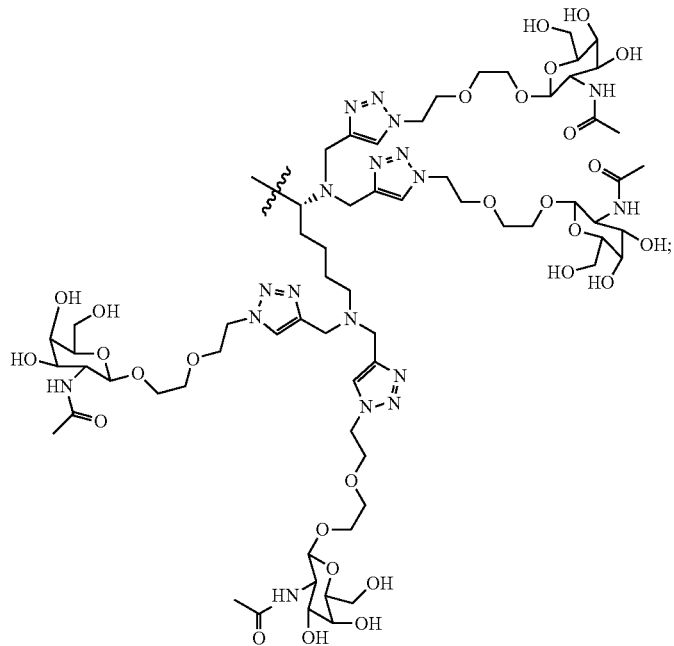 [SMILES: *[C@@H](CCCCN(Cc1cn(CCOCCOC2OC(CO)C(O)C(O)C2NC(C)=O)nn1)Cc1cn(CCOCCOC2OC(CO)C(O)C(O)C2NC(C)=O)nn1)N(Cc1cn(CCOCCOC2OC(CO)C(O)C(O)C2NC(C)=O)nn1)Cc1cn(CCOCCOC2OC(CO)C(O)C(O)C2NC(C)=O)nn1]
each of a and b is 1; and
(P)$_c$-(L)$_d$-(G)$_e$ of composition (2) is:
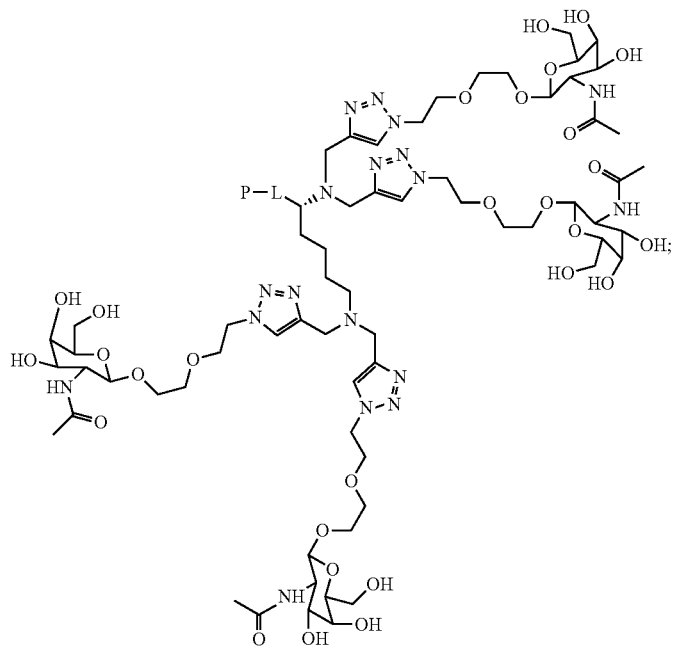
wherein P is a peptide selected from Table 2b; and wherein L of composition (2) is selected from:

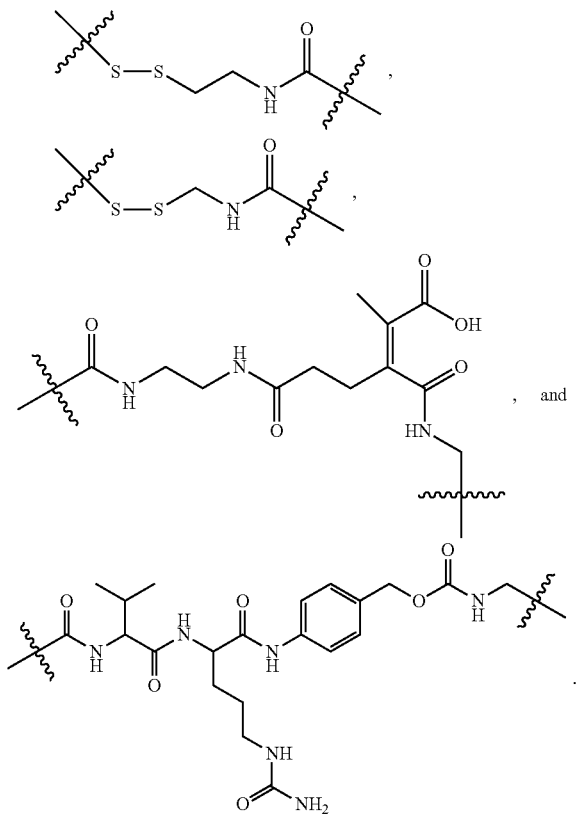

In one embodiment of the above methods, each L of compositions (1) and (2) is independently

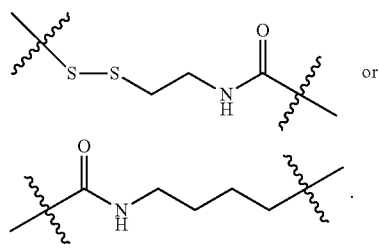

In one embodiment of the above methods, R-(L)$_a$-(G)$_b$ further comprises a lipid.

In one embodiment of the above methods, R-(L)$_a$-(G)$_b$ further comprises a peptide.

In one embodiment of the above methods, (P)$_c$-(L)$_d$-(G)$_e$ further comprises a lipid.

In one embodiment of the above methods, (P)$_c$-(L)$_d$-(G)$_e$ further comprises an oligonucleotide.

In one embodiment of the above methods, the composition comprising R-(L)$_a$-(G)$_b$ and the composition comprising (P)$_c$-(L)$_d$-(G)$_e$ are co-administered at the same time. In one embodiment, the two compositions are in the same formulation. In another embodiment, the two compositions are in different formulations.

In one embodiment of the above methods, the composition comprising (P)$_c$-(L)$_d$-(G)$_e$ and the composition comprising R-(L)$_a$-(G)$_b$ are sequentially administered about 0.1 hour to 2 hours apart.

In one embodiment of the above methods, the composition comprising (P)$_c$-(L)$_d$-(G)$_e$ and the composition comprising R-(L)$_a$-(G)$_b$ are sequentially administered to a subject about 0.1 hour to 24 hours apart. In another embodiment the sequential administrations are about 0.1 hour to 6 hours apart. In another embodiment the sequential administrations are about 0.25 hour to 2 hours apart. In another embodiment the sequential administrations are about 0.25 hour to 1 hour apart. In another embodiment the sequential administrations are about 0.25 hour to 0.5 hour apart. In another embodiment the sequential administrations are about 0.25 hour apart.

In one embodiment of the above methods, the composition comprising (P)$_c$-(L)$_d$-(G)$_e$ is administered about 0.1 hour to 2 hours before the composition comprising R-(L)$_a$-(G)$_b$ is administered to a subject. In another embodiment, the composition comprising (P)$_c$-(L)$_d$-(G)$_e$ is administered about 0.1 hour to 1 hour before the composition comprising R-(L)$_a$-(G)$_b$ is administered to a subject. In another embodiment, the composition comprising (P)$_c$-(L)$_d$-(G)$_e$ is administered about 0.25 hour to 0.5 hour before the composition comprising R-(L)$_a$-(G)$_b$ is administered to a subject.

In one embodiment of the above methods, the composition comprising (P)$_c$-(L)$_d$-(G)$_e$ is administered about 0.1 hour to 24 hours after the composition comprising R-(L)$_a$-(G)$_b$ is administered to a subject. In another embodiment, the composition comprising (P)$_c$-(L)$_d$-(G)$_e$ is administered about 0.1 hour to 12 hours after the composition comprising R-(L)$_a$-(G)$_b$ is administered to a subject. In another embodiment, the composition comprising (P)$_c$-(L)$_d$-(G)$_e$ is administered about 0.25 hour to 6 hours after the composition comprising R-(L)$_a$-(G)$_b$ is administered to a subject. In another embodiment, the composition comprising (P)$_c$-(L)$_d$-(G)$_e$ is administered about 0.25 hour to 2 hours after the composition comprising R-(L)$_a$-(G)$_b$ is administered to a subject. In another embodiment, the composition comprising (P)$_c$-(L)$_d$-(G)$_e$ is administered about 0.25 hour to 1 hour after the composition comprising R-(L)$_a$-(G)$_b$ is administered to a subject. In another embodiment, the composition comprising (P)$_c$-(L)$_d$-(G)$_e$ is administered about 0.25 hour to 0.5 hour after the composition comprising R-(L)$_a$-(G)$_b$ is administered to a subject.

In one embodiment of the above methods, the compositions of oligonucleotide and peptide are dosed either by intravenous (i.v.) or subcutaneous (s.c.) injections. In another embodiment, the compositions are dosed by intravenous (i.v.) injections. In another embodiment, the compositions are dosed by subcutaneous (s.c.) injections.

In one embodiment of the above methods, the oligonucleotide composition is administered at a dose of 0.1 to 20 mg/kg (mpk). In another embodiment, the oligonucleotide composition is administered at a dose of 0.1 to 10 mpk. In another embodiment, the oligonucleotide composition is administered at a dose of 0.1 to 5 mpk. In another embodiment, the oligonucleotide composition is administered at a dose of 0.1 to 2 mpk. In another embodiment, the oligonucleotide composition is administered at a dose of 0.1 to 1 mpk. In another embodiment, the oligonucleotide composition is administered at a dose of 0.5 mpk.

In one embodiment of the above methods, the peptide composition is administered at a dose of 0.1 to 500 mpk. In another embodiment, the peptide composition is administered at a dose of 1 to 200 mpk. In another embodiment, the peptide composition is administered at a dose of 1 to 100 mpk. In another embodiment, the peptide composition is administered at a dose of 5 to 60 mpk. In another embodiment, the peptide composition is administered at a dose of 10 to 50 mpk.

In one embodiment of the above methods, the oligonucleotide composition is administered at a dose of 0.1 to 5 mpk; and the peptide composition is administered at a dose of 1 to 100 mpk.

In one embodiment, a composition for dual molecular delivery of an oligonucleotide and a peptide conjugate comprises:

(1) R-(L)$_a$-(G)$_b$; and
(2) (P)$_c$-(L)$_d$-(G)$_e$; wherein:

R is an oligonucleotide selected from the group consisting of DNA, RNA, siRNA, and microRNA;

P is a peptide and each occurrence of P is independently selected from Table 2;

L is a linker and each occurrence of L is independently selected from Table 3;

G is a targeting ligand and each occurrence of G is independently selected from Table 4;

each of a and b is independently 0, 1, 2, 3 or 4; and
each of c, d and e is independently 1, 2, 3, 4, 5 or 6.

In one embodiment of the above composition, each occurrence of P is independently selected from Table 2a.

In one embodiment of the above composition, each occurrence of P is independently selected from Table 2b.

In one embodiment of the above composition, each occurrence of L is independently selected from Table 3a.

In one embodiment of the above composition, each occurrence of G is independently selected from Table 4a.

In one embodiment of the above composition, each of a and b is independently 0, 1 or 2. In another embodiment, each of a and b is 0. In another embodiment, each of a and b is 1.

In one embodiment of the above composition, each of c, d and e is independently 1, 2 or 3. In another embodiment, each of c, d and e is 1.

In one embodiment of the above composition:
R is an siRNA;
each occurrence of P is independently selected from Table 2b;
each occurrence of L is independently selected from Table 3a;

each occurrence of G is independently selected from Table 4a;
each of a and b is independently 0, 1 or 2;
c is 1 or 2; and
each of d and e is independently 1, 2 or 3.

In one embodiment of the above composition, G comprises a ligand of the following formula:

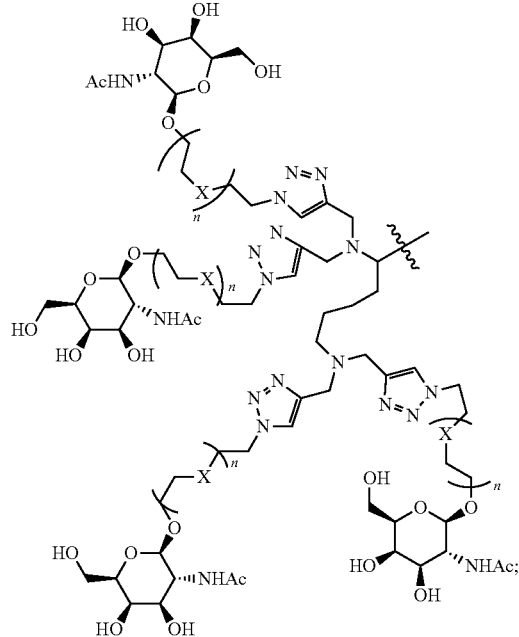

wherein each X is independently —O—, —S—, —CH$_2$— or —NH—; each n is independently 1, 2, 3, or 4; and the bond with "⌇" indicates the point of attachment.

In another embodiment, G of the above composition comprises a ligand of the following formula:

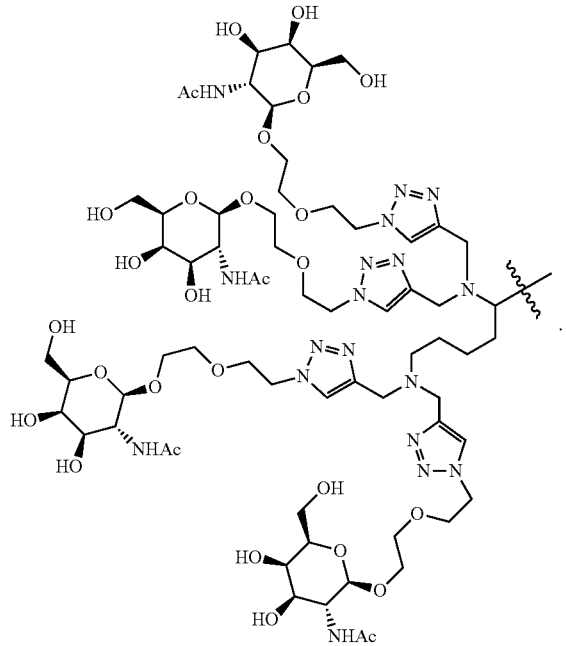 [SMILES: *C(CCCCN(Cc1cn(CCOCCO[C@@H]2O[C@H](CO)[C@H](O)[C@H](O)[C@H]2NC(C)=O)nn1)Cc1cn(CCOCCO[C@@H]2O[C@H](CO)[C@H](O)[C@H](O)[C@H]2NC(C)=O)nn1)N(Cc1cn(CCOCCO[C@@H]2O[C@H](CO)[C@H](O)[C@H](O)[C@H]2NC(C)=O)nn1)Cc1cn(CCOCCO[C@@H]2O[C@H](CO)[C@H](O)[C@H](O)[C@H]2NC(C)=O)nn1]

In one embodiment of the above composition, each of a and b is independently 0 or 1; c is 1; and each of d and e is 1.

In one embodiment of the above composition:
(1) G of R-(L)$_a$-(G)$_b$ is:
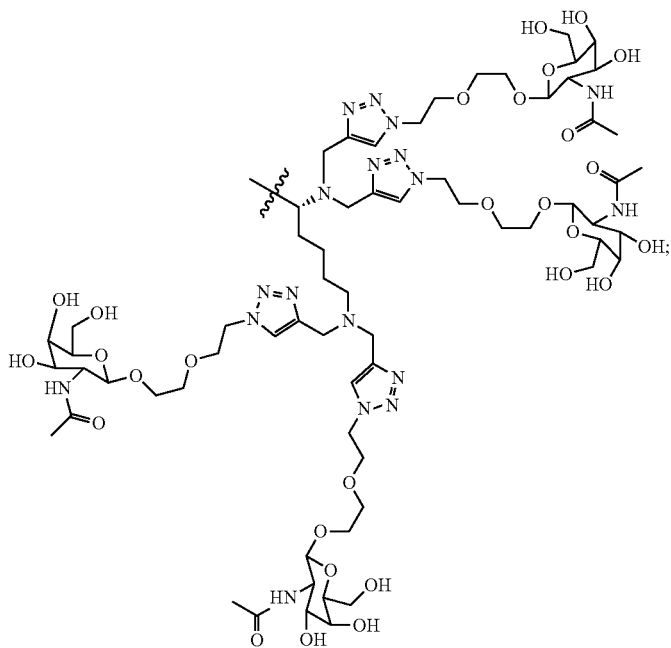 [SMILES: *[C@@H](CCCCN(Cc1cn(CCOCCOC2OC(CO)C(O)C(O)C2NC(C)=O)nn1)Cc1cn(CCOCCOC2OC(CO)C(O)C(O)C2NC(C)=O)nn1)N(Cc1cn(CCOCCOC2OC(CO)C(O)C(O)C2NC(C)=O)nn1)Cc1cn(CCOCCOC2OC(CO)C(O)C(O)C2NC(C)=O)nn1]
each of a and b is 1; and
(2) (P)$_c$-(L)$_d$-(G)$_e$ is:
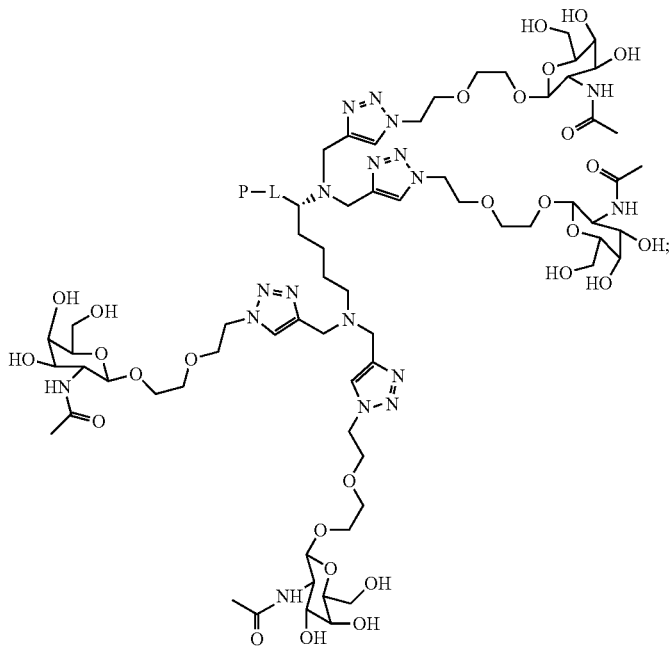
wherein P is a peptide selected from Table 2b; and
wherein each L of compositions (1) and (2) is independently selected from:
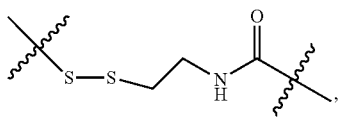
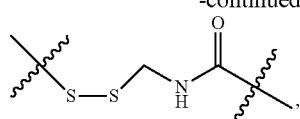
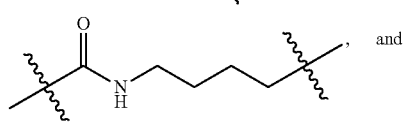
and

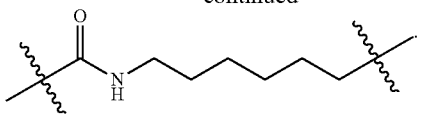

In one embodiment of the oligonucleotide composition, the oligonucleotide is a double stranded siRNA; and G is attached to the guide and/or passenger strand of the siRNA, wherein the point of attachment is at a 2'-position of a ribose ring and/or at a terminal 3' and/or 5'-position.

In one embodiment, the composition of R-(L)$_a$-(G)$_b$ further comprises a lipid or solubilizing agent.

In one embodiment, the composition of R-(L)$_a$-(G)$_b$ further comprises a lipid.

In one embodiment, the composition of R-(L)$_a$-(G)$_b$ further comprises a peptide.

In one embodiment, the composition of (P)$_c$-(L)$_d$-(G)$_e$ further comprises a lipid.

In one embodiment, the composition of (P)$_c$-(L)$_d$-(G)$_e$ further comprises an oligonucleotide.

In one embodiment, disclosed herein is a method for inhibiting the expression of one or more genes. The method comprises contacting one or more cells with a therapeutically effective amount of an oligonucleotide composition of the invention together with a peptide containing conjugate, wherein the effective amount is an amount that suppresses the expression of the one or more genes. The method can be performed in vitro, ex vivo or in vivo.

In one embodiment, disclosed herein is a method for expressing a protein or polypeptide of a gene. The method comprises contacting one or more cells with a therapeutically effective amount of an oligonucleotide composition of the invention together with a peptide containing conjugate, wherein the effective amount is an amount that suppresses the expression of the one or more genes. The method can be performed in vitro, ex vivo or in vivo.

The methods and compositions of the invention can be used for the treatment of any disease or disorder known in the art, and for the treatment of any subject, e.g., any animal, any mammal, such as any human. One of ordinary skill in the art will also recognize that the methods and compositions of the invention may be used for the treatment of any disease that would benefit from downregulating or silencing a gene or genes.

The methods and compositions of the invention may be used with any dosage and/or formulation described herein, or any dosage or formulation known in the art. In addition to the routes of administration described herein, a person skilled in the art will also appreciate that other routes of administration may be used to administer the modular composition of the invention.

Oligonucleotide

An "oligonucleotide" as used herein, is a double stranded or single stranded, unmodified or modified RNA or DNA, including mRNA. Examples of modified RNAs include those which have greater resistance to nuclease degradation than do unmodified RNAs. Further examples include those which have a 2' sugar modification, a base modification, a modification in a single strand overhang, for example a 3' single strand overhang, or, particularly if single stranded, a 5' modification which includes one or more phosphate groups or one or more analogs of a phosphate group. Examples and a further description of oligonucleotides can be found in WO2009/126933, which is hereby incorporated by reference.

In an embodiment, an oligonucleotide is an antisense, miRNA or siRNA. In one embodiment, the siRNA is a double stranded siRNA (ds siRNA). In another embodiment, the siRNA is a single stranded siRNA (ss siRNA). In an embodiment, the oligonucleotide is the passenger strand of an siRNA. In an embodiment, the oligonucleotide is the guide strand of an siRNA. In an embodiment, an oligonucleotide is mRNA.

siRNA siRNA directs the sequence-specific silencing of mRNA through a process known as RNA interference (RNAi). The process occurs in a wide variety of organisms, including mammals and other vertebrates. Methods for preparing and administering siRNA and their use for specifically inactivating gene function are known. siRNA includes modified and unmodified siRNA. Examples and a further description of siRNA can be found in WO2009/126933, which is hereby incorporated by reference.

A number of exemplary routes of delivery as described in the Example section can be used to administer siRNA to a subject. In addition, the siRNA can be formulated according to any exemplary method known in the art. Examples and a further description of siRNA formulation and administration can be found in WO2009/126933, which is hereby incorporated by reference.

In some embodiments, siRNA sequences shown in Table 1 as well as their unmodified equivalents are suitable for compositions and methods as described herein and used in the Example section.

TABLE 1

| Sequence Code | Gene Target | Strand | Sequence | SEQ ID NO |
|---|---|---|---|---|
| siRNA-I | CTNNB1 | passenger | [6 amiL][iB][omeC][omeU][fluG]omeU][omeU][fluG][fluG][fluA][omeU][omeU][fluG][fluA][omeU][omeU][omeC][fluG][fluA][fluA][fluA][omeUs][omeU][iB] | 1803 |
| | CTNNB1 | guide | [omeUs][fluUs][omeUs][fluC][omeG][fluA][omeA][fluU][omeC][fluA][omeA][fluU][omeC][fluC][omeA][fluA][omeC][fluA][omeG][omeUs][omeU] | 1804 |
| siRNA-II | CTNNB1 | passenger | [6amiL][iB][omeC][omeU][fluG][omeU][omeU][fluG][fluG][fluA][omeU][omeU][fluG][fluA][omeU][omeU][omeC][fluG][fluA][fluA][omeUs][omeU][iB] | 1803 |
| | CTNNB1 | guide | [vinylP3dTs][fluU]omeU][fluC][omeG][fluA][omeA][fluU][omeC][fluA][omeA][fluU][omeC][fluC][omeA][fluA][omeC][fluA][omeG][omeUs][omeU] | 1805 |
| siRNA-III | CTNNB1 | passenger | [6amiL][iB][omeC][omeU][fluG][omeU][omeU][fluG][fluG][fluA][omeU][omeU][fluG][fluA][omeU][omeU][omeC][fluG][fluA][fluA][fluA][omeUs][omeU][iB] | 1803 |
| | CTNNB1 | guide | [vinylPmoeT][fluU][omeU][fluC][omeG][fluA][omeA][fluU][omeC][fluA][omeA][fluU][omeC][fluC][omeA][fluA][omeC][fluA][omeG][omeUs][omeU] | 1806 |

TABLE 1-continued

| Sequence Code | Gene Target | Strand | Sequence | SEQ ID NO |
|---|---|---|---|---|
| sIRNA-IV | CTNNB1 | passenger | [6amiL][iB][omeC][omeU][fluG][omeU][omeU][fluG][fluG][fluA][omeU][omeU][fluG][fluA][omeU][omeU][omeC][fluG][clickA][fluA][fluA][omeUs][omeU][iB][5Chol] | 1807 |
| | CTNNB1 | guide | [vinylPmoeT][fluU][omeU][fluC][omeG][fluA][omeA][fluU][omeC][fluA][omeA][fluU][omeC][fluC][omeA][fluA][omeC][fluA][omeG][omeUs][omeU] | 1806 |
| sIRNA-V | CTNNB1 | passenger | [6amiL][iB][omeC][omeU][fluG][omeU][omeU][fluG][fluG][fluA][omeU][omeU][fluG][fluA][omeU][omeU][omeC][fluG][fluA][fluA][fluA][omeUs][omeU][iB] | 1803 |
| | CTNNB1 | guide | [omeU][fluU][omeU][fluC][omeG][fluA][omeA][fluU][omeC][fluA][omeA][fluU][omeC][fluC][omeA][fluA][omeC][fluA][omeG][omeUs][omeU] | 1808 |
| sIRNA-VI | CTNNB1 | passenger | [6amiL][iB][omeC][omeU][fluG][omeU][omeU][fluG][fluG][fluA][omeU][omeU][fluG][fluA][omeU][omeU][omeC][fluG][fluA][fluA][fluA][omeUs][omeU][iB] | 1803 |
| | CTNNB1 | guide | [fluU][fluU][fluU][omeC][fluG][fluA][fluA][omeU][omeC][fluA][fluA][omeU][omeC][fluC][fluA][fluA][omeC][fluA][fluG][omeUs][omeU] | 1809 |

Note:
As used herein, ome = 2' methoxy; flu = 2' fluoro; click = 2' propagyl; iB = inverted abasic; "s" subscript = phosphorothioate; r = 2' ribo; and 6amil = n-hexylamino.

vinylPmoeT

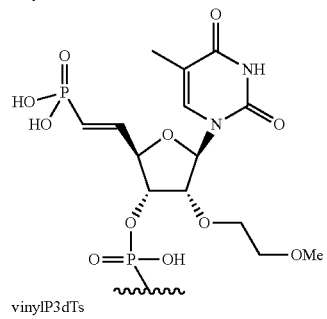

vinylP3dTs

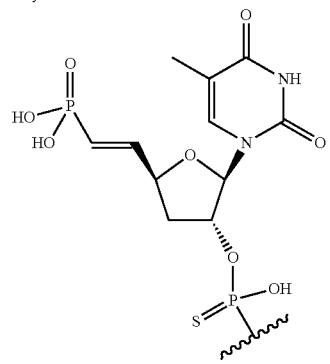

Peptides

For macromolecular drugs and hydrophilic drug molecules, which cannot easily cross bilayer membranes, entrapment in endosomal/lysosomal compartments of the cell is thought to be the biggest hurdle for effective delivery to their site of action. Without wishing to be bound by theory, it is believed that the use of peptides will facilitate oligonucleotide escape from these endosomal/lysosomal compartments or oligonucleotide translocation across a cellular membrane and release into the cytosolic compartment. In certain embodiments, the peptides of the present invention may be polycationic or amphiphilic or polyanionic peptides or peptidomimetics which show pH-dependent membrane activity and/or fusogenicity. A peptidomimetic may be a small protein-like chain designed to mimic a peptide.

In some embodiments, the peptide is a cell-permeation agent, preferably a helical cell-permeation agent. These peptides are commonly referred to as Cell Penetrating Peptides. See, for example, "Handbook of Cell Penetrating Peptides" Ed. Langel, U.; 2007, CRC Press, Boca Raton, Fla. Preferably, the component is amphipathic. The helical agent is preferably an alpha-helical agent, which preferably has a lipophilic and a lipophobic phase. A cell-permeation agent can be, for example, a cell permeation peptide, cationic peptide, amphipathic peptide or hydrophobic peptide, e.g. consisting primarily of Tyr, Trp and Phe, dendrimer peptide, constrained peptide or crosslinked peptide. Examples of cell penetrating peptides include Tat, Penetratin, and MPG. For the present invention, it is believed that the cell penetrating peptides can be a "delivery" peptide, which can carry large polar molecules including peptides, oligonucleotides, and proteins across cell membranes. Cell permeation peptides can be linear or cyclic, and include D-amino acids, "retro-inverso" sequences, nonpeptide or pseudo-peptide linkages, peptidyl mimics. In addition the peptide and peptide mimics can be modified, e.g. glycosylated, pegylated, or methylated. Examples and a further description of peptides can be found in WO2009/126933, which is hereby incorporated by reference. Synthesis of peptides is well known in the art.

The peptides may be conjugated through either end or both ends by addition of a cysteine or other thiol containing moiety to the C- or N-terminus. When not functionalized on the N-terminus, peptides may be capped by an acetyl group, or may be capped with a lipid, a PEG, or a targeting moiety. When the C-terminus of the peptides is unconjugated or unfunctionalized, it may be capped as an amide, or may be capped with a lipid, a PEG, or a targeting moiety.

Suitable peptides that can be used in the conjugates disclosed herein are listed in Table 2.

TABLE 2

Suitable Peptide Sequences

| Peptide SEQUENCE | SEQ ID No. |
|---|---|
| CGLFEAIEEFIENLWELLIDGWYGYGRKKRRQRR | SEQ ID NO: 1 |
| CGLFEAIEGFIENGWEGMIDGWYGYGHKKHHQHH | SEQ ID NO: 2 |
| C-bAla-LFEAIEGFIENGWEGMIDGWYGYGRKKRRQRR | SEQ ID NO: 3 |
| CGLFEAIEGFIENGLKGLIDWWYGYGRKKRRQRR | SEQ ID NO: 4 |
| CGLFEAIEGFIEWGWEGMIDGWYGYGRKKRRQRR | SEQ ID NO: 5 |
| CRRQRRKKRGYGYWGDIMGEWGNEIFGEIAEFLG | SEQ ID NO: 6 |
| CGLFEAIEGFIENGWEGMIDGWYGYGRKKRRQR | SEQ ID NO: 7 |
| CYGRKKRRQRRGLFEAIEGFIENGWEGMIDGWYG | SEQ ID NO: 8 |
| CIFGAIAGFIKNILKGLIDG | SEQ ID NO: 9 |
| CIFGAIAGFIRNIW | SEQ ID NO: 10 |
| CGLFHALLHLLHSLWHGLLHAWYGYGHKKHHQHR | SEQ ID NO: 11 |
| CGLFEAIEGLIENGWEGMIDGWYGYGRKKRRQRR | SEQ ID NO: 12 |
| CGLFELIEGFIENGWEGMIDGWYGYGRKKRRQRR | SEQ ID NO: 13 |
| CGLFEAIEGFIENGWEGLIDGWYGYGOOOOOQRR (O = ornithine) | SEQ ID NO: 14 |
| CGLFGAIEGFIENGWEGLIDGWYGYGRKKRRQRR | SEQ ID NO: 15 |
| CGLFEAIEGFLENGWEGMIDGWYGYGRKKRRQRR | SEQ ID NO: 16 |
| CGLFEAIEGFIENGLEGMIDGWYGYGRKKRRQRR | SEQ ID NO: 17 |
| CGLFGAIEGFIENGWEGMIDGWYGYGRKKRRQRR | SEQ ID NO: 18 |
| CGLFEAIEGFIENGWEG-Nle-IDGWYGYGRKKRRQRR | SEQ ID NO: 19 |
| CGIFGAIAGFIKNIWKGLIDW | SEQ ID NO: 20 |
| CYGRKKRRQRRGLFEAIEGFIENGWKGLIDAWYG | SEQ ID NO: 21 |
| CGLLEALEGLLESLWEGLLEAWYGYGRKKRRQRR | SEQ ID NO: 22 |
| CGLFEAIEGFIENGWEGMIDNWYGYGRKKRRQRR | SEQ ID NO: 23 |
| CIFGAIAGFIKNIWEGLIEAWYGLHLLHHLLHHLHHLLHHLLHL | SEQ ID NO: 24 |
| CIFGAIAGFIKNIWEGLIDAF | SEQ ID NO: 25 |
| CIFGAIAGFIKNIWEGLI | SEQ ID NO: 26 |
| CGLFEAIEGFIENGWEGMIDGWYGYGRKKRRQRRK(stearyl) | SEQ ID NO: 27 |
| CGLFEAIAGFIEGGWPGLINGWYGYGRKKRRQRRLHLLHHLLHHLHHLLHLLHHLLHHL | SEQ ID NO: 28 |
| CGLFEAIEGFIENGWEGMIDGWYGGGGLHLLHHLLHHLHHLLHHLLHLLHHLLHHL | SEQ ID NO: 29 |
| CGLFEAIEGFIENGWEGMIDGWYGLHLLHHLLHHLHHLLHHLLHL | SEQ ID NO: 30 |
| CGLFEALLELLESLWELLLEAYGRKKRRQRR | SEQ ID NO: 31 |
| CGLFEAIEGFIENGWEGMIDGWYGYGRKKRRQRR | SEQ ID NO: 32 |

TABLE 2-continued

Suitable Peptide Sequences

| Peptide SEQUENCE | SEQ ID No. |
|---|---|
| CGLFEAIEGFIENGWEGMADGWYGYGRKKRRQRR | SEQ ID NO: 33 |
| CGIFGAIAGFIKNIWEGLIDWWYGYGRKKRRQRR | SEQ ID NO: 34 |
| CGFLPAIAGILSQLFEGLIDGWYGYGRKKRRQRR | SEQ ID NO: 35 |
| CFFGAIWGFIKSIL | SEQ ID NO: 36 |
| CIFGAIAGFIKNIWKGLIDWWYG | SEQ ID NO: 37 |
| CGLFEAIEGFIWNGWEGMIDGWYGYGRKKRRQRR | SEQ ID NO: 38 |
| CGLFEAIAEFIENGWEGMIDGWYGYGRKKRRQRR | SEQ ID NO: 39 |
| CYGRKKRRQRRGLFEAIEGFIENGWKGLIDWWYG | SEQ ID NO: 40 |
| CGLFEAIEGFIEEGWEGMIDGWYGYGRKKRRQRR | SEQ ID NO: 41 |
| CGLFEAIEGFIENAWEGMIDGWYGYGRKKRRQRR | SEQ ID NO: 42 |
| CGLFEAIEGFIENGWEGMIDLWYGYGRKKRRQRR | SEQ ID NO: 43 |
| CRLLRLLLRLWRRLLRLLR | SEQ ID NO: 44 |
| CGGFEAIEGFIENGWEGMIDGWYGYGRKKRRQRR | SEQ ID NO: 45 |
| CGLFEKIEGFIENGWEGMIDGWYGYGRKKRRQRR | SEQ ID NO: 46 |
| CGLFEAIEGFIENGWENMIDGWYGYGRKKRRQRR | SEQ ID NO: 47 |
| CIFGAIAGFIKNILKGL | SEQ ID NO: 48 |
| CIFGAIAGFIKNILKGLIDGWYG | SEQ ID NO: 49 |
| CGLFEAIEGFIENGWEGMIDGWYG-(PEG)3-YGRKKRRQRR | SEQ ID NO: 50 |
| CGLFEALLELLESLWELLLEAYGRKKRRQRRLHLLHHLLHHLHHLLHHLLHL | SEQ ID NO: 51 |
| CYGRKKRRQRRWEAALAEALAEALAEHLAEALAEALEALAA | SEQ ID NO: 52 |
| CIFGAIAGFIKNIWEGLIDGWYGKLALKLALKALKAALKLA | SEQ ID NO: 53 |
| CFFGAIWEFIRSILEGLIDGWYGYGRKKRRQRR | SEQ ID NO: 54 |
| CGLFHALLHLLHSLWHLLLHAWYGYGRKKRRQRR | SEQ ID NO: 55 |
| CGLFHALLHLLHSLWHLLLHAWYGYGHKKHHQHR | SEQ ID NO: 56 |
| CGLFGALLELLESLWKGLLEWYGRKKRRQRR | SEQ ID NO: 57 |
| CRRQRRKKRGYGYWGDILGEWGNEIFGEIAEFLG | SEQ ID NO: 58 |
| CGLFEALEGFLENGWEGLLDGWYGYGROORRQRR (O = ornithine) | SEQ ID NO: 59 |
| CGLFGEIEELIENGLKNLIDWWYGYGRKKRRQRR | SEQ ID NO: 60 |
| CRRQRRKKRGYGYWWDILGKWGNEIFGEIAEFLG all (D) aminos | SEQ ID NO: 61 |
| CGIFGAIAGFIKNIL | SEQ ID NO: 62 |
| CGIFGAIAGLLKNIFK | SEQ ID NO: 63 |
| CIFGAIAGFIKNIWKGLIDW | SEQ ID NO: 64 |
| CIFGAIAGFIKNIWK | SEQ ID NO: 65 |
| CGLFEEIEGFIENGWEGLIDWWYGYGHKKHHQHR | SEQ ID NO: 66 |
| CGLFGEIEELIENGLKNLIDWWYGYGHKKHHQHR | SEQ ID NO: 67 |
| CGLFEEIEEFIENGWEGLIDWWYGYGHKKHHQHR | SEQ ID NO: 68 |
| stearyl-WEAALAEALAEALAEHLAEALAEALEALAAYGRKKRRQRRC | SEQ ID NO: 69 |
| CGLFEAIEGFIENGWKGLIDGWYGGLFEAIEGFIENGWKGLIDWWYG | SEQ ID NO: 70 |

TABLE 2-continued

Suitable Peptide Sequences

| Peptide SEQUENCE | SEQ ID No. |
| --- | --- |
| CGFFHAFFHFFHSFWHGFFEA | SEQ ID NO: 71 |
| CGNFGEIEELIEEGLENLIDWWNG | SEQ ID NO: 72 |
| CFFGAIWEFIRNILEGF | SEQ ID NO: 73 |
| CFFGAIWEFIHSIL | SEQ ID NO: 74 |
| CGLFHALLHLLHSLWHGLLEA | SEQ ID NO: 75 |
| CIFGAIAGFIKNIWEGL | SEQ ID NO: 76 |
| CIFGAIAGLLKNIFEGLIDGWYGYGRKKRRQRR | SEQ ID NO: 77 |
| CGFIGAIANLLSKIFEGLIDGWYGYGRKKRRQRR | SEQ ID NO: 78 |
| CGLFEAIEELIENLWKGLIDAWYGYGRKKRRQRR | SEQ ID NO: 79 |
| CGIFGAIAGLLKNIFKGLIDA | SEQ ID NO: 80 |
| CGIFGAIAGLLKNIFKGLIDW | SEQ ID NO: 81 |
| CGIFEAIAGLLKNIFK | SEQ ID NO: 82 |
| CGIFEEIAGLLKNIFK | SEQ ID NO: 83 |
| CGLFEAIAGFIEGGWPGLINGWYGYGRKKRRQRRLHLLHHLLHHLHHLLHHLLHL | SEQ ID NO: 84 |
| CGLFEAIEGFIENGWKGMIDWWYGYGRKKRRQRRK(stearyl) | SEQ ID NO: 85 |
| CGLFGEIEEFIENGWKGLIDWWYG | SEQ ID NO: 86 |
| CIFGAIAGFIKNIWLHLLHHLLHHLHHLLHHLLHL | SEQ ID NO: 87 |
| CGIFGAIEGFIENGWKGLIDAWYGYRKKRRQRR | SEQ ID NO: 88 |
| CELFGAIEGFIENGWKGLIDWWYGYGRKKRRQRR | SEQ ID NO: 89 |
| CIFGIDDLIIGLLFVAIVEAGIGGYLLGSYGRKKRRQRR | SEQ ID NO: 90 |
| GLFGALAEALAEALAEHLAEALAEALEALAAGGSC | SEQ ID NO: 91 |
| CGFIGAIANLLSKIFEGLIDGWYGYGRKKRRQRR all (D) | SEQ ID NO: 92 |
| CFFGAIWEFIRSILKGLI | SEQ ID NO: 93 |
| CFFGAIWEFIRSILK | SEQ ID NO: 94 |
| CFFGAIWEFIRSILE | SEQ ID NO: 95 |
| CIFGAIAGFIKNIWE | SEQ ID NO: 96 |
| CIFGAIAGFIKNIWKGLIDA | SEQ ID NO: 97 |
| CFFEAIEEFIKNILK | SEQ ID NO: 98 |
| CIFGAIAGLLRNIF | SEQ ID NO: 99 |
| CGIFGAIAGLLKNIW | SEQ ID NO: 100 |
| CLFGAIWEFIKSIL | SEQ ID NO: 101 |
| CFWGAIWEFIKSIL | SEQ ID NO: 102 |
| CFGGAIWEFIKSIL | SEQ ID NO: 103 |
| CFAGAIWEFIKSIL | SEQ ID NO: 104 |
| CGLFEAIEGFIENGWEGM(SO2)IDGWYGYGRKKRRQRR | SEQ ID NO: 105 |
| CGLFEAIEGFIENGWEGMIDWWYGYGRKKRRQRR | SEQ ID NO: 106 |
| CFFGAIWEFIKSIG | SEQ ID NO: 107 |
| CFFGAIWEFIKSIA | SEQ ID NO: 108 |

TABLE 2-continued

Suitable Peptide Sequences

| Peptide SEQUENCE | SEQ ID No. |
|---|---|
| CFFGAIWEFIKSIN | SEQ ID NO: 109 |
| CFFGAIWEFIKSIW | SEQ ID NO: 110 |
| CFFGAIWEFIKSILEGLIDWWYGYGHKKHHQHR | SEQ ID NO: 111 |
| Ac-CLHLLHHLLHHLHHLLHHLLHLLHHLLHHL | SEQ ID NO: 112 |
| Ac-LHLLHHLLHHLHHLLHHLLHHLLHHLGGGRKKRRQRRRPPQC | SEQ ID NO: 113 |
| CRKKRRQRRPPQGGGLHLLHHLLHHLHHLLHHLLHLLHHLLHHL | SEQ ID NO: 114 |
| CLHLLHHLLHHLHHLLHHLLHHLLHHLGGGRKKRRQRRRPPQ | SEQ ID NO: 115 |
| CGLFHAIAHFIHGGWHGLIHGWYGYGRKKRRQRR | SEQ ID NO: 116 |
| CGLFKAIAKFIKGGWKGLIKGWYGYGRKKRRQRR | SEQ ID NO: 117 |
| CGLFEAIAGFIENGWEGMIDGWYGYGRKKRRQRR | SEQ ID NO: 118 |
| CWEAALAEALAEALAEHLAEALAEALEALAAYGRKKRRQRR | SEQ ID NO: 119 |
| CGLFEAIEGFIENGWEGMIDGWYGRKKRRQRRRPPQ | SEQ ID NO: 120 |
| GLFEAIEGFIENGWEGMIDGWYGYGRKKRRQRRC | SEQ ID NO: 121 |
| Ac-LHLLHHLLHHLHHLLHHLLHHLLHHLRKKRRQRRRPPQ | SEQ ID NO: 122 |
| Ac-LHLLHHLLHHLHHLLHHLLHLLHHLLHHLGPGRKKRRQRRRPPQ | SEQ ID NO: 123 |
| Ac-LIRLWSHLIHIWFQNRRLKWKKK | SEQ ID NO: 124 |
| Ac-RKKRRQRRRPPQQQQQQ | SEQ ID NO: 125 |
| Ac-GLFEAIEGFIENGWEGMIDGWYGYGRKKRRQRR | SEQ ID NO: 126 |
| Ac-LHLLHHLLHHLHHLLHHLLHLLHHLLHHLGGGRRRRRRRRR | SEQ ID NO: 127 |
| Ac-LHLLHHLLHHLHHLLHHLLHLLHHLLHHL-(Peg)12-RKKRRQRRRPPQ | SEQ ID NO: 128 |
| Ac-GLFGAIAGFIENGWEGMIDGWYGLIRLWSHLIWFQNRRLKWLLL | SEQ ID NO: 129 |
| Ac-HHHHHRKKRRQRRRPPQGGGLHLLHHLLHHLHHLLHHLLHLLHHLLHHL | SEQ ID NO: 130 |
| Ac-LHLLHHLLHHLHHLLHHLLHLLHHLLHHL-(Peg)2-RKKRRQRRRPPQ | SEQ ID NO: 131 |
| Ac-LHLLHHLLHHLHHLLHHLLLLLHHLLHHLGGGRQIKIWFQNRRMKWKKGG | SEQ ID NO: 132 |
| Ac-KLLKLLLKLWLKLLKLLLKLLGGGRKKRRQRRRPPQ | SEQ ID NO: 133 |
| Ac-LHHLLHHLLHLLHHLLHHLHHLLHHLLHLC all (D) | SEQ ID NO: 134 |
| Ac-LHLLHHLLHHLHHLLHHLLHLLHHLLHHL-(PEG)6-RKKRRQRRRPPQC | SEQ ID NO: 135 |
| Ac-GLFEAIEGFIENGWEGMIDGWYGYGRKKRRQRRC | SEQ ID NO: 136 |
| CGLFEAIEGFIENGWEGMIDGWYGYGRKKRRQRR all (D) | SEQ ID NO: 137 |
| CGLFEAIEGFIENGWEGMIDGWYGYGRRRRRRRRR | SEQ ID NO: 138 |
| YGRKKRRQRRGLFEAIEGFIENGWEGMIDGWYGC | SEQ ID NO: 139 |
| CGVFVLGFLGFLATAGSYGRKKRRQRR | SEQ ID NO: 140 |
| CGLFKAIAKFIKGGWKGLIKGWYG | SEQ ID NO: 141 |
| CGLFEAIEGFIENGWEGMIDGWYGYGRKKR | SEQ ID NO: 142 |
| CGLFEAIEGFIENGWEGMIDGWYGYGRKKRRQRRYGRKKRRQRR | SEQ ID NO: 143 |
| CGLFEAIEGFIENGWEGMIDGWYGYGRKKRRQRRYGRKKRRQRR | SEQ ID NO: 144 |
| CGLFEAIKGFIENGWEGMIDGWYGYGRKKRRQRR | SEQ ID NO: 145 |

TABLE 2-continued

Suitable Peptide Sequences

| Peptide SEQUENCE | SEQ ID No. |
|---|---|
| CGLFEAIHGFIENGWEGMIDGWYGYGRKKRRQRR | SEQ ID NO: 146 |
| CGLFEAIRGFIENGWEGMIDGWYGYGRKKRRQRR | SEQ ID NO: 147 |
| CGLFEAIDGFIENGWEGMIDGWYGYGRKKRRQRR | SEQ ID NO: 148 |
| CRLFEAIEGFIENGWEGMIDGWYGYGRKKRRQRR | SEQ ID NO: 149 |
| CGGGLFEAIEGFIENGWEGMIDGWYGYGRKKRRQRR | SEQ ID NO: 150 |
| CGLFEAIEGFIENGWEGMIDGWYGGGGYGRKKRRQRR | SEQ ID NO: 151 |
| CGLFEAIEGFIENGWEGMIDGWYG-(PEG)11-YGRKKRRQRR | SEQ ID NO: 152 |
| CFLGFLLGVGSAIASGIAVSKVLHL | SEQ ID NO: 153 |
| CGVFVLGFLGFLATAGSAMGARSLTLSAYGRKKRRQRR | SEQ ID NO: 154 |
| Ac-GLWRALWRLLRSLWRLLWRA-mercaptoethylamide | SEQ ID NO: 155 |
| C-Nle-LFEAIEGFIENGWEGMIDGWYGYGRKKRRQRR | SEQ ID NO: 156 |
| CELFEAIEGFIENGWEGMIDGWYGYGRKKRRQRR | SEQ ID NO: 157 |
| CGFFGAIAGFLEGGWEGMIAGWHGYGRKKRRQRR | SEQ ID NO: 158 |
| CFLGFLLGVGSAIASGIAVSKVLHLYGRKKRRQRR | SEQ ID NO: 159 |
| GLFEAIEGFIENGWEGLAEALAEALEALAAGGSC | SEQ ID NO: 160 |
| CGLFEAIEGFIENGWEGMIDGWYGLHLLHHLLHHLHHLLHLLHHLLHHL | SEQ ID NO: 161 |
| CGLFEAIEGFIENGWEGMIDGWYGYGRKKRRQRRLHLLHHLLHHLHHLLHHLLHLLHHLLHHL | SEQ ID NO: 162 |
| CGLFGAIAGFIEGGWTGMIDGWYGYGRKKRRQRR | SEQ ID NO: 163 |
| CGLFGAIAGFIEGGWQGMVDGWYGYGRKKRRQRR | SEQ ID NO: 164 |
| CGLFGAIAGFIENGWQGLIDGWYGYGRKKRRQRR | SEQ ID NO: 165 |
| CGLFGAIAGFIENGWEGLVDGWYGYGRKKRRQRR | SEQ ID NO: 166 |
| CGLFGAIAGFIEGGWSGMIDGWYGYGRKKRRQRR | SEQ ID NO: 167 |
| CGLFGAIAGFIEGGWPGLVAGWYGYGRKKRRQRR | SEQ ID NO: 168 |
| CGLFGAIAGFIENGWEGMVDGWYGYGRKKRRQRR | SEQ ID NO: 169 |
| CGLFGAIAGFIEGGWPGLINGWYGYGRKKRRQRR | SEQ ID NO: 170 |
| CGLFGAIAGFIENGWEGLIDGWYGYGRKKRRQRR | SEQ ID NO: 171 |
| CGLFGAIAGFIENGWEGMIDGWYGYGRKKRRQRR | SEQ ID NO: 172 |
| CGLFGAIAGFIENGWEGMIDGWYGSSKKKK | SEQ ID NO: 173 |
| CGLFGAIAGFIENGWEGLIDGWYGYGRKKRRQRR | SEQ ID NO: 174 |
| CGLFEAIEGFIENGWEGLIDGWYGYGRKKRRQRR | SEQ ID NO: 175 |
| CGLFGAIAGFIENGWEGLIEGWYGGGRKKRRQRR | SEQ ID NO: 176 |
| CGLFEAIEGFIENGWEGMIDGWYGGGRKKRRQRR | SEQ ID NO: 177 |
| CGLFEAIAGFIENGWEGLIDGWYGYGRKKRRQRR | SEQ ID NO: 178 |
| CGLFEAIAEFIENGWEGLIEGWYGGRKKRRQRR | SEQ ID NO: 179 |
| CGLFEAIEGFIENGWEGMIDGWYGRKKRRQRRR | SEQ ID NO: 180 |
| CKLLKLLLKLWLKLLKLLLKLL | SEQ ID NO: 181 |
| CKLLKLLLKLWLKLLKLLLKLLYGRKKRRQRR | SEQ ID NO: 182 |

TABLE 2-continued

Suitable Peptide Sequences

| Peptide SEQUENCE | SEQ ID No. |
|---|---|
| GLFEAIEGFIENGWEGMIDGWYGC | SEQ ID NO: 183 |
| CVLFEAIEGFIENGWEGMIDGWYGYGRKKRRQRR | SEQ ID NO: 184 |
| CSLFEAIEGFIENGWEGMIDGWYGYGRKKRRQRR | SEQ ID NO: 185 |
| CGLFEAIEGFIENGWEGMIDGWYGYGRKKRRQ | SEQ ID NO: 186 |
| CGLFEAIEGFIENGWEGMIDGWYGYGRKKRR | SEQ ID NO: 187 |
| CGLFEAIEGFIENGWEGMIDGWYGYGKKKKKQKK | SEQ ID NO: 188 |
| CGLFEAIEGFIENGWEGMIDGWYGGLFEAIEGFIENGWEGMIDGWYG | SEQ ID NO: 189 |
| CGLFEAIEGFIENGWEGMIDGWYGYGRKKRRQRRGLFEAIEGFIENGWEGMIDGWYGYGRKKRRQRR | SEQ ID NO: 190 |
| RRQRRKKRGYGYWGDIMGEWGNEIFGEIAEFLGC | SEQ ID NO: 191 |
| CRRQRRKKRGYGYWGDIMGEWGNEIFGEIAEFLG | SEQ ID NO: 192 |
| GLFEAIEGFIENGWEGMIDGWYGYGRK-K(D)-RRQRR | SEQ ID NO: 193 |
| GLFEAIEGFIENGWEGMIDGWYGYGRKK-R(D)-RQRR | SEQ ID NO: 194 |
| GL-F(D)-EAIEGFIENGWEGMIDGWYGYGRKKRRQRR | SEQ ID NO: 195 |
| GLF-E(D)-AIEGFIENGWEGMIDGWYGYGRKKRRQRR | SEQ ID NO: 196 |
| CGLFEAIEGFIENGWEGMIDGWYG | SEQ ID NO: 197 |
| CYGRKKRRQRR | SEQ ID NO: 198 |
| YGRKKRRQRRC | SEQ ID NO: 199 |
| RRQRRKKRGYGYWGDIMGEWGNEIFGEIAEFLGC all(D) | SEQ ID NO: 200 |
| CRRQRRKKRGYGYWGDIMGEWGNEIFGEIAEFLG all(D) | SEQ ID NO: 201 |
| CGLFEAIEGFIENGWEGMIDGAYGYGRKKRRQRR | SEQ ID NO: 202 |
| CGLFEALLELLESLWELLLEAWYGYGRKKRRQRR | SEQ ID NO: 203 |
| CGLFEAIEGFNENGWEGMIDGWYGYGRKKRRQRR | SEQ ID NO: 204 |
| CGLFEAIEGFIENEWEGMIDGWYGYGRKKRRQRR | SEQ ID NO: 205 |
| K(stearyl)GLFEAIEGFIENGWEGMIDGWYGYGRKKRRQRRC | SEQ ID NO: 206 |
| CGLFEAIK(stearyl)GFIENGWEGMIDGWYGYGRKKRRQRR | SEQ ID NO: 207 |
| CGLFEAIKGFIENGWEGMIDGWYGYGRK(stearoyl)KRRQRR | SEQ ID NO: 208 |
| CGLFEAIEGFIENPWEGMIDGWYGYGRKKRRQRR | SEQ ID NO: 209 |
| (stearyl)GLFEAIEGFIENPWEGMIDGWYGYGRKKRRQRRC | SEQ ID NO: 210 |
| CGLFGAIAGFIEGGWPGLINGWYGYGRKKRRQRRLHLLHHLLHHLHHLLHHLLHLLHHLLHHL | SEQ ID NO: 211 |
| CGLFGAIAGFIEGGWPGLINGWYGYGRKKRRQRRLHLLHHLLHHLHHLLHHLLHL | SEQ ID NO: 212 |
| CGLFEAIAGFIEGGWPGLINGWYGYGRKKRRQRR | SEQ ID NO: 213 |
| CGLEEAIEGFIENGWEGMIDGWYGYGRKKRRQRR | SEQ ID NO: 214 |
| CGLFNAIEGFIENGWEGMIDGWYGYGRKKRRQRR | SEQ ID NO: 215 |
| CGLFAAIEGFIENGWEGMIDGWYGYGRKKRRQRR | SEQ ID NO: 216 |
| CGLFEAIENFIENGWEGMIDGWYGYGRKKRRQRR | SEQ ID NO: 217 |
| CGLFEAIEKFIENGWEGMIDGWYGYGRKKRRQRR | SEQ ID NO: 218 |
| CGLFEAIEGFAENGWEGMIDGWYGYGRKKRRQRR | SEQ ID NO: 219 |

TABLE 2-continued

Suitable Peptide Sequences

| Peptide SEQUENCE | SEQ ID No. |
|---|---|
| CGLFEAIEGFIENWWEGMIDGWYGYGRKKRRQRR | SEQ ID NO: 220 |
| CGLFEAIEGFIENNWEGMIDGWYGYGRKKRRQRR | SEQ ID NO: 221 |
| CGLFEAIEGFIENGEEGMIDGWYGYGRKKRRQRR | SEQ ID NO: 222 |
| CGLFEAIEGFIENGWAGMIDGWYGYGRKKRRQRR | SEQ ID NO: 223 |
| CGLFEAIEGFIENGWNGMIDGWYGYGRKKRRQRR | SEQ ID NO: 224 |
| CGLFEAIEGFIENGWGGMIDGWYGYGRKKRRQRR | SEQ ID NO: 225 |
| CGLFEAIEGFIENGWEGMIDAWYGYGRKKRRQRR | SEQ ID NO: 226 |
| CGLFEAIEGFIENGWLGMIDGWYGYGRKKRRQRR | SEQ ID NO: 227 |
| CGLFEAIEGFIENGWKGMIDGWYGYGRKKRRQRR | SEQ ID NO: 228 |
| CGLFEAIEGFIENGWEGMIDKWYGYGRKKRRQRR | SEQ ID NO: 229 |
| CGLFEAIEGFIENGWEGMIDEWYGYGRKKRRQRR | SEQ ID NO: 230 |
| CGLFEAIEGFIENGWEGMIDGLYGYGRKKRRQRR | SEQ ID NO: 231 |
| CGLFEAIEGFIENGWEGMIDGNYGYGRKKRRQRR | SEQ ID NO: 232 |
| CGLFEAIEGFIENGWEGMIDGKYGYGRKKRRQRR | SEQ ID NO: 233 |
| CGLFEAIEGFIENGWEGMIDGEYGYGRKKRRQRR | SEQ ID NO: 234 |
| CGLFEALEELLEGGWEGLIEAWYGYGRKKRRQRR | SEQ ID NO: 235 |
| CELFGAIWEFIEGGWEGLIEAWYGYGRKKRRQRR | SEQ ID NO: 236 |
| CGLFEALEEFIEGGWEGLLEAWYGYGRKKRRQRR | SEQ ID NO: 237 |
| CGLFEALEEFIENGWEGLLEAWYGYGRKKRRQRR | SEQ ID NO: 238 |
| CGLFEAIEGFIESGWEGLIDGWYGYGRKKRRQRR | SEQ ID NO: 239 |
| CGLFEAIEEFIEGGWEGLIEAWYGYGRKKRRQRR | SEQ ID NO: 240 |
| CGLFEAIEGFIENGWEGLIDAWYGYGRKKRRQRR | SEQ ID NO: 241 |
| CGLFEAIEGFILNGWEGMIDGWYGYGRKKRRQRR | SEQ ID NO: 242 |
| CGLFEAIEGFIKNGWEGMIDGWYGYGRKKRRQRR | SEQ ID NO: 243 |
| CGLFEAIEGFIGNGWEGMIDGWYGYGRKKRRQRR | SEQ ID NO: 244 |
| CGLFEAIEGFIELGWEGMIDGWYGYGRKKRRQRR | SEQ ID NO: 245 |
| CGLFEAIEGFIEKGWEGMIDGWYGYGRKKRRQRR | SEQ ID NO: 246 |
| CGLFEAIAEFIEGGWEGLIEGWYGYGRKKRRQRR | SEQ ID NO: 247 |
| CRGWEVLKYWWNLLQY | SEQ ID NO: 248 |
| CRGWEVLKYWWNLLQYYGRKKRRQRR | SEQ ID NO: 249 |
| CGLFGAIAGFIENGWEGMIDGWYGFRYGRKKRRQRR | SEQ ID NO: 250 |
| Ac-CGLFEAIEGFIENGWEGMIDGWYGYGRKKRRQRR-CO2H | SEQ ID NO: 251 |
| CGLLEALEGLLENGWEGLLEAWYGYGRKKRRQRR | SEQ ID NO: 252 |
| CLRHLLRHLLRHLRHLLRHLRHLLRHLLRH | SEQ ID NO: 253 |
| CGIFEAIEGFIENGWEGIIDGWYGYGROORRQRR (O = ornithine) | SEQ ID NO: 254 |
| CGIGAVLKVLTTGLPALISWIKRKRQQ | SEQ ID NO: 255 |
| CGIGAVLKVLTTGLPALISWIHHHHQQ | SEQ ID NO: 256 |
| CGAFEAIEGFIENGWEGMIDGWYGYGRKKRRQRR | SEQ ID NO: 257 |

TABLE 2-continued

Suitable Peptide Sequences

| Peptide SEQUENCE | SEQ ID No. |
|---|---|
| Ac-LHLLHHLLHHLHHLLHLLHHLLHHLLHHLRRRRR | SEQ ID NO: 258 |
| CGLFGAIWGFIENWWKGLIDWWYGYGRKKRRQRR | SEQ ID NO: 259 |
| CGLFGAIEGFIENGWKGLIDAWYGYGRKKRRQRR | SEQ ID NO: 260 |
| CGLFEAIAGFIENGWKGLIDWWYGYGRKKRRQRR | SEQ ID NO: 261 |
| GLFEAIEGFIENGWKGLIDWWYGYGRKKRRQRRC | SEQ ID NO: 262 |
| YGRKKRRQRRGLFEAIEGFIENGWKGLIDAWYGC | SEQ ID NO: 263 |
| YGRKKRRQRRGLFEAIEGFIENGWKGLIDWWYGC | SEQ ID NO: 264 |
| CGLFHAIHGFIENGWHGLIDWWYGYGRKKRRQRR | SEQ ID NO: 265 |
| CGLFEAIEGFIENGWKGLIDWWYGYGRKKRRQRRK(stearyl) | SEQ ID NO: 266 |
| CGLFKALLKLLKSLWKLLLKAWYGYGHKKHHQHR | SEQ ID NO: 267 |
| CGLFKALLKLLKSLWKGLLKAWYGYGHKKHHQHR | SEQ ID NO: 268 |
| CGLAKALLKLLKSLWKGLIEAWYGYGRKKRRQRR | SEQ ID NO: 269 |
| CGIFGAIAGFIKNIW | SEQ ID NO: 270 |
| CIFGAIAGFIKNIWEGLIDGWYGYGRKKRRQRR | SEQ ID NO: 271 |
| CGIFGAIAGFIKNIWEGLIDGYGRKKRRQRR | SEQ ID NO: 272 |
| CGIFGAIAGFIKNIWKGLIDAWYGYGRKKRRQRR | SEQ ID NO: 273 |
| CIFGAIAGFIKNIWKGLIDWWYGYGRKKRRQRR | SEQ ID NO: 274 |
| CLFGAIAGFIKNIW | SEQ ID NO: 275 |
| CGL(R5)EAIEGF(S8)ENGWEGMIDGWYGYGRKKRRQRR | SEQ ID NO: 276 |
| CGLFEA(S5)EGF(S5)ENGWEGMIDGWYGYGRKKRRQRR | SEQ ID NO: 277 |
| CGLFEAIEGFIENGWEGAIDGWYGYGRKKRRQRR | SEQ ID NO: 278 |
| CGLFEAIEGFIENGWEGEIDGWYGYGRKKRRQRR | SEQ ID NO: 279 |
| CGIFGAIAGFIKNGWEGMVDWYGYGRKKRRQRR | SEQ ID NO: 280 |
| CGLFEAIAGFIENGWEGMIDGWYGFYGRKKRRQRR | SEQ ID NO: 281 |
| CGIFGAIAGFIKNGWEGMIDGWYGYGRKKRRQRR | SEQ ID NO: 282 |
| CIFGAIAGFIKNIW | SEQ ID NO: 283 |
| CIFGAIAGFIKNIWYGRKKRRQRR | SEQ ID NO: 284 |
| CGIFGAIAGFIKNIWEGMIDGWYGYGRKKRRQRR | SEQ ID NO: 285 |
| CGLFEAIEGFIENGWEGLIEAYGRKKRRQRR | SEQ ID NO: 286 |
| CGLFEALLGFIENGWEGLIDGYGRKKRRQRR | SEQ ID NO: 287 |
| CGLFGAIEGFIENGWEGLIDGWYGYGRKKRRQRRR | SEQ ID NO: 288 |
| CELFGAIEGFIENGWEGMIDGWYGYGRKKRRQRRR | SEQ ID NO: 289 |
| CGLFEAIEGFIENGWEGMIDGWYGYGHKKHHQHR | SEQ ID NO: 290 |
| CGLFGAIEGFIEGGWPGLINGWYGYGRKKRRQRRR | SEQ ID NO: 291 |
| CGLFKALLKLLKSLWKLLLKAYGRKKRRQRR | SEQ ID NO: 292 |
| CGLFKALLKLLKSLWKLLLKAWYGRKKRRQRR | SEQ ID NO: 293 |
| CGLFRALLRLLRSLWRLLLRAYGRKKRRQRR | SEQ ID NO: 294 |
| CGLFEAILGFIENGWEGLIDGWYGYGRKKRRQRR | SEQ ID NO: 295 |

TABLE 2-continued

Suitable Peptide Sequences

| Peptide SEQUENCE | SEQ ID No. |
| --- | --- |
| CGLFEAIWEFIENGWEGLIDGWYGYGRKKRRQRR | SEQ ID NO: 296 |
| CGLFEAIEGFIENGWEGMIDGWYGGGGLHLLHHLLHHLHHLLHHLLHL | SEQ ID NO: 297 |
| CGPVEDAITAAIGRVADTVGTYGRKKRRQRR | SEQ ID NO: 298 |
| CMDGTLFPGDDDLAIPATEFFSTKA | SEQ ID NO: 299 |
| CGLFEALEEFIEGGWEGLLEAWYGYGRKKRRQRR | SEQ ID NO: 300 |
| CGLFEALEEFIENGWEGLLEAWYGYGRKKRRQRR | SEQ ID NO: 301 |
| CELFGAIWEFIEGGWEGLIEAYGRKKRRQRR | SEQ ID NO: 302 |
| CGLFEAIEGFIEEGWEGMIDGWYGYGRKKRRQRR | SEQ ID NO: 303 |
| CGLFEAIAEFIENGWEGMIDGWYGYGRKKRRQRR | SEQ ID NO: 304 |
| CGLFEAIAEFIEGLWEGLIEGWYGYGRKKRRQRR | SEQ ID NO: 305 |
| CGLLEALEGLLESLWEGLLEAWYGYGRKKRRQRR | SEQ ID NO: 306 |
| CGLFEAIEGFIENGWEGMIDIWYGYGRKKRRQRR | SEQ ID NO: 307 |
| CGLFEAIEGFIENGWRGMIDGWYGYGRKKRRQRR | SEQ ID NO: 308 |
| CGLFEAIEGFIENGWDGMIDGWYGYGRKKRRQRR | SEQ ID NO: 309 |
| CGLFEAIEGFIENHWEGMIDGWYGYGRKKRRQRR | SEQ ID NO: 310 |
| CGLFEAIEGFIENWWKGLIDWWYGYGRKKRRQRR | SEQ ID NO: 311 |
| GLFEAIEGFIENGWKGLIDAWYGYGRKKRRQRRC | SEQ ID NO: 312 |
| CGLFEAIEGFIENGWKGMIDAWYGYGRKKRRQRR | SEQ ID NO: 313 |
| CGLFEAIEGFIENGWKGMIDWWYGYGRKKRRQRR | SEQ ID NO: 314 |
| CGLAEAIEGFIENGLKGLIDWWYGYGRKKRRQRR | SEQ ID NO: 315 |
| RRQRRKKRGYGYWGDILGEWGNEIFGEIAEFLGC all(D) | SEQ ID NO: 316 |
| CRRQRRKKRGYGYWGDILGEWGNEIFGEIAEFLG all(D) | SEQ ID NO: 317 |
| CGLFEAIEGFIENGWKGLIDWWYGYGRKKRRQRR | SEQ ID NO: 318 |
| CGFFEAIEGFIENGLKGLIDAWYGYGRKKRRQRR | SEQ ID NO: 319 |
| CGLFEAIEGFIENGLKGLIDAWYGYGRKKRRQRR | SEQ ID NO: 320 |
| CELFGAIEGFIENGWKGLIDAWYGYGRKKRRQRR | SEQ ID NO: 321 |
| CGLFKAIKGFIKNGWKGLIKAWYGYGRKKRRQRR | SEQ ID NO: 322 |
| CGLAEALLELLESLWKGLIEAYGRKKRRQRR | SEQ ID NO: 323 |
| CGIFGAIEGFIENGWKGLIDAWYGYGRKKRRQRR | SEQ ID NO: 324 |
| CGIAGAIAGFIKNIWEGLIDWWYGYGRKKRRQRR | SEQ ID NO: 325 |
| CGIAGAIAGFIKNIWKGLIDAWYGYGRKKRRQRR | SEQ ID NO: 326 |
| CGIFGAIAGFIKNIWEGLIDGWYGKKKKKKKKK | SEQ ID NO: 327 |
| CG(R5)FEAIEG(S8)IENGWEGMIDGWYGYGRKKRRQRR | SEQ ID NO: 328 |
| CGLFEAIEGF(R5)ENGWEG(S8)IDGWYGYGRKKRRQRR | SEQ ID NO: 329 |
| GLFEAIEGFIENGWEGMIDGWYGCYGRKKRRQRR | SEQ ID NO: 330 |
| GLFEAIEGFIENGWEGMIDGWYGGCYGRKKRRQRR | SEQ ID NO: 331 |
| GLLEALEGLLENGWEGLLDGWYGYGRKKRRQRR | SEQ ID NO: 332 |
| CFFGAIWEFIRNIL | SEQ ID NO: 333 |

TABLE 2-continued

Suitable Peptide Sequences

| Peptide SEQUENCE | SEQ ID No. |
|---|---|
| CIFGAIAGFIRSIL | SEQ ID NO: 334 |
| CGLFEEIEEFIENGWEGLIDWWYGYGRKKRRQRR | SEQ ID NO: 335 |
| CGFFGAIWEFIKSIL | SEQ ID NO: 336 |
| GFFGAIWEFIKSILC | SEQ ID NO: 337 |
| CGLFEALEGFIENGWEGLLDGWYGYGROORRQRR (O = ornithine) | SEQ ID NO: 338 |
| CGLFEALLELLENGWELLLEAWYGYGRKKRRQRR | SEQ ID NO: 339 |
| CGLFEALLELLENGWELLLDGWYGYGRKKRRQRR | SEQ ID NO: 340 |
| CALFEAIEAFIENGWEAMIDAWYGYGRKKRRQRR | SEQ ID NO: 341 |
| CGLFGAIWGFIENGWEGLIDGWYGYGRKKRRQRR | SEQ ID NO: 342 |
| CGLFEAIEELIENLWKGLIDWWYGYGRKKRRQRR | SEQ ID NO: 343 |
| CGLFEEIEGFIENGWKGLIDWWYGYGRKKRRQRR | SEQ ID NO: 344 |
| CGLFEEIEGFIENGWKGLIDWWYGYGHKKHHQHR | SEQ ID NO: 345 |
| CFFGAIWEFIKNILKGLIDGWYG | SEQ ID NO: 346 |
| CGIFGAIAGFIRSIL | SEQ ID NO: 347 |
| CGLFEEIEGFIENGWEGMIDGWYGYGRKKRRQRR | SEQ ID NO: 348 |
| CGLFEAIEGFIENGWEGMIDGWNGYGRKKRRQRR | SEQ ID NO: 349 |
| AGYLLGKINLKALAALAKKILHHHHHKKKKKC | SEQ ID NO: 350 |
| Bis CGLFEAIEGFIENGWEGMIDWWYGYGRKKRRQRR | SEQ ID NO: 351 |
| CGLFEAIEGFIENGWEGMIDGWYG-(PEG)6-YGRKKRRQRR | SEQ ID NO: 352 |
| CGIFGAIWNGIKSLFEGLIDGWYGYGRKKRRQRR | SEQ ID NO: 353 |
| CGIFGAIEGFIENGWEGLIDWWYGYGRKKRRQRR | SEQ ID NO: 354 |
| CIFGAIAGFIKNIWEGLIDWWYGYGRKKRRQRR | SEQ ID NO: 355 |
| CGLFEAIEGFIENGWKGLIDGWYGGLFEAIEGFIENGWKGLIDWWYG | SEQ ID NO: 356 |
| CWEAALAEALAEALAEHLAEALAEALEALAAYGRKKRRQRRK(stearyl) | SEQ ID NO: 357 |
| CGLFEAIEGFIENGWKGLIDWWYGYGRKKRRQRR | SEQ ID NO: 358 |
| CGLFEELEELLEEGWEGLLEAYGRKKRRQRR | SEQ ID NO: 359 |
| CGNFEEIEEFIEEGLRNFIDWWYGYGHKKHHQHR | SEQ ID NO: 360 |
| CFFGAIWEFIRNILEGLIDWWYGYGRKKRRQRR | SEQ ID NO: 361 |
| CFFGAIWEFIKNILLHLLHHLLHHLHHLLHHLLHHLLHL | SEQ ID NO: 362 |
| CGLFEAIEGFIENGWEGMIDGWYGYGRKKRRQRR all(D) | SEQ ID NO: 363 |
| CGFFHAFFHFFHSFWHGFFEA | SEQ ID NO: 364 |
| CGLFHALLHLLHSLWHGLLHWWYGYGHKKHHQHR | SEQ ID NO: 365 |
| CGLFGALLELLESLWEGLLEWYGRKKRRQRR | SEQ ID NO: 366 |
| CGLFGALLELLESLWEGLLEWYGHKKHHQHR | SEQ ID NO: 367 |
| CGLFHALLHLLHSLWKGLLEWWYGF | SEQ ID NO: 368 |
| CIFGAIAGFIRSILEGF | SEQ ID NO: 369 |
| CGIFGAIAGFIKNIWKGLIDA | SEQ ID NO: 370 |
| CFFEAIEEFIKNIWK | SEQ ID NO: 371 |

TABLE 2-continued

Suitable Peptide Sequences

| Peptide SEQUENCE | SEQ ID No. |
| --- | --- |
| CGLFEAIEGFIENGWKGLIDWLAEALAEALEALAA | SEQ ID NO: 372 |
| GCGIFGAIAEFIKNIW | SEQ ID NO: 373 |
| CIFGAIAEFIKNIWKGLIDW | SEQ ID NO: 374 |
| CFFGAIWEFIKSILELLLEAYGHKKHHQHRR | SEQ ID NO: 375 |
| CWFGAIWEFIKSIL | SEQ ID NO: 376 |
| CAFGAIWEFIKSIL | SEQ ID NO: 377 |
| CFLGAIWEFIKSIL | SEQ ID NO: 378 |
| CFFGAIWEFIKSIK | SEQ ID NO: 379 |
| CGFIGAIANLLSKIFEGLIDGWYGYGRKKRRQRR all(D) | SEQ ID NO: 380 |
| CFFGAIWEFIKSIL | SEQ ID NO: 381 |
| CIFGAIAGFIKNIWLHLLHHLLHHLHHLLHHLLHL all(D) | SEQ ID NO: 382 |
| CFFGAIAEFIKNIW | SEQ ID NO: 383 |
| CIFEAIWGFIKNIW | SEQ ID NO: 384 |
| (stearyl)-AGYLLGKINLKALAALAKKILHHHHHHKKKKKKC | SEQ ID NO: 385 |
| CIFEAIAGFIKNIWKGLIDWWYGYGRKKRRQRR | SEQ ID NO: 386 |
| CGLFEAIEGFIENGWKGLIDWWYGGRPRESGKKRKRKRLKP | SEQ ID NO: 387 |
| C(b-Ala)GFGEIEEFIENGLKNLIDWWYGYGHKKHHQHR | SEQ ID NO: 388 |
| C(b-Ala)GFEFIEEFIENGLKNLIDWWYGYGRKKRRQRR | SEQ ID NO: 389 |
| C(b-Ala)GFEFIEEFIENGLKNLIDWWYGYGHKKHHQHR | SEQ ID NO: 390 |
| CGGIEEIAGLLSKILKGLIDWWYGYGHKKHHQHR | SEQ ID NO: 391 |
| CGFIGAIANLLSKIFEGLIDWWYGYGRKKRRQRR | SEQ ID NO: 392 |
| CGFIGAIAELLEKIFEGLIDWWYGYGRKKRRQRR | SEQ ID NO: 393 |
| CGFIGAIAELLEKIFEGLIDWWYGYGHKKHHQHR | SEQ ID NO: 394 |
| CFFGAIWEFIRNILEGLIDWWYGYGHKKHHQHR | SEQ ID NO: 395 |
| CFFGAIWEFIKSILLHLLHHLLHHLHHLLHHLLHL | SEQ ID NO: 396 |
| CFFGAIWEFIRSILLHLLHHLLHHLHHLLHHLLHL | SEQ ID NO: 397 |
| CGFFGAIWEFIRSILEGFIDWWYGYGYGHKKHHQHR | SEQ ID NO: 398 |
| CGLFEAIWEFIKSILEGLLEAYGHKKHHQHR | SEQ ID NO: 399 |
| CGLFEAIWEFIKSILEGLLEAWYGYGHKKHHQHR | SEQ ID NO: 400 |
| CGIFGAIAGFIKNIWKYGRKKRRQRR | SEQ ID NO: 401 |
| CGLFEALLELLESLWELLLEAWYGYGHKKHHQHR | SEQ ID NO: 402 |
| CIFGAIAGFIRNIWKGLIDGWYG | SEQ ID NO: 403 |
| CGIFGAIAGFIRNIWKGLIDGWYG | SEQ ID NO: 404 |
| CFFGAIWEFIKNILKLHLLHHLLHHLHHLLHHLLHL | SEQ ID NO: 405 |
| CFFGAIWEFIRNILLHLLHHLLHHLHHLLHHLLHL | SEQ ID NO: 406 |
| CFFGKIWEFIKSIL | SEQ ID NO: 407 |
| CYGRKKRRQRRGLFEALLELLESLWELLLEA | SEQ ID NO: 408 |
| FFGAIWEFIKSILC | SEQ ID NO: 409 |

TABLE 2-continued

Suitable Peptide Sequences

| Peptide SEQUENCE | SEQ ID No. |
|---|---|
| CWWGAIEGFIKSIL | SEQ ID NO: 410 |
| CFFGAIWEWIKSIL | SEQ ID NO: 411 |
| CFFGAIWEFWKSIL | SEQ ID NO: 412 |
| CFFGAIWEFIKFIL | SEQ ID NO: 413 |
| CFFGAIWEFIKKIL | SEQ ID NO: 414 |
| CFFGAIWEFIKGIL | SEQ ID NO: 415 |
| CFFGAIWEFIKLIL | SEQ ID NO: 416 |
| CFFGAIWEFIKWIL | SEQ ID NO: 417 |
| CFFGAIWEFIKSFL | SEQ ID NO: 418 |
| CFFGAIWEFIKSKL | SEQ ID NO: 419 |
| CFFGFIWEFIKSIL | SEQ ID NO: 420 |
| CIFGAIAGFIKNILKGLIDAF | SEQ ID NO: 421 |
| CFFGKIWELWEWIL | SEQ ID NO: 422 |
| CFFGAIWEFAKSIL | SEQ ID NO: 423 |
| CFFGAIWEFIKSAL | SEQ ID NO: 424 |
| CFFGAIWEFIKSWL | SEQ ID NO: 425 |
| CFFGAIWEFIKSILK | SEQ ID NO: 426 |
| CFFGAIWEFIKSILE | SEQ ID NO: 427 |
| CFFKAIWEFIKSIL | SEQ ID NO: 428 |
| CFFNAIWEFIKSIL | SEQ ID NO: 429 |
| CFFGGIWEFIKSIL | SEQ ID NO: 430 |
| CFFGNIWEFIKSIL | SEQ ID NO: 431 |
| CFFGALWEFIKSIL | SEQ ID NO: 432 |
| CFFGAAWEFIKSIL | SEQ ID NO: 433 |
| CGLFHALLHLLHSLWHGLLDG | SEQ ID NO: 434 |
| CGLFHALLHLLHSLWHGLLEW | SEQ ID NO: 435 |
| CGLFHALLHLLHSLWHLLLEA | SEQ ID NO: 436 |
| CGLFHALLHLLHSLWKLLLEW | SEQ ID NO: 437 |
| CKFGAIWEFIKSIL | SEQ ID NO: 438 |
| CFKGAIWEFIKSIL | SEQ ID NO: 439 |
| CFFGAIWKFIKSIL | SEQ ID NO: 440 |
| CFFGAIWAFIKSIL | SEQ ID NO: 441 |
| CFFGAIWLFIKSIL | SEQ ID NO: 442 |
| CFFGAIWFFIKSIL | SEQ ID NO: 443 |
| CFFGAIWNFIKSIL | SEQ ID NO: 444 |
| CFFGAIWELIKSIL | SEQ ID NO: 445 |
| CFFGAIWEAIKSIL | SEQ ID NO: 446 |
| CGLFEAIEGFIENGWEGLAEALAEALEALAAYGRKKRRQRR | SEQ ID NO: 447 |

TABLE 2-continued

Suitable Peptide Sequences

| Peptide SEQUENCE | SEQ ID No. |
| --- | --- |
| CIFGAIAGFIKNIWEGMIDGWYGYGRKKRRQRR | SEQ ID NO: 448 |
| CIFGAIAGFIKNIWEGLIDAWYGYGRKKRRQRR | SEQ ID NO: 449 |
| CIFGAIAGFIKNIWKGLIDAWYGYGRKKRRQRR | SEQ ID NO: 450 |
| CIFGAIAGFIKNIWIFGAIAGFIKNIWWYGYGRKKRRQRR | SEQ ID NO: 451 |
| CGLFGAIAGFIENGWEGLIEGWYG | SEQ ID NO: 452 |
| CGLFEAIEGFIENGWEGLIDGWYGYGOOOOOQRR (O = ornithine) | SEQ ID NO: 453 |
| CGLFEAIEGFIENGWKGLIDWWYGYGRKKRRQRR | SEQ ID NO: 454 |
| CGLFEAIEGFIENGWEGLIDGWYGYGRKKRRQRRK(stearyl) | SEQ ID NO: 455 |
| CYGHKKHHQHRGLFEAIEGFIENGWKGLIDWWYG | SEQ ID NO: 456 |
| CYGHKKHHQHRGLFEAIEEFIENGWEGLIDGWYG | SEQ ID NO: 457 |
| CGLFEAIEGFIENGWKGLIDWWYGYGRKKRRQRRK(stearyl) | SEQ ID NO: 458 |
| CGLFEAIEGFIENGWHGMIDGWYGYGRKKRRQRR | SEQ ID NO: 459 |
| IFGIDDLIIGLLFVAIVEAGIGGYLLGSYGRKKRRQRRC | SEQ ID NO: 460 |
| CGFFGEIAELIEEGLKGLIDWWNG | SEQ ID NO: 461 |
| CGLFGEIEELIEEGLENLIDWWNG | SEQ ID NO: 462 |
| CFFGAIWEFIHSIL all (D) | SEQ ID NO: 463 |
| CFFGAIWEFIHNIL | SEQ ID NO: 464 |
| CFFGAIWEFIHSIFK | SEQ ID NO: 465 |
| CGIFEAIAGLLKWIFK | SEQ ID NO: 466 |
| CGIFELIAGLLKNIFK | SEQ ID NO: 467 |
| CGIFEAIAGLLKSILKK(stearyl) | SEQ ID NO: 468 |
| CGIFGAIAGLLKSILKK(stearyl) | SEQ ID NO: 469 |
| CIFGAIAGFIKNILKGL all (D) | SEQ ID NO: 470 |
| CIFGAIAGFIKNILKGLIDGWWYG | SEQ ID NO: 471 |
| CIFGAIAGFIKNIWHGLI | SEQ ID NO: 472 |
| CIFGAIAGFIKNILKGLK(stearyl) | SEQ ID NO: 473 |
| GLGKLINKIFGAIAGFIC all (D) | SEQ ID NO: 474 |
| CGIFEAIAGLLKNIFD | SEQ ID NO: 475 |
| CGIFEAIAGLLKNIFE | SEQ ID NO: 476 |
| CGIFEAIAGLLKNIFR | SEQ ID NO: 477 |
| CGIFEAIAGLLKNIFH | SEQ ID NO: 478 |
| CGIFEAIAGLLKNIFO (O = ORNITHINE) | SEQ ID NO: 479 |
| CGIFEAIAGLLKNIFN | SEQ ID NO: 480 |
| CGIFEAIAGLLKNIFCit (Cit = citrulline) | SEQ ID NO: 481 |
| CGIFEAIWGLLKNIFK | SEQ ID NO: 482 |
| CGIFGAIWGLLKNIFK | SEQ ID NO: 483 |
| CIFGAIAGLLKNIFK | SEQ ID NO: 484 |
| CIFEAIAGLLKNIFK | SEQ ID NO: 485 |

TABLE 2-continued

Suitable Peptide Sequences

| Peptide SEQUENCE | SEQ ID No. |
|---|---|
| CFFGAIAGLLKNIFK | SEQ ID NO: 486 |
| CFFEAIAGLLKNIFK | SEQ ID NO: 487 |
| CGFFEAIAGLLKNIFK | SEQ ID NO: 488 |
| CIFGAIAGFIKNIWEGLI all (D) | SEQ ID NO: 489 |
| CIFGAIAGLLKNIFK all(D) | SEQ ID NO: 490 |
| CGLFGEIEELIEEGLENLIDWWNG all(D) | SEQ ID NO: 491 |
| CGNFGEIEELIEEGLENLIDWWNG all(D) | SEQ ID NO: 492 |
| CGFFGEIAELIEEGLKGLIDWWNG all(D) | SEQ ID NO: 493 |
| CGLFGEIEELIEEGLENLIDWWNE | SEQ ID NO: 494 |
| CGFFGAIAGLLKNIFK | SEQ ID NO: 495 |
| CGLFELIEGFIENGWEGMIDGWYGYGRKKRRQRRK(stearyl) | SEQ ID NO: 496 |
| CGLFELIEGFIEWGWEGMIDGWYGYGRKKRRQRRK(stearyl) | SEQ ID NO: 497 |
| CGLFEAIEGFIENGWEGMIDGWYGYGRKKRRQRRK(2H,2H,3H,3H-perfluorononanoyl) | SEQ ID NO: 498 |
| CGLFEAIEGFIENGWEGMIDGWYGYGRKKRRQRRK(2H,2H,3H,3H-perfluoro-10 methylundecanoyl) | SEQ ID NO: 499 |
| CIFGAIAGFIKNIWEGLIK(2H,2H,3H,3H-perfluorononanoyl) | SEQ ID NO: 500 |
| CIFGAIAGFIKNIWEGLIK(2H,2H,3H,3H-perfluoro-10 methylundecanoyl) | SEQ ID NO: 501 |
| CGLFEAIEGFIEWGWEGMIDGWYGYGRKKRRQRRK(2H,2H,3H,3H-perfluorononanoyl) | SEQ ID NO: 502 |
| CGLFEAIEGFIEWGWEGMIDGWYGYGRKKRRQRRK(2H,2H,3H,3H-perfluoro-10 methylundecanoyl) | SEQ ID NO: 503 |
| CGLFELIEGFIENGWEGMIDGWYGYGRKKRRQRRK(2H,2H,3H,3H-perfluorononanoyl) | SEQ ID NO: 504 |
| CGLFELIEGFIENGWEGMIDGWYGYGRKKRRQRRK(2H,2H,3H,3H-perfluoro-10 methylundecanoyl) | SEQ ID NO: 505 |
| CFFGAIWEFIHSILK(2H,2H,3H,3H-perfluorononanoyl) | SEQ ID NO: 506 |
| CFFGAIWEFIHSILK(2H,2H,3H,3H-perfluoro-10 methylundecanoyl) | SEQ ID NO: 507 |
| CIFGAIAGFIKNILKGLK(2H,2H,3H,3H-perfluorononanoyl) | SEQ ID NO: 508 |
| CIFGAIAGFIKNILKGLK(2H,2H,3H,3H-perfluoro-10 methylundecanoyl) | SEQ ID NO: 509 |
| CFFGAIWEFIRNILEGFK(2H,2H,3H,3H-perfluorononanoyl) | SEQ ID NO: 510 |
| CFFGAIWEFIRNILEGFK(2H,2H,3H,3H-perfluoro-10 methylundecanoyl) | SEQ ID NO: 511 |
| CGLFGEIEELIEEGLENLIDWWNQ | SEQ ID NO: 512 |
| CGIFGAIAGLLKSALK | SEQ ID NO: 513 |
| CGIFEAIAGLLKSIWK | SEQ ID NO: 514 |
| CGIFEAIAGLLKSILK | SEQ ID NO: 515 |
| CGIFEAIAGLLONIFK (O = Ornithine) | SEQ ID NO: 516 |
| CGIFEAIAGLLKNILKGLIDGWYG | SEQ ID NO: 517 |
| CGIFGAIAGLLKNILKGLIDGWYG | SEQ ID NO: 518 |
| CGIFGAIAGLLKNIFKGLIDGWYG | SEQ ID NO: 519 |
| CGIFGAIWELWEWILK | SEQ ID NO: 520 |

TABLE 2-continued

Suitable Peptide Sequences

| Peptide SEQUENCE | SEQ ID No. |
|---|---|
| CGIFEAIWELWEWILK | SEQ ID NO: 521 |
| CGLFEAIEGFIENGWEGMIDGWYGK(stearyl) | SEQ ID NO: 522 |
| (stearyl)GLFEAIEGFIENGWEGMIDGWYGC | SEQ ID NO: 523 |
| CFLE-Aib-LWKLLEHLL | SEQ ID NO: 524 |
| CFLE-Aib-LWELLEHLL | SEQ ID NO: 525 |
| CFLEALWE-Aib-LEHLL | SEQ ID NO: 526 |
| CFLE-Aib-LWE-Aib-LEHLL | SEQ ID NO: 527 |
| CFLE-Aib-LWEALEKLF | SEQ ID NO: 528 |
| (stearyl)IFGAIAGFIKNIWEGLIC | SEQ ID NO: 529 |
| CIFGAIAGFIKNIWEGLIK(stearyl) | SEQ ID NO: 530 |
| (stearyl)FFGAIWEFIKSILC | SEQ ID NO: 531 |
| CFFGAIWEFIKSILK(stearyl) | SEQ ID NO: 532 |
| (stearyl)FFGAIWEFIHSILC | SEQ ID NO: 533 |
| CFFGAIWEFIHSILK(stearyl) | SEQ ID NO: 534 |
| (stearyl)GIFEAIAGLLKNIFKC | SEQ ID NO: 535 |
| CGIFEAIAGLLKNIFK(stearyl) | SEQ ID NO: 536 |
| CGIFEAIAGLLKNIFKK(stearyl) | SEQ ID NO: 537 |
| (stearyl)IFGAIAGFIKNILKGLC | SEQ ID NO: 538 |
| CIFGAIAGFIKNILKGLK(stearyl) | SEQ ID NO: 539 |
| CIFGAIAGFIKNILKGL | SEQ ID NO: 540 |
| CGLFGEIEELIEEGLENLIDWWNS | SEQ ID NO: 541 |
| CGLFEAIEGFIENGWEGMIDGWYGYGRKKRRQRR | SEQ ID NO: 542 |
| CGFFGEIAELIEEGLKNLIDWWNG | SEQ ID NO: 543 |
| CGLFEAIEGFIENGWKGMIDGWYGYGRKKRRQRR | SEQ ID NO: 544 |
| CGLFEAIEGFIEWGWEGMIDGWYGYGRKKRRQRR | SEQ ID NO: 545 |
| CGLFELIEGFIENGWEGMIDGWYGYGRKKRRQRR | SEQ ID NO: 546 |
| CIFGAIAGFIKNIWEGLI | SEQ ID NO: 547 |
| CGLFGEIEELIEEGLENLIDWWNG | SEQ ID NO: 548 |
| CGLFEEIEGFIENGWEGLIDWWYGYGHKKGGQHR | SEQ ID NO: 549 |
| CGLFEAIEGFIENGWEGMIDGWYGYGRKKRRQRRK(stearyl) | SEQ ID NO: 550 |
| CGLFEALLELLESLWELLEAYGRKKRRQRR | SEQ ID NO: 551 |
| CGLFEALLELLESLWELLEAYGRKKRRQRR | SEQ ID NO: 552 |
| CFFGAIWEFIRNILEGF | SEQ ID NO: 553 |
| CFFGAIWEFIRNILEGFK(stearyl) | SEQ ID NO: 554 |
| CIFGAIAGFIKNIWEGLIK(lauryl) | SEQ ID NO: 555 |
| (lauryl)FFGAIWEFIKSILC | SEQ ID NO: 556 |
| CFFGAIWEFIKSILK(lauryl) | SEQ ID NO: 557 |
| (lauryl)FFGAIWEFIHSILC | SEQ ID NO: 558 |

TABLE 2-continued

Suitable Peptide Sequences

| Peptide SEQUENCE | SEQ ID No. |
|---|---|
| CFFGAIWEFIHSILK(lauryl) | SEQ ID NO: 559 |
| (lauryl)GIFEAIAGLLKNIFKC | SEQ ID NO: 560 |
| CGIFEAIAGLLKNIFK(lauryl) | SEQ ID NO: 561 |
| CFFGAIWEFIRNILEGFK(lauryl) | SEQ ID NO: 562 |
| (lauryl)GLFEAIEGFIENGWEGMIDGWYGC | SEQ ID NO: 563 |
| CGLFEAIEGFIENGWEGMIDGWYGK(lauryl) | SEQ ID NO: 564 |
| CGKFTIVFPHNQKGNWKNVPSNYHYK(stearyl) | SEQ ID NO: 565 |
| CMDGTLFPGDDDLAIPATEFFSTKAK(stearyl) | SEQ ID NO: 566 |
| CNPVENYIDEVLNEVLVVPNINSSNK(stearyl) | SEQ ID NO: 567 |
| CVTPHHVLVDEYTGEWVDSQFK(stearyl) | SEQ ID NO: 568 |
| CIFGIDDLIIGLLFVAIVEAGIGGYLLGSK(stearyl) | SEQ ID NO: 569 |
| CGAAIGLAWIPYFGPAAEK(stearyl) | SEQ ID NO: 570 |
| CFAGVVLAGAALGVATAAQITAGIALHK(stearyl) | SEQ ID NO: 571 |
| CFLGFLLGVGSAIASGIAVSKVLHLK(stearyl) | SEQ ID NO: 572 |
| CFFGAVIGTIALGVATSAQITAGIALAK(stearyl) | SEQ ID NO: 573 |
| CFFGAVIGTIALGVATAAQITAGIALAK(stearyl) | SEQ ID NO: 574 |
| GLFEAIAGFIENGGWEGMIDGGGK(stearyl) | SEQ ID NO: 575 |
| GLFKAIAKFIKGGWKGLIKGWYGK(stearyl) | SEQ ID NO: 576 |
| GLFHAIAHFIHGGWHGLIHGWYGK(stearyl) | SEQ ID NO: 577 |
| CGLFEAIAEFIENGWEGLIEGWYGK(stearyl) | SEQ ID NO: 578 |
| CGFFGAIAGFLEGGWEGMIAGWHGK(stearyl) | SEQ ID NO: 579 |
| CFAGVVIGLAALGVATAAQVTAAVALVKK(stearyl) | SEQ ID NO: 580 |
| CAVGIVGAMFLGFLGAAGSTMGAVSLTLTVQAK(stearyl) | SEQ ID NO: 581 |
| CGVFVLGFLGFLATAGSAMGARSLTLSAK(stearyl) | SEQ ID NO: 582 |
| CVPFVLGFLGFLGAAGTAMGAAATALTVK(stearyl) | SEQ ID NO: 583 |
| CAVPVAVWLVSALAMGAGVAGGITGSMSLASGK(stearyl) | SEQ ID NO: 584 |
| CGLASTLTRWAHYNALIRAFK(stearyl) | SEQ ID NO: 585 |
| CGPVEDAITAAIGRVADTVGTK(stearyl) | SEQ ID NO: 586 |
| CGLGQMLESMIDNTVREVGGAK(stearyl) | SEQ ID NO: 587 |
| CGLFEAIEGFIENGWEGMIDGWYGFK(stearyl) | SEQ ID NO: 588 |
| (D)-(cgl)FEAIEGFIENGWEGMIDGWYGYGRKKRR(D)-(qrr) | SEQ ID NO: 589 |
| CG(lf)LEAIEGFIENGWEGMIDGWYGYGRKKRRQRR | SEQ ID NO: 590 |
| CIFGIDDLIIGLLFVAIVEAGIGGYLLGS(stearyl) | SEQ ID NO: 591 |
| CVTVLALGALAGVGVG(stearyl) | SEQ ID NO: 592 |
| CLLGRRGWEVLKYWWNLLQYWSQEL(stearyl) | SEQ ID NO: 593 |
| CGIFEAIAGLLKNIFD | SEQ ID NO: 594 |
| CGIFEAIAGLLKNIFE | SEQ ID NO: 595 |
| CGIFEAIAGLLKNIFR | SEQ ID NO: 596 |

TABLE 2-continued

Suitable Peptide Sequences

| Peptide SEQUENCE | SEQ ID No. |
| --- | --- |
| CGIFEAIAGLLKNIFH | SEQ ID NO: 597 |
| CGIFEAIAGLLKNIFO (O = ORNITHINE) | SEQ ID NO: 598 |
| CGIFEAIAGLLKNIFN | SEQ ID NO: 599 |
| CGIFEAIAGLLKNIFCit (Cit = citrulline) | SEQ ID NO: 600 |
| CGIFGAIWGLLKNIFK | SEQ ID NO: 601 |
| CIFEAIAGLLKNIFK | SEQ ID NO: 602 |
| CFFEAIAGLLKNIFK | SEQ ID NO: 603 |
| CGFFEAIAGLLKNIFK | SEQ ID NO: 604 |
| CGIFEAIAGLLKNIFKG | SEQ ID NO: 605 |
| CGIFEAIAGLLKNIFKGL | SEQ ID NO: 606 |
| CGIFEAIAGLLKNIFKGLI | SEQ ID NO: 607 |
| CGIFEAIAGLLKNIFKGLID | SEQ ID NO: 608 |
| CGIFEAIAGLLKNIFKGLIDG | SEQ ID NO: 609 |
| CGIFEAIAGLLKNIFKGLIDGF | SEQ ID NO: 610 |
| CGIFEAIAGLLKNIFKGLIDGWYG | SEQ ID NO: 611 |
| CGIFEAIAGLLKNIFK all(D) | SEQ ID NO: 612 |
| CGIFEAIAGLLKSILK | SEQ ID NO: 613 |
| CGIFEAIAGLLKNIFKA | SEQ ID NO: 614 |
| CGIFEAIAGLLKNIFKL | SEQ ID NO: 615 |
| CGIFEAIAGLLKNIFKW | SEQ ID NO: 616 |
| CGIFEAIAGLLKNIFKF | SEQ ID NO: 617 |
| CGIFEAIAGLLKNAFK | SEQ ID NO: 618 |
| CGIFGAIAGLLKNAFK | SEQ ID NO: 619 |
| CGIFEAIAGLLONIFO (O = Ornithine) | SEQ ID NO: 620 |
| CGIFEAIAGLLKNIFKGIFEAIAGLLKNIFK | SEQ ID NO: 621 |
| CGIFEAIAGLLKNIFKFFGAIWEFIHSIL | SEQ ID NO: 622 |
| CFFGAIWEFIHSILGIFEAIAGLLKNIFK | SEQ ID NO: 623 |
| CFFGAIWEFIHSILFFGAIWEFIHSIL | SEQ ID NO: 624 |
| CFFGAIWEFIHSILGFFGAIWEFIHSIL | SEQ ID NO: 625 |
| CGIFEAIAGLLKNIFKGIFEAIAGLLKNIFK | SEQ ID NO: 626 |
| CGIFEAIAGLLKNIFKFFGAIWEFIHSIL | SEQ ID NO: 627 |
| CFFGAIWEFIHSILGIFEAIAGLLKNIFK | SEQ ID NO: 628 |
| CGLFHALLHLLHSLWHLLLEA | SEQ ID NO: 629 |
| CGLFHALLHLLHSLWHLLLEAK(stearyl) | SEQ ID NO: 630 |
| CGLFHALLHLLHSLWHLLLEAK(stearyl) | SEQ ID NO: 631 |
| (stearyl)GLFHALLHLLHSLWHLLLEAC | SEQ ID NO: 632 |
| CFFGNIWEFIKSIL | SEQ ID NO: 633 |
| CFFGAIWLFIKSIL | SEQ ID NO: 634 |

TABLE 2-continued

Suitable Peptide Sequences

| Peptide SEQUENCE | SEQ ID No. |
|---|---|
| CFFGAIWNFIKSIL | SEQ ID NO: 635 |
| CFFGAIWGFIKSIL | SEQ ID NO: 636 |
| CFLGALFKALSKLL | SEQ ID NO: 637 |
| CFLGALFHALSKLL | SEQ ID NO: 638 |
| CFLGALFKALSHLL | SEQ ID NO: 639 |
| CFLGALFHALSHLL | SEQ ID NO: 640 |
| FLGALFKALSKLLC | SEQ ID NO: 641 |
| FLGALFHALSKLLC | SEQ ID NO: 642 |
| FLGALFKALSHLLC | SEQ ID NO: 643 |
| FLGALFHALSHLLC | SEQ ID NO: 644 |
| CFLGALFKALKSLL | SEQ ID NO: 645 |
| CFLGALFHALKSLL | SEQ ID NO: 646 |
| CFLGALFKALHSLL | SEQ ID NO: 647 |
| CFLGALFHALHSLL | SEQ ID NO: 648 |
| FLGALFKALKSLLC | SEQ ID NO: 649 |
| FLGALFHALKSLLC | SEQ ID NO: 650 |
| FLGALFKALHSLLC | SEQ ID NO: 651 |
| FLGALFHALHSLLC | SEQ ID NO: 652 |
| CGIFGAIAGFIKNIWKGLIDW | SEQ ID NO: 653 |
| CGLFEAIEGFIENGWEG-Nle-IDGWYGYGRKKRRQRR | SEQ ID NO: 654 |
| CGLFEAIEGFIENGLKGLIDWWYGYGRKKRRQRR | SEQ ID NO: 655 |
| CGLFEAIEGFIENAWEGMIDGWYGYGRKKRRQRR | SEQ ID NO: 656 |
| CGLFEAIEGFIENGWEGMIDLWYGYGRKKRRQRR | SEQ ID NO: 657 |
| CRLLRLLLRLWRRLLRLLR | SEQ ID NO: 658 |
| CGIFGAIEGFIENGWKGLIDAWYGYRKKRRQRR | SEQ ID NO: 659 |
| CFFGAIWEFAHGIL | SEQ ID NO: 660 |
| CFFGAIWEFARGILEGF | SEQ ID NO: 661 |
| FFGAIWEFAHGILC | SEQ ID NO: 662 |
| FFGAIWEFARGILEGFC | SEQ ID NO: 663 |
| CFFGAIWEFAHSIL | SEQ ID NO: 664 |
| FFGAIWEFAHSILC | SEQ ID NO: 665 |
| CFFGAIWEFARSILK | SEQ ID NO: 666 |
| FFGAIWEFARSILKC | SEQ ID NO: 667 |
| CGIFEAIAGLAKNIFK | SEQ ID NO: 668 |
| GIFEAIAGLAKNIFKC | SEQ ID NO: 669 |
| CGIFEAIAGLAKNIFH | SEQ ID NO: 670 |
| CGIFEAIAGLAHNIFH | SEQ ID NO: 671 |
| CGIFEAIAGLAHNIFK | SEQ ID NO: 672 |

TABLE 2-continued

Suitable Peptide Sequences

| Peptide SEQUENCE | SEQ ID No. |
|---|---|
| GIFEAIAGLAKNIFHC | SEQ ID NO: 673 |
| GIFEAIAGLAHNIFHC | SEQ ID NO: 674 |
| CFLGALWKALSKLL | SEQ ID NO: 675 |
| CFLGALWHALSKLL | SEQ ID NO: 676 |
| CFLGALWKALSHLL | SEQ ID NO: 677 |
| CFLGALWHALSHLL | SEQ ID NO: 678 |
| FLGALWKALSKLLC | SEQ ID NO: 679 |
| FLGALWHALSKLLC | SEQ ID NO: 680 |
| FLGALWKALSHLLC | SEQ ID NO: 681 |
| FLGALWHALSHLLC | SEQ ID NO: 682 |
| CGIFGAIAGLLKNAFK | SEQ ID NO: 683 |
| CIFEAIAGLLKNAFK | SEQ ID NO: 684 |
| CIFGAIAGLLKNAFK | SEQ ID NO: 685 |
| CIFEAIWEFIKNIW | SEQ ID NO: 686 |
| CIFEAIAEFIKNIW | SEQ ID NO: 687 |
| CIFGAIWEFIKNIW | SEQ ID NO: 688 |
| CIFGAIAEFIKNIW | SEQ ID NO: 689 |
| CGIFGIAIGFKINIW | SEQ ID NO: 690 |
| CGIFEAIAGLLHNIFK | SEQ ID NO: 691 |
| CGIFEAIWGLLHNIFK | SEQ ID NO: 692 |
| CGFFEAIAGLLHNIFK | SEQ ID NO: 693 |
| CGIFEAIAALLKNIFK | SEQ ID NO: 694 |
| CGIFEAIEGLLKNIFK | SEQ ID NO: 695 |
| CGIFEAIAGFFKNIFK | SEQ ID NO: 696 |
| CGIFEAIAGWWKNIFK | SEQ ID NO: 697 |
| CGIFEAIAGLLKNIWK | SEQ ID NO: 698 |
| CGIFEAIAELLKNIFK | SEQ ID NO: 699 |
| CGIFGAIAGLLKSALK | SEQ ID NO: 700 |
| CGIFEAIAGLLKSIWK | SEQ ID NO: 701 |
| CGIFEAIAGLLKSILK | SEQ ID NO: 702 |
| CGIFEAIAGLLKNIFKGLIDA | SEQ ID NO: 703 |
| CGIFEAIAGLLKNIFKGLIDAF | SEQ ID NO: 704 |
| CGIFEAIAGLLKNIFKGLIDAWYG | SEQ ID NO: 705 |
| CGIFEAIAGLLKNIFKGLIDAWYGF | SEQ ID NO: 706 |
| CGIFEAIAGLLKNIFKGLIDGWYGF | SEQ ID NO: 707 |
| CGIFEAIAGLLKNIFKGLIDW | SEQ ID NO: 708 |
| CGIFEAIAGLLKNIFKGLIDWF | SEQ ID NO: 709 |
| CGIFEAIAGLLKNIFKGLIDWWYG | SEQ ID NO: 710 |

TABLE 2-continued

Suitable Peptide Sequences

| Peptide SEQUENCE | SEQ ID No. |
|---|---|
| CGIFEAIAGLLKNIFKGLIDWWYGF | SEQ ID NO: 711 |
| CGIFELIAGLLKNIFK | SEQ ID NO: 712 |
| CGIFEAIAGLLKWIFK | SEQ ID NO: 713 |
| CGIFELIAGLLKWIFK | SEQ ID NO: 714 |
| CGIFELIAGLLKNIFKG | SEQ ID NO: 715 |
| CGIFEAIAGLLKWIFKG | SEQ ID NO: 716 |
| CGIFELIAGLLKWIFKG | SEQ ID NO: 717 |
| CGLFEALLGLLESLWK | SEQ ID NO: 718 |
| CGIFEAIAELLKNIFK | SEQ ID NO: 719 |
| CGIFEALLGLLKSLWK | SEQ ID NO: 720 |
| CGIFEALLELLKSLWK | SEQ ID NO: 721 |
| CGIFEAIAGLLKNIFK | SEQ ID NO: 722 |
| CEIFEAIAGLLKNIFK | SEQ ID NO: 723 |
| CEIFGAIAGLLKNIFK | SEQ ID NO: 724 |
| CGLFEAIAGLLKNLFK | SEQ ID NO: 725 |
| CGIWEAIAGLLKNIWK | SEQ ID NO: 726 |
| CGLFGAIAGLLKNLFK | SEQ ID NO: 727 |
| CGIWGAIAGLLKNIWK | SEQ ID NO: 728 |
| CGIFDAIAGLLKNIFK | SEQ ID NO: 729 |
| CGIFDAIWGLLKNIFK | SEQ ID NO: 730 |
| CGIFGGIGGLLKNIFK | SEQ ID NO: 731 |
| CAIFAAIAALLKNIFK | SEQ ID NO: 732 |
| CGIFEAIAGLLKNIF | SEQ ID NO: 733 |
| CGIFEAIAGLLKNI | SEQ ID NO: 734 |
| CGIFEAIAGLLKN | SEQ ID NO: 735 |
| CGIFEAIAGLLK | SEQ ID NO: 736 |
| CVIFEAIAGLLKNIFK | SEQ ID NO: 737 |
| CSIFEAIAGLLKNIFK | SEQ ID NO: 738 |
| CGIFEEIAGLLKNIFK | SEQ ID NO: 739 |
| CGIFEEIWGLLKNIFK | SEQ ID NO: 740 |
| CGIFEAIEELLKNIFK | SEQ ID NO: 741 |
| CGIFEAIAGLWKNIFK | SEQ ID NO: 742 |
| CGIFEAIAGLLENIFK | SEQ ID NO: 743 |
| CGIFEAIAGLLWNIFK | SEQ ID NO: 744 |
| CGIFEAIAGLLKEIFK | SEQ ID NO: 745 |
| CGIFEAIAGLLKNILK | SEQ ID NO: 746 |
| CGIFEAIAGLLRNIFK | SEQ ID NO: 747 |
| CGIFEAIAGLLKSIFK | SEQ ID NO: 748 |

TABLE 2-continued

Suitable Peptide Sequences

| Peptide SEQUENCE | SEQ ID No. |
| --- | --- |
| CGIFEAIAGLLKNILK | SEQ ID NO: 749 |
| CGFFGAIWEFIKSILK | SEQ ID NO: 750 |
| CGFFEAIWEFIKSILK | SEQ ID NO: 751 |
| CGFFGAIWGLLKSILK | SEQ ID NO: 752 |
| CGFFEAIWGLLKSILK | SEQ ID NO: 753 |
| CGFFEAIAGLLKSILK | SEQ ID NO: 754 |
| CGFFGAIAGLLKSILK | SEQ ID NO: 755 |
| CGIFEAIAGLLKNIFEGLI | SEQ ID NO: 756 |
| CGIFEAIWGLLKNIFKGLI | SEQ ID NO: 757 |
| CGIFEAIWGLLKNIFEGLI | SEQ ID NO: 758 |
| CGIFEAIAGLLKNILKGLIDGWYG | SEQ ID NO: 759 |
| CGIFGAIAGLLKNILKGLIDGWYG | SEQ ID NO: 760 |
| CGIFGAIAGLLKNIFKGLIDGWYG | SEQ ID NO: 761 |
| CGIFGAIWELWEWILK | SEQ ID NO: 762 |
| CGIFEAIWELWEWILK | SEQ ID NO: 763 |
| CIFGAIWELWEWILK | SEQ ID NO: 764 |
| CIFEAIWELWEWILK | SEQ ID NO: 765 |
| CGIFEAIAELWKNIFK | SEQ ID NO: 766 |
| CGIFEAIAELWENIFK | SEQ ID NO: 767 |
| CGIFEAIAELWKWIFK | SEQ ID NO: 768 |
| CGIFEAIAELWEWIFK | SEQ ID NO: 769 |
| CGIFEAIAGLLKNILKGLIDWWYG | SEQ ID NO: 770 |
| CGIFGAIAGLLKNILKGLIDWWYG | SEQ ID NO: 771 |
| CGIFGAIAGLLKNIFKGLIDWWYG | SEQ ID NO: 772 |
| CGIFEAIAGLLKNILKGLIDGWYGF | SEQ ID NO: 773 |
| CGIFGAIAGLLKNILKGLIDGWYGF | SEQ ID NO: 774 |
| CGIFGAIAGLLKNIFKGLIDGWYGF | SEQ ID NO: 775 |
| CGIFGAIAELLEKIFE | SEQ ID NO: 776 |
| CGIFEAIAELLEKIFE | SEQ ID NO: 777 |
| CGFIGAIAELLEKIFE | SEQ ID NO: 778 |
| CGIFGAIAELLEKIFK | SEQ ID NO: 779 |
| CGIFEAIAELLEKIFK | SEQ ID NO: 780 |
| CGFIGAIAELLEKIFK | SEQ ID NO: 781 |
| CGLFHALLHLLHSLWHLLLEA | SEQ ID NO: 782 |
| GLFHALLHLLHSLWHGLLEAC | SEQ ID NO: 783 |
| GFFHAFFHFFHSFWHGFFEAC | SEQ ID NO: 784 |
| GLFHALLHLLHSLWHLLLEAC | SEQ ID NO: 785 |
| CGLFHALLHLLHSLWHGLLEAK(stearyl) | SEQ ID NO: 786 |

TABLE 2-continued

Suitable Peptide Sequences

| Peptide SEQUENCE | SEQ ID No. |
|---|---|
| CGFFHAFFHFFHSFWHGFFEAK(stearyl) | SEQ ID NO: 787 |
| CGLFHALLHLLHSLWHLLLEAK(stearyl) | SEQ ID NO: 788 |
| (stearyl)GLFHALLHLLHSLWHGLLEAC | SEQ ID NO: 789 |
| (stearyl)GFFHAFFHFFHSFWHGFFEAC | SEQ ID NO: 790 |
| (stearyl)GLFHALLHLLHSLWHLLLEAC | SEQ ID NO: 791 |
| CGFFHAFFHFFHSFWHFFFEA | SEQ ID NO: 792 |
| CGFFHAFFHFFHSFWHLFFEA | SEQ ID NO: 793 |
| CGLFHALLHLLHSLWHGLLEW | SEQ ID NO: 794 |
| CGLFHALLHLLHSLWHLLLEW | SEQ ID NO: 795 |
| CGFFHAFFHFFHSFWHGFFEW | SEQ ID NO: 796 |
| CFFGAIWEFAKSIL | SEQ ID NO: 797 |
| CFFGAIWEFAHSIL | SEQ ID NO: 798 |
| CFFGAIWEFAHGIL | SEQ ID NO: 799 |
| CFFGAIWEFIHSILK | SEQ ID NO: 800 |
| CFFGAIWEFIHSILH | SEQ ID NO: 801 |
| CFFGAIWEFIHSILD | SEQ ID NO: 802 |
| CFFGAIWEFIHSILR | SEQ ID NO: 803 |
| CFFGAIWEFIHSILO | SEQ ID NO: 804 |
| CFFGAIAEFIHSIL | SEQ ID NO: 805 |
| CIFGAIWEFIHSIL | SEQ ID NO: 806 |
| CGIFGAIWEFIHSIL | SEQ ID NO: 807 |
| CFFGAIWEFIHSILE | SEQ ID NO: 808 |
| CFFGAIWEFIHSILEG | SEQ ID NO: 809 |
| CFFGAIWEFIHSILEGL | SEQ ID NO: 810 |
| CFFGAIWEFIHSILEGLI | SEQ ID NO: 811 |
| CFFGAIWEFIHSILEGLID | SEQ ID NO: 812 |
| CFFGAIWEFIHSILEGLIDG | SEQ ID NO: 813 |
| CFFGAIWEFIHSILEGLIEA | SEQ ID NO: 814 |
| CFFGAIWEFIHSILEGLIDW | SEQ ID NO: 815 |
| CFFGAIWEFIHSILEGLIDGWYG | SEQ ID NO: 816 |
| CFFGAIWEFIHSILEGLIDGWYGF | SEQ ID NO: 817 |
| FFGAIWEFIHSILC | SEQ ID NO: 818 |
| CFWGAIWEFIHSIL | SEQ ID NO: 819 |
| CFFGAIWEFIHSILKGLIDW | SEQ ID NO: 820 |
| CAFGKIWEFAHSIL | SEQ ID NO: 821 |
| CAFGKIWEFIHSIL | SEQ ID NO: 822 |
| CFFGKIWEFIHSIL | SEQ ID NO: 823 |
| CAFGAIWEFIHSIL | SEQ ID NO: 824 |

TABLE 2-continued

Suitable Peptide Sequences

| Peptide SEQUENCE | SEQ ID No. |
|---|---|
| CAFGAIWEFAHSIL | SEQ ID NO: 825 |
| CGFFGAIAGLLHNIFK | SEQ ID NO: 826 |
| CFFGAIAGLLHNIFK | SEQ ID NO: 827 |
| CGFFEAIEGLLHNIFK | SEQ ID NO: 828 |
| CFFEAIAGLLHNIFK | SEQ ID NO: 829 |
| CFFEAIWGLLHNIFK | SEQ ID NO: 830 |
| CGFFGAIAELLHNIFK | SEQ ID NO: 831 |
| CFFGAIAELLHNIFK | SEQ ID NO: 832 |
| CGFFEAIAELLHNIFK | SEQ ID NO: 833 |
| CFFEAIAELLHNIFK | SEQ ID NO: 834 |
| CFFGAIWELLHNIFK | SEQ ID NO: 835 |
| CFFEAIWELLHNIFK | SEQ ID NO: 836 |
| CFFGAIWEFIHSILFFGAIWEFIHSIL | SEQ ID NO: 837 |
| CFFGAIWEFIHSILGGGFFGAIWEFIHSIL | SEQ ID NO: 838 |
| CFFGAIWEFIHSILGFFGAIWEFIHSIL | SEQ ID NO: 839 |
| GGLFEALLELLESLWELLLEW | SEQ ID NO: 840 |
| GGFFEAFFEFFESFWEFFFEA | SEQ ID NO: 841 |
| GGLFEALLELLESLWEGLLEA | SEQ ID NO: 842 |
| CGLFHALLHLLHSLWHLLLHA | SEQ ID NO: 843 |
| CGLFEALLHLLHSLWHLLLEA | SEQ ID NO: 844 |
| CGLFEALLELLHSLWHLLLEA | SEQ ID NO: 845 |
| CGLFEALLHLLESLWHLLLEA | SEQ ID NO: 846 |
| CGLFEALLHLLHSLWELLLEA | SEQ ID NO: 847 |
| CGLFHALLELLHSLWHLLLEA | SEQ ID NO: 848 |
| CGLFHALLHLLESLWHLLLEA | SEQ ID NO: 849 |
| CGLFHALLHLLHSLWELLLEA | SEQ ID NO: 850 |
| CGLFHALLELLESLWHLLLEA | SEQ ID NO: 851 |
| CGLFHALLELLHSLWELLLEA | SEQ ID NO: 852 |
| CGLFHALLHLLESLWELLLEA | SEQ ID NO: 853 |
| CGLFEALLHLLESLWELLLEA | SEQ ID NO: 854 |
| CGLFEALLELLHSLWELLLEA | SEQ ID NO: 855 |
| CGLEALLELLESLWHLLLEA | SEQ ID NO: 856 |
| CGLFHALLELLESLWELLLEA | SEQ ID NO: 857 |
| CFFGAIWEFIHSILHLLLEA | SEQ ID NO: 858 |
| CFFGAIWEFIHSILKLLLEA | SEQ ID NO: 859 |
| CGFFGAIWEFIHSILGFFGAIWEFIHSIL | SEQ ID NO: 860 |
| CFFGAIWEFAHSILFFGAIWEFAHSIL | SEQ ID NO: 861 |
| CFFGAIWEFAHSILGFFGAIWEFAHSIL | SEQ ID NO: 862 |

TABLE 2-continued

Suitable Peptide Sequences

| Peptide SEQUENCE | SEQ ID No. |
|---|---|
| CGFFGAIWEFAHSILGFFGAIWEFAHSIL | SEQ ID NO: 863 |
| CFFGAIWEFIHSILGLFEAIEGFIENGWEGMIDG | SEQ ID NO: 864 |
| CFFGAIWEFIHSILGLFEAIEGFIENGWEGMIDGWYG | SEQ ID NO: 865 |
| CFFGAIWEFIHSILGLFEAIEGFIENGWEGMIDGWYGF | SEQ ID NO: 866 |
| CFFGALLEFIHSILELLLEA | SEQ ID NO: 867 |
| CGLFGALLEFIHSILELLLEA | SEQ ID NO: 868 |
| CGFFGALLEFIHSILELLLEA | SEQ ID NO: 869 |
| CFFGALLEFIHSLWELLLEA | SEQ ID NO: 870 |
| CGLFGALLEFIHSLWELLLEA | SEQ ID NO: 871 |
| CGFFGALLEFIHSLWELLLEA | SEQ ID NO: 872 |
| CIFGAIAGFIKNIWK(stearyl) | SEQ ID NO: 873 |
| (stearyl)IFGAIAGFIKNIWC | SEQ ID NO: 874 |
| CFFGAIWEFIKSILK(stearyl) | SEQ ID NO: 875 |
| (stearyl)FFGAIWEFIKSILC | SEQ ID NO: 876 |
| CFFGAIWEFIHSILK(stearyl) | SEQ ID NO: 877 |
| (stearyl)FFGAIWEFIHSILC | SEQ ID NO: 878 |
| CIFGAIAGFIKNIWEGLIK(stearyl) | SEQ ID NO: 879 |
| (stearyl)IFGAIAGFIKNIWEGLIC | SEQ ID NO: 880 |
| (stearyl)IFGAIAGFIKNILKGLC | SEQ ID NO: 881 |
| (stearyl)GIFGAIAGFIKNILKGLC | SEQ ID NO: 882 |
| CIFGAIAGFIKNILKGLK(stearyl) | SEQ ID NO: 883 |
| CGLFGAIAGFIVNGWVGMIDG | SEQ ID NO: 884 |
| CGLFGAIAGFIVNGWVGMIDGWYG | SEQ ID NO: 885 |
| CGLFEAIEGFIVNGWVGMIDGWYG | SEQ ID NO: 886 |
| CGLFGAIAGFIVNGWVGMIDGWYGF | SEQ ID NO: 887 |
| CGLFEAIEAGFIVNGWVGMIDGWYGF | SEQ ID NO: 888 |
| CGLFGAIAGFIVNGWVGMIDGWYGK(stearyl) | SEQ ID NO: 889 |
| CGLFEAIEGFIVNGWVGMIDGWYGK(stearyl) | SEQ ID NO: 890 |
| (stearyl)GLFGAIAGFIVNGWVGMIDGWYGC | SEQ ID NO: 891 |
| (stearyl)GLFEAIEGFIVNGWVGMIDGWYGC | SEQ ID NO: 892 |
| (stearyl)GLFGAIAGFIVNGWVGMIDGWYGFC | SEQ ID NO: 893 |
| (stearyl)GLFEAIEAGFIVNGWVGMIDGWYGFC | SEQ ID NO: 894 |
| CFFGAIWGLLHSILH | SEQ ID NO: 895 |
| CFFGAIWELLHSIL | SEQ ID NO: 896 |
| CFFGAIWELLHSILH | SEQ ID NO: 897 |
| CFFGAIWGLLHSILK | SEQ ID NO: 898 |
| CFFGAIWELLHSILK | SEQ ID NO: 899 |
| CGLFGALLHLLHSLWELLLEA | SEQ ID NO: 900 |

TABLE 2-continued

Suitable Peptide Sequences

| Peptide SEQUENCE | SEQ ID No. |
|---|---|
| CGLFGALLELLHSLWELLLEA | SEQ ID NO: 901 |
| CFFGAIWEFIHSILELLLEA | SEQ ID NO: 902 |
| CFFGAIWEFIHSILHGLLEA | SEQ ID NO: 903 |
| CFFGAIWEFIHSILEGLLEA | SEQ ID NO: 904 |
| CGFFGAIWEFIHSILHLLLEA | SEQ ID NO: 905 |
| CGFFGAIWEFIHSILELLLEA | SEQ ID NO: 906 |
| CGFFGAIWEFIHSILHGLLEA | SEQ ID NO: 907 |
| CGFFGAIWEFIHSILEGLLEA | SEQ ID NO: 908 |
| CGFFGAIAGLLHSIL | SEQ ID NO: 909 |
| CGFFGAIWGLLHSIL | SEQ ID NO: 910 |
| CGFFGALLGLLHSIL | SEQ ID NO: 911 |
| CFFGAIWEFAKSAL | SEQ ID NO: 912 |
| CIFGAIAGFIHNILKGL | SEQ ID NO: 913 |
| CFFGAIAGFIKNILKGL | SEQ ID NO: 914 |
| CIFGAIWGFIKNILKGL | SEQ ID NO: 915 |
| CIFGAIWGFIHNILKGL | SEQ ID NO: 916 |
| CIFGAIAGLLKNILKGL | SEQ ID NO: 917 |
| CIFGAIAGLLHNILKGL | SEQ ID NO: 918 |
| CIFEAIAGFIKNILKGL | SEQ ID NO: 919 |
| CIFEAIAGFIHNILKGL | SEQ ID NO: 920 |
| CGNFGEIAELIEEGLKNLIDWWNG | SEQ ID NO: 921 |
| CGFFGEIAELIEEGLENLIDWWNG | SEQ ID NO: 922 |
| CGNFGEIEELIEEGLKNLIDWWNG | SEQ ID NO: 923 |
| CGNFGEIAELIEEGLENLIDWWNG | SEQ ID NO: 924 |
| CGFFGEIEELIEENGENLIDWWNG | SEQ ID NO: 925 |
| CGFFGAIEELIEEGLKNLIDWWNG | SEQ ID NO: 926 |
| CGFFGAIAELIEEGLKNLIDWWNG | SEQ ID NO: 927 |
| CGFFGEIAELIEEGLKNLIDWWNGF | SEQ ID NO: 928 |
| GFFGEIAELIEEGLKNLIDWWNGC | SEQ ID NO: 929 |
| GNWWDILNKLGEEILEAIEGFFGC | SEQ ID NO: 930 |
| CGNWWDILNKLGEEILEAIEGFFG | SEQ ID NO: 931 |
| CGFLGEIAELIEEGLKNLIDWWNG | SEQ ID NO: 932 |
| CGFFGEIWELIEEGLKNLIDWWNG | SEQ ID NO: 933 |
| CGFFGEIAELWEEGLKNLIDWWNG | SEQ ID NO: 934 |
| CGFFGEIAELIWEGLKNLIDWWNG | SEQ ID NO: 935 |
| CGFFGEIAELIEWGLKNLIDWWNG | SEQ ID NO: 936 |
| CGFFGEIAELIEEGLRNLIDWWNG | SEQ ID NO: 937 |
| CGFFGEIAELIEEGLDNLIDWWNG | SEQ ID NO: 938 |

TABLE 2-continued

Suitable Peptide Sequences

| Peptide SEQUENCE | SEQ ID No. |
|---|---|
| CGFFGEIAELIEEGLKNLNDWWNG | SEQ ID NO: 939 |
| CGFFGEIEELIEEGLKNLIDWWNG | SEQ ID NO: 940 |
| CGFLGEIEELIEEGLKNLIDWWNG | SEQ ID NO: 941 |
| CGFFGLIEELIEEGLKNLIDWWNG | SEQ ID NO: 942 |
| CGFFGEIAELIEEGLKNLIDWWNGK(stearyl) | SEQ ID NO: 943 |
| (stearyl)GFFGEIAELIEEGLKNLIDWWNGC | SEQ ID NO: 944 |
| CFFGAIWEFAKSILK(stearyl) | SEQ ID NO: 945 |
| CGFFGAIWEFAKSIL | SEQ ID NO: 946 |
| CFFGKIWEFIKSILK(stearyl) | SEQ ID NO: 947 |
| (stearyl)FFGKIWEFIKSILC | SEQ ID NO: 948 |
| CFFGAIWEFIKSIAK(stearyl) | SEQ ID NO: 949 |
| (stearyl)FFGAIWEFIKSIAC | SEQ ID NO: 950 |
| (stearyl)FFGAIWEFAKSILC | SEQ ID NO: 951 |
| CFFGGIWEFIKSILK(stearyl) | SEQ ID NO: 952 |
| (stearyl)FFGGIWEFIKSILC | SEQ ID NO: 953 |
| CFFKAIWEFIKSILK(stearyl) | SEQ ID NO: 954 |
| (stearyl)FFKAIWEFIKSILC | SEQ ID NO: 955 |
| CFFGAIWEAIKSILK(stearyl) | SEQ ID NO: 956 |
| (stearyl)FFGAIWEAIKSILC | SEQ ID NO: 957 |
| CFFKAIWEFAKSIL | SEQ ID NO: 958 |
| CFFKAIWEFAHSIL | SEQ ID NO: 959 |
| CFFKAIWEFAKSILK(stearyl) | SEQ ID NO: 960 |
| (stearyl)FFKAIWEFAKSILC | SEQ ID NO: 961 |
| CFFKAIWEFAHSILK(stearyl) | SEQ ID NO: 962 |
| CGLFGEIAELIEEGLENLIDWWNG | SEQ ID NO: 963 |
| CGLFGEIEELIEEGLKNLIDWWNG | SEQ ID NO: 964 |
| CFFGAIWEFAKSILK(stearyl) | SEQ ID NO: 965 |
| CGLFGEIEELIEEGLKGLIDWWNG | SEQ ID NO: 966 |
| CGLFGEIAELIEEGLKNLIDWWNG | SEQ ID NO: 967 |
| CGLFGEIAELIEEGLEGLIDWWNG | SEQ ID NO: 968 |
| GLFGEIEELIEEGLENLIDWWNGC | SEQ ID NO: 969 |
| (stearyl)GLFGEIEELIEEGLENLIDWWNGC | SEQ ID NO: 970 |
| CGLFGEIEELIEEGLENLIDWWNGK(stearyl) | SEQ ID NO: 971 |
| CGNWWDILNELGEEILEEIEGFLG | SEQ ID NO: 972 |
| CALFGEIEELIEEGLENLIDWWNG | SEQ ID NO: 973 |
| CELFGEIEELIEEGLENLIDWWNG | SEQ ID NO: 974 |
| CSLFGEIEELIEEGLENLIDWWNG | SEQ ID NO: 975 |
| CNLFGEIEELIEEGLENLIDWWNG | SEQ ID NO: 976 |

TABLE 2-continued

Suitable Peptide Sequences

| Peptide SEQUENCE | SEQ ID No. |
|---|---|
| CVLFGEIEELIEEGLENLIDWWNG | SEQ ID NO: 977 |
| CGFFGEIEELIEEGLENLIDWWNG | SEQ ID NO: 978 |
| CGVFGEIEELIEEGLENLIDWWNG | SEQ ID NO: 979 |
| CGIFGEIEELIEEGLENLIDWWNG | SEQ ID NO: 980 |
| CGWFGEIEELIEEGLENLIDWWNG | SEQ ID NO: 981 |
| CGYFGEIEELIEEGLENLIDWWNG | SEQ ID NO: 982 |
| CGLLGEIEELIEEGLENLIDWWNG | SEQ ID NO: 983 |
| CGLVGEIEELIEEGLENLIDWWNG | SEQ ID NO: 984 |
| CGLIGEIEELIEEGLENLIDWWNG | SEQ ID NO: 985 |
| CGLWGEIEELIEEGLENLIDWWNG | SEQ ID NO: 986 |
| CGLYGEIEELIEEGLENLIDWWNG | SEQ ID NO: 987 |
| CGLFEEIEELIEEGLENLIDWWNG | SEQ ID NO: 988 |
| CGLFAEIEELIEEGLENLIDWWNG | SEQ ID NO: 989 |
| CGLFNEIEELIEEGLENLIDWWNG | SEQ ID NO: 990 |
| CGLFSEIEELIEEGLENLIDWWNG | SEQ ID NO: 991 |
| CGLFGAIEELIEEGLENLIDWWNG | SEQ ID NO: 992 |
| CGLFGDIEELIEEGLENLIDWWNG | SEQ ID NO: 993 |
| CGLFGNIEELIEEGLENLIDWWNG | SEQ ID NO: 994 |
| CGLFGSIEELIEEGLENLIDWWNG | SEQ ID NO: 995 |
| CGLFGELEELIEEGLENLIDWWNG | SEQ ID NO: 996 |
| CGLFGEVEELIEEGLENLIDWWNG | SEQ ID NO: 997 |
| CGLFGEFEELIEEGLENLIDWWNG | SEQ ID NO: 998 |
| CGLFGEWEELIEEGLENLIDWWNG | SEQ ID NO: 999 |
| CGLFGEYEELIEEGLENLIDWWNG | SEQ ID NO: 1000 |
| CGLFGEIAELIEEGLENLIDWWNG | SEQ ID NO: 1001 |
| CGLFGEIGELIEEGLENLIDWWNG | SEQ ID NO: 1002 |
| CGLFGEILELIEEGLENLIDWWNG | SEQ ID NO: 1003 |
| CGLFGEIVELIEEGLENLIDWWNG | SEQ ID NO: 1004 |
| CGLFGEISELIEEGLENLIDWWNG | SEQ ID NO: 1005 |
| CGLFGEIEDLIEEGLENLIDWWNG | SEQ ID NO: 1006 |
| CGLFGEIENLIEEGLENLIDWWNG | SEQ ID NO: 1007 |
| CGLFGEIESLIEEGLENLIDWWNG | SEQ ID NO: 1008 |
| CGLFGEIEALIEEGLENLIDWWNG | SEQ ID NO: 1009 |
| CGLFGEIEGLIEEGLENLIDWWNG | SEQ ID NO: 1010 |
| CGLFGEIEEVIEEGLENLIDWWNG | SEQ ID NO: 1011 |
| CGLFGEIEEIIEEGLENLIDWWNG | SEQ ID NO: 1012 |
| CGLFGEIEEFIEEGLENLIDWWNG | SEQ ID NO: 1013 |
| CGLFGEIEEAIEEGLENLIDWWNG | SEQ ID NO: 1014 |

TABLE 2-continued

Suitable Peptide Sequences

| Peptide SEQUENCE | SEQ ID No. |
|---|---|
| CGLFGEIEEYIEEGLENLIDWWNG | SEQ ID NO: 1015 |
| CGLFGEIEEWIEEGLENLIDWWNG | SEQ ID NO: 1016 |
| CGLFGEIEELVEEGLENLIDWWNG | SEQ ID NO: 1017 |
| CGLFGEIEELLEEGLENLIDWWNG | SEQ ID NO: 1018 |
| CGLFGEIEELFEEGLENLIDWWNG | SEQ ID NO: 1019 |
| CGLFGEIEELAEEGLENLIDWWNG | SEQ ID NO: 1020 |
| CGLFGEIEELYEEGLENLIDWWNG | SEQ ID NO: 1021 |
| CGLFGEIEELWEEGLENLIDWWNG | SEQ ID NO: 1022 |
| CGLFGEIEELIDEGLENLIDWWNG | SEQ ID NO: 1023 |
| CGLFGEIEELINEGLENLIDWWNG | SEQ ID NO: 1024 |
| CGLFGEIEELISEGLENLIDWWNG | SEQ ID NO: 1025 |
| CGLFGEIEELIEDGLENLIDWWNG | SEQ ID NO: 1026 |
| CGLFGEIEELIEYGLENLIDWWNG | SEQ ID NO: 1027 |
| CGLFGEIEELIESGLENLIDWWNG | SEQ ID NO: 1028 |
| CGLFGEIEELIEQGLENLIDWWNG | SEQ ID NO: 1029 |
| CGLFGEIEELIENGLENLIDWWNG | SEQ ID NO: 1030 |
| CGLFGEIEELIEEALENLIDWWNG | SEQ ID NO: 1031 |
| CGLFGEIEELIEENLENLIDWWNG | SEQ ID NO: 1032 |
| CGLFGEIEELIEESLENLIDWWNG | SEQ ID NO: 1033 |
| CGLFGEIEELIEEQLENLIDWWNG | SEQ ID NO: 1034 |
| CGLFGEIEELIEEGWENLIDWWNG | SEQ ID NO: 1035 |
| CGLFGEIEELIEEGVENLIDWWNG | SEQ ID NO: 1036 |
| CGLFGEIEELIEEGIENLIDWWNG | SEQ ID NO: 1037 |
| CGLFGEIEELIEEGFENLIDWWNG | SEQ ID NO: 1038 |
| CGLFGEIEELIEEGAENLIDWWNG | SEQ ID NO: 1039 |
| CGLFGEIEELIEEGYENLIDWWNG | SEQ ID NO: 1040 |
| CGLFGEIEELIEEGLRNLIDWWNG | SEQ ID NO: 1041 |
| CGLFGEIEELIEEGLHNLIDWWNG | SEQ ID NO: 1042 |
| CGLFGEIEELIEEGLONLIDWWNG | SEQ ID NO: 1043 |
| CGLFGEIEELIEEGLDNLIDWWNG | SEQ ID NO: 1044 |
| CGLFGEIEELIEEGLKNLIDWWNG | SEQ ID NO: 1045 |
| CGLFGEIEELIEEGLEGLIDWWNG | SEQ ID NO: 1046 |
| CGLFGEIEELIEEGLEYLIDWWNG | SEQ ID NO: 1047 |
| CGLFGEIEELIEEGLEQLIDWWNG | SEQ ID NO: 1048 |
| CGLFGEIEELIEEGLESLIDWWNG | SEQ ID NO: 1049 |
| CGLFGEIEELIEEGLEALIDWWNG | SEQ ID NO: 1050 |
| CGLFGEIEELIEEGLE(Cit)LIDWWNG | SEQ ID NO: 1051 |
| CGLFGEIEELIEEGLENMIDWWNG | SEQ ID NO: 1052 |

TABLE 2-continued

Suitable Peptide Sequences

| Peptide SEQUENCE | SEQ ID No. |
|---|---|
| CGLFGEIEELIEEGLENFIDWWNG | SEQ ID NO: 1053 |
| CGLFGEIEELIEEGLENIIDWWNG | SEQ ID NO: 1054 |
| CGLFGEIEELIEEGLENWIDWWNG | SEQ ID NO: 1055 |
| CGLFGEIEELIEEGLENVIDWWNG | SEQ ID NO: 1056 |
| CGLFGEIEELIEEGLENYIDWWNG | SEQ ID NO: 1057 |
| CGLFGEIEELIEEGLEN(Nle)IDWWNG | SEQ ID NO: 1058 |
| CGLFGEIEELIEEGLENLIDWWNG | SEQ ID NO: 1059 |
| CGLFGEIEELIEEGLENLVDWWNG | SEQ ID NO: 1060 |
| CGLFGEIEELIEEGLENLFDWWNG | SEQ ID NO: 1061 |
| CGLFGEIEELIEEGLENLWDWWNG | SEQ ID NO: 1062 |
| CGLFGEIEELIEEGLENLYDWWNG | SEQ ID NO: 1063 |
| CGLFGEIEELIEEGLENLIEWWNG | SEQ ID NO: 1064 |
| CGLFGEIEELIEEGLENLINWWNG | SEQ ID NO: 1065 |
| CGLFGEIEELIEEGLENLISWWNG | SEQ ID NO: 1066 |
| CGLFGEIEELIEEGLENLIQWWNG | SEQ ID NO: 1067 |
| CGLFGEIEELIEEGLENLIDGWNG | SEQ ID NO: 1068 |
| CGLFGEIEELIEEGLENLIDAWNG | SEQ ID NO: 1069 |
| CGLFGEIEELIEEGLENLIDFWNG | SEQ ID NO: 1070 |
| CGLFGEIEELIEEGLENLIDLWNG | SEQ ID NO: 1071 |
| CGLFGEIEELIEEGLENLIDIWNG | SEQ ID NO: 1072 |
| CGLFGEIEELIEEGLENLIDVWNG | SEQ ID NO: 1073 |
| CGLFGEIEELIEEGLENLIDWGNG all (D) | SEQ ID NO: 1074 |
| CGLFGEIEELIEEGLENLIDWANG | SEQ ID NO: 1075 |
| CGLFGEIEELIEEGLENLIDWFNG | SEQ ID NO: 1076 |
| CGLFGEIEELIEEGLENLIDWING | SEQ ID NO: 1077 |
| CGLFGEIEELIEEGLENLIDWVNG | SEQ ID NO: 1078 |
| CGLFGEIEELIEEGLENLIDWYNG | SEQ ID NO: 1079 |
| CGLFGEIEELIEEGLENLIDWWQG | SEQ ID NO: 1080 |
| CGLFGEIEELIEEGLENLIDWWTG | SEQ ID NO: 1081 |
| CGLFGEIEELIEEGLENLIDWWSG | SEQ ID NO: 1082 |
| CGLFGEIEELIEEGLENLIDWWEG | SEQ ID NO: 1083 |
| CGLFGEIEELIEEGLENLIDWW(Cit)G | SEQ ID NO: 1084 |
| CGLFGEIEELIEEGLENLIDWWNA | SEQ ID NO: 1085 |
| CGLFGEIEELIEEGLENLIDWWNN | SEQ ID NO: 1086 |
| CGLFGEIEELIEEGLENLIDWWNS | SEQ ID NO: 1087 |
| CGLFGEIEELIEEGLENLIDWWNY | SEQ ID NO: 1088 |
| CGLFGEIEELIEEGLENLIDWWNW | SEQ ID NO: 1089 |
| CFFGAIWGLLHSIL | SEQ ID NO: 1090 |

TABLE 2-continued

Suitable Peptide Sequences

| Peptide SEQUENCE | SEQ ID No. |
|---|---|
| CFFGK(stearyl)IWEFIKSIL | SEQ ID NO: 1091 |
| CFFGK(stearyl)IWEFIHSIL | SEQ ID NO: 1092 |
| CFFK(stearyl)AIWEFIKSIL | SEQ ID NO: 1093 |
| CGFFGAIWGLLHSILK | SEQ ID NO: 1094 |
| CGFFEAIWGLLHSIL | SEQ ID NO: 1095 |
| CFFGAIWGLLKSIL | SEQ ID NO: 1096 |
| CGFFGAIWGLLKSIL | SEQ ID NO: 1097 |
| CFFEAIWGLLKSIL | SEQ ID NO: 1098 |
| CGFFEAIWGLLKSIL | SEQ ID NO: 1099 |
| CFFGAIWGLLHSILKGLIDWWNG | SEQ ID NO: 1100 |
| CFFGAIWGLLHSILKGLIDGWYG | SEQ ID NO: 1101 |
| CGIFGAIAGLLKNIFKG | SEQ ID NO: 1102 |
| CGIFGAIAGLLKNIFKA | SEQ ID NO: 1103 |
| CGIFGAIAGLLKNIFKL | SEQ ID NO: 1104 |
| CGIFGAIAGLLKNIFKW | SEQ ID NO: 1105 |
| CGIFGAIAGLLKNIFKF | SEQ ID NO: 1106 |
| CGIFGAIAGLLKNIFKN | SEQ ID NO: 1107 |
| CGIFGAIAGLLKNIFKE | SEQ ID NO: 1108 |
| CGIFGAIAGLLKNIFKS | SEQ ID NO: 1109 |
| CGIFGAIAGLLKNIFK(stearyl) | SEQ ID NO: 1110 |
| CGIFGAIAGLLKNIFKK(stearyl) | SEQ ID NO: 1111 |
| (stearyl)GIFGAIAGLLKNIFKC | SEQ ID NO: 1112 |
| CGIFGAIAGLLKNIFK(lauryl) | SEQ ID NO: 1113 |
| CGIFGAIAGLLKNIFKK(lauryl) | SEQ ID NO: 1114 |
| (lauryl)GIFGAIAGLLKNIFKC | SEQ ID NO: 1115 |
| CGIFGAIAGLLHNIFK | SEQ ID NO: 1116 |
| CGIFGAIAGLLONIFK | SEQ ID NO: 1117 |
| CGIFGAIAGLLRNIFK | SEQ ID NO: 1118 |
| CGIFGAIAGLLENIFK | SEQ ID NO: 1119 |
| CGIFGAIAGLLDNIFK | SEQ ID NO: 1120 |
| CGIFGAIAGLLKNIFH | SEQ ID NO: 1121 |
| CGIFGAIAGLLKNIFO | SEQ ID NO: 1122 |
| CGIFGAIAGLLKINFE | SEQ ID NO: 1123 |
| CGIFGAIAGLLKNIFD | SEQ ID NO: 1124 |
| CGIFGAIAGLLKNIFN | SEQ ID NO: 1125 |
| CGIFGAIAGLLNNIFK | SEQ ID NO: 1126 |
| CGIFGIAIGLLKNIFKGIFGAIAGLLKNIFK | SEQ ID NO: 1127 |
| CGIFGAIWGLLKNIFKG | SEQ ID NO: 1128 |

TABLE 2-continued

Suitable Peptide Sequences

| Peptide SEQUENCE | SEQ ID No. |
|---|---|
| CGIFGAIWGLLKNIFKA | SEQ ID NO: 1129 |
| CGIFGAIWGLLKNIFKL | SEQ ID NO: 1130 |
| CGIFGAIWGLLKNIFKW | SEQ ID NO: 1131 |
| CGIFGAIWGLLKNIFKF | SEQ ID NO: 1132 |
| CGIFGAIWGLLKNIFKN | SEQ ID NO: 1133 |
| CGIFGAIWGLLKNIFKE | SEQ ID NO: 1134 |
| CGIFGAIWGLLKNIFKS | SEQ ID NO: 1135 |
| CGIFGAIWGLLKNIFK(stearyl) | SEQ ID NO: 1136 |
| CGIFGAIWGLLKNIFKK(stearyl) | SEQ ID NO: 1137 |
| (stearyl)GIFGAIWGLLKNIFKC | SEQ ID NO: 1138 |
| CGIFGAIWGLLKNIFK(lauryl) | SEQ ID NO: 1139 |
| CGIFGAIWGLLKNIFKK(lauryl) | SEQ ID NO: 1140 |
| (lauryl)GIFGAIWGLLKNIFKC | SEQ ID NO: 1141 |
| CGIFGAIWGLLHNIFK | SEQ ID NO: 1142 |
| CGIFGAIWGLLONIFK | SEQ ID NO: 1143 |
| CGIFGAIWGLLRNIFK | SEQ ID NO: 1144 |
| CGIFGAIWGLLENIFK | SEQ ID NO: 1145 |
| CGIFGAIWGLLDNIFK | SEQ ID NO: 1146 |
| CGIFGAIWGLLKNIFH | SEQ ID NO: 1147 |
| CGIFGAIWGLLKNIFO | SEQ ID NO: 1148 |
| CGIFGAIWGLLKINFE | SEQ ID NO: 1149 |
| CGIFGAIWGLLKNIFD | SEQ ID NO: 1150 |
| CGIFGAIWGLLKNIFN | SEQ ID NO: 1151 |
| CGIFGAIWGLLNNIFK | SEQ ID NO: 1152 |
| CFFGAIWGLLKNIFK | SEQ ID NO: 1153 |
| CGFFGAIWGLLKNIFK | SEQ ID NO: 1154 |
| CIFGAIWGLLKNIFK | SEQ ID NO: 1155 |
| CGIFGAIWIGLLKNIFKGIFGAIWGLLKNIFK | SEQ ID NO: 1156 |
| CGIFGAIWGLLHNIFH | SEQ ID NO: 1157 |
| CGIFGAIWGLLONIFO | SEQ ID NO: 1158 |
| CGIFGAIAGLLHSILK | SEQ ID NO: 1159 |
| CGIFGAIWGLLHSILK | SEQ ID NO: 1160 |
| CGIFGAIAGLLHSIL | SEQ ID NO: 1161 |
| CGIFGAIWGLLHSIL | SEQ ID NO: 1162 |
| CGIFGAIWELLKNIFK | SEQ ID NO: 1163 |
| CGIFGAIWGLLHNIFHGIFGAIWGLLHNIFK | SEQ ID NO: 1164 |
| CGIFEAIWGLLHNIFHGIFEAIWGLLHNIFH | SEQ ID NO: 1165 |
| CGIFEAIWGLLKNIFHGIFEAIWGLLHNIFH | SEQ ID NO: 1166 |

TABLE 2-continued

Suitable Peptide Sequences

| Peptide SEQUENCE | SEQ ID No. |
|---|---|
| CGIFEAIWGLLKNIFKGIFEAIWELLKNIFH | SEQ ID NO: 1167 |
| CGIFEAIWGLLKNIFHGIFEAIWGLLKNIFH | SEQ ID NO: 1168 |
| CGLFEALLELLESLWELLLEAWNG | SEQ ID NO: 1169 |
| CGLFEALLELLESLWELLLEWWNG | SEQ ID NO: 1170 |
| CGLFGELEELLEEGLENLLDWWNG | SEQ ID NO: 1171 |
| CGLFGELEELLEEGLENLLEWWNG | SEQ ID NO: 1172 |
| CGLFGELEELLEEGWELLLEAWNG | SEQ ID NO: 1173 |
| CGLFGELEELLEEGWELLLEWWNG | SEQ ID NO: 1174 |
| CGLFGELEELLEEGWELLLDWWNG | SEQ ID NO: 1175 |
| CGLFGALLELLEEGLENLIDWWNG | SEQ ID NO: 1176 |
| CGLFEALLELLEEGLENLIDWWNG | SEQ ID NO: 1177 |
| CGLFEALLELLESLLENLIDWWNG | SEQ ID NO: 1178 |
| CGLFGELAELLEEGLENLLDWWNG | SEQ ID NO: 1179 |
| GLFGEIEELIEEGLENLIDWWNG | SEQ ID NO: 1180 |
| CFFGNIWEFIHSIL | SEQ ID NO: 1181 |
| CFFGAIWNFIHSIL | SEQ ID NO: 1182 |
| CFFGNIWNFIHSIL | SEQ ID NO: 1183 |
| CGIFGNIWNFIKNIFK | SEQ ID NO: 1184 |
| CGIFGNIWNLLKNIFK | SEQ ID NO: 1185 |
| CGIFGNIWGLLKNIFK | SEQ ID NO: 1186 |
| CGIFGNIWNFIKNIFH | SEQ ID NO: 1187 |
| CGIFGNIWNLLKNIFH | SEQ ID NO: 1188 |
| CGIFGNIWGLLKNIFH | SEQ ID NO: 1189 |
| CGIFENIWNFIKNIFK | SEQ ID NO: 1190 |
| CGIFENIWNFIKNIFH | SEQ ID NO: 1191 |
| CGIFENIWGLLKNIFK | SEQ ID NO: 1192 |
| CGIFENIWGLLKNIFH | SEQ ID NO: 1193 |
| CGIFENIWNLLKNIFK | SEQ ID NO: 1194 |
| CGIFENIWNLLKNIFH | SEQ ID NO: 1195 |
| CGLFGAIAGLLENIFENLIDWWNG | SEQ ID NO: 1196 |
| CGLFGAIAGLLNKIFKNLIDWWNG | SEQ ID NO: 1197 |
| CGLFGAIAGLLENIFKNLIDWWNG | SEQ ID NO: 1198 |
| CGLFGAIAGLLKNIFENLIDWWNG | SEQ ID NO: 1199 |
| CGLFGAIAGLLKNIFHNLIDWWNG | SEQ ID NO: 1200 |
| CLIGAILKVLATGLPTLISWIKNKRKQ | SEQ ID NO: 1201 |
| CGLLEEIEELLEEGLENLIDWWNG | SEQ ID NO: 1202 |
| CGLFEELEELLEEGLENLIDWWNG | SEQ ID NO: 1203 |
| CGLFEELEELLEEGLENLIEA | SEQ ID NO: 1204 |

TABLE 2-continued

Suitable Peptide Sequences

| Peptide SEQUENCE | SEQ ID No. |
| --- | --- |
| CGLFEELEELLEEGLENLIEAWNG | SEQ ID NO: 1205 |
| CGLFEELEELLEEGLENLIEW | SEQ ID NO: 1206 |
| CGLFEELEELLEEGLENLIEWWNG | SEQ ID NO: 1207 |
| CGLFEELEELLEEGLENLIDA | SEQ ID NO: 1208 |
| CGLFEELEELLEEGLENLIDAWNG | SEQ ID NO: 1209 |
| CGLFEELEELLEEGLENLIDW | SEQ ID NO: 1210 |
| CFLGALKFALKSLL | SEQ ID NO: 1211 |
| CFLGALHFALKSLL | SEQ ID NO: 1212 |
| CFLGALKFALHSLL | SEQ ID NO: 1213 |
| CFLGALHFALHSLL | SEQ ID NO: 1214 |
| FLGALKFALKSLLC | SEQ ID NO: 1215 |
| GFLGALKFALKSLLC | SEQ ID NO: 1216 |
| CGLFGELEELIEEGLENLLDWWNG | SEQ ID NO: 1217 |
| CGLFGEIEELLEEGLENLLDWWNG | SEQ ID NO: 1218 |
| CGLFGELEELLEEGLENLIDWWNG | SEQ ID NO: 1219 |
| CGLFGEIEELIEEGLENLMDWWNG | SEQ ID NO: 1220 |
| CGLFGEIEELIEEGLENLEDWWNG | SEQ ID NO: 1221 |
| CGLFGEIEELIEEGLENLDDWWNG | SEQ ID NO: 1222 |
| CGLFGEIEELIEEGLENLNDWWNG | SEQ ID NO: 1223 |
| CGLFGEIEELIEEGLENLSDWWNG | SEQ ID NO: 1224 |
| CGLFGEIEELIEEGLENLQDWWNG | SEQ ID NO: 1225 |
| CGLFGEIEELIEEGLENL-CIT-DWWNG | SEQ ID NO: 1226 |
| CGLFGEIEELIEELLENLIDWWNG | SEQ ID NO: 1227 |
| CGLFGEIEELIEEILENLIDWWNG | SEQ ID NO: 1228 |
| CGLFGEIEELIEEVLENLIDWWNG | SEQ ID NO: 1229 |
| CFLGALWKLLSHLL | SEQ ID NO: 1230 |
| CFLGALWKILSHLL | SEQ ID NO: 1231 |
| CFLGALWVKVLSHLL | SEQ ID NO: 1232 |
| CFLGALWKFLSHLL | SEQ ID NO: 1233 |
| CFLEALWKALSHLL | SEQ ID NO: 1234 |
| CFLHALWKALSHLL | SEQ ID NO: 1235 |
| CFLKALWKALSHLL | SEQ ID NO: 1236 |
| CFLNALWKALSHLL | SEQ ID NO: 1237 |
| CFLSALWKALSHLL | SEQ ID NO: 1238 |
| CFLQALWKALSHLL | SEQ ID NO: 1239 |
| CFLEALWEALSHLL | SEQ ID NO: 1240 |
| CFLGALWEALSHLL | SEQ ID NO: 1241 |
| CFLEALWKLLSHLL | SEQ ID NO: 1242 |

TABLE 2-continued

Suitable Peptide Sequences

| Peptide SEQUENCE | SEQ ID No. |
|---|---|
| CFLEALWEALEELL | SEQ ID NO: 1243 |
| CFLEELWEALEELL | SEQ ID NO: 1244 |
| CFLEALWEALEHLL | SEQ ID NO: 1245 |
| CFLEELWEALEHLL | SEQ ID NO: 1246 |
| CFLEELWELLEELL | SEQ ID NO: 1247 |
| CFLEELWELLEHLL | SEQ ID NO: 1248 |
| CGLFGEIEELLEEGLE-CIT-LIDWWNG | SEQ ID NO: 1249 |
| CGLFEEIEELLEEGLE-CIT-LIDWWNG | SEQ ID NO: 1250 |
| CGLFGEIAELLEEGLE-CIT-LIDWWNG | SEQ ID NO: 1251 |
| CGLFEEIAELLEEGLE-CIT-LIDWWNG | SEQ ID NO: 1252 |
| CGLFGEIEELLEEGLE-CIT-LVDWWNG | SEQ ID NO: 1253 |
| CGLFEEIEELLEEGLE-CIT-LVDWWNG | SEQ ID NO: 1254 |
| CGLFGEIAELLEEGLE-CIT-LVDWWNG | SEQ ID NO: 1255 |
| CGLFEEIAELLEEGLE-CIT-LVDWWNG | SEQ ID NO: 1256 |
| CGLFGEIEELLEEGLE-CIT-LIDWWNE | SEQ ID NO: 1257 |
| CGLFEEIEELLEEGLE-CIT-LIDWWNE | SEQ ID NO: 1258 |
| CGLFGEIAELLEEGLE-CIT-LIDWWNE | SEQ ID NO: 1259 |
| CGLFEEIAELLEEGLE-CIT-LIDWWNE | SEQ ID NO: 1260 |
| CGLFGEIEELLEEGLH-CIT-LIDWWNG | SEQ ID NO: 1261 |
| CGLFEEIEELLEEGLH-CIT-LIDWWNG | SEQ ID NO: 1262 |
| CGLFGEIAELLEEGLH-CIT-LIDWWNG | SEQ ID NO: 1263 |
| CGLFEEIAELLEEGLH-CIT-LIDWWNG | SEQ ID NO: 1264 |
| CGLFGEIEELLEEGLE-CIT-LVDWWNE | SEQ ID NO: 1265 |
| CGLFEEIEELLEEGLE-CIT-LVDWWNE | SEQ ID NO: 1266 |
| CGLFGEIAELLEEGLE-CIT-LVDWWNE | SEQ ID NO: 1267 |
| CGLFEEIAELLEEGLE-CIT-LVDWWNE | SEQ ID NO: 1268 |
| CFFKNIWEFIKSIL | SEQ ID NO: 1269 |
| CFFKNIWNFIKSIL | SEQ ID NO: 1270 |
| CFFKAIWEFIKSILE | SEQ ID NO: 1271 |
| CFFKAIWEFIKNIFK | SEQ ID NO: 1272 |
| CFFKAIWEFIKNIFKE | SEQ ID NO: 1273 |
| CFFKAIWELLKSIL | SEQ ID NO: 1274 |
| CFFKAIWGLLKSIL | SEQ ID NO: 1275 |
| CFFKAIWEFIKSILK | SEQ ID NO: 1276 |
| CFFKNIWGLLKSIL | SEQ ID NO: 1277 |
| CFFKAIWGLLKNIFK | SEQ ID NO: 1278 |
| CFFKAIWELLKNIFK | SEQ ID NO: 1279 |
| CFFKNIWGLLKNIFK | SEQ ID NO: 1280 |

TABLE 2-continued

Suitable Peptide Sequences

| Peptide SEQUENCE | SEQ ID No. |
|---|---|
| CFFKNIWELLKNIFK | SEQ ID NO: 1281 |
| CFFKAIWEFIRSIL | SEQ ID NO: 1282 |
| CFFKAIWEFIKSLL | SEQ ID NO: 1283 |
| CFFKAIWEFIKSAL | SEQ ID NO: 1284 |
| CFFKAIWEFIKSIF | SEQ ID NO: 1285 |
| CFFKALWEFLKSLL | SEQ ID NO: 1286 |
| CIFKAIWEFIKSIL | SEQ ID NO: 1287 |
| CFFKAIWEFIKSIW | SEQ ID NO: 1288 |
| CFFHAIWEFIKSIL | SEQ ID NO: 1289 |
| CFFEAIWEFIKSIL | SEQ ID NO: 1290 |
| CFFKAIAEFIKSIL | SEQ ID NO: 1291 |
| CFFKAIEEFIKSIL | SEQ ID NO: 1292 |
| CFFKAILEFIKSIL | SEQ ID NO: 1293 |
| CFFKAIFEFIKSIL | SEQ ID NO: 1294 |
| CFFKAIWGFIKSIL | SEQ ID NO: 1295 |
| CFFKAIWHFIKSIL | SEQ ID NO: 1296 |
| CFFKAIWKFIKSIL | SEQ ID NO: 1297 |
| CFFEAIWKFIKSIL | SEQ ID NO: 1298 |
| CFFKAIWELIKSIL | SEQ ID NO: 1299 |
| CFFKALWELLKSLL | SEQ ID NO: 1300 |
| CFFKAIWEAIKSIL | SEQ ID NO: 1301 |
| CFFKAIWEFLKSIL | SEQ ID NO: 1302 |
| CFFKAIWEFIHSIL | SEQ ID NO: 1303 |
| CFFKAIWEFIESIL | SEQ ID NO: 1304 |
| CFFKAIWEFIKNIL | SEQ ID NO: 1305 |
| CFFKAIWEFIKWIL | SEQ ID NO: 1306 |
| CFFKAIWEFIKEIL | SEQ ID NO: 1307 |
| CFFKAIWEFIKGIL | SEQ ID NO: 1308 |
| CFFKAIWEFIKSGL | SEQ ID NO: 1309 |
| CFFKAIWEFIKSII | SEQ ID NO: 1310 |
| CFFKAIWEFIK-CIT-IL | SEQ ID NO: 1311 |
| CFFKAIWEFIKSIA | SEQ ID NO: 1312 |
| CFFKAIWEFIKQIL | SEQ ID NO: 1313 |
| CGFFKAIWEFIKSIL | SEQ ID NO: 1314 |
| CFFKAIWEFIKSILKGLIDG | SEQ ID NO: 1315 |
| CFFKAIWEFIKSILKGLIDGWYG | SEQ ID NO: 1316 |
| CFFKAIWEFIKSILEGLIDG | SEQ ID NO: 1317 |
| CFFKAIWEFIKSILEGLIDGWYG | SEQ ID NO: 1318 |

TABLE 2-continued

Suitable Peptide Sequences

| Peptide SEQUENCE | SEQ ID No. |
|---|---|
| CFFKAIWEFIKNIFKGLIDG | SEQ ID NO: 1319 |
| CFFKAIWEFIKNIFKGLIDGWYG | SEQ ID NO: 1320 |
| CFFGNIWEFIKSILKGLIDG | SEQ ID NO: 1321 |
| CFFGNIWEFIKSILKGLIDGWYG | SEQ ID NO: 1322 |
| CFFGNIWEFIKSILEGLIDG | SEQ ID NO: 1323 |
| CFFGNIWEFIKSILEGLIDGWYG | SEQ ID NO: 1324 |
| CFFGNIWEFIKNIFKGLIDG | SEQ ID NO: 1325 |
| CFFGNIWEFIKNIFKGLIDGEYG | SEQ ID NO: 1326 |
| CFFKAIWGLLKSILKGLIDG | SEQ ID NO: 1327 |
| CFFKAIWGLLKSILKGLIDGWYG | SEQ ID NO: 1328 |
| CFFKAIWGLLKSILEGLIDG | SEQ ID NO: 1329 |
| CFFKAIWGLLKSILEGLIDGWYG | SEQ ID NO: 1330 |
| CFFKAIWGLLKNIFKGLIDG | SEQ ID NO: 1331 |
| CFFKAIWGLLKNIFKGLIDGWYG | SEQ ID NO: 1332 |
| CFFKAIWGLLKNIFEGLIDG | SEQ ID NO: 1333 |
| CFFKAIWGLLKNIFEGLIDGWYG | SEQ ID NO: 1334 |
| CFFKAIWEFIKSILKGLIDGWNG | SEQ ID NO: 1335 |
| CFFKAIWEFIKNIFKGLIDGWNG | SEQ ID NO: 1336 |
| CIFGAIAGLLKNILKGLIDG | SEQ ID NO: 1337 |
| CIFGAIAGLLKNILKGLIDGWYG | SEQ ID NO: 1338 |
| CFLEALWKALEHLL | SEQ ID NO: 1339 |
| CFLEALWEALSKLL | SEQ ID NO: 1340 |
| CFLEALWEALEKLL | SEQ ID NO: 1341 |
| CFLEALWEALEHLLK(stearyl) | SEQ ID NO: 1342 |
| (stearyl)FLEALWEALEHLLC | SEQ ID NO: 1343 |
| (stearyl)GFLEALWEALEHLLC | SEQ ID NO: 1344 |
| CFLEALWKALSKLL | SEQ ID NO: 1345 |
| CFLEALWEALDHLL | SEQ ID NO: 1346 |
| CFLEALWEALTHLL | SEQ ID NO: 1347 |
| CFLEALWEALNHLL | SEQ ID NO: 1348 |
| CFLEALWEALQHLL | SEQ ID NO: 1349 |
| CFLEALWEALEHLLH | SEQ ID NO: 1350 |
| CFLEALWEALEHLLK | SEQ ID NO: 1351 |
| CFLEALWEALEHLLE | SEQ ID NO: 1352 |
| CWLEALEALEHLL | SEQ ID NO: 1353 |
| CLLEALWEALEHLL | SEQ ID NO: 1354 |
| CFFEALWEALEHLL | SEQ ID NO: 1355 |
| CFLEALEEALEHLL | SEQ ID NO: 1356 |

TABLE 2-continued

Suitable Peptide Sequences

| Peptide SEQUENCE | SEQ ID No. |
|---|---|
| CFLEALAEALEHLL | SEQ ID NO: 1357 |
| CFLEALFEALEHLL | SEQ ID NO: 1358 |
| CLFEALWEALHHLL | SEQ ID NO: 1359 |
| CLFEALWEALKHLL | SEQ ID NO: 1360 |
| CFLEALWEALEHGL | SEQ ID NO: 1361 |
| CLFEALWEALEHLF | SEQ ID NO: 1362 |
| CLFEALWEALEHFL | SEQ ID NO: 1363 |
| CLFEALWEALEHLLEGLIDWWYG | SEQ ID NO: 1364 |
| CLFEALWEALEHLLEGLIDWWNG | SEQ ID NO: 1365 |
| CLFEALWEALEHLLENLIDWWNG | SEQ ID NO: 1366 |
| CFLEELWELLEKLL | SEQ ID NO: 1367 |
| CFLEELWELLEELLE | SEQ ID NO: 1368 |
| CFLEELWELLEELLELLE | SEQ ID NO: 1369 |
| CFLEELWELLEHLLELLD | SEQ ID NO: 1370 |
| CFLEELWELLEELLELID | SEQ ID NO: 1371 |
| CFLEELWELLEELLELLD | SEQ ID NO: 1372 |
| CFLEELWELLEHLLEGLE | SEQ ID NO: 1373 |
| CFLEELWELLEHLLEGLD | SEQ ID NO: 1374 |
| CFLEELWELLEHLLEEGLI | SEQ ID NO: 1375 |
| CFLEELWELLEHLLEGLIDWWYG | SEQ ID NO: 1376 |
| CFLEELWELLEHLLENLIDWWNG | SEQ ID NO: 1377 |
| CFLEALWEALEHLLELLD | SEQ ID NO: 1378 |
| CGLFGELEELLEEGLENLTDWWNG | SEQ ID NO: 1379 |
| CGLFGELEELLEEGLENL-(ALLO-I)-DWWNG | SEQ ID NO: 1380 |
| CFLEALWEALEHLLELID | SEQ ID NO: 1381 |
| CELFEELEELLEEGLENLIDWWNG | SEQ ID NO: 1382 |
| CGLFEELEELLEEGLELLIDWWNG | SEQ ID NO: 1383 |
| CGLFEELEELLEEGLELLIDWWNK | SEQ ID NO: 1384 |
| CGLFEELEELLEEGLENLIDWWNK | SEQ ID NO: 1385 |
| CGLFGELEELLEEGLENLIDWWNQ | SEQ ID NO: 1386 |
| CGLFGELEELLEEGLENLIDWWNE | SEQ ID NO: 1387 |
| CGLFGELEELLEEGLENLIDWWNN | SEQ ID NO: 1388 |
| CGLFGELEELLEEGLENLIDWWNS | SEQ ID NO: 1389 |
| CGLFEELEELLEEGLENLIDWWNQ | SEQ ID NO: 1390 |
| AC-CFLEELWELLEHLL | SEQ ID NO: 1391 |
| AC-CFLEELWELLEELL | SEQ ID NO: 1392 |
| CGLLGEIEELLEEGLENLIDWWNG | SEQ ID NO: 1393 |
| CGLLAEIEELLEEGLENLIDWWNG | SEQ ID NO: 1394 |

TABLE 2-continued

Suitable Peptide Sequences

| Peptide SEQUENCE | SEQ ID No. |
| --- | --- |
| CGLLGEIEELLEEGLENLIDWWNQ | SEQ ID NO: 1395 |
| CGLLAEIEELLEEGLENLIDWWNQ | SEQ ID NO: 1396 |
| CGLLEEIEELLEEGLENLIDWWNQ | SEQ ID NO: 1397 |
| CGLLGEIEELLEEGLENLIDWWNE | SEQ ID NO: 1398 |
| CGLLAEIEELLEEGLENLIDWWNE | SEQ ID NO: 1399 |
| CGLLEEIEELLEEGLENLIDWWNE | SEQ ID NO: 1400 |
| CGLLGEIEELLEEGLENLIDWWNS | SEQ ID NO: 1401 |
| CGLLAEIEELLEEGLENLIDWWNS | SEQ ID NO: 1402 |
| CGLLEEIEELLEEGLENLIDWWNS | SEQ ID NO: 1403 |
| CGLFAELEELLEEGLENLLEWWNG | SEQ ID NO: 1404 |
| CGLFEELEELLEEGLENLLEWWNG | SEQ ID NO: 1405 |
| CGLFGELEELLEEGLENLLEWWNE | SEQ ID NO: 1406 |
| CGLFAELEELLEEGLENLLEWWNE | SEQ ID NO: 1407 |
| CGLFEELEELLEEGLENLLEWWNE | SEQ ID NO: 1408 |
| CGLLGELEELLEEGLENLLEWWNG | SEQ ID NO: 1409 |
| CGLLGELEELLEEGLENLLEWWNE | SEQ ID NO: 1410 |
| CGILGEIEELLEEGLENLIDWWNG | SEQ ID NO: 1411 |
| CGILGEIEELLEEGLENLIDWWNE | SEQ ID NO: 1412 |
| CGILGEIEELLEEGLENLIDWWNS | SEQ ID NO: 1413 |
| CGILAEIEELLEEGLENLIDWWNG | SEQ ID NO: 1414 |
| CGILEEIEELLEEGLENLIDWWNG | SEQ ID NO: 1415 |
| CIFGAIAELLKNIFK | SEQ ID NO: 1416 |
| CIFGAIAELLENIFK | SEQ ID NO: 1417 |
| CIFGAIAGLLENIFK | SEQ ID NO: 1418 |
| CFLEELWGLLEHLL | SEQ ID NO: 1419 |
| CGILAEIEELLEEGLENLIDWWNQ | SEQ ID NO: 1420 |
| CGILAEIEELLEEGLENLIDWWNE | SEQ ID NO: 1421 |
| CGLFAEIEELLEEGLENLIDWWNQ | SEQ ID NO: 1422 |
| CGLFAEIEELLEEGLENLIDWWNE | SEQ ID NO: 1423 |
| CGLFGELEELLEEGLENLLEWWNQ | SEQ ID NO: 1424 |
| CGLFAEIAELLEEGLE-CIT-LIDWWNE | SEQ ID NO: 1425 |
| CGILAEIEELLEEGLENLLEWWNG | SEQ ID NO: 1426 |
| CGILEEIEELLEEGLENLIDWWNE | SEQ ID NO: 1427 |
| CGILEEIEELLEEGLENLIDWWNQ | SEQ ID NO: 1428 |
| CGLFGEIEELIWEGLENLIDWWNG | SEQ ID NO: 1429 |
| CGLFGEIAELIWEGLENLIDWWNG | SEQ ID NO: 1430 |
| CGLFEEIAELIEEGLENLIDWWNG | SEQ ID NO: 1431 |
| CGLFEEIAELIWEGLENLIDWWNG | SEQ ID NO: 1432 |

TABLE 2-continued

Suitable Peptide Sequences

| Peptide SEQUENCE | SEQ ID No. |
|---|---|
| CELFEEIAELIWEGLENLIDWWNG | SEQ ID NO: 1433 |
| CELFEEIAELLWEGLENLIDWWNG | SEQ ID NO: 1434 |
| CGLFEEIAELLWEGLENLIDWWNG | SEQ ID NO: 1435 |
| CGLFEELAELLWEGLENLIDWWNG | SEQ ID NO: 1436 |
| CELFEELAELLWEGLENLIDWWNG | SEQ ID NO: 1437 |
| CELFEELAELLWEGLENLIDWWNS | SEQ ID NO: 1438 |
| CGLFEELAELLWEGLENLIDWWNS | SEQ ID NO: 1439 |
| CGIFEELAELLWEGLENLIDWWNG | SEQ ID NO: 1440 |
| CGIFEELAELLWEGLENLIDWWNS | SEQ ID NO: 1441 |
| CGLFEELEELLEELLENLIDWWNS | SEQ ID NO: 1442 |
| CELFEELEELLEELLENLIDWWNS | SEQ ID NO: 1443 |
| CELFEELEELLEELLELLIDWWNS | SEQ ID NO: 1444 |
| CEFLEELEELLEELLENLIDWWNS | SEQ ID NO: 1445 |
| CELFEELEELLEHLLENLIDWWNS | SEQ ID NO: 1446 |
| CELFEELEELLHELLENLIDWWNS | SEQ ID NO: 1447 |
| CGLFGELEELLWEGLENLIDWWNG | SEQ ID NO: 1448 |
| CGLFGELEELLWEGLHNLIDWWNG | SEQ ID NO: 1449 |
| CGLFGELWELLEHGLENLIDWWNG | SEQ ID NO: 1450 |
| CGL-R6H-GELEEL-S7H-EEGLENLIDWWNG | SEQ ID NO: 1451 |
| CGLFEAIEGFIENGWEGMIDGWNG | SEQ ID NO: 1452 |
| CGLFEAIEGFIENGWEGMIDWWNG | SEQ ID NO: 1453 |
| CGLFGAIEGFIENGWEGMIDWWNG | SEQ ID NO: 1454 |
| CGLFAEIEELLEEGLENLLEWWNG | SEQ ID NO: 1455 |
| CGLFAELEELLEEGLENLIDWWNG | SEQ ID NO: 1456 |
| CGIFAEIEELLEEGLENLIDWWNG | SEQ ID NO: 1457 |
| CGLFAEIEELLEEGLENLIDWWNGF | SEQ ID NO: 1458 |
| CGLFAEIEELLEEGLENLIDWWNA | SEQ ID NO: 1459 |
| CGLFAEIEELLEEGLENLIDWWNS | SEQ ID NO: 1460 |
| CGLFAEIEELLEEGLENLIDWWN-CIT | SEQ ID NO: 1461 |
| CGLFGEIAGLLEEGLHNLIDWWNG | SEQ ID NO: 1462 |
| CGLFGEIAGLLEQGLHNLIDWWNG | SEQ ID NO: 1463 |
| CGLFGEIAGLLESGLHNLIDWWNG | SEQ ID NO: 1464 |
| CGLFAEIAGLLEQGLHNLIDWWNG | SEQ ID NO: 1465 |
| CGLFAEIAGLLEEGLHNLIDWWNG | SEQ ID NO: 1466 |
| CGLFAEIAGLLESGLHNLIDWWNG | SEQ ID NO: 1467 |
| CGIFEAIAGLLEQGLHNLIDWWNG | SEQ ID NO: 1468 |
| CGLFGAIAELLEEGLHNLIDWWNG | SEQ ID NO: 1469 |
| CGLFAAIAELLEEGLHNLIDWWNG | SEQ ID NO: 1470 |

TABLE 2-continued

Suitable Peptide Sequences

| Peptide SEQUENCE | SEQ ID No. |
|---|---|
| CGIFEAIAGLLKNIFKNLIDWWNG | SEQ ID NO: 1471 |
| CGIFGAIWELLEQGLHNLIDWWNG | SEQ ID NO: 1472 |
| CGLFAELAGLLEQGLHNLIDWWNG | SEQ ID NO: 1473 |
| CGILAELAGLLEQGLHNLIDWWNG | SEQ ID NO: 1474 |
| CGLFGEIEELLEHLL | SEQ ID NO: 1475 |
| CGLFGEIEELLEELL | SEQ ID NO: 1476 |
| CGLFGEIEELLEEGL | SEQ ID NO: 1477 |
| CGLFGEIEELLEHGL | SEQ ID NO: 1478 |
| CGLFHEIEELLEHLL | SEQ ID NO: 1479 |
| CFLGALWKALSELLE | SEQ ID NO: 1480 |
| CGLFGEIWELLEEGL | SEQ ID NO: 1481 |
| CGLFGEIWELLEEGLI | SEQ ID NO: 1482 |
| CGLFGEIWELLEELL | SEQ ID NO: 1483 |
| CGLFEEIEELLEELLE | SEQ ID NO: 1484 |
| CGLFELIEGFIEWGWEGMIDGWYGYGRKKRRQRR | SEQ ID NO: 1485 |
| CIFGAIAGFIKNIWLHLLHHLLHHLHHLLHHLLHL | SEQ ID NO: 1486 |
| CEALFGKINAIFIGKL | SEQ ID NO: 1487 |
| CEENWIGLFGGGNIWEEEEILDLL | SEQ ID NO: 1488 |
| CLELWLEHLFLELE | SEQ ID NO: 1489 |
| CGNFEEIEGFIENGWEGLIDGWYGYGRKKRRQRR | SEQ ID NO: 1490 |
| CRGKWYMGFGEIKRQGEGRRYGLFEDWIAENRGI | SEQ ID NO: 1491 |
| GLFEAIEGFIENGWEGLAELAEALEALAAGGSC | SEQ ID NO: 1492 |
| GLFGALAEALAEALAEHLAEALAEALEALAAGGSC | SEQ ID NO: 1493 |
| CGFFGEIAGLLENGLHNLIDWWNG | SEQ ID NO: 1494 |
| CGFFGEIAALLENGLENLIDWWNG | SEQ ID NO: 1495 |
| CGFFGEIAEFIHSGLKNLIDWWNG | SEQ ID NO: 1496 |
| CGFFGEIAGLLKNGLKNLIDWWNG | SEQ ID NO: 1497 |
| CGFFGEIAGFIKNGLKNLIDWWNG | SEQ ID NO: 1498 |
| CGFFGEIAEFIHSILKNLIDWWNG | SEQ ID NO: 1499 |
| CGFFGEIAGLLKNILKNLIDWWNG | SEQ ID NO: 1500 |
| CGFFGEIAGFIKNILKNLIDWWNG | SEQ ID NO: 1501 |
| CFLGALFHALSELL | SEQ ID NO: 1502 |
| CFLGALWHALSELL | SEQ ID NO: 1503 |
| CFLGALWHALSHLL | SEQ ID NO: 1504 |
| CFLGALWELLSHLL | SEQ ID NO: 1505 |
| CFLGALWKALSHLL | SEQ ID NO: 1506 |
| CFLGALWHALSKLL | SEQ ID NO: 1507 |
| CFLGALFHLLSHLL | SEQ ID NO: 1508 |

TABLE 2-continued

Suitable Peptide Sequences

| Peptide SEQUENCE | SEQ ID No. |
|---|---|
| CFLGALFHLLSELL | SEQ ID NO: 1509 |
| CFLGALWHLLSHLL | SEQ ID NO: 1510 |
| CFLGALWHLLSELL | SEQ ID NO: 1511 |
| CFLGALFHALSHLLE | SEQ ID NO: 1512 |
| CFLGALFHLLSHLLE | SEQ ID NO: 1513 |
| CGLFGALFHALSHLLE | SEQ ID NO: 1514 |
| CFLGALWKALSHLL | SEQ ID NO: 1515 |
| CGLFAEIEELLEEGLENLIDWWNG | SEQ ID NO: 1516 |
| CGLFGEIEELIEEGLE-Cit-LIDWWNG | SEQ ID NO: 1517 |
| CGLFGEIEELIEEGLENLIDWWNE | SEQ ID NO: 1518 |
| CFFGAIWEFIHSILK(stearyl) | SEQ ID NO: 1519 |
| CIFGAIAGFIKNIWEGLIK(stearyl) | SEQ ID NO: 1520 |
| CGIFEAIAGLLKNIFK(stearyl) | SEQ ID NO: 1521 |
| CGIFEAIAGLLKNIFKK(stearyl) | SEQ ID NO: 1522 |
| CFLGALFHALSHLL | SEQ ID NO: 1523 |
| Ac-CIFGAIAGFIKNILKGLIDG | SEQ ID NO: 1524 |
| CIFGAIAGFIKNILKGLK(stearylL) | SEQ ID NO: 1525 |
| Ac-CIFGAIAGFIKNILKGLK(stearyl) | SEQ ID NO: 1526 |
| CGLFGEIEELIEEGLENLIDWWNG | SEQ ID NO: 1527 |
| CFLGALWKALSELLKNLIDWWNG | SEQ ID NO: 1528 |
| CGFLGALWKALSELLKNLIDWWNG | SEQ ID NO: 1529 |
| CFLGALFHALSHLLENLIDWWNG | SEQ ID NO: 1530 |
| CGFLGALFHALSHLLENLIDWWNG | SEQ ID NO: 1531 |
| CGLFGELEGFIENGLKNLIDWWNG | SEQ ID NO: 1532 |
| CGLFGELEGLLWHGLKNLIDWWNG | SEQ ID NO: 1533 |
| CGLFGELAELLWHGLKNLIDWWNG | SEQ ID NO: 1534 |
| CGLFGELAELLWQGLKNLIDWWNG | SEQ ID NO: 1535 |
| CGLFGELWELLWHGLKNLIDWWNG | SEQ ID NO: 1536 |
| CGLFGELWELLWQGLKNLIDWWNG | SEQ ID NO: 1537 |
| CGLFEELAGLLWHGLKNLIDWWNG | SEQ ID NO: 1538 |
| CGLFEELWGLLWHGLKNLIDWWNG | SEQ ID NO: 1539 |
| CGLFEELAGLLWQGLKNLIDWWNG | SEQ ID NO: 1540 |
| CGLFEELWGLLWQGLKNLIDWWNG | SEQ ID NO: 1541 |
| CGLFGELAELLWHGLKNLIDWWNK | SEQ ID NO: 1542 |
| CGLFEELAELLWHGLKNLIDWWNK | SEQ ID NO: 1543 |
| CGLFGELAELLWHGLKNLIDWWNH | SEQ ID NO: 1544 |
| CGLFEELAELLWHGLKNLIDWWNH | SEQ ID NO: 1545 |
| CGLFAELWGLLWQGLKNLIDWWNG | SEQ ID NO: 1546 |

TABLE 2-continued

Suitable Peptide Sequences

| Peptide SEQUENCE | SEQ ID No. |
|---|---|
| CGLFAELWGLLWHGLKNLIDWWNG | SEQ ID NO: 1547 |
| CGLFAELWGLLWHGLHNLLDWWNG | SEQ ID NO: 1548 |
| CGLFAELAELLWEGLKNLIDWWNG | SEQ ID NO: 1549 |
| CGLFAELAELLWHGLKNLIDWWNG | SEQ ID NO: 1550 |
| CGLFAELELLWQGLKNLIDWWNG | SEQ ID NO: 1551 |
| CELFGELAGLLWHGLKNLIDWWNG | SEQ ID NO: 1552 |
| CLFEALWE-Aib-LEKLF | SEQ ID NO: 1553 |
| CFLEALWELLEHLL | SEQ ID NO: 1554 |
| CFLEALWKALEKLL | SEQ ID NO: 1555 |
| CGLF-Aib-EIAGLLEEGLHNLIDWWNG | SEQ ID NO: 1556 |
| CGLFGEI-Aib-GLLEEGLHNLIDWWNG | SEQ ID NO: 1557 |
| CGFFGEIAGLLEE-Aib-LHNLIDWWNG | SEQ ID NO: 1558 |
| CGLFGEIAGLLEEGLHNLIDWWN-Aib | SEQ ID NO: 1559 |
| CGLF-Aib-EIAGLLEE-Aib-LHNLIDWWNG | SEQ ID NO: 1560 |
| CGFFGEI-Aib-GLLEE-Aib-LHNLIDWWNG | SEQ ID NO: 1561 |
| CGFFGEI-Aib-ELIWEGLKNLIDWWNG | SEQ ID NO: 1562 |
| CGFFGEIAELIWELKNLIDWWN-Aib | SEQ ID NO: 1563 |
| CGFF Aib-EIAELIWE-Aib-LKNLIDWWNG | SEQ ID NO: 1564 |
| AC-CFLGALWKALSHLL | SEQ ID NO: 1565 |
| AC-CFLEELWELLEELLE | SEQ ID NO: 1566 |
| AC-CLFGALWKALSELL | SEQ ID NO: 1567 |
| AC-CGIGAVLKVLTTGLPALISWIKRKRQQ | SEQ ID NO: 1568 |
| AC-CGLFEAIEGFIENGWEGMIDGWYGYGRKKRRQRR | SEQ ID NO: 1569 |
| AC-CGLFEAIEGFIENGWEGMIDGWYGYGRKKRRQRRK(stearyl) | SEQ ID NO: 1570 |
| Ac-CFLGALWKALSHLL | SEQ ID NO: 1571 |
| Ac-CFLGALWKALSELL | SEQ ID NO: 1572 |
| CELFEEIAELLWEGLENLIDWWNG | SEQ ID NO: 1573 |
| CGLFGEIAELIWEGLENLIDWWNG | SEQ ID NO: 1574 |
| CGLFGEIEELLEEGLENLIDWWNG | SEQ ID NO: 1575 |
| CGLFAELAELLWEGLENLIDWWNG | SEQ ID NO: 1576 |
| CGLFAELAELLEEGLENLIDWWNG | SEQ ID NO: 1577 |
| CGLFAELAELLWEGLENLIDWWNS | SEQ ID NO: 1578 |
| CGLFAELAELLEEGLENLIDWWNS | SEQ ID NO: 1579 |
| CGLFAELAELLWEGLENLIDWWNQ | SEQ ID NO: 1580 |
| CGLFAELAELLEEGLENLIDWWNQ | SEQ ID NO: 1581 |
| CGLFAELAELLWEGLENLIDWWNE | SEQ ID NO: 1582 |
| CGLFAELAELLEEGLENLIDWWNE | SEQ ID NO: 1583 |
| CELFEELAELLWEGLENLIDWWNQ | SEQ ID NO: 1584 |

TABLE 2-continued

Suitable Peptide Sequences

| Peptide SEQUENCE | SEQ ID No. |
|---|---|
| CELFEELAELLWEGLENLIDWWNE | SEQ ID NO: 1585 |
| CELFEELAELLEEGLENLIDWWNG | SEQ ID NO: 1586 |
| CELFAELAELLWEGLENLIDWWNG | SEQ ID NO: 1587 |
| CELFAELAELLEEGLENLIDWWNG | SEQ ID NO: 1588 |
| CELFAELAELLWEGLENLIDWWNS | SEQ ID NO: 1589 |
| CELFAELAELLEEGLENLIDWWNS | SEQ ID NO: 1590 |
| CELFAELAELLWEGLENLIDWWNQ | SEQ ID NO: 1591 |
| CELFAELAELLEEGLENLIDWWNQ | SEQ ID NO: 1592 |
| CELFAELAELLWEGLENLIDWWNE | SEQ ID NO: 1593 |
| CELFAELAELLEEGLENLIDWWNE | SEQ ID NO: 1594 |
| CELFEELAELLWEGLHNLIDWWNG | SEQ ID NO: 1595 |
| CELFEELAELLWEGLHNLIDWWNS | SEQ ID NO: 1596 |
| CELFEELAELLWEGLHNLIDWWNQ | SEQ ID NO: 1597 |
| CELFEELAELLWEGLHNLIDWWNE | SEQ ID NO: 1598 |
| CELFGELEGFIENGLENLIDWWNG | SEQ ID NO: 1599 |
| CGLFEELEGFIENGLENLIDWWNG | SEQ ID NO: 1600 |
| CGLFAELAGFIENGLENLIDWWNG | SEQ ID NO: 1601 |
| CGLFAELEGFIENGLENLIDWWNG | SEQ ID NO: 1602 |
| CGLFGELAGFIENGLENLIDWWNG | SEQ ID NO: 1603 |
| CELFEELEGFIENGLENLIDWWNG | SEQ ID NO: 1604 |
| CELFAELAGFIENGLENLIDWWNG | SEQ ID NO: 1605 |
| CGLFGELEGFIWNGLENLIDWWNG | SEQ ID NO: 1606 |
| CGLFGELEGFIENGLENLIDWWNG | SEQ ID NO: 1607 |
| CGLFGELEGFIENGLENLIDWWNQ | SEQ ID NO: 1608 |
| CGLFGELEGFIENGLENLIDWWNE | SEQ ID NO: 1609 |
| CELFEELEGFIENGLENLIDWWNE | SEQ ID NO: 1610 |
| CGLLEEIAELLEEGLENLIDWWNS | SEQ ID NO: 1611 |
| CGLLEEIEELLWEGLENLIDWWNS | SEQ ID NO: 1612 |
| CELLEEIEELLEEGLENLIDWWNS | SEQ ID NO: 1613 |
| CGLLEEIAELLWEGLENLIDWWNS | SEQ ID NO: 1614 |
| CELLEEIAELLWEGLENLIDWWNS | SEQ ID NO: 1615 |
| CELLEEIEELLEEGLENLIDWWNE | SEQ ID NO: 1616 |
| CGLLEELEELLEEGLENLIDWWNS | SEQ ID NO: 1617 |
| CGLLEELEELLEEGLENLLEWWNS | SEQ ID NO: 1618 |
| CGLLEEIAELLEEGLENLIDWWNG | SEQ ID NO: 1619 |
| CGLLAEIAELLEEGLENLIDWWNS | SEQ ID NO: 1620 |
| CGLLAEIAELLWEGLENLIDWWNS | SEQ ID NO: 1621 |
| CGLLEEIEGFIENGLENLIDWWNS | SEQ ID NO: 1622 |

TABLE 2-continued

Suitable Peptide Sequences

| Peptide SEQUENCE | SEQ ID No. |
|---|---|
| CGLLEEIEGFIENGLENLIDWWNG | SEQ ID NO: 1623 |
| CGLLEEIEELLEEGLE-Cit-LIDWWNS | SEQ ID NO: 1624 |
| CGLLEEIEELLEQGLENLIDWWNS | SEQ ID NO: 1625 |
| CGLLAELAELLEEGLENLIDWWNS | SEQ ID NO: 1626 |
| CGLLEEIEELLEEGLENLIDWWNA | SEQ ID NO: 1627 |
| CGLL-Aib-EIEELLEEGLENLIDWWNS | SEQ ID NO: 1628 |
| CGLLEEIEELLEEGLENLIDWWN-Aib | SEQ ID NO: 1629 |
| CGLLEEIEELLEE-Aib-LENLIDWWNG | SEQ ID NO: 1630 |
| CGLFGHIHHLIHHGLHNLIDWWNG | SEQ ID NO: 1631 |
| CGLFGEIHHLIHHGLHNLIDWWNG | SEQ ID NO: 1632 |
| CGLFGEIHHLIHHGLENLIDWWNG | SEQ ID NO: 1633 |
| CGLFGEIHELIHHGLENLIDWWNG | SEQ ID NO: 1634 |
| CELLEEIEELLEEGLENLIDWWNS | SEQ ID NO: 1635 |
| CGLFGELEELIEEGLENLIDWWNG | SEQ ID NO: 1636 |
| CGLLAEIEELLWEGLENLIDWWNS | SEQ ID NO: 1637 |
| CGLLEEIEELLEEGLENLLEWWNS | SEQ ID NO: 1638 |
| C(b-ALA)LLEEIEELLEEGLENLIDWWNS | SEQ ID NO: 1639 |
| CGLLEEIEELLEEGLENLIDLWNS | SEQ ID NO: 1640 |
| CGLLEEIEELLEWGLENLIDWWNS | SEQ ID NO: 1641 |
| CGLFGEIEELIEEGLENLIDWGNG | SEQ ID NO: 1642 |
| CGFFGEIAELIEEGLKNLIDWGNG | SEQ ID NO: 1643 |
| CGLFGEIEELIEEGLENLIDWANG | SEQ ID NO: 1644 |
| CGLFGEIEELIEEGLENLIDWSNG | SEQ ID NO: 1645 |
| CGLFGEIEELIEEGLENLIDW-(Aib)-NG | SEQ ID NO: 1646 |
| CGLFGEIEELIEEGLENLIDWPNG | SEQ ID NO: 1647 |
| CGLFGEIEELIEEGLENLIDWHNG | SEQ ID NO: 1648 |
| CGLFGEIEELIEEGLENLIDWQNG | SEQ ID NO: 1649 |
| CGLFGEIEELIEEGLENLIDWENG | SEQ ID NO: 1650 |
| CGLFEEIAELIEEGLENLIDWGNG | SEQ ID NO: 1651 |
| CELFEELAELLWEGLENLIDWGNS | SEQ ID NO: 1652 |
| CGLFGEIAELIWEGLENLIDWGNG | SEQ ID NO: 1653 |
| CGLLEEIEELLEEGLENLIDWGNS | SEQ ID NO: 1654 |
| CGLFAEIEELLEEGLENLIDWGNG | SEQ ID NO: 1655 |
| CGLL-(Aib)-EIEELLEEGLENLIDWWNS | SEQ ID NO: 1656 |
| CGLFGEIEELIEEGLENLIDWNNG | SEQ ID NO: 1657 |
| CGLFGEIEELIEEGLENLIDWDNG | SEQ ID NO: 1658 |
| CGLFGEIEELIEEGLENLIDWONG | SEQ ID NO: 1659 |
| CGLFAEIEELLEEGLENLIDWGNG | SEQ ID NO: 1660 |

TABLE 2-continued

Suitable Peptide Sequences

| Peptide SEQUENCE | SEQ ID No. |
| --- | --- |
| CGLL-Aib-EIEELLEEGLENLIDWGNS | SEQ ID NO: 1661 |
| CGLFGEIEELIEEGLENLIDGWNG | SEQ ID NO: 1662 |
| CGLFGEIEELIEEGLENLIDLWNG | SEQ ID NO: 1663 |
| CGWFGEIEELIEEGLENLIDWWNG | SEQ ID NO: 1664 |
| CGLFGEVEELIEEGLENLIDWWNG | SEQ ID NO: 1665 |
| CGLFGEIEEVIEEGLENLIDWWNG | SEQ ID NO: 1666 |
| CGLFGEIEELVEEGLENLIDWWNG | SEQ ID NO: 1667 |
| CGLFGEIEELAEEGLENLIDWWNG | SEQ ID NO: 1668 |
| CGLFGEIEELIDEGLENLIDWWNG | SEQ ID NO: 1669 |
| CGLFGEIEELIEDGLENLIDWWNG | SEQ ID NO: 1670 |
| CGLFGEIEELIEEGLEALIDWWNG | SEQ ID NO: 1671 |
| CGLFGEIEELIEEGLENIIDWWNG | SEQ ID NO: 1672 |
| CGLFGEIEELIEEGLEN-(Nle)-IDWWNG | SEQ ID NO: 1673 |
| CGLFGEIEELIEEGLENLIGWWNG | SEQ ID NO: 1674 |
| CGLFELIEGFIENGWEGMIDGWYGYGRKKRRQRR all (D) | SEQ ID NO: 1675 |
| CGLFEAIEGFIENGWEGMIDGWYG all (D) | SEQ ID NO: 1676 |
| CGLFGEIEELIENGLKNLIDWWYGYGRKKRRQRR all (D) | SEQ ID NO: 1677 |
| CGLFEALLELLESLWELLLEAYGRKKRRQRR all (D) | SEQ ID NO: 1678 |
| CGLFEEIEGFIENGWEGLIDWWYGYGHKKHHQHR all (D) | SEQ ID NO: 1679 |
| CGLFGEIEELIEEGLENLIDWWNE all (D) | SEQ ID NO: 1680 |
| CGLFGEIEELIEEGLENLIDWWNS all (D) | SEQ ID NO: 1681 |
| CGLFGEIEELIEEGLENLIDWWNQ all (D) | SEQ ID NO: 1682 |
| CYGRKKRRQRRLIRLWSHLIHIWFQNRRLKWKKK | SEQ ID NO: 1683 |
| CGLFEAIEEFIENGWEGMIDGWYGYGRKKRRQRR | SEQ ID NO: 1684 |
| CGLFFAIEGFIENGWEGMIDWWYGYGRKKRRQRR ALL (D) | SEQ ID NO: 1685 |
| CGLFELIEGFIENGWEGMIDGWYGYGRKKRRQRRK(STEARYL) ALL (D) | SEQ ID NO: 1686 |
| (STEARYL)GLFELIEGFIENGWEGMIDGWYGYGRKKRRQRRC ALL (D) | SEQ ID NO: 1687 |
| CFFGAIWEFIKSILK(STEARYL) +C-TERM K(STEARYL) ALL(D) | SEQ ID NO: 1688 |
| CFFGAIWEFIKSILK(STEARYL) +C-TERM K(STEARYL) ALL(D) | SEQ ID NO: 1689 |
| LAURYL-FFGAIWEFIKSILC ALL (D) | SEQ ID NO: 1690 |
| CFFGAIWEFIHSILK(STEARYL) ALL (D) | SEQ ID NO: 1691 |
| CGFFGEIAELIEEGLKNLIDWWNG ALL (D) | SEQ ID NO: 1692 |
| CGIFEAIAGLLKNIFKGIFEAIAGLLKNIFK ALL (D) | SEQ ID NO: 1693 |
| CIFGAIAGFIKNILKGLIDG ALL (D) | SEQ ID NO: 1694 |
| CGLFEAIEGFIENGWEGMIDGWYGYGRKKRRQRRK(stearyl) all(D) | SEQ ID NO: 1695 |
| (LAURYL)FFGAIWEFIKSILC all (D) | SEQ ID NO: 1696 |
| CGLFGEIEELIEEGLENLIDWDNG | SEQ ID NO: 1696 |
| glfgeieeliecglenlidwgng | SEQ ID NO: 1697 |

TABLE 2-continued

Suitable Peptide Sequences

| Peptide SEQUENCE | SEQ ID No. |
|---|---|
| glfgeieelieeclenlidwgng | SEQ ID NO: 1698 |
| cglfgeeleelleeglenlidg | SEQ ID NO: 1699 |
| cglfgeeleelleeglenlieg | SEQ ID NO: 1700 |
| CGLFGEIEELIEEGLENLIDW-Aib-NG | SEQ ID NO: 1701 |
| AC-GLLEEIEELLEEGLENLIDWWNSC | SEQ ID NO: 1702 |
| GLLEEIEELLEEGLENLAELAEALEALAAGGSC | SEQ ID NO: 1703 |
| CGLFGEIEELIEEGLENLIDW | SEQ ID NO: 1704 |
| CGLFGEIEELIEEGLENLID | SEQ ID NO: 1705 |
| CGLFGEIEELIEEGLENLI | SEQ ID NO: 1706 |
| CELFEEIAELIEEGLENLIDWG | SEQ ID NO: 1707 |
| AC-GLFGEIEELIEEGLENLIDWGNGC | SEQ ID NO: 1708 |
| AC-CGLFGEIEELIEEGLENLIDWGNG | SEQ ID NO: 1709 |
| AC-CGLFGEIEELIEEGLENLIDWWNG | SEQ ID NO: 1710 |
| CGFFGEI-AIB-GLLEE-AIB-LHNLIDWWNG | SEQ ID NO: 1711 |
| CFLGALWKALSELLKNLIDWWNG | SEQ ID NO: 1712 |
| CGL-R6H-GELEEL-S7H-EEGLENLIDWWNG (STAPLED) | SEQ ID NO: 1713 |
| CGL-R6H-GELEEL-S7H-EEGLENLIDWWNG (STAPLED) | SEQ ID NO: 1714 |
| CGFFGEI-AIB-ELIWE-AIB-LKNLIDWWNG | SEQ ID NO: 1715 |
| CGLFEELAGLLWHGLKNLIDWWNG | SEQ ID NO: 1716 |
| CFLGALFHALSHLLENLIDWWNG | SEQ ID NO: 1717 |
| CGFF-AIB-EIAELIWE-AIB-LKNLIDWWNG | SEQ ID NO: 1718 |
| CGLFAEIEELIWEGLENLIDWWNQ | SEQ ID NO: 1719 |
| STEARYL-AGYLLGKLL-ORN-ORN-LAAAAL-ORN-ORN-LLC | SEQ ID NO: 1720 |
| R-AHX-R-AHX-RILFQYR-AHX-B_ALA-R-AHX-R-B_ALA-C | SEQ ID NO: 1721 |
| R-AHX-RR-BALA-R-AHX-EIFFQYR-AHX-R-BALA-R-AHX-R-B_ALA-C | SEQ ID NO: 1722 |
| R-AHX-RR-BALA-RR-AHX-RILFQYR-AHX-R-B_ALA-R-AHX-R-B_ALA-C | SEQ ID NO: 1723 |
| R-AHX-R-AHX-RR-AHX-RR-AHX-RIHILFQNRRMKWHK-B_ALA-C | SEQ ID NO: 1724 |
| CSSAWWSYWPPVA | SEQ ID NO: 1725 |
| CGLFAVIKKVASVIGGL | SEQ ID NO: 1726 |
| CGLFAVIHHVASVIGGL | SEQ ID NO: 1727 |
| CGLFAVIEEVASVIGGL | SEQ ID NO: 1728 |
| CGPSQPTYPGDDAPVRDLIRFYRDLRRYLNVVTRHRY | SEQ ID NO: 1729 |
| CGIGAVLHVLTTGLPALISWIKRKRQQ | SEQ ID NO: 1730 |
| CGIGAVLHVLTTGLPALISWIHHHHQQ | SEQ ID NO: 1731 |
| AC-GIFEAIAGLLKINFKC | SEQ ID NO: 1732 |
| AC-GLFGALAEALAEALAEHLAEALAEALEALAAGGSC | SEQ ID NO: 1733 |
| AC-GLFEAIEGFIENGWEGLAELAEALEALAAGGSC | SEQ ID NO: 1734 |

TABLE 2-continued

Suitable Peptide Sequences

| Peptide SEQUENCE | SEQ ID No. |
|---|---|
| AC-GIFEAIAGLLKINFKC | SEQ ID NO: 1735 |
| AC-GLFGALAEALAEALAEHLAEALAEALEALAAGGSC | SEQ ID NO: 1736 |
| AC-GLFGALAEALAEALAEHLAEALAEALEALAAGGSC | SEQ ID NO: 1737 |
| GLFGEIEELIEEGLENLIDWGNGLAELAEALEALAAGGSC | SEQ ID NO: 1738 |
| GLFGEIEELIEEGLENLIDWGNGLAELAEALEALAAGGSC | SEQ ID NO: 1739 |
| GLFEAIEGFIENGWEGLAELAEALEALAAGGSC | SEQ ID NO: 1740 |
| GLFGALAEALAEALAEHLAEALAEALEALAAGGSC | SEQ ID NO: 1741 |
| GLFEAIEGFIENGWEGLAELAEALEALAAGGSC | SEQ ID NO: 1742 |
| GLFEAIEGFIENGWEGLAELAEALEALAAGGSC | SEQ ID NO: 1743 |
| CEENWIGLFGGGNIWEEEEILDLL | SEQ ID NO: 1744 |
| CGLFGEIEELIEEGLENLIDWGNG | SEQ ID NO: 1745 |
| CEALFGKINAIFIGKL | SEQ ID NO: 1746 |
| CGLFGEIEELIEELEEGLENLIDWGNG | SEQ ID NO: 1747 |
| CGLFGEIEELIEEALENLIDWGNG | SEQ ID NO: 1748 |
| CGLFGEIEELIEEGFENLIDWGNG | SEQ ID NO: 1749 |
| CGLFGEIEELIEEGFENLIDWGNG | SEQ ID NO: 1750 |
| CGLFGEIEELIEEGWENLIDWGNG | SEQ ID NO: 1751 |
| CGLFGEIEEWIEEGLENLIDWGNG | SEQ ID NO: 1752 |
| CGLFGEIEEFIEEGLENLIDWGNG | SEQ ID NO: 1753 |
| CGLFGEIEEFIEEGLENLIDWGNG | SEQ ID NO: 1754 |
| CGLFGEIEELFEEGLENLIDWGNG | SEQ ID NO: 1755 |
| CGLFGEIEELIEEGLENLIDWGNE | SEQ ID NO: 1756 |
| CGLFGEIEELIEEGLENLIDWGNE | SEQ ID NO: 1757 |
| CGLFGEIEELIEEGLEELIDWGNG | SEQ ID NO: 1758 |
| CGLFGEIEELIEEGLESLIDWGNG | SEQ ID NO: 1759 |
| CGLFGEIEELIEEGLEQLIDWGNG | SEQ ID NO: 1760 |
| CGLFGEIEELIEEGLENWIDWGNG | SEQ ID NO: 1761 |
| CGLFGEIEELIEEGLENFIDWGNG | SEQ ID NO: 1762 |
| CGLFGEIEELIEEGLENLWDWGNG | SEQ ID NO: 1763 |
| CGLFGEIEELIEEGLENLVDWGNG | SEQ ID NO: 1764 |
| CGLFGEIEELIEEGLENLIEWGNG | SEQ ID NO: 1765 |
| CGLFGEIEELIEEGLENLIDFGNG | SEQ ID NO: 1766 |
| CGLFGEIEELIEEGLENLIDLGNG | SEQ ID NO: 1767 |
| CGLFGEIEELIEEGLENLIDWGYG | SEQ ID NO: 1768 |
| CGLFGEIEELIEEGLENLIDWGSG | SEQ ID NO: 1769 |
| CGLFGEIEELIEEGLENLIDWGNQ | SEQ ID NO: 1770 |
| CGLFGEIEELIEEGLENLIDWGN-AIB | SEQ ID NO: 1771 |
| CGLFEALLELLESLWELLLEAGYG | SEQ ID NO: 1772 |

TABLE 2-continued

Suitable Peptide Sequences

| Peptide SEQUENCE | SEQ ID No. |
|---|---|
| CGLFGEIEELIEEGLENLIDWGNS | SEQ ID NO: 1746 |
| CGLFEAIEGFIENGWEGMIDWGNG | SEQ ID NO: 1773 |
| CIFGIDDLEEGLLFVAIVEAGIGGYLLGS | SEQ ID NO: 1774 |
| CGLFEALLELLESLWELLLEA | SEQ ID NO: 1775 |
| CGLFGEIEELIEEGLENLIDWGNGC | SEQ ID NO: 1776 |
| CGNFGEIEELIEEGLENLIDWGNG | SEQ ID NO: 1777 |
| CGLFAEIEELIEEGLENLIDWGNG | SEQ ID NO: 1778 |
| CGLFEEIEELIEEGLENLIDWGNG | SEQ ID NO: 1779 |
| CGLFGEIAELIEEGLENLIDWGNG | SEQ ID NO: 1780 |
| CELFGEIEELIEEGLENLIDWGNG | SEQ ID NO: 1781 |
| CALFGEIEELIEEGLENLIDWGNG | SEQ ID NO: 1782 |
| C-AIB-LFGEIEELIEEGLENLIDWGNG | SEQ ID NO: 1783 |
| CGWFGEIEELIEEGLENLIDWGNG | SEQ ID NO: 1784 |
| CGLFGELEELIEEGLENLIDWGNG | SEQ ID NO: 1785 |
| CGLFGEIEELWEEGLENLIDWGNG | SEQ ID NO: 1786 |
| CGLFGEIEELWEEGLENLIDWGNG | SEQ ID NO: 1787 |
| CGLFGEIEELIEE-AIB-LENLIDWGNG | SEQ ID NO: 1788 |
| CGLFGEIEELIEE-AIB-LENLIDWGNG | SEQ ID NO: 1789 |
| CGLFGEIEELIEE-AIB-LENLIDWGNG | SEQ ID NO: 1790 |
| CGLFGEIEELIEE-AIB-LENLIDWGNG | SEQ ID NO: 1791 |
| CGLFGEIEELIEE-AIB-LENLIDWGNG | SEQ ID NO: 1792 |
| CGLLGEIEELIEEGLENLIDWGNG | SEQ ID NO: 1793 |
| CGLFGAIEELIEEGLENLIDWGNG | SEQ ID NO: 1794 |
| CGFFGEIEELIEEGLENLIDWGNG | SEQ ID NO: 1795 |
| CGLWGEIEELIEEGLENLIDWGNG | SEQ ID NO: 1796 |
| CGLFGEWEELIEEGLENLIDWGNG | SEQ ID NO: 1797 |
| CGLFGEFEELIEEGLENLIDWGNG | SEQ ID NO: 1798 |
| CGLFGEIEELIEEGLENLLDWGNG | SEQ ID NO: 1799 |
| CGLFGEIEELIEEGLENLIDWGQG | SEQ ID NO: 1800 |
| GLFGEIEELIEEGLENLIDWGNG | SEQ ID NO: 1801 |
| GFFGAIWEFIHSIL | SEQ ID NO: 1802 |

A subset of the peptides disclosed in Table 2 that can be used in the conjugates herein are listed in Table 2a.

TABLE 2a

Suitable Peptide Sequences and ID

| Peptide Sequence | SEQ ID NO: |
|---|---|
| CIFGAIAGFIKNIWEGLI | SEQ ID NO: 26 |
| CFFGAIWEFIHSIL | SEQ ID NO: 74 |

TABLE 2a-continued

Suitable Peptide Sequences and ID

| Peptide Sequence | SEQ ID NO: |
|---|---|
| CGIFEAIAGLLKNIFK | SEQ ID NO: 82 |
| CGIGAVLKVLTTGLPALISWIKRKRQQ | SEQ ID NO: 255 |
| CGFFGEIAELIEEGLKNLIDWWNG | SEQ ID NO: 543 |
| CGFFGEIAELIWEGLKNLIDWWNG | SEQ ID NO: 935 |
| CGLFGEIEELIEEGLENLIDWANG | SEQ ID NO: 1078 |
| CFLEELWELLEHLL | SEQ ID NO: 1248 |
| AC-CFLEELWELLEHLL | SEQ ID NO: 1391 |
| CGLLEEIEELLEEGLENLIDWWNS | SEQ ID NO: 1403 |
| CFLEELWGLLEHLL | SEQ ID NO: 1419 |
| CLELWLEHLFLELE | SEQ ID NO: 1489 |
| CGLFAEIEELLEEGLENLIDWWNG | SEQ ID NO: 1516 |
| CGLFGEIEELIEEGLE-CIT-LIDWWNG | SEQ ID NO: 1517 |
| CGLFGEIEELIEEGLENLIDWWNE | SEQ ID NO: 1518 |
| CGLL-AIB-EIEELLEEGLENLIDWWNS | SEQ ID NO: 1628 |
| CGLFGHIHHLIHHGLHNLIDWWNG | SEQ ID NO: 1631 |
| CGLFGEIHHLIHHGLHNLIDWWNG | SEQ ID NO: 1632 |
| CGLFGEIHHLIHHGLENLIDWWNG | SEQ ID NO: 1633 |
| CGLFGEIHELIHHGLENLIDWWNG | SEQ ID NO: 1634 |
| CGFFGEIAELIEEGLKNLIDWGNG | SEQ ID NO: 1643 |
| CGLFGEIEELIEEGLENLIDWSNG | SEQ ID NO: 1645 |
| CGLFGEIEELIEEGLENLIDWPNG | SEQ ID NO: 1647 |
| CGLFGEIEELIEEGLENLIDWHNG | SEQ ID NO: 1648 |
| CGLFGEIEELIEEGLENLIDWQNG | SEQ ID NO: 1649 |
| CGLFGEIEELIEEGLENLIDWENG | SEQ ID NO: 1650 |
| CGLFEEIAELIEEGLENLIDWGNG | SEQ ID NO: 1651 |
| CELFEELAELLWEGLENLIDWGNS | SEQ ID NO: 1652 |
| CGLFGEIAELIWEGLENLIDWGNG | SEQ ID NO: 1653 |
| CGLLEEIEELLEEGLENLIDWGNS | SEQ ID NO: 1654 |
| CGLFGEIEELIEEGLENLIDWNNG | SEQ ID NO: 1657 |
| CGLFAEIEELLEEGLENLIDWGNG | SEQ ID NO: 1660 |
| CGLFGEIEELIEEGLENLIDWONG | SEQ ID NO: 1662 |
| CGLFGEIEELIEEGLENLIDWDNG | SEQ ID NO: 1696 |
| GLFGEIEELIECGLENLIDWGNG | SEQ ID NO: 1697 |
| CGLFGEIEELIEEGLENLIDW-AIB-NG | SEQ ID NO: 1701 |
| AC-GLLEEIEELLEEGLENLIDWWNSC | SEQ ID NO: 1702 |
| GLLEEIEELLEEGLENLAELAEALEALAAGGSC | SEQ ID NO: 1703 |
| CGLFGEIEELIEEGLENLIDW | SEQ ID NO: 1704 |
| CGLFGEIEELIEEGLENLID | SEQ ID NO: 1705 |

TABLE 2a-continued

Suitable Peptide Sequences and ID

| Peptide Sequence | SEQ ID NO: |
| --- | --- |
| CGLFGEIEELIEEGLENLI | SEQ ID NO: 1706 |
| CELFEEIAELIEEGLENLIDWG | SEQ ID NO: 1707 |
| AC-GLFGEIEELIEEGLENLIDWGNGC | SEQ ID NO: 1708 |
| AC-CGLFGEIEELIEEGLENLIDWGNG | SEQ ID NO: 1709 |
| AC-CGLFGEIEELIEEGLENLIDWWNG | SEQ ID NO: 1710 |
| CGFFGEI-AIB-GLLEE-AIB-LHNLIDWWNG | SEQ ID NO: 1711 |
| CFLGALWKALSELLKNLIDWWNG | SEQ ID NO: 1712 |
| CGL-R6H-GELEEL-S7H-EEGLENLIDWWNG (STAPLED) | SEQ ID NO: 1713 |
| CGFFGEI-AIB-ELIWE-AIB-LKNLIDWWNG | SEQ ID NO: 1715 |
| CGLFEELAGLLWHGLKNLIDWWNG | SEQ ID NO: 1716 |
| CFLGALFHALSHLLENLIDWWNG | SEQ ID NO: 1717 |
| CGFF-AIB-EIAELIWE-AIB-LKNLIDWWNG | SEQ ID NO: 1718 |
| CGLFAEIEELIWEGLENLIDWWNQ | SEQ ID NO: 1719 |
| STEARYL-AGYLLGKLL-ORN-ORN-LAAAAL-ORN-ORN-LLC | SEQ ID NO: 1720 |
| R-AHX-R-AHX-RILFQYR-AHX-B_ALA-R-AHX-R-B_ALA-C | SEQ ID NO: 1721 |
| R-AHX-RR-B_ALA-R-AHX-EIFFQYR-AHX-R-B_ALA-R-AHX-R-B_ALA-C | SEQ ID NO: 1722 |
| R-AHX-RR-B_ALA-RR-AHX-RILFQYR-AHX-R-B_ALA-R-AHX-R-B_ALA-C | SEQ ID NO: 1723 |
| R-AHX-RR-AHX-RR-AHX-RIHILFQNRRMKWHK-B_ALA-C | SEQ ID NO: 1724 |
| CSSAWWSYWPPVA | SEQ ID NO: 1725 |
| CGLFAVIKKVASVIGGL | SEQ ID NO: 1726 |
| CGLFAVIHHVASVIGGL | SEQ ID NO: 1727 |
| CGLFAVIEEVASVIGGL | SEQ ID NO: 1728 |
| CGPSQPTYPGDDAPVRDLIRFYRDLRRYLNVVTRHRY | SEQ ID NO: 1729 |
| CGIGAVLHVLTTGLPALISWIKRKRQQ | SEQ ID NO: 1730 |
| CGIGAVLHVLTTGLPALISWIHHHHQQ | SEQ ID NO: 1731 |
| AC-GIFEAIAGLLKINFKC | SEQ ID NO: 1732 |
| AC-GLFGALAEALAEALAEHLAEALAEALEALAAGGSC | SEQ ID NO: 1733 |
| AC-GLFEAIEGFIENGWEGLAELAEALEALAAGGSC | SEQ ID NO: 1734 |
| GLFGEIEELIEEGLENLIDWGNGLAELAEALEALAAGGSC | SEQ ID NO: 1738 |
| GLFEAIEGFIENGWEGLAELAEALEALAAGGSC | SEQ ID NO: 1740 |
| GLFGALAEALAEALAEHLAEALAEALEALAAGGSC | SEQ ID NO: 1741 |
| CEENWIGLFGGGNIWEEEEILDLL | SEQ ID NO: 1744 |
| CGLFGEIEELIEEGLENLIDWGNG | SEQ ID NO: 1745 |
| CEALFGKINAIFIGKL | SEQ ID NO: 1746 |
| CGLFGEIEELEEGLENLIDWGNG | SEQ ID NO: 1747 |
| CGLFGEIEELIEEALENLIDWGNG | SEQ ID NO: 1748 |
| CGLFGEIEELIEEGFENLIDWGNG | SEQ ID NO: 1749 |

TABLE 2a-continued

Suitable Peptide Sequences and ID

| Peptide Sequence | SEQ ID NO: |
|---|---|
| CGLFGEIEELIEEGWENLIDWGNG | SEQ ID NO: 1751 |
| CGLFGEIEEWIEEGLENLIDWGNG | SEQ ID NO: 1752 |
| CGLFGEIEEFIEEGLENLIDWGNG | SEQ ID NO: 1753 |
| CGLFGEIEELFEEGLENLIDWGNG | SEQ ID NO: 1755 |
| CGLFGEIEELIEEGLENLIDWGNE | SEQ ID NO: 1756 |
| CGLFGEIEELIEEGLEELIDWGNG | SEQ ID NO: 1758 |
| CGLFGEIEELIEEGLESLIDWGNG | SEQ ID NO: 1759 |
| CGLFGEIEELIEEGLEQLIDWGNG | SEQ ID NO: 1760 |
| CGLFGEIEELIEEGLENWIDWGNG | SEQ ID NO: 1761 |
| CGLFGEIEELIEEGLENFIDWGNG | SEQ ID NO: 1762 |
| CGLFGEIEELIEEGLENLWDWGNG | SEQ ID NO: 1763 |
| CGLFGEIEELIEEGLENLVDWGNG | SEQ ID NO: 1764 |
| CGLFGEIEELIEEGLENLIEWGNG | SEQ ID NO: 1765 |
| CGLFGEIEELIEEGLENLIDFGNG | SEQ ID NO: 1766 |
| CGLFGEIEELIEEGLENLIDLGNG | SEQ ID NO: 1767 |
| CGLFGEIEELIEEGLENLIDWGYG | SEQ ID NO: 1768 |
| CGLFGEIEELIEEGLENLIDWGSG | SEQ ID NO: 1769 |
| CGLFGEIEELIEEGLENLIDWGNQ | SEQ ID NO: 1770 |
| CGLFGEIEELIEEGLENLIDWGN-AIB | SEQ ID NO: 1771 |
| CGLFEALLELLESLWELLLEAGYG | SEQ ID NO: 1772 |
| CGLFEAIEGFIENGWEGMIDWGNG | SEQ ID NO: 1773 |
| CIFGIDDLEEGLLFVAIVEAGIGGYLLGS | SEQ ID NO: 1774 |
| CGLFEALLELLESLWELLLEA | SEQ ID NO: 1775 |
| CGLFGEIEELIEEGLENLIDWGNGC | SEQ ID NO: 1776 |
| CGNFGEIEELIEEGLENLIDWGNG | SEQ ID NO: 1777 |
| CGLFAEIEELIEEGLENLIDWGNG | SEQ ID NO: 1778 |
| CGLFEEIEELIEEGLENLIDWGNG | SEQ ID NO: 1779 |
| CGLFGEIAELIEEGLENLIDWGNG | SEQ ID NO: 1780 |
| CELFGEIEELIEEGLENLIDWGNG | SEQ ID NO: 1781 |
| CALFGEIEELIEEGLENLIDWGNG | SEQ ID NO: 1782 |
| C-AIB-LFGEIEELIEEGLENLIDWGNG | SEQ ID NO: 1783 |
| CGWFGEIEELIEEGLENLIDWGNG | SEQ ID NO: 1784 |
| CGLFGELEELIEEGLENLIDWGNG | SEQ ID NO: 1785 |
| CGLFGEIEELWEEGLENLIDWGNG | SEQ ID NO: 1786 |
| CGLFGEIEELIEE-AIB-LENLIDWGNG | SEQ ID NO: 1788 |
| CGLLGEIEELIEEGLENLIDWGNG | SEQ ID NO: 1793 |
| CGLFGAIEELIEEGLENLIDWGNG | SEQ ID NO: 1794 |
| CGFFGEIEELIEEGLENLIDWGNG | SEQ ID NO: 1795 |

TABLE 2a-continued

Suitable Peptide Sequences and ID

| Peptide Sequence | SEQ ID NO: |
|---|---|
| CGLWGEIEELIEEGLENLIDWGNG | SEQ ID NO: 1796 |
| CGLFGEWEELIEEGLENLIDWGNG | SEQ ID NO: 1797 |
| CGLFGEFEELIEEGLENLIDWGNG | SEQ ID NO: 1798 |
| CGLFGEIEELIEEGLENLLDWGNG | SEQ ID NO: 1799 |
| CGLFGEIEELIEEGLENLIDWGQG | SEQ ID NO: 1800 |
| GLFGEIEELIEEGLENLIDWGNG | SEQ ID NO: 1801 |
| GFFGAIWEFIHSIL | SEQ ID NO: 1802 |

A subset of the peptides disclosed in table 2 that can be used in the conjugates herein are listed in Table 2b.

TABLE 2b

Suitable Peptide Sequences and ID

| Peptide Sequence | SEQ ID NO: |
|---|---|
| GLFGEIEELIECGLENLIDWGNG | SEQ ID NO: 1697 |
| CGLFGEIEELIEEGLENLIDW-AIB-NG | SEQ ID NO: 1701 |
| AC-GLLEEIEELLEEGLENLIDWWNSC | SEQ ID NO: 1702 |
| GLLEEIEELLEEGLENLAELAEALEALAAGGSC | SEQ ID NO: 1703 |
| CGLFGEIEELIEEGLENLIDW | SEQ ID NO: 1704 |
| CGLFGEIEELIEEGLENLID | SEQ ID NO: 1705 |
| CGLFGEIEELIEEGLENLI | SEQ ID NO: 1706 |
| CELFEEIAELIEEGLENLIDWG | SEQ ID NO: 1707 |
| AC-GLFGEIEELIEEGLENLIDWGNGC | SEQ ID NO: 1708 |
| AC-CGLFGEIEELIEEGLENLIDWGNG | SEQ ID NO: 1709 |
| AC-CGLFGEIEELIEEGLENLIDWWNG | SEQ ID NO: 1710 |
| CGFFGEI-AIB-GLLEE-AIB-LHNLIDWWNG | SEQ ID NO: 1711 |
| CFLGALWKALSELLKNLIDWWNG | SEQ ID NO: 1712 |
| CGL-R6H-GELEEL-S7H-EEGLENLIDWWNG (STAPLED) | SEQ ID NO: 1713 |
| CGFFGEI-AIB-ELIWE-AIB-LKNLIDWWNG | SEQ ID NO: 1715 |
| CGLFEELAGLLWHGLKNLIDWWNG | SEQ ID NO: 1716 |
| CFLGALFHALSHLLENLIDWWNG | SEQ ID NO: 1717 |
| CGFF-AIB-EIAELIWE-AIB-LKNLIDWWNG | SEQ ID NO: 1718 |
| CGLFAEIEELIWEGLENLIDWWNQ | SEQ ID NO: 1719 |
| STEARYL-AGYLLGKLL-ORN-ORN-LAAAAL-ORN-ORN-LLC | SEQ ID NO: 1720 |
| R-AHX-R-AHX-RILFQYR-AHX-B_ALA-R-AHX-R-B_ALA-C | SEQ ID NO: 1721 |
| R-AHX-RR-B_ALA-R-AHX-EIFFQYR-AHX-R-B_ALA-R-AHX-R-B_ALA-C | SEQ ID NO: 1722 |

TABLE 2b-continued

Suitable Peptide Sequences and ID

| Peptide Sequence | SEQ ID NO: |
|---|---|
| R-AHX-RR-B_ALA-RR-AHX-RILFQYR-AHX-R-B_ALA-R-AHX-R-B_ALA-C | SEQ ID NO: 1723 |
| R-AHX-RR-AHX-RR-AHX-RIHILFQNRRMKWHK-B_ALA-C | SEQ ID NO: 1724 |
| CSSAWWSYWPPVA | SEQ ID NO: 1725 |
| CGLFAVIKKVASVIGGL | SEQ ID NO: 1726 |
| CGLFAVIHHVASVIGGL | SEQ ID NO: 1727 |
| CGLFAVIEEVASVIGGL | SEQ ID NO: 1728 |
| CGPSQPTYPGDDAPVRDLIRFYRDLRRYLNVVTRHRY | SEQ ID NO: 1729 |
| CGIGAVLHVLTTGLPALISWIKRKRQQ | SEQ ID NO: 1730 |
| CGIGAVLHVLTTGLPALISWIHHHHQQ | SEQ ID NO: 1731 |
| AC-GIFEAIAGLLKINFKC | SEQ ID NO: 1732 |
| AC-GLFGALAEALAEALAEHLAEALAEALEALAAGGSC | SEQ ID NO: 1733 |
| AC-GLFEAIEGFIENGWEGLAELAEALEALAAGGSC | SEQ ID NO: 1734 |
| GLFGEIEELIEEGLENLIDWGNGLAELAEALEALAAGGSC | SEQ ID NO: 1738 |
| GLFEAIEGFIENGWEGLAELAEALEALAAGGSC | SEQ ID NO: 1740 |
| GLFGALAEALAEALAEHLAEALAEALEALAAGGSC | SEQ ID NO: 1741 |
| CEENWIGLFGGGNIWEEEEILDLL | SEQ ID NO: 1744 |
| CGLFGEIEELIEEGLENLIDWGNG | SEQ ID NO: 1745 |
| CEALFGKINAIFIGKL | SEQ ID NO: 1746 |
| CGLFGEIEELLEEGLENLIDWGNG | SEQ ID NO: 1747 |
| CGLFGEIEELIEEALENLIDWGNG | SEQ ID NO: 1748 |
| CGLFGEIEELIEEGFENLIDWGNG | SEQ ID NO: 1749 |
| CGLFGEIEELIEEGWENLIDWGNG | SEQ ID NO: 1751 |
| CGLFGEIEEWIEEGLENLIDWGNG | SEQ ID NO: 1752 |
| CGLFGEIEEFIEEGLENLIDWGNG | SEQ ID NO: 1753 |
| CGLFGEIEELFEEGLENLIDWGNG | SEQ ID NO: 1755 |
| CGLFGEIEELIEEGLENLIDWGNE | SEQ ID NO: 1756 |
| CGLFGEIEELIEEGLELIDWGNG | SEQ ID NO: 1758 |
| CGLFGEIEELIEEGLESLIDWGNG | SEQ ID NO: 1759 |
| CGLFGEIEELIEEGLEQLIDWGNG | SEQ ID NO: 1760 |
| CGLFGEIEELIEEGLENWIDWGNG | SEQ ID NO: 1761 |
| CGLFGEIEELIEEGLENFIDWGNG | SEQ ID NO: 1762 |
| CGLFGEIEELIEEGLENLWDWGNG | SEQ ID NO: 1763 |
| CGLFGEIEELIEEGLENLVDWGNG | SEQ ID NO: 1764 |
| CGLFGEIEELIEEGLENLIEWGNG | SEQ ID NO: 1765 |
| CGLFGEIEELIEEGLENLIDFGNG | SEQ ID NO: 1766 |
| CGLFGEIEELIEEGLENLIDLGNG | SEQ ID NO: 1767 |

TABLE 2b-continued

Suitable Peptide Sequences and ID

| Peptide Sequence | SEQ ID NO: |
| --- | --- |
| CGLFGEIEELIEEGLENLIDWGYG | SEQ ID NO: 1768 |
| CGLFGEIEELIEEGLENLIDWGSG | SEQ ID NO: 1769 |
| CGLFGEIEELIEEGLENLIDWGNQ | SEQ ID NO: 1770 |
| CGLFGEIEELIEEGLENLIDWGN-AIB | SEQ ID NO: 1771 |
| CGLFEALLELLESLWELLLEAGYG | SEQ ID NO: 1772 |
| CGLFEAIEGFIENGWEGMIDWGNG | SEQ ID NO: 1773 |
| CIFGIDDLEEGLLFVAIVEAGIGGYLLGS | SEQ ID NO: 1774 |
| CGLFEALLELLESLWELLLEA | SEQ ID NO: 1775 |
| CGLFGEIEELIEEGLENLIDWGNGC | SEQ ID NO: 1776 |
| CGNFGEIEELIEEGLENLIDWGNG | SEQ ID NO: 1777 |
| CGLFAEIEELIEEGLENLIDWGNG | SEQ ID NO: 1778 |
| CGLFEEIEELIEEGLENLIDWGNG | SEQ ID NO: 1779 |
| CGLFGEIAELIEEGLENLIDWGNG | SEQ ID NO: 1780 |
| CELFGEIEELIEEGLENLIDWGNG | SEQ ID NO: 1781 |
| CALFGEIEELIEEGLENLIDWGNG | SEQ ID NO: 1782 |
| C-AIB-LFGEIEELIEEGLENLIDWGNG | SEQ ID NO: 1783 |
| CGWFGEIEELIEEGLENLIDWGNG | SEQ ID NO: 1784 |
| CGLFGELEELIEEGLENLIDWGNG | SEQ ID NO: 1785 |
| CGLFGEIEELWEEGLENLIDWGNG | SEQ ID NO: 1786 |
| CGLFGEIEELIEE-AIB-LENLIDWGNG | SEQ ID NO: 1788 |
| CGLLGEIEELIEEGLENLIDWGNG | SEQ ID NO: 1793 |
| CGLFGAIEELIEEGLENLIDWGNG | SEQ ID NO: 1794 |
| CGFFGEIEELIEEGLENLIDWGNG | SEQ ID NO: 1795 |
| CGLWGEIEELIEEGLENLIDWGNG | SEQ ID NO: 1796 |
| CGLFGEWEELIEEGLENLIDWGNG | SEQ ID NO: 1797 |
| CGLFGEFEELIEEGLENLIDWGNG | SEQ ID NO: 1798 |
| CGLFGEIEELIEEGLENLLDWGNG | SEQ ID NO: 1799 |
| CGLFGEIEELIEEGLENLIDWGQG | SEQ ID NO: 1800 |
| GLFGEIEELIEEGLENLIDWGNG | SEQ ID NO: 1801 |
| GFFGAIWEFIHSIL | SEQ ID NO: 1802 |

Linkers

The attachment between a ligand G and an oligonucleotide and/or between a ligand G and a peptide may be mediated by a linker. This linker may be cleavable or non-cleavable, depending on the application. In certain embodiments, a cleavable linker may be used to release the oligonucleotide after transport from the endosome to the cytoplasm. The intended nature of the conjugation or coupling interaction, or the desired biological effect, will determine the choice of linker group. Linker groups may be combined or branched to provide more complex architectures. Suitable linkers include those as described in WO2009/126933, which is hereby incorporated by reference.

In one embodiment, a suitable linker is selected from Table 3:

TABLE 3

Suitable Linkers

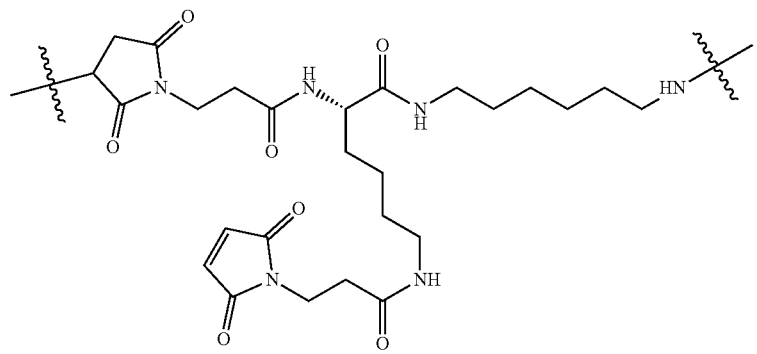 [SMILES: *NCCCCCCNC(=O)[C@H](CCCCNC(=O)CCN1C(=O)C=CC1=O)NC(=O)CCN1C(=O)CC(*)C1=O]

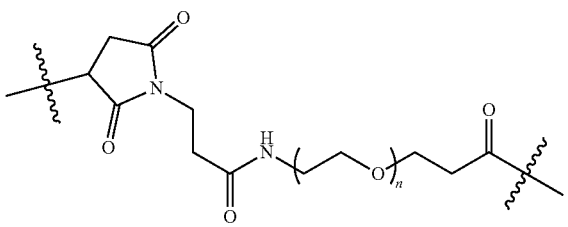

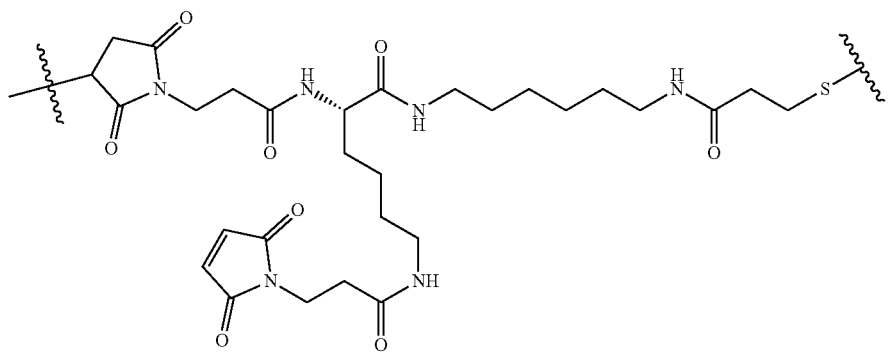 [SMILES: *SCCC(=O)NCCCCCCNC(=O)[C@H](CCCCNC(=O)CCN1C(=O)C=CC1=O)NC(=O)CCN1C(=O)CC(*)C1=O]

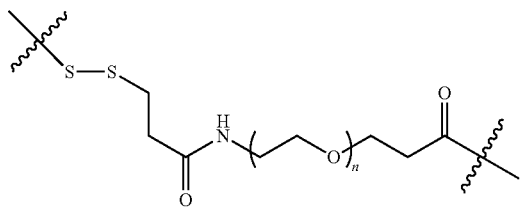

TABLE 3-continued
Suitable Linkers
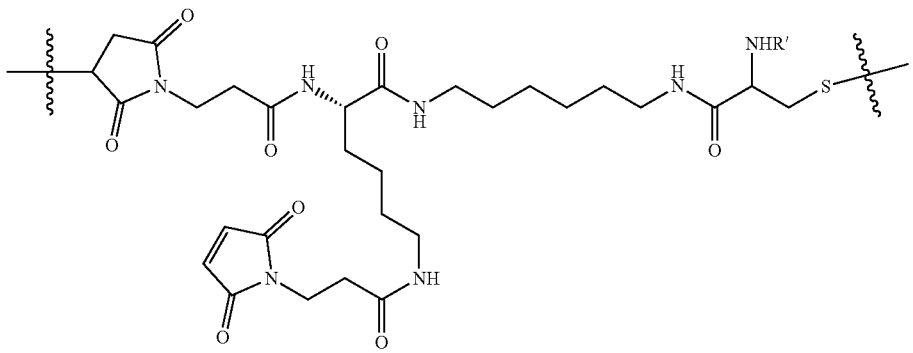
R' = H, Boc, Cbz, Ac, PEG, lipid, targeting ligand, linker(s) and/or peptides(s)
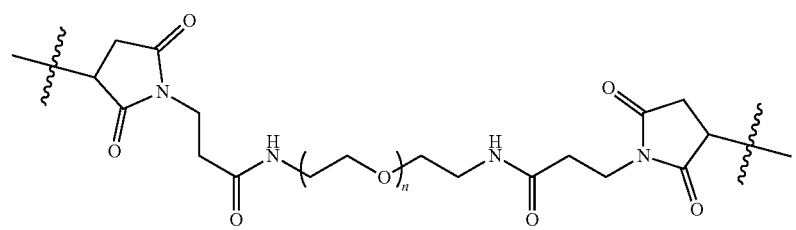
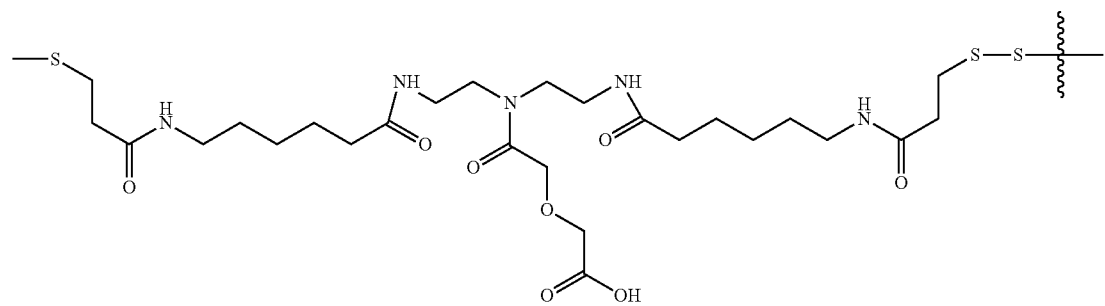 [SMILES: *SSCCC(=O)NCCCCCC(=O)NCCN(CCNC(=O)CCCCCNC(=O)CCSC)C(=O)COCC(=O)O]
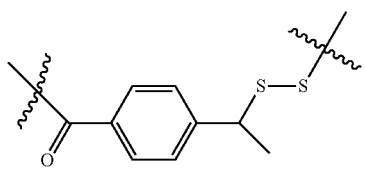 [SMILES: *SSC(C)c1ccc(C(*)=O)cc1]
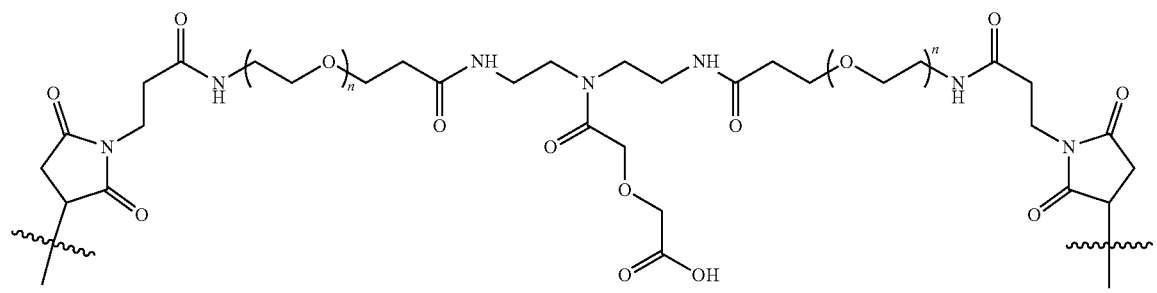
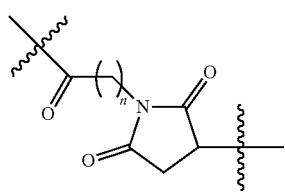

TABLE 3-continued
Suitable Linkers
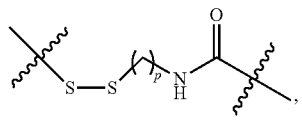
wherein p is 1 to 10
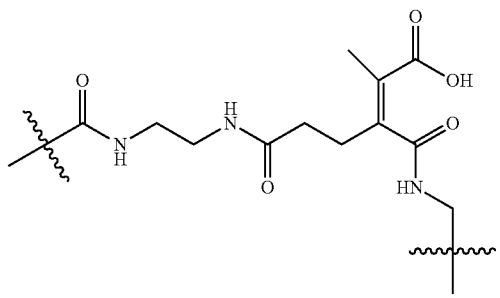
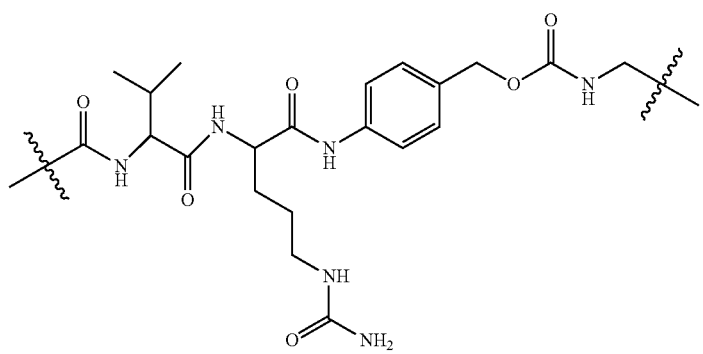
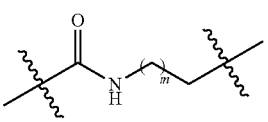
wherein m is 0 to 10
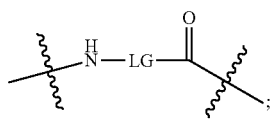
where "LG" is a linker selected from the group consisting of:
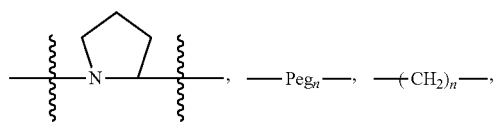
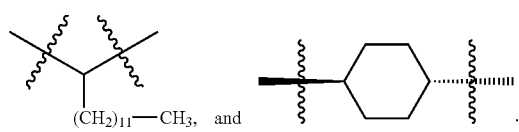
Note:
n = 0-750.

In one embodiment, a suitable linker is selected from Table 3a:
TABLE 3a
Suitable Linkers
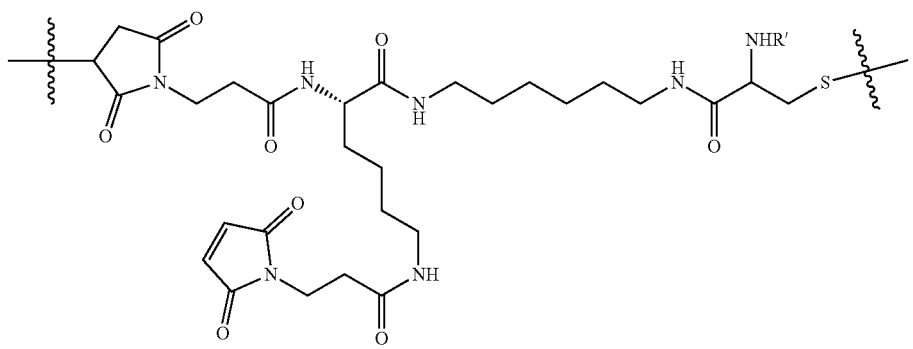
R' = H, Boc, Cbz, Ac, PEG, lipid, targeting ligand, linker(s) and/or peptides(s)
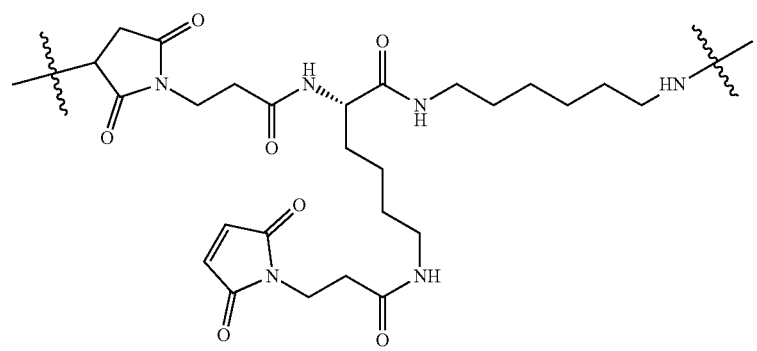 [SMILES: *NCCCCCCNC(=O)[C@H](CCCCNC(=O)CCN1C(=O)C=CC1=O)NC(=O)CCN1C(=O)CC(*)C1=O]
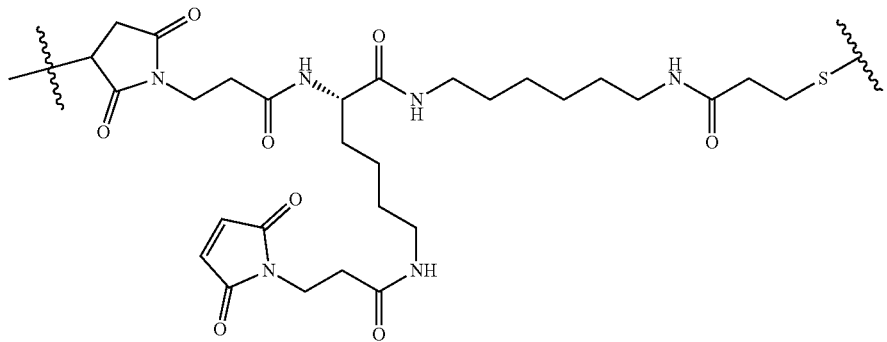 [SMILES: *SCCC(=O)NCCCCCCNC(=O)[C@H](CCCCNC(=O)CCN1C(=O)C=CC1=O)NC(=O)CCN1C(=O)CC(*)C1=O]
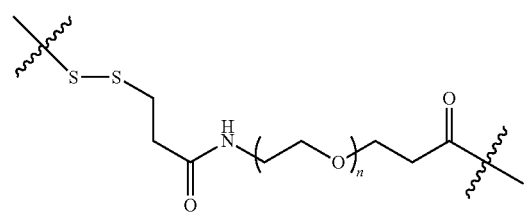

TABLE 3a-continued

Suitable Linkers

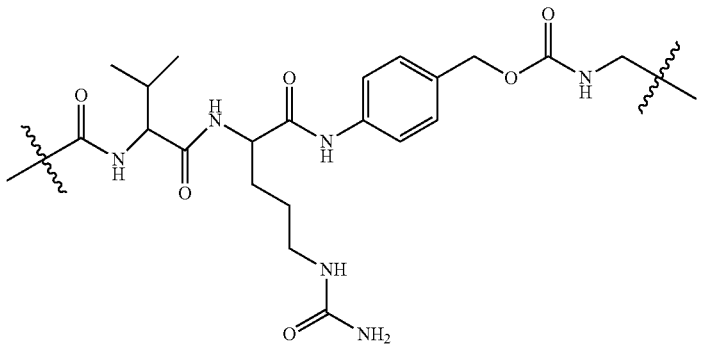

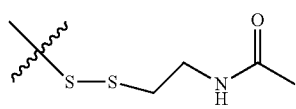

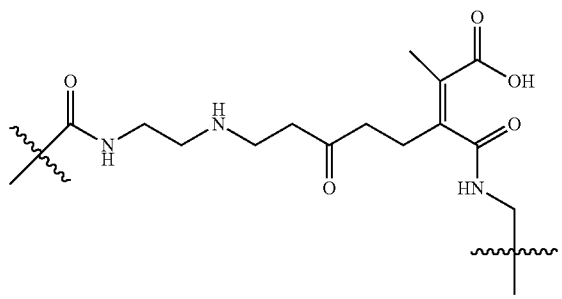

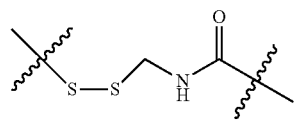

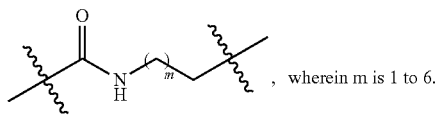, wherein m is 1 to 6.

Note:
n = 0-750

Commercial linkers are available from various suppliers such as Pierce or Quanta Biodesign including combinations of said linkers. The linkers may also be combined to produce more complex branched architectures accommodating from 1 to 6 targeting ligands and/or 1 to 6 peptides. In one embodiment, a combined targeting ligands and linkers has the structure T-L-1 as shown below:

T-L-1
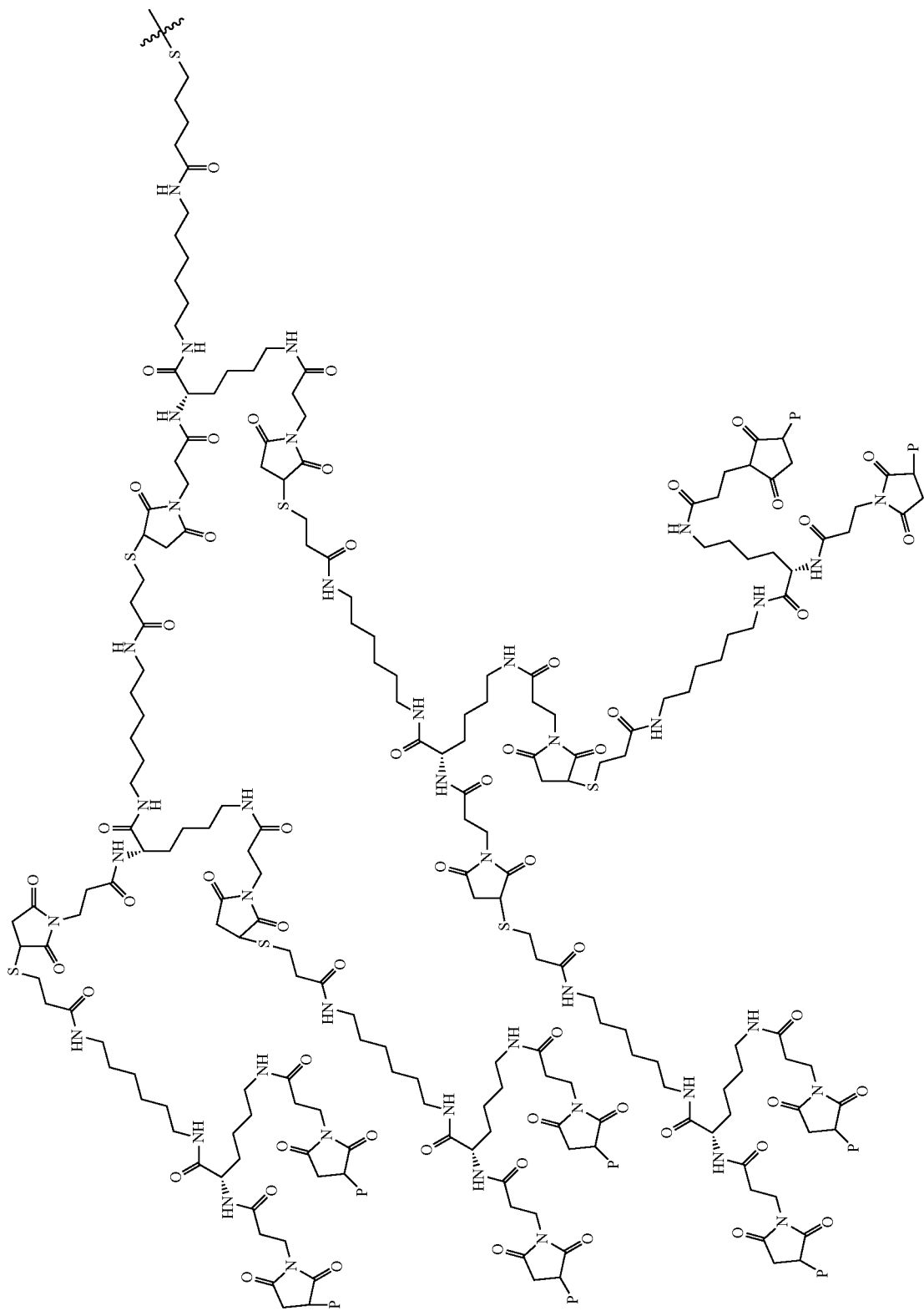

Targeting Ligands

The compositions and peptide conjugates of the present invention may comprise a targeting ligand. The term "targeting ligand" as used herein refers to its meaning as is generally accepted in the art. The term generally refers to a moiety that confers some degree of target specificity to one or more cells, tissues, or organs, such as in a subject or organism and thus the ability to target such cells, tissues, or organs with a compound or composition of interest.

In some embodiments, this targeting ligand may direct the modular composition to a particular cell. For example, the targeting ligand may specifically or non-specifically bind with a molecule on the surface of a target cell. The targeting moiety can be a molecule with a specific affinity for a target cell. Targeting moieties can include antibodies directed against a protein found on the surface of a target cell, or the ligand or a receptor-binding portion of a ligand for a molecule found on the surface of a target cell. Examples and a further description of targeting ligands can be found in WO2009/126933, which is hereby incorporated by reference.

The targeting ligands are selected from the group consisting of an antibody, a ligand-binding portion of a receptor, a ligand for a receptor, an aptamer, D-galactose, N-acetyl-D-galactose (GalNAc), multivalent N-acytyl-D-galactose, D-mannose, cholesterol, a fatty acid, a lipoprotein, folate, thyrotropin, melanotropin, surfactant protein A, mucin, carbohydrate, multivalent lactose, multivalent galactose, N-acetyl-galactosamine, N-acetyl-glucosamine, multivalent mannose, multivalent fructose, glycosylated polyaminoacids, transferrin, bisphosphonate, polyglutamate, polyaspartate, a lipophilic moiety that enhances plasma protein binding, a steroid, bile acid, vitamin B12, biotin, an RGD peptide, an RGD peptide mimic, ibuprofen, naproxen, aspirin, folate, and analogs and derivatives thereof.

In one embodiment, a targeting ligand is selected from the group consisting of D-galactose, N-acetyl-D-galactose (GalNAc), GalNAc2, and GalNAc3, cholesterol, folate, and analogs and derivatives thereof.

In one embodiment, each occurrence of the targeting ligand G of the above compositions and peptide conjugates is independently selected from Table 4.

TABLE 4

Suitable Ligands wherein each X is independently —O—, —S—, —CH$_2$— or —NH—; and each n is independently 1, 2, 3, or 4, TABLE 4-continued
Suitable Ligands
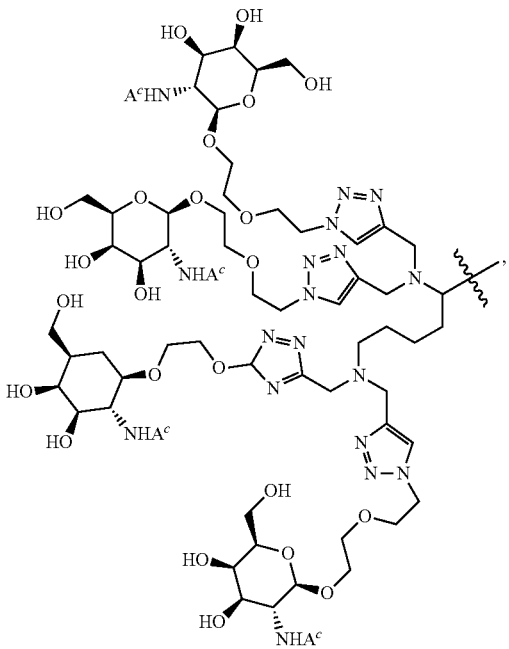
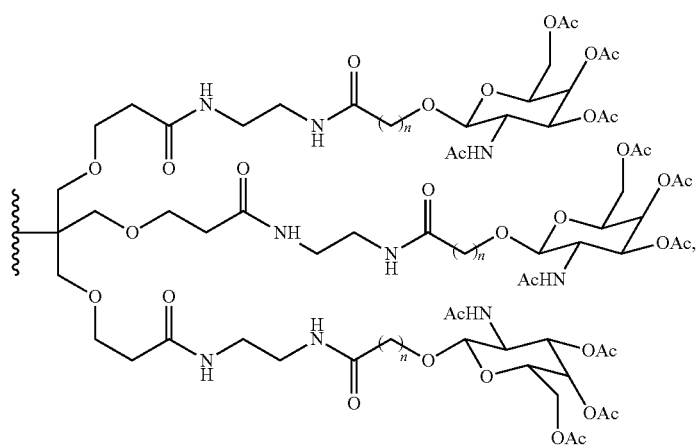
wherein each n is independently an interger from 1-20;

TABLE 4-continued
Suitable Ligands
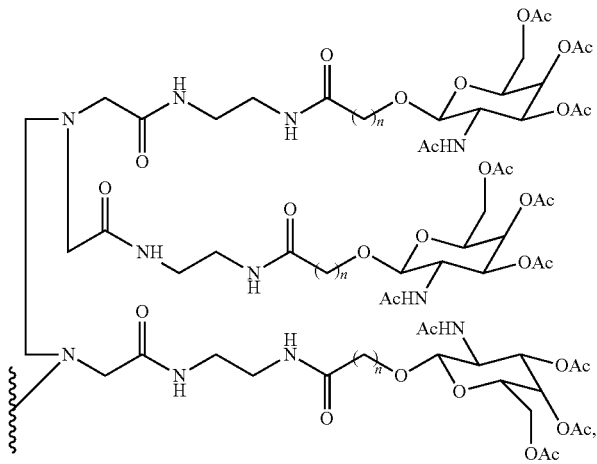
wherein each n is independently an integer from 1 to 20;
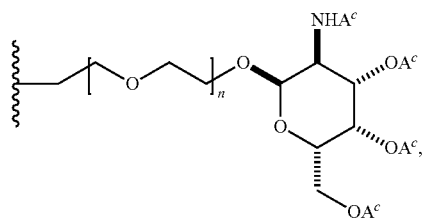
wherein n is an integer between 1 and 100,
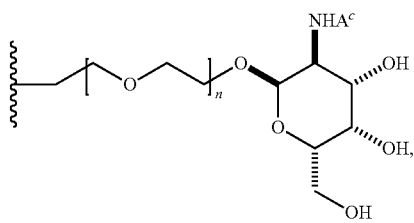
wherein n is an integer between 1 and 100,
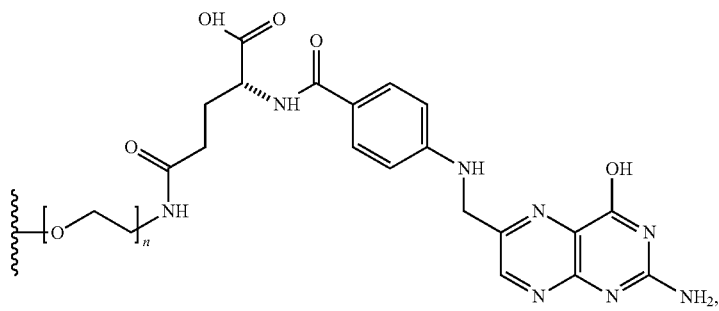
wherein n is an integer between 1 and 100.

In one embodiment, each occurrence of G is independently selected from Table 4a.

TABLE 4a

Suitable Ligands

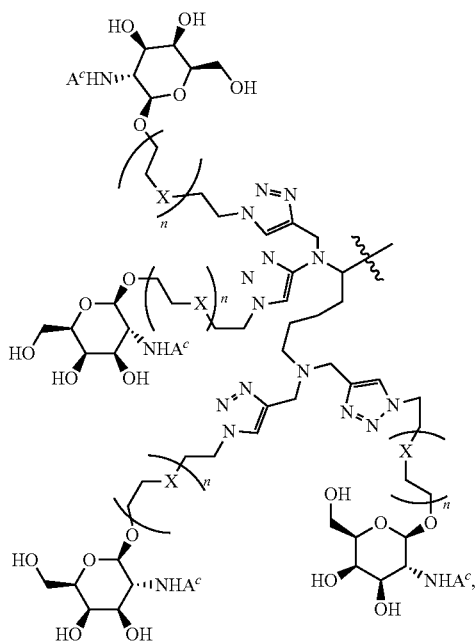

wherein each X is independently —O—, —S—, —CH$_2$— or —NH—; and each n is independently 1, 2, 3, or 4.

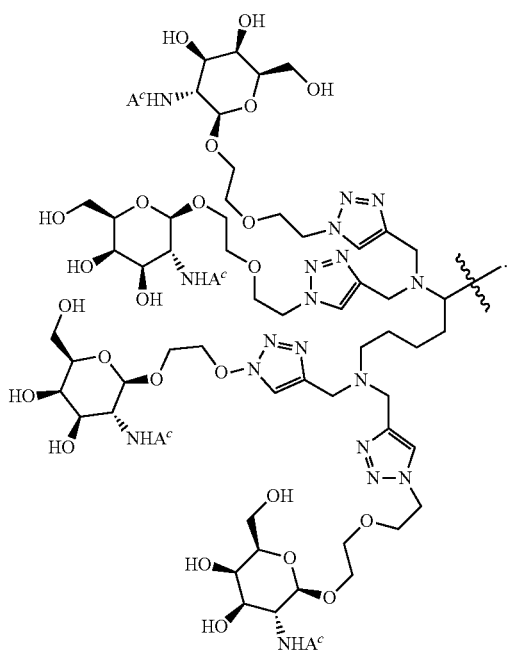

In one embodiment, G of the above compositions and peptide conjugates comprises a ligand of the following formula:

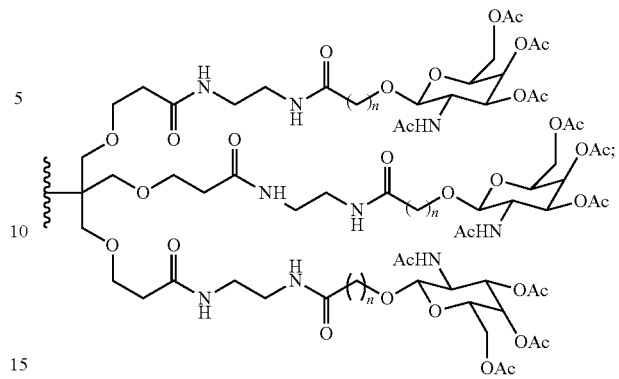

wherein each n is independently an integer from 1 to 20.

In another embodiment, G of the above compositions and peptide conjugates comprises a ligand of the following formula:

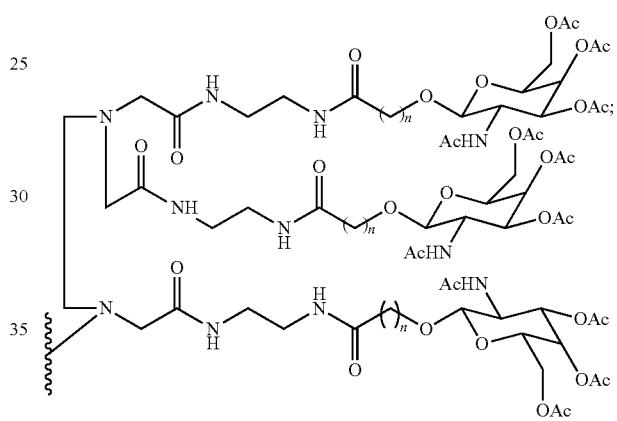

wherein each n is independently an integer from 1 to 20.

Lipids

In one embodiment, R-(L)$_a$-(G)$_b$ further comprises a lipid, either directly or through a suitable linker L.

In another embodiment, the peptide containing conjugate (P)$_c$-(L)$_d$-(G)$_e$ further comprises a lipid either directly or through a suitable linker.

Lipids, such as cholesterol or fatty acids, when attached to highly hydrophilic molecules such as nucleic acids can substantially enhance plasma protein binding and consequently circulation half life. In addition, lipophilic groups can increase cellular uptake. For example, lipids can bind to certain plasma proteins, such as lipoproteins, which have consequently been shown to increase uptake in specific tissues expressing the corresponding lipoprotein receptors (e.g., LDL-receptor or the scavenger receptor SR-B1). Lipophilic conjugates can also be considered as a targeted delivery approach and their intracellular trafficking could potentially be further improved by the combination with endosomolytic agents.

Exemplary lipids that enhance plasma protein binding include, but are not limited to, sterols, cholesterol, fatty acids, cholic acid, lithocholic acid, dialkylglycerides, diacylglyceride, phospholipids, sphingolipids, adamantane acetic acid, 1-pyrene butyric acid, dihydrotestosterone, 1,3-bis-O(hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, phenoxazine, aspirin, naproxen, ibuprofen, vitamin E and biotin etc. Examples of lipids can be found in WO2009/126933, which is hereby incorporated by reference.

In one embodiment, the lipid is cholesterol.

Solubilizing Agents

The R-$(L)_a$-$(G)_b$ composition and/or the peptide containing conjugate $(P)_c$-$(L)_d$-$(G)_e$ may further comprise one or more solubilizing agents that may enhance aqueous solubility, circulation half life and/or cellular uptake. These can include naturally occurring substances, such as a protein (e.g., human serum albumin (HSA), low-density lipoprotein (LDL), high-density lipoprotein (HDL), or globulin); or a carbohydrate (e.g., a dextran, pullulan, chitin, chitosan, inulin, cyclodextrin or hyaluronic acid). These moieties may also be a recombinant or synthetic molecule, such as a synthetic polymer or synthetic polyamino acids. Examples include polylysine (PLL), poly L-aspartic acid, poly L-glutamic acid, styrene-maleic acid anhydride copolymer, poly (L-lactide-co-glycolied) copolymer, divinyl ether-maleic anhydride copolymer, N-(2-hydroxypropyl)methacrylamide copolymer (HMPA), polyethylene glycol (PEG, e.g., PEG-0.5K, PEG-2K, PEG-5K, PEG-10K, PEG-12K, PEG-15K, PEG-20K, PEG-40K), methyl-PEG (mPEG), [mPEG]2, polyvinyl alcohol (PVA), polyurethane, poly(2 ethylacryllic acid), N-isopropylacrylamide polymers, or polyphosphazine. Examples and a further description of solubilizing agents can be found in WO2009/126933, which is hereby incorporated by reference.

In one embodiment, the solubilizing group is PEG 0.5K to 30K.

In one embodiment, R-$(L)_a$-$(G)_b$ comprises 1-4 targeting ligands. In another embodiment, R-$(L)_a$-$(G)_b$ comprises 1-2 targeting ligands. In yet another embodiment, the composition comprises 1 targeting ligand.

In one embodiment, $(P)_c$-$(L)_d$-$(G)_e$ comprises 1-6 peptides. In another embodiment, $(P)_c$-$(L)_d$-$(G)_e$ comprises 1-4 peptides. In another embodiment, $(P)_c$-$(L)_d$-$(G)_e$ comprises 1-2 peptides. In yet another embodiment, $(P)_c$-$(L)_d$-$(G)_e$ comprises 1 peptide.

In one embodiment, the oligonucleotide is mRNA, and the ligand is attached to one or more terminal positions or through 2'-position of a nucleotide ribose ring.

In one embodiment, the oligonucleotide or siRNA is double stranded and there is one targeting ligand which is attached to the guide strand at a 2'-position of a nucleotide ribose ring, optionally through a suitable linker.

In one embodiment, the oligonucleotide or siRNA is double stranded and there is one targeting ligand which is attached to the guide strand at a terminal 3' or 5'-position, optionally through a suitable linker.

In one embodiment, the oligonucleotide or siRNA is double stranded and there is one targeting ligand which is attached to the passenger strand at a 2'-position of a nucleotide ribose ring, optionally through a suitable linker.

In one embodiment, the oligonucleotide or siRNA is double stranded and there is one targeting ligand which is attached to the passenger strand at a terminal 3' or 5'-position, optionally through a suitable linker.

In one embodiment, the oligonucleotide or siRNA is double stranded and two or more targeting ligands are attached to the guide strand at different 2'-positions of the ribose rings, optionally through a suitable linkers.

In one embodiment, the oligonucleotide or siRNA is double stranded and two or more targeting ligands are attached to two or more nucleotides of the guide strand, optionally through a suitable linkers, wherein the points of attachment are at different terminal 3' and/or 5'-positions.

In one embodiment, the oligonucleotide or siRNA is double stranded and two or more targeting ligands are attached to two or more nucleotides of the passenger strand, optionally through a suitable linkers, wherein the points of attachment are at different terminal 3' and/or 5'-positions.

In one embodiment, the oligonucleotide or siRNA is double stranded and two or more targeting ligands are attached to two or more nucleotides of both the guide strand and the passenger strand, optionally through a suitable linkers, wherein the points of attachment are at different terminal 3' and/or 5'-positions.

In one embodiment, the oligonucleotide or siRNA is double stranded and optional targeting ligands, solubilizing agents, pharmacokinetics enhancing agents, lipids, and/or masking agents are attached to the same or different strands via linkers. In one embodiment, each linker is independently selected Table 3. In another embodiment, each linker is independently selected Table 3a.

To illustrate the invention, the invention features a modular composition, comprising an oligonucleotide or siRNA (R), one or more targeting ligands (G), one or more peptides (P), one or more optional linkers (L), and one or more optional ligands (X), solubilizing groups (X), pharmacokinetics enhancing agents (X), lipids (X), and/or masking agents (X). In one embodiment, the oligonucleotide is an siRNA. In another embodiment, the oligonucleotide is mRNA.

In one embodiment, the oligonucleotide composition has the formula:

G-R.

In one embodiment, the oligonucleotide composition has the formula:

G-L-R.

In one embodiment, the oligonucleotide composition has the formula:

G-L-R-X.

In one embodiment, the oligonucleotide composition has the formula:

G-L-R-L-X.

In one embodiment, the oligonucleotide composition has the formula:

G-R-L-P.

In one embodiment, the oligonucleotide composition has the formula:

G-L-R-L-P.

In one embodiment, the oligonucleotide composition has the formula:

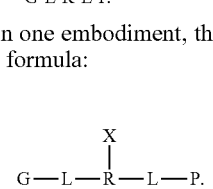

In one embodiment, the oligonucleotide composition has the formula:

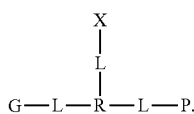

In one embodiment, a double stranded siRNA composition has the formula:

G-L-ds siRNA, wherein the ds siRNA is a double stranded siRNA that comprises a passenger (sense) strand and a guide (antisense) strand, wherein the passenger strand nucleotide sequence is complimentary to the guide strand nucleotide sequence, and wherein the G-L- is attached to the 5' end of the passenger strand. In one embodiment of the composition, the G-L- is attached to the 3' end of the passenger strand. In one embodiment of the composition, the G-L- is attached to the 5' end of the guide strand. In one embodiment of the composition, the G-L- is attached to the 3' end of the guide strand.

When the oligonucleotide or siRNA is a double stranded oligonucleotide or siRNA, the "G-L-", "P-L-" and "X-L-" may be located on the same strand or on different strands.

In one embodiment, a double stranded siRNA composition has the formula:

G-L-ds siRNA-L-P, wherein the ds siRNA is a double stranded siRNA that comprises a passenger (sense) strand and a guide (antisense) strand, wherein the passenger strand nucleotide sequence is complimentary to the guide strand nucleotide sequence, wherein the G-L- is attached to the 5' end of the passenger strand, and wherein the P-L- is attached to the 3' end of the passenger strand. In one embodiment of the composition, the G-L- is attached to the 5' end of the passenger strand, and the P-L- is attached to the 5' end of the guide strand. In one embodiment of the composition, the G-L- is attached to the 3' end of the guide strand, and the P-L- is attached to the 5' end of the guide strand. In one embodiment of the composition, the G-L- is attached to the 3' end of the guide strand, and the P-L- is attached to the 3' end of the passenger strand.

In one embodiment, a double stranded siRNA composition has the formula:

wherein the ds siRNA is a double stranded siRNA that comprises a passenger (sense) strand and a guide (antisense) strand, wherein the passenger strand nucleotide sequence is complimentary to the guide strand nucleotide sequence, wherein the G-L- is attached to the 5' end of the passenger strand, the P-L- is attached to the 3' end of the passenger strand, and the X-L- is attached to the 3' end of the guide strand. In one embodiment of the composition, the G-L- is attached to the 3' end of the guide strand, the P-L- is attached to the 3' end of the passenger strand, and the X-L- is attached to the 5' end of the passenger strand. In one embodiment of the composition, the G-L- is attached to the 3' end of the guide strand, the P-L- is attached to the 5' end of the guide strand, and the X-L- is attached to the 5' end of the passenger strand.

These examples are used as guidance. One skilled in the art will recognize that a variety of permutations for placing the desired components on the passenger and guide strand exist.

In some embodiments, when the oligonucleotide or siRNA is double-stranded and multiple "G-L", "P-L" and/or "X-L" components are present, such multiple "G-L", "P-L" and/or "X-L" components may all be present in one strand or both strands of the double stranded oligonucleotide or siRNA.

When multiple "G-L", "P-L" and/or "X-L" components are present, they may all be the same or different.

In some embodiments, the "G-L", "P-L" and "X-L" are on the same strand.

In some embodiments, the "G-L", "P-L" and "X-L" are on the passenger strand.

In some embodiments, the "G-L", "P-L" and "X-L" are on the guide strand.

In some embodiments, the "G-L", "P-L" and "X-L" are on different strands.

In some embodiments, the "G-L" is on the passenger strand and the "P-L" is on the guide strand.

In some embodiments, the "G-L" is on the guide strand and the "P-L" is on the passenger strand.

In some embodiments, the "G-L", "P-L" and "X-L" are on different strands but on the same terminal end of the double-stranded oligonucleotide or siRNA.

In some embodiments, the "G-L", "P-L" and "X-L" are on different strands and on the opposite terminal ends of the double-stranded oligonucleotide or siRNA.

In some embodiments, one or more "G-L", one or more "P-L" and/or one or more "X-L" of identical or different nature can be located on the guide strand or passenger strand in the above embodiments.

In some embodiments, the "G-L" and "P-L" may be located on multiple terminal ends of either the passenger or guide strand and the "X-L" may be located on the remaining terminal ends of the passenger and guide strands.

The method can be performed in vitro, ex vivo or in vivo, e.g., to treat a subject identified as being in need of an oligonucleotide or siRNA. A subject in need of said oligonucleotide is a subject, e.g., a human, in need of having the expression of a gene or genes, e.g., a gene related to a disorder, downregulated or silenced.

In one aspect, the invention provides a method for inhibiting the expression of one or more genes. The method comprising contacting one or more cells with an effective amount of an oligonucleotide of the invention, wherein the effective amount is an amount that suppresses the expression of the one or more genes. The method can be performed in vitro, ex vivo or in vivo.

The methods and compositions of the invention can be used with any oligonucleotides or siRNAs known in the art. In addition, the methods and compositions of the invention can be used for the treatment of any disease or disorder known in the art, and for the treatment of any subject, e.g., any animal, any mammal, such as any human. One of ordinary skill in the art will also recognize that the methods and compositions of the invention may be used for the treatment of any disease that would benefit from downregulating or silencing a gene or genes.

One of ordinary skill in the art will further recognize that the methods and compositions of the invention may be used for expressing genes encoding proteins or polypeptides.

The methods and compositions of the invention may be used with any dosage and/or formulation described herein, or any dosage or formulation known in the art. In addition to the routes of administration described herein, a person skilled in the art will also appreciate that other routes of administration may be used to administer the modular composition of the invention.

Method of Treatment

In one aspect, the invention features a method of treating a subject at risk for or afflicted with a disease that may benefit from the administration of the modular composition of the invention. The method comprises administering the modular composition of the invention to a subject in need thereof, thereby treating the subject. The oligonucleotide that is administered will depend on the disease being treated. See WO2009/126933 for additional details regarding methods of treatments for specific indications.

Formulation

There are numerous methods for preparing conjugates of oligonucleotide and peptide compounds. The techniques should be familiar to those skilled in the art. A useful reference for such reactions is Bioconjugate Techniques, Hermanson, G. T., Academic Press, San Diego, Calif., 1996. Other references include WO2005/041859; WO2008/036825 and WO2009/126933.

Unless otherwise noted, the following terminology and definitions apply as used in the present application.

As used in this specification and the appended claims, the singular forms "a," "an," and "the" include plural referents unless the content clearly dictates otherwise. Thus, for example, reference to "a cell" includes a combination of two or more cells, and the like.

Any concentration range, percentage range, ratio range or integer range is to be understood to include the value of any integer within the recited range, and when appropriate, fractions thereof (such as one tenth and one hundredth of an integer), unless otherwise indicated.

"About" or "approximately," as used herein, in reference to a number are generally taken to include numbers that fall within a range of 5% in either direction (greater than or less than) of the number unless otherwise stated or otherwise evident from the context (except where such number would exceed 100% of a possible value). Where ranges are stated, the endpoints are included within the range unless otherwise stated or otherwise evident from the context.

The phrase "biological system" as used herein refers to its meaning as is generally accepted in the art. The term generally refers to material, in a purified or unpurified form, from biological sources including, but not limited to, human or animal, wherein the system comprises the components required for RNAi activity. Thus, the phrase includes, for example, a cell, tissue, subject, or organism, or extract thereof. The term also includes reconstituted material from a biological source.

The term "cell" as used herein refers to its meaning as is generally accepted in the art. With reference to exemplary nucleic acid molecules of the invention, the term is used in its usual biological sense, and does not refer to an entire multicellular organism, e.g., specifically does not refer to a human being. The cell can be present in an organism, e.g., birds, plants and mammals, such as humans, cows, sheep, apes, monkeys, swine, dogs, and cats. The cell can be prokaryotic (e.g., bacterial cell) or eukaryotic (e.g., mammalian or plant cell). The cell can be of somatic or germ line origin, totipotent or pluripotent, dividing or non-dividing. The cell can also be derived from or can comprise a gamete or embryo, a stem cell, or a fully differentiated cell.

The terms "composition" or "formulation" as used herein refer to their generally accepted meaning in the art. These terms generally refer to a composition or formulation, such as in a pharmaceutically acceptable carrier or diluent, in a form suitable for administration, e.g., systemic or local administration, into a cell or subject, including, for example, a human. Suitable forms, in part, depend upon the use or the route of entry, for example oral, transdermal, inhalation, or by injection. Such forms should not prevent the composition or formulation from reaching a target cell. For example, compositions injected into the blood stream should be soluble. Other factors are known in the art, and include considerations such as toxicity and forms that prevent the composition or formulation from exerting its effect. As used herein, pharmaceutical formulations include formulations for human and veterinary use.

The term "including" (and any form thereof, such as "includes" and "include"), "comprising" (and any form thereof, such as "has" or "have") or "containing" (and any form thereof such as "contains" or "contain") are inclusive and open-ended and do not exclude additional, unrecited elements or method steps.

The terms "mammalian" or "mammal" as used herein refers to its meaning as is generally accepted in the art. The term generally refers to any warm blooded vertebrate species, such as a human, mouse, rat, dog, cat, hamster, guinea pig, rabbit, livestock, and the like.

The term "subject" as used herein refers to its meaning as is generally accepted in the art. The term generally refers an organism to which the nucleic acid molecules of the invention can be administered. A subject can be a mammal or mammalian cells, including a human or human cells. The term also refers to an organism, which is a donor or recipient of explanted cells or the cells themselves.

The phrase "systemic administration" as used herein refers to its meaning as is generally accepted in the art. The phrase generally refers in vivo systemic absorption or accumulation of drugs in the blood stream followed by distribution throughout the entire body.

The phrase "therapeutically effective amount" as used herein refers to its meaning as is generally accepted in the art. The term generally refers to the amount of the compound or composition that will elicit the biological or medical response of a cell, tissue, system, animal or human that is be sought by the researcher, veterinarian, medical doctor or other clinician. For example, if a given clinical treatment is considered effective when there is at least a 25% reduction in a measurable parameter associated with a disease or disorder, a therapeutically effective amount of a drug for the treatment of that disease or disorder is that amount necessary to effect at least a 25% reduction in that parameter.

EXAMPLES

The invention is further illustrated by the following examples, which should not be construed as further limiting. The contents of all references, pending patent applications and published patents, cited throughout this application are hereby expressly incorporated by reference. The siRNAs described herein were designed to target CTNNB1 (Beta Catenin).

Preparations of Compounds A9 and A10

TetraGalNAc Compounds A9 and A10 were prepared using steps and conditions as described in Scheme 1.

155 156
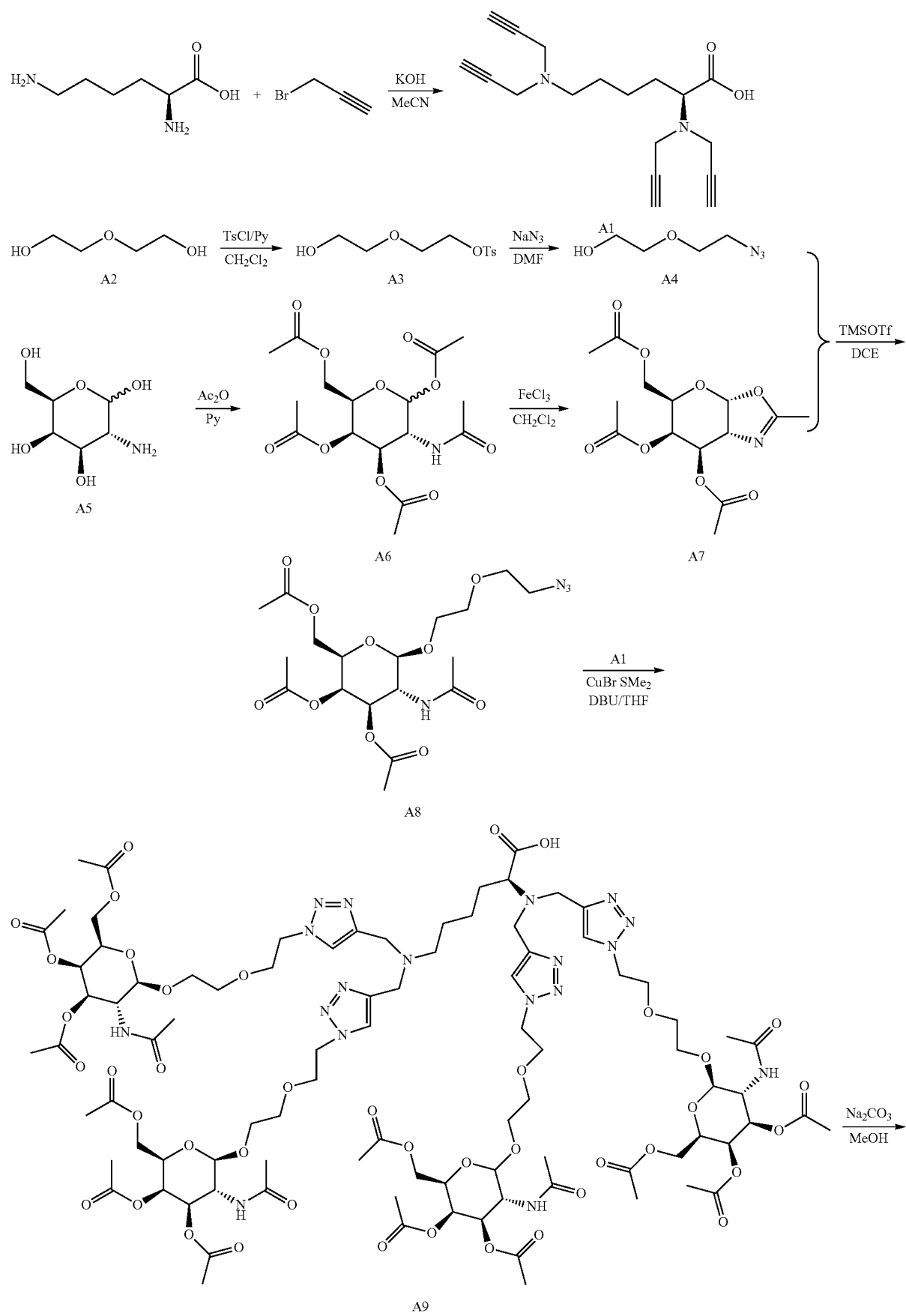

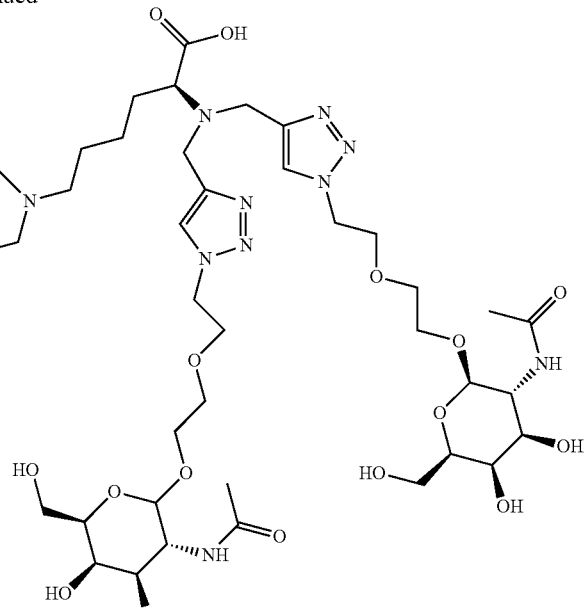

A10

Synthesis of (2S)-2, 6-bis[bis (prop-2-yn-1-yl)amino]hexanoic acid (Compound A1)

Into a 2000-mL 3-necked round-bottom flask purged and maintained with an inert atmosphere of nitrogen was placed a solution of (2S)-2,6-diaminohexanoic acid (50 g, 342.03 mmol, 1.00 equiv) in acetonitrile (1000 mL) and heated to 50° C. To this was added potassium hydroxide (22.6 g, 0.4025 mol, 1.00 equiv, 85%). The resulting solution was stirred for 30 min. Then 3-bromoprop-1-yne (29.5 mL, 1.00 equiv) was added. The resulting solution was stirred for 1 hour at 50° C. Additional potassium hydroxide (22.6 g, 0.4025 mol, 1.00 equiv) was added to the solution and stirred for 30 min at 50° C. To this was added 3-bromoprop-1-yne (29.5 mL, 1.00 equiv). The resulting solution was stirred for 1 hour. To this was added potassium hydroxide (22.6 g, 0.4025 mol, 1.00 equiv) again. The resulting solution was stirred for 30 min at 50° C., followed by addition of more 3-bromoprop-1-yne (29.5 mL, 1.00 equiv). The resulting solution was stirred for 1 hour. To this was added potassium hydroxide (22.6 g, 0.4025 mol, 1.00 equiv). The resulting solution was stirred for 30 min. To this was added 3-bromoprop-1-yne (29.5 mL, 1.00 equiv). The resulting solution was stirred for 3 hours. The reaction mixture was cooled to 25° C. with a water/ice bath. The solid was filtered out. The filtrate was adjusted to pH 4 with HCl (6M). The solid was filtered out. The filtrate was concentrated under vacuum. The residue was applied onto a silica gel column and eluted with dichloromethane/methanol (100:1-25:1). This resulted in Compound A1 as an oil.

MS (ES, m/z): 297.2, [M−H]$^{−1}$HNMR(CDCl$_3$, 500 MHz ppm): 3.62 (d, J=2.0 Hz, 4H), 3.52-3.49 (m, 1H), 3.50 (d, J=2.4 Hz, 4H), 2.62 (t, J=7.1 Hz, 2H), 2.30 (t, J=2.4 Hz, 2H), 2.27 (t, J=2.4 Hz, 2H), 1.88-1.79 (m, 2H), 1.60-1.53 (m, 2H), 1.52-1.43 (m, 2H).

Synthesis of 2-(2-hydroxyethoxy)ethyl 4-methylbenzenesulfonate (Compound A3)

Into a 2000-mL 3-necked round-bottom flask purged and maintained with an inert atmosphere of nitrogen was placed a solution of 2-(2-hydroxyethoxy)ethan-1-ol (A2, 42.4 g, 399.55 mmol, 1.00 equiv) in dichloromethane (1000 mL) and triethylamine (27.9 g, 275.72 mmol, 0.25 equiv). To the above was added p-toluenesulfonyl chloride (19.1 g, 100.18 mmol, 0.50 equiv). After stirring for 1 h at 25° C., the resulting mixture was washed with 1×500 mL of aq. potassium hydrosulfate (1M) and 1×500 mL of aq. sodium bicarbonate (5%) respectively. The organic layer was dried over anhydrous sodium sulfate and concentrated under vacuum. The residue was applied onto a silica gel column and eluted with dichloromethane/methanol (100:1). This resulted in Compound A3 as an oil.

Synthesis of 2-(2-azidoethoxy)ethan-1-ol (Compound A4)

Into a 500-mL round-bottom flask purged and maintained with an inert atmosphere of nitrogen was placed a solution of 2-(2-[[(4-2-(2-hydroxyethoxy)ethyl 4-methylbenzenesulfonate (A3, 50 g, 192.08 mmol, 1.00 equiv) in N,N-dimethylformamide (250 mL). This was followed by the addition of sodium azide (18.79 g, 289.03 mmol, 1.50 equiv) at 25° C. The resulting solution was stirred for 5 h at 100° C. in an oil bath. The reaction mixture was cooled and filtered. The filtrate was concentrated under vacuum. The residual solution was diluted with 1000 mL of dichloromethane and washed with 1×500 mL of water. The organic layer was dried over anhydrous sodium sulfate and concentrated under vacuum. The residue was applied onto a silica gel column and eluted with dichloromethane/methanol (80:1). This resulted in Compound A4 as an oil.

$^1$HNMR (CDCl$_3$, 400 MHz ppm): 3.42-3.45 (t, J=4.8 Hz, 2H), 3.63-3.65 (t, J=4.8 Hz, 2H), 3.71-3.74 (t, J=4.8 Hz, 2H), 3.71-3.79 (m, 2H).

Synthesis of (3R,4R,5R,6R)-3-acetamido-6-(acetoxymethyl)tetrahydro-2H-pyran-2,4,5-triyl triacetate (Compound A6)

Into a 2000-mL 3-necked round-bottom flask purged and maintained with an inert atmosphere of nitrogen was placed a solution of (3R,4R,5R,6R)-3-amino-6-(hydroxymethyl)tetrahydro-2H-pyran-2,4,5-triol hydrochloride (A5, 120 g, 556.50 mmol, 1.00 equiv) in pyridine (1200 mL). This was followed by the addition of acetic anhydride (341.6 g, 3.35 mol, 6.00 equiv) dropwise with stirring at 0° C. The resulting solution was stirred overnight at 25° C. The reaction was then quenched by the addition of 8000 mL of water/ice. The solid was collected by filtration. This resulted in Compound A6 as a solid.

Synthesis of (3aR,5R,6R,7R,7aR)-5-(acetoxymethyl)-2-methyl-5,6,7,7a-tetrahydro-3aH-pyrano[3,2-d]oxazole-6,7-diyl diacetate (Compound A7)

Into a 2000-mL round-bottom flask purged and maintained with an inert atmosphere of nitrogen was placed a solution of (3R,4R,5R,6R)-3-acetamido-6-(acetoxymethyl)tetrahydro-2H-pyran-2,4,5-triyl triacetate (A6, 30 g, 77.05 mmol, 1.00 equiv) in dichloromethane (1500 mL), then added iron (III) chloride (30 g, 184.95 mmol, 2.40 equiv). The resulting mixture was stirred for 2 h at 25° C. The reaction was then quenched by the addition of 1000 mL of water/ice. The organic layer was washed with 1×1000 mL of sodium aq. bicarbonate and 1×1000 mL of water, dried over anhydrous sodium sulfate and concentrated under vacuum. This resulted in Compound A7 as an oil.

$^1$HNMR (CDCl$_3$, 300 MHz ppm): 2.03 (s, 9H), 2.12 (s, 3H), 3.97-4.27 (m, 4H), 4.90-4.93 (m, J=3.3 Hz, 1H), 5.45-5.47 (t, J=3.0 Hz, 1H), 5.98-6.00 (d, J=6.6 Hz, 1H).

Synthesis of (2R,3R,4R,5R,6R)-5-acetamido-2-(acetoxymethyl)-6-[2-(2-azidoethoxy)ethoxy]tetrahydro-2H-pyran-3,4-diyl diacetate (Compound A8)

Into a 500-mL round-bottom flask purged and maintained with an inert atmosphere of nitrogen was placed a solution of (3aR,5R,6R,7R,7aR)-5-(acetoxymethyl)-2-methyl-5,6,7,7a-tetrahydro-3aH-pyrano[3,2-d]oxazole-6,7-diyl diacetate (A7, 40 g, 121.47 mmol, 1.00 equiv) in 1,2-dichloroethane (200 mL), 2-(2-azidoethoxy)ethan-1-ol (A4, 23.89 g, 182.18 mmol, 1.50 equiv). To the above several 4A zeolite was added. The resulting mixture was stirred for 1 h at 25° C. Then trimethylsilyl trifluoromethanesulfonate (10.8 mL, 0.50 equiv) was added. After stirred overnight at 25° C., the reaction mixture was diluted with 500 mL of dichloromethane and washed with 1×500 mL of water, 1×500 mL of aq. sodium bicarbonate and 1×500 mL of water. The organic layer was dried over anhydrous sodium sulfate and concentrated under vacuum. The residue was applied onto a silica gel column and eluted with dichloromethane/methanol (100:1). This resulted in Compound A8 as an oil. MS (m/z): 461.1, [M+H]$^+$ $^1$HNMR(CDCl$_3$, 500 MHz ppm) 5.78 (d, J=8.90 Hz, 1H), 5.36 (d, J=2.9 Hz, 1H), 5.22 (dd, J=11.2, 3.6 Hz, 1H), 4.77 (d, J=8.3 Hz, 1H), 4.19-4.12 (m, 2H), 4.11-4.05 (m, 1H), 3.98-3.92 (m, 2H), 3.82-3.78 (m, 1H), 3.71-3.63 (m, 4H), 3.49-3.38 (m, 2H), 2.16 (s, 3H), 2.05 (s, 3H), 2.01 (s, 3H), 1.97 (s, 3H).

Synthesis of (S)-2,6-bis(bis((1-(2-(2-(42R,3R,4R,5R,6R)-3-acetamido-4,5-diacetoxy-6-(acetoxymethyl)tetrahydro-2H-pyran-2-yl)oxy)ethoxy)ethyl)-1H-1,2,3-triazol-4-yl)methyl)amino)hexanoic acid (Compound A9, tetraGalNAc Acetate)

Into a 250-mL round bottom flask purged and maintained with an inert atmosphere of nitrogen was charged (2S)-2,6-bis [bis (prop-2-yn-1-yl) amino]hexanoic acid (A1, 1.0 g, 1.0 equiv), (2R,3R,4R,5R,6R)-5-acetamido-2-(acetoxymethyl)-6-[2-(2-azidoethoxy)ethoxy]tetrahydro-2H-pyran-3,4-diyl diacetate (A8, 9.26 g, 6.0 equiv), anhydrous THF 50 mL, CuBr.SMe$_2$ (0.138 g, 0.20 equiv), and anhydrous DBU (1.5 ml, 3.0 equiv) in respective order. The resulting solution was stirred for 16 h at room temperature, quenched with acetic acid (0.75 mL, 4.0 equiv), treated with MP-TMT resin (Part No: 801472, from Biotage) (9 g), aged at room temperature for 16 h, filtered, and concentrated the filtrate to a solid. The solid was then dissolved in $CH_2Cl_2$ (140 mL), and washed with AcOH/NaCl solution (140 mL). The AcOH/NaCl solution was prepared with 1 mL AcOH and 100 mL 20% NaCl solution. The bottom organic layer was concentrated, and purified on a $SiO_2$ column (220 g), eluting with $CH_2Cl_2$/MeOH. This resulted in Compound A9 as a solid (tetraGalNAc Acetate). MS (m/z): 2139.5, $[M+H]^+$ Synthesis of (S)-2,6-bis(bis((1-(2-(2-(((2R,3R,4R,5R,6R)-3-acetamido-4,5-dihydroxy-6-(hydroxymethyl)tetrahydro-2H-pyran-2-yl)oxy)ethoxy)ethyl)-1H-1,2,3-triazol-4-yl)methyl)amino)hexanoic acid (Compound A10, TetraGalNAc)

Into a 250-mL round-bottom flask purged and maintained with an inert atmosphere of nitrogen was charged (S)-2,6-bis(bis((1-(2-(2-(((2R,3R,4R,5R,6R)-3-acetamido-4,5-diacetoxy-6-(acetoxymethyl)tetrahydro-2H-pyran-2-yl)oxy)ethoxy)ethyl)-1H-1,2,3-triazol-4-yl)methyl)amino)hexanoic acid (A9, 6.9 g, 1.0 equiv), $Na_2CO_3$ (6.83 g, 20 eq), water (56 mL), and MeOH (32 mL) in respective order. The reaction was aged at room temperature for 16 h, concentrated to residue, redissolved in water (50 mL), and purified on Combiflash C18 gold reverse column (415 g), eluting with water/MeCN. After concentration under vacuum, the product was dissolved in minimum amount of water, and lyophilized to obtain Compound A10 (tetraGalNAc) as a solid.

MS (m/z): 1657 $[M+Na]^+$ $^1$HNMR ($D_2O$, 500 MHz, ppm): 8.05 (s, 2H), 7.91 (s, 2H), 4.62 (t, J=5.0 Hz, 4H), 4.57 (t, J=5.0 Hz, 4H), 4.45-4.41 (d, J=8.6 Hz, 4H), 3.99-3.82 (m, 28H), 3.80-3.61 (m, 28H), 3.14 (t, J=7.1 Hz, 1H), 2.52 (broad s, 2H), 1.99 (s, 6H), 1.98 (s, 6H), 1.73 (m, 2H), 1.60 (m, 2H), 1.29 (m, 2H).

Preparation of B2 to B4

Conjugates B2 to B4 were prepared using steps and conditions as described in Scheme 2.

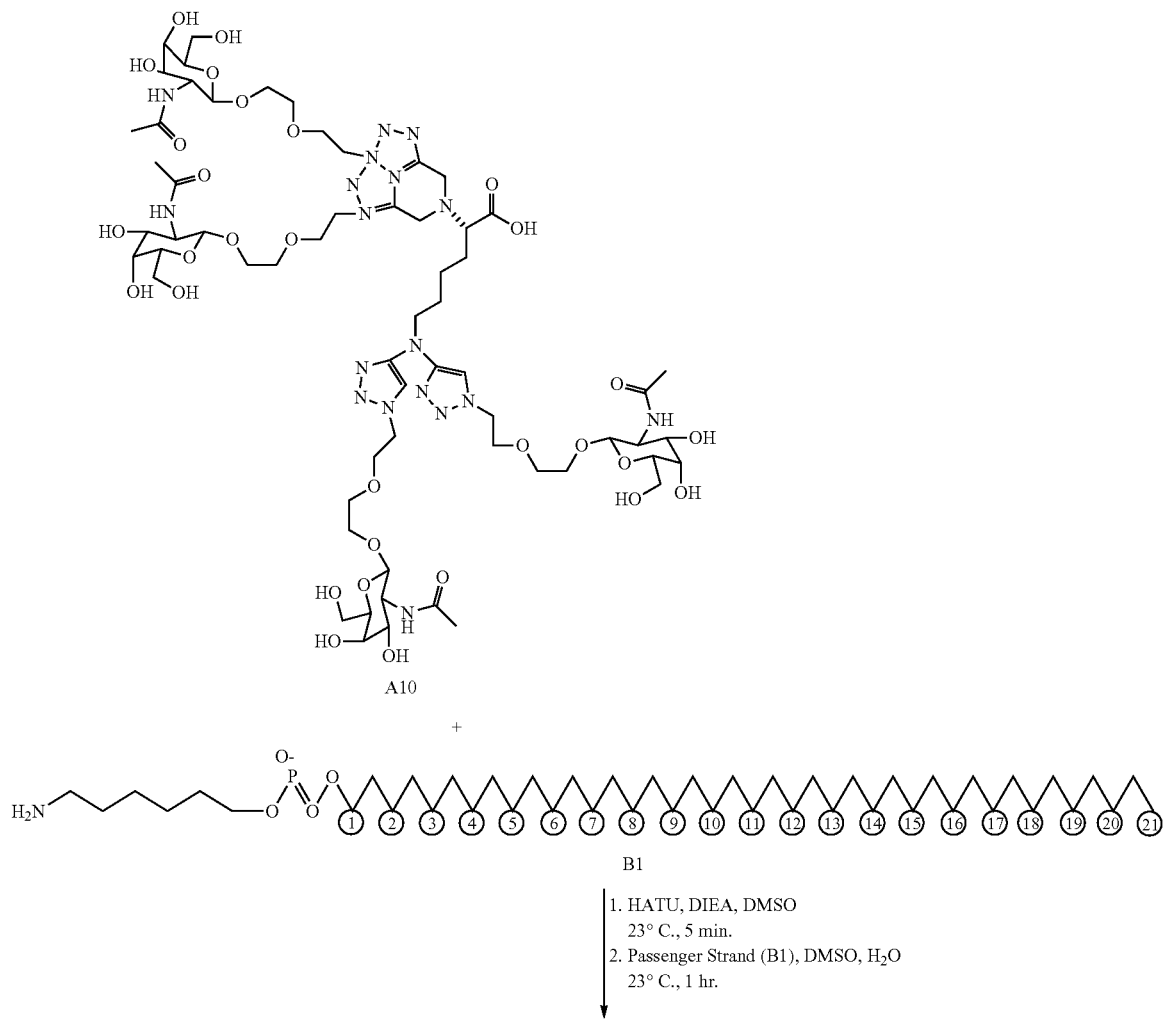

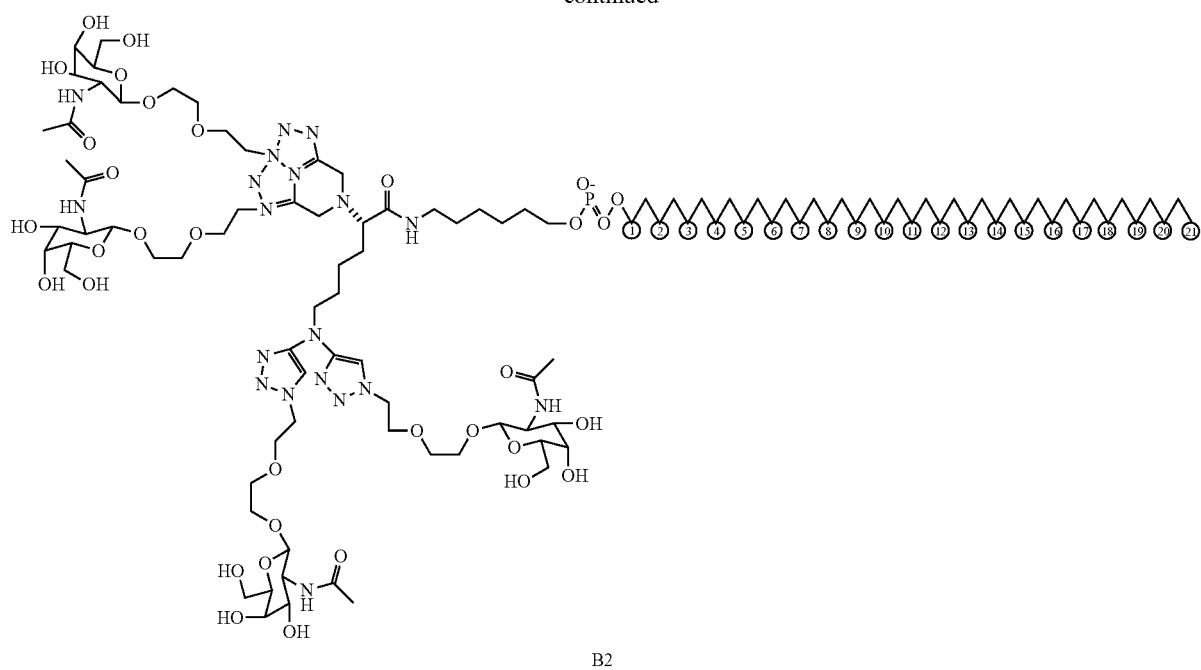
B2
B3
Duplexing
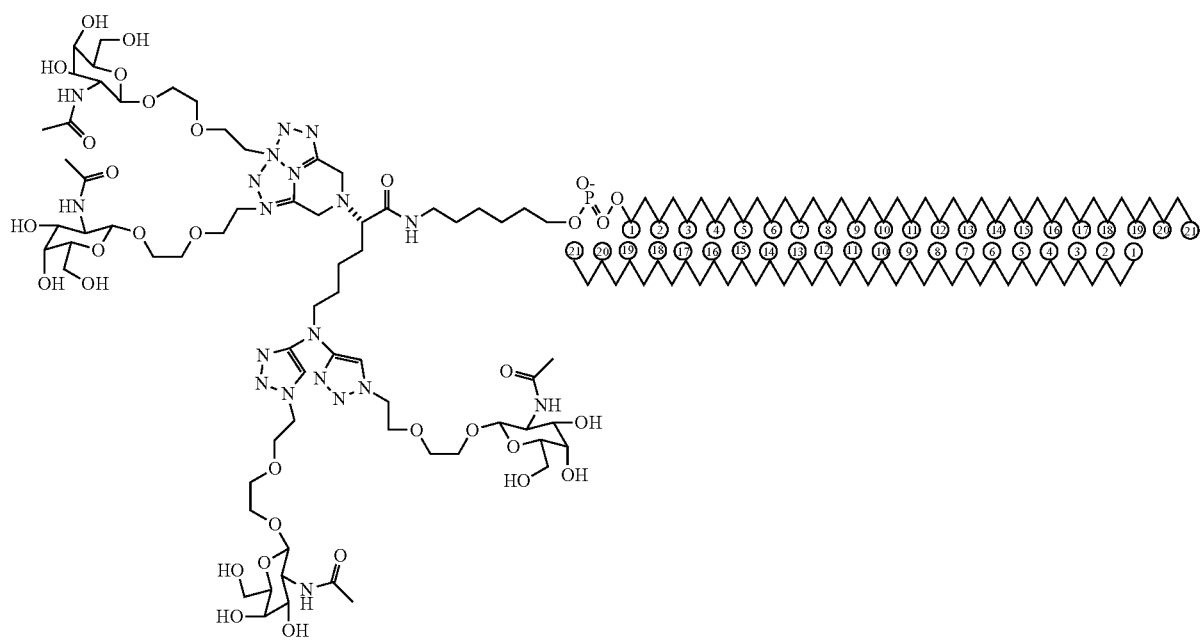
B4

Synthesis of B2

HATU (30 mg, 0.080 mmol, 3 eq.) was dissolved in DMSO (400 uL) and added to a vial containing A10 (130 mg, 0.080 mmol, 3 eq.). The solution color turned pale yellow as the tetra GalNAc (A10) dissolved. DIEA (28 uL, 0.16 mmol, 6 eq.) was then added to the solution. Starting material passenger strand B1 (200 mg, 0.027 mmol, 1 eq.) was dissolved in water (400 uL) and diluted with DMSO (800 uL). The HATU solution was added to the RNA solution and mixed thoroughly. The reaction mixture was left at room temperature for 20 minutes. The reaction mixture was diluted with water to bring the total DMSO content to 5% and centrifugal dialyzed two times against water over a 3K membrane. Expected mass: 9147.5, found mass: 9149.0

Synthesis of B4

Guide strand (B3, 58 mg) was dissolved in water (5 mL) and added to a vial containing B2 (79 mg). The solution was thoroughly mixed and left at room temperature for 2 hours. The solution was freeze dried to afford the duplex as a solid.

Synthesis of Compounds C1 and C2

Compounds C1 to C2 were prepared using steps and conditions as described in Scheme 3.

Scheme 3

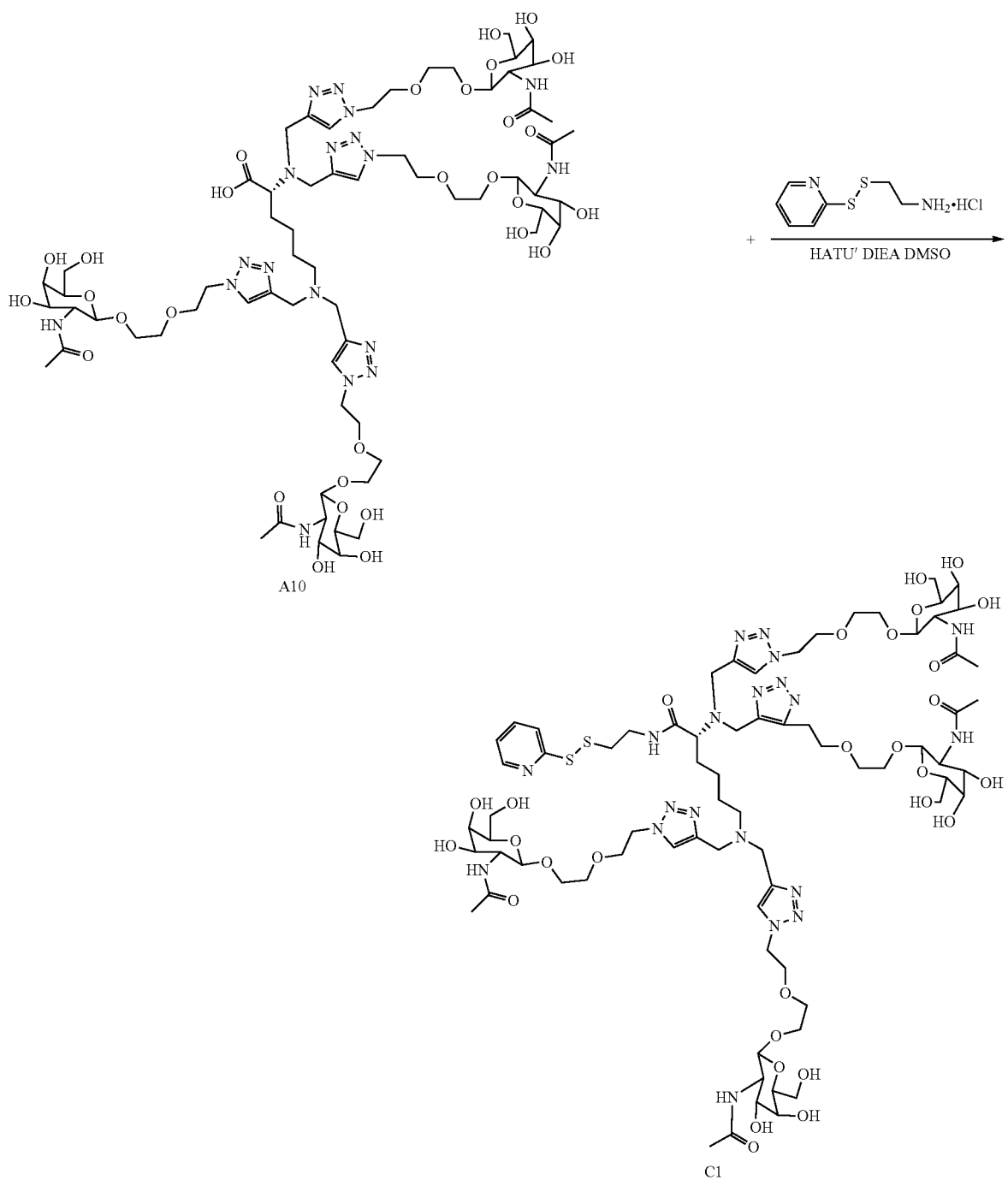

-continued
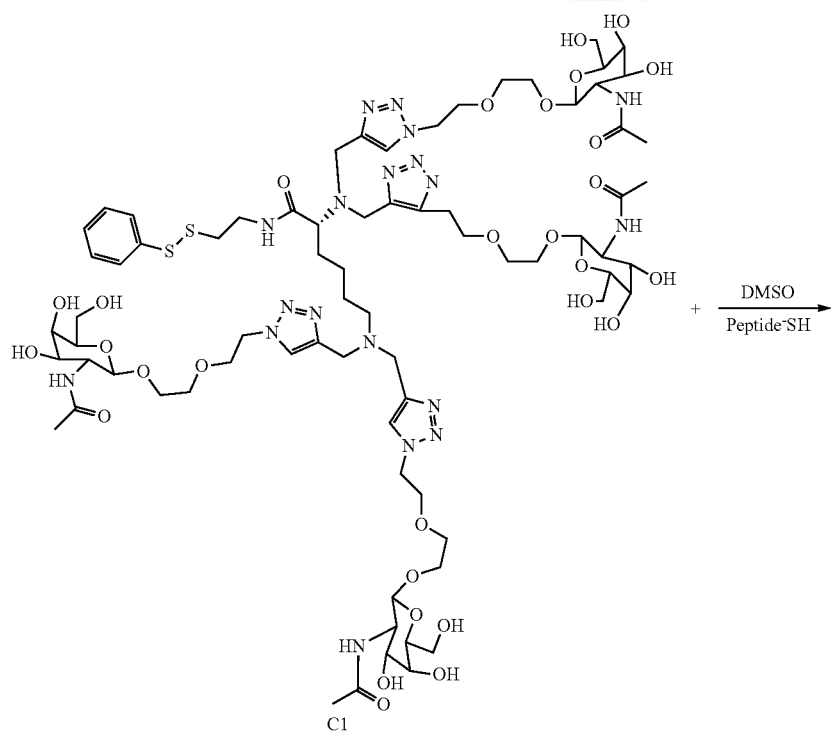
C1
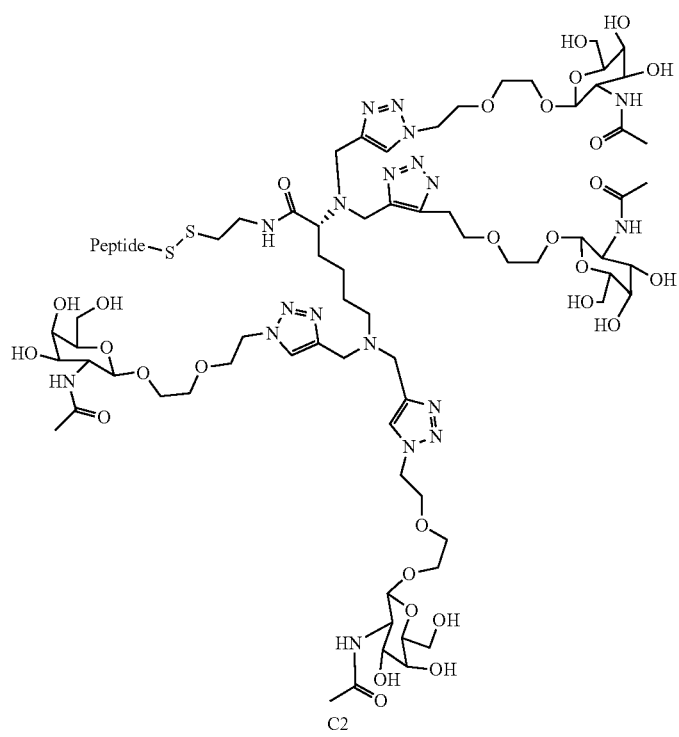
C2

Synthesis of N,N'-((2S,2'S,3S,3'S,4S,4'S,5S,5'S,6S,6'S)-2,2'-(((((4,4'-((((R)-6-(((1-(2-(2-(((2R,3R,4R,5R,6R)-3-acetamido-4,5-dihydroxy-6-(hydroxymethyl)tetrahydro-2H-pyran-2-yl)oxy)ethoxy)ethyl)-1H-1,2,3-triazol-4-yl)methyl)((1-(2-(2-(((2 S,3 S,4 S,5 S,6 S)-3-acetamido-4,5-dihydroxy-6-(hydroxymethyl)tetrahydro-2H-pyran-2-yl)oxy)ethoxy)ethyl)-1H-1,2,3-triazol-4-yl)methyl)amino)-1-oxo-1-((2-(pyridin-2-yldisulfanyl)ethyl)amino)hexan-2-yl)azanediyl)bis(methylene))bis(1H-1,2,3-triazole-4,1-diyl))bis(ethane-2,1-diyl))bis(oxy))bis(ethane-2,1-diyl))bis(oxy))bis(4,5-dihydroxy-6-(hydroxymethyl)tetrahydro-2H-pyran-3,2-diyl))diacetamide (Compound C1)

Into a 25-ml round bottom flask purged and maintained with an inert atmosphere of nitrogen was charged (S)-2,6-bis(bis((1-(2-(2-(((2R,3R,4R,5R,6R)-3-acetamido-4,5-dihydroxy-6-(hydroxymethyl)tetrahydro-2H-pyran-2-yl)oxy)ethoxy)ethyl)-1H-1,2,3-triazol-4-yl)methyl)amino)hexanoic acid (A10, 500 mg, 1.0 equiv), dimethyl sulfoxide (1.5 ml), 1-[bis(dimethylamino)methylene]-1H-1,2,3-triazolo[4,5-b]pyridinium 3-oxid hexafluorophosphate (HATU, 465 mg, 2 equiv.), and N,N-diisopropylethylamine (267 ul, 2.5 equiv.) in respective order. The reaction was aged at room temperature for 5 minutes. To the reaction mixture was added 2-(pyridin-2-yldisulfanyl) ethanamine hydrochloride (272 mg, 2 equiv.) and N,N-diisopropylethylamine (267 ul, 2.5 equiv.) in dimethyl sulfoxide (1.5 ml). The resulting mixture was aged at room temperature for 15 minutes and then, purified using Reverse-Phase Chromatography on C18 column, eluting with 0.05% TFA (v/v) in water and 0.05% (v/v) TFA in acetonitrile. After lyophilization, the product, Compound C1 (TGN-spdp), was obtained as a solid. MS (m/z): 1804.3 [M+H]

Synthesis of TGN-S-S-peptide (Compound C2)

Into a 4-dram scintillation vial purged and maintained with an inert atmosphere of nitrogen was charged dry peptide (cglfgeieelieeglenlidwwng all (D) SEQ ID NO: 1527, 100 mg, 1 equiv.). To the reaction was added TGN-spdp (C1, 195 mg, 3 equiv.) in dimethylsulfoxide (3.2 ml). The resulting mixture was aged at room temperature for 1 hour and then, purified using Reverse-Phase Chromatography on C18 column, eluting with 0.05% TFA (v/v) in water and 0.05% (v/v) TFA in acetonitrile. After lyophilization, the product, Compound C2 (TGN-S-S-peptide), was obtained as a solid. MS: theoretical MW (4470.852)

| m/z | Charge | Mass |
|---|---|---|
| 923.8 | 3 | 2774.4 |
| 1116.12 | 4 | 4468.48 |
| 1488.47 | 3 | 4468.41 |

Synthesis of Compounds C3a, C3b, and C4

Compounds C3a, C3b and C4 were prepared using steps and conditions as described in Scheme 4.

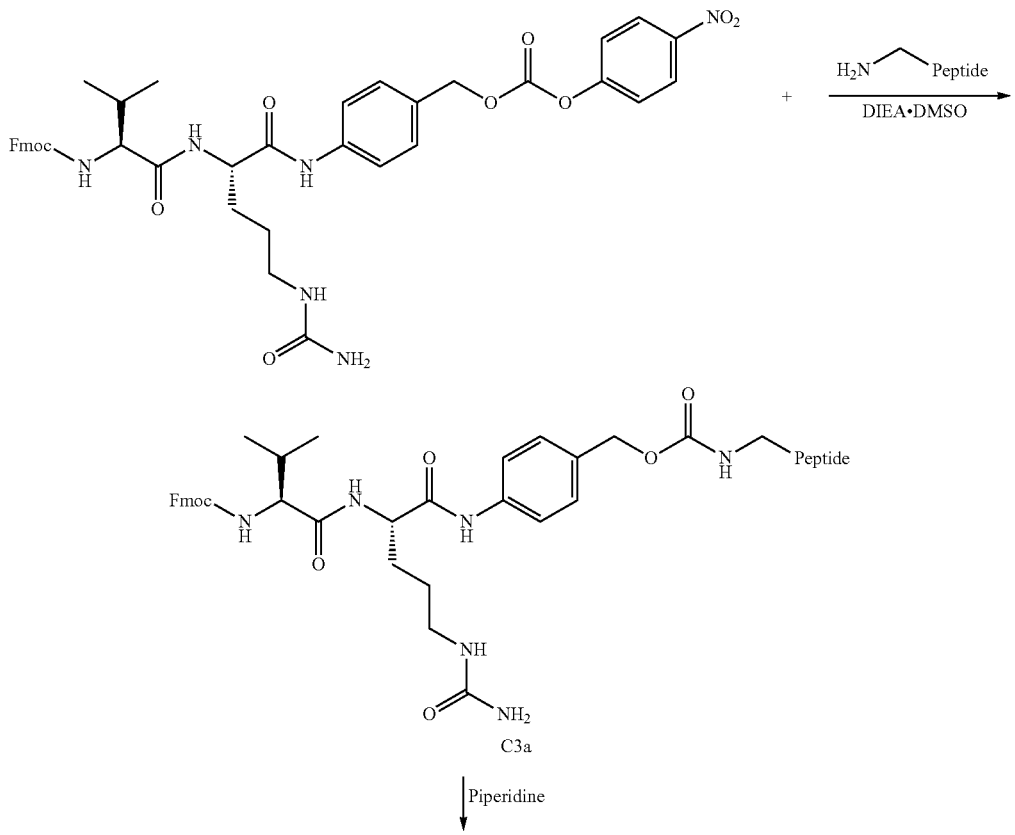

Scheme 4

-continued
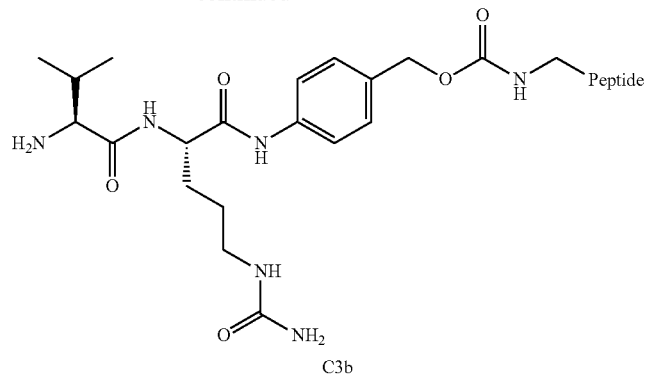
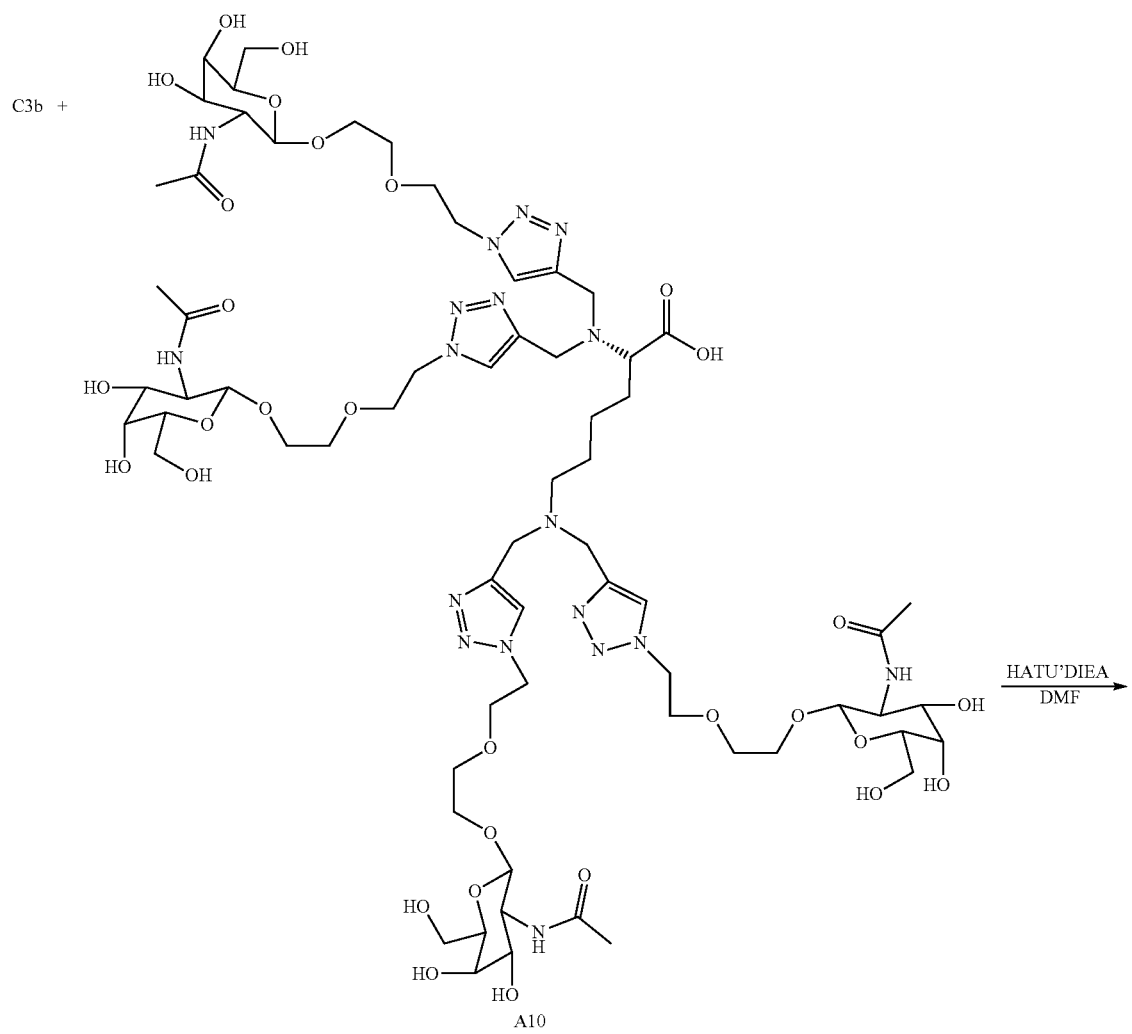

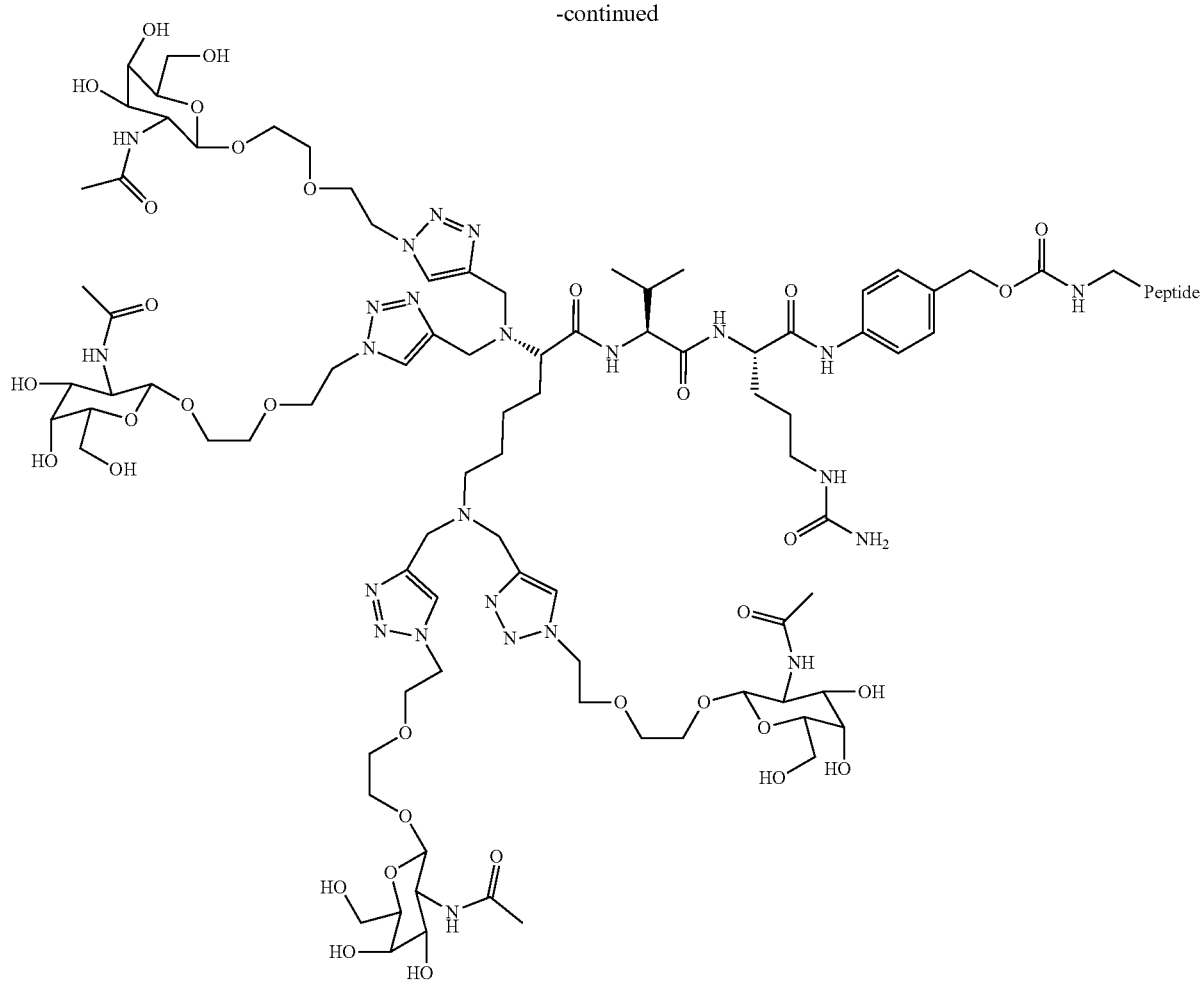

C4

Synthesis of Fmoc-ECL-peptide (C3a) and ECL-peptide (C3b)

Into a 4-dram scintillation vial purged and maintained with an inert atmosphere of nitrogen was charged peptide (glfgeieelieeglenlidwgng all (D), SEQ ID NO: 1074, 20 mg, 1 equiv.) in dimethyl sulfoxide (100 ul). To the reaction was added (9H-fluoren-9-yl)methyl ((S)-3-methyl-1-(((S)-1-((4-(((((4-nitrophenoxy)carbonyl)oxy)methyl)phenyl)amino)-1-oxo-5-ureidopentan-2-yl)amino)-1-oxobutan-2-yl)carbamate (13.26 mg, 2.2 equiv.) in dimethylsulfoxide (100 ul). The resulting mixture was aged at room temperature for 1 hour and then, purified using Reverse-Phase Chromatography on C18 column, eluting with 0.05% TFA (v/v) in water and 0.05% (v/v) TFA in acetonitrile. After lyophilization, the product, Fmoc-ECL-peptide (C3a), was obtained as a solid. MS (m/z): 1587.7 (M+2, theoretical and observed)

Into a 4-dram scintillation vial was charged Fmoc-ECL-peptide (C3a, 16.29 mg, 1.0 equiv.) in dimethylformamide (500 ul) and piperidine (3.11 ul, 6 equiv.) in respective order. The resulting reaction was aged at room temperature for 1 hour and then, purified using Reverse-Phase Chromatography on C18 column, eluting with 0.05% TFA (v/v) in water and 0.05% (v/v) TFA in acetonitrile. After lyophilization, the product, ECL-peptide (C3b), was obtained as a solid. MS (m/z): 1476.6 (M+2, theoretical), 1476.90 (M+2, observed)

Synthesis of TGN-ECL-peptide (C4)

Into a 4-dram scintillation vial purged and maintained with an inert atmosphere of nitrogen was charged TetraGal-NAc (A10, 25.2 mg, 4 equiv.) in dimethylformamide (193 ul), 1-[bis(dimethylamino)methylene]-1H-1,2,3-triazolo[4,5-b]pyridinium 3-oxid hexafluorophosphate (HATU, 2.2 mg, 1.5 equiv.), and N,N-Diisopropylethylamine (DIEA, 1.7 ul, 2.5 equiv.) in respective order. The reaction was aged at room temperature for 5 minutes. To the reaction mixture was added ECL-peptide (C3b, 11.37 mg, 1 equiv.) and N,N-diisopropylethylamine (1.7 ul, 2.5 equiv.) in dimethyl sulfoxide (193 ul). The resulting mixture was aged at room temperature for 15 minutes and then, purified using Reverse-Phase Chromatography on C18 column, eluting with 0.05% TFA (v/v) in water and 0.05% (v/v) TFA in Acetonitrile. After lyophilization, the product, TGN-ECL-peptide (C4), was obtained as a solid.

MS: theoretical MW (4568.86)

| m/z | charge | mass |
|---|---|---|
| 1140.33 | 4 | 4565.32 |
| 1520.78 | 3 | 4565.34 |

Synthesis of Compounds C5-C8

Compounds C5-C8 were prepared using steps and conditions as described in Scheme 5.

Scheme 5
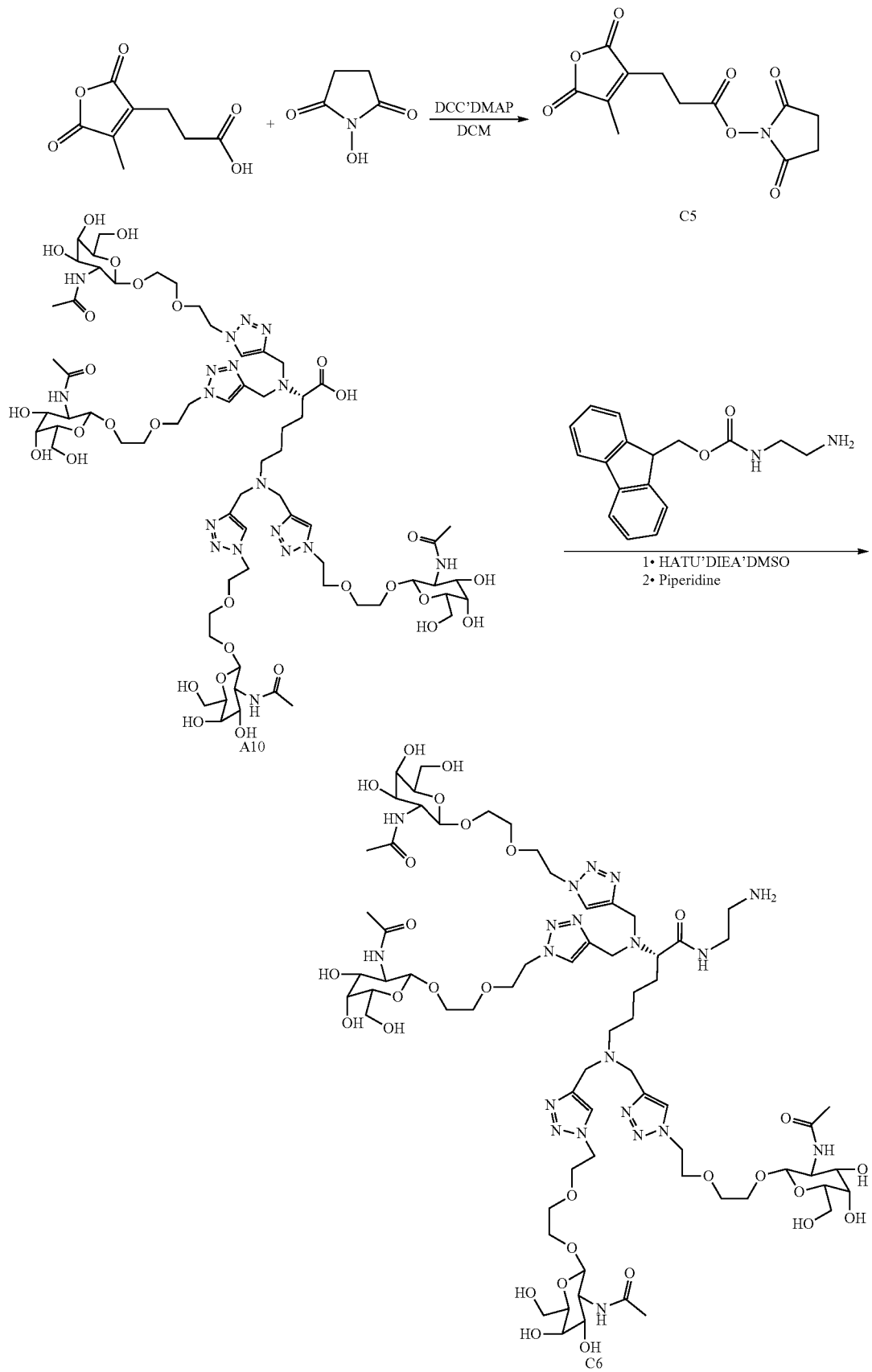

-continued
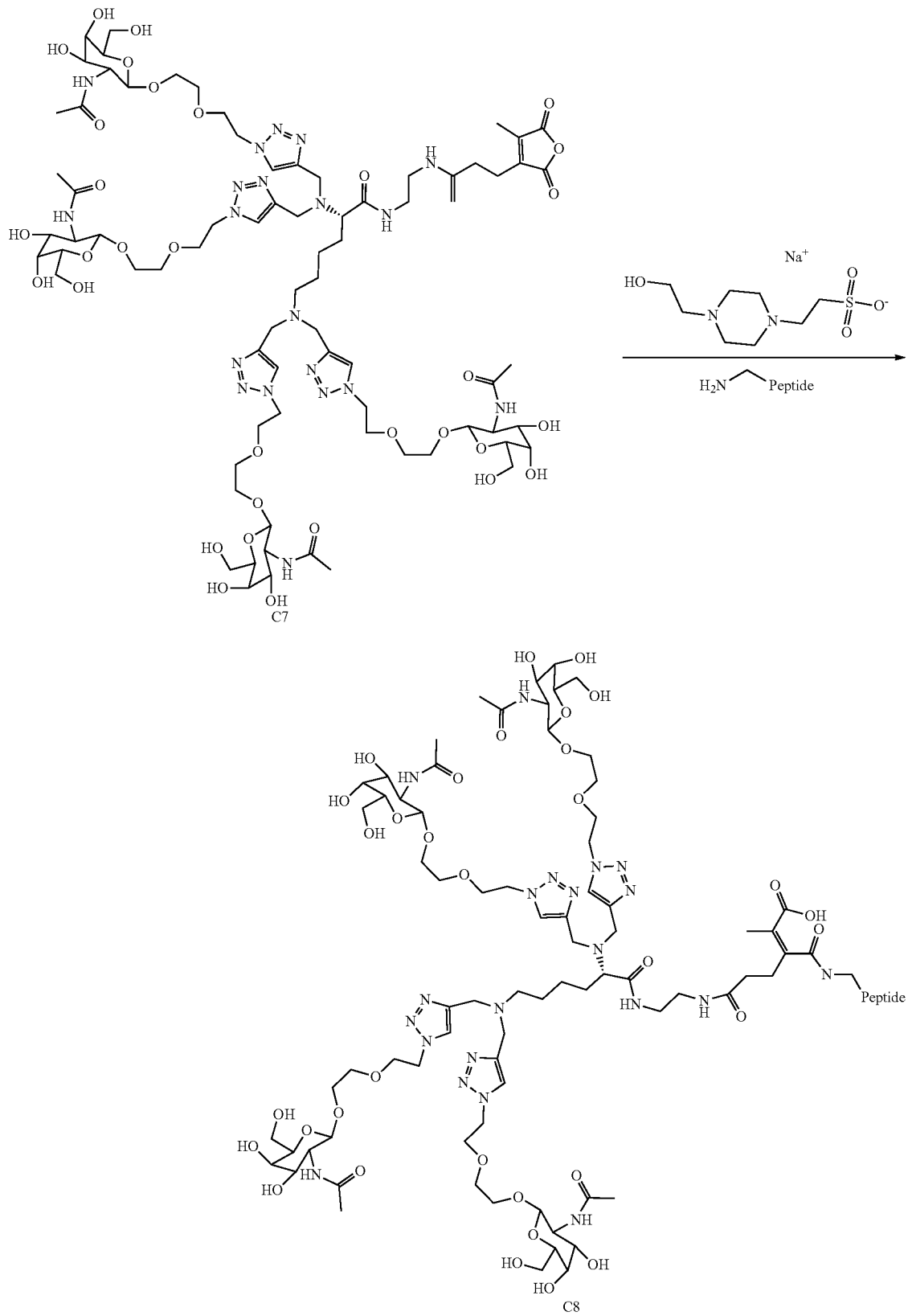

Synthesis of CDM-NHS (C5)

Into a 100-ml round bottom flask purged and maintained with an inert atmosphere of nitrogen was charged 3-(4-methyl-2,5-dioxo-2,5-dihydrofuran-3-yl)propanoic acid (2 g, 1 equiv.), 1-hydroxypyrrolidine-2,5-dione (NHS, 1.375 g, 1.1 equiv), 4-dimethylaminopyridine (DMAP, 0.066 g, 0.05 equiv.), and dichloromethane (50 ml) in respective order. To the reaction was added N,N'-dicyclohexylcarbodiimide (DCC, 11.95 ml, 1.0 M in DCM, 1.1 equiv.). The resulting reaction mixture was aged at room temperature overnight. The reaction mixture was filtered through a glass frit and concentrated in vacuo to give a tan solid which was dissolved in DCM and purified on a SiO$_2$ column (40 g), eluting with hexane/ethyl acetate to yield 2,5-dioxopyrrolidin-1-yl 3-(4-methyl-2,5-dioxo-2,5-dihydrofuran-3-yl)propanoate (CDM-NHS, C5) as a powder. MS (m/z): 282.1 [M+H]$^+$

Synthesis of NH$_2$-TGN (C6)

Into a 4-dram scintillation vial purged and maintained with an inert atmosphere of nitrogen was charged TetraGal-NAc (A10, 323 mg, 1 equiv.) in dimethyl sulfoxide (6.55 ml), 1-[bis(dimethylamino)methylene]-1H-1,2,3-triazolo[4,5-b]pyridinium 3-oxid hexafluorophosphate (HATU, 229 mg, 3 equiv.), and N,N-diisopropylethylamine (DIEA, 420 ul, 12 equiv.) in respective order. The reaction was aged at room temperature for 5 minutes. To the reaction mixture was added (9H-fluoren-9-yl)methyl (2-aminoethyl)carbamate (Fmoc-ethyl-diamine, 283 mg, 5 equiv.) in dimethyl sulfoxide (266 ul). The resulting reaction mixture was aged at room temperature for 5 minutes and then, purified using Reverse-Phase Chromatography on C18 column, eluting with 0.05% TFA (v/v) in water and 0.05% (v/v) TFA in acetonitrile. After lyophilization, the resulting solid was dissolved in DMF (1 ml) and added piperidine (496 ul, 25 equiv.). The resulting reaction mixture was aged at room temperature for 30 minutes and then, purified using Reverse-Phase Chromatography on C18 column, eluting with 0.05% TFA (v/v) in water and 0.05% (v/v) TFA in acetonitrile. After lyophilization, the product (NH$_2$-TGN, C6) was obtained as a solid. MS (m/z): 1678.7 [M+H]$^+$

Synthesis of CDM-TGN (C7)

Into a 10-ml round bottom flask purged and maintained with an inert atmosphere of nitrogen was charged NH$_2$-TGN (C6, 195 mg, 1 equiv.) in dimethyl sulfoxide (4 ml), CDM-NHS (C5, 131.2 mg, 4 equiv.) in dimethyl sulfoxide (1.64 ml), and N,N-diisopropylethylamine (DIEA, 60.9 ul, 3 equiv.) in respective order. The resulting reaction mixture was aged at room temperature for 1 hour and then, purified using Reverse-Phase Chromatography on C18 column, eluting with 0.05% TFA (v/v) in water and 0.05% (v/v) TFA in acetonitrile. After lyophilization, the product (CDM-TGN, C7) was obtained as a solid. MS (m/z): 1845.4 [M+H]$^+$

Synthesis of TGN-CDM peptide (C8)

Into a 4-dram scintillation vial purged and maintained with an inert atmosphere of nitrogen was charged peptide (glfgeieelieeglenlidwgng all (D), SEQ ID NO: 1074, 2.8 mg, 1 equiv.), dimethyl sulfoxide (30 ul), 10% glucose (106 ul), 1M Hepes buffer (pH=10.66, 160 ul) and water (56 ul) in respective order, maintaining pH at 8.85. The resulting reaction mixture was added to CDM-TGN (C7, 16.22 mg, 8 equiv.). The final pH was brought up from 8.12 to 8.5 by adding 1M Hepes buffer (150 ul). The CDM masking on the peptide was confirmed by MS and CE. MS (m/z): 1091.02 [M+4], 4368.08 observed, 4,446.698 theoretical CE: retention time at 27.234 min

Synthesis of Compounds C9 and C10

Compounds C9-C10 were prepared using steps and conditions as described in Scheme 6.

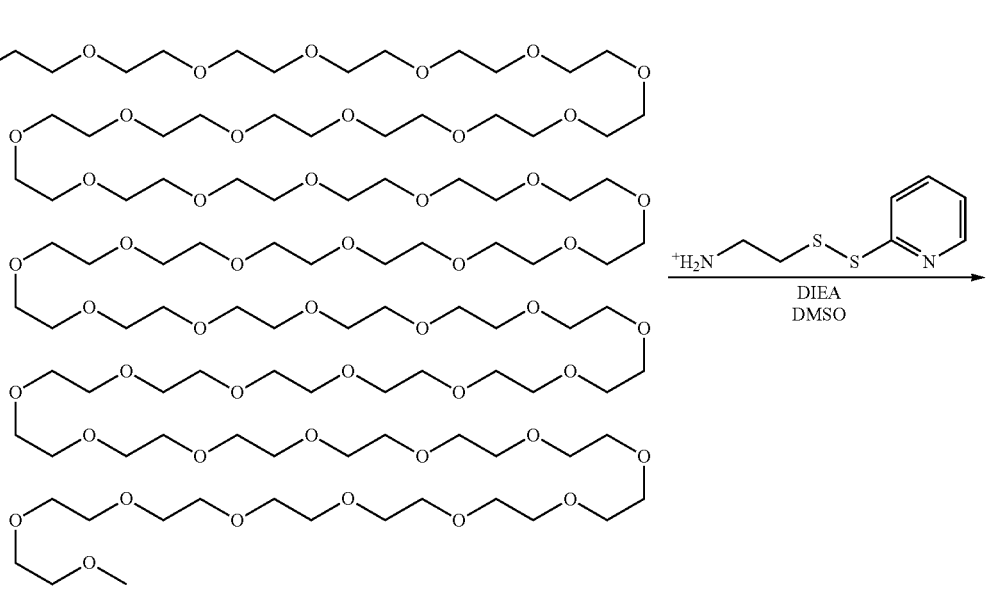

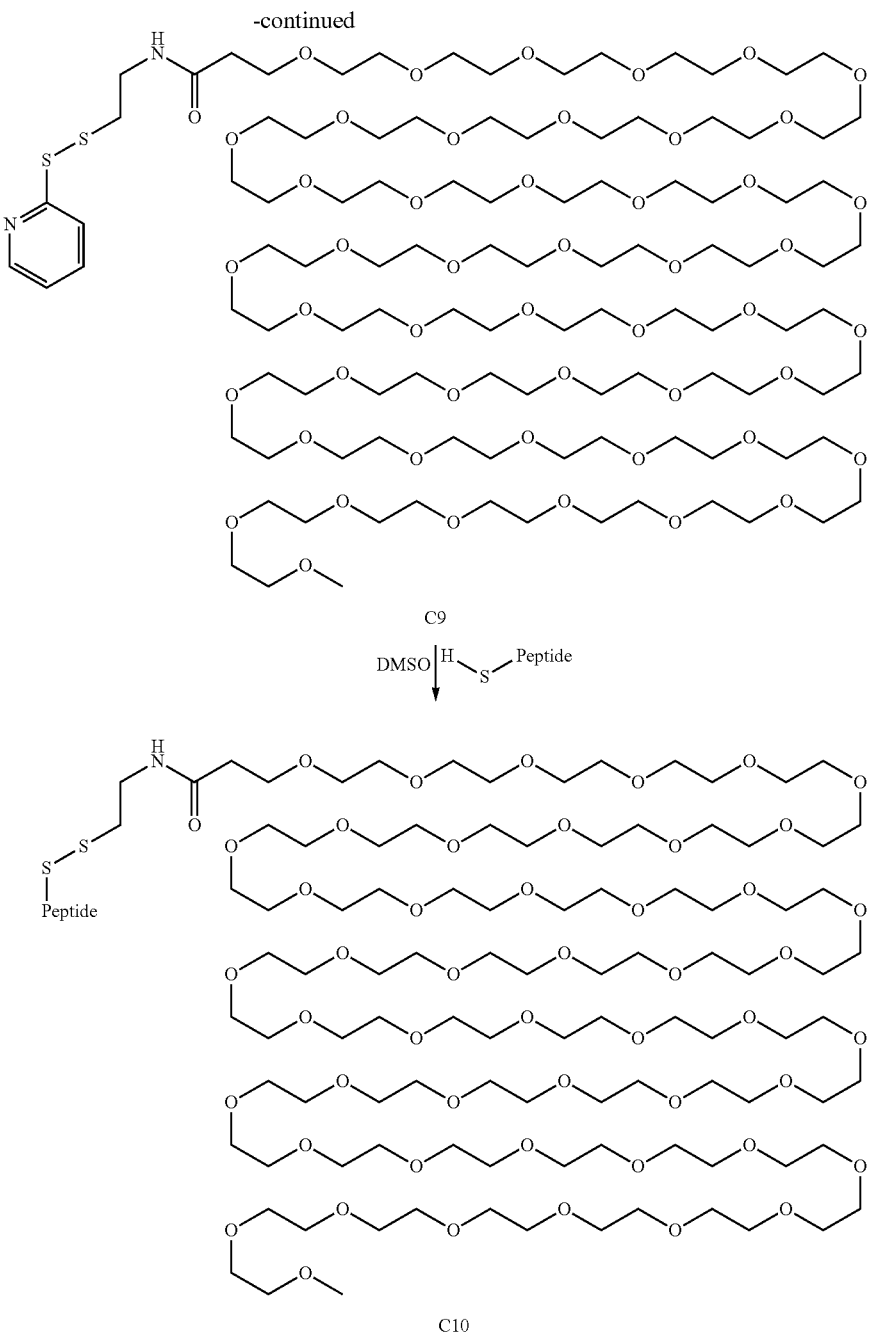

Synthesis of 2K-PEG-spdp (C9)

Into a 4-dram scintillation vial purged and maintained with an inert atmosphere of nitrogen was charged NHS-dPEG$_{49}$-ester (200 mg, 1 equiv.) in dimethylsulfoxide (883 ul), 2-(pyridin-2-yldisulfanyl)ethanamine (SPDP, 40.2 mg, 2.5 equiv.) in dimethyl sulfoxide (31 ul), and N,N-diisopropylethylamine (DIEA, 136 ul, 9 equiv.) in respective order. The resulting reaction mixture was aged at room temperature for 30 minutes and then, purified using Reverse-Phase Chromatography on C18 column, eluting with 0.05% TFA (v/v) in water and 0.05% (v/v) TFA in Acetonitrile. After lyophilization, the product (2K-PEG-spdp, C9) was obtained as a solid. MS (m/z): 796.5 [M+3], 1185.8 [M+2]

Synthesis of 2K-PEG-S-S-peptide (C10)

Into a 4-dram scintillation vial purged and maintained with an inert atmosphere of nitrogen was charged peptide (cgffgeiaelieeglknlidwwng, all D, SEQ ID NO: 1692, 10 mg, 1 equiv.) and 2K-PEG-spdp (C9, 25.9 mg, 3 equiv.) in dimethyl sulfoxide (914 ul) in respective order. The resulting reaction was aged at room temperature for 1 hour and then, purified using Reverse-Phase Chromatography on C18 column, eluting with 0.05% TFA (v/v) in water and 0.05% (v/v) TFA in acetonitrile. After lyophilization, the product (2K-PEG-S-S-peptide, C10) was obtained as a solid. MS (m/z): 1675.1[M+3], 5028.3 observed, 5,014.81 theoretical Formulation of Peptides and siRNA Conjugates Materials—

Tris base used for buffer preparation was obtained from Promega Corporation (Madison, Wis.). Sucrose used for tonicity modification was acquired from Macron Fine Chemicals (Center Valley, Pa.). All water used for dilutions was distilled, deionized to a resistivity of 18.2 MΩ*cm and filtered through a 0.2 μm filter. Unless otherwise indicated, all other reagents were acquired and used as received from Sigma Aldrich (St. Louis, Mo.).

Formulation Preparation for Sequential Dosing Experiments In Vivo—

Prior to formulation, purified peptide and siRNA solutions were dehydrated by lyophilization at −42° C. under $40 \times 10^{-3}$ mbar for 72 h. An isotonic sucrose formulation was prepared (292 mM, 10 wt %) and sterile filtered using aseptic handling techniques in a laminar flow hood. The lyophilized peptide product was either reconstituted in the sucrose formulation (for NHP model) or water (for mouse model) and allowed to equilibrate for 12 hr at 4° C. Rehydrated peptide was degassed via centrifugation (4000 g, 15 min) and sterile filtered using aseptic handling techniques. Following concentration analysis via UV and ICP spectroscopy (see Peptide Concentration Determination section), peptide stock solutions were diluted to target concentrations for dosing. Separately, siRNA was reconstituted in PBS and diluted to a target concentration for dosing. Both peptide and siRNA formulations were sterile filtered using aseptic handling techniques in a laminar flow hood. All formulations passed assessment for sterility and bioburden prior to dosing.

Formulation Preparation for Co-Dosing Experiments In Vivo—

Similar to previous formulations, purified peptide and siRNA solutions were dehydrated by lyophilization at −42° C. under $40 \times 10^{-3}$ mbar for 72 h. Peptide and siRNA were separately rehydrated in isotonic sucrose or water for analysis in NHP or mouse models, respectively. Peptide and siRNA stocks were sterile filtered using aseptic handling techniques and stored in sterile vials. Following analytical characterization of peptide/siRNA concentration and purity, co-dosing formulation were prepared by aseptically mixing peptide, siRNA, and the isotonic sucrose solution to the target concentrations for dosing. For NHP studies, solution pH was adjusted through the addition of a sucrose-tris buffer to a final formulation composition of 292 mM sucrose, 50 mM Tris (pH 7.50). Peptide or siRNA-only experimental controls were prepared using identical procedures and formulation compositions as co-dosing groups. All formulations passed assessment for sterility and bioburden prior to dosing.

Analysis of Peptides and siRNA Conjugates

Peptide Concentration Determination

UV Absorbance—

The concentration of peptides containing Tryptophan (W), Tyrosine (Y) or Cystine residues was determined based on the summation of theoretical molar extinction coefficients of the UV active residues. UV absorbance was measured at 280 nm using a Spectramax M5e UV spectrophotometer (Molecular Devices, Sunnyvale, Calif.)

Inductively Coupled Plasma Spectroscopy—

The concentration of peptide in constructs containing disulfide linker chemistry was determined indirectly by quantitating the amount of sulfur present in the conjugate, using an iCAP 6000 Inductively Coupled Plasma (ICP) Spectrophotometer (Thermo Fischer, Pittsburgh, Pa.). Samples were diluted with water containing) ppm Germanium (Ge) (Ricca Chemical Company, Arlington Tx.) internal standard. After injection, the sample was introduced to Nebulizer source with RF Power 1350 W, Aux gas flow 0.5 L/min and Nebulizer Gas flow 0.65 L/min. Sulfur content was quantitated using an external standard calibration curve (ranging from 0 ppm to 2 ppm) prepared from NIST Sulfur (S) ICP standard containing 1 ppm Ge as an internal standard. Raw ppm value for sulfur was reported and final peptide concentration was calculated using the peptide to sulfur molar ratio.

siRNA Concentration Determination

Inductively Coupled Plasma Spectroscopy—

The concentration of siRNA in constructs was determined directly by quantitating the amount of phosphorus present in the nucleotide backbone, using an iCAP 6000 Inductively Coupled Plasma (ICP) Spectrophotometer (Thermo Fischer, Pittsburgh, Pa.). Samples were diluted with water containing 1 ppm Germanium (Ge) (Ricca Chemical Company, Arlington Tx.) internal standard. After injection, the sample was introduced to Nebulizer source with RF Power 1350 W, Aux gas flow 0.5 L/min and Nebulizer Gas flow 0.65 L/min. Phosphorus content was quantitated using an external standard calibration curve (ranging from 0 ppm to 3 ppm) prepared from NIST Phosphorus ICP standard containing 1 ppm Ge as an internal standard. Raw ppm value for phosphorus was reported and final siRNA concentration was calculated using the siRNA to phosphorus molar ratio.

siRNA Duplex Purity siRNA duplex purity was determined by Capillary Electrophoresis using an Agilent G1600 (Agilent Technologies Sunnyvale, Ca.). Two techniques were employed based on siRNA conjugate composition: Capillary Zone Electrophoresis (CZE) or Micellar Electrokinetic Chromatography (MEKC). The sample was hydrodynamically injected onto a bare-fused silica capillary (Agilent extended light path 25 μm ID, 363 μm OD) at the anode end. The migration of analytes was initiated by applying positive 30 kV to the capillary. The siRNA signal was monitored by UV detection (abs. 260 nm). siRNA duplex purity was reported by area percent; excess single strand, functional duplex impurities and free peptide also reported. All siRNA duplex were >than 85% pure.

Peptide Purity Chromatographic Conditions

Peptide purity was determined by reverse-phase high performance liquid chromatography (RP-HPLC) using a Bio Basics 4 (150×4.6, 5μ particle size) column. The method conditions were as follows: Mobile Phase A: 0.1% trifluoroacetic acid (TFA) in water; Mobile Phase B: 0.1% TFA in acetonitrile; column temperature 60° C. and 1 ml/min flow rate. The gradient ramped from initial conditions of 5% B to 100% B in 60 minutes, followed by an 8 minute hold and returned to initial conditions. The peptide signal was monitored using fluorescence detection (ex. 280 nm and ex. 345 nm) and UV detection (abs. 214 nm). Peak purity was reported by area percent. All peptide conjugates were >70% pure.

Identity by Mass Spectrometry—Methodology and Data Analysis

Peptide and RNA samples were prepared for analysis by mass spectrometry by diluting stock sample solutions with DI water to create a working solution between 30-300 μg/mL. Mobile phase A (MPA) was an aqueous solution of 100 mM hexafluoroisopropanol (HFIP) and 8 mM Triethylamine (TEA), mobile phase B (MPB) was a 90:10 (v:v) acetonitrile:water mixture. Samples were analyzed by reverse-phase UPLC separation, followed by detection by Waters Synapt quadrupole time of flight (QToF) mass spectrometer operated in negative ion mode. The column used was a Waters Acquity UPLC BEH300 $C_4$ column (2.1 mm I.D.×100 mm length and the separation is performed at a flow rate of 0.35 mL/min at a column temperature of 65° C. The separation method starts with a 2 minute isocratic hold at 2% MPB, followed by a 5 minute gradient to 95% MPB, then another 2 minute isocratic hold at 95% MPB. The column is then equilibrated for 1 minute at 2% MPB prior to the next injection. The post-column eluent is introduced to the mass spectrometer by electrospray ionization. Data were collected ion negative ion mode between 650-4500 m/z, with no CID fragmentation. For all samples, a mass spectrum is obtained by averaging across the chromatographic peak in the MassLynx software. For RNA samples, raw mass spectra were deconvoluted from m/z to mass by using the MaxEnt1 algorithm in the MassLynx software. For peptide samples, the raw mass spectra were deconvoluted manually by determining charge states for all major peaks and calculating the resulting mass.

In Vitro DMD Assay

Cryopreserved primary Mouse hepatocytes (Bioreclamation, LLC) were placed into Collagen Type I coated 96-well plates at 25,000 cells per well in serum-containing InVitro-GRO CP media (Bioreclamation, LLC) and allowed 5 hours to attach. Media was replaced with InVitroGRO HI media and cells were treated with siRNA-IV at 125 nM [siRNA] for 1 hour. Media was replaced with InVitroGRO HI media and cells were treated for approximately 16 hours with experimental Peptide conjugates at various concentrations to establish a dose-response curve. Peptide conjugates were washed out after 16 hours with InVitroGRO HI media and cells allowed to incubate for an additional 24 hours. Cells were then lysed and mRNA expression of the siRNA target was measured by RT-qPCR (Applied Biosystems Taqman reagents). mRNA silencing activity of each Peptide conjugate was expressed as an enhancement above the baseline activity of 125 nM siRNA-IV alone with respect to the untreated cells and all siRNA target Ct values were normalized to PPIB mRNA for each well (dddCt) and summarized.

The structure of TGN-S-S-peptide is shown below and the activity data is listed in Table 5 (siRNA-IV concentration was kept at 125 mM).

TABLE 5

In Vitro Data

| Targeted peptide | Targeted peptide Dose (nM) | In vitro dddCt (vs. baseline SCE dose) |
| --- | --- | --- |
| TGN-S-S-SEQ ID NO: 1747 (D) | 5000 | -1.98 |
| TGN-S-S-SEQ ID NO: 1747 (D) | 1000 | -2.08 |
| TGN-S-S-SEQ ID NO: 1747 (D) | 200 | -1.53 |
| TGN-S-S-SEQ ID NO: 1747 (D) | 40 | -0.7 |
| TGN-S-S-SEQ ID NO: 1747 (D) | 8 | -0.23 |
| TGN-S-S-SEQ ID NO: 1748 (D) | 5000 | -2.01 |
| TGN-S-S-SEQ ID NO: 1748 (D) | 1000 | -1.92 |
| TGN-S-S-SEQ ID NO: 1748 (D) | 200 | -1.38 |
| TGN-S-S-SEQ ID NO: 1748 (D) | 40 | -0.5 |
| TGN-S-S-SEQ ID NO: 1748 (D) | 8 | -0.2 |
| TGN-S-S-SEQ ID NO: 1749 (D) | 5000 | -0.11 |
| TGN-S-S-SEQ ID NO: 1749 (D) | 1000 | -0.22 |
| TGN-S-S-SEQ ID NO: 1749 (D) | 200 | -0.26 |
| TGN-S-S-SEQ ID NO: 1749 (D) | 40 | -0.04 |
| TGN-S-S-SEQ ID NO: 1749 (D) | 8 | 0.02 |
| TGN-S-S-SEQ ID NO: 1751 (D) | 5000 | 0.01 |
| TGN-S-S-SEQ ID NO: 1751 (D) | 1000 | -0.05 |
| TGN-S-S-SEQ ID NO: 1751 (D) | 200 | 0.09 |
| TGN-S-S-SEQ ID NO: 1751 (D) | 40 | -0.12 |
| TGN-S-S-SEQ ID NO: 1751 (D) | 8 | -0.1 |

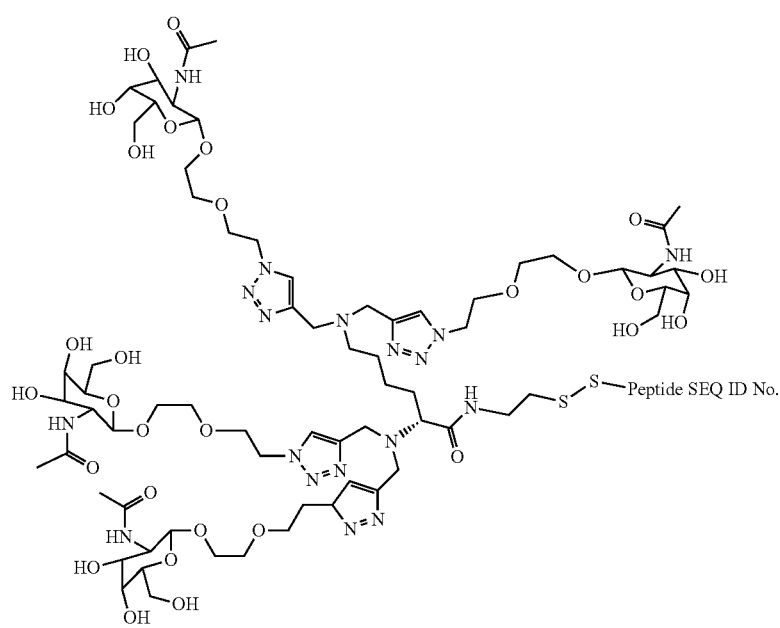

TABLE 5-continued

In Vitro Data

| Targeted peptide | Targeted peptide Dose (nM) | In vitro dddCt (vs. baseline SCE dose) |
|---|---|---|
| TGN-S-S-SEQ ID NO: 1752 (D) | 5000 | -1.02 |
| TGN-S-S-SEQ ID NO: 1752 (D) | 1000 | -0.95 |
| TGN-S-S-SEQ ID NO: 1752 (D) | 200 | -0.89 |
| TGN-S-S-SEQ ID NO: 1752 (D) | 40 | -0.48 |
| TGN-S-S-SEQ ID NO: 1752 (D) | 8 | -0.25 |
| TGN-S-S-SEQ ID NO: 1753 (D) | 5000 | -0.16 |
| TGN-S-S-SEQ ID NO: 1753 (D) | 1000 | -0.18 |
| TGN-S-S-SEQ ID NO: 1753 (D) | 200 | -0.2 |
| TGN-S-S-SEQ ID NO: 1753 (D) | 40 | 0.05 |
| TGN-S-S-SEQ ID NO: 1753 (D) | 8 | 0.15 |
| TGN-S-S-SEQ ID NO: 1755 (D) | 5000 | -0.24 |
| TGN-S-S-SEQ ID NO: 1755 (D) | 1000 | -0.49 |
| TGN-S-S-SEQ ID NO: 1755 (D) | 200 | -0.38 |
| TGN-S-S-SEQ ID NO: 1755 (D) | 40 | -0.24 |
| TGN-S-S-SEQ ID NO: 1755 (D) | 8 | -0.01 |
| TGN-S-S-SEQ ID NO: 1756 (D) | 5000 | -0.95 |
| TGN-S-S-SEQ ID NO: 1756 (D) | 1000 | -1.05 |
| TGN-S-S-SEQ ID NO: 1756 (D) | 200 | -0.76 |
| TGN-S-S-SEQ ID NO: 1756 (D) | 40 | -0.4 |
| TGN-S-S-SEQ ID NO: 1756 (D) | 8 | -0.15 |
| TGN-S-S-SEQ ID NO: 1758 (D) | 5000 | -0.64 |
| TGN-S-S-SEQ ID NO: 1758 (D) | 1000 | -0.77 |
| TGN-S-S-SEQ ID NO: 1758 (D) | 200 | -0.38 |
| TGN-S-S-SEQ ID NO: 1758 (D) | 40 | -0.02 |
| TGN-S-S-SEQ ID NO: 1758 (D) | 8 | 0.04 |
| TGN-S-S-Seq-ID-88 (D) | 5000 | -1.7 |
| TGN-S-S-SEQ ID NO: 1759 (D) | 1000 | -1.66 |
| TGN-S-S-SEQ ID NO: 1759 (D) | 200 | -1.65 |
| TGN-S-S-SEQ ID NO: 1759 (D) | 40 | -0.87 |
| TGN-S-S-SEQ ID NO: 1759 (D) | 8 | -0.15 |
| TGN-S-S-SEQ ID NO: 1760 (D) | 5000 | -1.46 |
| TGN-S-S-SEQ ID NO: 1760 (D) | 1000 | -1.8 |
| TGN-S-S-SEQ ID NO: 1760 (D) | 200 | -1.6 |
| TGN-S-S-SEQ ID NO: 1760 (D) | 40 | -1.01 |
| TGN-S-S-SEQ ID NO: 1760 (D) | 8 | -0.09 |
| TGN-S-S-SEQ ID NO: 1761 (D) | 5000 | -0.11 |
| TGN-S-S-SEQ ID NO: 1761 (D) | 1000 | -0.07 |
| TGN-S-S-SEQ ID NO: 1761 (D) | 200 | -0.22 |
| TGN-S-S-SEQ ID NO: 1761 (D) | 40 | -0.25 |
| TGN-S-S-SEQ ID NO: 1761 (D) | 8 | 0.08 |
| TGN-S-S-SEQ ID NO: 1762 (D) | 5000 | -0.08 |
| TGN-S-S-SEQ ID NO: 1762 (D) | 1000 | -0.39 |
| TGN-S-S-SEQ ID NO: 1762 (D) | 200 | -0.17 |
| TGN-S-S-SEQ ID NO: 1762 (D) | 40 | 0.03 |
| TGN-S-S-SEQ ID NO: 1762 (D) | 8 | -0.07 |
| TGN-S-S-SEQ ID NO: 1763 (D) | 5000 | -1.29 |
| TGN-S-S-SEQ ID NO: 1763 (D) | 1000 | -1.44 |
| TGN-S-S-SEQ ID NO: 1763 (D) | 200 | -1.26 |
| TGN-S-S-SEQ ID NO: 1763 (D) | 40 | -0.67 |
| TGN-S-S-SEQ ID NO: 1763 (D) | 8 | -0.13 |
| TGN-S-S-SEQ ID NO: 1764 (D) | 5000 | -0.75 |
| TGN-S-S-SEQ ID NO: 1764 (D) | 1000 | -0.62 |
| TGN-S-S-SEQ ID NO: 1764 (D) | 200 | -0.78 |
| TGN-S-S-SEQ ID NO: 1764 (D) | 40 | -0.41 |
| TGN-S-S-SEQ ID NO: 1764 (D) | 8 | -0.03 |
| TGN-S-S-SEQ ID NO: 1765(D) | 5000 | -1.23 |
| TGN-S-S-SEQ ID NO: 1765(D) | 1000 | -1.23 |
| TGN-S-S-SEQ ID NO: 1765(D) | 200 | -0.88 |
| TGN-S-S-SEQ ID NO: 1765(D) | 40 | -0.38 |
| TGN-S-S-SEQ ID NO: 1765(D) | 8 | -0.04 |
| TGN-S-S-SEQ ID NO: 1766 (D) | 5000 | -0.45 |
| TGN-S-S-SEQ ID NO: 1766 (D) | 1000 | -0.49 |
| TGN-S-S-SEQ ID NO: 1766 (D) | 200 | -0.31 |
| TGN-S-S-SEQ ID NO: 1766 (D) | 40 | -0.16 |
| TGN-S-S-SEQ ID NO: 1766 (D) | 8 | -0.05 |
| TGN-S-S-SEQ ID NO: 1767(D) | 5000 | -0.36 |
| TGN-S-S-SEQ ID NO: 1767(D) | 1000 | -0.4 |
| TGN-S-S-SEQ ID NO: 1767(D) | 200 | -0.16 |
| TGN-S-S-SEQ ID NO: 1767(D) | 40 | 0 |
| TGN-S-S-SEQ ID NO: 1767(D) | 8 | 0.15 |
| TGN-S-S-SEQ ID NO: 1768 (D) | 5000 | -1.73 |
| TGN-S-S-SEQ ID NO: 1768 (D) | 1000 | -1.55 |
| TGN-S-S-SEQ ID NO: 1768 (D) | 200 | -1.62 |
| TGN-S-S-SEQ ID NO: 1768 (D) | 40 | -1.04 |

TABLE 5-continued

In Vitro Data

| Targeted peptide | Targeted peptide Dose (nM) | In vitro dddCt (vs. baseline SCE dose) |
|---|---|---|
| TGN-S-S-SEQ ID NO: 1768 (D) | 8 | -0.34 |
| TGN-S-S-SEQ ID NO: 1769 (D) | 5000 | -1.83 |
| TGN-S-S-SEQ ID NO: 1769 (D) | 1000 | -1.82 |
| TGN-S-S-SEQ ID NO: 1769 (D) | 200 | -1.51 |
| TGN-S-S-SEQ ID NO: 1769 (D) | 40 | -0.71 |
| TGN-S-S-SEQ ID NO: 1769 (D) | 8 | -0.22 |
| TGN-S-S-SEQ ID NO: 1770 (D) | 5000 | -1.4 |
| TGN-S-S-SEQ ID NO: 1770 (D) | 1000 | -1.61 |
| TGN-S-S-SEQ ID NO: 1770 (D) | 200 | -1.13 |
| TGN-S-S-SEQ ID NO: 1770 (D) | 40 | -0.43 |
| TGN-S-S-SEQ ID NO: 1770 (D) | 8 | -0.27 |
| TGN-S-S-SEQ ID NO: 1771 (D) | 5000 | -1.97 |
| TGN-S-S-SEQ ID NO: 1771 (D) | 1000 | -1.7 |
| TGN-S-S-SEQ ID NO: 1771 (D) | 200 | -1.64 |
| TGN-S-S-SEQ ID NO: 1771 (D) | 40 | -0.79 |
| TGN-S-S-SEQ ID NO: 1771 (D) | 8 | -0.1 |
| TGN-S-S-SEQ ID NO: 1772 (D) | 5000 | -0.08 |
| TGN-S-S-SEQ ID NO: 1772 (D) | 1000 | -0.17 |
| TGN-S-S-SEQ ID NO: 1772 (D) | 200 | -0.15 |
| TGN-S-S-SEQ ID NO: 1772 (D) | 40 | -0.15 |
| TGN-S-S-SEQ ID NO: 1772 (D) | 8 | 0.03 |
| TGN-S-S-SEQ ID NO: 1746 (D) | 5000 | -0.04 |
| TGN-S-S-SEQ ID NO: 1746 (D) | 1000 | -0.09 |
| TGN-S-S-SEQ ID NO: 1746 (D) | 200 | -0.07 |
| TGN-S-S-SEQ ID NO: 1746 (D) | 40 | -0.09 |
| TGN-S-S-SEQ ID NO: 1746 (D) | 8 | -0.01 |
| TGN-S-S-SEQ ID NO: 1773 (D) | 5000 | 0.05 |
| TGN-S-S-SEQ ID NO: 1773 (D) | 1000 | 0.04 |
| TGN-S-S-SEQ ID NO: 1773 (D) | 200 | -0.06 |
| TGN-S-S-SEQ ID NO: 1773 (D) | 40 | -0.03 |
| TGN-S-S-SEQ ID NO: 1773 (D) | 8 | 0.03 |
| TGN-S-S-SEQ ID NO: 1774 (D) | 5000 | 0.37 |
| TGN-S-S-SEQ ID NO: 1774 (D) | 1000 | 0.17 |
| TGN-S-S-SEQ ID NO: 1774 (D) | 200 | 0.13 |
| TGN-S-S-SEQ ID NO: 1774 (D) | 40 | 0.14 |
| TGN-S-S-SEQ ID NO: 1774 (D) | 8 | 0.08 |
| TGN-S-S-SEQ ID NO: 1775 (D) | 5000 | -0.37 |
| TGN-S-S-SEQ ID NO: 1775 (D) | 1000 | -0.11 |
| TGN-S-S-SEQ ID NO: 1775 (D) | 200 | -0.14 |
| TGN-S-S-SEQ ID NO: 1775 (D) | 40 | -0.14 |
| TGN-S-S-SEQ ID NO: 1775 (D) | 8 | -0.1 |
| TGN-S-S-SEQ ID NO: 1710 (D) | 5000 | -3.45 |
| TGN-S-S-SEQ ID NO: 1710 (D) | 1000 | -3.1 |
| TGN-S-S-SEQ ID NO: 1710 (D) | 200 | -2.2 |
| TGN-S-S-SEQ ID NO: 1710 (D) | 40 | -0.71 |
| TGN-S-S-SEQ ID NO: 1710 (D) | 8 | -0.14 |
| TGN-S-S-SEQ ID NO: 1741 (L) | 15000 | -0.25 |
| TGN-S-S-SEQ ID NO: 1741 (L) | 3000 | -0.4 |
| TGN-S-S-SEQ ID NO: 1741 (L) | 600 | -0.08 |
| TGN-S-S-SEQ ID NO: 1741 (L) | 120 | 0.02 |
| TGN-S-S-SEQ ID NO: 1741 (L) | 24 | 0 |
| TGN-S-S-SEQ ID NO: 1776 (D) | 5000 | -0.27 |
| TGN-S-S-SEQ ID NO: 1776 (D) | 1000 | -0.29 |
| TGN-S-S-SEQ ID NO: 1776 (D) | 200 | -0.17 |
| TGN-S-S-SEQ ID NO: 1776 (D) | 40 | -0.12 |
| TGN-S-S-SEQ ID NO: 1776 (D) | 8 | -0.09 |
| TGN-S-S-SEQ ID NO: 1741 (D) | 5000 | -2.83 |
| TGN-S-S-SEQ ID NO: 1741 (D) | 1000 | -2.34 |
| TGN-S-S-SEQ ID NO: 1741 (D) | 200 | -1.36 |
| TGN-S-S-SEQ ID NO: 1741 (D) | 40 | -0.67 |
| TGN-S-S-SEQ ID NO: 1741 (D) | 8 | -0.23 |
| TGN-S-S-SEQ ID NO: 1709 (D) | 5000 | -0.89 |
| TGN-S-S-SEQ ID NO: 1709 (D) | 1000 | -1.03 |
| TGN-S-S-SEQ ID NO: 1709 (D) | 200 | -0.92 |
| TGN-S-S-SEQ ID NO: 1709 (D) | 40 | -0.62 |
| TGN-S-S-SEQ ID NO: 1709 (D) | 8 | -0.43 |
| TGN-S-S-SEQ ID NO: 1733 (D) | 5000 | -2.7 |
| TGN-S-S-SEQ ID NO: 1733 (D) | 1000 | -2.64 |
| TGN-S-S-SEQ ID NO: 1733 (D) | 200 | -1.39 |
| TGN-S-S-SEQ ID NO: 1733 (D) | 40 | -0.87 |
| TGN-S-S-SEQ ID NO: 1733 (D) | 8 | -0.51 |
| TGN-S-S-SEQ ID NO: 1702 (D) | 5000 | -2.47 |
| TGN-S-S-SEQ ID NO: 1702 (D) | 1000 | -2.1 |
| TGN-S-S-SEQ ID NO: 1702 (D) | 200 | -1.75 |

TABLE 5-continued

In Vitro Data

| Targeted peptide | Targeted peptide Dose (nM) | In vitro dddCt (vs. baseline SCE dose) |
|---|---|---|
| TGN-S-S-SEQ ID NO: 1702 (D) | 40 | -1.09 |
| TGN-S-S-SEQ ID NO: 1702 (D) | 8 | -0.68 |
| TGN-S-S-SEQ ID NO: 1776 (D) | 5000 | -0.01 |
| TGN-S-S-SEQ ID NO: 1776 (D) | 1000 | -0.21 |
| TGN-S-S-SEQ ID NO: 1776 (D) | 200 | -0.26 |
| TGN-S-S-SEQ ID NO: 1776 (D) | 40 | -0.1 |
| TGN-S-S-SEQ ID NO: 1776 (D) | 8 | 0.05 |
| TGN-S-S-SEQ ID NO: 1741 (D) | 5000 | -0.27 |
| TGN-S-S-SEQ ID NO: 1741 (D) | 1000 | -0.06 |
| TGN-S-S-SEQ ID NO: 1741 (D) | 200 | 0.08 |
| TGN-S-S-SEQ ID NO: 1741 (D) | 40 | 0.28 |
| TGN-S-S-SEQ ID NO: 1741 (D) | 8 | -0.04 |
| TGN-S-S-SEQ ID NO: 1738 (D) | 5000 | -2.19 |
| TGN-S-S-SEQ ID NO: 1738 (D) | 1000 | -1.69 |
| TGN-S-S-SEQ ID NO: 1738 (D) | 200 | -1.57 |
| TGN-S-S-SEQ ID NO: 1738 (D) | 40 | -0.67 |
| TGN-S-S-SEQ ID NO: 1738 (D) | 8 | -0.24 |
| TGN-S-S-SEQ ID NO: 1740 (L) | 5000 | -0.06 |
| TGN-S-S-SEQ ID NO: 1740 (L) | 1000 | -0.06 |
| TGN-S-S-SEQ ID NO: 1740 (L) | 200 | -0.07 |
| TGN-S-S-SEQ ID NO: 1740 (L) | 40 | 0.13 |
| TGN-S-S-SEQ ID NO: 1740 (L) | 8 | 0 |
| TGN-S-S-SEQ ID NO: 1741 (L) | 5000 | -0.58 |
| TGN-S-S-SEQ ID NO: 1741 (L) | 1000 | 0.98 |
| TGN-S-S-SEQ ID NO: 1741 (L) | 200 | -0.25 |
| TGN-S-S-SEQ ID NO: 1741 (L) | 40 | -0.11 |
| TGN-S-S-SEQ ID NO: 1741 (L) | 8 | 0.03 |
| TGN-S-S-SEQ ID NO: 1740 (D) | 5000 | -2.98 |
| TGN-S-S-SEQ ID NO: 1740 (D) | 1000 | -2.3 |
| TGN-S-S-SEQ ID NO: 1740 (D) | 200 | -1.29 |
| TGN-S-S-SEQ ID NO: 1740 (D) | 40 | -0.46 |
| TGN-S-S-SEQ ID NO: 1740 (D) | 8 | -0.19 |
| TGN-S-S-SEQ ID NO: 1777 (D) | 5000 | 0.09 |
| TGN-S-S-SEQ ID NO: 1777 (D) | 1000 | -0.13 |
| TGN-S-S-SEQ ID NO: 1777 (D) | 200 | -0.13 |
| TGN-S-S-SEQ ID NO: 1777 (D) | 40 | 0.28 |
| TGN-S-S-SEQ ID NO: 1777 (D) | 8 | -0.18 |
| TGN-S-S-Seq-ID-111 (D) | 5000 | -1.4 |
| TGN-S-S-SEQ ID NO: 1778 (D) | 1000 | -1.54 |
| TGN-S-S-SEQ ID NO: 1778 (D) | 200 | -0.91 |
| TGN-S-S-SEQ ID NO: 1778 (D) | 40 | -0.57 |
| TGN-S-S-SEQ ID NO: 1778 (D) | 8 | -0.38 |
| TGN-S-S-SEQ ID NO: 1779 (D) | 5000 | -1.51 |
| TGN-S-S-SEQ ID NO: 1779 (D) | 1000 | -1.52 |
| TGN-S-S-SEQ ID NO: 1779 (D) | 200 | -1.29 |
| TGN-S-S-SEQ ID NO: 1779 (D) | 40 | -0.24 |
| TGN-S-S-SEQ ID NO: 1779 (D) | 8 | -0.18 |
| TGN-S-S-SEQ ID NO: 1780 (D) | 5000 | -3.2 |
| TGN-S-S-SEQ ID NO: 1780 (D) | 1000 | 0.18 |
| TGN-S-S-SEQ ID NO: 1780 (D) | 200 | -2.83 |
| TGN-S-S-SEQ ID NO: 1780 (D) | 40 | -1.05 |
| TGN-S-S-SEQ ID NO: 1780 (D) | 8 | -0.11 |
| TGN-S-S-SEQ ID NO: 1781 (D) | 5000 | 0.01 |
| TGN-S-S-SEQ ID NO: 1781 (D) | 1000 | -0.01 |
| TGN-S-S-SEQ ID NO: 1781 (D) | 200 | 0.03 |
| TGN-S-S-SEQ ID NO: 1781 (D) | 40 | -0.02 |
| TGN-S-S-SEQ ID NO: 1781 (D) | 8 | -0.01 |
| TGN-S-S-SEQ-ID NO 115 (D) | 5000 | -0.17 |
| TGN-S-S-SEQ ID NO: 1782 (D) | 1000 | -0.21 |
| TGN-S-S-SEQ ID NO: 1782 (D) | 200 | -0.17 |
| TGN-S-S-SEQ ID NO: 1782 (D) | 40 | 0.43 |
| TGN-S-S-SEQ ID NO: 1782 (D) | 8 | -0.14 |
| TGN-S-S-SEQ ID NO: 1783 (D) | 5000 | -0.98 |
| TGN-S-S-SEQ ID NO: 1783 (D) | 1000 | -1.03 |
| TGN-S-S-SEQ ID NO: 1783 (D) | 200 | -0.61 |
| TGN-S-S-SEQ ID NO: 1783 (D) | 40 | -0.31 |
| TGN-S-S-SEQ ID NO: 1783 (D) | 8 | -0.15 |
| TGN-S-S-SEQ ID NO: 1784 (D) | 5000 | -0.81 |
| TGN-S-S-SEQ ID NO: 1784 (D) | 1000 | -1.01 |
| TGN-S-S-SEQ ID NO: 1784 (D) | 200 | -0.57 |
| TGN-S-S-SEQ ID NO: 1784 (D) | 40 | -0.22 |
| TGN-S-S-SEQ ID NO: 1784 (D) | 8 | 0.07 |
| TGN-S-S-SEQ ID NO: 1785 (D) | 5000 | -2.03 |
| TGN-S-S-SEQ ID NO: 1785 (D) | 1000 | 0.84 |

TABLE 5-continued

In Vitro Data

| Targeted peptide | Targeted peptide Dose (nM) | In vitro dddCt (vs. baseline SCE dose) |
|---|---|---|
| TGN-S-S-SEQ ID NO: 1785 (D) | 200 | -1.68 |
| TGN-S-S-SEQ ID NO: 1785 (D) | 40 | -0.44 |
| TGN-S-S-SEQ ID NO: 1785 (D) | 8 | -0.1 |
| TGN-S-S-SEQ ID NO: 1786 (D) | 5000 | 0.18 |
| TGN-S-S-SEQ ID NO: 1786 (D) | 1000 | 0.06 |
| TGN-S-S-SEQ ID NO: 1786 (D) | 200 | 0.06 |
| TGN-S-S-SEQ ID NO: 1786 (D) | 40 | 0.13 |
| TGN-S-S-SEQ ID NO: 1786 (D) | 8 | 0.17 |
| TGN-S-S-SEQ ID NO: 120 (D) | 5000 | -3.34 |
| TGN-S-S-SEQ ID NO: 1788 (D) | 1000 | -2.8 |
| TGN-S-S-SEQ ID NO: 1788 (D) | 200 | -1.91 |
| TGN-S-S-SEQ ID NO: 1788 (D) | 40 | -0.18 |
| TGN-S-S-SEQ ID NO: 1788 (D) | 8 | -0.17 |
| TGN-S-S-SEQ ID NO: 1793 (D) | 5000 | -2.65 |
| TGN-S-S-SEQ ID NO: 1793 (D) | 1000 | -2.75 |
| TGN-S-S-SEQ ID NO: 1793 (D) | 200 | -2.36 |
| TGN-S-S-SEQ ID NO: 1793 (D) | 40 | -1.04 |
| TGN-S-S-SEQ ID NO: 1793 (D) | 8 | -0.02 |
| TGN-S-S-SEQ ID NO: 1794 (D) | 5000 | -2.61 |
| TGN-S-S-SEQ ID NO: 1794 (D) | 1000 | -2.71 |
| TGN-S-S-SEQ ID NO: 1794 (D) | 200 | -2.22 |
| TGN-S-S-SEQ ID NO: 1794 (D) | 40 | -0.8 |
| TGN-S-S-SEQ ID NO: 1794 (D) | 8 | -0.09 |
| TGN-S-S-SEQ ID NO: 1795 (D) | 5000 | -0.71 |
| TGN-S-S-SEQ ID NO: 1795 (D) | 1000 | 0.94 |
| TGN-S-S-SEQ ID NO: 1795 (D) | 200 | -0.71 |
| TGN-S-S-SEQ ID NO: 1795 (D) | 40 | -0.33 |
| TGN-S-S-SEQ ID NO: 1795 (D) | 8 | -0.1 |
| TGN-S-S-SEQ ID NO: 1796 (D) | 5000 | -1.81 |
| TGN-S-S-SEQ ID NO: 1796 (D) | 1000 | -1.98 |
| TGN-S-S-SEQ ID NO: 1796 (D) | 200 | -1.13 |
| TGN-S-S-SEQ ID NO: 1796 (D) | 40 | -0.56 |
| TGN-S-S-SEQ ID NO: 1796 (D) | 8 | 0.05 |
| TGN-S-S-SEQ ID NO: 1797 (D) | 5000 | 0.24 |
| TGN-S-S-SEQ ID NO: 1797 (D) | 1000 | 0.05 |
| TGN-S-S-SEQ ID NO: 1797 (D) | 200 | 0.08 |
| TGN-S-S-SEQ ID NO: 1797 (D) | 40 | 0.41 |
| TGN-S-S-SEQ ID NO: 1797 (D) | 8 | 0 |
| TGN-S-S-SEQ ID NO: 1798 (D) | 5000 | -0.18 |
| TGN-S-S-SEQ ID NO: 1798 (D) | 1000 | -0.26 |
| TGN-S-S-SEQ ID NO: 1798 (D) | 200 | -0.13 |
| TGN-S-S-SEQ ID NO: 1798 (D) | 40 | -0.69 |
| TGN-S-S-SEQ ID NO: 1798 (D) | 8 | -0.09 |
| TGN-S-S-SSEQ ID NO: 1799(D) | 5000 | -2.22 |
| TGN-S-S-SSEQ ID NO: 1799(D) | 1000 | -2.13 |
| TGN-S-S-SSEQ ID NO: 1799(D) | 200 | -1.63 |
| TGN-S-S-SSEQ ID NO: 1799(D) | 40 | -0.45 |
| TGN-S-S-SSEQ ID NO: 1799(D) | 8 | 0.03 |
| TGN-S-S-SEQ ID NO: 1800 (D) | 5000 | -1.46 |
| TGN-S-S-SEQ ID NO: 1800 (D) | 1000 | 0.96 |
| TGN-S-S-SEQ ID NO: 1800 (D) | 200 | -1.11 |
| TGN-S-S-SEQ ID NO: 1800 (D) | 40 | -0.33 |
| TGN-S-S-SEQ ID NO: 1800 (D) | 8 | 0.14 |
| TGN-S-S-SEQ ID NO: 1710 (D) | 5000 | -4.01 |
| TGN-S-S-SEQ ID NO: 1710 (D) | 1000 | -3.47 |
| TGN-S-S-SEQ ID NO: 1710 (D) | 200 | -2.74 |
| TGN-S-S-SEQ ID NO: 1710 (D) | 40 | -1.06 |
| TGN-S-S-SEQ ID NO: 1710 (D) | 8 | -0.13 |
| TGN-S-S-SEQ ID NO: 1704 (D) | 5000 | -1.74 |
| TGN-S-S-SEQ ID NO: 1704 (D) | 1000 | -1.76 |
| TGN-S-S-SEQ ID NO: 1704 (D) | 200 | -1.28 |
| TGN-S-S-SEQ ID NO: 1704 (D) | 40 | 0.1 |
| TGN-S-S-SEQ ID NO: 1704 (D) | 8 | -0.09 |
| TGN-S-S-SEQ ID NO: 1733(D) | 5000 | -2.46 |
| TGN-S-S-SEQ ID NO: 1733(D) | 1000 | -2.42 |
| TGN-S-S-SEQ ID NO: 1733(D) | 200 | -1.42 |
| TGN-S-S-SEQ ID NO: 1733(D) | 40 | -0.72 |
| TGN-S-S-SEQ ID NO: 1733(D) | 8 | -0.19 |
| TGN-S-S-SEQ ID NO: 1730 (D) | 1000 | -3.39 |
| TGN-S-S-SEQ ID NO: 1730 (D) | 200 | -1 |
| TGN-S-S-SEQ ID NO: 1730 (D) | 40 | -0.08 |
| TGN-S-S-SEQ ID NO: 1730 (D) | 8 | 0.11 |
| TGN-S-S-SEQ ID NO: 1705 (D) | 5000 | -1.1 |
| TGN-S-S-SEQ ID NO: 1705 (D) | 1000 | 0.99 |

TABLE 5-continued

In Vitro Data

| Targeted peptide | Targeted peptide Dose (nM) | In vitro dddCt (vs. baseline SCE dose) |
|---|---|---|
| TGN-S-S-SEQ ID NO: 1705 (D) | 200 | -0.68 |
| TGN-S-S-SEQ ID NO: 1705 (D) | 40 | -0.1 |
| TGN-S-S-SEQ ID NO: 1705 (D) | 8 | 0.16 |
| TGN-S-S-SEQ ID NO: 1708 (L) | 5000 | 0.14 |
| TGN-S-S-SEQ ID NO: 1708 (L) | 1000 | 0.07 |
| TGN-S-S-SEQ ID NO: 1708 (L) | 200 | 0.04 |
| TGN-S-S-SEQ ID NO: 1708 (L) | 40 | 0.06 |
| TGN-S-S-SEQ ID NO: 1708 (L) | 8 | 0 |
| TGN-S-S-SEQ ID NO: 1711 (L) | 5000 | -0.18 |
| TGN-S-S-SEQ ID NO: 1711 (L) | 1000 | -0.07 |
| TGN-S-S-SEQ ID NO: 1711 (L) | 200 | -0.03 |
| TGN-S-S-SEQ ID NO: 1711 (L) | 40 | -0.13 |
| TGN-S-S-SEQ ID NO: 1711 (L) | 8 | -0.07 |
| TGN-S-S-SEQ ID NO: 1712 (L) | 5000 | -0.2 |
| TGN-S-S-SEQ ID NO: 1712 (L) | 1000 | 0 |
| TGN-S-S-SEQ ID NO: 1712 (L) | 200 | -0.08 |
| TGN-S-S-SEQ ID NO: 1712 (L) | 40 | 0.07 |
| TGN-S-S-SEQ ID NO: 1712 (L) | 8 | 0.03 |
| TGN-S-S-SEQ ID NO: 1713 (L) | 5000 | 0 |
| TGN-S-S-SEQ ID NO: 1713 (L) | 1000 | -0.04 |
| TGN-S-S-SEQ ID NO: 1713 (L) | 200 | 0.15 |
| TGN-S-S-SEQ ID NO: 1713 (L) | 40 | 0.21 |
| TGN-S-S-SEQ ID NO: 1713 (L) | 8 | 0.21 |
| TGN-S-S-SEQ ID NO: 1715 (L) | 5000 | -0.3 |
| TGN-S-S-SEQ ID NO: 1715 (L) | 1000 | -0.1 |
| TGN-S-S-SEQ ID NO: 1715 (L) | 200 | -0.04 |
| TGN-S-S-SEQ ID NO: 1715 (L) | 40 | -0.02 |
| TGN-S-S-SEQ ID NO: 1715 (L) | 8 | 0.07 |
| TGN-S-S-Seq-ID-37 (L) | 5000 | -0.79 |
| TGN-S-S-Seq-ID-37 (L) | 1000 | -0.19 |
| TGN-S-S-Seq-ID-37 (L) | 200 | -0.01 |
| TGN-S-S-Seq-ID-37 (L) | 40 | 0.14 |
| TGN-S-S-Seq-ID-37 (L) | 8 | 0.02 |
| TGN-S-S-Seq-ID-40 (L) | 5000 | -0.2 |
| TGN-S-S-Seq-ID-40 (L) | 1000 | -0.12 |
| TGN-S-S-Seq-ID-40 (L) | 200 | -0.12 |
| TGN-S-S-Seq-ID-40 (L) | 40 | -0.07 |
| TGN-S-S-Seq-ID-40 (L) | 8 | -0.14 |
| TGN-S-S-Seq-ID-41 (L) | 5000 | -0.11 |
| TGN-S-S-Seq-ID-41 (L) | 1000 | -0.2 |
| TGN-S-S-Seq-ID-41 (L) | 200 | -0.06 |
| TGN-S-S-Seq-ID-41 (L) | 40 | -0.14 |
| TGN-S-S-Seq-ID-41 (L) | 8 | -0.11 |
| TGN-S-S-Seq-ID-45 (L) | 5000 | -0.26 |
| TGN-S-S-Seq-ID-45 (L) | 1000 | -0.01 |
| TGN-S-S-Seq-ID-45 (L) | 200 | -0.08 |
| TGN-S-S-Seq-ID-45 (L) | 40 | 0.04 |
| TGN-S-S-Seq-ID-45 (L) | 8 | -0.14 |
| TGN-S-S-Seq-ID-50 (D) | 5000 | -0.3 |
| TGN-S-S-Seq-ID-50 (D) | 1000 | -0.17 |
| TGN-S-S-Seq-ID-50 (D) | 200 | 0.07 |
| TGN-S-S-Seq-ID-50 (D) | 40 | 0.03 |
| TGN-S-S-Seq-ID-50 (D) | 8 | -0.01 |
| TGN-S-S-Seq-ID-53 (L) | 5000 | 0.01 |
| TGN-S-S-Seq-ID-53 (L) | 1000 | -0.02 |
| TGN-S-S-Seq-ID-53 (L) | 200 | -0.11 |
| TGN-S-S-Seq-ID-53 (L) | 40 | -0.08 |
| TGN-S-S-Seq-ID-53 (L) | 8 | -0.11 |
| TGN-S-S-Seq-ID-54 (L) | 5000 | 0.07 |
| TGN-S-S-Seq-ID-54 (L) | 1000 | -0.03 |
| TGN-S-S-Seq-ID-54 (L) | 200 | -0.16 |
| TGN-S-S-Seq-ID-54 (L) | 40 | -0.07 |
| TGN-S-S-Seq-ID-54 (L) | 8 | 0.03 |
| TGN-S-S-Seq-ID-55 (L) | 5000 | -0.01 |
| TGN-S-S-Seq-ID-55 (L) | 1000 | 0.05 |
| TGN-S-S-Seq-ID-55 (L) | 200 | 0.12 |
| TGN-S-S-Seq-ID-55 (L) | 40 | 0.08 |
| TGN-S-S-Seq-ID-55 (L) | 8 | 0.11 |
| TGN-S-S-Seq-ID-56 (L) | 5000 | -0.58 |
| TGN-S-S-Seq-ID-56 (L) | 1000 | -0.08 |
| TGN-S-S-Seq-ID-56 (L) | 200 | -0.12 |
| TGN-S-S-Seq-ID-56 (L) | 40 | 0.05 |
| TGN-S-S-Seq-ID-56 (L) | 8 | 0.02 |
| TGN-S-S-Seq-ID-57 (L) | 5000 | 0.09 |

TABLE 5-continued

In Vitro Data

| Targeted peptide | Targeted peptide Dose (nM) | In vitro dddCt (vs. baseline SCE dose) |
|---|---|---|
| TGN-S-S-Seq-ID-57 (L) | 1000 | 0.1 |
| TGN-S-S-Seq-ID-57 (L) | 200 | 0.02 |
| TGN-S-S-Seq-ID-57 (L) | 40 | 0 |
| TGN-S-S-Seq-ID-57 (L) | 8 | 0.1 |
| TGN-S-S-Seq-ID-58 (D) | 5000 | -0.3 |
| TGN-S-S-Seq-ID-58 (D) | 1000 | -0.26 |
| TGN-S-S-Seq-ID-58 (D) | 200 | -0.25 |
| TGN-S-S-Seq-ID-58 (D) | 40 | -0.03 |
| TGN-S-S-Seq-ID-58 (D) | 8 | -0.05 |
| TGN-S-S-Seq-ID-59 (D) | 5000 | 0.25 |
| TGN-S-S-Seq-ID-59 (D) | 1000 | 0.17 |
| TGN-S-S-Seq-ID-59 (D) | 200 | -0.02 |
| TGN-S-S-Seq-ID-59 (D) | 40 | -0.03 |
| TGN-S-S-Seq-ID-59 (D) | 8 | -0.13 |
| TGN-S-S-Seq-ID-61 (D) | 5000 | -0.55 |
| TGN-S-S-Seq-ID-61 (D) | 1000 | 0 |
| TGN-S-S-Seq-ID-61 (D) | 200 | 0.01 |
| TGN-S-S-Seq-ID-61 (D) | 40 | 0.08 |
| TGN-S-S-Seq-ID-61 (D) | 8 | 0.13 |
| TGN-S-S-Seq-ID-65 (D) | 5000 | -2.68 |
| TGN-S-S-Seq-ID-65 (D) | 1000 | -1.88 |
| TGN-S-S-Seq-ID-65 (D) | 200 | -1.48 |
| TGN-S-S-Seq-ID-65 (D) | 40 | -0.73 |
| TGN-S-S-Seq-ID-65 (D) | 8 | 0 |
| TGN-S-S-Seq-ID-29 (D) | 5000 | -0.72 |
| TGN-S-S-Seq-ID-29 (D) | 1000 | -0.52 |
| TGN-S-S-Seq-ID-29 (D) | 200 | -0.44 |
| TGN-S-S-Seq-ID-29 (D) | 40 | -0.12 |
| TGN-S-S-Seq-ID-29 (D) | 8 | 0.05 |
| TGN-S-S-Seq-ID-28 (D) | 5000 | -1.67 |
| TGN-S-S-Seq-ID-28 (D) | 1000 | -1.65 |
| TGN-S-S-Seq-ID-28 (D) | 200 | -1.47 |
| TGN-S-S-Seq-ID-28 (D) | 40 | -1.14 |
| TGN-S-S-Seq-ID-28 (D) | 8 | -0.27 |
| TGN-S-S-Seq-ID-27 (D) | 5000 | -0.65 |
| TGN-S-S-Seq-ID-27 (D) | 1000 | -0.61 |
| TGN-S-S-Seq-ID-27 (D) | 200 | -0.53 |
| TGN-S-S-Seq-ID-27 (D) | 40 | -0.38 |
| TGN-S-S-Seq-ID-27 (D) | 8 | -0.05 |
| TGN-S-S-Seq-ID-26 (D) | 5000 | -0.69 |
| TGN-S-S-Seq-ID-26 (D) | 1000 | 0.12 |
| TGN-S-S-Seq-ID-26 (D) | 200 | 0.21 |
| TGN-S-S-Seq-ID-26 (D) | 40 | 0.1 |
| TGN-S-S-Seq-ID-26 (D) | 8 | 0.1 |
| TGN-S-S-Seq-ID-25 (D) | 5000 | -1.72 |
| TGN-S-S-Seq-ID-25 (D) | 1000 | 0.01 |
| TGN-S-S-Seq-ID-25 (D) | 200 | -0.13 |
| TGN-S-S-Seq-ID-25 (D) | 40 | 0.2 |
| TGN-S-S-Seq-ID-25 (D) | 8 | -0.06 |
| TGN-S-S-SEQ ID NO: 1710 (D) | 5000 | -3.12 |
| TGN-S-S-SEQ ID NO: 1710 (D) | 1000 | -2.83 |
| TGN-S-S-SEQ ID NO: 1710 (D) | 200 | -2 |
| TGN-S-S-SEQ ID NO: 1710 (D) | 40 | -1.04 |
| TGN-S-S-SEQ ID NO: 1710 (D) | 8 | -0.2 |
| TGN-S-S-SEQ ID NO: 1732 (D) | 3125 | 0.67 |
| TGN-S-S-SEQ ID NO: 1732 (D) | 625 | 0.66 |
| TGN-S-S-SEQ ID NO: 1732 (D) | 125 | 0.47 |
| TGN-S-S-SEQ ID NO: 1732 (D) | 25 | 0.47 |
| TGN-S-S-SEQ ID NO: 1078 (D) | 3125 | -1.06 |
| TGN-S-S-SEQ ID NO: 1078 (D) | 625 | -0.96 |
| TGN-S-S-SEQ ID NO: 1078 (D) | 125 | -0.82 |
| TGN-S-S-SEQ ID NO: 1078 (D) | 25 | -0.34 |
| TGN-S-S-SEQ ID NO: 1633 (D) | 3125 | -0.2 |
| TGN-S-S-SEQ ID NO: 1633 (D) | 625 | -0.2 |
| TGN-S-S-SEQ ID NO: 1633 (D) | 25 | -0.33 |
| TGN-S-S-SEQ ID NO: 1703 (D) | 3125 | -0.57 |
| TGN-S-S-SEQ ID NO: 1703 (D) | 625 | -0.43 |
| TGN-S-S-SEQ ID NO: 1703 (D) | 125 | -0.38 |
| TGN-S-S-SEQ ID NO: 1703 (D) | 25 | -0.09 |
| TGN-S-S-SEQ ID NO: 1654 (D) | 3125 | -1.48 |
| TGN-S-S-SEQ ID NO: 1654 (D) | 625 | -1.3 |
| TGN-S-S-SEQ ID NO: 1654 (D)) | 125 | -1.05 |
| TGN-S-S-SEQ ID NO: 1654 (D) | 25 | -0.39 |
| TGN-S-S-SEQ ID NO: 1631 (D) | 3125 | -0.37 |

TABLE 5-continued

In Vitro Data

| Targeted peptide | Targeted peptide Dose (nM) | In vitro dddCt (vs. baseline SCE dose) |
|---|---|---|
| TGN-S-S-SEQ ID NO: 1631 (D) | 625 | 0.07 |
| TGN-S-S-SEQ ID NO: 1631 (D) | 125 | 0.25 |
| TGN-S-S-SEQ ID NO: 1704 (D) | 3125 | -0.39 |
| TGN-S-S-SEQ ID NO: 1704 (D) | 625 | -0.56 |
| TGN-S-S-SEQ ID NO: 1704 (D) | 125 | -0.32 |
| TGN-S-S-SEQ ID NO: 1704 (D) | 25 | -0.08 |
| TGN-S-S-SEQ ID NO: 1653 (D) | 3125 | -2.46 |
| TGN-S-S-SEQ ID NO: 1653 (D) | 625 | -1.97 |
| TGN-S-S-SEQ ID NO: 1653 (D) | 125 | -1.45 |
| TGN-S-S-SEQ ID NO: 1653 (D) | 25 | -0.76 |
| TGN-S-S-SEQ ID NO: 1717 (L) | 3125 | 0.15 |
| TGN-S-S-SEQ ID NO: 1717 (L) | 625 | 0.37 |
| TGN-S-S-SEQ ID NO: 1717 (L) | 25 | 0.61 |
| TGN-S-S-SEQ ID NO: 1705 (D) | 3125 | -0.17 |
| TGN-S-S-SEQ ID NO: 1705 (D) | 625 | -0.69 |
| TGN-S-S-SEQ ID NO: 1705 (D) | 125 | -0.21 |
| TGN-S-S-SEQ ID NO: 1705 (D) | 25 | -0.06 |
| TGN-S-S-SEQ ID NO: 1706 (D) | 3125 | -1.01 |
| TGN-S-S-SEQ ID NO: 1706 (D) | 625 | -1.05 |
| TGN-S-S-SEQ ID NO: 1706 (D) | 125 | -0.95 |
| TGN-S-S-SEQ ID NO: 1706 (D) | 25 | -0.77 |
| TGN-S-S-SEQ ID NO: 1730 (D) | 3125 | -3.38 |
| TGN-S-S-SEQ ID NO: 1730 (D) | 625 | -0.67 |
| TGN-S-S-SEQ ID NO: 1730 (D) | 125 | 0.15 |
| TGN-S-S-SEQ ID NO: 1730 (D) | 25 | 0.44 |
| TGN-S-S-SEQ ID NO: 1707 (D) | 3125 | -0.39 |
| TGN-S-S-SEQ ID NO: 1707 (D) | 625 | -0.54 |
| TGN-S-S-SEQ ID NO: 1707 (D) | 125 | -0.21 |
| TGN-S-S-SEQ ID NO: 1707 (D) | 25 | -0.35 |
| TGN-S-S-SEQ ID NO: 1647 (D) | 3125 | -0.21 |
| TGN-S-S-SEQ ID NO: 1647 (D) | 625 | -0.41 |
| TGN-S-S-SEQ ID NO: 1647 (D) | 125 | -0.32 |
| TGN-S-S-SEQ ID NO: 1647 (D) | 25 | -0.05 |
| TGN-S-S-SEQ ID NO: 1720 (L) | 625 | -0.57 |
| TGN-S-S-SEQ ID NO: 1720 (L) | 125 | 0.13 |
| TGN-S-S-SEQ ID NO: 1720 (L) | 25 | 0.04 |
| TGN-S-S-SEQ ID NO: 1733 (D) | 3125 | -1.93 |
| TGN-S-S-SEQ ID NO: 1733 (D) | 625 | -1.92 |
| TGN-S-S-SEQ ID NO: 1733 (D) | 125 | -1.16 |
| TGN-S-S-SEQ ID NO: 1733 (D) | 25 | -0.85 |
| TGN-S-S-SEQ ID NO: 1701 (D) | 3125 | -1.69 |
| TGN-S-S-SEQ ID NO: 1701 (D) | 625 | -1.46 |
| TGN-S-S-SEQ ID NO: 1701 (D) | 125 | -1.55 |
| TGN-S-S-SEQ ID NO: 1701 (D) | 25 | -0.58 |
| TGN-S-S-SEQ ID NO: 1518 (L) | 3125 | 0.19 |
| TGN-S-S-SEQ ID NO: 1518 (L) | 625 | 0.3 |
| TGN-S-S-SEQ ID NO: 1518 (L) | 125 | 0.37 |
| TGN-S-S-SEQ ID NO: 1518 (L) | 25 | 0.54 |
| TGN-S-S-SEQ ID NO: 1734 (D) | 3125 | -1.14 |
| TGN-S-S-SEQ ID NO: 1734 (D) | 625 | -0.86 |
| TGN-S-S-SEQ ID NO: 1734 (D) | 125 | -0.42 |
| TGN-S-S-SEQ ID NO: 1734 (D) | 25 | -0.2 |
| TGN-S-S-SEQ ID NO: 1628 (D) | 3125 | -2.24 |
| TGN-S-S-SEQ ID NO: 1628 (D) | 625 | -1.64 |
| TGN-S-S-SEQ ID NO: 1628 (D) | 125 | -1.17 |
| TGN-S-S-SEQ ID NO: 1628 (D) | 25 | -0.54 |
| TGN-S-SEQ ID NO: 1517 (L) | 3125 | 0.33 |
| TGN-S-SEQ ID NO: 1517 (L) | 625 | 0.48 |
| TGN-S-SEQ ID NO: 1517 (L) | 125 | 0.49 |
| TGN-S-SEQ ID NO: 1517 (L) | 25 | 0.54 |
| TGN-S-S-SEQ ID NO: 1652 (D) | 15625 | -2.03 |
| TGN-S-S-SEQ ID NO: 1652 (D) | 3125 | -1.6 |
| TGN-S-S-SEQ ID NO: 1652 (D) | 625 | -1.5 |
| TGN-S-S-SEQ ID NO: 1652 (D) | 125 | -1.27 |
| TGN-S-S-SEQ ID NO: 1701 (D) | 15625 | -2.15 |
| TGN-S-S-SEQ ID NO: 1701 (D) | 3125 | -1.65 |
| TGN-S-S-SEQ ID NO: 1701 (D) | 625 | -1.35 |
| TGN-S-S-SEQ ID NO: 1701 (D) | 125 | -1.14 |
| TGN-S-S-SEQ ID NO: 1078(D) | 15625 | -1.44 |
| TGN-S-S-SEQ ID NO: 1078(D) | 3125 | -1.17 |
| TGN-S-S-SEQ ID NO: 1078(D) | 625 | -1.24 |
| TGN-S-S-SEQ ID NO: 1078(D) | 125 | -1.04 |
| TGN-S-S-SEQ ID NO: 1651 (D) | 15625 | -1.48 |
| TGN-S-S-SEQ ID NO: 1651 (D) | 3125 | -1.55 |

TABLE 5-continued

In Vitro Data

| Targeted peptide | Targeted peptide Dose (nM) | In vitro dddCt (vs. baseline SCE dose) |
|---|---|---|
| TGN-S-S-SEQ ID NO: 1651 (D) | 625 | -1.11 |
| TGN-S-S-SEQ ID NO: 1651 (D) | 125 | -0.84 |
| TGN-S-S-SEQ ID NO: 1628 (D) | 15625 | -2.67 |
| TGN-S-S-SEQ ID NO: 1628 (D) | 3125 | -2.15 |
| TGN-S-S-SEQ ID NO: 1628 (D) | 625 | -1.86 |
| TGN-S-S-SEQ ID NO: 1628 (D) | 125 | -1.17 |
| TGN-S-S-SEQ ID NO: 1662 | 15625 | -0.45 |
| TGN-S-S-SEQ ID NO: 1662 | 3125 | -0.48 |
| TGN-S-S-SEQ ID NO: 1662 | 625 | -0.47 |
| TGN-S-S-SEQ ID NO: 1662 | 125 | -0.31 |
| TGN-S-S-SEQ ID NO: 1650 (D) | 15625 | -0.57 |
| TGN-S-S-SEQ ID NO: 1650 (D) | 3125 | -0.21 |
| TGN-S-S-SEQ ID NO: 1650 (D) | 625 | -0.45 |
| TGN-S-S-SEQ ID NO: 1650 (D) | 125 | -0.33 |
| TGN-S-S-SEQ ID NO: 1633 (D) | 15625 | -0.69 |
| TGN-S-S-SEQ ID NO: 1633 (D) | 3125 | -0.37 |
| TGN-S-S-SEQ ID NO: 1633 (D) | 625 | -0.57 |
| TGN-S-S-SEQ ID NO: 1633 (D) | 125 | -0.39 |
| TGN-S-S-SEQ ID NO: 1696 | 15625 | -0.54 |
| TGN-S-S-SEQ ID NO: 1696 | 3125 | -0.4 |
| TGN-S-S-SEQ ID NO: 1696 | 625 | -0.59 |
| TGN-S-S-SEQ ID NO: 1696 | 125 | -0.41 |
| TGN-S-S-SEQ ID NO: 1632 (D) | 15625 | -0.47 |
| TGN-S-S-SEQ ID NO: 1632 (D) | 3125 | -0.19 |
| TGN-S-S-SEQ ID NO: 1632 (D) | 625 | -0.44 |
| TGN-S-S-SEQ ID NO: 1632 (D) | 125 | -0.29 |
| TGN-S-S-SEQ ID NO: 1657 (D) | 15625 | -0.56 |
| TGN-S-S-SEQ ID NO: 1657 (D) | 3125 | -0.4 |
| TGN-S-S-SEQ ID NO: 1657 (D) | 625 | -0.49 |
| TGN-S-S-SEQ ID NO: 1657 (D) | 125 | -0.42 |
| TGN-S-S-SEQ ID NO: 1634 (D) | 15625 | -0.74 |
| TGN-S-S-SEQ ID NO: 1634 (D) | 3125 | -0.3 |
| TGN-S-S-SEQ ID NO: 1634 (D) | 625 | -0.41 |
| TGN-S-S-SEQ ID NO: 1634 (D) | 125 | -0.3 |
| TGN-S-S-SEQ ID NO: 1660 (D) | 15625 | -0.7 |
| TGN-S-S-SEQ ID NO: 1660 (D) | 3125 | -0.69 |
| TGN-S-S-SEQ ID NO: 1660 (D) | 625 | -0.9 |
| TGN-S-S-SEQ ID NO: 1660 (D) | 125 | -0.57 |
| TGN-S-S-SEQ ID NO: 1649 (D) | 15625 | -0.77 |
| TGN-S-S-SEQ ID NO: 1649 (D) | 3125 | -0.61 |
| TGN-S-S-SEQ ID NO: 1649 (D) | 625 | -0.48 |
| TGN-S-S-SEQ ID NO: 1649 (D) | 125 | -0.3 |
| TGN-S-S-SEQ ID NO: 1631 (D) | 15625 | -2.11 |
| TGN-S-S-SEQ ID NO: 1631 (D) | 3125 | -0.45 |
| TGN-S-S-SEQ ID NO: 1631 (D) | 625 | -0.3 |
| TGN-S-S-SEQ ID NO: 1631 (D) | 125 | -0.19 |
| TGN-S-S-SEQ ID NO: 1654 (D) | 15625 | -1.61 |
| TGN-S-S-SEQ ID NO: 1654 (D) | 3125 | -1.48 |
| TGN-S-S-SEQ ID NO: 1654 (D) | 625 | -1.08 |
| TGN-S-S-SEQ ID NO: 1654 (D) | 125 | -1.05 |
| TGN-S-S-SEQ ID NO: 1648 (D) | 15625 | -0.59 |
| TGN-S-S-SEQ ID NO: 1648 (D) | 3125 | -0.39 |
| TGN-S-S-SEQ ID NO: 1648 (D) | 625 | -0.57 |
| TGN-S-S-SEQ ID NO: 1648 (D) | 125 | -0.27 |
| TGN-S-S-SEQ ID NO: 255 (D) | 625 | -1.59 |
| TGN-S-S-SEQ ID NO: 255 (D) | 125 | -0.37 |
| TGN-S-S-SEQ ID NO: 1653 (D) | 15625 | -2.13 |
| TGN-S-S-SEQ ID NO: 1653 (D) | 3125 | -1.92 |
| TGN-S-S-SEQ ID NO: 1653 (D) | 625 | -1.53 |
| TGN-S-S-SEQ ID NO: 1653 (D) | 125 | -1.31 |
| TGN-S-S-SEQ ID NO: 1647 (D) | 15625 | -0.68 |
| TGN-S-S-SEQ ID NO: 1647 (D) | 3125 | -0.58 |
| TGN-S-S-SEQ ID NO: 1647 (D) | 625 | -0.59 |
| TGN-S-S-SEQ ID NO: 1647 (D) | 125 | -0.52 |

Note:
Every amino acid (except glycine) can occur in two isomeric forms, because of the possibility of forming two different enantiomers (stereoisomers) around the central carbon atom. By convention, these are called L- and D-forms, analogous to left-handed and right-handed configurations.

In Vivo Assay—In Vivo Evaluation in Mice:

Female CD-1 mice (Charles River) were injected in accordance with either a sequential dosing paradigm or a co-dosing paradigm. In the sequential dosing paradigm, the targeted siRNA (SCE) is dosed at t=0 and the targeted peptide is separately dosed up to 2 hr before the SCE (−2 hr) or up to 24 hr after the SCE (+24 hr). In the co-dosing paradigm, the SCE and peptides are co-formulated and dosed together in the same formulation as a single injection at t=0. The mice were dosed either by intravenous (i.v.) or subcutaneous (s.c.) injection of SCE and peptide. For the i.v.

doses, the compounds were injected into the tail vein of the mice. For the s.c. doses, the compounds were injected in the subcutaneous space on the back of the mouse between the shoulder blades. At the indicated harvest times (measured from t=0 when the siRNA was dosed, regardless of when the peptide was dosed), the animals were sacrificed and 3 mm liver punches were collected, preserved in RNAlater (Ambion), and stored at 4° C. Separate 5 mm liver punches were collected, placed in 96-well plates, frozen on dry ice, and stored at −80° C. until use.

mRNA Knockdown Measurement:

The 3 mm liver punches were removed from RNAlater and homogenized in Trizol (Invitrogen) using a bead mill tissue lyser (Qiagen); disruption was performed for two 5-minute cycles at 30 Hz. RNA extraction was performed using 1-bromo-2-chloropropane (Acros Organics) and total RNA was isolated from the aqueous phase using the MagMax RNA isolation method (Ambion). RNA (125 ng) was reverse transcribed using the High Capacity cDNA Reverse Transcription kit (Applied Biosystems). TaqMan qPCR analysis was performed with an ABI 7900 Real-Time PCR System using TaqMan Fast Advanced Master Mix (Applied Biosystems). All TaqMan probes and primers for CTNNB1 and PPIB (housekeeping gene) were purchased from Applied Biosystems as pre-validated gene expression assays. Results are calculated by the comparative Ct method, where the difference between the CTNNB1 Ct value and the PPIB Ct value (ΔCt) is calculated and then further normalized relative to the PBS control by taking a second difference (ΔΔCt), as described previously (1).

Table-3, shows the mRNA knockdown data of multiple peptide conjugates dosed sequentially with peptide dosed 15 min after siRNA via intravenous (IV) route Stem-Loop qPCR:

The same liver homogenates used to measure mRNA knockdown were also used to measure the concentration of CTNNB1 siRNA in the liver using a modified quantitative stem-loop RT-PCR protocol (2). Liver homogenate samples were diluted in TE buffer and then the antisense strand of the siRNA (5'-UUUCGAAUCAAUCCAACAGUU-3'; Seq. ID No. 1810) was reverse transcribed with 25 nM of a CTNNB1-specific stem-loop primer (5'-GTCGTATCCAGT-GCAGGGTCCGAGGTATTCGCACTGGATACGA-CAACTGTTG-3'; Seq. ID No. 1811) using a TaqMan MicroRNA reverse transcription kit (Applied Biosystems) using 0.5 μL MultiScribe RT enzyme per reaction. A standard curve was generated by spiking CTNNB1 siRNA into untreated liver homogenate and then serially diluting with TE buffer. The cDNA from the RT step was utilized for real-time PCR using TaqMan Universal Master Mix (Applied Biosystems) with 1.5 μM of forward primer (5'-GGCGG CTTTCGAATCAATCCA-3'; Seq. ID No. 1812), 0.75 μM of reverse primer (5'-AGTGCAGGGTCCGAG-3'; Seq. ID No. 1813), and 0.2 μM of probe (5'-6FAM-TGGA-TACGACAACTGTTG-3'; Seq. ID No. 1814). Quantitative PCR reactions were performed using standard cycling conditions in an ABI 7900HT Fast Real-Time PCR System. Normalized Ct values were transformed into plasma concentrations using the linear equation derived from the standard curve.

Quantitation of siRNA Bound to RISC:

The 5 mm liver punches were homogenized in lysis buffer (50 mM Tris, 200 mM NaCl, 2 mM EDTA, 0.5% Triton-X-100, 1 mg/mL heparin, 1 tablet/50 mL of cOmplete EDTA-free protease inhibitor cocktail, and 200 U/mL benzonase), using a Geno/Grinder (SPEX SamplePrep Corp) with a stainless steel grinding ball (5/32", 4 mm SPEX SamplePrep Corp) in a 96-well plate at 1100 strokes per minute for five intervals of one min each at 4° C. Samples were then centrifuged at 14,000 rpm for 30 min at 4° C. and protein levels were determined using a Peirce BCA Kit. Mouse anti mouse Ago2 monoclonal antibody (018-22021, Wako) was bound to magnetic beads (Invitrogen Dynabeads Protein G) in a 96-well microtiter plate. Liver lysates were incubated overnight at 4° C. with the antibody-magnetic bead complex. Post-incubation the samples were washed, incubated with 10 U/mL of benzonase (Sigma Aldrich) to reduce background, resuspended in 0.01% NP-40 detergent, and eluted off of the magnetic bead using heat (95° C. for 15 min). Using the 0.01% NP-40 samples, the antisense strand of the siRNA was quantitated using the stem-loop procedure described above, except that the standard curve was generated by spiking CTNNB siRNA into 0.01% NP-40 and then serially diluting with 0.01% NP-40. Simultaneously, the 0.01% NP-40 samples were used to quantitate miR-16 (5'-UAGCAGCACGUAAAUAUUGGCG-3'; Seq. ID No. 1815) using TaqMan MicroRNA Assay hsa-mir-16 (Applied Biosystems assay ID 000391) following the manufacturer's kit instructions. A standard curve was generated by spiking miR-16 into 0.01% NP-40 and then serially diluting with 0.01% NP-40. Quantitative PCR reactions were performed using standard cycling conditions in an ABI 7900HT Fast Real-Time PCR System. Normalized Ct values were transformed into liver concentrations using the linear equation derived from the standard curve. Using the concentrations derived from the standard curves of both the CTNNB1 siRNA and the miR-16, a ratio of RISC-bound siRNA to RISC-bound miR-16 was determined.

In Vivo Evaluation in Non-Human Primates:

Chair-trained rhesus monkeys were dosed with siRNA at t=0 by i.v. injection into the saphenous vein and then dosed with peptide (or sucrose buffer) by i.v. injection into the saphenous vein 15 min later. At indicated harvest times, monkeys were sedated using ketamine and/or telazol (5-30 mg/kg or 4-6 mg/kg, respectively) and then a ~500 mg liver biopsy sample was obtained during a minimally invasive surgery (MIS) procedure. The liver tissue was stored in RNAlater and processed for mRNA knockdown as described above. The liver tissue was also processed for stem-loop qPCR and RISC binding as described above. The only differences were that rhesus-specific TaqMan probes and primers for CTNNB1 and PPM (housekeeping gene) were purchased from Applied Biosystems and that a mouse anti human Ago2 monoclonal antibody (018-22033, Wako) was used during the immunoprecipitation step in the RISC analysis The structure of TGN-S-S-peptide is the same as that shown above for Table 5 and the structure of TGN-L-siRNA is shown below. The activity data is listed in Table 6.

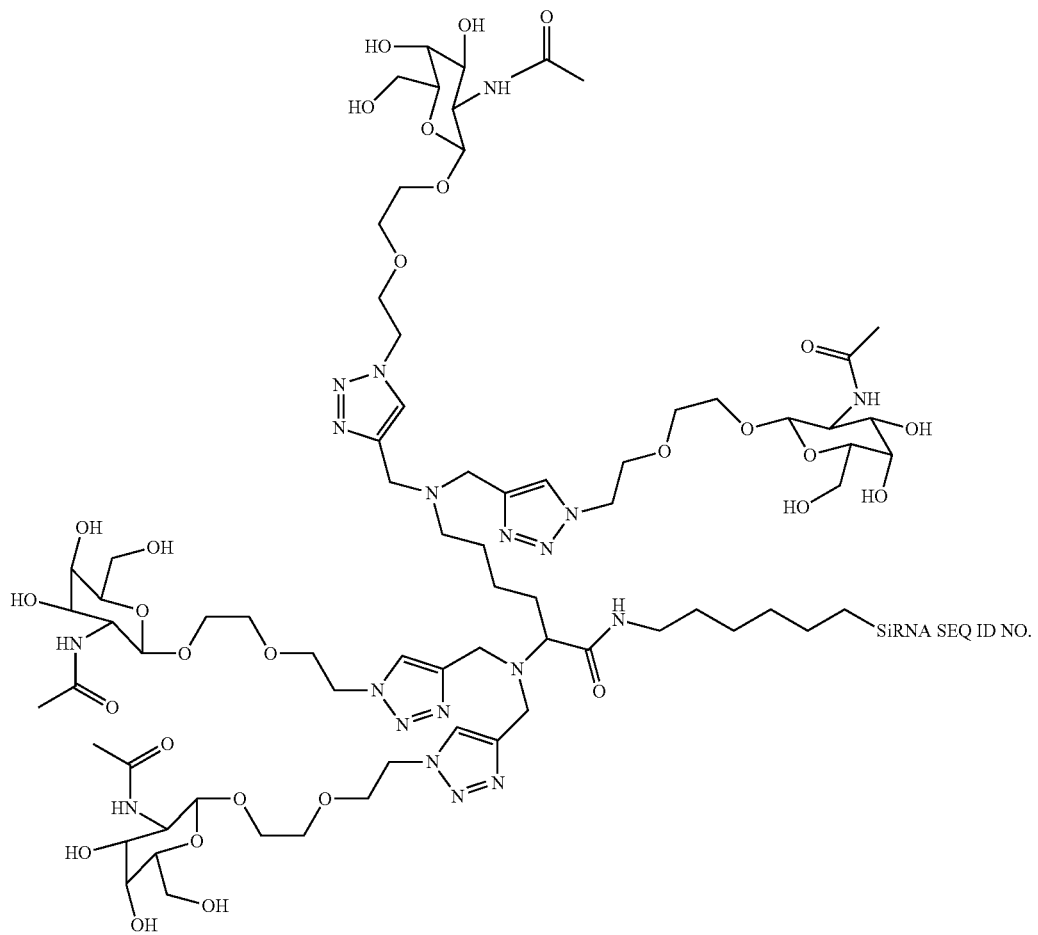

TABLE 6 mRNA Knockdown Data - Sequential Dosing with Peptide
Dosed 15 min After siRNA via Intravenous (IV) Route

| Targeted siRNA | Targeted peptide | Targeted siRNA dose-IV (mg/kg) | Targeted peptide dose-IV (mg/kg) | In vivo mRNA knockdown (%) |
|---|---|---|---|---|
| siRNA-IV | TGN-S-S-SEQ ID NO: 1710 (D) | 5 | 2 | 66 |
| siRNA-IV | TGN-S-S-SEQ ID NO: 1710 (D) | 5 | 10 | 79 |
| siRNA-IV | TGN-S-S-SEQ ID NO: 1710 (D) | 2 | 2 | 58 |
| siRNA-IV | TGN-S-S-SEQ ID NO: 1710 (D) | 2 | 10 | 64 |
| siRNA-IV | TGN-S-S-SEQ ID NO: 1710 (D) | 0.5 | 2 | 30 |
| siRNA-IV | TGN-S-S-SEQ ID NO: 1710 (D) | 0.5 | 10 | 67 |
| siRNA-IV | — | 5 | 0 | 35 |
| siRNA-IV | — | 2 | 0 | 25 |
| siRNA-IV | — | 0.5 | 0 | 25 |
| TGN-L-siRNA-III | — | 0.5 | 0 | 30 |
| TGN-L-siRNA-III | — | 0.25 | 0 | 15 |
| TGN-LsiRNA-III | TGN-S-S-SEQ ID NO: 1710 (D) | 0.5 | 25 | 63 |
| TGN-L-siRNA-III | TGN-S-S-SEQ ID NO: 1710 (D) | 0.5 | 18 | 68 |

TABLE 6-continued mRNA Knockdown Data - Sequential Dosing with Peptide
Dosed 15 min After siRNA via Intravenous (IV) Route

| Targeted siRNA | Targeted peptide | Targeted siRNA dose-IV (mg/kg) | Targeted peptide dose-IV (mg/kg) | In vivo mRNA knockdown (%) |
|---|---|---|---|---|
| TGN-L-siRNA-III | TGN-S-S-SEQ ID NO: 1710 (D) | 0.25 | 10 | 69 |
| TGN-L-siRNA-III | TGN-S-S-SEQ ID NO: 1710 (D) | 0.25 | 5 | 50 |
| TGN-L-siRNA-III | TGN-S-S-SEQ ID NO: 1643 (D) | 0.25 | 10 | 41 |
| TGN-L-siRNA-III | TGN-S-S-SEQ ID NO: 1078 (D) | 0.25 | 10 | 53 |
| TGN-L-siRNA-III | TGN-S-S-SEQ ID NO: 1662 (D) | 0.25 | 10 | 32 |
| TGN-L-siRNA-III | TGN-S-S-SEQ ID NO: 1696 (D) | 0.25 | 10 | 44 |
| TGN-L-siRNA-III | TGN-S-S-SEQ ID NO: 1657 (D) | 0.25 | 10 | 35 |
| TGN-L-siRNA-III | TGN-S-S-SEQ ID NO: 1660 (D) | 0.25 | 10 | 34 |
| TGN-L-siRNA-III | TGN-S-S-SEQ ID NO: 1654 (D) | 0.25 | 2 | 51 |
| TGN-L-siRNA-III | TGN-S-S-SEQ ID NO: 1654 (D) | 0.25 | 10 | 72 |
| TGN-L-siRNA-III | TGN-S-S-SEQ ID NO: 1654 (D) | 0.25 | 50* | 65 |
| TGN-L-siRNA-III | TGN-S-S-SEQ ID NO: 1653 (D) | 0.25 | 50 | 69 |
| TGN-L-siRNA-III | TGN-S-S-SEQ ID NO: 1653 (D) | 0.25 | 10 | 63 |
| TGN-L-siRNA-III | TGN-S-S-SEQ ID NO: 1652 (D) | 0.25 | 10 | 37 |
| TGN-L-siRNA-III | TGN-S-S-SEQ ID NO: 1651 (D) | 0.25 | 10 | 49 |
| TGN-L-siRNA-III | TGN-S-S-SEQ ID NO: 1650 (D) | 0.25 | 10 | 49 |
| TGN-L-siRNA-III | TGN-S-S-SEQ ID NO: 1649 (D) | 0.25 | 10 | 41 |
| TGN-L-siRNA-III | TGN-S-S-SEQ ID NO: 1648 (D) | 0.25 | 10 | 41 |
| TGN-L-siRNA-III | TGN-S-S-SEQ ID NO: 1647 (D) | 0.25 | 10 | 29 |
| TGN-L-siRNA-III | TGN-S-S-SEQ ID NO: 1701 (D) | 0.25 | 2 | 57 |
| TGN-L-siRNA-III | TGN-S-S-SEQ ID NO: 1701 (D) | 0.25 | 10 | 68 |
| TGN-L-siRNA-III | TGN-S-S-SEQ ID NO: 1701 (D) | 0.25 | 25 | 77 |
| TGN-L-siRNA-III | TGN-S-S-SEQ ID NO: 1701 (D) | 0.25 | 50* | 82 |
| TGN-L-siRNA-III | TGN-S-S-SEQ ID NO: 1645 (D) | 0.25 | 10 | 37 |
| TGN-L-siRNA-III | TGN-S-S-SEQ ID NO: 1628 (D) | 0.25 | 10* | All mice died |
| TGN-L-siRNA-III | TGN-S-S-SEQ ID NO: 1633 (D) | 0.25 | 10 | 55 |
| TGN-L-siRNA-III | TGN-S-S-SEQ ID NO: 1632 (D) | 0.25 | 10 | 36 |
| TGN-L-siRNA-III | TGN-S-S-SEQ ID NO: 1634 (D) | 0.25 | 10 | 17 |
| TGN-L-siRNA-III | TGN-S-S-SEQ ID NO: 1631 (D) | 0.25 | 10 | 17 |
| TGN-L-siRNA-III | TGN-S-S-SEQ ID NO: 1697 (D) | 0.25 | 10 | 52 |
| TGN-L-siRNA-III | TGN-S-S-SEQ ID NO: 1702(D) | 0.25 | 5 | 75 |
| TGN-L-siRNA-III | TGN-S-S-SEQ ID NO: 1703 (D) | 0.25 | 5 | 54 |
| TGN-L-siRNA-III | TGN-S-S-SEQ ID NO: 1704 (D) | 0.25 | 5 | 64 |
| TGN-L-siRNA-III | TGN-S-S-SEQ ID NO: 1705 (D) | 0.25 | 5 | 59 |
| TGN-L-siRNA-III | TGN-S-S-SEQ ID NO: 1706 (D) | 0.25 | 5 | 61 |
| TGN-L-siRNA-III | TGN-S-S-SEQ ID NO: 1707 (D) | 0.25 | 5 | 56 |
| TGN-L-siRNA-III | TGN-S-S-SEQ ID NO: 1708 (L) | 0.25 | 5 | 46 |

TABLE 6-continued mRNA Knockdown Data - Sequential Dosing with Peptide
Dosed 15 min After siRNA via Intravenous (IV) Route

| Targeted siRNA | Targeted peptide | Targeted siRNA dose-IV (mg/kg) | Targeted peptide dose-IV (mg/kg) | In vivo mRNA knockdown (%) |
|---|---|---|---|---|
| TGN-L-siRNA-III | TGN-S-S-SEQ ID NO: 1709 (L) | 0.5 | 5 | 16 |
| TGN-L-siRNA-III | TGN-S-S-SEQ ID NO: 1710 (L) | 0.5 | 5 | 21 |
| TGN-L-siRNA-III | TGN-S-S-SEQ ID NO: 1711 (L) | 0.5 | 5 | 36 |
| TGN-L-siRNA-III | TGN-S-S-SEQ ID NO: 1712 (L) | 0.5 | 5 | 34 |
| TGN-L-siRNA-III | TGN-S-S-SEQ ID NO: 1713 (L) | 0.25 | 2 | 0 |
| TGN-L-siRNA-III | TGN-S-S-SEQ ID NO: 1713 (L) | 0.25 | 10 | 2 |
| TGN-L-siRNA-III | TGN-S-S-SEQ ID NO: 1715 (L) | 0.5 | 5 | 28 |
| TGN-L-siRNA-III | TGN-S-S-SEQ ID NO: 1716 (L) | 0.5 | 5 | 39 |
| TGN-L-siRNA-III | TGN-S-S-SEQ ID NO: 1717(L) | 0.5 | 5 | 16 |
| TGN-L-siRNA-III | TGN-S-S-SEQ ID NO: 1718 (L) | 0.25 | 10 | 6 |
| TGN-L-siRNA-III | TGN-S-S-SEQ ID NO: 1719 (L) | 0.25 | 5 | 25 |
| TGN-L-siRNA-III | TGN-S-S-SEQ ID NO: 1403 (L) | 0.25 | 2 | 22 |
| TGN-L-siRNA-III | TGN-S-S-SEQ ID NO: 1403(L) | 0.25 | 10 | 24 |
| TGN-L-siRNA-III | TGN-S-S-SEQ ID NO: 1518(L) | 0.25 | 2 | 18.3 |
| TGN-L-siRNA-III | TGN-S-S-SEQ ID NO: 1518 (L) | 0.25 | 10 | 13 |
| TGN-L-siRNA-III | TGN-S-S-SEQ ID NO: 1517 (L) | 0.25 | 2, | 18 |
| TGN-L-siRNA-III | TGN-S-S-SEQ ID NO: 1517 (L) | 0.25 | 10 | 18 |
| TGN-L-siRNA-III | TGN-S-S-SEQ ID NO: 1516 (L) | 0.25 | 5 | 14 |
| TGN-L-siRNA-III | TGN-S-S-SEQ ID NO: 935 (L) | 0.25 | 2 | 17 |
| TGN-L-siRNA-III | TGN-S-S-SEQ ID NO: 935 (L) | 0.25 | 10 | 23 |
| TGN-L-siRNA-III | TGN-S-S-SEQ ID NO: 1391 (L) | 0.5 | 10 | 6 |
| TGN-L-siRNA-III | TGN-S-S-SEQ ID NO: 1248 (L) | 0.5 | 5 | 24 |
| TGN-L-siRNA-III | TGN-S-S-SEQ ID NO: 1720 (L) | 0.5 | 10 | 31 |
| TGN-L-siRNA-III | TGN-S-S-SEQ ID NO: 1721 (L) | 0.5 | 10 | 8 |
| TGN-L-siRNA-III | TGN-S-S-SEQ ID NO: 1722 (L) | 0.5 | 10 | 21 |
| TGN-L-siRNA-III | TGN-S-S-SEQ ID NO: 1723 (L) | 0.5 | 10 | 5 |
| TGN-L-siRNA-III | TGN-S-S-SEQ ID NO: 1724 (L) | 0.5 | 10 | 21 |
| TGN-L-siRNA-III | TGN-S-S-SEQ ID NO: 1725 (L) | 0.25 | 10 | 19 |
| TGN-L-siRNA-III | TGN-S-S-SEQ ID NO: 1726(D) | 0.25 | 10 | 23 |
| TGN-L-siRNA-III | TGN-S-S-SEQ ID NO: 1727 (D) | 0.25 | 10 | 26 |
| TGN-L-siRNA-III | TGN-S-S-SEQ ID NO: 1728(D) | 0.25 | 10 | 23 |
| TGN-L-siRNA-III | TGN-S-S-SEQ ID NO: 1729 (L) | 0.25 | 10 | 10 |
| TGN-L-siRNA-III | TGN-S-S-SEQ ID NO: 1730 (D) | 0.25 | 10 | 43 |
| TGN-L-siRNA-III | TGN-S-S-SEQ ID NO: 1731(D) | 0.25 | 10 | 30 |
| TGN-L-siRNA-III | TGN-S-S-SEQ ID NO: 1732 (D) | 0.25 | 5 | |
| TGN-L-siRNA-III | TGN-S-S-SEQ ID NO: 1733 (D) | 0.25 | 5 | 73 |

TABLE 6-continued mRNA Knockdown Data - Sequential Dosing with Peptide
Dosed 15 min After siRNA via Intravenous (IV) Route

| Targeted siRNA | Targeted peptide | Targeted siRNA dose-IV (mg/kg) | Targeted peptide dose-IV (mg/kg) | In vivo mRNA knockdown (%) |
|---|---|---|---|---|
| TGN-L-siRNA-III | TGN-S-S-SEQ ID NO: 1734 (D) | 0.25 | 5 | 61 |
| TGN-L-siRNA-III | TGN-S-S-SEQ ID NO: 1732 (D) | 0.25 | 5 | 35 |
| TGN-L-siRNA-II | TGN-S-S-SEQ ID NO: 1733(D) | 0.25 | 1 | 60 |
| TGN-L-siRNA-II | TGN-S-S-SEQ ID NO: 1733(D) | 0.25 | 3 | 75 |
| TGN-L-siRNA-II | TGN-S-S-SEQ ID NO: 1733(D) | 0.25 | 10 | 58 |
| TGN-L-siRNA-II | TGN-S-S-SEQ ID NO: 1733(D) | 0.25 | 50 | 50 |
| TGN-L-siRNA-II | TGN-S-S-SEQ ID NO: 1738 (D) | 0.25 | 1 | 25 |
| TGN-L-siRNA-II | TGN-S-S-SEQ ID NO: 1738 (D) | 0.25 | 3 | 44 |
| TGN-L-siRNA-II | TGN-S-S-SEQ ID NO: 1740 (L) | 0.25 | 3 | 20 |
| TGN-L-siRNA-II | TGN-S-S-SEQ ID NO: 1741(L) | 0.25 | 3 | 24 |
| TGN-L-siRNA-II | TGN-S-S-SEQ ID NO: 1740 (D) | 0.25 | 1 | 23 |
| TGN-L-siRNA-II | TGN-S-S-SEQ ID NO: 1740 (D) | 0.25 | 3 | 42 |
| TGN-L-siRNA-III | TGN-S-S-SEQ ID NO: 1709 (D) | 0.25 | 2 | 54 |
| TGN-L-siRNA-III | TGN-S-S-SEQ ID NO: 1709 (D) | 0.25 | 10 | 65 |
| TGN-L-siRNA-III | TGN-S-S-SEQ ID NO: 1709 (D) | 0.25 | 25 | 77 |
| TGN-L-siRNA-III | TGN-S-S-SEQ ID NO: 1709 (D) | 0.25 | 35 | 81 |
| TGN-L-siRNA-III | TGN-S-S-SEQ ID NO: 1744 (D) | 0.5 | 2 | 28 |
| TGN-L-siRNA-III | TGN-S-S-SEQ ID NO: 1744 (D) | 0.5 | 10 | 33 |
| TGN-L-siRNA-III | TGN-S-S-SEQ ID NO: 1745 (D) | 0.5 | 2 | 54 |
| TGN-L-siRNA-III | TGN-S-S-SEQ ID NO: 1745 (D) | 0.5 | 10 | 69 |
| TGN-L-siRNA-III | TGN-S-S-SEQ ID NO: 1745 (D) | 0.5 | 25 | 66 |
| TGN-L-siRNA-III | TGN-S-S-SEQ ID NO: 1746 (D) | 0.5 | 2 | 31 |
| TGN-L-siRNA-III | TGN-S-S-SEQ ID NO: 1746 (D) | 0.5 | 10 | 25 |
| TGN-L-siRNA-III | TGN-S-S-SEQ ID NO: 1489 (D) | 0.5 | 2 | 37 |
| TGN-L-siRNA-III | TGN-S-S-SEQ ID NO: 1489 (D) | 0.5 | 10 | 26 |
| TGN-L-siRNA-III | TGN-S-S-SEQ ID NO: 1489 (D) | 0.5 | 25 | 34 |
| TGN-L-siRNA-III | TGN-S-S-SEQ ID NO: 1419 (D) | 0.5 | 2 | 43 |
| TGN-L-siRNA-III | TGN-S-S-SEQ ID NO: 1419 (D) | 0.5 | 10 | 78 |
| TGN-L-siRNA-III | TGN-S-S-SEQ ID NO: 1419 (D) | 0.5 | 25* | 76 |
| TGN-L-siRNA-III | TGN-S-S-SEQ ID NO: 1248 (D) | 0.5 | 2 | 42 |
| TGN-L-siRNA-III | TGN-S-S-SEQ ID NO: 1248 (D) | 0.5 | 10 | 74 |
| TGN-L-siRNA-III | TGN-S-S-SEQ ID NO: 1248 (D) | 0.5 | 25* | 58 |
| TGN-L-siRNA-III | TGN-S-S-SEQ ID NO: 26 (D) | 0.5 | 0.5 | 26 |
| TGN-L-siRNA-III | TGN-S-S-SEQ ID NO: 26 (D) | 0.5 | 2 | 40 |
| TGN-L-siRNA-III | TGN-S-S-SEQ ID NO: 26 (D) | 0.5 | 5 | 65 |

TABLE 6-continued mRNA Knockdown Data - Sequential Dosing with Peptide
Dosed 15 min After siRNA via Intravenous (IV) Route

| Targeted siRNA | Targeted peptide | Targeted siRNA dose-IV (mg/kg) | Targeted peptide dose-IV (mg/kg) | In vivo mRNA knockdown (%) |
|---|---|---|---|---|
| TGN-L-siRNA-III | TGN-S-S-SEQ ID NO: 26 (D) | 0.5 | 10 | 70 |
| TGN-L-siRNA-III | TGN-S-S-SEQ ID NO: 74 (D) | 0.5 | 0.5 | 26 |
| TGN-L-siRNA-III | TGN-S-S-SEQ ID NO: 74 (D) | 0.5 | 2 | 44 |
| TGN-L-siRNA-III | TGN-S-S-SEQ ID NO: 74 (D) | 0.5 | 5 | 51 |
| TGN-L-siRNA-III | TGN-S-S-SEQ ID NO: 74 (D) | 0.5 | 10 | 68 |
| TGN-L-siRNA-III | TGN-S-S-SEQ ID NO: 82 (D) | 0.5 | 0.5 | 40 |
| TGN-L-siRNA-III | TGN-S-S-SEQ ID NO: 82 (D) | 0.5 | 2 | 42 |
| TGN-L-siRNA-III | TGN-S-S-SEQ ID NO: 82 (D) | 0.5 | 5 | 50 |
| TGN-L-siRNA-III | TGN-S-S-SEQ ID NO: 82 (D) | 0.5 | 10 | 60 |
| TGN-L-siRNA-III | TGN-S-S-SEQ ID NO: 543 (D) | 0.5 | 0.5 | 35 |
| TGN-L-siRNA-III | TGN-S-S-SEQ ID NO: 543 (D) | 0.5 | 2 | 60 |
| TGN-L-siRNA-III | TGN-S-S-SEQ ID NO: 543 (D) | 0.5 | 5 | 65 |
| TGN-L-siRNA-III | TGN-S-S-SEQ ID NO: 543 (D) | 0.5 | 10 | 75 |
| TGN-L-siRNA-I | — | 0.5 | 0 | 20 |
| TGN-L-siRNA-I | 2K-PEG-S-S-Seq-ID-50 (D) | 0.5 | 0.5 | 22 |
| TGN-L-siRNA-I | 2K-PEG-S-S-SEQ ID NO: 26 (D) | 0.5 | 2 | 25 |
| TGN-L-siRNA-I | 2K-PEG-S-S-SEQ ID NO: 26 (D) | 0.5 | 5 | 45 |
| TGN-L-siRNA-I | 2K-PEG-S-S-SEQ ID NO: 26 (D) | 0.5 | 10 | 45 |
| TGN-L-siRNA-I | 2K-PEG-S-S-SEQ ID NO: 74 (D) | 0.5 | 0.5 | 20 |
| TGN-L-siRNA-I | 2K-PEG-S-S-SEQ ID NO: 74 (D) | 0.5 | 2 | 20 |
| TGN-L-siRNA-I | 2K-PEG-S-S-SEQ ID NO: 74 (D) | 0.5 | 5 | 20 |
| TGN-L-siRNA-I | 2K-PEG-S-S-SEQ ID NO: 74 (D) | 0.5 | 10 | 20 |
| TGN-L-siRNA-I | 2K-PEG-S-S-SEQ ID NO: 82 (D) | 0.5 | 2 | 15 |
| TGN-L-siRNA-I | 2K-PEG-S-S-SEQ ID NO: 82 (D) | 0.5 | 5 | 30 |
| TGN-L-siRNA-I | 2K-PEG-S-S-SEQ ID NO: 82 (D) | 0.5 | 10 | 45 |
| TGN-L-siRNA-I | 2K-PEG-S-S-SEQ ID NO: 1710 (D) | 0.5 | 2 | 25 |
| TGN-L-siRNA-I | 2K-PEG-S-S-SEQ ID NO: 1710 (D) | 0.5 | 5 | 15 |
| TGN-L-siRNA-I | 2K-PEG-S-S-SEQ ID NO: 1710 (D) | 0.5 | 10 | 25 |
| TGN-L-siRNA-I | 2K-PEG-S-S-SEQ ID NO: 543 (D) | 0.5 | 2 | 25 |
| TGN-L-siRNA-I | 2K-PEG-S-S-SEQ ID NO: 543 (D) | 0.5 | 5 | 25 |

Note:
D—D isomer of peptide;
L—L isomer of peptide;
2K-S-S-PEG-SEQ ID NO = 2K-PEG-S-S-peptide;
*lethal at this dose Comparison of Sequential Dosing (Peptide Dosed 15 Min after siRNA) Vs. Co-Dosing and Comparison of SC Vs. IV Dosing The structure of TGN-S-S-peptide is the same as that shown above for Table 5 and the structure of TGN-L-siRNA is the same as that shown above for Table 6. The activity data is listed in Table 7.

TABLE 7

(i) Comparison of sequential dosing (peptide dosed 15 min after siRNA) vs. co-dosing (ii) Comparison of s.c. vs. i.v. dosing

| Targeted siRNA | Targeted peptide | Targeted siRNA dose (mg/kg) | Targeted peptide dose (mg/kg) | In vivo mRNA knockdown (%) | Route of administration |
|---|---|---|---|---|---|
| TGN-L-siRNA-III | | 0.5 | 0 | 40 | IV |
| TGN-L-siRNA-III | TGN-S-S-SEQ ID NO: 26 (D) | 0.5 | 2 | 30 | Sequential dosing-IV |
| TGN-L-siRNA-III | TGN-S-S-SEQ ID NO: 26 (D) | 0.5 | 5 | 60 | Sequential dosing-IV |
| TGN-L-siRNA-III | TGN-S-S-SEQ ID NO: 26 (D) | 0.5 | 10 | 70 | Sequential dosing-IV |
| TGN-L-siRNA-III | TGN-S-S-SEQ ID NO: 26 (D) | 0.5 | 2 | 30 | Sequential dosing-SC |
| TGN-L-siRNA-III | TGN-S-S-SEQ ID NO: 26 (D) | 0.5 | 5 | 25 | Sequential dosing-SC |
| TGN-L-siRNA-III | TGN-S-S-SEQ ID NO: 26 (D) | 0.5 | 10 | 25 | Sequential dosing-SC |
| TGN-L-siRNA-III | TGN-S-S-SEQ ID NO: 1710 (D) | 0.5 | 2 | 60 | Sequential dosing-IV |
| TGN-L-siRNA-III | TGN-S-S-SEQ ID NO: 1710 (D) | 0.5 | 5 | 66 | Sequential dosing-IV |
| TGN-L-siRNA-III | TGN-S-S-SEQ ID NO: 1710 (D) | 0.5 | 10 | 75 | Sequential dosing-IV |
| TGN-L-siRNA-III | TGN-S-S-SEQ ID NO: 1710 (D) | 0.5 | 2 | 65 | Sequential dosing-SC |
| TGN-L-siRNA-III | TGN-S-SSEQ ID NO: 1710(D) | 0.5 | 5 | 64 | Sequential dosing-SC |
| TGN-L-siRNA-III | TGN-S-S-SEQ ID NO: 1710 (D) | 0.5 | 10 | 66 | Sequential dosing-SC |
| TGN-L-siRNA-III | TGN-S-S-SEQ ID NO: 26 (D) | 0.5 | 2 | 30 | Co-dosing-IV |
| TGN-L-siRNA-III | TGN-S-S-SEQ ID NO: 26 (D) | 0.5 | 5 | 60 | Co-dosing-IV |
| TGN-L-siRNA-III | TGN-S-S-SEQ ID NO: 26 (D) | 0.5 | 10 | 70 | Co-dosing-IV |
| TGN-L-siRNA-III | TGN-S-S-SEQ ID NO: 26 (D) | 0.5 | 2 | 30 | Co-dosing-SC |
| TGN-L-siRNA-III | TGN-S-S-SEQ ID NO: 26 (D) | 0.5 | 5 | 25 | Co-dosing-SC |
| TGN-L-siRNA-III | TGN-S-S-SEQ ID NO: 26 (D) | 0.5 | 10 | 25 | Co-dosing-SC |
| TGN-L-siRNA-II | — | 0.5 | 0 | 25 | SC |
| TGN-L-siRNA-II | TGN-S-S-SEQ ID NO: 1709 (D) | 0.5 | 2 | 66 | Co-dosing-SC |
| TGN-L-siRNA-II | TGN-S-S-SEQ ID NO: 1709 (D) | 0.5 | 10 | 77 | Co-dosing-SC |

TABLE 7-continued (i) Comparison of sequential dosing (peptide dosed 15 min after siRNA) vs. co-dosing (ii) Comparison of s.c. vs. i.v. dosing

| Targeted siRNA | Targeted peptide | Targeted siRNA dose (mg/kg) | Targeted peptide dose (mg/kg) | In vivo mRNA knockdown (%) | Route of administration |
| --- | --- | --- | --- | --- | --- |
| TGN-L-siRNA-II | TGN-S-S-SEQ ID NO: 1709 (D) | 0.5 | 2 | 54 | Sequential dosing-SC |
| TGN-L-siRNA-II | TGN-S-S-SEQ ID NO: 1709 (D) | 0.5 | 10 | 72 | Sequential dosing-SC |
| TGN-L-siRNA-II | — | 0.25 | 0 | 25 | IV |
| TGN-L-siRNA-II | — | 0.25 | 0 | 9 | SC |
| TGN-L-siRNA-II | TGN-S-S-SEQ ID NO: 1733 (D) | 0.25 | 3 | 69 | Sequential dosing-IV |
| TGN-L-siRNA-II | TGN-S-S-SEQ ID NO: 1733 (D) | 0.25 | 10 | 58 | Sequential dosing-IV |
| TGN-L-siRNA-II | TGN-S-S-SEQ ID NO: 1733 (D) | 0.25 | 3 | 47 | Sequential dosing-SC |
| TGN-L-siRNA-II | TGN-S-S-SEQ ID NO: 1733 (D) | 0.25 | 10 | 67 | Sequential dosing-SC |

Note:
D-D isomer of peptide.

Comparison of Disulfide Vs. ECL Vs. CDM Linkages Between Targeting Ligand and Peptide The structure of TGN-S-S-peptide is the same as that shown above for Table 5 and the structure of TGN-L-siRNA is the same as that shown above for Table 6. The activity data is listed in Table 8.

TABLE 8

Comparison of Disulfide vs. ECL vs. CDM Linkages between Targeting Ligand and Peptide

| Targeted siRNA | Targeted peptide | Targeted siRNA dose (mg/kg) | Targeted peptide dose (mg/kg) | In vivo mRNA knockdown (%) | Peptide sequence | SEQ ID No. |
| --- | --- | --- | --- | --- | --- | --- |
| TGN-L-siRNA-II | TGN-S-S-SEQ ID NO: 1745 (D) | 0.25 | 3 | 46.1 | cglfgeieelieeglenlidwgng | 1745 |
| TGN-L-siRNA-II | TGN-S-S-SEQ ID NO: 1745 (D) | 0.25 | 1 | 44.4 | cglfgeieelieeglenlidwgng | 1745 |
| TGN-L-siRNA-II | TGN-ECL-SEQ ID NO: 1801 (D) | 0.25 | 3 | 47.4 | glfgeieelieeglenlidwgng | 1801 |
| TGN-L-siRNA-II | TGN-ECL-SEQ ID NO: 1801 (D) | 0.25 | 1 | 29.6 | glfgeieelieeglenlidwgng | 1801 |
| TGN-L-siRNA-II | TGN-CDM-SEQ ID NO: 1801 (D) | 0.25 | 3 | 24.9 | glfgeieelieeglenlidwgng | 1801 |
| TGN-L-siRNA-II | TGN-CDM-SEQ ID NO: 1801 (D) | 0.25 | 1 | 23.0 | glfgeieelieeglenlidwgng | 1801 |
| TGN-L-siRNA-II | TGN-S-S-SEQ ID NO: 74 (D) | 0.25 | 3 | 33.9 | cffgaiwefihsil | 74 |
| TGN-L-siRNA-II | TGN-S-S-SEQ ID NO: 74 (D) | 0.25 | 1 | 15.8 | cffgaiwefihsil | 74 |
| TGN-L-siRNA-II | TGN-ECL-SEQ ID NO: 1802 (D) | 0.25 | 3 | 64.0 | gffgaiwefihsil | 1802 |

TABLE 8-continued

Comparison of Disulfide vs. ECL vs. CDM Linkages between Targeting Ligand and Peptide

| Targeted siRNA | Targeted peptide | Targeted siRNA dose (mg/kg) | Targeted peptide dose (mg/kg) | In vivo mRNA knockdown (%) | Peptide sequence | SEQ ID No. |
|---|---|---|---|---|---|---|
| TGN-L-siRNA-II | TGN-ECL-SEQ ID NO: 1802 (D) | 0.25 | 1 | 28.7 | gffgaiwefihsil | 1802 |

One skilled in the art would readily appreciate that the present invention is well adapted to carry out the objects and obtain the ends and advantages mentioned, as well as those inherent therein. The methods and compositions described herein, as presently representative of preferred embodiments, are exemplary and are not intended as limitations on the scope of the invention. Changes therein and other uses will occur to those skilled in the art, which are encompassed within the spirit of the invention, are defined by the scope of the claims.

What is claimed is:

1. A method for inhibiting expression of a gene of a subject comprising administering:

(1) a composition comprising R-(L)$_a$-(G)$_b$ to the subject; wherein:

R is an oligonucleotide selected from the group consisting of DNA, RNA, siRNA, and microRNA;

L is a linker and each occurrence of L is independently selected from Table 3:

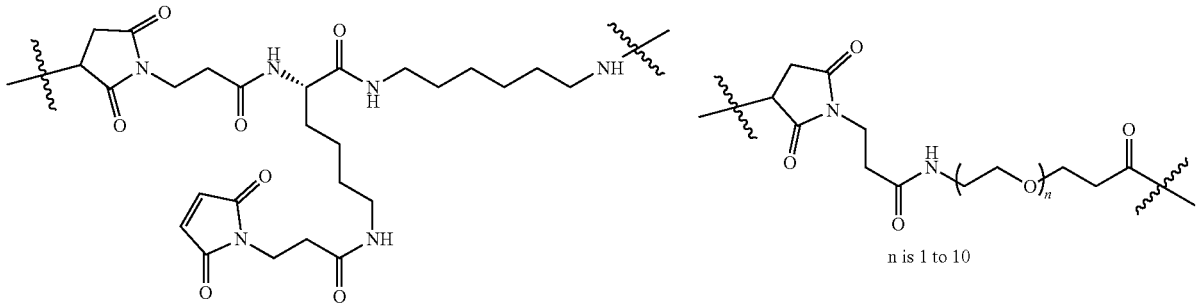

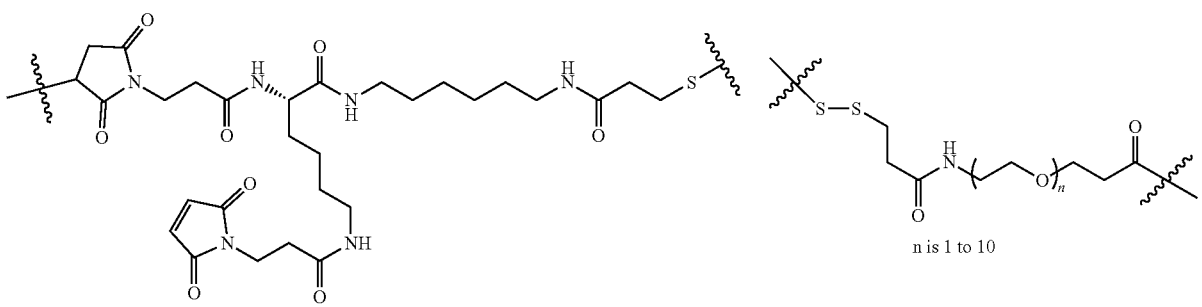

887 888
-continued
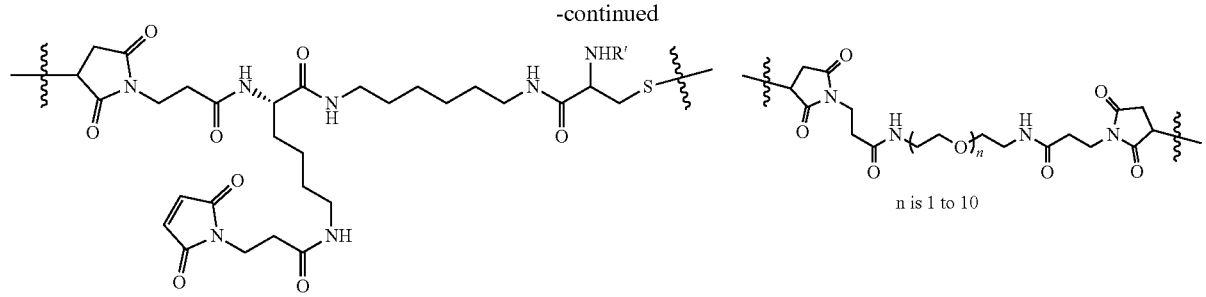
R' = H, Boc, Cbz, Ac, PEG, lipid, targeting ligand, linker(s) and/or peptide(s)
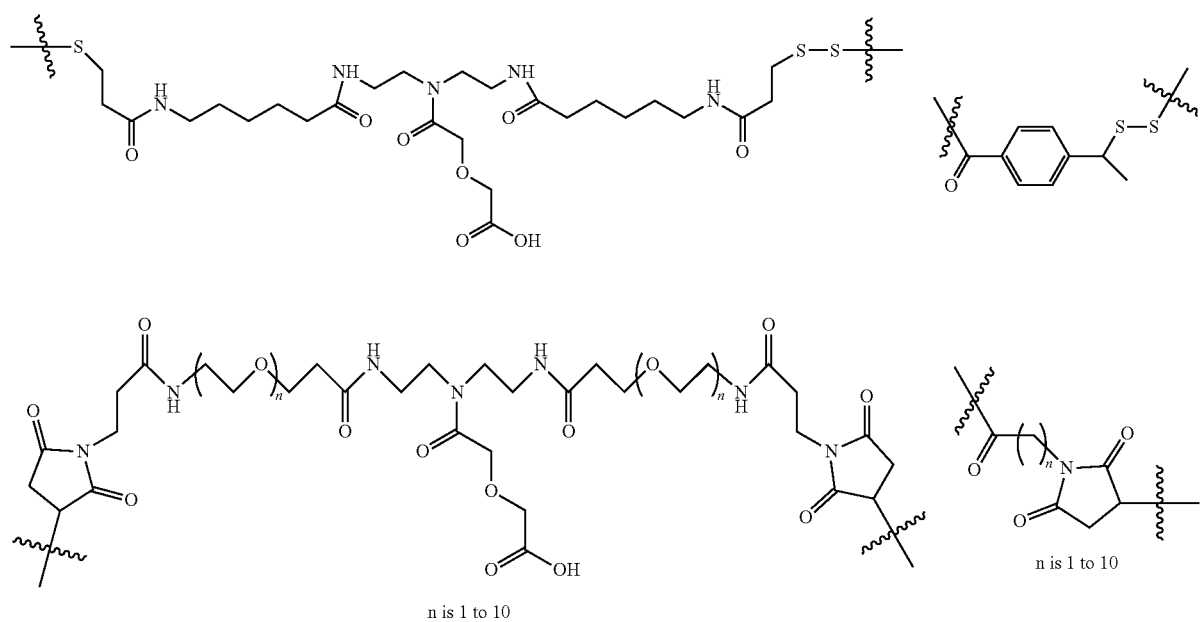
n is 1 to 10
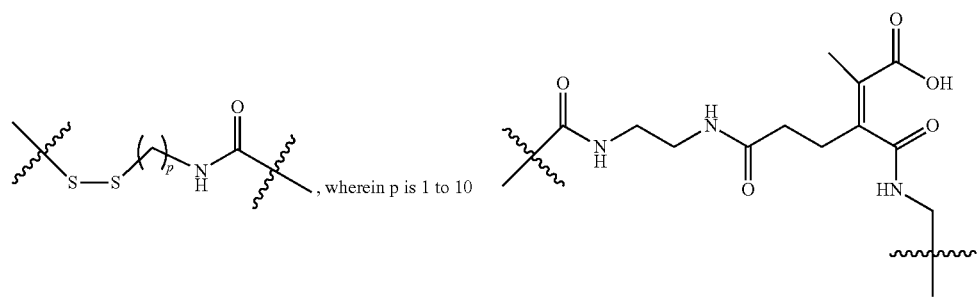
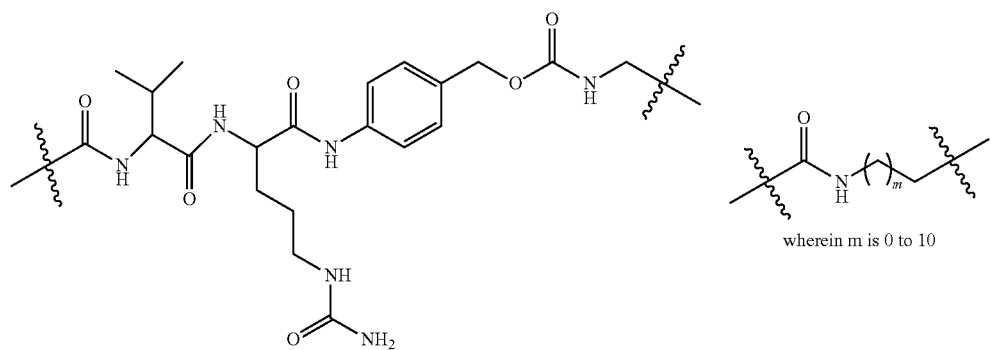
wherein m is 0 to 10

-continued
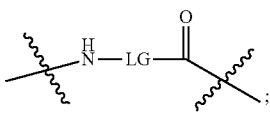
where "LG" is a linker selected from the group consisting of:
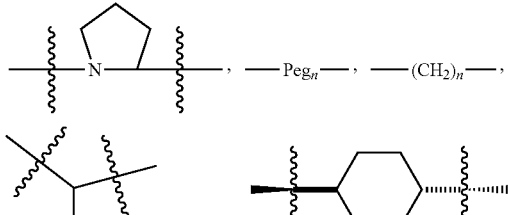
and n is 1 to 10;
G is a targeting ligand and each occurrence of G is independently selected from Table 4:
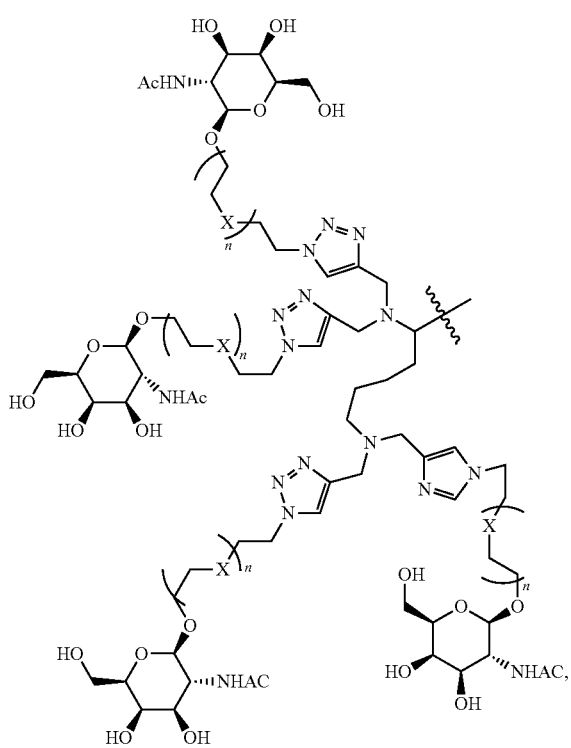
wherein each X is independently —O—, —S—, —CH$_2$— or —NH—; and each n is independently 1, 2, 3, or 4,
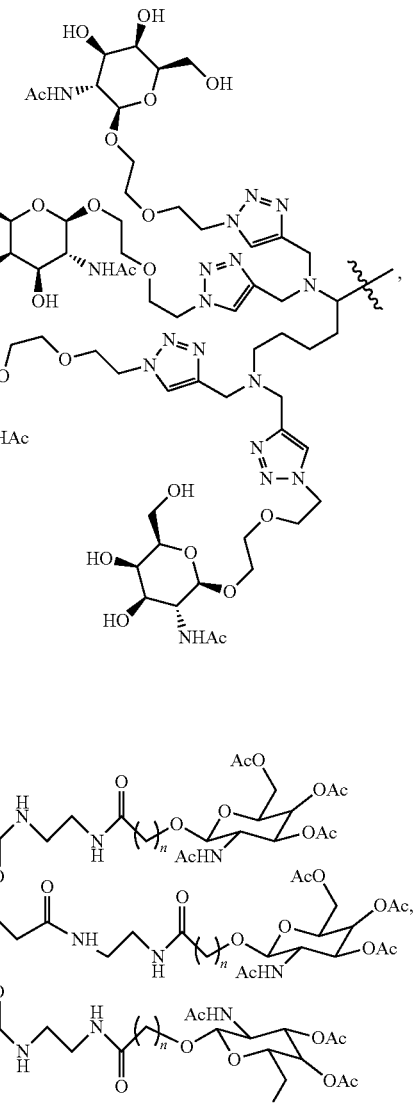
wherein each n is independently an integer from 1 to 20;

891
-continued

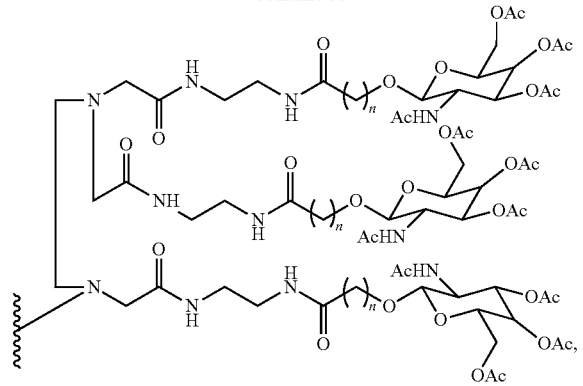

wherein each n is independently an integer from 1 to 20;

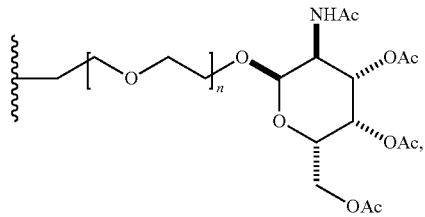

wherein n is an integer between 1 and 100,

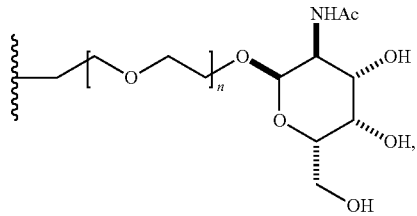

wherein n is an integer between 1 and 100,

892
-continued

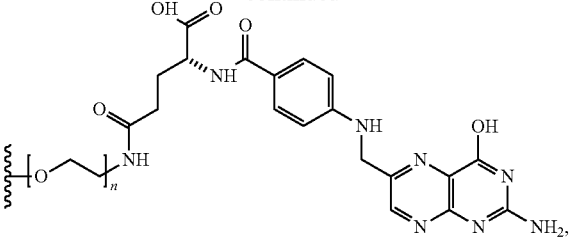

wherein n is an integer between 1 and 100; and each of a and b is independently 0, 1, 2, or 3; and (2) a composition comprising $(P)_c$-$(L)_d$-$(G)_e$ to the subject; wherein:

P is a peptide and each occurrence of P is independently selected from SEQ ID NOS: 1-1802;

L is a linker and each occurrence of L is independently selected from Table 3;

G is a targeting ligand and each occurrence of G is independently selected from Table 4;

d is 0, 1, 2, 3, or 4; and each of c and e is independently 1, 2, 3, or 4.

2. The method of claim 1, wherein R is a double stranded siRNA or single stranded siRNA.

3. The method of claim 1, wherein each occurrence of L is independently selected from Table 3a:

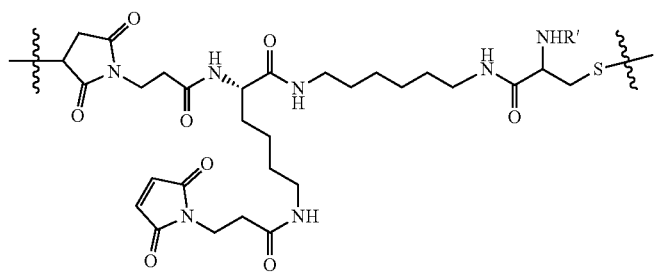

wherein R' = H, Boc, Cbz, Ac, PEG, lipid, targeting ligand, linker(s) and/or peptide(s)

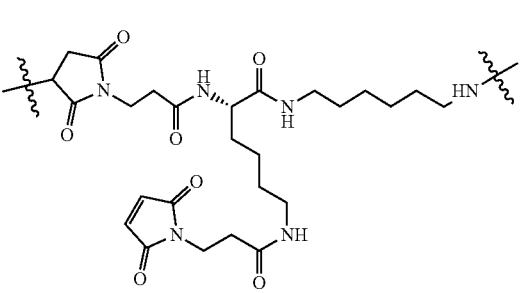

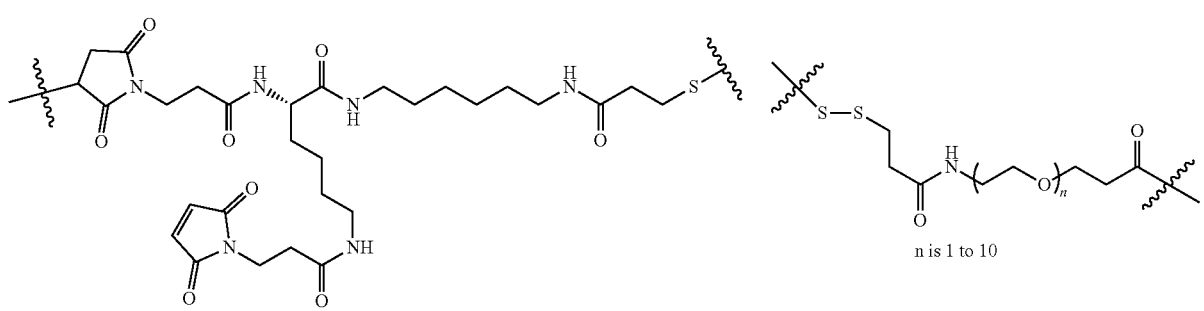

n is 1 to 10

-continued
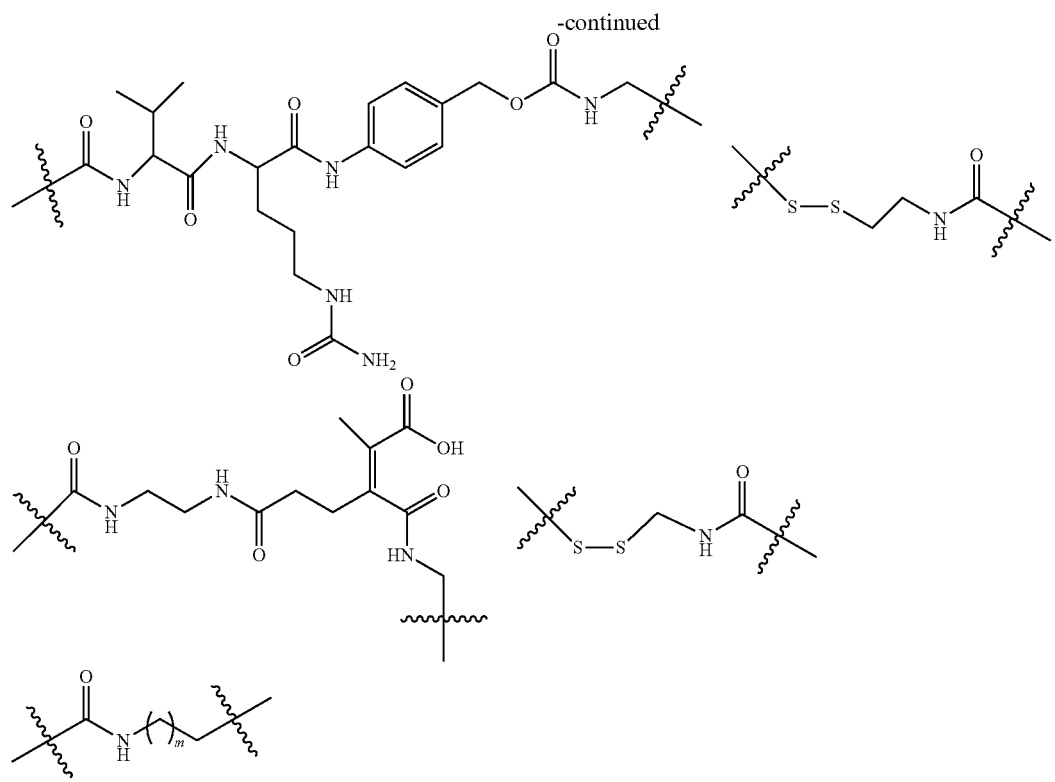
wherein m is 1 to 6.
4. The method of claim 1, wherein each occurrence of G is independently selected from Table 4a:
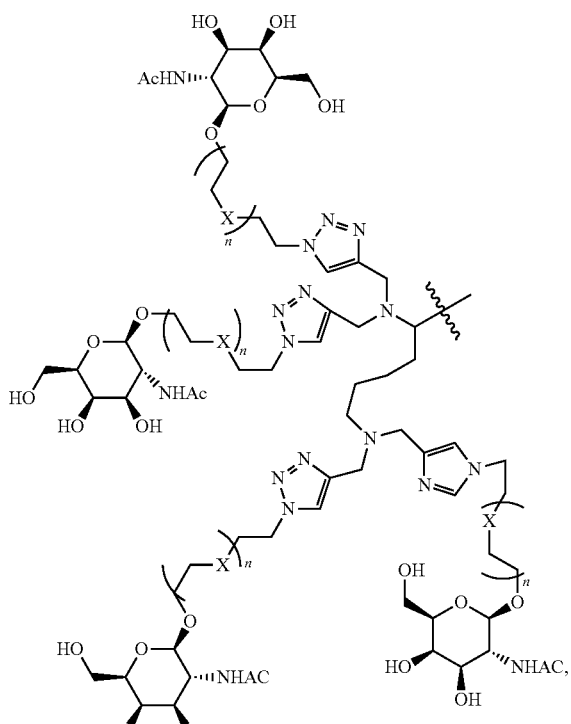
wherein each X is independently —O—, —S—, —CH$_2$— or —NH—; and each n is independently 1, 2, 3, or 4,
-continued
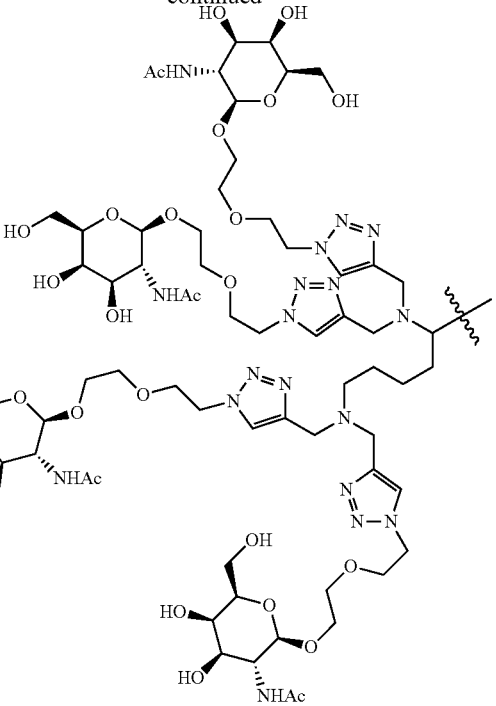
5. The method of claim 4, wherein G is a ligand of the following formula:

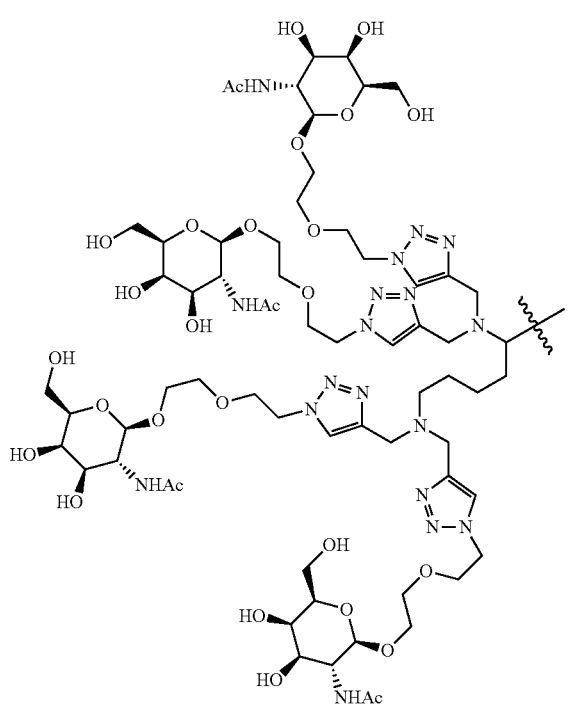

6. The method of claim 1, wherein:

each of a and b is independently 0, 1 or 2;

c is 1 or 2; and each of d and e is independently 1 or 2.

7. The method of claim 1, comprising administering:

(1) a composition comprising R-(L)$_a$-(G)$_b$ to the subject; wherein:

R is an siRNA;

L is a linker and each occurrence of L is independently selected from Table 3a:

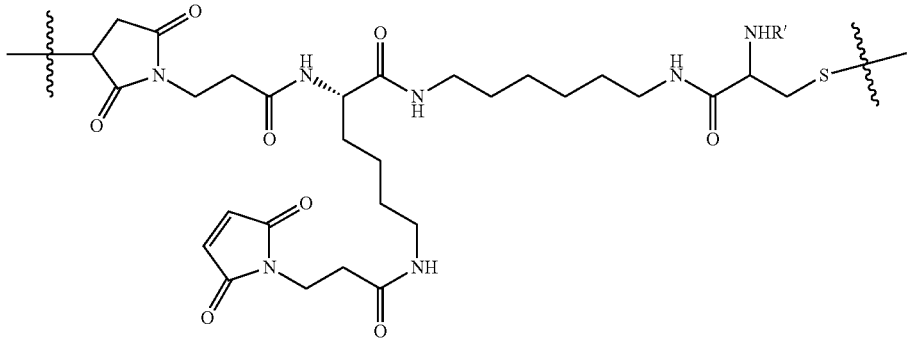

wherein R' = H, Boc, Cbz, Ac, PEG, lipid, targeting ligand, linker(s) and/or peptide(s)

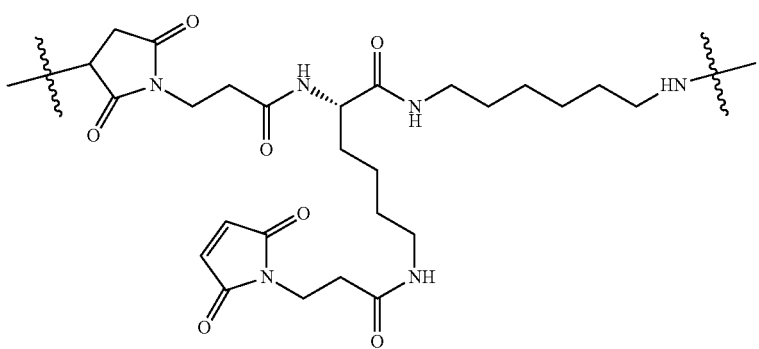

897
898
-continued
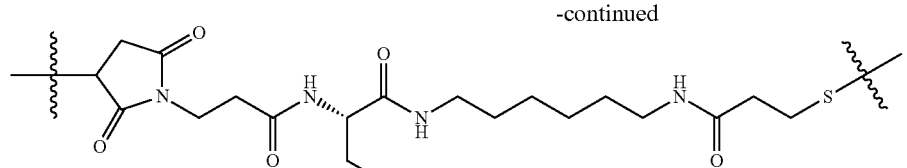
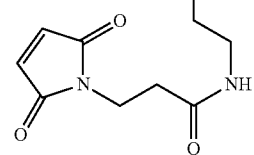
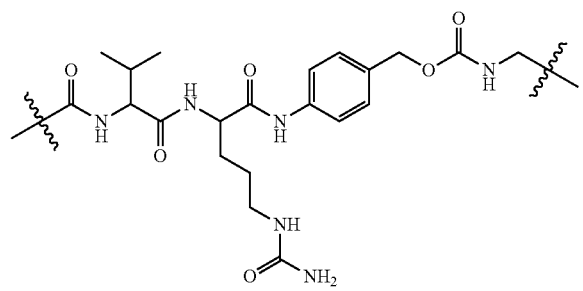
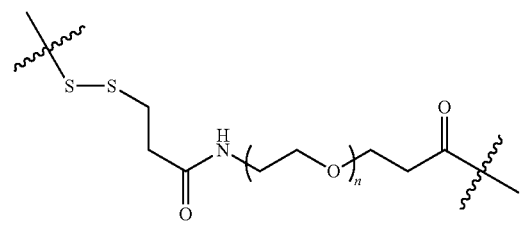
n is 1 to 10
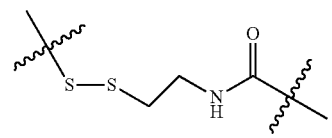
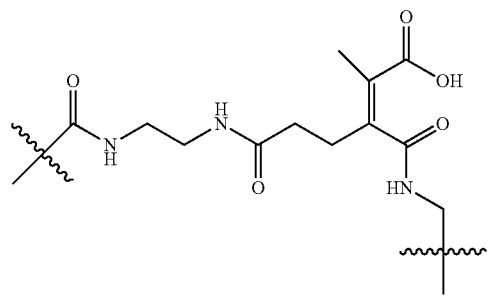
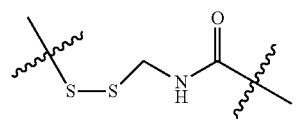
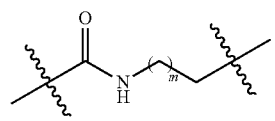
wherein m is 1 to 6;

G is a targeting ligand and each occurrence of G is independently selected from Table 4a:

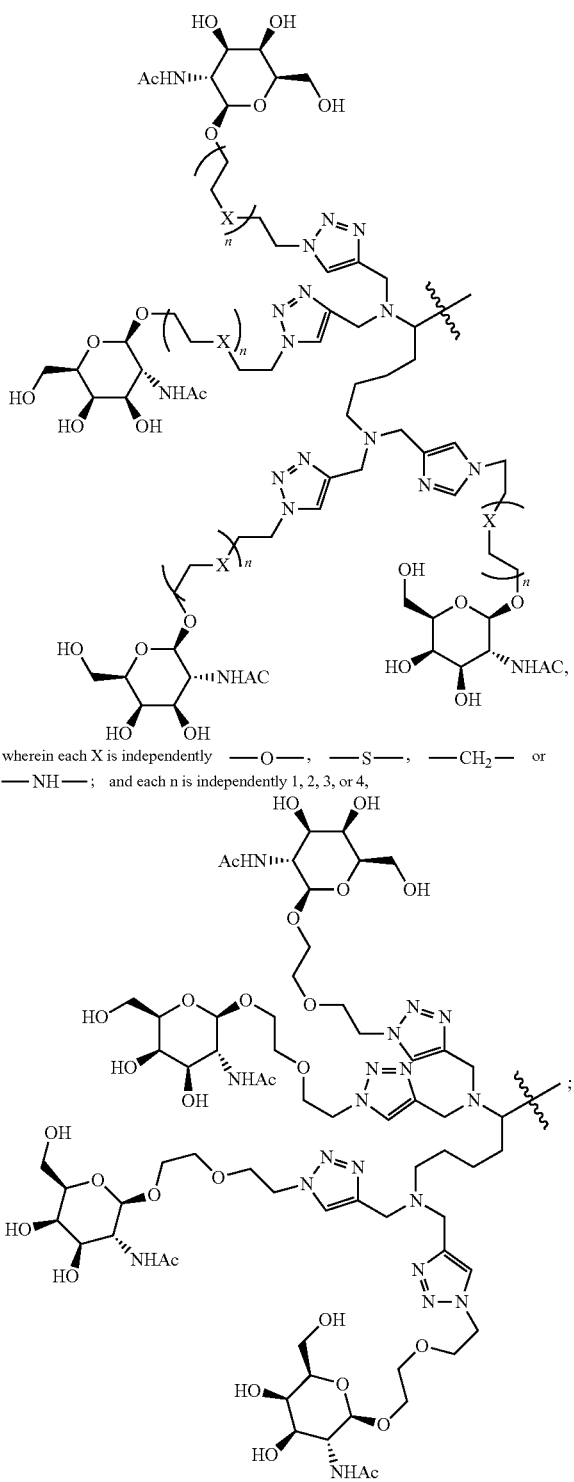

wherein each X is independently —O—, —S—, —CH$_2$— or —NH—; and each n is independently 1, 2, 3, or 4, each of a and b is independently 0, 1 or 2; and
(2) a composition comprising (P)$_c$-(L)$_d$-(G)$_e$ to the subject; wherein:
P is a peptide and each occurrence of P is independently selected from SEQ ID NOS: 1697, 1701-1713, 1715-1734, 1738, 1740, 1741, 1744-1749, 1751-1753, 1755, 1756, 1758-1786, 1788, and 1793-1802;
L is a linker and each occurrence of L is independently selected from Table 3a;
G is a targeting ligand and each occurrence of G is independently selected from Table 4a; and
each of c, d and e is independently 1 or 2.

8. The method of claim 7, wherein:
L of R-(L)$_a$-(G)$_b$ is selected from

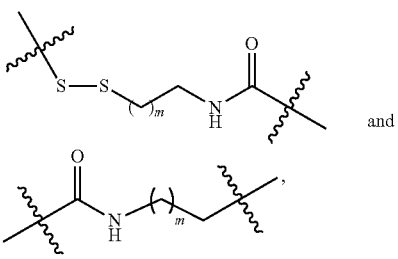

wherein m is an integer selected from 0 to 10;
G of R-(L)$_a$-(G)$_b$ is:

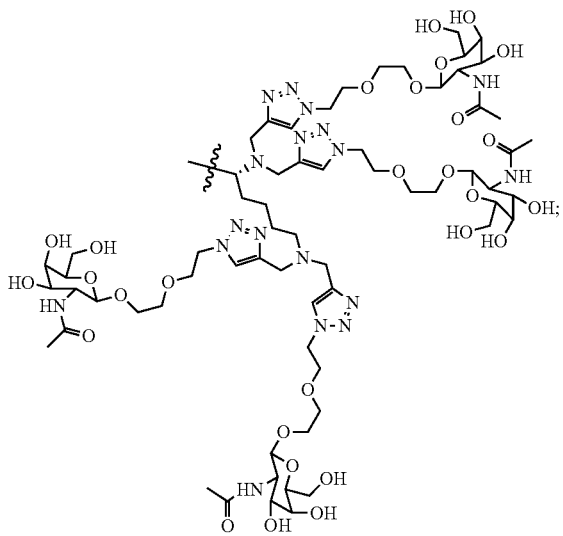 [SMILES: *[C@@H](CCCCN(Cc1cn(CCOCCOC2OC(CO)C(O)C(O)C2NC(C)=O)nn1)Cc1cn(CCOCCOC2OC(CO)C(O)C(O)C2NC(C)=O)nn1)N(Cc1cn(CCOCCOC2OC(CO)C(O)C(O)C2NC(C)=O)nn1)Cc1cn(CCOCCOC2OC(CO)C(O)C(O)C2NC(C)=O)nn1]

and
(P)$_c$-(L)$_d$-(G)$_e$ of composition (2) is:

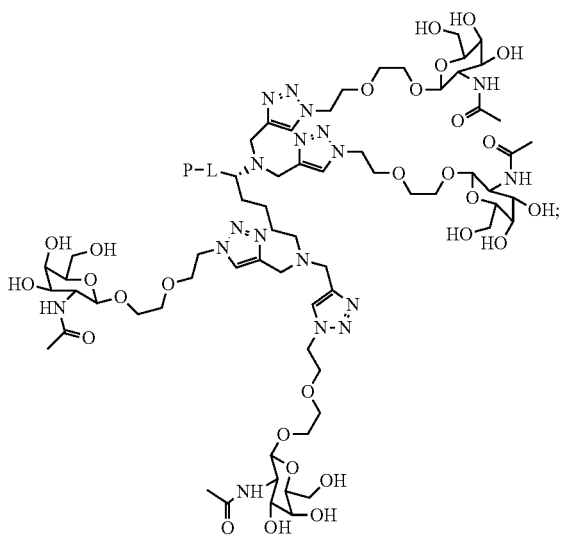

wherein P is a peptide selected from SEQ ID NOS: 1697, 1701-1713, 1715-1734, 1738, 1740, 1741, 1744-1749, 1751-1753, 1755, 1756, 1758-1786, 1788, and 1793-1802; and wherein L of composition (2) is selected from:

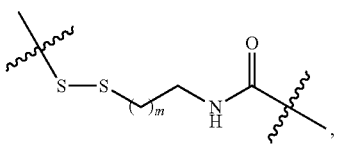

wherein m is an integer selected from 0 to 10,

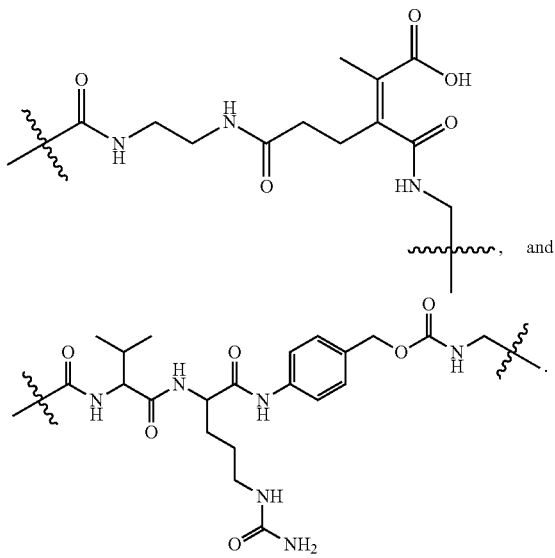

9. The method of claim 8, wherein each L of compositions (1) and (2) is independently

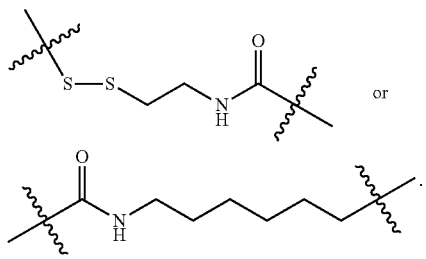

10. The method of claim 1, wherein:
the composition comprising R-(L)$_a$-(G)$_b$ and the composition comprising (P)$_c$-(L)$_d$-(G)$_e$ are co-administered at the same time.

11. The method of claim 1, wherein:
the composition comprising R-(L)$_a$-(G)$_b$ and the composition comprising (P)$_c$-(L)$_d$-(G)$_e$ are sequentially administered about 0.1 to 1 hour apart.

12. The method of claim 1, wherein the oligonucleotide is administered at a dose of 0.1 to 5 mpk; and the peptide is administered at a dose of 1 to 100 mpk.

13. A composition for dual molecular delivery of an oligonucleotide and a peptide conjugate comprising:
(1) R-(L)$_a$-(G)$_b$; and
(2) (P)$_c$-(L)$_d$-(G)$_e$; wherein:
R is an oligonucleotide selected from the group consisting of DNA, RNA, siRNA, and microRNA;
P is a peptide and each occurrence of P is independently selected from SEQ ID NOS: 1697, 1701-1713, 1715-1734, 1738, 1740, 1741, 1744-1749, 1751-1753, 1755, 1756, 1758-1786, 1788, and 1793-1802;

L is a linker and each occurrence of L is independently selected from Table 3 of claim 1;
G is a targeting ligand and each occurrence of G is independently selected from Table 4 of claim 1;
each of a and b is independently 0, 1, 2, or 3; and
each of c, d and e is independently 1, 2, 3, 4, or 5.

14. The composition of claim 13, wherein Y comprises a ligand of the following formula:

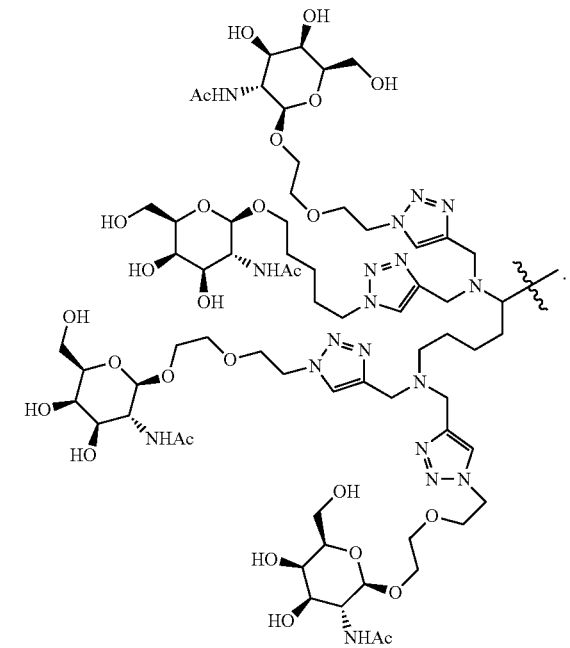

15. The composition of claim 13, wherein each of a and b is independently 0 or 1;
c is 1; and
each of d and e is an 1.

16. The composition of claim 13, wherein:
(1) G of R-(L)$_a$-(G)$_b$ is:

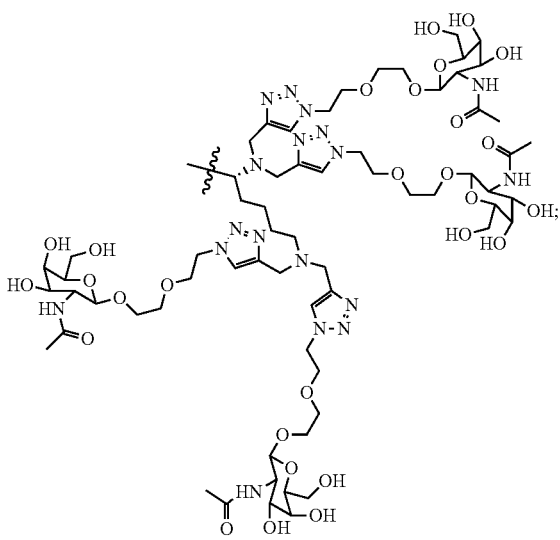 [SMILES: *[C@@H](CCCCN(Cc1cn(CCOCCOC2OC(CO)C(O)C(O)C2NC(C)=O)nn1)Cc1cn(CCOCCOC2OC(CO)C(O)C(O)C2NC(C)=O)nn1)N(Cc1cn(CCOCCOC2OC(CO)C(O)C(O)C2NC(C)=O)nn1)Cc1cn(CCOCCOC2OC(CO)C(O)C(O)C2NC(C)=O)nn1]

and
each of a and b is 1; and (2) $(P)_c\text{-}(L)_d\text{-}(G)_e$ is:

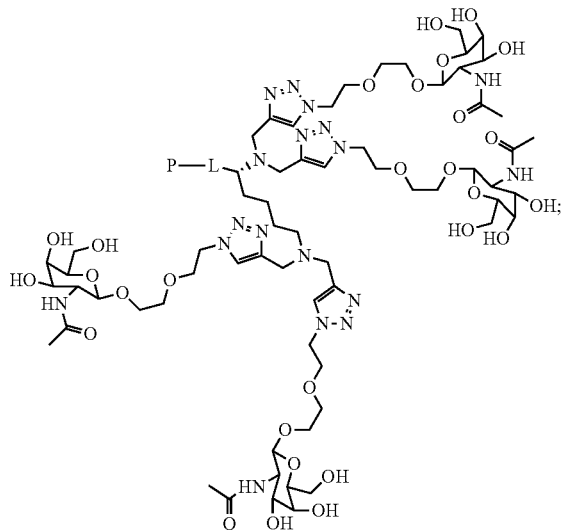

and wherein each L of compositions (1) and (2) is independently selected from:

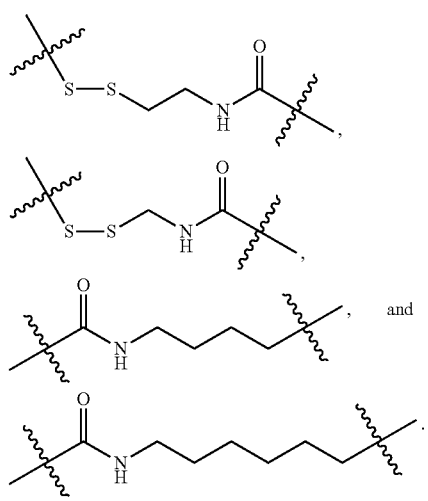

17. The composition of claim 13, wherein $R\text{-}(L)_a\text{-}(G)_b$ further comprises a lipid and/or solubilizing agent.

18. The composition of claim 13, wherein:
the oligonucleotide is a double stranded siRNA; and
G is attached to the guide strand or the passenger strand of the siRNA at different 2'-positions of the ribose rings and/or at different terminal 3' and/or 5'-positions.

* * * * *

SEQUENCE LISTING

```
<160> NUMBER OF SEQ ID NOS: 1815

<210> SEQ ID NO 1
<211> LENGTH: 34
<212> TYPE: PRT
<213> ORGANISM: Homo sapiens

<400> SEQUENCE: 1

Cys Gly Leu Phe Glu Ala Ile Glu Glu Phe Ile Glu Asn Leu Trp Glu
1               5                   10                  15

Leu Leu Ile Asp Gly Trp Tyr Gly Tyr Gly Arg Lys Lys Arg Arg Gln
            20                  25                  30

Arg Arg

<210> SEQ ID NO 2
<211> LENGTH: 34
<212> TYPE: PRT
<213> ORGANISM: Homo sapiens

<400> SEQUENCE: 2

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly His Lys Lys His His Gln
            20                  25                  30

His His

<210> SEQ ID NO 3
<211> LENGTH: 37
<212> TYPE: PRT
<213> ORGANISM: Homo sapiens

<400> SEQUENCE: 3

Cys Asx Ala Leu Ala Leu Phe Glu Ala Ile Gly Phe Ile Glu Asn
1               5                   10                  15

Gly Trp Glu Gly Met Ile Asp Gly Trp Tyr Gly Tyr Gly Arg Lys Lys
            20                  25                  30

Arg Arg Gln Arg Arg
            35

<210> SEQ ID NO 4
<211> LENGTH: 34
<212> TYPE: PRT
<213> ORGANISM: Homo sapiens
```

-continued

<400> SEQUENCE: 4

Cys Gly Leu Phe Glu Ala Ile Glu Gly Phe Ile Glu Asn Gly Leu Lys
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 5
<211> LENGTH: 34
<212> TYPE: PRT
<213> ORGANISM: Homo sapiens

<400> SEQUENCE: 5

Cys Gly Leu Phe Glu Ala Ile Glu Gly Phe Ile Glu Trp Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 6
<211> LENGTH: 34
<212> TYPE: PRT
<213> ORGANISM: Homo sapiens

<400> SEQUENCE: 6

Cys Arg Arg Gln Arg Arg Lys Lys Arg Gly Tyr Gly Tyr Trp Gly Asp
1               5                   10                  15

Ile Met Gly Glu Trp Gly Asn Glu Ile Phe Gly Glu Ile Ala Glu Phe
            20                  25                  30

Leu Gly

<210> SEQ ID NO 7
<211> LENGTH: 33
<212> TYPE: PRT
<213> ORGANISM: Homo sapiens

<400> SEQUENCE: 7

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg

<210> SEQ ID NO 8
<211> LENGTH: 34
<212> TYPE: PRT
<213> ORGANISM: Homo sapiens

<400> SEQUENCE: 8

Cys Tyr Gly Arg Lys Lys Arg Arg Gln Arg Arg Gly Leu Phe Glu Ala
1               5                   10                  15

Ile Glu Gly Phe Ile Glu Asn Gly Trp Glu Gly Met Ile Asp Gly Trp
            20                  25                  30

Tyr Gly

<210> SEQ ID NO 9
<211> LENGTH: 20
<212> TYPE: PRT
<213> ORGANISM: Homo sapiens

<400> SEQUENCE: 9

Cys Ile Phe Gly Ala Ile Ala Gly Phe Ile Lys Asn Ile Leu Lys Gly
1               5                   10                  15

Leu Ile Asp Gly
            20

<210> SEQ ID NO 10
<211> LENGTH: 14
<212> TYPE: PRT
<213> ORGANISM: Homo sapiens

<400> SEQUENCE: 10

Cys Ile Phe Gly Ala Ile Ala Gly Phe Ile Arg Asn Ile Trp
1               5                   10

<210> SEQ ID NO 11
<211> LENGTH: 34
<212> TYPE: PRT
<213> ORGANISM: Homo sapiens

<400> SEQUENCE: 11

Cys Gly Leu Phe His Ala Leu Leu His Leu Leu His Ser Leu Trp His
1               5                   10                  15

Gly Leu Leu His Ala Trp Tyr Gly Tyr Gly His Lys Lys His His Gln
            20                  25                  30

His Arg

<210> SEQ ID NO 12
<211> LENGTH: 34
<212> TYPE: PRT
<213> ORGANISM: Homo sapiens

<400> SEQUENCE: 12

Cys Gly Leu Phe Glu Ala Ile Glu Gly Leu Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 13
<211> LENGTH: 34
<212> TYPE: PRT
<213> ORGANISM: Homo sapiens

<400> SEQUENCE: 13

Cys Gly Leu Phe Glu Leu Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 14
<211> LENGTH: 34
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: misc_feature
<222> LOCATION: (27)..(31)
<223> OTHER INFORMATION: Xaa = ornithine -continued

<400> SEQUENCE: 14

Cys Gly Leu Phe Glu Ala Ile Glu Gly Phe Ile Glu Asn Gly Trp Glu
1               5                   10                  15

Gly Leu Ile Asp Gly Trp Tyr Gly Tyr Gly Xaa Xaa Xaa Xaa Xaa Gln
            20                  25                  30

Arg Arg

<210> SEQ ID NO 15
<211> LENGTH: 34
<212> TYPE: PRT
<213> ORGANISM: Homo sapiens

<400> SEQUENCE: 15

Cys Gly Leu Phe Gly Ala Ile Glu Gly Phe Ile Glu Asn Gly Trp Glu
1               5                   10                  15

Gly Leu Ile Asp Gly Trp Tyr Gly Tyr Gly Arg Lys Lys Arg Arg Gln
            20                  25                  30

Arg Arg

<210> SEQ ID NO 16
<211> LENGTH: 34
<212> TYPE: PRT
<213> ORGANISM: Homo sapiens

<400> SEQUENCE: 16

Cys Gly Leu Phe Glu Ala Ile Glu Gly Phe Leu Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 17
<211> LENGTH: 34
<212> TYPE: PRT
<213> ORGANISM: Homo sapiens

<400> SEQUENCE: 17

Cys Gly Leu Phe Glu Ala Ile Glu Gly Phe Ile Glu Asn Gly Leu Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 18
<211> LENGTH: 34
<212> TYPE: PRT
<213> ORGANISM: Homo sapiens

<400> SEQUENCE: 18

Cys Gly Leu Phe Gly Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 19
<211> LENGTH: 36
<212> TYPE: PRT

<213> ORGANISM: Homo sapiens

<400> SEQUENCE: 19

Cys Gly Leu Phe Glu Ala Ile Glu Gly Phe Ile Glu Asn Gly Trp Glu
1               5                   10                  15
Gly Asn Leu Glu Ile Asp Gly Trp Tyr Gly Tyr Gly Arg Lys Lys Arg
            20                  25                  30
Arg Gln Arg Arg
        35

<210> SEQ ID NO 20
<211> LENGTH: 21
<212> TYPE: PRT
<213> ORGANISM: Homo sapiens

<400> SEQUENCE: 20

Cys Gly Ile Phe Gly Ala Ile Ala Gly Phe Ile Lys Asn Ile Trp Lys
1               5                   10                  15
Gly Leu Ile Asp Trp
            20

<210> SEQ ID NO 21
<211> LENGTH: 34
<212> TYPE: PRT
<213> ORGANISM: Homo sapiens

<400> SEQUENCE: 21

Cys Tyr Gly Arg Lys Lys Arg Gln Arg Arg Gly Leu Phe Glu Ala
1               5                   10                  15
Ile Glu Gly Phe Ile Glu Asn Gly Trp Lys Gly Leu Ile Asp Ala Trp
            20                  25                  30
Tyr Gly

<210> SEQ ID NO 22
<211> LENGTH: 34
<212> TYPE: PRT
<213> ORGANISM: Homo sapiens

<400> SEQUENCE: 22

Cys Gly Leu Leu Glu Ala Leu Glu Gly Leu Leu Glu Ser Leu Trp Glu
1               5                   10                  15
Gly Leu Leu Glu Ala Trp Tyr Gly Tyr Gly Arg Lys Lys Arg Arg Gln
            20                  25                  30
Arg Arg

<210> SEQ ID NO 23
<211> LENGTH: 34
<212> TYPE: PRT
<213> ORGANISM: Homo sapiens

<400> SEQUENCE: 23

Cys Gly Leu Phe Glu Ala Ile Glu Gly Phe Ile Glu Asn Gly Trp Glu
1               5                   10                  15
Gly Met Ile Asp Asn Trp Tyr Gly Tyr Gly Arg Lys Lys Arg Arg Gln
            20                  25                  30
Arg Arg

<210> SEQ ID NO 24
<211> LENGTH: 44
<212> TYPE: PRT

<213> ORGANISM: Homo sapiens

<400> SEQUENCE: 24

Cys Ile Phe Gly Ala Ile Ala Gly Phe Ile Lys Asn Ile Trp Glu Gly
1               5                   10                  15

Leu Ile Glu Ala Trp Tyr Gly Leu His Leu Leu His His Leu Leu His
            20                  25                  30

His Leu His His Leu Leu His His Leu Leu His Leu
        35                  40

<210> SEQ ID NO 25
<211> LENGTH: 21
<212> TYPE: PRT
<213> ORGANISM: Homo sapiens

<400> SEQUENCE: 25

Cys Ile Phe Gly Ala Ile Ala Gly Phe Ile Lys Asn Ile Trp Glu Gly
1               5                   10                  15

Leu Ile Asp Ala Phe
            20

<210> SEQ ID NO 26
<211> LENGTH: 18
<212> TYPE: PRT
<213> ORGANISM: Homo sapiens

<400> SEQUENCE: 26

Cys Ile Phe Gly Ala Ile Ala Gly Phe Ile Lys Asn Ile Trp Glu Gly
1               5                   10                  15

Leu Ile

<210> SEQ ID NO 27
<211> LENGTH: 35
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (35)..(35)
<223> OTHER INFORMATION: Lys is conjugated to Stearyl

<400> SEQUENCE: 27

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg Lys
        35

<210> SEQ ID NO 28
<211> LENGTH: 63
<212> TYPE: PRT
<213> ORGANISM: Homo sapiens

<400> SEQUENCE: 28

Cys Gly Leu Phe Glu Ala Ile Ala Gly Phe Ile Glu Gly Gly Trp Pro
1               5                   10                  15

Gly Leu Ile Asn Gly Trp Tyr Gly Tyr Gly Arg Lys Lys Arg Arg Gln
            20                  25                  30

Arg Arg Leu His Leu Leu His His Leu Leu His Leu His His Leu
        35                  40                  45

Leu His His Leu Leu His Leu Leu His Leu Leu His His Leu
            50                  55                  60

<210> SEQ ID NO 29
<211> LENGTH: 56
<212> TYPE: PRT
<213> ORGANISM: Homo sapiens

<400> SEQUENCE: 29

Cys Gly Leu Phe Glu Ala Ile Glu Gly Phe Ile Glu Asn Gly Trp Glu
1               5                   10                  15

Gly Met Ile Asp Gly Trp Tyr Gly Gly Gly Leu His Leu Leu His
            20                  25                  30

His Leu Leu His His Leu His His Leu Leu His Leu Leu His Leu
        35                  40                  45

Leu His His Leu Leu His His Leu
        50                  55

<210> SEQ ID NO 30
<211> LENGTH: 45
<212> TYPE: PRT
<213> ORGANISM: Homo sapiens

<400> SEQUENCE: 30

Cys Gly Leu Phe Glu Ala Ile Glu Gly Phe Ile Glu Asn Gly Trp Glu
1               5                   10                  15

Gly Met Ile Asp Gly Trp Tyr Gly Leu His Leu Leu His His Leu Leu
            20                  25                  30

His His Leu His His Leu Leu His His Leu Leu His Leu
        35                  40                  45

<210> SEQ ID NO 31
<211> LENGTH: 31
<212> TYPE: PRT
<213> ORGANISM: Homo sapiens

<400> SEQUENCE: 31

Cys Gly Leu Phe Glu Ala Leu Leu Glu Leu Leu Glu Ser Leu Trp Glu
1               5                   10                  15

Leu Leu Leu Glu Ala Tyr Gly Arg Lys Lys Arg Arg Gln Arg Arg
            20                  25                  30

<210> SEQ ID NO 32
<211> LENGTH: 34
<212> TYPE: PRT
<213> ORGANISM: Homo sapiens

<400> SEQUENCE: 32

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 33
<211> LENGTH: 34
<212> TYPE: PRT
<213> ORGANISM: Homo sapiens

<400> SEQUENCE: 33

```
Cys Gly Leu Phe Glu Ala Ile Glu Gly Phe Ile Asn Gly Trp Glu
1               5                   10                  15

Gly Met Ala Asp Gly Trp Tyr Gly Tyr Gly Arg Lys Lys Arg Arg Gln
            20                  25                  30

Arg Arg
```

<210> SEQ ID NO 34
<211> LENGTH: 34
<212> TYPE: PRT
<213> ORGANISM: Homo sapiens

<400> SEQUENCE: 34

```
Cys Gly Ile Phe Gly Ala Ile Ala Gly Phe Ile Lys Asn Ile Trp Glu
1               5                   10                  15

Gly Leu Ile Asp Trp Trp Tyr Gly Tyr Gly Arg Lys Lys Arg Arg Gln
            20                  25                  30

Arg Arg
```

<210> SEQ ID NO 35
<211> LENGTH: 34
<212> TYPE: PRT
<213> ORGANISM: Homo sapiens

<400> SEQUENCE: 35

```
Cys Gly Phe Leu Pro Ala Ile Ala Gly Ile Leu Ser Gln Leu Phe Glu
1               5                   10                  15

Gly Leu Ile Asp Gly Trp Tyr Gly Tyr Gly Arg Lys Lys Arg Arg Gln
            20                  25                  30

Arg Arg
```

<210> SEQ ID NO 36
<211> LENGTH: 14
<212> TYPE: PRT
<213> ORGANISM: Homo sapiens

<400> SEQUENCE: 36

```
Cys Phe Phe Gly Ala Ile Trp Gly Phe Ile Lys Ser Ile Leu
1               5                   10
```

<210> SEQ ID NO 37
<211> LENGTH: 23
<212> TYPE: PRT
<213> ORGANISM: Homo sapiens

<400> SEQUENCE: 37

```
Cys Ile Phe Gly Ala Ile Ala Gly Phe Ile Lys Asn Ile Trp Lys Gly
1               5                   10                  15

Leu Ile Asp Trp Trp Tyr Gly
            20
```

<210> SEQ ID NO 38
<211> LENGTH: 34
<212> TYPE: PRT
<213> ORGANISM: Homo sapiens

<400> SEQUENCE: 38

```
Cys Gly Leu Phe Glu Ala Ile Glu Gly Phe Ile Trp Asn Gly Trp Glu
1               5                   10                  15

Gly Met Ile Asp Gly Trp Tyr Gly Tyr Gly Arg Lys Lys Arg Arg Gln
            20                  25                  30
```

Arg Arg

<210> SEQ ID NO 39
<211> LENGTH: 34
<212> TYPE: PRT
<213> ORGANISM: Homo sapiens

<400> SEQUENCE: 39

Cys Gly Leu Phe Glu Ala Ile Ala Glu Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 40
<211> LENGTH: 34
<212> TYPE: PRT
<213> ORGANISM: Homo sapiens

<400> SEQUENCE: 40

Cys Tyr Gly Arg Lys Lys Arg Arg Gln Arg Arg Gly Leu Phe Glu Ala
1               5                   10                  15

Ile Glu Gly Phe Ile Glu Asn Gly Trp Lys Gly Leu Ile Asp Trp Trp
            20                  25                  30

Tyr Gly

<210> SEQ ID NO 41
<211> LENGTH: 34
<212> TYPE: PRT
<213> ORGANISM: Homo sapiens

<400> SEQUENCE: 41

Cys Gly Leu Phe Glu Ala Ile Glu Gly Phe Ile Glu Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 42
<211> LENGTH: 34
<212> TYPE: PRT
<213> ORGANISM: Homo sapiens

<400> SEQUENCE: 42

Cys Gly Leu Phe Glu Ala Ile Glu Gly Phe Ile Glu Asn Ala Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 43
<211> LENGTH: 34
<212> TYPE: PRT
<213> ORGANISM: Homo sapiens

<400> SEQUENCE: 43

Cys Gly Leu Phe Glu Ala Ile Glu Gly Phe Ile Glu Asn Gly Trp Glu
1               5                   10                  15

Gly Met Ile Asp Leu Trp Tyr Gly Tyr Gly Arg Lys Lys Arg Arg Gln
            20                  25                  30

-continued

Arg Arg

<210> SEQ ID NO 44
<211> LENGTH: 19
<212> TYPE: PRT
<213> ORGANISM: Homo sapiens

<400> SEQUENCE: 44

Cys Arg Leu Leu Arg Leu Leu Arg Leu Trp Arg Arg Leu Leu Arg
1               5                   10                  15

Leu Leu Arg

<210> SEQ ID NO 45
<211> LENGTH: 34
<212> TYPE: PRT
<213> ORGANISM: Homo sapiens

<400> SEQUENCE: 45

Cys Gly Gly Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 46
<211> LENGTH: 34
<212> TYPE: PRT
<213> ORGANISM: Homo sapiens

<400> SEQUENCE: 46

Cys Gly Leu Phe Glu Lys Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 47
<211> LENGTH: 34
<212> TYPE: PRT
<213> ORGANISM: Homo sapiens

<400> SEQUENCE: 47

Cys Gly Leu Phe Glu Ala Ile Glu Gly Phe Ile Glu Asn Gly Trp Glu
1               5                   10                  15

Asn Met Ile Asp Gly Trp Tyr Gly Tyr Gly Arg Lys Lys Arg Arg Gln
            20                  25                  30

Arg Arg

<210> SEQ ID NO 48
<211> LENGTH: 17
<212> TYPE: PRT
<213> ORGANISM: Homo sapiens

<400> SEQUENCE: 48

Cys Ile Phe Gly Ala Ile Ala Gly Phe Ile Lys Asn Ile Leu Lys Gly
1               5                   10                  15

Leu

<210> SEQ ID NO 49

```
<211> LENGTH: 23
<212> TYPE: PRT
<213> ORGANISM: Homo sapiens

<400> SEQUENCE: 49

Cys Ile Phe Gly Ala Ile Ala Gly Phe Ile Lys Asn Ile Leu Lys Gly
1               5                   10                  15

Leu Ile Asp Gly Trp Tyr Gly
            20

<210> SEQ ID NO 50
<211> LENGTH: 37
<212> TYPE: PRT
<213> ORGANISM: Homo sapiens

<400> SEQUENCE: 50

Cys Gly Leu Phe Glu Ala Ile Glu Gly Phe Ile Glu Asn Gly Trp Glu
1               5                   10                  15

Gly Met Ile Asp Gly Trp Tyr Gly Pro Glu Gly Tyr Gly Arg Lys Lys
            20                  25                  30

Arg Arg Gln Arg Arg
        35

<210> SEQ ID NO 51
<211> LENGTH: 52
<212> TYPE: PRT
<213> ORGANISM: Homo sapiens

<400> SEQUENCE: 51

Cys Gly Leu Phe Glu Ala Leu Leu Glu Leu Leu Glu Ser Leu Trp Glu
1               5                   10                  15

Leu Leu Leu Glu Ala Tyr Gly Arg Lys Lys Arg Arg Gln Arg Arg Leu
            20                  25                  30

His Leu Leu His His Leu Leu His His Leu His His Leu Leu His His
        35                  40                  45

Leu Leu His Leu
    50

<210> SEQ ID NO 52
<211> LENGTH: 41
<212> TYPE: PRT
<213> ORGANISM: Homo sapiens

<400> SEQUENCE: 52

Cys Tyr Gly Arg Lys Lys Arg Arg Gln Arg Arg Trp Glu Ala Ala Leu
1               5                   10                  15

Ala Glu Ala Leu Ala Glu Ala Leu Ala Glu His Leu Ala Glu Ala Leu
            20                  25                  30

Ala Glu Ala Leu Glu Ala Leu Ala Ala
        35                  40

<210> SEQ ID NO 53
<211> LENGTH: 41
<212> TYPE: PRT
<213> ORGANISM: Homo sapiens

<400> SEQUENCE: 53

Cys Ile Phe Gly Ala Ile Ala Gly Phe Ile Lys Asn Ile Trp Glu Gly
1               5                   10                  15

Leu Ile Asp Gly Trp Tyr Gly Lys Leu Ala Leu Lys Leu Ala Leu Lys
            20                  25                  30
```

Ala Leu Lys Ala Ala Leu Lys Leu Ala
         35                  40

<210> SEQ ID NO 54
<211> LENGTH: 33
<212> TYPE: PRT
<213> ORGANISM: Homo sapiens

<400> SEQUENCE: 54

Cys Phe Phe Gly Ala Ile Trp Glu Phe Ile Arg Ser Ile Leu Glu Gly
1               5                   10                  15

Leu Ile Asp Gly Trp Tyr Gly Tyr Gly Arg Lys Lys Arg Arg Gln Arg
            20                  25                  30

Arg

<210> SEQ ID NO 55
<211> LENGTH: 34
<212> TYPE: PRT
<213> ORGANISM: Homo sapiens

<400> SEQUENCE: 55

Cys Gly Leu Phe His Ala Leu Leu His Leu His Ser Leu Trp His
1               5                   10                  15

Leu Leu Leu His Ala Trp Tyr Gly Tyr Gly Arg Lys Lys Arg Arg Gln
            20                  25                  30

Arg Arg

<210> SEQ ID NO 56
<211> LENGTH: 34
<212> TYPE: PRT
<213> ORGANISM: Homo sapiens

<400> SEQUENCE: 56

Cys Gly Leu Phe His Ala Leu Leu His Leu His Ser Leu Trp His
1               5                   10                  15

Leu Leu Leu His Ala Trp Tyr Gly Tyr Gly His Lys Lys His His Gln
            20                  25                  30

His Arg

<210> SEQ ID NO 57
<211> LENGTH: 31
<212> TYPE: PRT
<213> ORGANISM: Homo sapiens

<400> SEQUENCE: 57

Cys Gly Leu Phe Gly Ala Leu Leu Glu Leu Leu Glu Ser Leu Trp Lys
1               5                   10                  15

Gly Leu Leu Glu Trp Tyr Gly Arg Lys Lys Arg Arg Gln Arg Arg
            20                  25                  30

<210> SEQ ID NO 58
<211> LENGTH: 34
<212> TYPE: PRT
<213> ORGANISM: Homo sapiens

<400> SEQUENCE: 58

Cys Arg Arg Gln Arg Arg Lys Lys Arg Gly Tyr Gly Tyr Trp Gly Asp
1               5                   10                  15

Ile Leu Gly Glu Trp Gly Asn Glu Ile Phe Gly Glu Ile Ala Glu Phe
            20                  25                  30

-continued

Leu Gly

<210> SEQ ID NO 59
<211> LENGTH: 34
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: misc_feature
<222> LOCATION: (28)..(29)
<223> OTHER INFORMATION: Xaa = ornithine

<400> SEQUENCE: 59

Cys Gly Leu Phe Glu Ala Leu Glu Gly Phe Leu Glu Asn Gly Trp Glu
1               5                   10                  15

Gly Leu Leu Asp Gly Trp Tyr Gly Tyr Gly Arg Xaa Xaa Arg Arg Gln
            20                  25                  30

Arg Arg

<210> SEQ ID NO 60
<211> LENGTH: 34
<212> TYPE: PRT
<213> ORGANISM: Homo sapiens

<400> SEQUENCE: 60

Cys Gly Leu Phe Gly Glu Ile Glu Glu Leu Ile Glu Asn Gly Leu Lys
1               5                   10                  15

Asn Leu Ile Asp Trp Trp Tyr Gly Tyr Gly Arg Lys Lys Arg Arg Gln
            20                  25                  30

Arg Arg

<210> SEQ ID NO 61
<211> LENGTH: 34
<212> TYPE: PRT
<213> ORGANISM: Homo sapiens

<400> SEQUENCE: 61

Cys Arg Arg Gln Arg Arg Lys Lys Arg Gly Tyr Gly Tyr Trp Trp Asp
1               5                   10                  15

Ile Leu Gly Lys Trp Gly Asn Glu Ile Phe Gly Glu Ile Ala Glu Phe
            20                  25                  30

Leu Gly

<210> SEQ ID NO 62
<211> LENGTH: 15
<212> TYPE: PRT
<213> ORGANISM: Homo sapiens

<400> SEQUENCE: 62

Cys Gly Ile Phe Gly Ala Ile Ala Gly Phe Ile Lys Asn Ile Leu
1               5                   10                  15

<210> SEQ ID NO 63
<211> LENGTH: 16
<212> TYPE: PRT
<213> ORGANISM: Homo sapiens

<400> SEQUENCE: 63

Cys Gly Ile Phe Gly Ala Ile Ala Gly Leu Leu Lys Asn Ile Phe Lys
1               5                   10                  15

```
<210> SEQ ID NO 64
<211> LENGTH: 20
<212> TYPE: PRT
<213> ORGANISM: Homo sapiens

<400> SEQUENCE: 64

Cys Ile Phe Gly Ala Ile Ala Gly Phe Ile Lys Asn Ile Trp Lys Gly
1               5                   10                  15

Leu Ile Asp Trp
            20

<210> SEQ ID NO 65
<211> LENGTH: 15
<212> TYPE: PRT
<213> ORGANISM: Homo sapiens

<400> SEQUENCE: 65

Cys Ile Phe Gly Ala Ile Ala Gly Phe Ile Lys Asn Ile Trp Lys
1               5                   10                  15

<210> SEQ ID NO 66
<211> LENGTH: 34
<212> TYPE: PRT
<213> ORGANISM: Homo sapiens

<400> SEQUENCE: 66

Cys Gly Leu Phe Glu Glu Ile Glu Gly Phe Ile Glu Asn Gly Trp Glu
1               5                   10                  15

Gly Leu Ile Asp Trp Trp Tyr Gly Tyr Gly His Lys Lys His His Gln
            20                  25                  30

His Arg

<210> SEQ ID NO 67
<211> LENGTH: 34
<212> TYPE: PRT
<213> ORGANISM: Homo sapiens

<400> SEQUENCE: 67

Cys Gly Leu Phe Gly Glu Ile Glu Glu Leu Ile Glu Asn Gly Leu Lys
1               5                   10                  15

Asn Leu Ile Asp Trp Trp Tyr Gly Tyr Gly His Lys Lys His His Gln
            20                  25                  30

His Arg

<210> SEQ ID NO 68
<211> LENGTH: 34
<212> TYPE: PRT
<213> ORGANISM: Homo sapiens

<400> SEQUENCE: 68

Cys Gly Leu Phe Glu Glu Ile Glu Glu Phe Ile Glu Asn Gly Trp Glu
1               5                   10                  15

Gly Leu Ile Asp Trp Trp Tyr Gly Tyr Gly His Lys Lys His His Gln
            20                  25                  30

His Arg

<210> SEQ ID NO 69
<211> LENGTH: 41
<212> TYPE: PRT
<213> ORGANISM: Homo sapiens
```

```
<400> SEQUENCE: 69

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala Tyr Gly
            20                  25                  30

Arg Lys Lys Arg Gln Arg Cys
        35              40

<210> SEQ ID NO 70
<211> LENGTH: 47
<212> TYPE: PRT
<213> ORGANISM: Homo sapiens

<400> SEQUENCE: 70

Cys Gly Leu Phe Glu Ala Ile Glu Gly Phe Ile Glu Asn Gly Trp Lys
1               5                   10                  15

Gly Leu Ile Asp Gly Trp Tyr Gly Leu Phe Glu Ala Ile Glu Gly
            20                  25                  30

Phe Ile Glu Asn Gly Trp Lys Gly Leu Ile Asp Trp Trp Tyr Gly
        35              40                  45

<210> SEQ ID NO 71
<211> LENGTH: 21
<212> TYPE: PRT
<213> ORGANISM: Homo sapiens

<400> SEQUENCE: 71

Cys Gly Phe Phe His Ala Phe Phe His Phe His Ser Phe Trp His
1               5                   10                  15

Gly Phe Phe Glu Ala
            20

<210> SEQ ID NO 72
<211> LENGTH: 21
<212> TYPE: PRT
<213> ORGANISM: Homo sapiens

<400> SEQUENCE: 72

Cys Gly Phe Phe His Ala Phe Phe His Phe His Ser Phe Trp His
1               5                   10                  15

Gly Phe Phe Glu Ala
            20

<210> SEQ ID NO 73
<211> LENGTH: 17
<212> TYPE: PRT
<213> ORGANISM: Homo sapiens

<400> SEQUENCE: 73

Cys Phe Phe Gly Ala Ile Trp Glu Phe Ile Arg Asn Ile Leu Glu Gly
1               5                   10                  15

Phe

<210> SEQ ID NO 74
<211> LENGTH: 14
<212> TYPE: PRT
<213> ORGANISM: Homo sapiens

<400> SEQUENCE: 74

Cys Phe Phe Gly Ala Ile Trp Glu Phe Ile His Ser Ile Leu
1               5                   10
```

```
<210> SEQ ID NO 75
<211> LENGTH: 21
<212> TYPE: PRT
<213> ORGANISM: Homo sapiens

<400> SEQUENCE: 75

Cys Gly Leu Phe His Ala Leu Leu His Leu His Ser Leu Trp His
1               5                   10                  15

Gly Leu Leu Glu Ala
            20

<210> SEQ ID NO 76
<211> LENGTH: 17
<212> TYPE: PRT
<213> ORGANISM: Homo sapiens

<400> SEQUENCE: 76

Cys Ile Phe Gly Ala Ile Ala Gly Phe Ile Lys Asn Ile Trp Glu Gly
1               5                   10                  15

Leu

<210> SEQ ID NO 77
<211> LENGTH: 33
<212> TYPE: PRT
<213> ORGANISM: Homo sapiens

<400> SEQUENCE: 77

Cys Ile Phe Gly Ala Ile Ala Gly Leu Leu Lys Asn Ile Phe Glu Gly
1               5                   10                  15

Leu Ile Asp Gly Trp Tyr Gly Tyr Gly Arg Lys Lys Arg Arg Gln Arg
            20                  25                  30

Arg

<210> SEQ ID NO 78
<211> LENGTH: 34
<212> TYPE: PRT
<213> ORGANISM: Homo sapiens

<400> SEQUENCE: 78

Cys Gly Phe Ile Gly Ala Ile Ala Asn Leu Leu Ser Lys Ile Phe Glu
1               5                   10                  15

Gly Leu Ile Asp Gly Trp Tyr Gly Tyr Gly Arg Lys Lys Arg Arg Gln
            20                  25                  30

Arg Arg

<210> SEQ ID NO 79
<211> LENGTH: 34
<212> TYPE: PRT
<213> ORGANISM: Homo sapiens

<400> SEQUENCE: 79

Cys Gly Leu Phe Glu Ala Ile Glu Glu Leu Ile Glu Asn Leu Trp Lys
1               5                   10                  15

Gly Leu Ile Asp Ala Trp Tyr Gly Tyr Gly Arg Lys Lys Arg Arg Gln
            20                  25                  30

Arg Arg

<210> SEQ ID NO 80
<211> LENGTH: 21
```

```
<212> TYPE: PRT
<213> ORGANISM: Homo sapiens

<400> SEQUENCE: 80

Cys Gly Ile Phe Gly Ala Ile Ala Gly Leu Leu Lys Asn Ile Phe Lys
1               5                   10                  15

Gly Leu Ile Asp Ala
            20

<210> SEQ ID NO 81
<211> LENGTH: 21
<212> TYPE: PRT
<213> ORGANISM: Homo sapiens

<400> SEQUENCE: 81

Cys Gly Ile Phe Gly Ala Ile Ala Gly Leu Leu Lys Asn Ile Phe Lys
1               5                   10                  15

Gly Leu Ile Asp Trp
            20

<210> SEQ ID NO 82
<211> LENGTH: 16
<212> TYPE: PRT
<213> ORGANISM: Homo sapiens

<400> SEQUENCE: 82

Cys Gly Ile Phe Glu Ala Ile Ala Gly Leu Leu Lys Asn Ile Phe Lys
1               5                   10                  15

<210> SEQ ID NO 83
<211> LENGTH: 16
<212> TYPE: PRT
<213> ORGANISM: Homo sapiens

<400> SEQUENCE: 83

Cys Gly Ile Phe Glu Glu Ile Ala Gly Leu Leu Lys Asn Ile Phe Lys
1               5                   10                  15

<210> SEQ ID NO 84
<211> LENGTH: 55
<212> TYPE: PRT
<213> ORGANISM: Homo sapiens

<400> SEQUENCE: 84

Cys Gly Leu Phe Glu Ala Ile Ala Gly Phe Ile Glu Gly Gly Trp Pro
1               5                   10                  15

Gly Leu Ile Asn Gly Trp Tyr Gly Tyr Gly Arg Lys Lys Arg Arg Gln
            20                  25                  30

Arg Arg Leu His Leu Leu His His Leu Leu His His Leu His His Leu
        35                  40                  45

Leu His His Leu Leu His Leu
    50                  55

<210> SEQ ID NO 85
<211> LENGTH: 36
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (35)..(35)
<223> OTHER INFORMATION: Lys is conjugated to Stearyl
```

```
<400> SEQUENCE: 85

Gly Cys Gly Leu Phe Glu Ala Ile Glu Gly Phe Ile Glu Asn Gly Trp
1               5                   10                  15

Lys Gly Met Ile Asp Trp Trp Tyr Gly Tyr Gly Arg Lys Lys Arg Arg
                20                  25                  30

Gln Arg Arg Lys
            35

<210> SEQ ID NO 86
<211> LENGTH: 24
<212> TYPE: PRT
<213> ORGANISM: Homo sapiens

<400> SEQUENCE: 86

Cys Gly Leu Phe Gly Glu Ile Glu Gly Phe Ile Glu Asn Gly Trp Lys
1               5                   10                  15

Gly Leu Ile Asp Trp Trp Tyr Gly
                20

<210> SEQ ID NO 87
<211> LENGTH: 35
<212> TYPE: PRT
<213> ORGANISM: Homo sapiens

<400> SEQUENCE: 87

Cys Ile Phe Gly Ala Ile Ala Gly Phe Ile Lys Asn Ile Trp Leu His
1               5                   10                  15

Leu Leu His His Leu Leu His His Leu His His Leu Leu His His Leu
                20                  25                  30

Leu His Leu
        35

<210> SEQ ID NO 88
<211> LENGTH: 33
<212> TYPE: PRT
<213> ORGANISM: Homo sapiens

<400> SEQUENCE: 88

Cys Gly Ile Phe Gly Ala Ile Glu Gly Phe Ile Glu Asn Gly Trp Lys
1               5                   10                  15

Gly Leu Ile Asp Ala Trp Tyr Gly Tyr Arg Lys Lys Arg Arg Gln Arg
                20                  25                  30

Arg

<210> SEQ ID NO 89
<211> LENGTH: 34
<212> TYPE: PRT
<213> ORGANISM: Homo sapiens

<400> SEQUENCE: 89

Cys Glu Leu Phe Gly Ala Ile Glu Gly Phe Ile Glu Asn Gly Trp Lys
1               5                   10                  15

Gly Leu Ile Asp Trp Trp Tyr Gly Tyr Gly Arg Lys Lys Arg Arg Gln
                20                  25                  30

Arg Arg

<210> SEQ ID NO 90
<211> LENGTH: 39
<212> TYPE: PRT
<213> ORGANISM: Homo sapiens
```

<400> SEQUENCE: 90

Cys Ile Phe Gly Ile Asp Asp Leu Ile Ile Gly Leu Leu Phe Val Ala
1               5                   10                  15

Ile Val Glu Ala Gly Ile Gly Gly Tyr Leu Leu Gly Ser Tyr Gly Arg
            20                  25                  30

Lys Lys Arg Arg Gln Arg Arg
            35

<210> SEQ ID NO 91
<211> LENGTH: 35
<212> TYPE: PRT
<213> ORGANISM: Homo sapiens

<400> SEQUENCE: 91

Gly Leu Phe Gly Ala Leu Ala Glu Ala Leu Ala Glu Ala Leu Ala Glu
1               5                   10                  15

His Leu Ala Glu Ala Leu Ala Glu Ala Leu Glu Ala Leu Ala Ala Gly
            20                  25                  30

Gly Ser Cys
        35

<210> SEQ ID NO 92
<211> LENGTH: 34
<212> TYPE: PRT
<213> ORGANISM: Homo sapiens

<400> SEQUENCE: 92

Cys Gly Phe Ile Gly Ala Ile Ala Asn Leu Leu Ser Lys Ile Phe Glu
1               5                   10                  15

Gly Leu Ile Asp Gly Trp Tyr Gly Tyr Gly Arg Lys Lys Arg Arg Gln
            20                  25                  30

Arg Arg

<210> SEQ ID NO 93
<211> LENGTH: 18
<212> TYPE: PRT
<213> ORGANISM: Homo sapiens

<400> SEQUENCE: 93

Cys Phe Phe Gly Ala Ile Trp Glu Phe Ile Arg Ser Ile Leu Lys Gly
1               5                   10                  15

Leu Ile

<210> SEQ ID NO 94
<211> LENGTH: 15
<212> TYPE: PRT
<213> ORGANISM: Homo sapiens

<400> SEQUENCE: 94

Cys Phe Phe Gly Ala Ile Trp Glu Phe Ile Arg Ser Ile Leu Lys
1               5                   10                  15

<210> SEQ ID NO 95
<211> LENGTH: 15
<212> TYPE: PRT
<213> ORGANISM: Homo sapiens

<400> SEQUENCE: 95

Cys Phe Phe Gly Ala Ile Trp Glu Phe Ile Arg Ser Ile Leu Glu
1               5                   10                  15

```
<210> SEQ ID NO 96
<211> LENGTH: 15
<212> TYPE: PRT
<213> ORGANISM: Homo sapiens

<400> SEQUENCE: 96

Cys Ile Phe Gly Ala Ile Ala Gly Phe Ile Lys Asn Ile Trp Glu
1               5                   10                  15

<210> SEQ ID NO 97
<211> LENGTH: 20
<212> TYPE: PRT
<213> ORGANISM: Homo sapiens

<400> SEQUENCE: 97

Cys Ile Phe Gly Ala Ile Ala Gly Phe Ile Lys Asn Ile Trp Lys Gly
1               5                   10                  15

Leu Ile Asp Ala
            20

<210> SEQ ID NO 98
<211> LENGTH: 15
<212> TYPE: PRT
<213> ORGANISM: Homo sapiens

<400> SEQUENCE: 98

Cys Phe Phe Glu Ala Ile Glu Glu Phe Ile Lys Asn Ile Leu Lys
1               5                   10                  15

<210> SEQ ID NO 99
<211> LENGTH: 14
<212> TYPE: PRT
<213> ORGANISM: Homo sapiens

<400> SEQUENCE: 99

Cys Ile Phe Gly Ala Ile Ala Gly Leu Leu Arg Asn Ile Phe
1               5                   10

<210> SEQ ID NO 100
<211> LENGTH: 15
<212> TYPE: PRT
<213> ORGANISM: Homo sapiens

<400> SEQUENCE: 100

Cys Gly Ile Phe Gly Ala Ile Ala Gly Leu Leu Lys Asn Ile Trp
1               5                   10                  15

<210> SEQ ID NO 101
<211> LENGTH: 14
<212> TYPE: PRT
<213> ORGANISM: Homo sapiens

<400> SEQUENCE: 101

Cys Leu Phe Gly Ala Ile Trp Glu Phe Ile Lys Ser Ile Leu
1               5                   10

<210> SEQ ID NO 102
<211> LENGTH: 14
<212> TYPE: PRT
<213> ORGANISM: Homo sapiens

<400> SEQUENCE: 102

Cys Phe Trp Gly Ala Ile Trp Glu Phe Ile Lys Ser Ile Leu
```

```
1               5                   10
```

<210> SEQ ID NO 103
<211> LENGTH: 14
<212> TYPE: PRT
<213> ORGANISM: Homo sapiens

<400> SEQUENCE: 103

```
Cys Phe Gly Gly Ala Ile Trp Glu Phe Ile Lys Ser Ile Leu
1               5                   10
```

<210> SEQ ID NO 104
<211> LENGTH: 14
<212> TYPE: PRT
<213> ORGANISM: Homo sapiens

<400> SEQUENCE: 104

```
Cys Phe Ala Gly Ala Ile Trp Glu Phe Ile Lys Ser Ile Leu
1               5                   10
```

<210> SEQ ID NO 105
<211> LENGTH: 35
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (18)..(18)
<223> OTHER INFORMATION: methionine is conjugated to SO2

<400> SEQUENCE: 105

```
Cys Gly Leu Phe Glu Ala Ile Glu Gly Phe Ile Glu Asn Gly Trp Glu
1               5                   10                  15

Gly Met Ser Ile Asp Gly Trp Tyr Gly Tyr Gly Arg Lys Lys Arg Arg
            20                  25                  30

Gln Arg Arg
        35
```

<210> SEQ ID NO 106
<211> LENGTH: 34
<212> TYPE: PRT
<213> ORGANISM: Homo sapiens

<400> SEQUENCE: 106

```
Cys Gly Leu Phe Glu Ala Ile Glu Gly Phe Ile Glu Asn Gly Trp Glu
1               5                   10                  15

Gly Met Ile Asp Trp Trp Tyr Gly Tyr Gly Arg Lys Lys Arg Arg Gln
            20                  25                  30

Arg Arg
```

<210> SEQ ID NO 107
<211> LENGTH: 14
<212> TYPE: PRT
<213> ORGANISM: Homo sapiens

<400> SEQUENCE: 107

```
Cys Phe Phe Gly Ala Ile Trp Glu Phe Ile Lys Ser Ile Gly
1               5                   10
```

<210> SEQ ID NO 108
<211> LENGTH: 14
<212> TYPE: PRT
<213> ORGANISM: Homo sapiens

```
<400> SEQUENCE: 108

Cys Phe Phe Gly Ala Ile Trp Glu Phe Ile Lys Ser Ile Ala
1               5                   10

<210> SEQ ID NO 109
<211> LENGTH: 14
<212> TYPE: PRT
<213> ORGANISM: Homo sapiens

<400> SEQUENCE: 109

Cys Phe Phe Gly Ala Ile Trp Glu Phe Ile Lys Ser Ile Asn
1               5                   10

<210> SEQ ID NO 110
<211> LENGTH: 14
<212> TYPE: PRT
<213> ORGANISM: Homo sapiens

<400> SEQUENCE: 110

Cys Phe Phe Gly Ala Ile Trp Glu Phe Ile Lys Ser Ile Trp
1               5                   10

<210> SEQ ID NO 111
<211> LENGTH: 33
<212> TYPE: PRT
<213> ORGANISM: Homo sapiens

<400> SEQUENCE: 111

Cys Phe Phe Gly Ala Ile Trp Glu Phe Ile Lys Ser Ile Leu Glu Gly
1               5                   10                  15

Leu Ile Asp Trp Trp Tyr Gly Tyr Gly His Lys Lys His His Gln His
                20                  25                  30

Arg

<210> SEQ ID NO 112
<211> LENGTH: 32
<212> TYPE: PRT
<213> ORGANISM: Homo sapiens

<400> SEQUENCE: 112

Ala Cys Cys Leu His Leu Leu His His Leu Leu His His Leu His His
1               5                   10                  15

Leu Leu His His Leu Leu His Leu Leu His His Leu Leu His His Leu
                20                  25                  30

<210> SEQ ID NO 113
<211> LENGTH: 47
<212> TYPE: PRT
<213> ORGANISM: Homo sapiens

<400> SEQUENCE: 113

Ala Cys Leu His Leu Leu His His Leu Leu His His Leu His His Leu
1               5                   10                  15

Leu His His Leu Leu His Leu Leu His His Leu Leu His His Leu Gly
                20                  25                  30

Gly Gly Arg Lys Lys Arg Arg Gln Arg Arg Pro Pro Gln Cys
                35                  40                  45

<210> SEQ ID NO 114
<211> LENGTH: 45
<212> TYPE: PRT
```

<213> ORGANISM: Homo sapiens

<400> SEQUENCE: 114

Cys Arg Lys Lys Arg Arg Gln Arg Arg Pro Pro Gln Gly Gly Gly
1               5                   10                  15
Leu His Leu Leu His His Leu Leu His His Leu His His Leu His
                20                  25                  30
His Leu Leu His Leu Leu His His Leu Leu His His Leu
        35                  40                  45

<210> SEQ ID NO 115
<211> LENGTH: 45
<212> TYPE: PRT
<213> ORGANISM: Homo sapiens

<400> SEQUENCE: 115

Cys Leu His Leu Leu His His Leu His Leu His His Leu His Leu
1               5                   10                  15
His His Leu Leu His Leu Leu His His Leu Leu His His Leu Gly Gly
                20                  25                  30
Gly Arg Lys Lys Arg Arg Gln Arg Arg Pro Pro Gln
        35                  40                  45

<210> SEQ ID NO 116
<211> LENGTH: 34
<212> TYPE: PRT
<213> ORGANISM: Homo sapiens

<400> SEQUENCE: 116

Cys Gly Leu Phe His Ala Ile Ala His Phe Ile His Gly Gly Trp His
1               5                   10                  15
Gly Leu Ile His Gly Trp Tyr Gly Tyr Gly Arg Lys Lys Arg Arg Gln
                20                  25                  30
Arg Arg

<210> SEQ ID NO 117
<211> LENGTH: 34
<212> TYPE: PRT
<213> ORGANISM: Homo sapiens

<400> SEQUENCE: 117

Cys Gly Leu Phe Lys Ala Ile Ala Lys Phe Ile Lys Gly Gly Trp Lys
1               5                   10                  15
Gly Leu Ile Lys Gly Trp Tyr Gly Tyr Gly Arg Lys Lys Arg Arg Gln
                20                  25                  30
Arg Arg

<210> SEQ ID NO 118
<211> LENGTH: 34
<212> TYPE: PRT
<213> ORGANISM: Homo sapiens

<400> SEQUENCE: 118

Cys Gly Leu Phe Glu Ala Ile Ala Gly Phe Ile Glu Asn Gly Trp Glu
1               5                   10                  15
Gly Met Ile Asp Gly Trp Tyr Gly Tyr Gly Arg Lys Lys Arg Arg Gln
                20                  25                  30
Arg Arg

```
<210> SEQ ID NO 119
<211> LENGTH: 41
<212> TYPE: PRT
<213> ORGANISM: Homo sapiens

<400> SEQUENCE: 119

Cys Trp Glu Ala Ala Leu Ala Glu Ala Leu Ala Glu Ala Leu Ala Glu
1               5                   10                  15

His Leu Ala Glu Ala Leu Ala Glu Ala Leu Glu Ala Leu Ala Ala Tyr
            20                  25                  30

Gly Arg Lys Lys Arg Arg Gln Arg Arg
        35                  40

<210> SEQ ID NO 120
<211> LENGTH: 36
<212> TYPE: PRT
<213> ORGANISM: Homo sapiens

<400> SEQUENCE: 120

Cys Gly Leu Phe Glu Ala Ile Glu Gly Phe Ile Glu Asn Gly Trp Glu
1               5                   10                  15

Gly Met Ile Asp Gly Trp Tyr Gly Arg Lys Lys Arg Arg Gln Arg Arg
            20                  25                  30

Arg Pro Pro Gln
        35

<210> SEQ ID NO 121
<211> LENGTH: 34
<212> TYPE: PRT
<213> ORGANISM: Homo sapiens

<400> SEQUENCE: 121

Gly Leu Phe Glu Ala Ile Glu Gly Phe Ile Glu Asn Gly Trp Glu Gly
1               5                   10                  15

Met Ile Asp Gly Trp Tyr Gly Tyr Gly Arg Lys Lys Arg Arg Gln Arg
            20                  25                  30

Arg Cys

<210> SEQ ID NO 122
<211> LENGTH: 43
<212> TYPE: PRT
<213> ORGANISM: Homo sapiens

<400> SEQUENCE: 122

Ala Cys Leu His Leu Leu His His Leu His His Leu His His Leu
1               5                   10                  15

Leu His His Leu Leu His Leu Leu His His Leu Leu His His Leu Arg
            20                  25                  30

Lys Lys Arg Arg Gln Arg Arg Pro Pro Gln
        35                  40

<210> SEQ ID NO 123
<211> LENGTH: 46
<212> TYPE: PRT
<213> ORGANISM: Homo sapiens

<400> SEQUENCE: 123

Ala Cys Leu His Leu Leu His Leu His His Leu His His Leu
1               5                   10                  15

Leu His His Leu Leu His Leu Leu His His Leu Leu His His Leu Gly
            20                  25                  30
```

```
Pro Gly Arg Lys Lys Arg Arg Gln Arg Arg Pro Pro Gln
        35                  40                  45

<210> SEQ ID NO 124
<211> LENGTH: 25
<212> TYPE: PRT
<213> ORGANISM: Homo sapiens

<400> SEQUENCE: 124

Ala Cys Leu Ile Arg Leu Trp Ser His Leu Ile His Ile Trp Phe Gln
1               5                   10                  15

Asn Arg Arg Leu Lys Trp Lys Lys Lys
            20                  25

<210> SEQ ID NO 125
<211> LENGTH: 19
<212> TYPE: PRT
<213> ORGANISM: Homo sapiens

<400> SEQUENCE: 125

Ala Cys Arg Lys Lys Arg Arg Gln Arg Arg Pro Pro Gln Gln Gln
1               5                   10                  15

Gln Gln Gln

<210> SEQ ID NO 126
<211> LENGTH: 35
<212> TYPE: PRT
<213> ORGANISM: Homo sapiens

<400> SEQUENCE: 126

Ala Cys Gly Leu Phe Glu Ala Ile Glu Gly Phe Ile Glu Asn Gly Trp
1               5                   10                  15

Glu Gly Met Ile Asp Gly Trp Tyr Gly Tyr Gly Arg Lys Lys Arg Arg
            20                  25                  30

Gln Arg Arg
        35

<210> SEQ ID NO 127
<211> LENGTH: 43
<212> TYPE: PRT
<213> ORGANISM: Homo sapiens

<400> SEQUENCE: 127

Ala Cys Leu His Leu Leu His Leu Leu His His Leu His His Leu
1               5                   10                  15

Leu His His Leu Leu His Leu Leu His His Leu Leu His His Leu Gly
            20                  25                  30

Gly Gly Arg Arg Arg Arg Arg Arg Arg Arg
        35                  40

<210> SEQ ID NO 128
<211> LENGTH: 46
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (31)..(31)
<223> OTHER INFORMATION: Leucine is conjugated to Peg

<400> SEQUENCE: 128
```

-continued

```
Ala Cys Leu His Leu Leu His His Leu His Leu His His Leu
1               5                   10                  15

Leu His His Leu Leu His Leu Leu His His Leu Leu His His Leu Pro
            20                  25                  30

Glu Gly Arg Lys Lys Arg Arg Gln Arg Arg Arg Pro Pro Gln
        35                  40                  45

<210> SEQ ID NO 129
<211> LENGTH: 46
<212> TYPE: PRT
<213> ORGANISM: Homo sapiens

<400> SEQUENCE: 129

Ala Cys Gly Leu Phe Gly Ala Ile Ala Gly Phe Ile Glu Asn Gly Trp
1               5                   10                  15

Glu Gly Met Ile Asp Gly Trp Tyr Gly Leu Ile Arg Leu Trp Ser His
            20                  25                  30

Leu Ile Trp Phe Gln Asn Arg Arg Leu Lys Trp Leu Leu Leu
        35                  40                  45

<210> SEQ ID NO 130
<211> LENGTH: 51
<212> TYPE: PRT
<213> ORGANISM: Homo sapiens

<400> SEQUENCE: 130

Ala Cys His His His His His Arg Lys Lys Arg Arg Gln Arg Arg Arg
1               5                   10                  15

Pro Pro Gln Gly Gly Gly Leu His Leu Leu His His Leu His Leu His
            20                  25                  30

Leu His His Leu Leu His Leu Leu His Leu Leu His His Leu Leu
        35                  40                  45

His His Leu
    50

<210> SEQ ID NO 131
<211> LENGTH: 46
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (31)..(31)
<223> OTHER INFORMATION: Leucine is conjugated to Peg

<400> SEQUENCE: 131

Ala Cys Leu His Leu Leu His His Leu His Leu His His Leu
1               5                   10                  15

Leu His His Leu Leu His Leu Leu His His Leu Leu His His Leu Pro
            20                  25                  30

Glu Gly Arg Lys Lys Arg Arg Gln Arg Arg Arg Pro Pro Gln
        35                  40                  45

<210> SEQ ID NO 132
<211> LENGTH: 51
<212> TYPE: PRT
<213> ORGANISM: Homo sapiens

<400> SEQUENCE: 132

Ala Cys Leu His Leu Leu His His Leu Leu His His Leu His Leu
1               5                   10                  15
```

Leu His Leu Leu Leu His His Leu Leu His His Leu Gly Gly
            20                  25                  30

Gly Arg Gln Ile Lys Ile Trp Phe Gln Asn Arg Arg Met Lys Trp Lys
        35                  40                  45

Lys Gly Gly
    50

<210> SEQ ID NO 133
<211> LENGTH: 38
<212> TYPE: PRT
<213> ORGANISM: Homo sapiens

<400> SEQUENCE: 133

Ala Cys Lys Leu Leu Lys Leu Leu Lys Leu Trp Leu Lys Leu Leu
1               5                   10                  15

Lys Leu Leu Lys Leu Leu Gly Gly Gly Arg Lys Lys Arg Arg Gln
            20                  25                  30

Arg Arg Arg Pro Pro Gln
            35

<210> SEQ ID NO 134
<211> LENGTH: 32
<212> TYPE: PRT
<213> ORGANISM: Homo sapiens

<400> SEQUENCE: 134

Ala Cys Leu His His Leu Leu His His Leu Leu His Leu His His
1               5                   10                  15

Leu Leu His His Leu His His Leu Leu His His Leu Leu His Leu Cys
            20                  25                  30

<210> SEQ ID NO 135
<211> LENGTH: 47
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (31)..(31)
<223> OTHER INFORMATION: Leucine is conjugated to PEG

<400> SEQUENCE: 135

Ala Cys Leu His Leu Leu His His Leu Leu His His Leu His Leu
1               5                   10                  15

Leu His His Leu Leu His Leu Leu His Leu Leu His His Leu Pro
            20                  25                  30

Glu Gly Arg Lys Lys Arg Arg Gln Arg Arg Pro Pro Gln Cys
        35                  40                  45

<210> SEQ ID NO 136
<211> LENGTH: 36
<212> TYPE: PRT
<213> ORGANISM: Homo sapiens

<400> SEQUENCE: 136

Ala Cys Gly Leu Phe Glu Ala Ile Glu Gly Phe Ile Glu Asn Gly Trp
1               5                   10                  15

Glu Gly Met Ile Asp Gly Trp Tyr Gly Tyr Gly Arg Lys Lys Arg Arg
            20                  25                  30

Gln Arg Arg Cys

<210> SEQ ID NO 137
<211> LENGTH: 34
<212> TYPE: PRT
<213> ORGANISM: Homo sapiens

<400> SEQUENCE: 137

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 138
<211> LENGTH: 35
<212> TYPE: PRT
<213> ORGANISM: Homo sapiens

<400> SEQUENCE: 138

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Arg Arg Arg Arg Arg
            20                  25                  30

Arg Arg Arg
        35

<210> SEQ ID NO 139
<211> LENGTH: 34
<212> TYPE: PRT
<213> ORGANISM: Homo sapiens

<400> SEQUENCE: 139

Tyr Gly Arg Lys Lys Arg Arg Gln Arg Arg Gly Leu Phe Glu Ala Ile
1               5                   10                  15

Glu Gly Phe Ile Glu Asn Gly Trp Glu Gly Met Ile Asp Gly Trp Tyr
            20                  25                  30

Gly Cys

<210> SEQ ID NO 140
<211> LENGTH: 27
<212> TYPE: PRT
<213> ORGANISM: Homo sapiens

<400> SEQUENCE: 140

Cys Gly Val Phe Val Leu Gly Phe Leu Gly Phe Leu Ala Thr Ala Gly
1               5                   10                  15

Ser Tyr Gly Arg Lys Lys Arg Arg Gln Arg Arg
            20                  25

<210> SEQ ID NO 141
<211> LENGTH: 24
<212> TYPE: PRT
<213> ORGANISM: Homo sapiens

<400> SEQUENCE: 141

Cys Gly Leu Phe Lys Ala Ile Ala Lys Phe Ile Lys Gly Trp Lys
1               5                   10                  15

Gly Leu Ile Lys Gly Trp Tyr Gly
            20

<210> SEQ ID NO 142
<211> LENGTH: 30
<212> TYPE: PRT
<213> ORGANISM: Homo sapiens

<400> SEQUENCE: 142

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg
            20                  25                  30

<210> SEQ ID NO 143
<211> LENGTH: 44
<212> TYPE: PRT
<213> ORGANISM: Homo sapiens

<400> SEQUENCE: 143

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg Tyr Gly Arg Lys Lys Arg Arg Gln Arg Arg
        35                  40

<210> SEQ ID NO 144
<211> LENGTH: 44
<212> TYPE: PRT
<213> ORGANISM: Homo sapiens

<400> SEQUENCE: 144

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg Tyr Gly Arg Lys Lys Arg Arg Gln Arg Arg
        35                  40

<210> SEQ ID NO 145
<211> LENGTH: 34
<212> TYPE: PRT
<213> ORGANISM: Homo sapiens

<400> SEQUENCE: 145

Cys Gly Leu Phe Glu Ala Ile Lys Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 146
<211> LENGTH: 34
<212> TYPE: PRT
<213> ORGANISM: Homo sapiens

<400> SEQUENCE: 146

Cys Gly Leu Phe Glu Ala Ile His Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 147
<211> LENGTH: 34
<212> TYPE: PRT
<213> ORGANISM: Homo sapiens

<400> SEQUENCE: 147

Cys Gly Leu Phe Glu Ala Ile Arg Gly Phe Ile Glu Asn Gly Trp Glu
1               5                   10                  15
Gly Met Ile Asp Gly Trp Tyr Gly Tyr Gly Arg Lys Lys Arg Arg Gln
            20                  25                  30
Arg Arg

<210> SEQ ID NO 148
<211> LENGTH: 34
<212> TYPE: PRT
<213> ORGANISM: Homo sapiens

<400> SEQUENCE: 148

Cys Gly Leu Phe Glu Ala Ile Asp Gly Phe Ile Glu Asn Gly Trp Glu
1               5                   10                  15
Gly Met Ile Asp Gly Trp Tyr Gly Tyr Gly Arg Lys Lys Arg Arg Gln
            20                  25                  30
Arg Arg

<210> SEQ ID NO 149
<211> LENGTH: 34
<212> TYPE: PRT
<213> ORGANISM: Homo sapiens

<400> SEQUENCE: 149

Cys Arg Leu Phe Glu Ala Ile Glu Gly Phe Ile Glu Asn Gly Trp Glu
1               5                   10                  15
Gly Met Ile Asp Gly Trp Tyr Gly Tyr Gly Arg Lys Lys Arg Arg Gln
            20                  25                  30
Arg Arg

<210> SEQ ID NO 150
<211> LENGTH: 36
<212> TYPE: PRT
<213> ORGANISM: Homo sapiens

<400> SEQUENCE: 150

Cys Gly Gly Gly Leu Phe Glu Ala Ile Glu Gly Phe Ile Glu Asn Gly
1               5                   10                  15
Trp Glu Gly Met Ile Asp Gly Trp Tyr Gly Tyr Gly Arg Lys Lys Arg
            20                  25                  30
Arg Gln Arg Arg
        35

<210> SEQ ID NO 151
<211> LENGTH: 37
<212> TYPE: PRT
<213> ORGANISM: Homo sapiens

<400> SEQUENCE: 151

Cys Gly Leu Phe Glu Ala Ile Glu Gly Phe Ile Glu Asn Gly Trp Glu
1               5                   10                  15
Gly Met Ile Asp Gly Trp Tyr Gly Gly Gly Tyr Gly Arg Lys Lys
            20                  25                  30

Arg Arg Gln Arg Arg
        35

<210> SEQ ID NO 152
<211> LENGTH: 37
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (27)..(27)
<223> OTHER INFORMATION: Glycine is conjugated to PEG

<400> SEQUENCE: 152

Cys Gly Leu Phe Glu Ala Ile Glu Gly Phe Ile Glu Asn Gly Trp Glu
1               5                   10                  15

Gly Met Ile Asp Gly Trp Tyr Gly Pro Glu Gly Tyr Gly Arg Lys Lys
            20                  25                  30

Arg Arg Gln Arg Arg
        35

<210> SEQ ID NO 153
<211> LENGTH: 25
<212> TYPE: PRT
<213> ORGANISM: Homo sapiens

<400> SEQUENCE: 153

Cys Phe Leu Gly Phe Leu Leu Gly Val Gly Ser Ala Ile Ala Ser Gly
1               5                   10                  15

Ile Ala Val Ser Lys Val Leu His Leu
            20                  25

<210> SEQ ID NO 154
<211> LENGTH: 38
<212> TYPE: PRT
<213> ORGANISM: Homo sapiens

<400> SEQUENCE: 154

Cys Gly Val Phe Val Leu Gly Phe Leu Gly Phe Leu Ala Thr Ala Gly
1               5                   10                  15

Ser Ala Met Gly Ala Arg Ser Leu Thr Leu Ser Ala Tyr Gly Arg Lys
            20                  25                  30

Lys Arg Arg Gln Arg Arg
        35

<210> SEQ ID NO 155
<211> LENGTH: 39
<212> TYPE: PRT
<213> ORGANISM: Homo sapiens

<400> SEQUENCE: 155

Ala Cys Gly Leu Trp Arg Ala Leu Trp Arg Leu Leu Arg Ser Leu Trp
1               5                   10                  15

Arg Leu Leu Trp Arg Ala Met Glu Arg Cys Ala Pro Thr Glu Thr His
            20                  25                  30

Tyr Leu Ala Met Ile Asp Glu
        35

<210> SEQ ID NO 156
<211> LENGTH: 36
<212> TYPE: PRT

<213> ORGANISM: Homo sapiens

<400> SEQUENCE: 156

Cys Asn Leu Glu Leu Phe Glu Ala Ile Glu Gly Phe Ile Glu Asn Gly
1               5                   10                  15

Trp Glu Gly Met Ile Asp Gly Trp Tyr Gly Tyr Gly Arg Lys Lys Arg
            20                  25                  30

Arg Gln Arg Arg
        35

<210> SEQ ID NO 157
<211> LENGTH: 34
<212> TYPE: PRT
<213> ORGANISM: Homo sapiens

<400> SEQUENCE: 157

Cys Glu Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 158
<211> LENGTH: 34
<212> TYPE: PRT
<213> ORGANISM: Homo sapiens

<400> SEQUENCE: 158

Cys Gly Phe Phe Gly Ala Ile Ala Gly Phe Leu Glu Gly Gly Trp Glu
1               5                   10                  15

Gly Met Ile Ala Gly Trp His Gly Tyr Gly Arg Lys Lys Arg Arg Gln
            20                  25                  30

Arg Arg

<210> SEQ ID NO 159
<211> LENGTH: 35
<212> TYPE: PRT
<213> ORGANISM: Homo sapiens

<400> SEQUENCE: 159

Cys Phe Leu Gly Phe Leu Leu Gly Val Gly Ser Ala Ile Ala Ser Gly
1               5                   10                  15

Ile Ala Val Ser Lys Val Leu His Leu Tyr Gly Arg Lys Lys Arg Arg
            20                  25                  30

Gln Arg Arg
        35

<210> SEQ ID NO 160
<211> LENGTH: 34
<212> TYPE: PRT
<213> ORGANISM: Homo sapiens

<400> SEQUENCE: 160

Gly Leu Phe Glu Ala Ile Glu Gly Phe Ile Glu Asn Gly Trp Glu Gly
1               5                   10                  15

Leu Ala Glu Ala Leu Ala Glu Ala Leu Glu Ala Leu Ala Ala Gly Gly
            20                  25                  30

Ser Cys

```
<210> SEQ ID NO 161
<211> LENGTH: 53
<212> TYPE: PRT
<213> ORGANISM: Homo sapiens

<400> SEQUENCE: 161

Cys Gly Leu Phe Glu Ala Ile Glu Gly Phe Ile Glu Asn Gly Trp Glu
1               5                   10                  15

Gly Met Ile Asp Gly Trp Tyr Gly Leu His Leu Leu His His Leu Leu
            20                  25                  30

His His Leu His His Leu Leu His Leu Leu His Leu Leu His His
        35                  40                  45

Leu Leu His His Leu
    50

<210> SEQ ID NO 162
<211> LENGTH: 63
<212> TYPE: PRT
<213> ORGANISM: Homo sapiens

<400> SEQUENCE: 162

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg Leu His Leu Leu His Leu Leu His Leu Leu His His Leu
        35                  40                  45

Leu His His Leu Leu His Leu Leu His His Leu Leu His His Leu
    50                  55                  60

<210> SEQ ID NO 163
<211> LENGTH: 34
<212> TYPE: PRT
<213> ORGANISM: Homo sapiens

<400> SEQUENCE: 163

Cys Gly Leu Phe Gly Ala Ile Ala Gly Phe Ile Glu Gly Gly Trp Thr
1               5                   10                  15

Gly Met Ile Asp Gly Trp Tyr Gly Tyr Gly Arg Lys Lys Arg Arg Gln
            20                  25                  30

Arg Arg

<210> SEQ ID NO 164
<211> LENGTH: 34
<212> TYPE: PRT
<213> ORGANISM: Homo sapiens

<400> SEQUENCE: 164

Cys Gly Leu Phe Gly Ala Ile Ala Gly Phe Ile Glu Gly Gly Trp Gln
1               5                   10                  15

Gly Met Val Asp Gly Trp Tyr Gly Tyr Gly Arg Lys Lys Arg Arg Gln
            20                  25                  30

Arg Arg

<210> SEQ ID NO 165
<211> LENGTH: 34
<212> TYPE: PRT
<213> ORGANISM: Homo sapiens

<400> SEQUENCE: 165
```

Cys Gly Leu Phe Gly Ala Ile Ala Gly Phe Ile Glu Asn Gly Trp Gln
1               5                   10                  15

Gly Leu Ile Asp Gly Trp Tyr Gly Tyr Gly Arg Lys Lys Arg Arg Gln
            20                  25                  30

Arg Arg

<210> SEQ ID NO 166
<211> LENGTH: 34
<212> TYPE: PRT
<213> ORGANISM: Homo sapiens

<400> SEQUENCE: 166

Cys Gly Leu Phe Gly Ala Ile Ala Gly Phe Ile Glu Asn Gly Trp Glu
1               5                   10                  15

Gly Leu Val Asp Gly Trp Tyr Gly Tyr Gly Arg Lys Lys Arg Arg Gln
            20                  25                  30

Arg Arg

<210> SEQ ID NO 167
<211> LENGTH: 34
<212> TYPE: PRT
<213> ORGANISM: Homo sapiens

<400> SEQUENCE: 167

Cys Gly Leu Phe Gly Ala Ile Ala Gly Phe Ile Glu Gly Gly Trp Ser
1               5                   10                  15

Gly Met Ile Asp Gly Trp Tyr Gly Tyr Gly Arg Lys Lys Arg Arg Gln
            20                  25                  30

Arg Arg

<210> SEQ ID NO 168
<211> LENGTH: 34
<212> TYPE: PRT
<213> ORGANISM: Homo sapiens

<400> SEQUENCE: 168

Cys Gly Leu Phe Gly Ala Ile Ala Gly Phe Ile Glu Gly Gly Trp Pro
1               5                   10                  15

Gly Leu Val Ala Gly Trp Tyr Gly Tyr Gly Arg Lys Lys Arg Arg Gln
            20                  25                  30

Arg Arg

<210> SEQ ID NO 169
<211> LENGTH: 34
<212> TYPE: PRT
<213> ORGANISM: Homo sapiens

<400> SEQUENCE: 169

Cys Gly Leu Phe Gly Ala Ile Ala Gly Phe Ile Glu Asn Gly Trp Glu
1               5                   10                  15

Gly Met Val Asp Gly Trp Tyr Gly Tyr Gly Arg Lys Lys Arg Arg Gln
            20                  25                  30

Arg Arg

<210> SEQ ID NO 170
<211> LENGTH: 34
<212> TYPE: PRT
<213> ORGANISM: Homo sapiens

<400> SEQUENCE: 170

Cys Gly Leu Phe Gly Ala Ile Ala Gly Phe Ile Glu Gly Gly Trp Pro
1               5                   10                  15

Gly Leu Ile Asn Gly Trp Tyr Gly Tyr Gly Arg Lys Lys Arg Arg Gln
            20                  25                  30

Arg Arg

<210> SEQ ID NO 171
<211> LENGTH: 34
<212> TYPE: PRT
<213> ORGANISM: Homo sapiens

<400> SEQUENCE: 171

Cys Gly Leu Phe Gly Ala Ile Ala Gly Phe Ile Glu Asn Gly Trp Glu
1               5                   10                  15

Gly Leu Ile Asp Gly Trp Tyr Gly Tyr Gly Arg Lys Lys Arg Arg Gln
            20                  25                  30

Arg Arg

<210> SEQ ID NO 172
<211> LENGTH: 34
<212> TYPE: PRT
<213> ORGANISM: Homo sapiens

<400> SEQUENCE: 172

Cys Gly Leu Phe Gly Ala Ile Ala Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 173
<211> LENGTH: 30
<212> TYPE: PRT
<213> ORGANISM: Homo sapiens

<400> SEQUENCE: 173

Cys Gly Leu Phe Gly Ala Ile Ala Gly Phe Ile Glu Asn Gly Trp Glu
1               5                   10                  15

Gly Met Ile Asp Gly Trp Tyr Gly Ser Ser Lys Lys Lys Lys
            20                  25                  30

<210> SEQ ID NO 174
<211> LENGTH: 34
<212> TYPE: PRT
<213> ORGANISM: Homo sapiens

<400> SEQUENCE: 174

Cys Gly Leu Phe Gly Ala Ile Ala Gly Phe Ile Glu Asn Gly Trp Glu
1               5                   10                  15

Gly Leu Ile Asp Gly Trp Tyr Gly Tyr Gly Arg Lys Lys Arg Arg Gln
            20                  25                  30

Arg Arg

<210> SEQ ID NO 175
<211> LENGTH: 34
<212> TYPE: PRT
<213> ORGANISM: Homo sapiens

<400> SEQUENCE: 175

-continued

Cys Gly Leu Phe Glu Ala Ile Glu Gly Phe Ile Glu Asn Gly Trp Glu
1               5                   10                  15
Gly Leu Ile Asp Gly Trp Tyr Gly Tyr Gly Arg Lys Lys Arg Arg Gln
            20                  25                  30
Arg Arg

<210> SEQ ID NO 176
<211> LENGTH: 34
<212> TYPE: PRT
<213> ORGANISM: Homo sapiens

<400> SEQUENCE: 176

Cys Gly Leu Phe Gly Ala Ile Ala Gly Phe Ile Glu Asn Gly Trp Glu
1               5                   10                  15
Gly Leu Ile Glu Gly Trp Tyr Gly Gly Arg Lys Lys Arg Arg Gln
            20                  25                  30
Arg Arg

<210> SEQ ID NO 177
<211> LENGTH: 34
<212> TYPE: PRT
<213> ORGANISM: Homo sapiens

<400> SEQUENCE: 177

Cys Gly Leu Phe Glu Ala Ile Glu Gly Phe Ile Glu Asn Gly Trp Glu
1               5                   10                  15
Gly Met Ile Asp Gly Trp Tyr Gly Gly Arg Lys Lys Arg Arg Gln
            20                  25                  30
Arg Arg

<210> SEQ ID NO 178
<211> LENGTH: 34
<212> TYPE: PRT
<213> ORGANISM: Homo sapiens

<400> SEQUENCE: 178

Cys Gly Leu Phe Glu Ala Ile Ala Gly Phe Ile Glu Asn Gly Trp Glu
1               5                   10                  15
Gly Leu Ile Asp Gly Trp Tyr Gly Tyr Gly Arg Lys Lys Arg Arg Gln
            20                  25                  30
Arg Arg

<210> SEQ ID NO 179
<211> LENGTH: 33
<212> TYPE: PRT
<213> ORGANISM: Homo sapiens

<400> SEQUENCE: 179

Cys Gly Leu Phe Glu Ala Ile Ala Glu Phe Ile Glu Asn Gly Trp Glu
1               5                   10                  15
Gly Leu Ile Glu Gly Trp Tyr Gly Gly Arg Lys Lys Arg Arg Gln Arg
            20                  25                  30
Arg

<210> SEQ ID NO 180
<211> LENGTH: 33
<212> TYPE: PRT
<213> ORGANISM: Homo sapiens

<400> SEQUENCE: 180

Cys Gly Leu Phe Glu Ala Ile Glu Gly Phe Ile Glu Asn Gly Trp Glu
1               5                   10                  15

Gly Met Ile Asp Gly Trp Tyr Gly Arg Lys Lys Arg Arg Gln Arg Arg
            20                  25                  30

Arg

<210> SEQ ID NO 181
<211> LENGTH: 22
<212> TYPE: PRT
<213> ORGANISM: Homo sapiens

<400> SEQUENCE: 181

Cys Lys Leu Leu Lys Leu Leu Lys Leu Trp Leu Lys Leu Leu Lys
1               5                   10                  15

Leu Leu Leu Lys Leu Leu
            20

<210> SEQ ID NO 182
<211> LENGTH: 32
<212> TYPE: PRT
<213> ORGANISM: Homo sapiens

<400> SEQUENCE: 182

Cys Lys Leu Leu Lys Leu Leu Leu Lys Leu Trp Leu Lys Leu Leu Lys
1               5                   10                  15

Leu Leu Leu Lys Leu Leu Tyr Gly Arg Lys Lys Arg Arg Gln Arg Arg
            20                  25                  30

<210> SEQ ID NO 183
<211> LENGTH: 24
<212> TYPE: PRT
<213> ORGANISM: Homo sapiens

<400> SEQUENCE: 183

Gly Leu Phe Glu Ala Ile Glu Gly Phe Ile Glu Asn Gly Trp Glu Gly
1               5                   10                  15

Met Ile Asp Gly Trp Tyr Gly Cys
            20

<210> SEQ ID NO 184
<211> LENGTH: 34
<212> TYPE: PRT
<213> ORGANISM: Homo sapiens

<400> SEQUENCE: 184

Cys Val Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 185
<211> LENGTH: 34
<212> TYPE: PRT
<213> ORGANISM: Homo sapiens

<400> SEQUENCE: 185

Cys Ser Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln

Arg Arg

<210> SEQ ID NO 186
<211> LENGTH: 32
<212> TYPE: PRT
<213> ORGANISM: Homo sapiens

<400> SEQUENCE: 186

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

<210> SEQ ID NO 187
<211> LENGTH: 31
<212> TYPE: PRT
<213> ORGANISM: Homo sapiens

<400> SEQUENCE: 187

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg
            20                  25                  30

<210> SEQ ID NO 188
<211> LENGTH: 34
<212> TYPE: PRT
<213> ORGANISM: Homo sapiens

<400> SEQUENCE: 188

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Lys Lys Lys Lys Lys Gln
            20                  25                  30

Lys Lys

<210> SEQ ID NO 189
<211> LENGTH: 47
<212> TYPE: PRT
<213> ORGANISM: Homo sapiens

<400> SEQUENCE: 189

Cys Gly Leu Phe Glu Ala Ile Glu Gly Phe Ile Glu Asn Gly Trp Glu
1               5                   10                  15

Gly Met Ile Asp Gly Trp Tyr Gly Gly Leu Phe Glu Ala Ile Glu Gly
            20                  25                  30

Phe Ile Glu Asn Gly Trp Glu Gly Met Ile Asp Gly Trp Tyr Gly
        35                  40                  45

<210> SEQ ID NO 190
<211> LENGTH: 67
<212> TYPE: PRT
<213> ORGANISM: Homo sapiens

<400> SEQUENCE: 190

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

```
Arg Arg Gly Leu Phe Glu Ala Ile Glu Gly Phe Ile Glu Asn Gly Trp
         35                  40                  45
Glu Gly Met Ile Asp Gly Trp Tyr Gly Tyr Gly Arg Lys Lys Arg Arg
 50                  55                  60
Gln Arg Arg
 65

<210> SEQ ID NO 191
<211> LENGTH: 34
<212> TYPE: PRT
<213> ORGANISM: Homo sapiens

<400> SEQUENCE: 191

Arg Arg Gln Arg Arg Lys Lys Arg Gly Tyr Gly Tyr Trp Gly Asp Ile
 1               5                  10                  15
Met Gly Glu Trp Gly Asn Glu Ile Phe Gly Ile Ala Glu Phe Leu
             20                  25                  30
Gly Cys

<210> SEQ ID NO 192
<211> LENGTH: 34
<212> TYPE: PRT
<213> ORGANISM: Homo sapiens

<400> SEQUENCE: 192

Cys Arg Arg Gln Arg Arg Lys Lys Arg Gly Tyr Gly Tyr Trp Gly Asp
 1               5                  10                  15
Ile Met Gly Glu Trp Gly Asn Glu Ile Phe Gly Ile Ala Glu Phe
             20                  25                  30
Leu Gly

<210> SEQ ID NO 193
<211> LENGTH: 34
<212> TYPE: PRT
<213> ORGANISM: Homo sapiens

<400> SEQUENCE: 193

Gly Leu Phe Glu Ala Ile Glu Gly Phe Ile Glu Asn Gly Trp Glu Gly
 1               5                  10                  15
Met Ile Asp Gly Trp Tyr Gly Tyr Gly Arg Lys Lys Asp Arg Arg Gln
             20                  25                  30
Arg Arg

<210> SEQ ID NO 194
<211> LENGTH: 34
<212> TYPE: PRT
<213> ORGANISM: Homo sapiens

<400> SEQUENCE: 194

Gly Leu Phe Glu Ala Ile Glu Gly Phe Ile Glu Asn Gly Trp Glu Gly
 1               5                  10                  15
Met Ile Asp Gly Trp Tyr Gly Tyr Gly Arg Lys Lys Arg Asp Arg Gln
             20                  25                  30
Arg Arg

<210> SEQ ID NO 195
<211> LENGTH: 34
<212> TYPE: PRT
<213> ORGANISM: Homo sapiens
```

```
<400> SEQUENCE: 195

Gly Leu Phe Asp Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 196
<211> LENGTH: 34
<212> TYPE: PRT
<213> ORGANISM: Homo sapiens

<400> SEQUENCE: 196

Gly Leu Phe Glu Asp Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 197
<211> LENGTH: 24
<212> TYPE: PRT
<213> ORGANISM: Homo sapiens

<400> SEQUENCE: 197

Cys Gly Leu Phe Glu Ala Ile Glu Gly Phe Ile Glu Asn Gly Trp Glu
1               5                   10                  15

Gly Met Ile Asp Gly Trp Tyr Gly
            20

<210> SEQ ID NO 198
<211> LENGTH: 11
<212> TYPE: PRT
<213> ORGANISM: Homo sapiens

<400> SEQUENCE: 198

Cys Tyr Gly Arg Lys Lys Arg Arg Gln Arg Arg
1               5                   10

<210> SEQ ID NO 199
<211> LENGTH: 11
<212> TYPE: PRT
<213> ORGANISM: Homo sapiens

<400> SEQUENCE: 199

Tyr Gly Arg Lys Lys Arg Arg Gln Arg Arg Cys
1               5                   10

<210> SEQ ID NO 200
<211> LENGTH: 34
<212> TYPE: PRT
<213> ORGANISM: Homo sapiens

<400> SEQUENCE: 200

Arg Arg Gln Arg Arg Lys Lys Arg Gly Tyr Gly Tyr Trp Gly Asp Ile
1               5                   10                  15

Met Gly Glu Trp Gly Asn Glu Ile Phe Gly Glu Ile Ala Glu Phe Leu
            20                  25                  30

Gly Cys
```

```
<210> SEQ ID NO 201
<211> LENGTH: 34
<212> TYPE: PRT
<213> ORGANISM: Homo sapiens

<400> SEQUENCE: 201

Cys Arg Arg Gln Arg Arg Lys Lys Arg Gly Tyr Gly Tyr Trp Gly Asp
1               5                   10                  15

Ile Met Gly Glu Trp Gly Asn Glu Ile Phe Gly Glu Ile Ala Glu Phe
            20                  25                  30

Leu Gly

<210> SEQ ID NO 202
<211> LENGTH: 34
<212> TYPE: PRT
<213> ORGANISM: Homo sapiens

<400> SEQUENCE: 202

Cys Gly Leu Phe Glu Ala Ile Glu Gly Phe Ile Glu Asn Gly Trp Glu
1               5                   10                  15

Gly Met Ile Asp Gly Ala Tyr Gly Tyr Gly Arg Lys Lys Arg Arg Gln
            20                  25                  30

Arg Arg

<210> SEQ ID NO 203
<211> LENGTH: 34
<212> TYPE: PRT
<213> ORGANISM: Homo sapiens

<400> SEQUENCE: 203

Cys Gly Leu Phe Glu Ala Leu Leu Glu Leu Leu Glu Ser Leu Trp Glu
1               5                   10                  15

Leu Leu Leu Glu Ala Trp Tyr Gly Tyr Gly Arg Lys Lys Arg Arg Gln
            20                  25                  30

Arg Arg

<210> SEQ ID NO 204
<211> LENGTH: 34
<212> TYPE: PRT
<213> ORGANISM: Homo sapiens

<400> SEQUENCE: 204

Cys Gly Leu Phe Glu Ala Ile Glu Gly Phe Asn Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 205
<211> LENGTH: 34
<212> TYPE: PRT
<213> ORGANISM: Homo sapiens

<400> SEQUENCE: 205

Cys Gly Leu Phe Glu Ala Ile Glu Gly Phe Ile Glu Asn Glu Trp Glu
1               5                   10                  15

Gly Met Ile Asp Gly Trp Tyr Gly Tyr Gly Arg Lys Lys Arg Arg Gln
            20                  25                  30

Arg Arg
```

<210> SEQ ID NO 206
<211> LENGTH: 42
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (1)..(1)
<223> OTHER INFORMATION: Lys is conjugated to stearyl

<400> SEQUENCE: 206

Lys Ser Thr Glu Ala Arg Tyr Leu Gly Leu Phe Glu Ala Ile Glu Gly
1               5                   10                  15

Phe Ile Glu Asn Gly Trp Glu Gly Met Ile Asp Gly Trp Tyr Gly Tyr
            20                  25                  30

Gly Arg Lys Lys Arg Arg Gln Arg Arg Cys
        35                  40

<210> SEQ ID NO 207
<211> LENGTH: 41
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (8)..(8)
<223> OTHER INFORMATION: Lys is conjugated to stearyl

<400> SEQUENCE: 207

Cys Gly Leu Phe Glu Ala Ile Lys Ser Thr Glu Ala Arg Tyr Leu Gly
1               5                   10                  15

Phe Ile Glu Asn Gly Trp Glu Gly Met Ile Asp Gly Trp Tyr Gly Tyr
            20                  25                  30

Gly Arg Lys Lys Arg Arg Gln Arg Arg
        35                  40

<210> SEQ ID NO 208
<211> LENGTH: 34
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (28)..(28)
<223> OTHER INFORMATION: Lysine is conjugated to Stearyl

<400> SEQUENCE: 208

Cys Gly Leu Phe Glu Ala Ile Lys Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 209
<211> LENGTH: 34
<212> TYPE: PRT
<213> ORGANISM: Homo sapiens

<400> SEQUENCE: 209

Cys Gly Leu Phe Glu Ala Ile Glu Gly Phe Ile Glu Asn Pro Trp Glu
1               5                   10                  15

```
Gly Met Ile Asp Gly Trp Tyr Gly Tyr Gly Arg Lys Arg Arg Gln
            20                  25                  30

Arg Arg

<210> SEQ ID NO 210
<211> LENGTH: 41
<212> TYPE: PRT
<213> ORGANISM: Homo sapiens

<400> SEQUENCE: 210

Ser Thr Glu Ala Arg Tyr Leu Gly Leu Phe Glu Ala Ile Glu Gly Phe
1               5                   10                  15

Ile Glu Asn Pro Trp Glu Gly Met Ile Asp Gly Trp Tyr Gly Tyr Gly
            20                  25                  30

Arg Lys Lys Arg Arg Gln Arg Arg Cys
        35                  40

<210> SEQ ID NO 211
<211> LENGTH: 63
<212> TYPE: PRT
<213> ORGANISM: Homo sapiens

<400> SEQUENCE: 211

Cys Gly Leu Phe Gly Ala Ile Ala Gly Phe Ile Glu Gly Gly Trp Pro
1               5                   10                  15

Gly Leu Ile Asn Gly Trp Tyr Gly Tyr Gly Arg Lys Lys Arg Arg Gln
            20                  25                  30

Arg Arg Leu His Leu Leu His His Leu His His Leu His His Leu
        35                  40                  45

Leu His His Leu Leu His Leu Leu His His Leu Leu His His Leu
    50                  55                  60

<210> SEQ ID NO 212
<211> LENGTH: 55
<212> TYPE: PRT
<213> ORGANISM: Homo sapiens

<400> SEQUENCE: 212

Cys Gly Leu Phe Gly Ala Ile Ala Gly Phe Ile Glu Gly Gly Trp Pro
1               5                   10                  15

Gly Leu Ile Asn Gly Trp Tyr Gly Tyr Gly Arg Lys Lys Arg Arg Gln
            20                  25                  30

Arg Arg Leu His Leu Leu His His Leu His His Leu His His Leu
        35                  40                  45

Leu His His Leu Leu His Leu
    50                  55

<210> SEQ ID NO 213
<211> LENGTH: 34
<212> TYPE: PRT
<213> ORGANISM: Homo sapiens

<400> SEQUENCE: 213

Cys Gly Leu Phe Glu Ala Ile Ala Gly Phe Ile Glu Gly Gly Trp Pro
1               5                   10                  15

Gly Leu Ile Asn Gly Trp Tyr Gly Tyr Gly Arg Lys Lys Arg Arg Gln
            20                  25                  30

Arg Arg
```

-continued

```
<210> SEQ ID NO 214
<211> LENGTH: 34
<212> TYPE: PRT
<213> ORGANISM: Homo sapiens

<400> SEQUENCE: 214

Cys Gly Leu Glu Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 215
<211> LENGTH: 34
<212> TYPE: PRT
<213> ORGANISM: Homo sapiens

<400> SEQUENCE: 215

Cys Gly Leu Phe Asn Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 216
<211> LENGTH: 34
<212> TYPE: PRT
<213> ORGANISM: Homo sapiens

<400> SEQUENCE: 216

Cys Gly Leu Phe Ala Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 217
<211> LENGTH: 34
<212> TYPE: PRT
<213> ORGANISM: Homo sapiens

<400> SEQUENCE: 217

Cys Gly Leu Phe Glu Ala Ile Glu Asn Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 218
<211> LENGTH: 34
<212> TYPE: PRT
<213> ORGANISM: Homo sapiens

<400> SEQUENCE: 218

Cys Gly Leu Phe Glu Ala Ile Glu Lys Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg
```

<210> SEQ ID NO 219
<211> LENGTH: 34
<212> TYPE: PRT
<213> ORGANISM: Homo sapiens

<400> SEQUENCE: 219

Cys Gly Leu Phe Glu Ala Ile Glu Gly Phe Ala Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 220
<211> LENGTH: 34
<212> TYPE: PRT
<213> ORGANISM: Homo sapiens

<400> SEQUENCE: 220

Cys Gly Leu Phe Glu Ala Ile Glu Gly Phe Ile Glu Asn Trp Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 221
<211> LENGTH: 34
<212> TYPE: PRT
<213> ORGANISM: Homo sapiens

<400> SEQUENCE: 221

Cys Gly Leu Phe Glu Ala Ile Glu Gly Phe Ile Glu Asn Asn Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 222
<211> LENGTH: 34
<212> TYPE: PRT
<213> ORGANISM: Homo sapiens

<400> SEQUENCE: 222

Cys Gly Leu Phe Glu Ala Ile Glu Gly Phe Ile Glu Asn Gly Glu Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 223
<211> LENGTH: 34
<212> TYPE: PRT
<213> ORGANISM: Homo sapiens

<400> SEQUENCE: 223

Cys Gly Leu Phe Glu Ala Ile Glu Gly Phe Ile Glu Asn Gly Trp Ala
1               5                   10                  15

Gly Met Ile Asp Gly Trp Tyr Gly Tyr Gly Arg Lys Lys Arg Arg Gln
            20                  25                  30

Arg Arg

<210> SEQ ID NO 224
<211> LENGTH: 34
<212> TYPE: PRT
<213> ORGANISM: Homo sapiens

<400> SEQUENCE: 224

Cys Gly Leu Phe Glu Ala Ile Glu Gly Phe Ile Glu Asn Gly Trp Asn
1               5                   10                  15

Gly Met Ile Asp Gly Trp Tyr Gly Tyr Gly Arg Lys Lys Arg Arg Gln
            20                  25                  30

Arg Arg

<210> SEQ ID NO 225
<211> LENGTH: 34
<212> TYPE: PRT
<213> ORGANISM: Homo sapiens

<400> SEQUENCE: 225

Cys Gly Leu Phe Glu Ala Ile Glu Gly Phe Ile Glu Asn Gly Trp Gly
1               5                   10                  15

Gly Met Ile Asp Gly Trp Tyr Gly Tyr Gly Arg Lys Lys Arg Arg Gln
            20                  25                  30

Arg Arg

<210> SEQ ID NO 226
<211> LENGTH: 34
<212> TYPE: PRT
<213> ORGANISM: Homo sapiens

<400> SEQUENCE: 226

Cys Gly Leu Phe Glu Ala Ile Glu Gly Phe Ile Glu Asn Gly Trp Glu
1               5                   10                  15

Gly Met Ile Asp Ala Trp Tyr Gly Tyr Gly Arg Lys Lys Arg Arg Gln
            20                  25                  30

Arg Arg

<210> SEQ ID NO 227
<211> LENGTH: 34
<212> TYPE: PRT
<213> ORGANISM: Homo sapiens

<400> SEQUENCE: 227

Cys Gly Leu Phe Glu Ala Ile Glu Gly Phe Ile Glu Asn Gly Trp Leu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 228
<211> LENGTH: 34
<212> TYPE: PRT
<213> ORGANISM: Homo sapiens

<400> SEQUENCE: 228

Cys Gly Leu Phe Glu Ala Ile Glu Gly Phe Ile Glu Asn Gly Trp Lys
1               5                   10                  15

Gly Met Ile Asp Gly Trp Tyr Gly Tyr Gly Arg Lys Lys Arg Arg Gln
            20                  25                  30

Arg Arg

<210> SEQ ID NO 229
<211> LENGTH: 34
<212> TYPE: PRT
<213> ORGANISM: Homo sapiens

<400> SEQUENCE: 229

Cys Gly Leu Phe Glu Ala Ile Glu Gly Phe Ile Glu Asn Gly Trp Glu
1               5                   10                  15

Gly Met Ile Asp Lys Trp Tyr Gly Tyr Gly Arg Lys Lys Arg Arg Gln
            20                  25                  30

Arg Arg

<210> SEQ ID NO 230
<211> LENGTH: 34
<212> TYPE: PRT
<213> ORGANISM: Homo sapiens

<400> SEQUENCE: 230

Cys Gly Leu Phe Glu Ala Ile Glu Gly Phe Ile Glu Asn Gly Trp Glu
1               5                   10                  15

Gly Met Ile Asp Glu Trp Tyr Gly Tyr Gly Arg Lys Lys Arg Arg Gln
            20                  25                  30

Arg Arg

<210> SEQ ID NO 231
<211> LENGTH: 34
<212> TYPE: PRT
<213> ORGANISM: Homo sapiens

<400> SEQUENCE: 231

Cys Gly Leu Phe Glu Ala Ile Glu Gly Phe Ile Glu Asn Gly Trp Glu
1               5                   10                  15

Gly Met Ile Asp Gly Leu Tyr Gly Tyr Gly Arg Lys Lys Arg Arg Gln
            20                  25                  30

Arg Arg

<210> SEQ ID NO 232
<211> LENGTH: 34
<212> TYPE: PRT
<213> ORGANISM: Homo sapiens

<400> SEQUENCE: 232

Cys Gly Leu Phe Glu Ala Ile Glu Gly Phe Ile Glu Asn Gly Trp Glu
1               5                   10                  15

Gly Met Ile Asp Gly Asn Tyr Gly Tyr Gly Arg Lys Lys Arg Arg Gln
            20                  25                  30

Arg Arg

<210> SEQ ID NO 233
<211> LENGTH: 34
<212> TYPE: PRT
<213> ORGANISM: Homo sapiens

<400> SEQUENCE: 233

Cys Gly Leu Phe Glu Ala Ile Glu Gly Phe Ile Glu Asn Gly Trp Glu
1               5                   10                  15

Gly Met Ile Asp Gly Lys Tyr Gly Tyr Gly Arg Lys Lys Arg Arg Gln
            20                  25                  30

Arg Arg

<210> SEQ ID NO 234
<211> LENGTH: 34
<212> TYPE: PRT
<213> ORGANISM: Homo sapiens

<400> SEQUENCE: 234

Cys Gly Leu Phe Glu Ala Ile Glu Gly Phe Ile Glu Asn Gly Trp Glu
1               5                   10                  15

Gly Met Ile Asp Gly Glu Tyr Gly Tyr Gly Arg Lys Lys Arg Arg Gln
            20                  25                  30

Arg Arg

<210> SEQ ID NO 235
<211> LENGTH: 34
<212> TYPE: PRT
<213> ORGANISM: Homo sapiens

<400> SEQUENCE: 235

Cys Gly Leu Phe Glu Ala Leu Glu Glu Leu Leu Glu Gly Gly Trp Glu
1               5                   10                  15

Gly Leu Ile Glu Ala Trp Tyr Gly Tyr Gly Arg Lys Lys Arg Arg Gln
            20                  25                  30

Arg Arg

<210> SEQ ID NO 236
<211> LENGTH: 34
<212> TYPE: PRT
<213> ORGANISM: Homo sapiens

<400> SEQUENCE: 236

Cys Glu Leu Phe Gly Ala Ile Trp Glu Phe Ile Glu Gly Gly Trp Glu
1               5                   10                  15

Gly Leu Ile Glu Ala Trp Tyr Gly Tyr Gly Arg Lys Lys Arg Arg Gln
            20                  25                  30

Arg Arg

<210> SEQ ID NO 237
<211> LENGTH: 34
<212> TYPE: PRT
<213> ORGANISM: Homo sapiens

<400> SEQUENCE: 237

Cys Gly Leu Phe Glu Ala Leu Glu Glu Phe Ile Glu Gly Gly Trp Glu
1               5                   10                  15

Gly Leu Leu Glu Ala Trp Tyr Gly Tyr Gly Arg Lys Lys Arg Arg Gln
            20                  25                  30

Arg Arg

<210> SEQ ID NO 238
<211> LENGTH: 34
<212> TYPE: PRT
<213> ORGANISM: Homo sapiens

<400> SEQUENCE: 238

Cys Gly Leu Phe Glu Ala Leu Glu Glu Phe Ile Glu Asn Gly Trp Glu
1               5                   10                  15

Gly Leu Leu Glu Ala Trp Tyr Gly Tyr Gly Arg Lys Lys Arg Arg Gln 20                  25                  30

Arg Arg

<210> SEQ ID NO 239
<211> LENGTH: 34
<212> TYPE: PRT
<213> ORGANISM: Homo sapiens

<400> SEQUENCE: 239

Cys Gly Leu Phe Glu Ala Ile Glu Gly Phe Ile Glu Ser Gly Trp Glu
1               5                   10                  15

Gly Leu Ile Asp Gly Trp Tyr Gly Tyr Gly Arg Lys Lys Arg Arg Gln
            20                  25                  30

Arg Arg

<210> SEQ ID NO 240
<211> LENGTH: 34
<212> TYPE: PRT
<213> ORGANISM: Homo sapiens

<400> SEQUENCE: 240

Cys Gly Leu Phe Glu Ala Ile Glu Glu Phe Ile Glu Gly Gly Trp Glu
1               5                   10                  15

Gly Leu Ile Glu Ala Trp Tyr Gly Tyr Gly Arg Lys Lys Arg Arg Gln
            20                  25                  30

Arg Arg

<210> SEQ ID NO 241
<211> LENGTH: 34
<212> TYPE: PRT
<213> ORGANISM: Homo sapiens

<400> SEQUENCE: 241

Cys Gly Leu Phe Glu Ala Ile Glu Gly Phe Ile Glu Asn Gly Trp Glu
1               5                   10                  15

Gly Leu Ile Asp Ala Trp Tyr Gly Tyr Gly Arg Lys Lys Arg Arg Gln
            20                  25                  30

Arg Arg

<210> SEQ ID NO 242
<211> LENGTH: 34
<212> TYPE: PRT
<213> ORGANISM: Homo sapiens

<400> SEQUENCE: 242

Cys Gly Leu Phe Glu Ala Ile Glu Gly Phe Ile Leu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 243
<211> LENGTH: 34
<212> TYPE: PRT
<213> ORGANISM: Homo sapiens

<400> SEQUENCE: 243

Cys Gly Leu Phe Glu Ala Ile Glu Gly Phe Ile Lys Asn Gly Trp Glu
1               5                   10                  15

```
Gly Met Ile Asp Gly Trp Tyr Gly Tyr Gly Arg Lys Arg Gln
            20                  25                  30

Arg Arg

<210> SEQ ID NO 244
<211> LENGTH: 34
<212> TYPE: PRT
<213> ORGANISM: Homo sapiens

<400> SEQUENCE: 244

Cys Gly Leu Phe Glu Ala Ile Glu Gly Phe Ile Gly Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 245
<211> LENGTH: 34
<212> TYPE: PRT
<213> ORGANISM: Homo sapiens

<400> SEQUENCE: 245

Cys Gly Leu Phe Glu Ala Ile Glu Gly Phe Ile Glu Leu Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 246
<211> LENGTH: 34
<212> TYPE: PRT
<213> ORGANISM: Homo sapiens

<400> SEQUENCE: 246

Cys Gly Leu Phe Glu Ala Ile Glu Gly Phe Ile Glu Lys Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 247
<211> LENGTH: 34
<212> TYPE: PRT
<213> ORGANISM: Homo sapiens

<400> SEQUENCE: 247

Cys Gly Leu Phe Glu Ala Ile Ala Glu Phe Ile Glu Gly Gly Trp Glu
1               5                   10                  15

Gly Leu Ile Glu Gly Trp Tyr Gly Tyr Gly Arg Lys Lys Arg Arg Gln
            20                  25                  30

Arg Arg

<210> SEQ ID NO 248
<211> LENGTH: 16
<212> TYPE: PRT
<213> ORGANISM: Homo sapiens

<400> SEQUENCE: 248

Cys Arg Gly Trp Glu Val Leu Lys Tyr Trp Trp Asn Leu Leu Gln Tyr
1               5                   10                  15
```

```
<210> SEQ ID NO 249
<211> LENGTH: 26
<212> TYPE: PRT
<213> ORGANISM: Homo sapiens

<400> SEQUENCE: 249

Cys Arg Gly Trp Glu Val Leu Lys Tyr Trp Trp Asn Leu Leu Gln Tyr
1               5                   10                  15

Tyr Gly Arg Lys Lys Arg Arg Gln Arg Arg
            20                  25

<210> SEQ ID NO 250
<211> LENGTH: 36
<212> TYPE: PRT
<213> ORGANISM: Homo sapiens

<400> SEQUENCE: 250

Cys Gly Leu Phe Gly Ala Ile Ala Gly Phe Ile Glu Asn Gly Trp Glu
1               5                   10                  15

Gly Met Ile Asp Gly Trp Tyr Gly Phe Arg Tyr Gly Arg Lys Lys Arg
            20                  25                  30

Arg Gln Arg Arg
        35

<210> SEQ ID NO 251
<211> LENGTH: 38
<212> TYPE: PRT
<213> ORGANISM: Homo sapiens

<400> SEQUENCE: 251

Ala Cys Cys Gly Leu Phe Glu Ala Ile Glu Gly Phe Ile Glu Asn Gly
1               5                   10                  15

Trp Glu Gly Met Ile Asp Gly Trp Tyr Gly Tyr Gly Arg Lys Lys Arg
            20                  25                  30

Arg Gln Arg Arg Cys His
        35

<210> SEQ ID NO 252
<211> LENGTH: 34
<212> TYPE: PRT
<213> ORGANISM: Homo sapiens

<400> SEQUENCE: 252

Cys Gly Leu Leu Glu Ala Leu Glu Gly Leu Leu Glu Asn Gly Trp Glu
1               5                   10                  15

Gly Leu Leu Glu Ala Trp Tyr Gly Tyr Gly Arg Lys Lys Arg Arg Gln
            20                  25                  30

Arg Arg

<210> SEQ ID NO 253
<211> LENGTH: 30
<212> TYPE: PRT
<213> ORGANISM: Homo sapiens

<400> SEQUENCE: 253

Cys Leu Arg His Leu Leu Arg His Leu Leu Arg His Leu Arg His Leu
1               5                   10                  15

Leu Arg His Leu Arg His Leu Leu Arg His Leu Leu Arg His
            20                  25                  30
```

```
<210> SEQ ID NO 254
<211> LENGTH: 34
<212> TYPE: PRT
<213> ORGANISM: Artificial Sequence
<220> FEATURE:
<223> OTHER INFORMATION: Synthetically generated peptide
<220> FEATURE:
<221> NAME/KEY: misc_feature
<222> LOCATION: (28)..(29)
<223> OTHER INFORMATION: Xaa = ornithine

<400> SEQUENCE: 254

Cys Gly Ile Phe Glu Ala Ile Glu Gly Phe Ile Glu Asn Gly Trp Glu
1               5                   10                  15

Gly Ile Ile Asp Gly Trp Tyr Gly Tyr Gly Arg Xaa Xaa Arg Arg Gln
            20                  25                  30

Arg Arg

<210> SEQ ID NO 255
<211> LENGTH: 27
<212> TYPE: PRT
<213> ORGANISM: Homo sapiens

<400> SEQUENCE: 255

Cys Gly Ile Gly Ala Val Leu Lys Val Leu Thr Thr Gly Leu Pro Ala
1               5                   10                  15

Leu Ile Ser Trp Ile Lys Arg Lys Arg Gln Gln
            20                  25

<210> SEQ ID NO 256
<211> LENGTH: 27
<212> TYPE: PRT
<213> ORGANISM: Homo sapiens

<400> SEQUENCE: 256

Cys Gly Ile Gly Ala Val Leu Lys Val Leu Thr Thr Gly Leu Pro Ala
1               5                   10                  15

Leu Ile Ser Trp Ile His His His His Gln Gln
            20                  25

<210> SEQ ID NO 257
<211> LENGTH: 34
<212> TYPE: PRT
<213> ORGANISM: Homo sapiens

<400> SEQUENCE: 257

Cys Gly Ala Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 258
<211> LENGTH: 36
<212> TYPE: PRT
<213> ORGANISM: Homo sapiens

<400> SEQUENCE: 258

Ala Cys Leu His Leu Leu His Leu Leu His His Leu His Leu His Leu
1               5                   10                  15

Leu His His Leu Leu His Leu Leu His His Leu Leu His Leu His Leu Arg
            20                  25                  30
```

-continued

Arg Arg Arg Arg
        35

<210> SEQ ID NO 259
<211> LENGTH: 34
<212> TYPE: PRT
<213> ORGANISM: Homo sapiens

<400> SEQUENCE: 259

Cys Gly Leu Phe Gly Ala Ile Trp Gly Phe Ile Glu Asn Trp Trp Lys
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 260
<211> LENGTH: 34
<212> TYPE: PRT
<213> ORGANISM: Homo sapiens

<400> SEQUENCE: 260

Cys Gly Leu Phe Gly Ala Ile Glu Gly Phe Ile Glu Asn Gly Trp Lys
1               5                   10                  15

Gly Leu Ile Asp Ala Trp Tyr Gly Tyr Gly Arg Lys Lys Arg Arg Gln
            20                  25                  30

Arg Arg

<210> SEQ ID NO 261
<211> LENGTH: 34
<212> TYPE: PRT
<213> ORGANISM: Homo sapiens

<400> SEQUENCE: 261

Cys Gly Leu Phe Glu Ala Ile Ala Gly Phe Ile Glu Asn Gly Trp Lys
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 262
<211> LENGTH: 34
<212> TYPE: PRT
<213> ORGANISM: Homo sapiens

<400> SEQUENCE: 262

Gly Leu Phe Glu Ala Ile Glu Gly Phe Ile Glu Asn Gly Trp Lys Gly
1               5                   10                  15

Leu Ile Asp Trp Trp Tyr Gly Tyr Gly Arg Lys Lys Arg Arg Gln Arg
            20                  25                  30

Arg Cys

<210> SEQ ID NO 263
<211> LENGTH: 34
<212> TYPE: PRT
<213> ORGANISM: Homo sapiens

<400> SEQUENCE: 263

Tyr Gly Arg Lys Lys Arg Arg Gln Arg Arg Gly Leu Phe Glu Ala Ile
1               5                   10                  15

Glu Gly Phe Ile Glu Asn Gly Trp Lys Gly Leu Ile Asp Ala Trp Tyr
            20                  25                  30

Gly Cys

<210> SEQ ID NO 264
<211> LENGTH: 34
<212> TYPE: PRT
<213> ORGANISM: Homo sapiens

<400> SEQUENCE: 264

Tyr Gly Arg Lys Lys Arg Arg Gln Arg Arg Gly Leu Phe Glu Ala Ile
1               5                   10                  15

Glu Gly Phe Ile Glu Asn Gly Trp Lys Gly Leu Ile Asp Trp Trp Tyr
            20                  25                  30

Gly Cys

<210> SEQ ID NO 265
<211> LENGTH: 34
<212> TYPE: PRT
<213> ORGANISM: Homo sapiens

<400> SEQUENCE: 265

Cys Gly Leu Phe His Ala Ile His Gly Phe Ile Glu Asn Gly Trp His
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 266
<211> LENGTH: 35
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (35)..(35)
<223> OTHER INFORMATION: Lys is conjugated to Stearyl

<400> SEQUENCE: 266

Cys Gly Leu Phe Glu Ala Ile Glu Gly Phe Ile Glu Asn Gly Trp Lys
1               5                   10                  15

Gly Leu Ile Asp Trp Trp Tyr Gly Tyr Gly Arg Lys Lys Arg Arg Gln
            20                  25                  30

Arg Arg Lys
        35

<210> SEQ ID NO 267
<211> LENGTH: 34
<212> TYPE: PRT
<213> ORGANISM: Homo sapiens

<400> SEQUENCE: 267

Cys Gly Leu Phe Lys Ala Leu Leu Lys Leu Leu Lys Ser Leu Trp Lys
1               5                   10                  15

Leu Leu Leu Lys Ala Trp Tyr Gly Tyr Gly His Lys Lys His His Gln
            20                  25                  30

His Arg

<210> SEQ ID NO 268
<211> LENGTH: 34

<212> TYPE: PRT
<213> ORGANISM: Homo sapiens

<400> SEQUENCE: 268

Cys Gly Leu Phe Lys Ala Leu Leu Lys Leu Leu Lys Ser Leu Trp Lys
1               5                   10                  15

Gly Leu Leu Lys Ala Trp Tyr Gly Tyr Gly His Lys Lys His His Gln
            20                  25                  30

His Arg

<210> SEQ ID NO 269
<211> LENGTH: 34
<212> TYPE: PRT
<213> ORGANISM: Homo sapiens

<400> SEQUENCE: 269

Cys Gly Leu Ala Lys Ala Leu Leu Lys Leu Leu Lys Ser Leu Trp Lys
1               5                   10                  15

Gly Leu Ile Glu Ala Trp Tyr Gly Tyr Gly Arg Lys Lys Arg Arg Gln
            20                  25                  30

Arg Arg

<210> SEQ ID NO 270
<211> LENGTH: 15
<212> TYPE: PRT
<213> ORGANISM: Homo sapiens

<400> SEQUENCE: 270

Cys Gly Ile Phe Gly Ala Ile Ala Gly Phe Ile Lys Asn Ile Trp
1               5                   10                  15

<210> SEQ ID NO 271
<211> LENGTH: 33
<212> TYPE: PRT
<213> ORGANISM: Homo sapiens

<400> SEQUENCE: 271

Cys Ile Phe Gly Ala Ile Ala Gly Phe Ile Lys Asn Ile Trp Glu Gly
1               5                   10                  15

Leu Ile Asp Gly Trp Tyr Gly Tyr Gly Arg Lys Lys Arg Arg Gln Arg
            20                  25                  30

Arg

<210> SEQ ID NO 272
<211> LENGTH: 31
<212> TYPE: PRT
<213> ORGANISM: Homo sapiens

<400> SEQUENCE: 272

Cys Gly Ile Phe Gly Ala Ile Ala Gly Phe Ile Lys Asn Ile Trp Glu
1               5                   10                  15

Gly Leu Ile Asp Gly Tyr Gly Arg Lys Lys Arg Arg Gln Arg Arg
            20                  25                  30

<210> SEQ ID NO 273
<211> LENGTH: 34
<212> TYPE: PRT
<213> ORGANISM: Homo sapiens

<400> SEQUENCE: 273

Cys Gly Ile Phe Gly Ala Ile Ala Gly Phe Ile Lys Asn Ile Trp Lys

```
                1               5                  10                 15
        Gly Leu Ile Asp Ala Trp Tyr Gly Tyr Gly Arg Lys Lys Arg Arg Gln
                        20                  25                  30

Arg Arg

<210> SEQ ID NO 274
<211> LENGTH: 33
<212> TYPE: PRT
<213> ORGANISM: Homo sapiens

<400> SEQUENCE: 274

Cys Ile Phe Gly Ala Ile Ala Gly Phe Ile Lys Asn Ile Trp Lys Gly
        1               5                  10                 15

Leu Ile Asp Trp Trp Tyr Gly Tyr Gly Arg Lys Lys Arg Arg Gln Arg
                        20                  25                  30

Arg

<210> SEQ ID NO 275
<211> LENGTH: 14
<212> TYPE: PRT
<213> ORGANISM: Homo sapiens

<400> SEQUENCE: 275

Cys Leu Phe Gly Ala Ile Ala Gly Phe Ile Lys Asn Ile Trp
        1               5                  10

<210> SEQ ID NO 276
<211> LENGTH: 34
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (3)..(3)
<223> OTHER INFORMATION: Leucine is conjugated to R5
<220> FEATURE:
<221> NAME/KEY: MISC_FEATURE
<222> LOCATION: (10)..(10)
<223> OTHER INFORMATION: Phenylalanine is conjugated to S8

<400> SEQUENCE: 276

Cys Gly Leu Arg Glu Ala Ile Glu Gly Phe Ser Glu Asn Gly Trp Glu
        1               5                  10                 15

Gly Met Ile Asp Gly Trp Tyr Gly Tyr Gly Arg Lys Lys Arg Arg Gln
                        20                  25                  30

Arg Arg

<210> SEQ ID NO 277
<211> LENGTH: 34
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (6)..(6)
<223> OTHER INFORMATION: Ala  is conjugated to S5
<220> FEATURE:
<221> NAME/KEY: MISC_FEATURE
<222> LOCATION: (10)..(10)
<223> OTHER INFORMATION: phe  is conjugated to S5

<400> SEQUENCE: 277

Cys Gly Leu Phe Glu Ala Ser Glu Gly Phe Ser Glu Asn Gly Trp Glu
```

```
                1               5                  10                 15
Gly Met Ile Asp Gly Trp Tyr Gly Tyr Gly Arg Lys Lys Arg Arg Gln
            20                 25                 30

Arg Arg

<210> SEQ ID NO 278
<211> LENGTH: 34
<212> TYPE: PRT
<213> ORGANISM: Homo sapiens

<400> SEQUENCE: 278

Cys Gly Leu Phe Glu Ala Ile Glu Gly Phe Ile Glu Asn Gly Trp Glu
1               5                  10                 15

Gly Ala Ile Asp Gly Trp Tyr Gly Tyr Gly Arg Lys Lys Arg Arg Gln
            20                 25                 30

Arg Arg

<210> SEQ ID NO 279
<211> LENGTH: 34
<212> TYPE: PRT
<213> ORGANISM: Homo sapiens

<400> SEQUENCE: 279

Cys Gly Leu Phe Glu Ala Ile Glu Gly Phe Ile Glu Asn Gly Trp Glu
1               5                  10                 15

Gly Glu Ile Asp Gly Trp Tyr Gly Tyr Gly Arg Lys Lys Arg Arg Gln
            20                 25                 30

Arg Arg

<210> SEQ ID NO 280
<211> LENGTH: 33
<212> TYPE: PRT
<213> ORGANISM: Homo sapiens

<400> SEQUENCE: 280

Cys Gly Ile Phe Gly Ala Ile Ala Gly Phe Ile Lys Asn Gly Trp Glu
1               5                  10                 15

Gly Met Val Asp Trp Tyr Gly Tyr Gly Arg Lys Lys Arg Arg Gln Arg
            20                 25                 30

Arg

<210> SEQ ID NO 281
<211> LENGTH: 35
<212> TYPE: PRT
<213> ORGANISM: Homo sapiens

<400> SEQUENCE: 281

Cys Gly Leu Phe Glu Ala Ile Ala Gly Phe Ile Glu Asn Gly Trp Glu
1               5                  10                 15

Gly Met Ile Asp Gly Trp Tyr Gly Phe Tyr Gly Arg Lys Lys Arg Arg
            20                 25                 30

Gln Arg Arg
        35

<210> SEQ ID NO 282
<211> LENGTH: 34
<212> TYPE: PRT
<213> ORGANISM: Homo sapiens

<400> SEQUENCE: 282
```

```
Cys Gly Ile Phe Gly Ala Ile Ala Gly Phe Ile Lys Asn Gly Trp Glu
1               5                   10                  15

Gly Met Ile Asp Gly Trp Tyr Gly Tyr Gly Arg Lys Lys Arg Arg Gln
            20                  25                  30

Arg Arg
```

<210> SEQ ID NO 283
<211> LENGTH: 14
<212> TYPE: PRT
<213> ORGANISM: Homo sapiens

<400> SEQUENCE: 283

```
Cys Ile Phe Gly Ala Ile Ala Gly Phe Ile Lys Asn Ile Trp
1               5                   10
```

<210> SEQ ID NO 284
<211> LENGTH: 24
<212> TYPE: PRT
<213> ORGANISM: Homo sapiens

<400> SEQUENCE: 284

```
Cys Ile Phe Gly Ala Ile Ala Gly Phe Ile Lys Asn Ile Trp Tyr Gly
1               5                   10                  15

Arg Lys Lys Arg Arg Gln Arg Arg
            20
```

<210> SEQ ID NO 285
<211> LENGTH: 34
<212> TYPE: PRT
<213> ORGANISM: Homo sapiens

<400> SEQUENCE: 285

```
Cys Gly Ile Phe Gly Ala Ile Ala Gly Phe Ile Lys Asn Ile Trp Glu
1               5                   10                  15

Gly Met Ile Asp Gly Trp Tyr Gly Tyr Gly Arg Lys Lys Arg Arg Gln
            20                  25                  30

Arg Arg
```

<210> SEQ ID NO 286
<211> LENGTH: 31
<212> TYPE: PRT
<213> ORGANISM: Homo sapiens

<400> SEQUENCE: 286

```
Cys Gly Leu Phe Glu Ala Ile Glu Gly Phe Ile Glu Asn Gly Trp Glu
1               5                   10                  15

Gly Leu Ile Glu Ala Tyr Gly Arg Lys Lys Arg Arg Gln Arg Arg
            20                  25                  30
```

<210> SEQ ID NO 287
<211> LENGTH: 31
<212> TYPE: PRT
<213> ORGANISM: Homo sapiens

<400> SEQUENCE: 287

```
Cys Gly Leu Phe Glu Ala Leu Leu Gly Phe Ile Glu Asn Gly Trp Glu
1               5                   10                  15

Gly Leu Ile Asp Gly Tyr Gly Arg Lys Lys Arg Arg Gln Arg Arg
            20                  25                  30
```

-continued

<210> SEQ ID NO 288
<211> LENGTH: 35
<212> TYPE: PRT
<213> ORGANISM: Homo sapiens

<400> SEQUENCE: 288

Cys Gly Leu Phe Gly Ala Ile Glu Gly Phe Ile Glu Asn Gly Trp Glu
1               5                   10                  15

Gly Leu Ile Asp Gly Trp Tyr Gly Tyr Gly Arg Lys Lys Arg Arg Gln
            20                  25                  30

Arg Arg Arg
        35

<210> SEQ ID NO 289
<211> LENGTH: 35
<212> TYPE: PRT
<213> ORGANISM: Homo sapiens

<400> SEQUENCE: 289

Cys Glu Leu Phe Gly Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg Arg
        35

<210> SEQ ID NO 290
<211> LENGTH: 34
<212> TYPE: PRT
<213> ORGANISM: Homo sapiens

<400> SEQUENCE: 290

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly His Lys Lys His His Gln
            20                  25                  30

His Arg

<210> SEQ ID NO 291
<211> LENGTH: 35
<212> TYPE: PRT
<213> ORGANISM: Homo sapiens

<400> SEQUENCE: 291

Cys Gly Leu Phe Gly Ala Ile Glu Gly Phe Ile Glu Gly Gly Trp Pro
1               5                   10                  15

Gly Leu Ile Asn Gly Trp Tyr Gly Tyr Gly Arg Lys Lys Arg Arg Gln
            20                  25                  30

Arg Arg Arg
        35

<210> SEQ ID NO 292
<211> LENGTH: 31
<212> TYPE: PRT
<213> ORGANISM: Homo sapiens

<400> SEQUENCE: 292

Cys Gly Leu Phe Lys Ala Leu Leu Lys Leu Leu Lys Ser Leu Trp Lys
1               5                   10                  15

Leu Leu Leu Lys Ala Tyr Gly Arg Lys Lys Arg Arg Gln Arg Arg
            20                  25                  30

```
<210> SEQ ID NO 293
<211> LENGTH: 34
<212> TYPE: PRT
<213> ORGANISM: Homo sapiens

<400> SEQUENCE: 293

Cys Gly Leu Phe Lys Ala Leu Leu Lys Leu Leu Lys Ser Leu Trp Lys
1               5                   10                  15

Leu Leu Leu Lys Ala Trp Tyr Gly Tyr Gly Arg Lys Lys Arg Arg Gln
            20                  25                  30

Arg Arg

<210> SEQ ID NO 294
<211> LENGTH: 31
<212> TYPE: PRT
<213> ORGANISM: Homo sapiens

<400> SEQUENCE: 294

Cys Gly Leu Phe Arg Ala Leu Leu Arg Leu Leu Arg Ser Leu Trp Arg
1               5                   10                  15

Leu Leu Leu Arg Ala Tyr Gly Arg Lys Lys Arg Arg Gln Arg Arg
            20                  25                  30

<210> SEQ ID NO 295
<211> LENGTH: 34
<212> TYPE: PRT
<213> ORGANISM: Homo sapiens

<400> SEQUENCE: 295

Cys Gly Leu Phe Glu Ala Ile Leu Gly Phe Ile Glu Asn Gly Trp Glu
1               5                   10                  15

Gly Leu Ile Asp Gly Trp Tyr Gly Tyr Gly Arg Lys Lys Arg Arg Gln
            20                  25                  30

Arg Arg

<210> SEQ ID NO 296
<211> LENGTH: 34
<212> TYPE: PRT
<213> ORGANISM: Homo sapiens

<400> SEQUENCE: 296

Cys Gly Leu Phe Glu Ala Ile Trp Glu Phe Ile Glu Asn Gly Trp Glu
1               5                   10                  15

Gly Leu Ile Asp Gly Trp Tyr Gly Tyr Gly Arg Lys Lys Arg Arg Gln
            20                  25                  30

Arg Arg

<210> SEQ ID NO 297
<211> LENGTH: 48
<212> TYPE: PRT
<213> ORGANISM: Homo sapiens

<400> SEQUENCE: 297

Cys Gly Leu Phe Glu Ala Ile Glu Gly Phe Ile Glu Asn Gly Trp Glu
1               5                   10                  15

Gly Met Ile Asp Gly Trp Tyr Gly Gly Gly Leu His Leu Leu His
            20                  25                  30

His Leu Leu His His Leu His Leu Leu His Leu Leu His Leu
        35                  40                  45
```

<210> SEQ ID NO 298
<211> LENGTH: 31
<212> TYPE: PRT
<213> ORGANISM: Homo sapiens

<400> SEQUENCE: 298

Cys Gly Pro Val Glu Asp Ala Ile Thr Ala Ala Ile Gly Arg Val Ala
1               5                   10                  15

Asp Thr Val Gly Thr Tyr Gly Arg Lys Lys Arg Gln Arg Arg
            20                  25                  30

<210> SEQ ID NO 299
<211> LENGTH: 25
<212> TYPE: PRT
<213> ORGANISM: Homo sapiens

<400> SEQUENCE: 299

Cys Met Asp Gly Thr Leu Phe Pro Gly Asp Asp Leu Ala Ile Pro
1               5                   10                  15

Ala Thr Glu Phe Phe Ser Thr Lys Ala
            20                  25

<210> SEQ ID NO 300
<211> LENGTH: 34
<212> TYPE: PRT
<213> ORGANISM: Homo sapiens

<400> SEQUENCE: 300

Cys Gly Leu Phe Glu Ala Leu Glu Glu Phe Ile Glu Gly Gly Trp Glu
1               5                   10                  15

Gly Leu Leu Glu Ala Trp Tyr Gly Tyr Gly Arg Lys Lys Arg Arg Gln
            20                  25                  30

Arg Arg

<210> SEQ ID NO 301
<211> LENGTH: 34
<212> TYPE: PRT
<213> ORGANISM: Homo sapiens

<400> SEQUENCE: 301

Cys Gly Leu Phe Glu Ala Leu Glu Glu Phe Ile Glu Asn Gly Trp Glu
1               5                   10                  15

Gly Leu Leu Glu Ala Trp Tyr Gly Tyr Gly Arg Lys Lys Arg Arg Gln
            20                  25                  30

Arg Arg

<210> SEQ ID NO 302
<211> LENGTH: 31
<212> TYPE: PRT
<213> ORGANISM: Homo sapiens

<400> SEQUENCE: 302

Cys Glu Leu Phe Gly Ala Ile Trp Glu Phe Ile Glu Gly Gly Trp Glu
1               5                   10                  15

Gly Leu Ile Glu Ala Tyr Gly Arg Lys Lys Arg Arg Gln Arg Arg
            20                  25                  30

<210> SEQ ID NO 303
<211> LENGTH: 34
<212> TYPE: PRT

-continued

<213> ORGANISM: Homo sapiens

<400> SEQUENCE: 303

Cys Gly Leu Phe Glu Ala Ile Glu Gly Phe Ile Glu Glu Gly Trp Glu
1               5                   10                  15
Gly Met Ile Asp Gly Trp Tyr Gly Tyr Gly Arg Lys Lys Arg Arg Gln
            20                  25                  30
Arg Arg

<210> SEQ ID NO 304
<211> LENGTH: 34
<212> TYPE: PRT
<213> ORGANISM: Homo sapiens

<400> SEQUENCE: 304

Cys Gly Leu Phe Glu Ala Ile Ala Glu Phe Ile Glu Asn Gly Trp Glu
1               5                   10                  15
Gly Met Ile Asp Gly Trp Tyr Gly Tyr Gly Arg Lys Lys Arg Arg Gln
            20                  25                  30
Arg Arg

<210> SEQ ID NO 305
<211> LENGTH: 34
<212> TYPE: PRT
<213> ORGANISM: Homo sapiens

<400> SEQUENCE: 305

Cys Gly Leu Phe Glu Ala Ile Ala Glu Phe Ile Glu Gly Leu Trp Glu
1               5                   10                  15
Gly Leu Ile Glu Gly Trp Tyr Gly Tyr Gly Arg Lys Lys Arg Arg Gln
            20                  25                  30
Arg Arg

<210> SEQ ID NO 306
<211> LENGTH: 34
<212> TYPE: PRT
<213> ORGANISM: Homo sapiens

<400> SEQUENCE: 306

Cys Gly Leu Leu Glu Ala Leu Glu Gly Leu Leu Glu Ser Leu Trp Glu
1               5                   10                  15
Gly Leu Leu Glu Ala Trp Tyr Gly Tyr Gly Arg Lys Lys Arg Arg Gln
            20                  25                  30
Arg Arg

<210> SEQ ID NO 307
<211> LENGTH: 34
<212> TYPE: PRT
<213> ORGANISM: Homo sapiens

<400> SEQUENCE: 307

Cys Gly Leu Phe Glu Ala Ile Glu Gly Phe Ile Glu Asn Gly Trp Glu
1               5                   10                  15
Gly Met Ile Asp Ile Trp Tyr Gly Tyr Gly Arg Lys Lys Arg Arg Gln
            20                  25                  30
Arg Arg

<210> SEQ ID NO 308
<211> LENGTH: 34

<212> TYPE: PRT
<213> ORGANISM: Homo sapiens

<400> SEQUENCE: 308

Cys Gly Leu Phe Glu Ala Ile Glu Gly Phe Ile Glu Asn Gly Trp Arg
1               5                   10                  15

Gly Met Ile Asp Gly Trp Tyr Gly Tyr Gly Arg Lys Lys Arg Arg Gln
            20                  25                  30

Arg Arg

<210> SEQ ID NO 309
<211> LENGTH: 34
<212> TYPE: PRT
<213> ORGANISM: Homo sapiens

<400> SEQUENCE: 309

Cys Gly Leu Phe Glu Ala Ile Glu Gly Phe Ile Glu Asn Gly Trp Asp
1               5                   10                  15

Gly Met Ile Asp Gly Trp Tyr Gly Tyr Gly Arg Lys Lys Arg Arg Gln
            20                  25                  30

Arg Arg

<210> SEQ ID NO 310
<211> LENGTH: 34
<212> TYPE: PRT
<213> ORGANISM: Homo sapiens

<400> SEQUENCE: 310

Cys Gly Leu Phe Glu Ala Ile Glu Gly Phe Ile Glu Asn His Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 311
<211> LENGTH: 34
<212> TYPE: PRT
<213> ORGANISM: Homo sapiens

<400> SEQUENCE: 311

Cys Gly Leu Phe Glu Ala Ile Glu Gly Phe Ile Glu Asn Trp Trp Lys
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 312
<211> LENGTH: 34
<212> TYPE: PRT
<213> ORGANISM: Homo sapiens

<400> SEQUENCE: 312

Gly Leu Phe Glu Ala Ile Glu Gly Phe Ile Glu Asn Gly Trp Lys Gly
1               5                   10                  15

Leu Ile Asp Ala Trp Tyr Gly Tyr Gly Arg Lys Lys Arg Gln Arg
            20                  25                  30

Arg Cys

<210> SEQ ID NO 313

-continued

```
<211> LENGTH: 34
<212> TYPE: PRT
<213> ORGANISM: Homo sapiens

<400> SEQUENCE: 313

Cys Gly Leu Phe Glu Ala Ile Glu Gly Phe Ile Glu Asn Gly Trp Lys
1               5                   10                  15

Gly Met Ile Asp Ala Trp Tyr Gly Tyr Gly Arg Lys Lys Arg Arg Gln
            20                  25                  30

Arg Arg

<210> SEQ ID NO 314
<211> LENGTH: 34
<212> TYPE: PRT
<213> ORGANISM: Homo sapiens

<400> SEQUENCE: 314

Cys Gly Leu Phe Glu Ala Ile Glu Gly Phe Ile Glu Asn Gly Trp Lys
1               5                   10                  15

Gly Met Ile Asp Trp Trp Tyr Gly Tyr Gly Arg Lys Lys Arg Arg Gln
            20                  25                  30

Arg Arg

<210> SEQ ID NO 315
<211> LENGTH: 34
<212> TYPE: PRT
<213> ORGANISM: Homo sapiens

<400> SEQUENCE: 315

Cys Gly Leu Ala Glu Ala Ile Glu Gly Phe Ile Glu Asn Gly Leu Lys
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 316
<211> LENGTH: 34
<212> TYPE: PRT
<213> ORGANISM: Homo sapiens

<400> SEQUENCE: 316

Arg Arg Gln Arg Arg Lys Lys Arg Gly Tyr Gly Tyr Trp Gly Asp Ile
1               5                   10                  15

Leu Gly Glu Trp Gly Asn Glu Ile Phe Gly Glu Ile Ala Glu Phe Leu
            20                  25                  30

Gly Cys

<210> SEQ ID NO 317
<211> LENGTH: 34
<212> TYPE: PRT
<213> ORGANISM: Homo sapiens

<400> SEQUENCE: 317

Cys Arg Arg Gln Arg Arg Lys Lys Arg Gly Tyr Gly Tyr Trp Gly Asp
1               5                   10                  15

Ile Leu Gly Glu Trp Gly Asn Glu Ile Phe Gly Glu Ile Ala Glu Phe
            20                  25                  30

Leu Gly
```

-continued

<210> SEQ ID NO 318
<211> LENGTH: 34
<212> TYPE: PRT
<213> ORGANISM: Homo sapiens

<400> SEQUENCE: 318

Cys Gly Leu Phe Glu Ala Ile Glu Gly Phe Ile Glu Asn Gly Trp Lys
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 319
<211> LENGTH: 34
<212> TYPE: PRT
<213> ORGANISM: Homo sapiens

<400> SEQUENCE: 319

Cys Gly Phe Phe Glu Ala Ile Glu Gly Phe Ile Glu Asn Gly Leu Lys
1               5                   10                  15

Gly Leu Ile Asp Ala Trp Tyr Gly Tyr Gly Arg Lys Lys Arg Arg Gln
            20                  25                  30

Arg Arg

<210> SEQ ID NO 320
<211> LENGTH: 34
<212> TYPE: PRT
<213> ORGANISM: Homo sapiens

<400> SEQUENCE: 320

Cys Gly Leu Phe Glu Ala Ile Glu Gly Phe Ile Glu Asn Gly Leu Lys
1               5                   10                  15

Gly Leu Ile Asp Ala Trp Tyr Gly Tyr Gly Arg Lys Lys Arg Arg Gln
            20                  25                  30

Arg Arg

<210> SEQ ID NO 321
<211> LENGTH: 34
<212> TYPE: PRT
<213> ORGANISM: Homo sapiens

<400> SEQUENCE: 321

Cys Glu Leu Phe Gly Ala Ile Glu Gly Phe Ile Glu Asn Gly Trp Lys
1               5                   10                  15

Gly Leu Ile Asp Ala Trp Tyr Gly Tyr Gly Arg Lys Lys Arg Arg Gln
            20                  25                  30

Arg Arg

<210> SEQ ID NO 322
<211> LENGTH: 34
<212> TYPE: PRT
<213> ORGANISM: Homo sapiens

<400> SEQUENCE: 322

Cys Gly Leu Phe Lys Ala Ile Lys Gly Phe Ile Lys Asn Gly Trp Lys
1               5                   10                  15

Gly Leu Ile Lys Ala Trp Tyr Gly Tyr Gly Arg Lys Lys Arg Arg Gln
            20                  25                  30

Arg Arg

```
<210> SEQ ID NO 323
<211> LENGTH: 31
<212> TYPE: PRT
<213> ORGANISM: Homo sapiens

<400> SEQUENCE: 323

Cys Gly Leu Ala Glu Ala Leu Leu Glu Leu Leu Glu Ser Leu Trp Lys
1               5                   10                  15

Gly Leu Ile Glu Ala Tyr Gly Arg Lys Lys Arg Arg Gln Arg Arg
            20                  25                  30

<210> SEQ ID NO 324
<211> LENGTH: 34
<212> TYPE: PRT
<213> ORGANISM: Homo sapiens

<400> SEQUENCE: 324

Cys Gly Ile Phe Gly Ala Ile Glu Gly Phe Ile Glu Asn Gly Trp Lys
1               5                   10                  15

Gly Leu Ile Asp Ala Trp Tyr Gly Tyr Gly Arg Lys Lys Arg Arg Gln
            20                  25                  30

Arg Arg

<210> SEQ ID NO 325
<211> LENGTH: 34
<212> TYPE: PRT
<213> ORGANISM: Homo sapiens

<400> SEQUENCE: 325

Cys Gly Ile Ala Gly Ala Ile Ala Gly Phe Ile Lys Asn Ile Trp Glu
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 326
<211> LENGTH: 34
<212> TYPE: PRT
<213> ORGANISM: Homo sapiens

<400> SEQUENCE: 326

Cys Gly Ile Ala Gly Ala Ile Ala Gly Phe Ile Lys Asn Ile Trp Lys
1               5                   10                  15

Gly Leu Ile Asp Ala Trp Tyr Gly Tyr Gly Arg Lys Lys Arg Arg Gln
            20                  25                  30

Arg Arg

<210> SEQ ID NO 327
<211> LENGTH: 33
<212> TYPE: PRT
<213> ORGANISM: Homo sapiens

<400> SEQUENCE: 327

Cys Gly Ile Phe Gly Ala Ile Ala Gly Phe Ile Lys Asn Ile Trp Glu
1               5                   10                  15

Gly Leu Ile Asp Gly Trp Tyr Gly Lys Lys Lys Lys Lys Lys Lys
            20                  25                  30

Lys
```

```
<210> SEQ ID NO 328
<211> LENGTH: 34
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (2)..(2)
<223> OTHER INFORMATION: Gly is conjugated to R5
<220> FEATURE:
<221> NAME/KEY: MISC_FEATURE
<222> LOCATION: (9)..(9)
<223> OTHER INFORMATION: Gly is conjugated to S8

<400> SEQUENCE: 328

Cys Gly Arg Phe Glu Ala Ile Glu Gly Ser Ile Glu Asn Gly Trp Glu
 1               5                  10                  15

Gly Met Ile Asp Gly Trp Tyr Gly Tyr Gly Arg Lys Lys Arg Arg Gln
             20                  25                  30

Arg Arg

<210> SEQ ID NO 329
<211> LENGTH: 34
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (10)..(10)
<223> OTHER INFORMATION: Phe is conjugated to R5
<220> FEATURE:
<221> NAME/KEY: MISC_FEATURE
<222> LOCATION: (17)..(17)
<223> OTHER INFORMATION: Gly  is conjugated to S8

<400> SEQUENCE: 329

Cys Gly Leu Phe Glu Ala Ile Glu Gly Phe Arg Glu Asn Gly Trp Glu
 1               5                  10                  15

Gly Ser Ile Asp Gly Trp Tyr Gly Tyr Gly Arg Lys Lys Arg Arg Gln
             20                  25                  30

Arg Arg

<210> SEQ ID NO 330
<211> LENGTH: 34
<212> TYPE: PRT
<213> ORGANISM: Homo sapiens

<400> SEQUENCE: 330

Gly Leu Phe Glu Ala Ile Glu Gly Phe Ile Glu Asn Gly Trp Glu Gly
 1               5                  10                  15

Met Ile Asp Gly Trp Tyr Gly Cys Tyr Gly Arg Lys Lys Arg Arg Gln
             20                  25                  30

Arg Arg

<210> SEQ ID NO 331
<211> LENGTH: 36
<212> TYPE: PRT
<213> ORGANISM: Homo sapiens

<400> SEQUENCE: 331

Gly Leu Phe Glu Ala Ile Glu Gly Phe Ile Glu Asn Gly Trp Glu Gly
 1               5                  10                  15

Met Ile Asp Gly Trp Tyr Gly Gly Cys Gly Tyr Gly Arg Lys Lys Arg
             20                  25                  30
```

20                  25                  30

Arg Gln Arg Arg
        35

<210> SEQ ID NO 332
<211> LENGTH: 33
<212> TYPE: PRT
<213> ORGANISM: Homo sapiens

<400> SEQUENCE: 332

Gly Leu Leu Glu Ala Leu Glu Gly Leu Leu Glu Asn Gly Trp Glu Gly
1               5                   10                  15

Leu Leu Asp Gly Trp Tyr Gly Tyr Gly Arg Lys Lys Arg Gln Arg
            20                  25                  30

Arg

<210> SEQ ID NO 333
<211> LENGTH: 14
<212> TYPE: PRT
<213> ORGANISM: Homo sapiens

<400> SEQUENCE: 333

Cys Phe Phe Gly Ala Ile Trp Glu Phe Ile Arg Asn Ile Leu
1               5                   10

<210> SEQ ID NO 334
<211> LENGTH: 14
<212> TYPE: PRT
<213> ORGANISM: Homo sapiens

<400> SEQUENCE: 334

Cys Ile Phe Gly Ala Ile Ala Gly Phe Ile Arg Ser Ile Leu
1               5                   10

<210> SEQ ID NO 335
<211> LENGTH: 34
<212> TYPE: PRT
<213> ORGANISM: Homo sapiens

<400> SEQUENCE: 335

Cys Gly Leu Phe Glu Glu Ile Glu Glu Phe Ile Glu Asn Gly Trp Glu
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 336
<211> LENGTH: 15
<212> TYPE: PRT
<213> ORGANISM: Homo sapiens

<400> SEQUENCE: 336

Cys Gly Phe Phe Gly Ala Ile Trp Glu Phe Ile Lys Ser Ile Leu
1               5                   10                  15

<210> SEQ ID NO 337
<211> LENGTH: 15
<212> TYPE: PRT
<213> ORGANISM: Homo sapiens

<400> SEQUENCE: 337

Gly Phe Phe Gly Ala Ile Trp Glu Phe Ile Lys Ser Ile Leu Cys

```
                   1               5              10              15

<210> SEQ ID NO 338
<211> LENGTH: 34
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: misc_feature
<222> LOCATION: (28)..(29)
<223> OTHER INFORMATION: Xaa  = ornithine

<400> SEQUENCE: 338

Cys Gly Leu Phe Glu Ala Leu Glu Gly Phe Ile Glu Asn Gly Trp Glu
1               5                   10                  15

Gly Leu Leu Asp Gly Trp Tyr Gly Tyr Gly Arg Xaa Xaa Arg Arg Gln
            20                  25                  30

Arg Arg

<210> SEQ ID NO 339
<211> LENGTH: 34
<212> TYPE: PRT
<213> ORGANISM: Homo sapiens

<400> SEQUENCE: 339

Cys Gly Leu Phe Glu Ala Leu Leu Glu Leu Leu Glu Asn Gly Trp Glu
1               5                   10                  15

Leu Leu Leu Glu Ala Trp Tyr Gly Tyr Gly Arg Lys Lys Arg Arg Gln
            20                  25                  30

Arg Arg

<210> SEQ ID NO 340
<211> LENGTH: 34
<212> TYPE: PRT
<213> ORGANISM: Homo sapiens

<400> SEQUENCE: 340

Cys Gly Leu Phe Glu Ala Leu Leu Glu Leu Leu Glu Asn Gly Trp Glu
1               5                   10                  15

Leu Leu Leu Glu Ala Trp Tyr Gly Tyr Gly Arg Lys Lys Arg Arg Gln
            20                  25                  30

Arg Arg

<210> SEQ ID NO 341
<211> LENGTH: 34
<212> TYPE: PRT
<213> ORGANISM: Homo sapiens

<400> SEQUENCE: 341

Cys Ala Leu Phe Glu Ala Ile Glu Ala Phe Ile Glu Asn Gly Trp Glu
1               5                   10                  15

Ala Met Ile Asp Ala Trp Tyr Gly Tyr Gly Arg Lys Lys Arg Arg Gln
            20                  25                  30

Arg Arg

<210> SEQ ID NO 342
<211> LENGTH: 34
<212> TYPE: PRT
<213> ORGANISM: Homo sapiens

<400> SEQUENCE: 342
```

-continued

Cys Gly Leu Phe Gly Ala Ile Trp Gly Phe Ile Glu Asn Gly Trp Glu
1               5                   10                  15

Gly Leu Ile Asp Gly Trp Tyr Gly Tyr Gly Arg Lys Lys Arg Arg Gln
            20                  25                  30

Arg Arg

<210> SEQ ID NO 343
<211> LENGTH: 34
<212> TYPE: PRT
<213> ORGANISM: Homo sapiens

<400> SEQUENCE: 343

Cys Gly Leu Phe Glu Ala Ile Glu Glu Leu Ile Glu Asn Leu Trp Lys
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 344
<211> LENGTH: 34
<212> TYPE: PRT
<213> ORGANISM: Homo sapiens

<400> SEQUENCE: 344

Cys Gly Leu Phe Glu Glu Ile Glu Gly Phe Ile Glu Asn Gly Trp Lys
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 345
<211> LENGTH: 34
<212> TYPE: PRT
<213> ORGANISM: Homo sapiens

<400> SEQUENCE: 345

Cys Gly Leu Phe Glu Glu Ile Glu Gly Phe Ile Glu Asn Gly Trp Lys
1               5                   10                  15

Gly Leu Ile Asp Trp Trp Tyr Gly Tyr Gly His Lys Lys His His Gln
            20                  25                  30

His Arg

<210> SEQ ID NO 346
<211> LENGTH: 23
<212> TYPE: PRT
<213> ORGANISM: Homo sapiens

<400> SEQUENCE: 346

Cys Phe Phe Gly Ala Ile Trp Glu Phe Ile Lys Asn Ile Leu Lys Gly
1               5                   10                  15

Leu Ile Asp Gly Trp Tyr Gly
            20

<210> SEQ ID NO 347
<211> LENGTH: 15
<212> TYPE: PRT
<213> ORGANISM: Homo sapiens

<400> SEQUENCE: 347

Cys Gly Ile Phe Gly Ala Ile Ala Gly Phe Ile Arg Ser Ile Leu
1               5                   10                  15

<210> SEQ ID NO 348
<211> LENGTH: 34
<212> TYPE: PRT
<213> ORGANISM: Homo sapiens

<400> SEQUENCE: 348

Cys Gly Leu Phe Glu Glu Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 349
<211> LENGTH: 34
<212> TYPE: PRT
<213> ORGANISM: Homo sapiens

<400> SEQUENCE: 349

Cys Gly Leu Phe Glu Ala Ile Glu Gly Phe Ile Glu Asn Gly Trp Glu
1               5                   10                  15

Gly Met Ile Asp Gly Trp Asn Gly Tyr Gly Arg Lys Lys Arg Arg Gln
            20                  25                  30

Arg Arg

<210> SEQ ID NO 350
<211> LENGTH: 34
<212> TYPE: PRT
<213> ORGANISM: Homo sapiens

<400> SEQUENCE: 350

Cys Gly Leu Phe Glu Ala Ile Glu Gly Phe Ile Glu Asn Gly Trp Glu
1               5                   10                  15

Gly Met Ile Asp Gly Trp Asn Gly Tyr Gly Arg Lys Lys Arg Arg Gln
            20                  25                  30

Arg Arg

<210> SEQ ID NO 351
<211> LENGTH: 37
<212> TYPE: PRT
<213> ORGANISM: Homo sapiens

<400> SEQUENCE: 351

Asx Ile Ser Cys Gly Leu Phe Glu Ala Ile Glu Gly Phe Ile Glu Asn
1               5                   10                  15

Gly Trp Glu Gly Met Ile Asp Trp Trp Tyr Gly Tyr Gly Arg Lys Lys
            20                  25                  30

Arg Arg Gln Arg Arg
        35

<210> SEQ ID NO 352
<211> LENGTH: 37
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (27)..(27)
<223> OTHER INFORMATION: Gly is conjugated to PEG

<400> SEQUENCE: 352

Cys Gly Leu Phe Glu Ala Ile Glu Gly Phe Ile Glu Asn Gly Trp Glu
1               5                   10                  15

Gly Met Ile Asp Gly Trp Tyr Gly Pro Glu Gly Tyr Gly Arg Lys Lys
            20                  25                  30

Arg Arg Gln Arg Arg
        35

<210> SEQ ID NO 353
<211> LENGTH: 34
<212> TYPE: PRT
<213> ORGANISM: Homo sapiens

<400> SEQUENCE: 353

Cys Gly Ile Phe Gly Ala Ile Trp Asn Gly Ile Lys Ser Leu Phe Glu
1               5                   10                  15

Gly Leu Ile Asp Gly Trp Tyr Gly Tyr Gly Arg Lys Lys Arg Arg Gln
            20                  25                  30

Arg Arg

<210> SEQ ID NO 354
<211> LENGTH: 34
<212> TYPE: PRT
<213> ORGANISM: Homo sapiens

<400> SEQUENCE: 354

Cys Gly Ile Phe Gly Ala Ile Glu Gly Phe Ile Glu Asn Gly Trp Glu
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 355
<211> LENGTH: 33
<212> TYPE: PRT
<213> ORGANISM: Homo sapiens

<400> SEQUENCE: 355

Cys Ile Phe Gly Ala Ile Ala Gly Phe Ile Lys Asn Ile Trp Glu Gly
1               5                   10                  15

Leu Ile Asp Trp Trp Tyr Gly Tyr Gly Arg Lys Lys Arg Arg Gln Arg
            20                  25                  30

Arg

<210> SEQ ID NO 356
<211> LENGTH: 47
<212> TYPE: PRT
<213> ORGANISM: Homo sapiens

<400> SEQUENCE: 356

Cys Gly Leu Phe Glu Ala Ile Glu Gly Phe Ile Glu Asn Gly Trp Lys
1               5                   10                  15

Gly Leu Ile Asp Gly Trp Tyr Gly Gly Leu Phe Glu Ala Ile Glu Gly
            20                  25                  30

Phe Ile Glu Asn Gly Trp Lys Gly Leu Ile Asp Trp Trp Tyr Gly
        35                  40                  45

<210> SEQ ID NO 357

```
<211> LENGTH: 42
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (42)..(42)
<223> OTHER INFORMATION: Lys is conjugated to stearyl

<400> SEQUENCE: 357

Cys Trp Glu Ala Ala Leu Ala Glu Ala Leu Ala Glu Ala Leu Ala Glu
1               5                   10                  15

His Leu Ala Glu Ala Leu Ala Glu Ala Leu Glu Ala Leu Ala Ala Tyr
            20                  25                  30

Gly Arg Lys Lys Arg Arg Gln Arg Arg Lys
        35                  40

<210> SEQ ID NO 358
<211> LENGTH: 34
<212> TYPE: PRT
<213> ORGANISM: Homo sapiens

<400> SEQUENCE: 358

Cys Gly Leu Phe Glu Ala Ile Glu Gly Phe Ile Glu Asn Gly Trp Lys
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 359
<211> LENGTH: 31
<212> TYPE: PRT
<213> ORGANISM: Homo sapiens

<400> SEQUENCE: 359

Cys Gly Leu Phe Glu Glu Leu Glu Glu Leu Leu Glu Glu Gly Trp Glu
1               5                   10                  15

Gly Leu Leu Glu Ala Tyr Gly Arg Lys Lys Arg Arg Gln Arg Arg
            20                  25                  30

<210> SEQ ID NO 360
<211> LENGTH: 34
<212> TYPE: PRT
<213> ORGANISM: Homo sapiens

<400> SEQUENCE: 360

Cys Gly Asn Phe Glu Glu Ile Glu Glu Phe Ile Glu Glu Gly Leu Arg
1               5                   10                  15

Asn Phe Ile Asp Trp Trp Tyr Gly Tyr Gly His Lys Lys His His Gln
            20                  25                  30

His Arg

<210> SEQ ID NO 361
<211> LENGTH: 33
<212> TYPE: PRT
<213> ORGANISM: Homo sapiens

<400> SEQUENCE: 361

Cys Phe Phe Gly Ala Ile Trp Glu Phe Ile Arg Asn Ile Leu Glu Gly
1               5                   10                  15

Leu Ile Asp Trp Trp Tyr Gly Tyr Gly Arg Lys Lys Arg Arg Gln Arg
```

-continued

```
                20                  25                  30

Arg

<210> SEQ ID NO 362
<211> LENGTH: 35
<212> TYPE: PRT
<213> ORGANISM: Homo sapiens

<400> SEQUENCE: 362

Cys Phe Phe Gly Ala Ile Trp Glu Phe Ile Lys Asn Ile Leu Leu His
1               5                   10                  15

Leu Leu His His Leu Leu His His Leu His His Leu Leu His His Leu
            20                  25                  30

Leu His Leu
        35

<210> SEQ ID NO 363
<211> LENGTH: 34
<212> TYPE: PRT
<213> ORGANISM: Homo sapiens

<400> SEQUENCE: 363

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 364
<211> LENGTH: 21
<212> TYPE: PRT
<213> ORGANISM: Homo sapiens

<400> SEQUENCE: 364

Cys Gly Phe Phe His Ala Phe Phe His Phe His Ser Phe Trp His
1               5                   10                  15

Gly Phe Phe Glu Ala
            20

<210> SEQ ID NO 365
<211> LENGTH: 34
<212> TYPE: PRT
<213> ORGANISM: Homo sapiens

<400> SEQUENCE: 365

Cys Gly Leu Phe His Ala Leu Leu His Leu Leu His Ser Leu Trp His
1               5                   10                  15

Gly Leu Leu His Trp Trp Tyr Gly Tyr Gly His Lys Lys His His Gln
            20                  25                  30

His Arg

<210> SEQ ID NO 366
<211> LENGTH: 31
<212> TYPE: PRT
<213> ORGANISM: Homo sapiens

<400> SEQUENCE: 366

Cys Gly Leu Phe Gly Ala Leu Leu Glu Leu Leu Glu Ser Leu Trp Glu
1               5                   10                  15

Gly Leu Leu Glu Trp Tyr Gly Arg Lys Lys Arg Arg Gln Arg Arg
```

-continued

```
                20                  25                  30
```

<210> SEQ ID NO 367
<211> LENGTH: 31
<212> TYPE: PRT
<213> ORGANISM: Homo sapiens

<400> SEQUENCE: 367

```
Cys Gly Leu Phe Gly Ala Leu Leu Glu Leu Leu Glu Ser Leu Trp Glu
1               5                   10                  15

Gly Leu Leu Glu Trp Tyr Gly His Lys Lys His His Gln His Arg
            20                  25                  30
```

<210> SEQ ID NO 368
<211> LENGTH: 25
<212> TYPE: PRT
<213> ORGANISM: Homo sapiens

<400> SEQUENCE: 368

```
Cys Gly Leu Phe His Ala Leu Leu His Leu Leu His Ser Leu Trp Lys
1               5                   10                  15

Gly Leu Leu Glu Trp Trp Tyr Gly Phe
            20                  25
```

<210> SEQ ID NO 369
<211> LENGTH: 17
<212> TYPE: PRT
<213> ORGANISM: Homo sapiens

<400> SEQUENCE: 369

```
Cys Ile Phe Gly Ala Ile Ala Gly Phe Ile Arg Ser Ile Leu Glu Gly
1               5                   10                  15

Phe
```

<210> SEQ ID NO 370
<211> LENGTH: 21
<212> TYPE: PRT
<213> ORGANISM: Homo sapiens

<400> SEQUENCE: 370

```
Cys Gly Ile Phe Gly Ala Ile Ala Gly Phe Ile Lys Asn Ile Trp Lys
1               5                   10                  15

Gly Leu Ile Asp Ala
            20
```

<210> SEQ ID NO 371
<211> LENGTH: 15
<212> TYPE: PRT
<213> ORGANISM: Homo sapiens

<400> SEQUENCE: 371

```
Cys Phe Phe Glu Ala Ile Glu Glu Phe Ile Lys Asn Ile Trp Lys
1               5                   10                  15
```

<210> SEQ ID NO 372
<211> LENGTH: 35
<212> TYPE: PRT
<213> ORGANISM: Homo sapiens

<400> SEQUENCE: 372

```
Cys Gly Leu Phe Glu Ala Ile Glu Gly Phe Ile Glu Asn Gly Trp Lys
1               5                   10                  15
```

```
Gly Leu Ile Asp Trp Leu Ala Glu Leu Ala Glu Ala Leu Glu Ala
            20                  25                  30

Leu Ala Ala
        35

<210> SEQ ID NO 373
<211> LENGTH: 16
<212> TYPE: PRT
<213> ORGANISM: Homo sapiens

<400> SEQUENCE: 373

Gly Cys Gly Ile Phe Gly Ala Ile Ala Glu Phe Ile Lys Asn Ile Trp
1               5                   10                  15

<210> SEQ ID NO 374
<211> LENGTH: 20
<212> TYPE: PRT
<213> ORGANISM: Homo sapiens

<400> SEQUENCE: 374

Cys Ile Phe Gly Ala Ile Ala Glu Phe Ile Lys Asn Ile Trp Lys Gly
1               5                   10                  15

Leu Ile Asp Trp
            20

<210> SEQ ID NO 375
<211> LENGTH: 31
<212> TYPE: PRT
<213> ORGANISM: Homo sapiens

<400> SEQUENCE: 375

Cys Phe Phe Gly Ala Ile Trp Glu Phe Ile Lys Ser Ile Leu Glu Leu
1               5                   10                  15

Leu Leu Glu Ala Tyr Gly His Lys Lys His His Gln His Arg Arg
            20                  25                  30

<210> SEQ ID NO 376
<211> LENGTH: 14
<212> TYPE: PRT
<213> ORGANISM: Homo sapiens

<400> SEQUENCE: 376

Cys Trp Phe Gly Ala Ile Trp Glu Phe Ile Lys Ser Ile Leu
1               5                   10

<210> SEQ ID NO 377
<211> LENGTH: 14
<212> TYPE: PRT
<213> ORGANISM: Homo sapiens

<400> SEQUENCE: 377

Cys Ala Phe Gly Ala Ile Trp Glu Phe Ile Lys Ser Ile Leu
1               5                   10

<210> SEQ ID NO 378
<211> LENGTH: 14
<212> TYPE: PRT
<213> ORGANISM: Homo sapiens

<400> SEQUENCE: 378

Cys Phe Leu Gly Ala Ile Trp Glu Phe Ile Lys Ser Ile Leu
1               5                   10
```

```
<210> SEQ ID NO 379
<211> LENGTH: 14
<212> TYPE: PRT
<213> ORGANISM: Homo sapiens

<400> SEQUENCE: 379

Cys Phe Phe Gly Ala Ile Trp Glu Phe Ile Lys Ser Ile Lys
1               5                   10

<210> SEQ ID NO 380
<211> LENGTH: 34
<212> TYPE: PRT
<213> ORGANISM: Homo sapiens

<400> SEQUENCE: 380

Cys Gly Phe Ile Gly Ala Ile Ala Asn Leu Leu Ser Lys Ile Phe Glu
1               5                   10                  15

Gly Leu Ile Asp Gly Trp Tyr Gly Tyr Gly Arg Lys Lys Arg Arg Gln
            20                  25                  30

Arg Arg

<210> SEQ ID NO 381
<211> LENGTH: 14
<212> TYPE: PRT
<213> ORGANISM: Homo sapiens

<400> SEQUENCE: 381

Cys Phe Phe Gly Ala Ile Trp Glu Phe Ile Lys Ser Ile Leu
1               5                   10

<210> SEQ ID NO 382
<211> LENGTH: 35
<212> TYPE: PRT
<213> ORGANISM: Homo sapiens

<400> SEQUENCE: 382

Cys Ile Phe Gly Ala Ile Ala Gly Phe Ile Lys Asn Ile Trp Leu His
1               5                   10                  15

Leu Leu His His Leu Leu His His Leu His His Leu Leu His His Leu
            20                  25                  30

Leu His Leu
        35

<210> SEQ ID NO 383
<211> LENGTH: 14
<212> TYPE: PRT
<213> ORGANISM: Homo sapiens

<400> SEQUENCE: 383

Cys Phe Phe Gly Ala Ile Ala Glu Phe Ile Lys Asn Ile Trp
1               5                   10

<210> SEQ ID NO 384
<211> LENGTH: 14
<212> TYPE: PRT
<213> ORGANISM: Homo sapiens

<400> SEQUENCE: 384

Cys Ile Phe Glu Ala Ile Trp Gly Phe Ile Lys Asn Ile Trp
1               5                   10

<210> SEQ ID NO 385
<211> LENGTH: 34
```

-continued

```
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (1)..(1)
<223> OTHER INFORMATION: Ala is conjugated to stearyl

<400> SEQUENCE: 385

Ala Gly Tyr Leu Leu Gly Lys Ile Asn Leu Lys Ala Leu Ala Ala Leu
1               5                   10                  15

Ala Lys Lys Ile Leu His His His His His Lys Lys Lys Lys
            20                  25                  30

Lys Cys

<210> SEQ ID NO 386
<211> LENGTH: 33
<212> TYPE: PRT
<213> ORGANISM: Homo sapiens

<400> SEQUENCE: 386

Cys Ile Phe Glu Ala Ile Ala Gly Phe Ile Lys Asn Ile Trp Lys Gly
1               5                   10                  15

Leu Ile Asp Trp Trp Tyr Gly Tyr Gly Arg Lys Lys Arg Gln Arg
            20                  25                  30

Arg

<210> SEQ ID NO 387
<211> LENGTH: 41
<212> TYPE: PRT
<213> ORGANISM: Homo sapiens

<400> SEQUENCE: 387

Cys Gly Leu Phe Glu Ala Ile Glu Gly Phe Ile Glu Asn Gly Trp Lys
1               5                   10                  15

Gly Leu Ile Asp Trp Trp Tyr Gly Gly Arg Pro Arg Glu Ser Gly Lys
            20                  25                  30

Lys Arg Lys Arg Lys Arg Leu Lys Pro
            35                  40

<210> SEQ ID NO 388
<211> LENGTH: 33
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (1)..(1)
<223> OTHER INFORMATION: Cys is conjugated to b-Ala

<400> SEQUENCE: 388

Cys Gly Phe Gly Glu Ile Glu Glu Phe Ile Glu Asn Gly Leu Lys Asn
1               5                   10                  15

Leu Ile Asp Trp Trp Tyr Gly Tyr Gly His Lys Lys His His Gln His
            20                  25                  30

Arg

<210> SEQ ID NO 389
<211> LENGTH: 33
<212> TYPE: PRT
<213> ORGANISM: Artificial Sequence
```

```
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Cys is conjugated to b-Ala

<400> SEQUENCE: 389

Cys Gly Phe Glu Phe Ile Glu Glu Phe Ile Glu Asn Gly Leu Lys Asn
1               5                   10                  15

Leu Ile Asp Trp Trp Tyr Gly Tyr Gly Arg Lys Lys Arg Gln Arg
            20                  25                  30

Arg

<210> SEQ ID NO 390
<211> LENGTH: 33
<212> TYPE: PRT
<213> ORGANISM: Artificial Sequence
<220> FEATURE:
<223> OTHER INFORMATION: Synthetically generated peptide

<400> SEQUENCE: 390

Cys Gly Phe Glu Phe Ile Glu Glu Phe Ile Glu Asn Gly Leu Lys Asn
1               5                   10                  15

Leu Ile Asp Trp Trp Tyr Gly Tyr Gly His Lys Lys His His Gln His
            20                  25                  30

Arg

<210> SEQ ID NO 391
<211> LENGTH: 34
<212> TYPE: PRT
<213> ORGANISM: Homo sapiens

<400> SEQUENCE: 391

Cys Gly Gly Ile Glu Glu Ile Ala Gly Leu Leu Ser Lys Ile Leu Lys
1               5                   10                  15

Gly Leu Ile Asp Trp Trp Tyr Gly Tyr Gly His Lys Lys His His Gln
            20                  25                  30

His Arg

<210> SEQ ID NO 392
<211> LENGTH: 34
<212> TYPE: PRT
<213> ORGANISM: Homo sapiens

<400> SEQUENCE: 392

Cys Gly Phe Ile Gly Ala Ile Ala Asn Leu Leu Ser Lys Ile Phe Glu
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 393
<211> LENGTH: 34
<212> TYPE: PRT
<213> ORGANISM: Homo sapiens

<400> SEQUENCE: 393

Cys Gly Phe Ile Gly Ala Ile Ala Glu Leu Leu Glu Lys Ile Phe Glu
1               5                   10                  15

Gly Leu Ile Asp Trp Trp Tyr Gly Tyr Gly Arg Lys Lys Arg Arg Gln
```

```
                20              25              30
Arg Arg

<210> SEQ ID NO 394
<211> LENGTH: 34
<212> TYPE: PRT
<213> ORGANISM: Homo sapiens

<400> SEQUENCE: 394

Cys Gly Phe Ile Gly Ala Ile Ala Glu Leu Leu Glu Lys Ile Phe Glu
1               5                   10                  15

Gly Leu Ile Asp Trp Trp Tyr Gly Tyr Gly His Lys Lys His His Gln
            20                  25                  30

His Arg

<210> SEQ ID NO 395
<211> LENGTH: 33
<212> TYPE: PRT
<213> ORGANISM: Homo sapiens

<400> SEQUENCE: 395

Cys Phe Phe Gly Ala Ile Trp Glu Phe Ile Arg Asn Ile Leu Glu Gly
1               5                   10                  15

Leu Ile Asp Trp Trp Tyr Gly Tyr Gly His Lys Lys His His Gln His
            20                  25                  30

Arg

<210> SEQ ID NO 396
<211> LENGTH: 35
<212> TYPE: PRT
<213> ORGANISM: Homo sapiens

<400> SEQUENCE: 396

Cys Phe Phe Gly Ala Ile Trp Glu Phe Ile Lys Ser Ile Leu Leu His
1               5                   10                  15

Leu Leu His His Leu Leu His His Leu His His Leu Leu His His Leu
            20                  25                  30

Leu His Leu
        35

<210> SEQ ID NO 397
<211> LENGTH: 35
<212> TYPE: PRT
<213> ORGANISM: Homo sapiens

<400> SEQUENCE: 397

Cys Phe Phe Gly Ala Ile Trp Glu Phe Ile Arg Ser Ile Leu Leu His
1               5                   10                  15

Leu Leu His His Leu Leu His His Leu His His Leu Leu His His Leu
            20                  25                  30

Leu His Leu
        35

<210> SEQ ID NO 398
<211> LENGTH: 36
<212> TYPE: PRT
<213> ORGANISM: Homo sapiens

<400> SEQUENCE: 398

Cys Gly Phe Phe Gly Ala Ile Trp Glu Phe Ile Arg Ser Ile Leu Glu
```

```
                1               5                  10                  15
Gly Phe Ile Asp Trp Trp Tyr Gly Tyr Gly Tyr Gly His Lys Lys His
                20                  25                  30

His Gln His Arg
        35
```

<210> SEQ ID NO 399
<211> LENGTH: 31
<212> TYPE: PRT
<213> ORGANISM: Homo sapiens

<400> SEQUENCE: 399

```
Cys Gly Leu Phe Glu Ala Ile Trp Glu Phe Ile Lys Ser Ile Leu Glu
1               5                   10                  15
Gly Leu Leu Glu Ala Tyr Gly His Lys Lys His His Gln His Arg
                20                  25                  30
```

<210> SEQ ID NO 400
<211> LENGTH: 34
<212> TYPE: PRT
<213> ORGANISM: Homo sapiens

<400> SEQUENCE: 400

```
Cys Gly Leu Phe Glu Ala Ile Trp Glu Phe Ile Lys Ser Ile Leu Glu
1               5                   10                  15
Gly Leu Leu Glu Ala Trp Tyr Gly Tyr Gly His Lys Lys His His Gln
                20                  25                  30
His Arg
```

<210> SEQ ID NO 401
<211> LENGTH: 26
<212> TYPE: PRT
<213> ORGANISM: Homo sapiens

<400> SEQUENCE: 401

```
Cys Gly Ile Phe Gly Ala Ile Ala Gly Phe Ile Lys Asn Ile Trp Lys
1               5                   10                  15
Tyr Gly Arg Lys Lys Arg Arg Gln Arg Arg
                20                  25
```

<210> SEQ ID NO 402
<211> LENGTH: 34
<212> TYPE: PRT
<213> ORGANISM: Homo sapiens

<400> SEQUENCE: 402

```
Cys Gly Leu Phe Glu Ala Leu Leu Glu Leu Leu Glu Ser Leu Trp Glu
1               5                   10                  15
Leu Leu Leu Glu Ala Trp Tyr Gly Tyr Gly His Lys Lys His His Gln
                20                  25                  30
His Arg
```

<210> SEQ ID NO 403
<211> LENGTH: 23
<212> TYPE: PRT
<213> ORGANISM: Homo sapiens

<400> SEQUENCE: 403

```
Cys Ile Phe Gly Ala Ile Ala Gly Phe Ile Arg Asn Ile Trp Lys Gly
1               5                   10                  15
```

```
Leu Ile Asp Gly Trp Tyr Gly
        20

<210> SEQ ID NO 404
<211> LENGTH: 24
<212> TYPE: PRT
<213> ORGANISM: Homo sapiens

<400> SEQUENCE: 404

Cys Gly Ile Phe Gly Ala Ile Ala Gly Phe Ile Arg Asn Ile Trp Lys
1               5                   10                  15

Gly Leu Ile Asp Gly Trp Tyr Gly
        20

<210> SEQ ID NO 405
<211> LENGTH: 36
<212> TYPE: PRT
<213> ORGANISM: Homo sapiens

<400> SEQUENCE: 405

Cys Phe Phe Gly Ala Ile Trp Glu Phe Ile Lys Asn Ile Leu Lys Leu
1               5                   10                  15

His Leu Leu His His Leu Leu His His Leu His His Leu Leu His His
            20                  25                  30

Leu Leu His Leu
        35

<210> SEQ ID NO 406
<211> LENGTH: 35
<212> TYPE: PRT
<213> ORGANISM: Homo sapiens

<400> SEQUENCE: 406

Cys Phe Phe Gly Ala Ile Trp Glu Phe Ile Arg Asn Ile Leu Leu His
1               5                   10                  15

Leu Leu His His Leu Leu His His Leu His His Leu Leu His His Leu
            20                  25                  30

Leu His Leu
        35

<210> SEQ ID NO 407
<211> LENGTH: 14
<212> TYPE: PRT
<213> ORGANISM: Homo sapiens

<400> SEQUENCE: 407

Cys Phe Phe Gly Lys Ile Trp Glu Phe Ile Lys Ser Ile Leu
1               5                   10

<210> SEQ ID NO 408
<211> LENGTH: 31
<212> TYPE: PRT
<213> ORGANISM: Homo sapiens

<400> SEQUENCE: 408

Cys Tyr Gly Arg Lys Lys Arg Arg Gln Arg Arg Gly Leu Phe Glu Ala
1               5                   10                  15

Leu Leu Glu Leu Leu Glu Ser Leu Trp Glu Leu Leu Leu Glu Ala
            20                  25                  30

<210> SEQ ID NO 409
<211> LENGTH: 14
```

```
<212> TYPE: PRT
<213> ORGANISM: Homo sapiens

<400> SEQUENCE: 409

Phe Phe Gly Ala Ile Trp Glu Phe Ile Lys Ser Ile Leu Cys
1               5                   10

<210> SEQ ID NO 410
<211> LENGTH: 14
<212> TYPE: PRT
<213> ORGANISM: Homo sapiens

<400> SEQUENCE: 410

Cys Trp Trp Gly Ala Ile Glu Gly Phe Ile Lys Ser Ile Leu
1               5                   10

<210> SEQ ID NO 411
<211> LENGTH: 14
<212> TYPE: PRT
<213> ORGANISM: Homo sapiens

<400> SEQUENCE: 411

Cys Phe Phe Gly Ala Ile Trp Glu Trp Ile Lys Ser Ile Leu
1               5                   10

<210> SEQ ID NO 412
<211> LENGTH: 14
<212> TYPE: PRT
<213> ORGANISM: Homo sapiens

<400> SEQUENCE: 412

Cys Phe Phe Gly Ala Ile Trp Glu Phe Trp Lys Ser Ile Leu
1               5                   10

<210> SEQ ID NO 413
<211> LENGTH: 14
<212> TYPE: PRT
<213> ORGANISM: Homo sapiens

<400> SEQUENCE: 413

Cys Phe Phe Gly Ala Ile Trp Glu Phe Ile Lys Phe Ile Leu
1               5                   10

<210> SEQ ID NO 414
<211> LENGTH: 14
<212> TYPE: PRT
<213> ORGANISM: Homo sapiens

<400> SEQUENCE: 414

Cys Phe Phe Gly Ala Ile Trp Glu Phe Ile Lys Lys Ile Leu
1               5                   10

<210> SEQ ID NO 415
<211> LENGTH: 14
<212> TYPE: PRT
<213> ORGANISM: Homo sapiens

<400> SEQUENCE: 415

Cys Phe Phe Gly Ala Ile Trp Glu Phe Ile Lys Gly Ile Leu
1               5                   10

<210> SEQ ID NO 416
<211> LENGTH: 14
<212> TYPE: PRT
<213> ORGANISM: Homo sapiens
```

<400> SEQUENCE: 416

Cys Phe Phe Gly Ala Ile Trp Glu Phe Ile Lys Leu Ile Leu
1               5                   10

<210> SEQ ID NO 417
<211> LENGTH: 14
<212> TYPE: PRT
<213> ORGANISM: Homo sapiens

<400> SEQUENCE: 417

Cys Phe Phe Gly Ala Ile Trp Glu Phe Ile Lys Trp Ile Leu
1               5                   10

<210> SEQ ID NO 418
<211> LENGTH: 14
<212> TYPE: PRT
<213> ORGANISM: Homo sapiens

<400> SEQUENCE: 418

Cys Phe Phe Gly Ala Ile Trp Glu Phe Ile Lys Ser Phe Leu
1               5                   10

<210> SEQ ID NO 419
<211> LENGTH: 14
<212> TYPE: PRT
<213> ORGANISM: Homo sapiens

<400> SEQUENCE: 419

Cys Phe Phe Gly Ala Ile Trp Glu Phe Ile Lys Ser Lys Leu
1               5                   10

<210> SEQ ID NO 420
<211> LENGTH: 14
<212> TYPE: PRT
<213> ORGANISM: Homo sapiens

<400> SEQUENCE: 420

Cys Phe Phe Gly Phe Ile Trp Glu Phe Ile Lys Ser Ile Leu
1               5                   10

<210> SEQ ID NO 421
<211> LENGTH: 21
<212> TYPE: PRT
<213> ORGANISM: Homo sapiens

<400> SEQUENCE: 421

Cys Ile Phe Gly Ala Ile Ala Gly Phe Ile Lys Asn Ile Leu Lys Gly
1               5                   10                  15

Leu Ile Asp Ala Phe
            20

<210> SEQ ID NO 422
<211> LENGTH: 14
<212> TYPE: PRT
<213> ORGANISM: Homo sapiens

<400> SEQUENCE: 422

Cys Phe Phe Gly Lys Ile Trp Glu Leu Trp Glu Trp Ile Leu
1               5                   10

<210> SEQ ID NO 423
<211> LENGTH: 14
<212> TYPE: PRT

<213> ORGANISM: Homo sapiens

<400> SEQUENCE: 423

Cys Phe Phe Gly Ala Ile Trp Glu Phe Ala Lys Ser Ile Leu
1               5                   10

<210> SEQ ID NO 424
<211> LENGTH: 14
<212> TYPE: PRT
<213> ORGANISM: Homo sapiens

<400> SEQUENCE: 424

Cys Phe Phe Gly Ala Ile Trp Glu Phe Ile Lys Ser Ala Leu
1               5                   10

<210> SEQ ID NO 425
<211> LENGTH: 14
<212> TYPE: PRT
<213> ORGANISM: Homo sapiens

<400> SEQUENCE: 425

Cys Phe Phe Gly Ala Ile Trp Glu Phe Ile Lys Ser Trp Leu
1               5                   10

<210> SEQ ID NO 426
<211> LENGTH: 15
<212> TYPE: PRT
<213> ORGANISM: Homo sapiens

<400> SEQUENCE: 426

Cys Phe Phe Gly Ala Ile Trp Glu Phe Ile Lys Ser Ile Leu Lys
1               5                   10                  15

<210> SEQ ID NO 427
<211> LENGTH: 15
<212> TYPE: PRT
<213> ORGANISM: Homo sapiens

<400> SEQUENCE: 427

Cys Phe Phe Gly Ala Ile Trp Glu Phe Ile Lys Ser Ile Leu Glu
1               5                   10                  15

<210> SEQ ID NO 428
<211> LENGTH: 14
<212> TYPE: PRT
<213> ORGANISM: Homo sapiens

<400> SEQUENCE: 428

Cys Phe Phe Lys Ala Ile Trp Glu Phe Ile Lys Ser Ile Leu
1               5                   10

<210> SEQ ID NO 429
<211> LENGTH: 14
<212> TYPE: PRT
<213> ORGANISM: Homo sapiens

<400> SEQUENCE: 429

Cys Phe Phe Asn Ala Ile Trp Glu Phe Ile Lys Ser Ile Leu
1               5                   10

<210> SEQ ID NO 430
<211> LENGTH: 14
<212> TYPE: PRT
<213> ORGANISM: Homo sapiens

```
<400> SEQUENCE: 430

Cys Phe Phe Gly Gly Ile Trp Glu Phe Ile Lys Ser Ile Leu
1               5                   10

<210> SEQ ID NO 431
<211> LENGTH: 14
<212> TYPE: PRT
<213> ORGANISM: Homo sapiens

<400> SEQUENCE: 431

Cys Phe Phe Gly Asn Ile Trp Glu Phe Ile Lys Ser Ile Leu
1               5                   10

<210> SEQ ID NO 432
<211> LENGTH: 14
<212> TYPE: PRT
<213> ORGANISM: Homo sapiens

<400> SEQUENCE: 432

Cys Phe Phe Gly Ala Leu Trp Glu Phe Ile Lys Ser Ile Leu
1               5                   10

<210> SEQ ID NO 433
<211> LENGTH: 14
<212> TYPE: PRT
<213> ORGANISM: Homo sapiens

<400> SEQUENCE: 433

Cys Phe Phe Gly Ala Ala Trp Glu Phe Ile Lys Ser Ile Leu
1               5                   10

<210> SEQ ID NO 434
<211> LENGTH: 21
<212> TYPE: PRT
<213> ORGANISM: Homo sapiens

<400> SEQUENCE: 434

Cys Gly Leu Phe His Ala Leu Leu His Leu His Ser Leu Trp His
1               5                   10                  15

Gly Leu Leu Asp Gly
            20

<210> SEQ ID NO 435
<211> LENGTH: 21
<212> TYPE: PRT
<213> ORGANISM: Homo sapiens

<400> SEQUENCE: 435

Cys Gly Leu Phe His Ala Leu Leu His Leu His Ser Leu Trp His
1               5                   10                  15

Gly Leu Leu Glu Trp
            20

<210> SEQ ID NO 436
<211> LENGTH: 21
<212> TYPE: PRT
<213> ORGANISM: Homo sapiens

<400> SEQUENCE: 436

Cys Gly Leu Phe His Ala Leu Leu His Leu His Ser Leu Trp His
1               5                   10                  15

Leu Leu Leu Glu Ala
            20
```

```
<210> SEQ ID NO 437
<211> LENGTH: 21
<212> TYPE: PRT
<213> ORGANISM: Homo sapiens

<400> SEQUENCE: 437

Cys Gly Leu Phe His Ala Leu Leu His Leu His Ser Leu Trp Lys
1               5                   10                  15

Leu Leu Leu Glu Trp
            20

<210> SEQ ID NO 438
<211> LENGTH: 14
<212> TYPE: PRT
<213> ORGANISM: Homo sapiens

<400> SEQUENCE: 438

Cys Lys Phe Gly Ala Ile Trp Glu Phe Ile Lys Ser Ile Leu
1               5                   10

<210> SEQ ID NO 439
<211> LENGTH: 14
<212> TYPE: PRT
<213> ORGANISM: Homo sapiens

<400> SEQUENCE: 439

Cys Phe Lys Gly Ala Ile Trp Glu Phe Ile Lys Ser Ile Leu
1               5                   10

<210> SEQ ID NO 440
<211> LENGTH: 14
<212> TYPE: PRT
<213> ORGANISM: Homo sapiens

<400> SEQUENCE: 440

Cys Phe Phe Gly Ala Ile Trp Lys Phe Ile Lys Ser Ile Leu
1               5                   10

<210> SEQ ID NO 441
<211> LENGTH: 14
<212> TYPE: PRT
<213> ORGANISM: Homo sapiens

<400> SEQUENCE: 441

Cys Phe Phe Gly Ala Ile Trp Ala Phe Ile Lys Ser Ile Leu
1               5                   10

<210> SEQ ID NO 442
<211> LENGTH: 14
<212> TYPE: PRT
<213> ORGANISM: Homo sapiens

<400> SEQUENCE: 442

Cys Phe Phe Gly Ala Ile Trp Leu Phe Ile Lys Ser Ile Leu
1               5                   10

<210> SEQ ID NO 443
<211> LENGTH: 14
<212> TYPE: PRT
<213> ORGANISM: Homo sapiens

<400> SEQUENCE: 443

Cys Phe Phe Gly Ala Ile Trp Phe Phe Ile Lys Ser Ile Leu
```

-continued

```
1               5                   10

<210> SEQ ID NO 444
<211> LENGTH: 14
<212> TYPE: PRT
<213> ORGANISM: Homo sapiens

<400> SEQUENCE: 444

Cys Phe Phe Gly Ala Ile Trp Asn Phe Ile Lys Ser Ile Leu
1               5                   10

<210> SEQ ID NO 445
<211> LENGTH: 14
<212> TYPE: PRT
<213> ORGANISM: Homo sapiens

<400> SEQUENCE: 445

Cys Phe Phe Gly Ala Ile Trp Glu Leu Ile Lys Ser Ile Leu
1               5                   10

<210> SEQ ID NO 446
<211> LENGTH: 14
<212> TYPE: PRT
<213> ORGANISM: Homo sapiens

<400> SEQUENCE: 446

Cys Phe Phe Gly Ala Ile Trp Glu Ala Ile Lys Ser Ile Leu
1               5                   10

<210> SEQ ID NO 447
<211> LENGTH: 41
<212> TYPE: PRT
<213> ORGANISM: Homo sapiens

<400> SEQUENCE: 447

Cys Gly Leu Phe Glu Ala Ile Glu Gly Phe Ile Glu Asn Gly Trp Glu
1               5                   10                  15

Gly Leu Ala Glu Ala Leu Ala Glu Ala Leu Glu Ala Leu Ala Ala Tyr
            20                  25                  30

Gly Arg Lys Lys Arg Arg Gln Arg Arg
        35                  40

<210> SEQ ID NO 448
<211> LENGTH: 33
<212> TYPE: PRT
<213> ORGANISM: Homo sapiens

<400> SEQUENCE: 448

Cys Ile Phe Gly Ala Ile Ala Gly Phe Ile Lys Asn Ile Trp Glu Gly
1               5                   10                  15

Met Ile Asp Gly Trp Tyr Gly Tyr Gly Arg Lys Lys Arg Gln Arg
            20                  25                  30

Arg

<210> SEQ ID NO 449
<211> LENGTH: 33
<212> TYPE: PRT
<213> ORGANISM: Homo sapiens

<400> SEQUENCE: 449

Cys Ile Phe Gly Ala Ile Ala Gly Phe Ile Lys Asn Ile Trp Glu Gly
1               5                   10                  15
```

-continued

```
Leu Ile Asp Ala Trp Tyr Gly Tyr Gly Arg Lys Lys Arg Arg Gln Arg
            20                  25                  30

Arg

<210> SEQ ID NO 450
<211> LENGTH: 33
<212> TYPE: PRT
<213> ORGANISM: Homo sapiens

<400> SEQUENCE: 450

Cys Ile Phe Gly Ala Ile Ala Gly Phe Ile Lys Asn Ile Trp Lys Gly
1               5                   10                  15

Leu Ile Asp Ala Trp Tyr Gly Tyr Gly Arg Lys Lys Arg Arg Gln Arg
            20                  25                  30

Arg

<210> SEQ ID NO 451
<211> LENGTH: 40
<212> TYPE: PRT
<213> ORGANISM: Homo sapiens

<400> SEQUENCE: 451

Cys Ile Phe Gly Ala Ile Ala Gly Phe Ile Lys Asn Ile Trp Ile Phe
1               5                   10                  15

Gly Ala Ile Ala Gly Phe Ile Lys Asn Ile Trp Trp Tyr Gly Tyr Gly
            20                  25                  30

Arg Lys Lys Arg Arg Gln Arg Arg
        35                  40

<210> SEQ ID NO 452
<211> LENGTH: 24
<212> TYPE: PRT
<213> ORGANISM: Homo sapiens

<400> SEQUENCE: 452

Cys Gly Leu Phe Gly Ala Ile Ala Gly Phe Ile Glu Asn Gly Trp Glu
1               5                   10                  15

Gly Leu Ile Glu Gly Trp Tyr Gly
            20

<210> SEQ ID NO 453
<211> LENGTH: 34
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: misc_feature
<222> LOCATION: (27)..(31)
<223> OTHER INFORMATION: Xaa = ornithine

<400> SEQUENCE: 453

Cys Gly Leu Phe Glu Ala Ile Glu Gly Phe Ile Glu Asn Gly Trp Glu
1               5                   10                  15

Gly Leu Ile Asp Gly Trp Tyr Gly Tyr Gly Xaa Xaa Xaa Xaa Xaa Gln
            20                  25                  30

Arg Arg

<210> SEQ ID NO 454
<211> LENGTH: 34
<212> TYPE: PRT
<213> ORGANISM: Homo sapiens
```

<400> SEQUENCE: 454

Cys Gly Leu Phe Glu Ala Ile Glu Gly Phe Ile Glu Asn Gly Trp Lys
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 455
<211> LENGTH: 35
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (35)..(35)
<223> OTHER INFORMATION: Lys is conjugated to stearyl

<400> SEQUENCE: 455

Cys Gly Leu Phe Glu Ala Ile Glu Gly Phe Ile Glu Asn Gly Trp Glu
1               5                   10                  15

Gly Leu Ile Asp Gly Trp Tyr Gly Tyr Gly Arg Lys Lys Arg Arg Gln
            20                  25                  30

Arg Arg Lys
        35

<210> SEQ ID NO 456
<211> LENGTH: 34
<212> TYPE: PRT
<213> ORGANISM: Homo sapiens

<400> SEQUENCE: 456

Cys Tyr Gly His Lys Lys His His Gln His Arg Gly Leu Phe Glu Ala
1               5                   10                  15

Ile Glu Glu Phe Ile Glu Asn Gly Trp Glu Gly Leu Ile Asp Gly Trp
            20                  25                  30

Tyr Gly

<210> SEQ ID NO 457
<211> LENGTH: 34
<212> TYPE: PRT
<213> ORGANISM: Homo sapiens

<400> SEQUENCE: 457

Cys Tyr Gly His Lys Lys His His Gln His Arg Gly Leu Phe Glu Ala
1               5                   10                  15

Ile Glu Glu Phe Ile Glu Asn Gly Trp Glu Gly Leu Ile Asp Gly Trp
            20                  25                  30

Tyr Gly

<210> SEQ ID NO 458
<211> LENGTH: 35
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (35)..(35)
<223> OTHER INFORMATION: Lys is conjugated to Stearyl

<400> SEQUENCE: 458

Cys Gly Leu Phe Glu Ala Ile Glu Gly Phe Ile Glu Asn Gly Trp Lys
1               5                   10                  15

Gly Leu Ile Asp Gly Trp Tyr Gly Tyr Gly Arg Lys Lys Arg Arg Gln
            20                  25                  30

Arg Arg Lys
        35

<210> SEQ ID NO 459
<211> LENGTH: 34
<212> TYPE: PRT
<213> ORGANISM: Homo sapiens

<400> SEQUENCE: 459

Cys Gly Leu Phe Glu Ala Ile Glu Gly Phe Ile Glu Asn Gly Trp His
1               5                   10                  15

Gly Met Ile Asp Gly Trp Tyr Gly Tyr Gly Arg Lys Lys Arg Arg Gln
            20                  25                  30

Arg Arg

<210> SEQ ID NO 460
<211> LENGTH: 39
<212> TYPE: PRT
<213> ORGANISM: Homo sapiens

<400> SEQUENCE: 460

Ile Phe Gly Ile Asp Asp Leu Ile Ile Gly Leu Leu Phe Val Ala Ile
1               5                   10                  15

Val Glu Ala Gly Ile Gly Gly Tyr Leu Leu Gly Ser Tyr Gly Arg Lys
            20                  25                  30

Lys Arg Arg Gln Arg Arg Cys
        35

<210> SEQ ID NO 461
<211> LENGTH: 24
<212> TYPE: PRT
<213> ORGANISM: Homo sapiens

<400> SEQUENCE: 461

Cys Gly Phe Phe Gly Glu Ile Ala Glu Leu Ile Glu Glu Gly Leu Lys
1               5                   10                  15

Gly Leu Ile Asp Trp Trp Asn Gly
            20

<210> SEQ ID NO 462
<211> LENGTH: 24
<212> TYPE: PRT
<213> ORGANISM: Homo sapiens

<400> SEQUENCE: 462

Cys Gly Leu Phe Gly Glu Ile Glu Glu Leu Ile Glu Glu Gly Leu Glu
1               5                   10                  15

Asn Leu Ile Asp Trp Trp Asn Gly
            20

<210> SEQ ID NO 463
<211> LENGTH: 14
<212> TYPE: PRT
<213> ORGANISM: Homo sapiens

<400> SEQUENCE: 463

Cys Phe Phe Gly Ala Ile Trp Glu Phe Ile His Ser Ile Leu
1               5                   10

<210> SEQ ID NO 464
<211> LENGTH: 14
<212> TYPE: PRT
<213> ORGANISM: Homo sapiens

<400> SEQUENCE: 464

Cys Phe Phe Gly Ala Ile Trp Glu Phe Ile His Asn Ile Leu
1               5                   10

<210> SEQ ID NO 465
<211> LENGTH: 15
<212> TYPE: PRT
<213> ORGANISM: Homo sapiens

<400> SEQUENCE: 465

Cys Phe Phe Gly Ala Ile Trp Glu Phe Ile His Ser Ile Phe Lys
1               5                   10                  15

<210> SEQ ID NO 466
<211> LENGTH: 16
<212> TYPE: PRT
<213> ORGANISM: Homo sapiens

<400> SEQUENCE: 466

Cys Gly Ile Phe Glu Ala Ile Ala Gly Leu Leu Lys Trp Ile Phe Lys
1               5                   10                  15

<210> SEQ ID NO 467
<211> LENGTH: 16
<212> TYPE: PRT
<213> ORGANISM: Homo sapiens

<400> SEQUENCE: 467

Cys Gly Ile Phe Glu Leu Ile Ala Gly Leu Leu Lys Asn Ile Phe Lys
1               5                   10                  15

<210> SEQ ID NO 468
<211> LENGTH: 17
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (16)..(16)
<223> OTHER INFORMATION: Lys is conjugated to stearyl

<400> SEQUENCE: 468

Cys Gly Ile Phe Glu Ala Ile Ala Gly Leu Leu Lys Ser Ile Leu Lys
1               5                   10                  15
Lys

<210> SEQ ID NO 469
<211> LENGTH: 17
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (17)..(17)
<223> OTHER INFORMATION: Lys is conjugated to stearyl

<400> SEQUENCE: 469

Cys Gly Ile Phe Gly Ala Ile Ala Gly Leu Leu Lys Ser Ile Leu Lys
1               5                   10                  15

Lys

<210> SEQ ID NO 470
<211> LENGTH: 17
<212> TYPE: PRT
<213> ORGANISM: Homo sapiens

<400> SEQUENCE: 470

Cys Ile Phe Gly Ala Ile Ala Gly Phe Ile Lys Asn Ile Leu Lys Gly
1               5                   10                  15

Leu

<210> SEQ ID NO 471
<211> LENGTH: 24
<212> TYPE: PRT
<213> ORGANISM: Homo sapiens

<400> SEQUENCE: 471

Cys Ile Phe Gly Ala Ile Ala Gly Phe Ile Lys Asn Ile Leu Lys Gly
1               5                   10                  15

Leu Ile Asp Gly Trp Trp Tyr Gly
            20

<210> SEQ ID NO 472
<211> LENGTH: 18
<212> TYPE: PRT
<213> ORGANISM: Homo sapiens

<400> SEQUENCE: 472

Cys Ile Phe Gly Ala Ile Ala Gly Phe Ile Lys Asn Ile Trp His Gly
1               5                   10                  15

Leu Ile

<210> SEQ ID NO 473
<211> LENGTH: 18
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (18)..(18)
<223> OTHER INFORMATION: Lys is conjugated to stearyl

<400> SEQUENCE: 473

Cys Ile Phe Gly Ala Ile Ala Gly Phe Ile Lys Asn Ile Leu Lys Gly
1               5                   10                  15

Leu Lys

<210> SEQ ID NO 474
<211> LENGTH: 18
<212> TYPE: PRT
<213> ORGANISM: Homo sapiens

<400> SEQUENCE: 474

Gly Leu Gly Lys Leu Ile Asn Lys Ile Phe Gly Ala Ile Ala Gly Phe
1               5                   10                  15

Ile Cys

```
<210> SEQ ID NO 475
<211> LENGTH: 16
<212> TYPE: PRT
<213> ORGANISM: Homo sapiens

<400> SEQUENCE: 475

Cys Gly Ile Phe Glu Ala Ile Ala Gly Leu Leu Lys Asn Ile Phe Asp
1               5                   10                  15

<210> SEQ ID NO 476
<211> LENGTH: 16
<212> TYPE: PRT
<213> ORGANISM: Homo sapiens

<400> SEQUENCE: 476

Cys Gly Ile Phe Glu Ala Ile Ala Gly Leu Leu Lys Asn Ile Phe Glu
1               5                   10                  15

<210> SEQ ID NO 477
<211> LENGTH: 16
<212> TYPE: PRT
<213> ORGANISM: Homo sapiens

<400> SEQUENCE: 477

Cys Gly Ile Phe Glu Ala Ile Ala Gly Leu Leu Lys Asn Ile Phe Arg
1               5                   10                  15

<210> SEQ ID NO 478
<211> LENGTH: 16
<212> TYPE: PRT
<213> ORGANISM: Homo sapiens

<400> SEQUENCE: 478

Cys Gly Ile Phe Glu Ala Ile Ala Gly Leu Leu Lys Asn Ile Phe His
1               5                   10                  15

<210> SEQ ID NO 479
<211> LENGTH: 16
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: misc_feature
<222> LOCATION: (16)..(16)
<223> OTHER INFORMATION: Xaa = ornithine

<400> SEQUENCE: 479

Cys Gly Ile Phe Glu Ala Ile Ala Gly Leu Leu Lys Asn Ile Phe Xaa
1               5                   10                  15

<210> SEQ ID NO 480
<211> LENGTH: 16
<212> TYPE: PRT
<213> ORGANISM: Homo sapiens

<400> SEQUENCE: 480

Cys Gly Ile Phe Glu Ala Ile Ala Gly Leu Leu Lys Asn Ile Phe Asn
1               5                   10                  15

<210> SEQ ID NO 481
<211> LENGTH: 15
<212> TYPE: PRT
<213> ORGANISM: Artificial Sequence
<220> FEATURE:
<223> OTHER INFORMATION: Synthetically Generated Peptide
<220> FEATURE:
```

```
<221> NAME/KEY: MISC_FEATURE
<222> LOCATION: (15)..(15)
<223> OTHER INFORMATION: Phe is conjugated to Citrulline

<400> SEQUENCE: 481

Cys Gly Ile Phe Glu Ala Ile Ala Gly Leu Leu Lys Asn Ile Phe
1               5                   10                  15

<210> SEQ ID NO 482
<211> LENGTH: 16
<212> TYPE: PRT
<213> ORGANISM: Homo sapiens

<400> SEQUENCE: 482

Cys Gly Ile Phe Glu Ala Ile Trp Gly Leu Leu Lys Asn Ile Phe Lys
1               5                   10                  15

<210> SEQ ID NO 483
<211> LENGTH: 16
<212> TYPE: PRT
<213> ORGANISM: Homo sapiens

<400> SEQUENCE: 483

Cys Gly Ile Phe Gly Ala Ile Trp Gly Leu Leu Lys Asn Ile Phe Lys
1               5                   10                  15

<210> SEQ ID NO 484
<211> LENGTH: 15
<212> TYPE: PRT
<213> ORGANISM: Homo sapiens

<400> SEQUENCE: 484

Cys Ile Phe Gly Ala Ile Ala Gly Leu Leu Lys Asn Ile Phe Lys
1               5                   10                  15

<210> SEQ ID NO 485
<211> LENGTH: 15
<212> TYPE: PRT
<213> ORGANISM: Homo sapiens

<400> SEQUENCE: 485

Cys Ile Phe Glu Ala Ile Ala Gly Leu Leu Lys Asn Ile Phe Lys
1               5                   10                  15

<210> SEQ ID NO 486
<211> LENGTH: 15
<212> TYPE: PRT
<213> ORGANISM: Homo sapiens

<400> SEQUENCE: 486

Cys Phe Phe Gly Ala Ile Ala Gly Leu Leu Lys Asn Ile Phe Lys
1               5                   10                  15

<210> SEQ ID NO 487
<211> LENGTH: 15
<212> TYPE: PRT
<213> ORGANISM: Homo sapiens

<400> SEQUENCE: 487

Cys Phe Phe Glu Ala Ile Ala Gly Leu Leu Lys Asn Ile Phe Lys
1               5                   10                  15

<210> SEQ ID NO 488
<211> LENGTH: 16
<212> TYPE: PRT
```

<213> ORGANISM: Homo sapiens

<400> SEQUENCE: 488

Cys Gly Phe Phe Glu Ala Ile Ala Gly Leu Leu Lys Asn Ile Phe Lys
1               5                   10                  15

<210> SEQ ID NO 489
<211> LENGTH: 18
<212> TYPE: PRT
<213> ORGANISM: Homo sapiens

<400> SEQUENCE: 489

Cys Ile Phe Gly Ala Ile Ala Gly Phe Ile Lys Asn Ile Trp Glu Gly
1               5                   10                  15

Leu Ile

<210> SEQ ID NO 490
<211> LENGTH: 15
<212> TYPE: PRT
<213> ORGANISM: Homo sapiens

<400> SEQUENCE: 490

Cys Ile Phe Gly Ala Ile Ala Gly Leu Leu Lys Asn Ile Phe Lys
1               5                   10                  15

<210> SEQ ID NO 491
<211> LENGTH: 24
<212> TYPE: PRT
<213> ORGANISM: Homo sapiens

<400> SEQUENCE: 491

Cys Gly Leu Phe Gly Glu Ile Glu Glu Leu Ile Glu Glu Gly Leu Glu
1               5                   10                  15

Asn Leu Ile Asp Trp Trp Asn Gly
            20

<210> SEQ ID NO 492
<211> LENGTH: 24
<212> TYPE: PRT
<213> ORGANISM: Homo sapiens

<400> SEQUENCE: 492

Cys Gly Asn Phe Gly Glu Ile Glu Glu Leu Ile Glu Glu Gly Leu Glu
1               5                   10                  15

Asn Leu Ile Asp Trp Trp Asn Gly
            20

<210> SEQ ID NO 493
<211> LENGTH: 24
<212> TYPE: PRT
<213> ORGANISM: Homo sapiens

<400> SEQUENCE: 493

Cys Gly Phe Phe Gly Glu Ile Ala Glu Leu Ile Glu Glu Gly Leu Lys
1               5                   10                  15

Gly Leu Ile Asp Trp Trp Asn Gly
            20

<210> SEQ ID NO 494
<211> LENGTH: 24
<212> TYPE: PRT
<213> ORGANISM: Homo sapiens

```
<400> SEQUENCE: 494

Cys Gly Leu Phe Gly Glu Ile Glu Glu Leu Ile Glu Glu Gly Leu Glu
1               5                   10                  15

Asn Leu Ile Asp Trp Trp Asn Glu
            20

<210> SEQ ID NO 495
<211> LENGTH: 16
<212> TYPE: PRT
<213> ORGANISM: Homo sapiens

<400> SEQUENCE: 495

Cys Gly Phe Phe Gly Ala Ile Ala Gly Leu Leu Lys Asn Ile Phe Lys
1               5                   10                  15

<210> SEQ ID NO 496
<211> LENGTH: 35
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (35)..(35)
<223> OTHER INFORMATION: Lys is conjugated to stearyl

<400> SEQUENCE: 496

Cys Gly Leu Phe Glu Leu Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg Lys
        35

<210> SEQ ID NO 497
<211> LENGTH: 35
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (35)..(35)
<223> OTHER INFORMATION: Lys is conjugated to stearyl

<400> SEQUENCE: 497

Cys Gly Leu Phe Glu Leu Ile Glu Gly Phe Ile Glu Trp Gly Trp Glu
1               5                   10                  15

Gly Met Ile Asp Gly Trp Tyr Gly Tyr Gly Arg Lys Lys Arg Arg Gln
            20                  25                  30

Arg Arg Lys
        35

<210> SEQ ID NO 498
<211> LENGTH: 35
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (35)..(35)
<223> OTHER INFORMATION: Lys is conjugated to 2H, 2h, 3h, 3h-Perfluroro-
      10 methylundecanoyl

<400> SEQUENCE: 498
```

```
Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg Lys
        35

<210> SEQ ID NO 499
<211> LENGTH: 35
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (35)..(35)
<223> OTHER INFORMATION: Lys is conjugated to 2H, 2h, 3h, 3h-perfluoro-
      10 methylundecanoyl

<400> SEQUENCE: 499

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg Lys
        35

<210> SEQ ID NO 500
<211> LENGTH: 19
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (19)..(19)
<223> OTHER INFORMATION: Lys is conjugated to 2H, 2H, 3H, 3H,-perfluoro-
      10 perfluorononanyoyl

<400> SEQUENCE: 500

Cys Ile Phe Gly Ala Ile Ala Gly Phe Ile Lys Asn Ile Trp Glu Gly
1               5                   10                  15

Leu Ile Lys

<210> SEQ ID NO 501
<211> LENGTH: 19
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (19)..(19)
<223> OTHER INFORMATION: Lys is conjugated to 2H, 2H, 3H, 3H-perfluoro-
      10-methylundecanoyl

<400> SEQUENCE: 501

Cys Ile Phe Gly Ala Ile Ala Gly Phe Ile Lys Asn Ile Trp Glu Gly
1               5                   10                  15

Leu Ile Lys

<210> SEQ ID NO 502
<211> LENGTH: 35
<212> TYPE: PRT
<213> ORGANISM: Artificial Sequence
```

```
<220> FEATURE:
<223> OTHER INFORMATION: Synthetically generated peptide
<220> FEATURE:
<221> NAME/KEY: MISC_FEATURE
<222> LOCATION: (35)..(35)
<223> OTHER INFORMATION: Lys is conjugated to 2H, 2H, 3H, 3H,-
      perfluorononanoyl

<400> SEQUENCE: 502

Cys Gly Leu Phe Glu Ala Ile Glu Gly Phe Ile Glu Trp Gly Trp Glu
1               5                   10                  15

Gly Met Ile Asp Gly Trp Tyr Gly Tyr Gly Arg Lys Lys Arg Arg Gln
            20                  25                  30

Arg Arg Lys
        35

<210> SEQ ID NO 503
<211> LENGTH: 35
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (35)..(35)
<223> OTHER INFORMATION: Lys is conjugated to 2H, 2H, 3H, 3H-perfluoro-
      10 methylundecanoyl

<400> SEQUENCE: 503

Cys Gly Leu Phe Glu Ala Ile Glu Gly Phe Ile Glu Trp Gly Trp Glu
1               5                   10                  15

Gly Met Ile Asp Gly Trp Tyr Gly Tyr Gly Arg Lys Lys Arg Arg Gln
            20                  25                  30

Arg Arg Lys
        35

<210> SEQ ID NO 504
<211> LENGTH: 35
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (35)..(35)
<223> OTHER INFORMATION: Lys is conjugated to 2H, 2H, 3H, 3H-
      perfluorononanoyl

<400> SEQUENCE: 504

Cys Gly Leu Phe Glu Leu Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg Lys
        35

<210> SEQ ID NO 505
<211> LENGTH: 35
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (35)..()
<223> OTHER INFORMATION: Lys is conjugated to 2H, 2H, 3H, 3H-perfluoro-
      10 methylundecanoyl
```

```
<220> FEATURE:
<221> NAME/KEY: MISC_FEATURE
<222> LOCATION: (35)..(35)
<223> OTHER INFORMATION: Lys is conjugated to 2H, 2H, 3H, 3H-perfluoro-
      10 methylundecanoyl

<400> SEQUENCE: 505

Cys Gly Leu Phe Glu Leu Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg Lys
        35

<210> SEQ ID NO 506
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(15)
<223> OTHER INFORMATION: Lys is conjugated to 2H, 2H, 3H, 3H-
      perfluorononanoyl

<400> SEQUENCE: 506

Cys Phe Phe Gly Ala Ile Trp Glu Phe Ile His Ser Ile Leu Lys
1               5                   10                  15

<210> SEQ ID NO 507
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(15)
<223> OTHER INFORMATION: Lys is conjugated to 2H, 2H, 3H, 3H-
      methylundecanoyl

<400> SEQUENCE: 507

Cys Phe Phe Gly Ala Ile Trp Glu Phe Ile His Ser Ile Leu Lys
1               5                   10                  15

<210> SEQ ID NO 508
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (18)..(18)
<223> OTHER INFORMATION: Lys is conjugated to 2H, 2H, 3H, 3H-
      perfluorononanoyl

<400> SEQUENCE: 508

Cys Ile Phe Gly Ala Ile Ala Gly Phe Ile Lys Asn Ile Leu Lys Gly
1               5                   10                  15

Leu Lys

<210> SEQ ID NO 509
<211> LENGTH: 18
<212> TYPE: PRT
<213> ORGANISM: Artificial Sequence
<220> FEATURE:
```

```
<223> OTHER INFORMATION: Synthetically generated peptide
<220> FEATURE:
<221> NAME/KEY: MISC_FEATURE
<222> LOCATION: (18)..(18)
<223> OTHER INFORMATION: Lys is conjugated to 2h, 2h, 3h, 3h-perfluoro-
      10 methylundecanoyl

<400> SEQUENCE: 509

Cys Ile Phe Gly Ala Ile Ala Gly Phe Ile Lys Asn Ile Leu Lys Gly
1               5                   10                  15

Leu Lys

<210> SEQ ID NO 510
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (18)..(18)
<223> OTHER INFORMATION: Lys is conjugated to 2H, 2H, 3H, 3H-
      perfluorononanoyl

<400> SEQUENCE: 510

Cys Phe Phe Gly Ala Ile Trp Glu Phe Ile Arg Asn Ile Leu Glu Gly
1               5                   10                  15

Phe Lys

<210> SEQ ID NO 511
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (18)..(18)
<223> OTHER INFORMATION: Lys is conjugated to 2H, 2H, 3H, 3H-perfluoro-
      1-methylundecanoyl

<400> SEQUENCE: 511

Cys Phe Phe Gly Ala Ile Trp Glu Phe Ile Arg Asn Ile Leu Glu Gly
1               5                   10                  15

Phe Lys

<210> SEQ ID NO 512
<211> LENGTH: 24
<212> TYPE: PRT
<213> ORGANISM: Homo sapiens

<400> SEQUENCE: 512

Cys Gly Leu Phe Gly Glu Ile Glu Glu Leu Ile Glu Glu Gly Leu Glu
1               5                   10                  15

Asn Leu Ile Asp Trp Trp Asn Gln
            20

<210> SEQ ID NO 513
<211> LENGTH: 16
<212> TYPE: PRT
<213> ORGANISM: Homo sapiens

<400> SEQUENCE: 513

Cys Gly Ile Phe Gly Ala Ile Ala Gly Leu Leu Lys Ser Ala Leu Lys
1               5                   10                  15
```

```
<210> SEQ ID NO 514
<211> LENGTH: 16
<212> TYPE: PRT
<213> ORGANISM: Homo sapiens

<400> SEQUENCE: 514

Cys Gly Ile Phe Glu Ala Ile Ala Gly Leu Leu Lys Ser Ile Trp Lys
1               5                   10                  15

<210> SEQ ID NO 515
<211> LENGTH: 16
<212> TYPE: PRT
<213> ORGANISM: Homo sapiens

<400> SEQUENCE: 515

Cys Gly Ile Phe Glu Ala Ile Ala Gly Leu Leu Lys Ser Ile Leu Lys
1               5                   10                  15

<210> SEQ ID NO 516
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: misc_feature
<222> LOCATION: (12)..(12)
<223> OTHER INFORMATION: Xaa = ornithine

<400> SEQUENCE: 516

Cys Gly Ile Phe Glu Ala Ile Ala Gly Leu Leu Xaa Asn Ile Phe Lys
1               5                   10                  15

<210> SEQ ID NO 517
<211> LENGTH: 24
<212> TYPE: PRT
<213> ORGANISM: Homo sapiens

<400> SEQUENCE: 517

Cys Gly Ile Phe Glu Ala Ile Ala Gly Leu Leu Lys Asn Ile Leu Lys
1               5                   10                  15

Gly Leu Ile Asp Gly Trp Tyr Gly
            20

<210> SEQ ID NO 518
<211> LENGTH: 24
<212> TYPE: PRT
<213> ORGANISM: Homo sapiens

<400> SEQUENCE: 518

Cys Gly Ile Phe Gly Ala Ile Ala Gly Leu Leu Lys Asn Ile Leu Lys
1               5                   10                  15

Gly Leu Ile Asp Gly Trp Tyr Gly
            20

<210> SEQ ID NO 519
<211> LENGTH: 24
<212> TYPE: PRT
<213> ORGANISM: Homo sapiens

<400> SEQUENCE: 519

Cys Gly Ile Phe Gly Ala Ile Ala Gly Leu Leu Lys Asn Ile Phe Lys
1               5                   10                  15

Gly Leu Ile Asp Gly Trp Tyr Gly
```

20

<210> SEQ ID NO 520
<211> LENGTH: 16
<212> TYPE: PRT
<213> ORGANISM: Homo sapiens

<400> SEQUENCE: 520

Cys Gly Ile Phe Gly Ala Ile Trp Glu Leu Trp Glu Trp Ile Leu Lys
1               5                   10                  15

<210> SEQ ID NO 521
<211> LENGTH: 16
<212> TYPE: PRT
<213> ORGANISM: Homo sapiens

<400> SEQUENCE: 521

Cys Gly Ile Phe Glu Ala Ile Trp Glu Leu Trp Glu Trp Ile Leu Lys
1               5                   10                  15

<210> SEQ ID NO 522
<211> LENGTH: 25
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (25)..(25)
<223> OTHER INFORMATION: Lys is conjugated to stearyl

<400> SEQUENCE: 522

Cys Gly Leu Phe Glu Ala Ile Glu Gly Phe Ile Glu Asn Gly Trp Glu
1               5                   10                  15

Gly Met Ile Asp Gly Trp Tyr Gly Lys
            20                  25

<210> SEQ ID NO 523
<211> LENGTH: 24
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Gly is conjugated to stearyl

<400> SEQUENCE: 523

Gly Leu Phe Glu Ala Ile Glu Gly Phe Ile Glu Asn Gly Trp Glu Gly
1               5                   10                  15

Met Ile Asp Gly Trp Tyr Gly Cys
            20

<210> SEQ ID NO 524
<211> LENGTH: 16
<212> TYPE: PRT
<213> ORGANISM: Homo sapiens

<400> SEQUENCE: 524

Cys Phe Leu Glu Ala Ile Asx Leu Trp Lys Leu Leu Glu His Leu Leu
1               5                   10                  15

<210> SEQ ID NO 525
<211> LENGTH: 16
<212> TYPE: PRT

<213> ORGANISM: Homo sapiens

<400> SEQUENCE: 525

Cys Phe Leu Glu Ala Ile Asx Leu Trp Glu Leu Leu Glu His Leu Leu
1               5                   10                  15

<210> SEQ ID NO 526
<211> LENGTH: 16
<212> TYPE: PRT
<213> ORGANISM: Homo sapiens

<400> SEQUENCE: 526

Cys Phe Leu Glu Ala Leu Trp Glu Ala Ile Asx Leu Glu His Leu Leu
1               5                   10                  15

<210> SEQ ID NO 527
<211> LENGTH: 18
<212> TYPE: PRT
<213> ORGANISM: Homo sapiens

<400> SEQUENCE: 527

Cys Phe Leu Glu Ala Ile Asx Leu Trp Glu Ala Ile Asx Leu Glu His
1               5                   10                  15

Leu Leu

<210> SEQ ID NO 528
<211> LENGTH: 16
<212> TYPE: PRT
<213> ORGANISM: Homo sapiens

<400> SEQUENCE: 528

Cys Phe Leu Glu Ala Ile Asx Leu Trp Glu Ala Leu Glu Lys Leu Phe
1               5                   10                  15

<210> SEQ ID NO 529
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Ile is conjugated to stearyl

<400> SEQUENCE: 529

Ile Phe Gly Ala Ile Ala Gly Phe Ile Lys Asn Ile Trp Glu Gly Leu
1               5                   10                  15

Ile Cys

<210> SEQ ID NO 530
<211> LENGTH: 19
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (19)..(19)
<223> OTHER INFORMATION: Lys is conjugated to stearyl

<400> SEQUENCE: 530

Cys Ile Phe Gly Ala Ile Ala Gly Phe Ile Lys Asn Ile Trp Glu Gly
1               5                   10                  15

Leu Ile Lys

```
<210> SEQ ID NO 531
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Phe is conjugated is stearyl

<400> SEQUENCE: 531

Phe Phe Gly Ala Ile Trp Glu Phe Ile Lys Ser Ile Leu Cys
1               5                   10

<210> SEQ ID NO 532
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(15)
<223> OTHER INFORMATION: Lys is conjugated to stearyl

<400> SEQUENCE: 532

Cys Phe Phe Gly Ala Ile Trp Glu Phe Ile Lys Ser Ile Leu Lys
1               5                   10                  15

<210> SEQ ID NO 533
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Phe is conjugated to stearyl

<400> SEQUENCE: 533

Phe Phe Gly Ala Ile Trp Glu Phe Ile His Ser Ile Leu Cys
1               5                   10

<210> SEQ ID NO 534
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(15)
<223> OTHER INFORMATION: Lys is conjugated to stearyl

<400> SEQUENCE: 534

Cys Phe Phe Gly Ala Ile Trp Glu Phe Ile His Ser Ile Leu Lys
1               5                   10                  15

<210> SEQ ID NO 535
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
```

<223> OTHER INFORMATION: Gly is conjugated to stearyl

<400> SEQUENCE: 535

Gly Ile Phe Glu Ala Ile Ala Gly Leu Leu Lys Asn Ile Phe Lys Cys
1               5                   10                  15

<210> SEQ ID NO 536
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (16)..(16)
<223> OTHER INFORMATION: Lys is conjugated to stearyl

<400> SEQUENCE: 536

Cys Gly Ile Phe Glu Ala Ile Ala Gly Leu Leu Lys Asn Ile Phe Lys
1               5                   10                  15

<210> SEQ ID NO 537
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (17)..(17)
<223> OTHER INFORMATION: Lys is conjugated to stearyl

<400> SEQUENCE: 537

Cys Gly Ile Phe Glu Ala Ile Ala Gly Leu Leu Lys Asn Ile Phe Lys
1               5                   10                  15

Lys

<210> SEQ ID NO 538
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Ile is conjugated to isoleucine

<400> SEQUENCE: 538

Ile Phe Gly Ala Ile Ala Gly Phe Ile Lys Asn Ile Leu Lys Gly Leu
1               5                   10                  15

Cys

<210> SEQ ID NO 539
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(15)
<223> OTHER INFORMATION: Lys is conjugated to stearyl

<400> SEQUENCE: 539

Cys Ile Phe Gly Ala Ile Ala Gly Phe Ile Lys Asn Ile Leu Lys Gly
1               5                   10                  15

Leu Lys

<210> SEQ ID NO 540
<211> LENGTH: 17
<212> TYPE: PRT
<213> ORGANISM: Homo sapiens

<400> SEQUENCE: 540

Cys Ile Phe Gly Ala Ile Ala Gly Phe Ile Lys Asn Ile Leu Lys Gly
1               5                   10                  15

Leu

<210> SEQ ID NO 541
<211> LENGTH: 24
<212> TYPE: PRT
<213> ORGANISM: Homo sapiens

<400> SEQUENCE: 541

Cys Gly Leu Phe Gly Glu Ile Glu Glu Leu Ile Glu Glu Gly Leu Glu
1               5                   10                  15

Asn Leu Ile Asp Trp Trp Asn Ser
            20

<210> SEQ ID NO 542
<211> LENGTH: 34
<212> TYPE: PRT
<213> ORGANISM: Homo sapiens

<400> SEQUENCE: 542

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 543
<211> LENGTH: 24
<212> TYPE: PRT
<213> ORGANISM: Homo sapiens

<400> SEQUENCE: 543

Cys Gly Phe Phe Gly Glu Ile Ala Glu Leu Ile Glu Glu Gly Leu Lys
1               5                   10                  15

Asn Leu Ile Asp Trp Trp Asn Gly
            20

<210> SEQ ID NO 544
<211> LENGTH: 34
<212> TYPE: PRT
<213> ORGANISM: Homo sapiens

<400> SEQUENCE: 544

Cys Gly Leu Phe Glu Ala Ile Glu Gly Phe Ile Glu Asn Gly Trp Lys
1               5                   10                  15

Gly Met Ile Asp Gly Trp Tyr Gly Tyr Gly Arg Lys Lys Arg Arg Gln
            20                  25                  30

Arg Arg

<210> SEQ ID NO 545
<211> LENGTH: 34
<212> TYPE: PRT

<213> ORGANISM: Homo sapiens

<400> SEQUENCE: 545

Cys Gly Leu Phe Glu Ala Ile Glu Gly Phe Ile Glu Trp Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 546
<211> LENGTH: 34
<212> TYPE: PRT
<213> ORGANISM: Homo sapiens

<400> SEQUENCE: 546

Cys Gly Leu Phe Glu Leu Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 547
<211> LENGTH: 18
<212> TYPE: PRT
<213> ORGANISM: Homo sapiens

<400> SEQUENCE: 547

Cys Ile Phe Gly Ala Ile Ala Gly Phe Ile Lys Asn Ile Trp Glu Gly
1               5                   10                  15

Leu Ile

<210> SEQ ID NO 548
<211> LENGTH: 24
<212> TYPE: PRT
<213> ORGANISM: Homo sapiens

<400> SEQUENCE: 548

Cys Gly Leu Phe Gly Glu Ile Glu Glu Leu Ile Glu Glu Gly Leu Glu
1               5                   10                  15

Asn Leu Ile Asp Trp Trp Asn Gly
            20

<210> SEQ ID NO 549
<211> LENGTH: 34
<212> TYPE: PRT
<213> ORGANISM: Homo sapiens

<400> SEQUENCE: 549

Cys Gly Leu Phe Glu Glu Ile Glu Gly Phe Ile Glu Asn Gly Trp Glu
1               5                   10                  15

Gly Leu Ile Asp Trp Trp Tyr Gly Tyr Gly His Lys Lys Gly Gly Gln
            20                  25                  30

His Arg

<210> SEQ ID NO 550
<211> LENGTH: 35
<212> TYPE: PRT
<213> ORGANISM: Artificial Sequence
<220> FEATURE:
<223> OTHER INFORMATION: Synthetically Generated Peptide
<220> FEATURE:

```
<221> NAME/KEY: MISC_FEATURE
<222> LOCATION: (35)..(35)
<223> OTHER INFORMATION: Lys is conjugated to stearyl

<400> SEQUENCE: 550
```

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg Lys
        35

```
<210> SEQ ID NO 551
<211> LENGTH: 30
<212> TYPE: PRT
<213> ORGANISM: Homo sapiens

<400> SEQUENCE: 551
```

Cys Gly Leu Phe Glu Ala Leu Leu Glu Leu Leu Glu Ser Leu Trp Glu
1               5                   10                  15

Leu Leu Glu Ala Tyr Gly Arg Lys Lys Arg Arg Gln Arg Arg
            20                  25                  30

```
<210> SEQ ID NO 552
<211> LENGTH: 30
<212> TYPE: PRT
<213> ORGANISM: Homo sapiens

<400> SEQUENCE: 552
```

Cys Gly Leu Phe Glu Ala Leu Leu Glu Leu Leu Glu Ser Leu Trp Glu
1               5                   10                  15

Leu Leu Glu Ala Tyr Gly Arg Lys Lys Arg Arg Gln Arg Arg
            20                  25                  30

```
<210> SEQ ID NO 553
<211> LENGTH: 17
<212> TYPE: PRT
<213> ORGANISM: Homo sapiens

<400> SEQUENCE: 553
```

Cys Phe Phe Gly Ala Ile Trp Glu Phe Ile Arg Asn Ile Leu Glu Gly
1               5                   10                  15

Phe

```
<210> SEQ ID NO 554
<211> LENGTH: 18
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (18)..(18)
<223> OTHER INFORMATION: Lys is conjugated to stearyl

<400> SEQUENCE: 554
```

Cys Phe Phe Gly Ala Ile Trp Glu Phe Ile Arg Asn Ile Leu Glu Gly
1               5                   10                  15

Phe Lys

```
<210> SEQ ID NO 555
<211> LENGTH: 19
<212> TYPE: PRT
```

```
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (19)..(19)
<223> OTHER INFORMATION: Lys is conjugated to lauryl

<400> SEQUENCE: 555

Cys Ile Phe Gly Ala Ile Ala Gly Phe Ile Lys Asn Ile Trp Glu Gly
1               5                   10                  15

Leu Ile Lys

<210> SEQ ID NO 556
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Phe is conjugated to lauryl

<400> SEQUENCE: 556

Phe Phe Gly Ala Ile Trp Glu Phe Ile Lys Ser Ile Leu Cys
1               5                   10

<210> SEQ ID NO 557
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(15)
<223> OTHER INFORMATION: Lys is conjugated to lauryl

<400> SEQUENCE: 557

Cys Phe Phe Gly Ala Ile Trp Glu Phe Ile Lys Ser Ile Leu Lys
1               5                   10                  15

<210> SEQ ID NO 558
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Phe is conjugated to lauryl

<400> SEQUENCE: 558

Phe Phe Gly Ala Ile Trp Glu Phe Ile His Ser Ile Leu Cys
1               5                   10

<210> SEQ ID NO 559
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(15)
<223> OTHER INFORMATION: Lys is conjugated to lauryl

<400> SEQUENCE: 559
```

```
Cys Phe Phe Gly Ala Ile Trp Glu Phe Ile His Ser Ile Leu Lys
1               5                   10                  15

<210> SEQ ID NO 560
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Gly is conjugated to lauryl

<400> SEQUENCE: 560

Gly Ile Phe Glu Ala Ile Ala Gly Leu Leu Lys Asn Ile Phe Lys Cys
1               5                   10                  15

<210> SEQ ID NO 561
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (16)..(16)
<223> OTHER INFORMATION: Lys is conjugated to lauryl

<400> SEQUENCE: 561

Cys Gly Ile Phe Glu Ala Ile Ala Gly Leu Leu Lys Asn Ile Phe Lys
1               5                   10                  15

<210> SEQ ID NO 562
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (18)..(18)
<223> OTHER INFORMATION: Lys is conjugated to lauryl

<400> SEQUENCE: 562

Cys Phe Phe Gly Ala Ile Trp Glu Phe Ile Arg Asn Ile Leu Glu Gly
1               5                   10                  15

Phe Lys

<210> SEQ ID NO 563
<211> LENGTH: 24
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Gly is conjugated to lauryl

<400> SEQUENCE: 563

Gly Leu Phe Glu Ala Ile Glu Gly Phe Ile Glu Asn Gly Trp Glu Gly
1               5                   10                  15

Met Ile Asp Gly Trp Tyr Gly Cys
                20

<210> SEQ ID NO 564
```

```
<211> LENGTH: 25
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (25)..(25)
<223> OTHER INFORMATION: Lys is conjugated to lauryl

<400> SEQUENCE: 564

Cys Gly Leu Phe Glu Ala Ile Glu Gly Phe Ile Glu Asn Gly Trp Glu
1               5                   10                  15

Gly Met Ile Asp Gly Trp Tyr Gly Lys
            20                  25

<210> SEQ ID NO 565
<211> LENGTH: 26
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (26)..(26)
<223> OTHER INFORMATION: Lys is conjugated to stearyl

<400> SEQUENCE: 565

Cys Gly Lys Phe Thr Ile Val Phe Pro His Asn Gln Lys Gly Asn Trp
1               5                   10                  15

Lys Asn Val Pro Ser Asn Tyr His Tyr Lys
            20                  25

<210> SEQ ID NO 566
<211> LENGTH: 26
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (26)..(26)
<223> OTHER INFORMATION: Lys is conjugated to stearyl

<400> SEQUENCE: 566

Cys Met Asp Gly Thr Leu Phe Pro Gly Asp Asp Asp Leu Ala Ile Pro
1               5                   10                  15

Ala Thr Glu Phe Phe Ser Thr Lys Ala Lys
            20                  25

<210> SEQ ID NO 567
<211> LENGTH: 26
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (26)..(26)
<223> OTHER INFORMATION: Lys is conjugated to stearyl

<400> SEQUENCE: 567

Cys Asn Pro Val Glu Asn Tyr Ile Asp Glu Val Leu Asn Glu Val Leu
1               5                   10                  15

Val Val Pro Asn Ile Asn Ser Ser Asn Lys
            20                  25
```

```
<210> SEQ ID NO 568
<211> LENGTH: 22
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (22)..(22)
<223> OTHER INFORMATION: Lys is conjugated to stearyl

<400> SEQUENCE: 568

Cys Val Thr Pro His His Val Leu Val Asp Glu Tyr Thr Gly Glu Trp
1               5                   10                  15

Val Asp Ser Gln Phe Lys
            20

<210> SEQ ID NO 569
<211> LENGTH: 30
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (30)..(30)
<223> OTHER INFORMATION: Lys is conjugated to stearyl

<400> SEQUENCE: 569

Cys Ile Phe Gly Ile Asp Asp Leu Ile Ile Gly Leu Leu Phe Val Ala
1               5                   10                  15

Ile Val Glu Ala Gly Ile Gly Gly Tyr Leu Leu Gly Ser Lys
            20                  25                  30

<210> SEQ ID NO 570
<211> LENGTH: 19
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (19)..(19)
<223> OTHER INFORMATION: Lys is conjugated to stearyl

<400> SEQUENCE: 570

Cys Gly Ala Ala Ile Gly Leu Ala Trp Ile Pro Tyr Phe Gly Pro Ala
1               5                   10                  15

Ala Glu Lys

<210> SEQ ID NO 571
<211> LENGTH: 28
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (28)..(28)
<223> OTHER INFORMATION: Lys is conjugated to stearyl

<400> SEQUENCE: 571

Cys Phe Ala Gly Val Val Leu Ala Gly Ala Ala Leu Gly Val Ala Thr
1               5                   10                  15

Ala Ala Gln Ile Thr Ala Gly Ile Ala Leu His Lys
            20                  25
```

```
<210> SEQ ID NO 572
<211> LENGTH: 26
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (26)..(26)
<223> OTHER INFORMATION: Lys is conjugated to stearyl

<400> SEQUENCE: 572

Cys Phe Leu Gly Phe Leu Leu Gly Val Gly Ser Ala Ile Ala Ser Gly
1               5                   10                  15

Ile Ala Val Ser Lys Val Leu His Leu Lys
            20                  25

<210> SEQ ID NO 573
<211> LENGTH: 28
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (28)..(28)
<223> OTHER INFORMATION: Lys is conjugated to stearyl

<400> SEQUENCE: 573

Cys Phe Phe Gly Ala Val Ile Gly Thr Ile Ala Leu Gly Val Ala Thr
1               5                   10                  15

Ser Ala Gln Ile Thr Ala Gly Ile Ala Leu Ala Lys
            20                  25

<210> SEQ ID NO 574
<211> LENGTH: 28
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (28)..(28)
<223> OTHER INFORMATION: Lys is conjugated to stearyl

<400> SEQUENCE: 574

Cys Phe Phe Gly Ala Val Ile Gly Thr Ile Ala Leu Gly Val Ala Thr
1               5                   10                  15

Ala Ala Gln Ile Thr Ala Gly Ile Ala Leu Ala Lys
            20                  25

<210> SEQ ID NO 575
<211> LENGTH: 24
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (24)..(24)
<223> OTHER INFORMATION: Lys is conjugated to stearyl

<400> SEQUENCE: 575

Gly Leu Phe Glu Ala Ile Ala Gly Phe Ile Glu Asn Gly Gly Trp Glu
1               5                   10                  15

Gly Met Ile Asp Gly Gly Gly Lys
            20
```

<210> SEQ ID NO 576
<211> LENGTH: 24
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (24)..(24)
<223> OTHER INFORMATION: Lys  is conjugated to stearyl

<400> SEQUENCE: 576

Gly Leu Phe Lys Ala Ile Ala Lys Phe Ile Lys Gly Gly Trp Lys Gly
1               5                   10                  15

Leu Ile Lys Gly Trp Tyr Gly Lys
            20

<210> SEQ ID NO 577
<211> LENGTH: 24
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (24)..(24)
<223> OTHER INFORMATION: Lys is conjugated to stearyl

<400> SEQUENCE: 577

Gly Leu Phe His Ala Ile Ala His Phe Ile His Gly Gly Trp His Gly
1               5                   10                  15

Leu Ile His Gly Trp Tyr Gly Lys
            20

<210> SEQ ID NO 578
<211> LENGTH: 25
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (25)..(25)
<223> OTHER INFORMATION: Lys is conjugated to stearyl

<400> SEQUENCE: 578

Cys Gly Leu Phe Glu Ala Ile Ala Glu Phe Ile Glu Asn Gly Trp Glu
1               5                   10                  15

Gly Leu Ile Glu Gly Trp Tyr Gly Lys
            20                  25

<210> SEQ ID NO 579
<211> LENGTH: 25
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (25)..(25)
<223> OTHER INFORMATION: Lys is conjugated to stearyl

<400> SEQUENCE: 579

Cys Gly Phe Phe Gly Ala Ile Ala Gly Phe Leu Glu Gly Gly Trp Glu
1               5                   10                  15

Gly Met Ile Ala Gly Trp His Gly Lys
            20                  25

```
<210> SEQ ID NO 580
<211> LENGTH: 29
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (29)..(29)
<223> OTHER INFORMATION: Lys is conjugated to stearyl

<400> SEQUENCE: 580

Cys Phe Ala Gly Val Val Ile Gly Leu Ala Ala Leu Gly Val Ala Thr
1               5                   10                  15

Ala Ala Gln Val Thr Ala Ala Val Ala Leu Val Lys Lys
            20                  25

<210> SEQ ID NO 581
<211> LENGTH: 33
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (33)..(33)
<223> OTHER INFORMATION: Lys is conjugated to stearyl

<400> SEQUENCE: 581

Cys Ala Val Gly Ile Val Gly Ala Met Phe Leu Gly Phe Leu Gly Ala
1               5                   10                  15

Ala Gly Ser Thr Met Gly Ala Val Ser Leu Thr Leu Thr Val Gln Ala
            20                  25                  30

Lys

<210> SEQ ID NO 582
<211> LENGTH: 29
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (29)..(29)
<223> OTHER INFORMATION: Lys is conjugated to stearyl

<400> SEQUENCE: 582

Cys Gly Val Phe Val Leu Gly Phe Leu Gly Phe Leu Ala Thr Ala Gly
1               5                   10                  15

Ser Ala Met Gly Ala Arg Ser Leu Thr Leu Ser Ala Lys
            20                  25

<210> SEQ ID NO 583
<211> LENGTH: 29
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (29)..(29)
<223> OTHER INFORMATION: Lys is conjugated to stearyl

<400> SEQUENCE: 583

Cys Val Pro Phe Val Leu Gly Phe Leu Gly Phe Leu Gly Ala Ala Gly
1               5                   10                  15
```

```
Thr Ala Met Gly Ala Ala Ala Thr Ala Leu Thr Val Lys
            20                  25
```

<210> SEQ ID NO 584
<211> LENGTH: 33
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (33)..(33)
<223> OTHER INFORMATION: Lys is conjugated to stearyl

<400> SEQUENCE: 584

```
Cys Ala Val Pro Val Ala Val Trp Leu Val Ser Ala Leu Ala Met Gly
1               5                   10                  15

Ala Gly Val Ala Gly Gly Ile Thr Gly Ser Met Ser Leu Ala Ser Gly
            20                  25                  30

Lys
```

<210> SEQ ID NO 585
<211> LENGTH: 21
<212> TYPE: PRT
<213> ORGANISM: Homo sapiens

<400> SEQUENCE: 585

```
Cys Gly Leu Ala Ser Thr Leu Thr Arg Trp Ala His Tyr Asn Ala Leu
1               5                   10                  15

Ile Arg Ala Phe Lys
            20
```

<210> SEQ ID NO 586
<211> LENGTH: 22
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (22)..(22)
<223> OTHER INFORMATION: Lys is conjugated to stearyl

<400> SEQUENCE: 586

```
Cys Gly Pro Val Glu Asp Ala Ile Thr Ala Ala Ile Gly Arg Val Ala
1               5                   10                  15

Asp Thr Val Gly Thr Lys
            20
```

<210> SEQ ID NO 587
<211> LENGTH: 22
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (23)..(23)
<223> OTHER INFORMATION: Lys is conjugated to stearyl

<400> SEQUENCE: 587

```
Cys Gly Leu Gly Gln Met Leu Glu Ser Met Ile Asp Asn Thr Val Arg
1               5                   10                  15

Glu Val Gly Gly Ala Lys
            20
```

```
<210> SEQ ID NO 588
<211> LENGTH: 26
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (26)..(26)
<223> OTHER INFORMATION: Lys is conjugated to stearyl

<400> SEQUENCE: 588

Cys Gly Leu Phe Glu Ala Ile Glu Gly Phe Ile Glu Asn Gly Trp Glu
1               5                   10                  15

Gly Met Ile Asp Gly Trp Tyr Gly Phe Lys
            20                  25

<210> SEQ ID NO 589
<211> LENGTH: 28
<212> TYPE: PRT
<213> ORGANISM: Homo sapiens

<400> SEQUENCE: 589

Phe Glu Ala Ile Glu Gly Phe Ile Glu Asn Gly Trp Glu Gly Met Ile
1               5                   10                  15

Asp Gly Trp Tyr Gly Tyr Gly Arg Lys Lys Arg Arg
            20                  25

<210> SEQ ID NO 590
<211> LENGTH: 31
<212> TYPE: PRT
<213> ORGANISM: Homo sapiens

<400> SEQUENCE: 590

Leu Glu Ala Ile Glu Gly Phe Ile Glu Asn Gly Trp Glu Gly Met Ile
1               5                   10                  15

Asp Gly Trp Tyr Gly Tyr Gly Arg Lys Lys Arg Arg Gln Arg Arg
            20                  25                  30

<210> SEQ ID NO 591
<211> LENGTH: 29
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (29)..(29)
<223> OTHER INFORMATION: Ser is conjugated to stearyl

<400> SEQUENCE: 591

Cys Ile Phe Gly Ile Asp Asp Leu Ile Ile Gly Leu Leu Phe Val Ala
1               5                   10                  15

Ile Val Glu Ala Gly Ile Gly Gly Tyr Leu Leu Gly Ser
            20                  25

<210> SEQ ID NO 592
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (16)..(16)
```

<223> OTHER INFORMATION: Gly is conjugated to stearyl

<400> SEQUENCE: 592

Cys Val Thr Val Leu Ala Leu Gly Ala Leu Ala Gly Val Gly Val Gly
1               5                   10                  15

<210> SEQ ID NO 593
<211> LENGTH: 25
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (25)..(25)
<223> OTHER INFORMATION: Leu is conjugated to stearyl

<400> SEQUENCE: 593

Cys Leu Leu Gly Arg Arg Gly Trp Glu Val Leu Lys Tyr Trp Trp Asn
1               5                   10                  15
Leu Leu Gln Tyr Trp Ser Gln Glu Leu
            20                  25

<210> SEQ ID NO 594
<211> LENGTH: 16
<212> TYPE: PRT
<213> ORGANISM: Homo sapiens

<400> SEQUENCE: 594

Cys Gly Ile Phe Glu Ala Ile Ala Gly Leu Leu Lys Asn Ile Phe Asp
1               5                   10                  15

<210> SEQ ID NO 595
<211> LENGTH: 16
<212> TYPE: PRT
<213> ORGANISM: Homo sapiens

<400> SEQUENCE: 595

Cys Gly Ile Phe Glu Ala Ile Ala Gly Leu Leu Lys Asn Ile Phe Glu
1               5                   10                  15

<210> SEQ ID NO 596
<211> LENGTH: 16
<212> TYPE: PRT
<213> ORGANISM: Homo sapiens

<400> SEQUENCE: 596

Cys Gly Ile Phe Glu Ala Ile Ala Gly Leu Leu Lys Asn Ile Phe Arg
1               5                   10                  15

<210> SEQ ID NO 597
<211> LENGTH: 16
<212> TYPE: PRT
<213> ORGANISM: Homo sapiens

<400> SEQUENCE: 597

Cys Gly Ile Phe Glu Ala Ile Ala Gly Leu Leu Lys Asn Ile Phe His
1               5                   10                  15

<210> SEQ ID NO 598
<211> LENGTH: 16
<212> TYPE: PRT
<213> ORGANISM: Artificial Sequence
<220> FEATURE:
<223> OTHER INFORMATION: Synthetically Generated Peptide
<220> FEATURE:

```
<221> NAME/KEY: misc_feature
<222> LOCATION: (16)..(16)
<223> OTHER INFORMATION: Xaa = Ornithine

<400> SEQUENCE: 598

Cys Gly Ile Phe Glu Ala Ile Ala Gly Leu Leu Lys Asn Ile Phe Xaa
1               5                   10                  15

<210> SEQ ID NO 599
<211> LENGTH: 16
<212> TYPE: PRT
<213> ORGANISM: Homo sapiens

<400> SEQUENCE: 599

Cys Gly Ile Phe Glu Ala Ile Ala Gly Leu Leu Lys Asn Ile Phe Asn
1               5                   10                  15

<210> SEQ ID NO 600
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(15)
<223> OTHER INFORMATION: Phe is conjugated to Citrulline

<400> SEQUENCE: 600

Cys Gly Ile Phe Glu Ala Ile Ala Gly Leu Leu Lys Asn Ile Phe
1               5                   10                  15

<210> SEQ ID NO 601
<211> LENGTH: 16
<212> TYPE: PRT
<213> ORGANISM: Homo sapiens

<400> SEQUENCE: 601

Cys Gly Ile Phe Gly Ala Ile Trp Gly Leu Leu Lys Asn Ile Phe Lys
1               5                   10                  15

<210> SEQ ID NO 602
<211> LENGTH: 15
<212> TYPE: PRT
<213> ORGANISM: Homo sapiens

<400> SEQUENCE: 602

Cys Ile Phe Glu Ala Ile Ala Gly Leu Leu Lys Asn Ile Phe Lys
1               5                   10                  15

<210> SEQ ID NO 603
<211> LENGTH: 15
<212> TYPE: PRT
<213> ORGANISM: Homo sapiens

<400> SEQUENCE: 603

Cys Phe Phe Glu Ala Ile Ala Gly Leu Leu Lys Asn Ile Phe Lys
1               5                   10                  15

<210> SEQ ID NO 604
<211> LENGTH: 16
<212> TYPE: PRT
<213> ORGANISM: Homo sapiens

<400> SEQUENCE: 604

Cys Gly Phe Phe Glu Ala Ile Ala Gly Leu Leu Lys Asn Ile Phe Lys
```

-continued

```
1               5                   10                  15

<210> SEQ ID NO 605
<211> LENGTH: 17
<212> TYPE: PRT
<213> ORGANISM: Homo sapiens

<400> SEQUENCE: 605

Cys Gly Ile Phe Glu Ala Ile Ala Gly Leu Leu Lys Asn Ile Phe Lys
1               5                   10                  15

Gly

<210> SEQ ID NO 606
<211> LENGTH: 18
<212> TYPE: PRT
<213> ORGANISM: Homo sapiens

<400> SEQUENCE: 606

Cys Gly Ile Phe Glu Ala Ile Ala Gly Leu Leu Lys Asn Ile Phe Lys
1               5                   10                  15

Gly Leu

<210> SEQ ID NO 607
<211> LENGTH: 19
<212> TYPE: PRT
<213> ORGANISM: Homo sapiens

<400> SEQUENCE: 607

Cys Gly Ile Phe Glu Ala Ile Ala Gly Leu Leu Lys Asn Ile Phe Lys
1               5                   10                  15

Gly Leu Ile

<210> SEQ ID NO 608
<211> LENGTH: 20
<212> TYPE: PRT
<213> ORGANISM: Homo sapiens

<400> SEQUENCE: 608

Cys Gly Ile Phe Glu Ala Ile Ala Gly Leu Leu Lys Asn Ile Phe Lys
1               5                   10                  15

Gly Leu Ile Asp
            20

<210> SEQ ID NO 609
<211> LENGTH: 21
<212> TYPE: PRT
<213> ORGANISM: Homo sapiens

<400> SEQUENCE: 609

Cys Gly Ile Phe Glu Ala Ile Ala Gly Leu Leu Lys Asn Ile Phe Lys
1               5                   10                  15

Gly Leu Ile Asp Gly
            20

<210> SEQ ID NO 610
<211> LENGTH: 22
<212> TYPE: PRT
<213> ORGANISM: Homo sapiens

<400> SEQUENCE: 610

Cys Gly Ile Phe Glu Ala Ile Ala Gly Leu Leu Lys Asn Ile Phe Lys
1               5                   10                  15
```

Gly Leu Ile Asp Gly Phe
        20

<210> SEQ ID NO 611
<211> LENGTH: 24
<212> TYPE: PRT
<213> ORGANISM: Homo sapiens

<400> SEQUENCE: 611

Cys Gly Ile Phe Glu Ala Ile Ala Gly Leu Leu Lys Asn Ile Phe Lys
1               5                   10                  15

Gly Leu Ile Asp Gly Trp Tyr Gly
        20

<210> SEQ ID NO 612
<211> LENGTH: 16
<212> TYPE: PRT
<213> ORGANISM: Homo sapiens

<400> SEQUENCE: 612

Cys Gly Ile Phe Glu Ala Ile Ala Gly Leu Leu Lys Asn Ile Phe Lys
1               5                   10                  15

<210> SEQ ID NO 613
<211> LENGTH: 16
<212> TYPE: PRT
<213> ORGANISM: Homo sapiens

<400> SEQUENCE: 613

Cys Gly Ile Phe Glu Ala Ile Ala Gly Leu Leu Lys Ser Ile Leu Lys
1               5                   10                  15

<210> SEQ ID NO 614
<211> LENGTH: 17
<212> TYPE: PRT
<213> ORGANISM: Homo sapiens

<400> SEQUENCE: 614

Cys Gly Ile Phe Glu Ala Ile Ala Gly Leu Leu Lys Asn Ile Phe Lys
1               5                   10                  15

Ala

<210> SEQ ID NO 615
<211> LENGTH: 17
<212> TYPE: PRT
<213> ORGANISM: Homo sapiens

<400> SEQUENCE: 615

Cys Gly Ile Phe Glu Ala Ile Ala Gly Leu Leu Lys Asn Ile Phe Lys
1               5                   10                  15

Leu

<210> SEQ ID NO 616
<211> LENGTH: 17
<212> TYPE: PRT
<213> ORGANISM: Homo sapiens

<400> SEQUENCE: 616

Cys Gly Ile Phe Glu Ala Ile Ala Gly Leu Leu Lys Asn Ile Phe Lys
1               5                   10                  15

Trp

<210> SEQ ID NO 617
<211> LENGTH: 17
<212> TYPE: PRT
<213> ORGANISM: Homo sapiens

<400> SEQUENCE: 617

Cys Gly Ile Phe Glu Ala Ile Ala Gly Leu Leu Lys Asn Ile Phe Lys
1               5                   10                  15

Phe

<210> SEQ ID NO 618
<211> LENGTH: 16
<212> TYPE: PRT
<213> ORGANISM: Homo sapiens

<400> SEQUENCE: 618

Cys Gly Ile Phe Glu Ala Ile Ala Gly Leu Leu Lys Asn Ala Phe Lys
1               5                   10                  15

<210> SEQ ID NO 619
<211> LENGTH: 16
<212> TYPE: PRT
<213> ORGANISM: Homo sapiens

<400> SEQUENCE: 619

Cys Gly Ile Phe Gly Ala Ile Ala Gly Leu Leu Lys Asn Ala Phe Lys
1               5                   10                  15

<210> SEQ ID NO 620
<211> LENGTH: 16
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: misc_feature
<222> LOCATION: (12)..(12)
<223> OTHER INFORMATION: Xaa = Ornithine
<220> FEATURE:
<221> NAME/KEY: misc_feature
<222> LOCATION: (16)..(16)
<223> OTHER INFORMATION: Xaa = Ornithine

<400> SEQUENCE: 620

Cys Gly Ile Phe Glu Ala Ile Ala Gly Leu Leu Xaa Asn Ile Phe Xaa
1               5                   10                  15

<210> SEQ ID NO 621
<211> LENGTH: 31
<212> TYPE: PRT
<213> ORGANISM: Homo sapiens

<400> SEQUENCE: 621

Cys Gly Ile Phe Glu Ala Ile Ala Gly Leu Leu Lys Asn Ile Phe Lys
1               5                   10                  15

Gly Ile Phe Glu Ala Ile Ala Gly Leu Leu Lys Asn Ile Phe Lys
            20                  25                  30

<210> SEQ ID NO 622
<211> LENGTH: 29
<212> TYPE: PRT
<213> ORGANISM: Homo sapiens

<400> SEQUENCE: 622

Cys Gly Ile Phe Glu Ala Ile Ala Gly Leu Leu Lys Asn Ile Phe Lys

```
                1               5                  10                  15
Phe Phe Gly Ala Ile Trp Glu Phe Ile His Ser Ile Leu
            20                  25

<210> SEQ ID NO 623
<211> LENGTH: 29
<212> TYPE: PRT
<213> ORGANISM: Homo sapiens

<400> SEQUENCE: 623

Cys Phe Phe Gly Ala Ile Trp Glu Phe Ile His Ser Ile Leu Gly Ile
1               5                  10                  15

Phe Glu Ala Ile Ala Gly Leu Leu Lys Asn Ile Phe Lys
            20                  25

<210> SEQ ID NO 624
<211> LENGTH: 27
<212> TYPE: PRT
<213> ORGANISM: Homo sapiens

<400> SEQUENCE: 624

Cys Phe Phe Gly Ala Ile Trp Glu Phe Ile His Ser Ile Leu Phe Phe
1               5                  10                  15

Gly Ala Ile Trp Glu Phe Ile His Ser Ile Leu
            20                  25

<210> SEQ ID NO 625
<211> LENGTH: 28
<212> TYPE: PRT
<213> ORGANISM: Homo sapiens

<400> SEQUENCE: 625

Cys Phe Phe Gly Ala Ile Trp Glu Phe Ile His Ser Ile Leu Gly Phe
1               5                  10                  15

Phe Gly Ala Ile Trp Glu Phe Ile His Ser Ile Leu
            20                  25

<210> SEQ ID NO 626
<211> LENGTH: 31
<212> TYPE: PRT
<213> ORGANISM: Homo sapiens

<400> SEQUENCE: 626

Cys Gly Ile Phe Glu Ala Ile Ala Gly Leu Leu Lys Asn Ile Phe Lys
1               5                  10                  15

Gly Ile Phe Glu Ala Ile Ala Gly Leu Leu Lys Asn Ile Phe Lys
            20                  25                  30

<210> SEQ ID NO 627
<211> LENGTH: 29
<212> TYPE: PRT
<213> ORGANISM: Homo sapiens

<400> SEQUENCE: 627

Cys Gly Ile Phe Glu Ala Ile Ala Gly Leu Leu Lys Asn Ile Phe Lys
1               5                  10                  15

Phe Phe Gly Ala Ile Trp Glu Phe Ile His Ser Ile Leu
            20                  25

<210> SEQ ID NO 628
<211> LENGTH: 29
<212> TYPE: PRT
```

```
<213> ORGANISM: Homo sapiens

<400> SEQUENCE: 628

Cys Phe Phe Gly Ala Ile Trp Glu Phe Ile His Ser Ile Leu Gly Ile
1               5                   10                  15

Phe Glu Ala Ile Ala Gly Leu Leu Lys Asn Ile Phe Lys
            20                  25

<210> SEQ ID NO 629
<211> LENGTH: 21
<212> TYPE: PRT
<213> ORGANISM: Homo sapiens

<400> SEQUENCE: 629

Cys Gly Leu Phe His Ala Leu Leu His Leu Leu His Ser Leu Trp His
1               5                   10                  15

Leu Leu Leu Glu Ala
            20

<210> SEQ ID NO 630
<211> LENGTH: 22
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (22)..(22)
<223> OTHER INFORMATION: Lys is conjugated to stearyl

<400> SEQUENCE: 630

Cys Gly Leu Phe His Ala Leu Leu His Leu Leu His Ser Leu Trp His
1               5                   10                  15

Leu Leu Leu Glu Ala Lys
            20

<210> SEQ ID NO 631
<211> LENGTH: 22
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (22)..(22)
<223> OTHER INFORMATION: Lys is conjugated to stearyl

<400> SEQUENCE: 631

Cys Gly Leu Phe His Ala Leu Leu His Leu Leu His Ser Leu Trp His
1               5                   10                  15

Leu Leu Leu Glu Ala Lys
            20

<210> SEQ ID NO 632
<211> LENGTH: 21
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Gly is conjugated to stearyl

<400> SEQUENCE: 632

Gly Leu Phe His Ala Leu Leu His Leu Leu His Ser Leu Trp His Leu
```

```
                1               5                  10                  15

Leu Leu Glu Ala Cys
            20

<210> SEQ ID NO 633
<211> LENGTH: 14
<212> TYPE: PRT
<213> ORGANISM: Homo sapiens

<400> SEQUENCE: 633

Cys Phe Phe Gly Asn Ile Trp Glu Phe Ile Lys Ser Ile Leu
1               5                   10

<210> SEQ ID NO 634
<211> LENGTH: 14
<212> TYPE: PRT
<213> ORGANISM: Homo sapiens

<400> SEQUENCE: 634

Cys Phe Phe Gly Ala Ile Trp Leu Phe Ile Lys Ser Ile Leu
1               5                   10

<210> SEQ ID NO 635
<211> LENGTH: 14
<212> TYPE: PRT
<213> ORGANISM: Homo sapiens

<400> SEQUENCE: 635

Cys Phe Phe Gly Ala Ile Trp Asn Phe Ile Lys Ser Ile Leu
1               5                   10

<210> SEQ ID NO 636
<211> LENGTH: 14
<212> TYPE: PRT
<213> ORGANISM: Homo sapiens

<400> SEQUENCE: 636

Cys Phe Phe Gly Ala Ile Trp Gly Phe Ile Lys Ser Ile Leu
1               5                   10

<210> SEQ ID NO 637
<211> LENGTH: 14
<212> TYPE: PRT
<213> ORGANISM: Homo sapiens

<400> SEQUENCE: 637

Cys Phe Leu Gly Ala Leu Phe Lys Ala Leu Ser Lys Leu Leu
1               5                   10

<210> SEQ ID NO 638
<211> LENGTH: 14
<212> TYPE: PRT
<213> ORGANISM: Homo sapiens

<400> SEQUENCE: 638

Cys Phe Leu Gly Ala Leu Phe His Ala Leu Ser Lys Leu Leu
1               5                   10

<210> SEQ ID NO 639
<211> LENGTH: 14
<212> TYPE: PRT
<213> ORGANISM: Homo sapiens

<400> SEQUENCE: 639
```

Cys Phe Leu Gly Ala Leu Phe Lys Ala Leu Ser His Leu Leu
1               5                   10

<210> SEQ ID NO 640
<211> LENGTH: 14
<212> TYPE: PRT
<213> ORGANISM: Homo sapiens

<400> SEQUENCE: 640

Cys Phe Leu Gly Ala Leu Phe His Ala Leu Ser His Leu Leu
1               5                   10

<210> SEQ ID NO 641
<211> LENGTH: 14
<212> TYPE: PRT
<213> ORGANISM: Homo sapiens

<400> SEQUENCE: 641

Phe Leu Gly Ala Leu Phe Lys Ala Leu Ser Lys Leu Leu Cys
1               5                   10

<210> SEQ ID NO 642
<211> LENGTH: 14
<212> TYPE: PRT
<213> ORGANISM: Homo sapiens

<400> SEQUENCE: 642

Phe Leu Gly Ala Leu Phe His Ala Leu Ser Lys Leu Leu Cys
1               5                   10

<210> SEQ ID NO 643
<211> LENGTH: 14
<212> TYPE: PRT
<213> ORGANISM: Homo sapiens

<400> SEQUENCE: 643

Phe Leu Gly Ala Leu Phe Lys Ala Leu Ser His Leu Leu Cys
1               5                   10

<210> SEQ ID NO 644
<211> LENGTH: 14
<212> TYPE: PRT
<213> ORGANISM: Homo sapiens

<400> SEQUENCE: 644

Phe Leu Gly Ala Leu Phe His Ala Leu Ser His Leu Leu Cys
1               5                   10

<210> SEQ ID NO 645
<211> LENGTH: 14
<212> TYPE: PRT
<213> ORGANISM: Homo sapiens

<400> SEQUENCE: 645

Cys Phe Leu Gly Ala Leu Phe Lys Ala Leu Lys Ser Leu Leu
1               5                   10

<210> SEQ ID NO 646
<211> LENGTH: 14
<212> TYPE: PRT
<213> ORGANISM: Homo sapiens

<400> SEQUENCE: 646

Cys Phe Leu Gly Ala Leu Phe His Ala Leu Lys Ser Leu Leu
1               5                   10

<210> SEQ ID NO 647
<211> LENGTH: 14
<212> TYPE: PRT
<213> ORGANISM: Homo sapiens

<400> SEQUENCE: 647

Cys Phe Leu Gly Ala Leu Phe Lys Ala Leu His Ser Leu Leu
1               5                   10

<210> SEQ ID NO 648
<211> LENGTH: 14
<212> TYPE: PRT
<213> ORGANISM: Homo sapiens

<400> SEQUENCE: 648

Cys Phe Leu Gly Ala Leu Phe His Ala Leu His Ser Leu Leu
1               5                   10

<210> SEQ ID NO 649
<211> LENGTH: 14
<212> TYPE: PRT
<213> ORGANISM: Homo sapiens

<400> SEQUENCE: 649

Phe Leu Gly Ala Leu Phe Lys Ala Leu Lys Ser Leu Leu Cys
1               5                   10

<210> SEQ ID NO 650
<211> LENGTH: 14
<212> TYPE: PRT
<213> ORGANISM: Homo sapiens

<400> SEQUENCE: 650

Phe Leu Gly Ala Leu Phe His Ala Leu Lys Ser Leu Leu Cys
1               5                   10

<210> SEQ ID NO 651
<211> LENGTH: 14
<212> TYPE: PRT
<213> ORGANISM: Homo sapiens

<400> SEQUENCE: 651

Phe Leu Gly Ala Leu Phe Lys Ala Leu His Ser Leu Leu Cys
1               5                   10

<210> SEQ ID NO 652
<211> LENGTH: 14
<212> TYPE: PRT
<213> ORGANISM: Homo sapiens

<400> SEQUENCE: 652

Phe Leu Gly Ala Leu Phe His Ala Leu His Ser Leu Leu Cys
1               5                   10

<210> SEQ ID NO 653
<211> LENGTH: 21
<212> TYPE: PRT
<213> ORGANISM: Homo sapiens

<400> SEQUENCE: 653

Cys Gly Ile Phe Gly Ala Ile Ala Gly Phe Ile Lys Asn Ile Trp Lys
1               5                   10                  15

Gly Leu Ile Asp Trp

```
                    20

<210> SEQ ID NO 654
<211> LENGTH: 36
<212> TYPE: PRT
<213> ORGANISM: Homo sapiens

<400> SEQUENCE: 654

Cys Gly Leu Phe Glu Ala Ile Glu Gly Phe Ile Glu Asn Gly Trp Glu
1               5                   10                  15

Gly Asn Leu Glu Ile Asp Gly Trp Tyr Gly Tyr Gly Arg Lys Lys Arg
            20                  25                  30

Arg Gln Arg Arg
            35

<210> SEQ ID NO 655
<211> LENGTH: 34
<212> TYPE: PRT
<213> ORGANISM: Homo sapiens

<400> SEQUENCE: 655

Cys Gly Leu Phe Glu Ala Ile Glu Gly Phe Ile Glu Asn Gly Leu Lys
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 656
<211> LENGTH: 34
<212> TYPE: PRT
<213> ORGANISM: Homo sapiens

<400> SEQUENCE: 656

Cys Gly Leu Phe Glu Ala Ile Glu Gly Phe Ile Glu Asn Ala Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 657
<211> LENGTH: 34
<212> TYPE: PRT
<213> ORGANISM: Homo sapiens

<400> SEQUENCE: 657

Cys Gly Leu Phe Glu Ala Ile Glu Gly Phe Ile Glu Asn Gly Trp Glu
1               5                   10                  15

Gly Met Ile Asp Leu Trp Tyr Gly Tyr Gly Arg Lys Lys Arg Arg Gln
            20                  25                  30

Arg Arg

<210> SEQ ID NO 658
<211> LENGTH: 19
<212> TYPE: PRT
<213> ORGANISM: Homo sapiens

<400> SEQUENCE: 658

Cys Arg Leu Leu Arg Leu Leu Leu Arg Leu Trp Arg Arg Leu Leu Arg
1               5                   10                  15

Leu Leu Arg
```

<210> SEQ ID NO 659
<211> LENGTH: 33
<212> TYPE: PRT
<213> ORGANISM: Homo sapiens

<400> SEQUENCE: 659

Cys Gly Ile Phe Gly Ala Ile Glu Gly Phe Ile Glu Asn Gly Trp Lys
1               5                   10                  15

Gly Leu Ile Asp Ala Trp Tyr Gly Tyr Arg Lys Arg Arg Gln Arg
            20                  25                  30

Arg

<210> SEQ ID NO 660
<211> LENGTH: 14
<212> TYPE: PRT
<213> ORGANISM: Homo sapiens

<400> SEQUENCE: 660

Cys Phe Phe Gly Ala Ile Trp Glu Phe Ala His Gly Ile Leu
1               5                   10

<210> SEQ ID NO 661
<211> LENGTH: 17
<212> TYPE: PRT
<213> ORGANISM: Homo sapiens

<400> SEQUENCE: 661

Cys Phe Phe Gly Ala Ile Trp Glu Phe Ala Arg Gly Ile Leu Glu Gly
1               5                   10                  15

Phe

<210> SEQ ID NO 662
<211> LENGTH: 14
<212> TYPE: PRT
<213> ORGANISM: Homo sapiens

<400> SEQUENCE: 662

Phe Phe Gly Ala Ile Trp Glu Phe Ala His Gly Ile Leu Cys
1               5                   10

<210> SEQ ID NO 663
<211> LENGTH: 17
<212> TYPE: PRT
<213> ORGANISM: Homo sapiens

<400> SEQUENCE: 663

Phe Phe Gly Ala Ile Trp Glu Phe Ala Arg Gly Ile Leu Glu Gly Phe
1               5                   10                  15

Cys

<210> SEQ ID NO 664
<211> LENGTH: 14
<212> TYPE: PRT
<213> ORGANISM: Homo sapiens

<400> SEQUENCE: 664

Cys Phe Phe Gly Ala Ile Trp Glu Phe Ala His Ser Ile Leu
1               5                   10

<210> SEQ ID NO 665
<211> LENGTH: 14

```
<212> TYPE: PRT
<213> ORGANISM: Homo sapiens

<400> SEQUENCE: 665

Phe Phe Gly Ala Ile Trp Glu Phe Ala His Ser Ile Leu Cys
1               5                   10

<210> SEQ ID NO 666
<211> LENGTH: 15
<212> TYPE: PRT
<213> ORGANISM: Homo sapiens

<400> SEQUENCE: 666

Cys Phe Phe Gly Ala Ile Trp Glu Phe Ala Arg Ser Ile Leu Lys
1               5                   10                  15

<210> SEQ ID NO 667
<211> LENGTH: 15
<212> TYPE: PRT
<213> ORGANISM: Homo sapiens

<400> SEQUENCE: 667

Phe Phe Gly Ala Ile Trp Glu Phe Ala Arg Ser Ile Leu Lys Cys
1               5                   10                  15

<210> SEQ ID NO 668
<211> LENGTH: 16
<212> TYPE: PRT
<213> ORGANISM: Homo sapiens

<400> SEQUENCE: 668

Cys Gly Ile Phe Glu Ala Ile Ala Gly Leu Ala Lys Asn Ile Phe Lys
1               5                   10                  15

<210> SEQ ID NO 669
<211> LENGTH: 16
<212> TYPE: PRT
<213> ORGANISM: Homo sapiens

<400> SEQUENCE: 669

Gly Ile Phe Glu Ala Ile Ala Gly Leu Ala Lys Asn Ile Phe Lys Cys
1               5                   10                  15

<210> SEQ ID NO 670
<211> LENGTH: 16
<212> TYPE: PRT
<213> ORGANISM: Homo sapiens

<400> SEQUENCE: 670

Cys Gly Ile Phe Glu Ala Ile Ala Gly Leu Ala Lys Asn Ile Phe His
1               5                   10                  15

<210> SEQ ID NO 671
<211> LENGTH: 16
<212> TYPE: PRT
<213> ORGANISM: Homo sapiens

<400> SEQUENCE: 671

Cys Gly Ile Phe Glu Ala Ile Ala Gly Leu Ala His Asn Ile Phe His
1               5                   10                  15

<210> SEQ ID NO 672
<211> LENGTH: 16
<212> TYPE: PRT
```

-continued

<400> SEQUENCE: 672

Cys Gly Ile Phe Glu Ala Ile Ala Gly Leu Ala His Asn Ile Phe Lys
1               5                   10                  15

<210> SEQ ID NO 673
<211> LENGTH: 16
<212> TYPE: PRT
<213> ORGANISM: Homo sapiens

<400> SEQUENCE: 673

Gly Ile Phe Glu Ala Ile Ala Gly Leu Ala Lys Asn Ile Phe His Cys
1               5                   10                  15

<210> SEQ ID NO 674
<211> LENGTH: 16
<212> TYPE: PRT
<213> ORGANISM: Homo sapiens

<400> SEQUENCE: 674

Gly Ile Phe Glu Ala Ile Ala Gly Leu Ala His Asn Ile Phe His Cys
1               5                   10                  15

<210> SEQ ID NO 675
<211> LENGTH: 14
<212> TYPE: PRT
<213> ORGANISM: Homo sapiens

<400> SEQUENCE: 675

Cys Phe Leu Gly Ala Leu Trp Lys Ala Leu Ser Lys Leu Leu
1               5                   10

<210> SEQ ID NO 676
<211> LENGTH: 14
<212> TYPE: PRT
<213> ORGANISM: Homo sapiens

<400> SEQUENCE: 676

Cys Phe Leu Gly Ala Leu Trp His Ala Leu Ser Lys Leu Leu
1               5                   10

<210> SEQ ID NO 677
<211> LENGTH: 14
<212> TYPE: PRT
<213> ORGANISM: Homo sapiens

<400> SEQUENCE: 677

Cys Phe Leu Gly Ala Leu Trp Lys Ala Leu Ser His Leu Leu
1               5                   10

<210> SEQ ID NO 678
<211> LENGTH: 14
<212> TYPE: PRT
<213> ORGANISM: Homo sapiens

<400> SEQUENCE: 678

Cys Phe Leu Gly Ala Leu Trp His Ala Leu Ser His Leu Leu
1               5                   10

<210> SEQ ID NO 679
<211> LENGTH: 14
<212> TYPE: PRT
<213> ORGANISM: Homo sapiens

<400> SEQUENCE: 679

Phe Leu Gly Ala Leu Trp Lys Ala Leu Ser Lys Leu Leu Cys
1               5                   10

<210> SEQ ID NO 680
<211> LENGTH: 14
<212> TYPE: PRT
<213> ORGANISM: Homo sapiens

<400> SEQUENCE: 680

Phe Leu Gly Ala Leu Trp His Ala Leu Ser Lys Leu Leu Cys
1               5                   10

<210> SEQ ID NO 681
<211> LENGTH: 14
<212> TYPE: PRT
<213> ORGANISM: Homo sapiens

<400> SEQUENCE: 681

Phe Leu Gly Ala Leu Trp Lys Ala Leu Ser His Leu Leu Cys
1               5                   10

<210> SEQ ID NO 682
<211> LENGTH: 14
<212> TYPE: PRT
<213> ORGANISM: Homo sapiens

<400> SEQUENCE: 682

Phe Leu Gly Ala Leu Trp His Ala Leu Ser His Leu Leu Cys
1               5                   10

<210> SEQ ID NO 683
<211> LENGTH: 16
<212> TYPE: PRT
<213> ORGANISM: Homo sapiens

<400> SEQUENCE: 683

Cys Gly Ile Phe Gly Ala Ile Ala Gly Leu Leu Lys Asn Ala Phe Lys
1               5                   10                  15

<210> SEQ ID NO 684
<211> LENGTH: 15
<212> TYPE: PRT
<213> ORGANISM: Homo sapiens

<400> SEQUENCE: 684

Cys Ile Phe Glu Ala Ile Ala Gly Leu Leu Lys Asn Ala Phe Lys
1               5                   10                  15

<210> SEQ ID NO 685
<211> LENGTH: 15
<212> TYPE: PRT
<213> ORGANISM: Homo sapiens

<400> SEQUENCE: 685

Cys Ile Phe Gly Ala Ile Ala Gly Leu Leu Lys Asn Ala Phe Lys
1               5                   10                  15

<210> SEQ ID NO 686
<211> LENGTH: 14
<212> TYPE: PRT
<213> ORGANISM: Homo sapiens

<400> SEQUENCE: 686

Cys Ile Phe Glu Ala Ile Trp Glu Phe Ile Lys Asn Ile Trp

```
1               5                   10
```

<210> SEQ ID NO 687
<211> LENGTH: 14
<212> TYPE: PRT
<213> ORGANISM: Homo sapiens

<400> SEQUENCE: 687

```
Cys Ile Phe Glu Ala Ile Ala Glu Phe Ile Lys Asn Ile Trp
1               5                   10
```

<210> SEQ ID NO 688
<211> LENGTH: 14
<212> TYPE: PRT
<213> ORGANISM: Homo sapiens

<400> SEQUENCE: 688

```
Cys Ile Phe Gly Ala Ile Trp Glu Phe Ile Lys Asn Ile Trp
1               5                   10
```

<210> SEQ ID NO 689
<211> LENGTH: 14
<212> TYPE: PRT
<213> ORGANISM: Homo sapiens

<400> SEQUENCE: 689

```
Cys Ile Phe Gly Ala Ile Ala Glu Phe Ile Lys Asn Ile Trp
1               5                   10
```

<210> SEQ ID NO 690
<211> LENGTH: 15
<212> TYPE: PRT
<213> ORGANISM: Homo sapiens

<400> SEQUENCE: 690

```
Cys Gly Ile Phe Gly Ile Ala Ile Gly Phe Lys Ile Asn Ile Trp
1               5                   10                  15
```

<210> SEQ ID NO 691
<211> LENGTH: 16
<212> TYPE: PRT
<213> ORGANISM: Homo sapiens

<400> SEQUENCE: 691

```
Cys Gly Ile Phe Glu Ala Ile Ala Gly Leu Leu His Asn Ile Phe Lys
1               5                   10                  15
```

<210> SEQ ID NO 692
<211> LENGTH: 16
<212> TYPE: PRT
<213> ORGANISM: Homo sapiens

<400> SEQUENCE: 692

```
Cys Gly Ile Phe Glu Ala Ile Trp Gly Leu Leu His Asn Ile Phe Lys
1               5                   10                  15
```

<210> SEQ ID NO 693
<211> LENGTH: 16
<212> TYPE: PRT
<213> ORGANISM: Homo sapiens

<400> SEQUENCE: 693

```
Cys Gly Phe Phe Glu Ala Ile Ala Gly Leu Leu His Asn Ile Phe Lys
1               5                   10                  15
```

```
<210> SEQ ID NO 694
<211> LENGTH: 16
<212> TYPE: PRT
<213> ORGANISM: Homo sapiens

<400> SEQUENCE: 694

Cys Gly Ile Phe Glu Ala Ile Ala Ala Leu Leu Lys Asn Ile Phe Lys
1               5                   10                  15

<210> SEQ ID NO 695
<211> LENGTH: 16
<212> TYPE: PRT
<213> ORGANISM: Homo sapiens

<400> SEQUENCE: 695

Cys Gly Ile Phe Glu Ala Ile Glu Gly Leu Leu Lys Asn Ile Phe Lys
1               5                   10                  15

<210> SEQ ID NO 696
<211> LENGTH: 16
<212> TYPE: PRT
<213> ORGANISM: Homo sapiens

<400> SEQUENCE: 696

Cys Gly Ile Phe Glu Ala Ile Ala Gly Phe Phe Lys Asn Ile Phe Lys
1               5                   10                  15

<210> SEQ ID NO 697
<211> LENGTH: 16
<212> TYPE: PRT
<213> ORGANISM: Homo sapiens

<400> SEQUENCE: 697

Cys Gly Ile Phe Glu Ala Ile Ala Gly Trp Trp Lys Asn Ile Phe Lys
1               5                   10                  15

<210> SEQ ID NO 698
<211> LENGTH: 16
<212> TYPE: PRT
<213> ORGANISM: Homo sapiens

<400> SEQUENCE: 698

Cys Gly Ile Phe Glu Ala Ile Ala Gly Leu Leu Lys Asn Ile Trp Lys
1               5                   10                  15

<210> SEQ ID NO 699
<211> LENGTH: 16
<212> TYPE: PRT
<213> ORGANISM: Homo sapiens

<400> SEQUENCE: 699

Cys Gly Ile Phe Glu Ala Ile Ala Glu Leu Leu Lys Asn Ile Phe Lys
1               5                   10                  15

<210> SEQ ID NO 700
<211> LENGTH: 16
<212> TYPE: PRT
<213> ORGANISM: Homo sapiens

<400> SEQUENCE: 700

Cys Gly Ile Phe Gly Ala Ile Ala Gly Leu Leu Lys Ser Ala Leu Lys
1               5                   10                  15

<210> SEQ ID NO 701
```

```
<211> LENGTH: 16
<212> TYPE: PRT
<213> ORGANISM: Homo sapiens

<400> SEQUENCE: 701

Cys Gly Ile Phe Glu Ala Ile Ala Gly Leu Leu Lys Ser Ile Trp Lys
1               5                   10                  15

<210> SEQ ID NO 702
<211> LENGTH: 16
<212> TYPE: PRT
<213> ORGANISM: Homo sapiens

<400> SEQUENCE: 702

Cys Gly Ile Phe Glu Ala Ile Ala Gly Leu Leu Lys Ser Ile Leu Lys
1               5                   10                  15

<210> SEQ ID NO 703
<211> LENGTH: 21
<212> TYPE: PRT
<213> ORGANISM: Homo sapiens

<400> SEQUENCE: 703

Cys Gly Ile Phe Glu Ala Ile Ala Gly Leu Leu Lys Asn Ile Phe Lys
1               5                   10                  15

Gly Leu Ile Asp Ala
            20

<210> SEQ ID NO 704
<211> LENGTH: 22
<212> TYPE: PRT
<213> ORGANISM: Homo sapiens

<400> SEQUENCE: 704

Cys Gly Ile Phe Glu Ala Ile Ala Gly Leu Leu Lys Asn Ile Phe Lys
1               5                   10                  15

Gly Leu Ile Asp Ala Phe
            20

<210> SEQ ID NO 705
<211> LENGTH: 24
<212> TYPE: PRT
<213> ORGANISM: Homo sapiens

<400> SEQUENCE: 705

Cys Gly Ile Phe Glu Ala Ile Ala Gly Leu Leu Lys Asn Ile Phe Lys
1               5                   10                  15

Gly Leu Ile Asp Ala Trp Tyr Gly
            20

<210> SEQ ID NO 706
<211> LENGTH: 24
<212> TYPE: PRT
<213> ORGANISM: Homo sapiens

<400> SEQUENCE: 706

Cys Gly Ile Phe Glu Ala Ile Ala Gly Leu Leu Lys Asn Ile Phe Lys
1               5                   10                  15

Gly Leu Ile Asp Ala Trp Tyr Gly
            20

<210> SEQ ID NO 707
<211> LENGTH: 25
```

```
<212> TYPE: PRT
<213> ORGANISM: Homo sapiens

<400> SEQUENCE: 707

Cys Gly Ile Phe Glu Ala Ile Ala Gly Leu Leu Lys Asn Ile Phe Lys
1               5                   10                  15

Gly Leu Ile Asp Gly Trp Tyr Gly Phe
            20                  25

<210> SEQ ID NO 708
<211> LENGTH: 21
<212> TYPE: PRT
<213> ORGANISM: Homo sapiens

<400> SEQUENCE: 708

Cys Gly Ile Phe Glu Ala Ile Ala Gly Leu Leu Lys Asn Ile Phe Lys
1               5                   10                  15

Gly Leu Ile Asp Trp
            20

<210> SEQ ID NO 709
<211> LENGTH: 22
<212> TYPE: PRT
<213> ORGANISM: Homo sapiens

<400> SEQUENCE: 709

Cys Gly Ile Phe Glu Ala Ile Ala Gly Leu Leu Lys Asn Ile Phe Lys
1               5                   10                  15

Gly Leu Ile Asp Trp Phe
            20

<210> SEQ ID NO 710
<211> LENGTH: 24
<212> TYPE: PRT
<213> ORGANISM: Homo sapiens

<400> SEQUENCE: 710

Cys Gly Ile Phe Glu Ala Ile Ala Gly Leu Leu Lys Asn Ile Phe Lys
1               5                   10                  15

Gly Leu Ile Asp Trp Trp Tyr Gly
            20

<210> SEQ ID NO 711
<211> LENGTH: 25
<212> TYPE: PRT
<213> ORGANISM: Homo sapiens

<400> SEQUENCE: 711

Cys Gly Ile Phe Glu Ala Ile Ala Gly Leu Leu Lys Asn Ile Phe Lys
1               5                   10                  15

Gly Leu Ile Asp Trp Trp Tyr Gly Phe
            20                  25

<210> SEQ ID NO 712
<211> LENGTH: 16
<212> TYPE: PRT
<213> ORGANISM: Homo sapiens

<400> SEQUENCE: 712

Cys Gly Ile Phe Glu Leu Ile Ala Gly Leu Leu Lys Asn Ile Phe Lys
1               5                   10                  15
```

```
<210> SEQ ID NO 713
<211> LENGTH: 16
<212> TYPE: PRT
<213> ORGANISM: Homo sapiens

<400> SEQUENCE: 713

Cys Gly Ile Phe Glu Ala Ile Ala Gly Leu Leu Lys Trp Ile Phe Lys
1               5                   10                  15

<210> SEQ ID NO 714
<211> LENGTH: 16
<212> TYPE: PRT
<213> ORGANISM: Homo sapiens

<400> SEQUENCE: 714

Cys Gly Ile Phe Glu Leu Ile Ala Gly Leu Leu Lys Trp Ile Phe Lys
1               5                   10                  15

<210> SEQ ID NO 715
<211> LENGTH: 17
<212> TYPE: PRT
<213> ORGANISM: Homo sapiens

<400> SEQUENCE: 715

Cys Gly Ile Phe Glu Leu Ile Ala Gly Leu Leu Lys Asn Ile Phe Lys
1               5                   10                  15
Gly

<210> SEQ ID NO 716
<211> LENGTH: 17
<212> TYPE: PRT
<213> ORGANISM: Homo sapiens

<400> SEQUENCE: 716

Cys Gly Ile Phe Glu Ala Ile Ala Gly Leu Leu Lys Trp Ile Phe Lys
1               5                   10                  15
Gly

<210> SEQ ID NO 717
<211> LENGTH: 17
<212> TYPE: PRT
<213> ORGANISM: Homo sapiens

<400> SEQUENCE: 717

Cys Gly Ile Phe Glu Leu Ile Ala Gly Leu Leu Lys Trp Ile Phe Lys
1               5                   10                  15
Gly

<210> SEQ ID NO 718
<211> LENGTH: 16
<212> TYPE: PRT
<213> ORGANISM: Homo sapiens

<400> SEQUENCE: 718

Cys Gly Leu Phe Glu Ala Leu Leu Gly Leu Leu Glu Ser Leu Trp Lys
1               5                   10                  15

<210> SEQ ID NO 719
<211> LENGTH: 16
<212> TYPE: PRT
<213> ORGANISM: Homo sapiens

<400> SEQUENCE: 719
```

```
Cys Gly Ile Phe Glu Ala Ile Ala Glu Leu Leu Lys Asn Ile Phe Lys
1               5                   10                  15
```

<210> SEQ ID NO 720
<211> LENGTH: 16
<212> TYPE: PRT
<213> ORGANISM: Homo sapiens

<400> SEQUENCE: 720

```
Cys Gly Ile Phe Glu Ala Leu Leu Gly Leu Leu Lys Ser Leu Trp Lys
1               5                   10                  15
```

<210> SEQ ID NO 721
<211> LENGTH: 16
<212> TYPE: PRT
<213> ORGANISM: Homo sapiens

<400> SEQUENCE: 721

```
Cys Gly Ile Phe Glu Ala Leu Leu Gly Leu Leu Lys Ser Leu Trp Lys
1               5                   10                  15
```

<210> SEQ ID NO 722
<211> LENGTH: 16
<212> TYPE: PRT
<213> ORGANISM: Homo sapiens

<400> SEQUENCE: 722

```
Cys Gly Ile Phe Glu Ala Ile Ala Gly Leu Leu Lys Asn Ile Phe Lys
1               5                   10                  15
```

<210> SEQ ID NO 723
<211> LENGTH: 16
<212> TYPE: PRT
<213> ORGANISM: Homo sapiens

<400> SEQUENCE: 723

```
Cys Glu Ile Phe Glu Ala Ile Ala Gly Leu Leu Lys Asn Ile Phe Lys
1               5                   10                  15
```

<210> SEQ ID NO 724
<211> LENGTH: 16
<212> TYPE: PRT
<213> ORGANISM: Homo sapiens

<400> SEQUENCE: 724

```
Cys Glu Ile Phe Gly Ala Ile Ala Gly Leu Leu Lys Asn Ile Phe Lys
1               5                   10                  15
```

<210> SEQ ID NO 725
<211> LENGTH: 16
<212> TYPE: PRT
<213> ORGANISM: Homo sapiens

<400> SEQUENCE: 725

```
Cys Gly Leu Phe Glu Ala Ile Ala Gly Leu Leu Lys Asn Leu Phe Lys
1               5                   10                  15
```

<210> SEQ ID NO 726
<211> LENGTH: 16
<212> TYPE: PRT
<213> ORGANISM: Homo sapiens

<400> SEQUENCE: 726

```
Cys Gly Ile Trp Glu Ala Ile Ala Gly Leu Leu Lys Asn Ile Trp Lys
1               5                   10                  15
```

```
<210> SEQ ID NO 727
<211> LENGTH: 16
<212> TYPE: PRT
<213> ORGANISM: Homo sapiens

<400> SEQUENCE: 727

Cys Gly Leu Phe Gly Ala Ile Ala Gly Leu Leu Lys Asn Leu Phe Lys
1               5                   10                  15

<210> SEQ ID NO 728
<211> LENGTH: 16
<212> TYPE: PRT
<213> ORGANISM: Homo sapiens

<400> SEQUENCE: 728

Cys Gly Ile Trp Gly Ala Ile Ala Gly Leu Leu Lys Asn Ile Trp Lys
1               5                   10                  15

<210> SEQ ID NO 729
<211> LENGTH: 16
<212> TYPE: PRT
<213> ORGANISM: Homo sapiens

<400> SEQUENCE: 729

Cys Gly Ile Phe Asp Ala Ile Ala Gly Leu Leu Lys Asn Ile Phe Lys
1               5                   10                  15

<210> SEQ ID NO 730
<211> LENGTH: 16
<212> TYPE: PRT
<213> ORGANISM: Homo sapiens

<400> SEQUENCE: 730

Cys Gly Ile Phe Asp Ala Ile Trp Gly Leu Leu Lys Asn Ile Phe Lys
1               5                   10                  15

<210> SEQ ID NO 731
<211> LENGTH: 16
<212> TYPE: PRT
<213> ORGANISM: Homo sapiens

<400> SEQUENCE: 731

Cys Gly Ile Phe Gly Gly Ile Gly Gly Leu Leu Lys Asn Ile Phe Lys
1               5                   10                  15

<210> SEQ ID NO 732
<211> LENGTH: 16
<212> TYPE: PRT
<213> ORGANISM: Homo sapiens

<400> SEQUENCE: 732

Cys Ala Ile Phe Ala Ala Ile Ala Ala Leu Leu Lys Asn Ile Phe Lys
1               5                   10                  15

<210> SEQ ID NO 733
<211> LENGTH: 15
<212> TYPE: PRT
<213> ORGANISM: Homo sapiens

<400> SEQUENCE: 733

Cys Gly Ile Phe Glu Ala Ile Ala Gly Leu Leu Lys Asn Ile Phe
1               5                   10                  15
```

```
<210> SEQ ID NO 734
<211> LENGTH: 14
<212> TYPE: PRT
<213> ORGANISM: Homo sapiens

<400> SEQUENCE: 734

Cys Gly Ile Phe Glu Ala Ile Ala Gly Leu Leu Lys Asn Ile
1               5                   10

<210> SEQ ID NO 735
<211> LENGTH: 13
<212> TYPE: PRT
<213> ORGANISM: Homo sapiens

<400> SEQUENCE: 735

Cys Gly Ile Phe Glu Ala Ile Ala Gly Leu Leu Lys Asn
1               5                   10

<210> SEQ ID NO 736
<211> LENGTH: 12
<212> TYPE: PRT
<213> ORGANISM: Homo sapiens

<400> SEQUENCE: 736

Cys Gly Ile Phe Glu Ala Ile Ala Gly Leu Leu Lys
1               5                   10

<210> SEQ ID NO 737
<211> LENGTH: 16
<212> TYPE: PRT
<213> ORGANISM: Homo sapiens

<400> SEQUENCE: 737

Cys Val Ile Phe Glu Ala Ile Ala Gly Leu Leu Lys Asn Ile Phe Lys
1               5                   10                  15

<210> SEQ ID NO 738
<211> LENGTH: 16
<212> TYPE: PRT
<213> ORGANISM: Homo sapiens

<400> SEQUENCE: 738

Cys Ser Ile Phe Glu Ala Ile Ala Gly Leu Leu Lys Asn Ile Phe Lys
1               5                   10                  15

<210> SEQ ID NO 739
<211> LENGTH: 16
<212> TYPE: PRT
<213> ORGANISM: Homo sapiens

<400> SEQUENCE: 739

Cys Gly Ile Phe Glu Glu Ile Ala Gly Leu Leu Lys Asn Ile Phe Lys
1               5                   10                  15

<210> SEQ ID NO 740
<211> LENGTH: 16
<212> TYPE: PRT
<213> ORGANISM: Homo sapiens

<400> SEQUENCE: 740

Cys Gly Ile Phe Glu Glu Ile Trp Gly Leu Leu Lys Asn Ile Phe Lys
1               5                   10                  15

<210> SEQ ID NO 741
<211> LENGTH: 16
```

-continued

<212> TYPE: PRT
<213> ORGANISM: Homo sapiens

<400> SEQUENCE: 741

Cys Gly Ile Phe Glu Ala Ile Glu Glu Leu Leu Lys Asn Ile Phe Lys
1               5                   10                  15

<210> SEQ ID NO 742
<211> LENGTH: 16
<212> TYPE: PRT
<213> ORGANISM: Homo sapiens

<400> SEQUENCE: 742

Cys Gly Ile Phe Glu Ala Ile Ala Gly Leu Trp Lys Asn Ile Phe Lys
1               5                   10                  15

<210> SEQ ID NO 743
<211> LENGTH: 16
<212> TYPE: PRT
<213> ORGANISM: Homo sapiens

<400> SEQUENCE: 743

Cys Gly Ile Phe Glu Ala Ile Ala Gly Leu Leu Glu Asn Ile Phe Lys
1               5                   10                  15

<210> SEQ ID NO 744
<211> LENGTH: 16
<212> TYPE: PRT
<213> ORGANISM: Homo sapiens

<400> SEQUENCE: 744

Cys Gly Ile Phe Glu Ala Ile Ala Gly Leu Leu Trp Asn Ile Phe Lys
1               5                   10                  15

<210> SEQ ID NO 745
<211> LENGTH: 16
<212> TYPE: PRT
<213> ORGANISM: Homo sapiens

<400> SEQUENCE: 745

Cys Gly Ile Phe Glu Ala Ile Ala Gly Leu Leu Lys Glu Ile Phe Lys
1               5                   10                  15

<210> SEQ ID NO 746
<211> LENGTH: 16
<212> TYPE: PRT
<213> ORGANISM: Homo sapiens

<400> SEQUENCE: 746

Cys Gly Ile Phe Glu Ala Ile Ala Gly Leu Leu Lys Asn Ile Leu Lys
1               5                   10                  15

<210> SEQ ID NO 747
<211> LENGTH: 16
<212> TYPE: PRT
<213> ORGANISM: Homo sapiens

<400> SEQUENCE: 747

Cys Gly Ile Phe Glu Ala Ile Ala Gly Leu Leu Arg Asn Ile Phe Lys
1               5                   10                  15

<210> SEQ ID NO 748
<211> LENGTH: 16
<212> TYPE: PRT

```
<400> SEQUENCE: 748

Cys Gly Ile Phe Glu Ala Ile Ala Gly Leu Leu Lys Ser Ile Phe Lys
1               5                   10                  15

<210> SEQ ID NO 749
<211> LENGTH: 16
<212> TYPE: PRT
<213> ORGANISM: Homo sapiens

<400> SEQUENCE: 749

Cys Gly Ile Phe Glu Ala Ile Ala Gly Leu Leu Lys Asn Ile Leu Lys
1               5                   10                  15

<210> SEQ ID NO 750
<211> LENGTH: 16
<212> TYPE: PRT
<213> ORGANISM: Homo sapiens

<400> SEQUENCE: 750

Cys Gly Phe Phe Gly Ala Ile Trp Glu Phe Ile Lys Ser Ile Leu Lys
1               5                   10                  15

<210> SEQ ID NO 751
<211> LENGTH: 16
<212> TYPE: PRT
<213> ORGANISM: Homo sapiens

<400> SEQUENCE: 751

Cys Gly Phe Phe Glu Ala Ile Trp Glu Phe Ile Lys Ser Ile Leu Lys
1               5                   10                  15

<210> SEQ ID NO 752
<211> LENGTH: 16
<212> TYPE: PRT
<213> ORGANISM: Homo sapiens

<400> SEQUENCE: 752

Cys Gly Phe Phe Gly Ala Ile Trp Gly Leu Leu Lys Ser Ile Leu Lys
1               5                   10                  15

<210> SEQ ID NO 753
<211> LENGTH: 16
<212> TYPE: PRT
<213> ORGANISM: Homo sapiens

<400> SEQUENCE: 753

Cys Gly Phe Phe Glu Ala Ile Trp Gly Leu Leu Lys Ser Ile Leu Lys
1               5                   10                  15

<210> SEQ ID NO 754
<211> LENGTH: 16
<212> TYPE: PRT
<213> ORGANISM: Homo sapiens

<400> SEQUENCE: 754

Cys Gly Phe Phe Glu Ala Ile Ala Gly Leu Leu Lys Ser Ile Leu Lys
1               5                   10                  15

<210> SEQ ID NO 755
<211> LENGTH: 16
<212> TYPE: PRT
<213> ORGANISM: Homo sapiens

<400> SEQUENCE: 755
```

Cys Gly Phe Phe Gly Ala Ile Ala Gly Leu Leu Lys Ser Ile Leu Lys
1               5                   10                  15

<210> SEQ ID NO 756
<211> LENGTH: 19
<212> TYPE: PRT
<213> ORGANISM: Homo sapiens

<400> SEQUENCE: 756

Cys Gly Ile Phe Glu Ala Ile Ala Gly Leu Leu Lys Asn Ile Phe Glu
1               5                   10                  15

Gly Leu Ile

<210> SEQ ID NO 757
<211> LENGTH: 19
<212> TYPE: PRT
<213> ORGANISM: Homo sapiens

<400> SEQUENCE: 757

Cys Gly Ile Phe Glu Ala Ile Trp Gly Leu Leu Lys Asn Ile Phe Lys
1               5                   10                  15

Gly Leu Ile

<210> SEQ ID NO 758
<211> LENGTH: 19
<212> TYPE: PRT
<213> ORGANISM: Homo sapiens

<400> SEQUENCE: 758

Cys Gly Ile Phe Glu Ala Ile Trp Gly Leu Leu Lys Asn Ile Phe Glu
1               5                   10                  15

Gly Leu Ile

<210> SEQ ID NO 759
<211> LENGTH: 24
<212> TYPE: PRT
<213> ORGANISM: Homo sapiens

<400> SEQUENCE: 759

Cys Gly Ile Phe Glu Ala Ile Ala Gly Leu Leu Lys Asn Ile Leu Lys
1               5                   10                  15

Gly Leu Ile Asp Gly Trp Tyr Gly
            20

<210> SEQ ID NO 760
<211> LENGTH: 24
<212> TYPE: PRT
<213> ORGANISM: Homo sapiens

<400> SEQUENCE: 760

Cys Gly Ile Phe Gly Ala Ile Ala Gly Leu Leu Lys Asn Ile Leu Lys
1               5                   10                  15

Gly Leu Ile Asp Gly Trp Tyr Gly
            20

<210> SEQ ID NO 761
<211> LENGTH: 24
<212> TYPE: PRT
<213> ORGANISM: Homo sapiens

<400> SEQUENCE: 761

```
Cys Gly Ile Phe Gly Ala Ile Ala Gly Leu Leu Lys Asn Ile Phe Lys
1               5                   10                  15

Gly Leu Ile Asp Gly Trp Tyr Gly
            20
```

<210> SEQ ID NO 762
<211> LENGTH: 16
<212> TYPE: PRT
<213> ORGANISM: Homo sapiens

<400> SEQUENCE: 762

```
Cys Gly Ile Phe Gly Ala Ile Trp Glu Leu Trp Glu Trp Ile Leu Lys
1               5                   10                  15
```

<210> SEQ ID NO 763
<211> LENGTH: 16
<212> TYPE: PRT
<213> ORGANISM: Homo sapiens

<400> SEQUENCE: 763

```
Cys Gly Ile Phe Glu Ala Ile Trp Glu Leu Trp Glu Trp Ile Leu Lys
1               5                   10                  15
```

<210> SEQ ID NO 764
<211> LENGTH: 15
<212> TYPE: PRT
<213> ORGANISM: Homo sapiens

<400> SEQUENCE: 764

```
Cys Ile Phe Gly Ala Ile Trp Glu Leu Trp Glu Trp Ile Leu Lys
1               5                   10                  15
```

<210> SEQ ID NO 765
<211> LENGTH: 15
<212> TYPE: PRT
<213> ORGANISM: Homo sapiens

<400> SEQUENCE: 765

```
Cys Ile Phe Glu Ala Ile Trp Glu Leu Trp Glu Trp Ile Leu Lys
1               5                   10                  15
```

<210> SEQ ID NO 766
<211> LENGTH: 16
<212> TYPE: PRT
<213> ORGANISM: Homo sapiens

<400> SEQUENCE: 766

```
Cys Gly Ile Phe Glu Ala Ile Ala Glu Leu Trp Lys Asn Ile Phe Lys
1               5                   10                  15
```

<210> SEQ ID NO 767
<211> LENGTH: 16
<212> TYPE: PRT
<213> ORGANISM: Homo sapiens

<400> SEQUENCE: 767

```
Cys Gly Ile Phe Glu Ala Ile Ala Glu Leu Trp Glu Asn Ile Phe Lys
1               5                   10                  15
```

<210> SEQ ID NO 768
<211> LENGTH: 16
<212> TYPE: PRT
<213> ORGANISM: Homo sapiens

<400> SEQUENCE: 768

```
Cys Gly Ile Phe Glu Ala Ile Ala Glu Leu Trp Lys Trp Ile Phe Lys
1               5                   10                  15
```

<210> SEQ ID NO 769
<211> LENGTH: 16
<212> TYPE: PRT
<213> ORGANISM: Homo sapiens

<400> SEQUENCE: 769

```
Cys Gly Ile Phe Glu Ala Ile Ala Glu Leu Trp Glu Trp Ile Phe Lys
1               5                   10                  15
```

<210> SEQ ID NO 770
<211> LENGTH: 24
<212> TYPE: PRT
<213> ORGANISM: Homo sapiens

<400> SEQUENCE: 770

```
Cys Gly Ile Phe Glu Ala Ile Ala Gly Leu Leu Lys Asn Ile Leu Lys
1               5                   10                  15

Gly Leu Ile Asp Trp Trp Tyr Gly
            20
```

<210> SEQ ID NO 771
<211> LENGTH: 24
<212> TYPE: PRT
<213> ORGANISM: Homo sapiens

<400> SEQUENCE: 771

```
Cys Gly Ile Phe Gly Ala Ile Ala Gly Leu Leu Lys Asn Ile Leu Lys
1               5                   10                  15

Gly Leu Ile Asp Trp Trp Tyr Gly
            20
```

<210> SEQ ID NO 772
<211> LENGTH: 24
<212> TYPE: PRT
<213> ORGANISM: Homo sapiens

<400> SEQUENCE: 772

```
Cys Gly Ile Phe Gly Ala Ile Ala Gly Leu Leu Lys Asn Ile Phe Lys
1               5                   10                  15

Gly Leu Ile Asp Trp Trp Tyr Gly
            20
```

<210> SEQ ID NO 773
<211> LENGTH: 25
<212> TYPE: PRT
<213> ORGANISM: Homo sapiens

<400> SEQUENCE: 773

```
Cys Gly Ile Phe Glu Ala Ile Ala Gly Leu Leu Lys Asn Ile Leu Lys
1               5                   10                  15

Gly Leu Ile Asp Gly Trp Tyr Gly Phe
            20                  25
```

<210> SEQ ID NO 774
<211> LENGTH: 25
<212> TYPE: PRT
<213> ORGANISM: Homo sapiens

<400> SEQUENCE: 774

Cys Gly Ile Phe Gly Ala Ile Ala Gly Leu Leu Lys Asn Ile Leu Lys
1               5                   10                  15

Gly Leu Ile Asp Gly Trp Tyr Gly Phe
            20                  25

<210> SEQ ID NO 775
<211> LENGTH: 25
<212> TYPE: PRT
<213> ORGANISM: Homo sapiens

<400> SEQUENCE: 775

Cys Gly Ile Phe Gly Ala Ile Ala Gly Leu Leu Lys Asn Ile Phe Lys
1               5                   10                  15

Gly Leu Ile Asp Gly Trp Tyr Gly Phe
            20                  25

<210> SEQ ID NO 776
<211> LENGTH: 16
<212> TYPE: PRT
<213> ORGANISM: Homo sapiens

<400> SEQUENCE: 776

Cys Gly Ile Phe Gly Ala Ile Ala Glu Leu Leu Glu Lys Ile Phe Glu
1               5                   10                  15

<210> SEQ ID NO 777
<211> LENGTH: 16
<212> TYPE: PRT
<213> ORGANISM: Homo sapiens

<400> SEQUENCE: 777

Cys Gly Ile Phe Glu Ala Ile Ala Glu Leu Leu Glu Lys Ile Phe Glu
1               5                   10                  15

<210> SEQ ID NO 778
<211> LENGTH: 16
<212> TYPE: PRT
<213> ORGANISM: Homo sapiens

<400> SEQUENCE: 778

Cys Gly Phe Ile Gly Ala Ile Ala Glu Leu Leu Glu Lys Ile Phe Glu
1               5                   10                  15

<210> SEQ ID NO 779
<211> LENGTH: 16
<212> TYPE: PRT
<213> ORGANISM: Homo sapiens

<400> SEQUENCE: 779

Cys Gly Ile Phe Gly Ala Ile Ala Glu Leu Leu Glu Lys Ile Phe Lys
1               5                   10                  15

<210> SEQ ID NO 780
<211> LENGTH: 16
<212> TYPE: PRT
<213> ORGANISM: Homo sapiens

<400> SEQUENCE: 780

Cys Gly Ile Phe Glu Ala Ile Ala Glu Leu Leu Glu Lys Ile Phe Lys
1               5                   10                  15

<210> SEQ ID NO 781
<211> LENGTH: 16
<212> TYPE: PRT

-continued

<213> ORGANISM: Homo sapiens

<400> SEQUENCE: 781

Cys Gly Phe Ile Gly Ala Ile Ala Glu Leu Leu Glu Lys Ile Phe Lys
1               5                   10                  15

<210> SEQ ID NO 782
<211> LENGTH: 21
<212> TYPE: PRT
<213> ORGANISM: Homo sapiens

<400> SEQUENCE: 782

Cys Gly Leu Phe His Ala Leu Leu His Leu Leu His Ser Leu Trp His
1               5                   10                  15

Leu Leu Leu Glu Ala
            20

<210> SEQ ID NO 783
<211> LENGTH: 21
<212> TYPE: PRT
<213> ORGANISM: Homo sapiens

<400> SEQUENCE: 783

Gly Leu Phe His Ala Leu Leu His Leu Leu His Ser Leu Trp His Gly
1               5                   10                  15

Leu Leu Glu Ala Cys
            20

<210> SEQ ID NO 784
<211> LENGTH: 21
<212> TYPE: PRT
<213> ORGANISM: Homo sapiens

<400> SEQUENCE: 784

Gly Phe Phe His Ala Phe Phe His Phe Phe His Ser Phe Trp His Gly
1               5                   10                  15

Phe Phe Glu Ala Cys
            20

<210> SEQ ID NO 785
<211> LENGTH: 21
<212> TYPE: PRT
<213> ORGANISM: Homo sapiens

<400> SEQUENCE: 785

Gly Leu Phe His Ala Leu Leu His Leu Leu His Ser Leu Trp His Leu
1               5                   10                  15

Leu Leu Glu Ala Cys
            20

<210> SEQ ID NO 786
<211> LENGTH: 22
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (22)..(22)
<223> OTHER INFORMATION: Lys is conjugated to stearyl

<400> SEQUENCE: 786

Cys Gly Leu Phe His Ala Leu Leu His Leu Leu His Ser Leu Trp His
1               5                   10                  15

Gly Leu Leu Glu Ala Lys
            20

<210> SEQ ID NO 787
<211> LENGTH: 22
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (22)..(22)
<223> OTHER INFORMATION: Lys is conjugated to stearyl

<400> SEQUENCE: 787

Cys Gly Phe Phe His Ala Phe Phe His Phe Phe His Ser Phe Trp His
1               5                   10                  15

Gly Phe Phe Glu Ala Lys
            20

<210> SEQ ID NO 788
<211> LENGTH: 22
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (22)..(22)
<223> OTHER INFORMATION: Lys is conjugated to stearyl

<400> SEQUENCE: 788

Cys Gly Leu Phe His Ala Leu Leu His Leu Leu His Ser Leu Trp His
1               5                   10                  15

Leu Leu Leu Glu Ala Lys
            20

<210> SEQ ID NO 789
<211> LENGTH: 21
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Gly is conjugated to stearyl

<400> SEQUENCE: 789

Gly Leu Phe His Ala Leu Leu His Leu Leu His Ser Leu Trp His Gly
1               5                   10                  15

Leu Leu Glu Ala Cys
            20

<210> SEQ ID NO 790
<211> LENGTH: 21
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Gly is conjugated to stearyl

<400> SEQUENCE: 790

Gly Phe Phe His Ala Phe Phe His Phe Phe His Ser Phe Trp His Gly

-continued

```
1               5                   10                  15

Phe Phe Glu Ala Cys
            20

<210> SEQ ID NO 791
<211> LENGTH: 21
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Gly is conjugated to stearyl

<400> SEQUENCE: 791

Gly Leu Phe His Ala Leu Leu His Leu Leu His Ser Leu Trp His Leu
1               5                   10                  15

Leu Leu Glu Ala Cys
            20

<210> SEQ ID NO 792
<211> LENGTH: 21
<212> TYPE: PRT
<213> ORGANISM: Homo sapiens

<400> SEQUENCE: 792

Cys Gly Phe Phe His Ala Phe Phe His Phe Phe His Ser Phe Trp His
1               5                   10                  15

Phe Phe Phe Glu Ala
            20

<210> SEQ ID NO 793
<211> LENGTH: 21
<212> TYPE: PRT
<213> ORGANISM: Homo sapiens

<400> SEQUENCE: 793

Cys Gly Phe Phe His Ala Phe Phe His Phe Phe His Ser Phe Trp His
1               5                   10                  15

Leu Phe Phe Glu Ala
            20

<210> SEQ ID NO 794
<211> LENGTH: 21
<212> TYPE: PRT
<213> ORGANISM: Homo sapiens

<400> SEQUENCE: 794

Cys Gly Leu Phe His Ala Leu Leu His Leu Leu His Ser Leu Trp His
1               5                   10                  15

Gly Leu Leu Glu Trp
            20

<210> SEQ ID NO 795
<211> LENGTH: 21
<212> TYPE: PRT
<213> ORGANISM: Homo sapiens

<400> SEQUENCE: 795

Cys Gly Leu Phe His Ala Leu Leu His Leu Leu His Ser Leu Trp His
1               5                   10                  15

Leu Leu Leu Glu Trp
```

```
              20

<210> SEQ ID NO 796
<211> LENGTH: 21
<212> TYPE: PRT
<213> ORGANISM: Homo sapiens

<400> SEQUENCE: 796

Cys Gly Phe Phe His Ala Phe Phe His Phe Phe His Ser Phe Trp His
1               5                   10                  15

Gly Phe Phe Glu Trp
            20

<210> SEQ ID NO 797
<211> LENGTH: 14
<212> TYPE: PRT
<213> ORGANISM: Homo sapiens

<400> SEQUENCE: 797

Cys Phe Phe Gly Ala Ile Trp Glu Phe Ala Lys Ser Ile Leu
1               5                   10

<210> SEQ ID NO 798
<211> LENGTH: 14
<212> TYPE: PRT
<213> ORGANISM: Homo sapiens

<400> SEQUENCE: 798

Cys Phe Phe Gly Ala Ile Trp Glu Phe Ala His Ser Ile Leu
1               5                   10

<210> SEQ ID NO 799
<211> LENGTH: 14
<212> TYPE: PRT
<213> ORGANISM: Homo sapiens

<400> SEQUENCE: 799

Cys Phe Phe Gly Ala Ile Trp Glu Phe Ala His Gly Ile Leu
1               5                   10

<210> SEQ ID NO 800
<211> LENGTH: 15
<212> TYPE: PRT
<213> ORGANISM: Homo sapiens

<400> SEQUENCE: 800

Cys Phe Phe Gly Ala Ile Trp Glu Phe Ile His Ser Ile Leu Lys
1               5                   10                  15

<210> SEQ ID NO 801
<211> LENGTH: 15
<212> TYPE: PRT
<213> ORGANISM: Homo sapiens

<400> SEQUENCE: 801

Cys Phe Phe Gly Ala Ile Trp Glu Phe Ile His Ser Ile Leu His
1               5                   10                  15

<210> SEQ ID NO 802
<211> LENGTH: 15
<212> TYPE: PRT
<213> ORGANISM: Homo sapiens

<400> SEQUENCE: 802
```

```
Cys Phe Phe Gly Ala Ile Trp Glu Phe Ile His Ser Ile Leu Asp
1               5                   10                  15
```

<210> SEQ ID NO 803
<211> LENGTH: 15
<212> TYPE: PRT
<213> ORGANISM: Homo sapiens

<400> SEQUENCE: 803

```
Cys Phe Phe Gly Ala Ile Trp Glu Phe Ile His Ser Ile Leu Arg
1               5                   10                  15
```

<210> SEQ ID NO 804
<211> LENGTH: 14
<212> TYPE: PRT
<213> ORGANISM: Homo sapiens

<400> SEQUENCE: 804

```
Cys Phe Phe Gly Ala Ile Trp Glu Phe Ile His Ser Ile Leu
1               5                   10
```

<210> SEQ ID NO 805
<211> LENGTH: 14
<212> TYPE: PRT
<213> ORGANISM: Homo sapiens

<400> SEQUENCE: 805

```
Cys Phe Phe Gly Ala Ile Ala Glu Phe Ile His Ser Ile Leu
1               5                   10
```

<210> SEQ ID NO 806
<211> LENGTH: 14
<212> TYPE: PRT
<213> ORGANISM: Homo sapiens

<400> SEQUENCE: 806

```
Cys Ile Phe Gly Ala Ile Trp Glu Phe Ile His Ser Ile Leu
1               5                   10
```

<210> SEQ ID NO 807
<211> LENGTH: 15
<212> TYPE: PRT
<213> ORGANISM: Homo sapiens

<400> SEQUENCE: 807

```
Cys Gly Ile Phe Gly Ala Ile Trp Glu Phe Ile His Ser Ile Leu
1               5                   10                  15
```

<210> SEQ ID NO 808
<211> LENGTH: 15
<212> TYPE: PRT
<213> ORGANISM: Homo sapiens

<400> SEQUENCE: 808

```
Cys Phe Phe Gly Ala Ile Trp Glu Phe Ile His Ser Ile Leu Glu
1               5                   10                  15
```

<210> SEQ ID NO 809
<211> LENGTH: 16
<212> TYPE: PRT
<213> ORGANISM: Homo sapiens

<400> SEQUENCE: 809

```
Cys Phe Phe Gly Ala Ile Trp Glu Phe Ile His Ser Ile Leu Glu Gly
1               5                   10                  15
```

<210> SEQ ID NO 810
<211> LENGTH: 17
<212> TYPE: PRT
<213> ORGANISM: Homo sapiens

<400> SEQUENCE: 810

Cys Phe Phe Gly Ala Ile Trp Glu Phe Ile His Ser Ile Leu Glu Gly
1               5                   10                  15

Leu

<210> SEQ ID NO 811
<211> LENGTH: 18
<212> TYPE: PRT
<213> ORGANISM: Homo sapiens

<400> SEQUENCE: 811

Cys Phe Phe Gly Ala Ile Trp Glu Phe Ile His Ser Ile Leu Glu Gly
1               5                   10                  15

Leu Ile

<210> SEQ ID NO 812
<211> LENGTH: 19
<212> TYPE: PRT
<213> ORGANISM: Homo sapiens

<400> SEQUENCE: 812

Cys Phe Phe Gly Ala Ile Trp Glu Phe Ile His Ser Ile Leu Glu Gly
1               5                   10                  15

Leu Ile Asp

<210> SEQ ID NO 813
<211> LENGTH: 20
<212> TYPE: PRT
<213> ORGANISM: Homo sapiens

<400> SEQUENCE: 813

Cys Phe Phe Gly Ala Ile Trp Glu Phe Ile His Ser Ile Leu Glu Gly
1               5                   10                  15

Leu Ile Asp Gly
            20

<210> SEQ ID NO 814
<211> LENGTH: 20
<212> TYPE: PRT
<213> ORGANISM: Homo sapiens

<400> SEQUENCE: 814

Cys Phe Phe Gly Ala Ile Trp Glu Phe Ile His Ser Ile Leu Glu Gly
1               5                   10                  15

Leu Ile Glu Ala
            20

<210> SEQ ID NO 815
<211> LENGTH: 20
<212> TYPE: PRT
<213> ORGANISM: Homo sapiens

<400> SEQUENCE: 815

Cys Phe Phe Gly Ala Ile Trp Glu Phe Ile His Ser Ile Leu Glu Gly
1               5                   10                  15

Leu Ile Asp Trp
        20

<210> SEQ ID NO 816
<211> LENGTH: 23
<212> TYPE: PRT
<213> ORGANISM: Homo sapiens

<400> SEQUENCE: 816

Cys Phe Phe Gly Ala Ile Trp Glu Phe Ile His Ser Ile Leu Glu Gly
1               5                   10                  15

Leu Ile Asp Gly Trp Tyr Gly
        20

<210> SEQ ID NO 817
<211> LENGTH: 24
<212> TYPE: PRT
<213> ORGANISM: Homo sapiens

<400> SEQUENCE: 817

Cys Phe Phe Gly Ala Ile Trp Glu Phe Ile His Ser Ile Leu Glu Gly
1               5                   10                  15

Leu Ile Asp Gly Trp Tyr Gly Phe
        20

<210> SEQ ID NO 818
<211> LENGTH: 14
<212> TYPE: PRT
<213> ORGANISM: Homo sapiens

<400> SEQUENCE: 818

Phe Phe Gly Ala Ile Trp Glu Phe Ile His Ser Ile Leu Cys
1               5                   10

<210> SEQ ID NO 819
<211> LENGTH: 14
<212> TYPE: PRT
<213> ORGANISM: Homo sapiens

<400> SEQUENCE: 819

Cys Phe Trp Gly Ala Ile Trp Glu Phe Ile His Ser Ile Leu
1               5                   10

<210> SEQ ID NO 820
<211> LENGTH: 20
<212> TYPE: PRT
<213> ORGANISM: Homo sapiens

<400> SEQUENCE: 820

Cys Phe Phe Gly Ala Ile Trp Glu Phe Ile His Ser Ile Leu Lys Gly
1               5                   10                  15

Leu Ile Asp Trp
        20

<210> SEQ ID NO 821
<211> LENGTH: 14
<212> TYPE: PRT
<213> ORGANISM: Homo sapiens

<400> SEQUENCE: 821

Cys Ala Phe Gly Lys Ile Trp Glu Phe Ala His Ser Ile Leu
1               5                   10

```
<210> SEQ ID NO 822
<211> LENGTH: 14
<212> TYPE: PRT
<213> ORGANISM: Homo sapiens

<400> SEQUENCE: 822

Cys Ala Phe Gly Lys Ile Trp Glu Phe Ile His Ser Ile Leu
1               5                   10

<210> SEQ ID NO 823
<211> LENGTH: 14
<212> TYPE: PRT
<213> ORGANISM: Homo sapiens

<400> SEQUENCE: 823

Cys Phe Phe Gly Lys Ile Trp Glu Phe Ile His Ser Ile Leu
1               5                   10

<210> SEQ ID NO 824
<211> LENGTH: 14
<212> TYPE: PRT
<213> ORGANISM: Homo sapiens

<400> SEQUENCE: 824

Cys Ala Phe Gly Ala Ile Trp Glu Phe Ile His Ser Ile Leu
1               5                   10

<210> SEQ ID NO 825
<211> LENGTH: 14
<212> TYPE: PRT
<213> ORGANISM: Homo sapiens

<400> SEQUENCE: 825

Cys Ala Phe Gly Ala Ile Trp Glu Phe Ala His Ser Ile Leu
1               5                   10

<210> SEQ ID NO 826
<211> LENGTH: 16
<212> TYPE: PRT
<213> ORGANISM: Homo sapiens

<400> SEQUENCE: 826

Cys Gly Phe Phe Gly Ala Ile Ala Gly Leu Leu His Asn Ile Phe Lys
1               5                   10                  15

<210> SEQ ID NO 827
<211> LENGTH: 15
<212> TYPE: PRT
<213> ORGANISM: Homo sapiens

<400> SEQUENCE: 827

Cys Phe Phe Gly Ala Ile Ala Gly Leu Leu His Asn Ile Phe Lys
1               5                   10              15

<210> SEQ ID NO 828
<211> LENGTH: 16
<212> TYPE: PRT
<213> ORGANISM: Homo sapiens

<400> SEQUENCE: 828

Cys Gly Phe Phe Glu Ala Ile Glu Gly Leu Leu His Asn Ile Phe Lys
1               5                   10                  15

<210> SEQ ID NO 829
<211> LENGTH: 15
```

```
<212> TYPE: PRT
<213> ORGANISM: Homo sapiens

<400> SEQUENCE: 829

Cys Phe Phe Glu Ala Ile Ala Gly Leu Leu His Asn Ile Phe Lys
1               5                   10                  15

<210> SEQ ID NO 830
<211> LENGTH: 15
<212> TYPE: PRT
<213> ORGANISM: Homo sapiens

<400> SEQUENCE: 830

Cys Phe Phe Glu Ala Ile Trp Gly Leu Leu His Asn Ile Phe Lys
1               5                   10                  15

<210> SEQ ID NO 831
<211> LENGTH: 16
<212> TYPE: PRT
<213> ORGANISM: Homo sapiens

<400> SEQUENCE: 831

Cys Gly Phe Phe Gly Ala Ile Ala Glu Leu Leu His Asn Ile Phe Lys
1               5                   10                  15

<210> SEQ ID NO 832
<211> LENGTH: 15
<212> TYPE: PRT
<213> ORGANISM: Homo sapiens

<400> SEQUENCE: 832

Cys Phe Phe Gly Ala Ile Ala Glu Leu Leu His Asn Ile Phe Lys
1               5                   10                  15

<210> SEQ ID NO 833
<211> LENGTH: 16
<212> TYPE: PRT
<213> ORGANISM: Homo sapiens

<400> SEQUENCE: 833

Cys Gly Phe Phe Glu Ala Ile Ala Glu Leu Leu His Asn Ile Phe Lys
1               5                   10                  15

<210> SEQ ID NO 834
<211> LENGTH: 15
<212> TYPE: PRT
<213> ORGANISM: Homo sapiens

<400> SEQUENCE: 834

Cys Phe Phe Glu Ala Ile Ala Glu Leu Leu His Asn Ile Phe Lys
1               5                   10                  15

<210> SEQ ID NO 835
<211> LENGTH: 15
<212> TYPE: PRT
<213> ORGANISM: Homo sapiens

<400> SEQUENCE: 835

Cys Phe Phe Gly Ala Ile Trp Glu Leu Leu His Asn Ile Phe Lys
1               5                   10                  15

<210> SEQ ID NO 836
<211> LENGTH: 15
<212> TYPE: PRT
<213> ORGANISM: Homo sapiens
```

```
<400> SEQUENCE: 836

Cys Phe Phe Glu Ala Ile Trp Glu Leu Leu His Asn Ile Phe Lys
1               5                   10                  15

<210> SEQ ID NO 837
<211> LENGTH: 27
<212> TYPE: PRT
<213> ORGANISM: Homo sapiens

<400> SEQUENCE: 837

Cys Phe Phe Gly Ala Ile Trp Glu Phe Ile His Ser Ile Leu Phe Phe
1               5                   10                  15

Gly Ala Ile Trp Glu Phe Ile His Ser Ile Leu
            20                  25

<210> SEQ ID NO 838
<211> LENGTH: 30
<212> TYPE: PRT
<213> ORGANISM: Homo sapiens

<400> SEQUENCE: 838

Cys Phe Phe Gly Ala Ile Trp Glu Phe Ile His Ser Ile Leu Gly Gly
1               5                   10                  15

Gly Phe Phe Gly Ala Ile Trp Glu Phe Ile His Ser Ile Leu
            20                  25                  30

<210> SEQ ID NO 839
<211> LENGTH: 28
<212> TYPE: PRT
<213> ORGANISM: Homo sapiens

<400> SEQUENCE: 839

Cys Phe Phe Gly Ala Ile Trp Glu Phe Ile His Ser Ile Leu Gly Phe
1               5                   10                  15

Phe Gly Ala Ile Trp Glu Phe Ile His Ser Ile Leu
            20                  25

<210> SEQ ID NO 840
<211> LENGTH: 21
<212> TYPE: PRT
<213> ORGANISM: Homo sapiens

<400> SEQUENCE: 840

Gly Gly Leu Phe Glu Ala Leu Leu Glu Leu Leu Glu Ser Leu Trp Glu
1               5                   10                  15

Leu Leu Leu Glu Trp
            20

<210> SEQ ID NO 841
<211> LENGTH: 21
<212> TYPE: PRT
<213> ORGANISM: Homo sapiens

<400> SEQUENCE: 841

Gly Gly Phe Phe Glu Ala Phe Phe Glu Phe Phe Glu Ser Phe Trp Glu
1               5                   10                  15

Phe Phe Phe Glu Ala
            20

<210> SEQ ID NO 842
<211> LENGTH: 21
```

```
<212> TYPE: PRT
<213> ORGANISM: Homo sapiens

<400> SEQUENCE: 842

Gly Gly Leu Phe Glu Ala Leu Leu Glu Leu Leu Ser Leu Trp Glu
1               5                   10                  15

Gly Leu Leu Glu Ala
            20

<210> SEQ ID NO 843
<211> LENGTH: 21
<212> TYPE: PRT
<213> ORGANISM: Homo sapiens

<400> SEQUENCE: 843

Cys Gly Leu Phe His Ala Leu Leu His Leu Leu His Ser Leu Trp His
1               5                   10                  15

Leu Leu Leu His Ala
            20

<210> SEQ ID NO 844
<211> LENGTH: 21
<212> TYPE: PRT
<213> ORGANISM: Homo sapiens

<400> SEQUENCE: 844

Cys Gly Leu Phe His Ala Leu Leu His Leu Leu His Ser Leu Trp His
1               5                   10                  15

Leu Leu Leu His Ala
            20

<210> SEQ ID NO 845
<211> LENGTH: 21
<212> TYPE: PRT
<213> ORGANISM: Homo sapiens

<400> SEQUENCE: 845

Cys Gly Leu Phe Glu Ala Leu Leu His Leu Leu His Ser Leu Trp His
1               5                   10                  15

Leu Leu Leu Glu Ala
            20

<210> SEQ ID NO 846
<211> LENGTH: 21
<212> TYPE: PRT
<213> ORGANISM: Homo sapiens

<400> SEQUENCE: 846

Cys Gly Leu Phe Glu Ala Leu Leu His Leu Leu Glu Ser Leu Trp His
1               5                   10                  15

Leu Leu Leu Glu Ala
            20

<210> SEQ ID NO 847
<211> LENGTH: 21
<212> TYPE: PRT
<213> ORGANISM: Homo sapiens

<400> SEQUENCE: 847

Cys Gly Leu Phe Glu Ala Leu Leu His Leu Leu His Ser Leu Trp Glu
1               5                   10                  15

Leu Leu Leu Glu Ala
```

<210> SEQ ID NO 848
<211> LENGTH: 21
<212> TYPE: PRT
<213> ORGANISM: Homo sapiens

<400> SEQUENCE: 848

Cys Gly Leu Phe His Ala Leu Leu Glu Leu Leu His Ser Leu Trp His
1               5                   10                  15

Leu Leu Leu Glu Ala
            20

<210> SEQ ID NO 849
<211> LENGTH: 21
<212> TYPE: PRT
<213> ORGANISM: Homo sapiens

<400> SEQUENCE: 849

Cys Gly Leu Phe His Ala Leu Leu His Leu Leu Glu Ser Leu Trp His
1               5                   10                  15

Leu Leu Leu Glu Ala
            20

<210> SEQ ID NO 850
<211> LENGTH: 21
<212> TYPE: PRT
<213> ORGANISM: Homo sapiens

<400> SEQUENCE: 850

Cys Gly Leu Phe His Ala Leu Leu His Leu Leu His Ser Leu Trp Glu
1               5                   10                  15

Leu Leu Leu Glu Ala
            20

<210> SEQ ID NO 851
<211> LENGTH: 21
<212> TYPE: PRT
<213> ORGANISM: Homo sapiens

<400> SEQUENCE: 851

Cys Gly Leu Phe His Ala Leu Leu Glu Leu Leu Glu Ser Leu Trp His
1               5                   10                  15

Leu Leu Leu Glu Ala
            20

<210> SEQ ID NO 852
<211> LENGTH: 21
<212> TYPE: PRT
<213> ORGANISM: Homo sapiens

<400> SEQUENCE: 852

Cys Gly Leu Phe His Ala Leu Leu Glu Leu Leu His Ser Leu Trp Glu
1               5                   10                  15

Leu Leu Leu Glu Ala
            20

<210> SEQ ID NO 853
<211> LENGTH: 21
<212> TYPE: PRT
<213> ORGANISM: Homo sapiens

<400> SEQUENCE: 853

Cys Gly Leu Phe His Ala Leu Leu His Leu Leu Glu Ser Leu Trp Glu
1               5                   10                  15

Leu Leu Leu Glu Ala
            20

<210> SEQ ID NO 854
<211> LENGTH: 21
<212> TYPE: PRT
<213> ORGANISM: Homo sapiens

<400> SEQUENCE: 854

Cys Gly Leu Phe Glu Ala Leu Leu His Leu Leu Glu Ser Leu Trp Glu
1               5                   10                  15

Leu Leu Leu Glu Ala
            20

<210> SEQ ID NO 855
<211> LENGTH: 21
<212> TYPE: PRT
<213> ORGANISM: Homo sapiens

<400> SEQUENCE: 855

Cys Gly Leu Phe Glu Ala Leu Leu Glu Leu Leu His Ser Leu Trp Glu
1               5                   10                  15

Leu Leu Leu Glu Ala
            20

<210> SEQ ID NO 856
<211> LENGTH: 20
<212> TYPE: PRT
<213> ORGANISM: Homo sapiens

<400> SEQUENCE: 856

Cys Gly Leu Glu Ala Leu Leu Glu Leu Leu Glu Ser Leu Trp His Leu
1               5                   10                  15

Leu Leu Glu Ala
            20

<210> SEQ ID NO 857
<211> LENGTH: 21
<212> TYPE: PRT
<213> ORGANISM: Homo sapiens

<400> SEQUENCE: 857

Cys Gly Leu Phe His Ala Leu Leu Glu Leu Leu Glu Ser Leu Trp Glu
1               5                   10                  15

Leu Leu Leu Glu Ala
            20

<210> SEQ ID NO 858
<211> LENGTH: 20
<212> TYPE: PRT
<213> ORGANISM: Homo sapiens

<400> SEQUENCE: 858

Cys Phe Phe Gly Ala Ile Trp Glu Phe Ile His Ser Ile Leu His Leu
1               5                   10                  15

Leu Leu Glu Ala
            20

<210> SEQ ID NO 859

```
<211> LENGTH: 20
<212> TYPE: PRT
<213> ORGANISM: Homo sapiens

<400> SEQUENCE: 859

Cys Phe Phe Gly Ala Ile Trp Glu Phe Ile His Ser Ile Leu Lys Leu
1               5                   10                  15

Leu Leu Glu Ala
            20

<210> SEQ ID NO 860
<211> LENGTH: 29
<212> TYPE: PRT
<213> ORGANISM: Homo sapiens

<400> SEQUENCE: 860

Cys Gly Phe Phe Gly Ala Ile Trp Glu Phe Ile His Ser Ile Leu Gly
1               5                   10                  15

Phe Phe Gly Ala Ile Trp Glu Phe Ile His Ser Ile Leu
            20                  25

<210> SEQ ID NO 861
<211> LENGTH: 27
<212> TYPE: PRT
<213> ORGANISM: Homo sapiens

<400> SEQUENCE: 861

Cys Phe Phe Gly Ala Ile Trp Glu Phe Ala His Ser Ile Leu Phe Phe
1               5                   10                  15

Gly Ala Ile Trp Glu Phe Ala His Ser Ile Leu
            20                  25

<210> SEQ ID NO 862
<211> LENGTH: 28
<212> TYPE: PRT
<213> ORGANISM: Homo sapiens

<400> SEQUENCE: 862

Cys Phe Phe Gly Ala Ile Trp Glu Phe Ala His Ser Ile Leu Gly Phe
1               5                   10                  15

Phe Gly Ala Ile Trp Glu Phe Ala His Ser Ile Leu
            20                  25

<210> SEQ ID NO 863
<211> LENGTH: 29
<212> TYPE: PRT
<213> ORGANISM: Homo sapiens

<400> SEQUENCE: 863

Cys Gly Phe Phe Gly Ala Ile Trp Glu Phe Ala His Ser Ile Leu Gly
1               5                   10                  15

Phe Phe Gly Ala Ile Trp Glu Phe Ala His Ser Ile Leu
            20                  25

<210> SEQ ID NO 864
<211> LENGTH: 34
<212> TYPE: PRT
<213> ORGANISM: Homo sapiens

<400> SEQUENCE: 864

Cys Phe Phe Gly Ala Ile Trp Glu Phe Ile His Ser Ile Leu Gly Leu
1               5                   10                  15
```

Phe Glu Ala Ile Glu Gly Phe Ile Glu Asn Gly Trp Glu Gly Met Ile
            20                  25                  30

Asp Gly

<210> SEQ ID NO 865
<211> LENGTH: 37
<212> TYPE: PRT
<213> ORGANISM: Homo sapiens

<400> SEQUENCE: 865

Cys Phe Phe Gly Ala Ile Trp Glu Phe Ile His Ser Ile Leu Gly Leu
1               5                   10                  15

Phe Glu Ala Ile Glu Gly Phe Ile Glu Asn Gly Trp Glu Gly Met Ile
            20                  25                  30

Asp Gly Trp Tyr Gly
        35

<210> SEQ ID NO 866
<211> LENGTH: 38
<212> TYPE: PRT
<213> ORGANISM: Homo sapiens

<400> SEQUENCE: 866

Cys Phe Phe Gly Ala Ile Trp Glu Phe Ile His Ser Ile Leu Gly Leu
1               5                   10                  15

Phe Glu Ala Ile Glu Gly Phe Ile Glu Asn Gly Trp Glu Gly Met Ile
            20                  25                  30

Asp Gly Trp Tyr Gly Phe
        35

<210> SEQ ID NO 867
<211> LENGTH: 20
<212> TYPE: PRT
<213> ORGANISM: Homo sapiens

<400> SEQUENCE: 867

Cys Phe Phe Gly Ala Leu Leu Glu Phe Ile His Ser Ile Leu Glu Leu
1               5                   10                  15

Leu Leu Glu Ala
            20

<210> SEQ ID NO 868
<211> LENGTH: 21
<212> TYPE: PRT
<213> ORGANISM: Homo sapiens

<400> SEQUENCE: 868

Cys Gly Leu Phe Gly Ala Leu Leu Glu Phe Ile His Ser Ile Leu Glu
1               5                   10                  15

Leu Leu Leu Glu Ala
            20

<210> SEQ ID NO 869
<211> LENGTH: 21
<212> TYPE: PRT
<213> ORGANISM: Homo sapiens

<400> SEQUENCE: 869

Cys Gly Phe Phe Gly Ala Leu Leu Glu Phe Ile His Ser Ile Leu Glu
1               5                   10                  15

Leu Leu Leu Glu Ala

20

<210> SEQ ID NO 870
<211> LENGTH: 20
<212> TYPE: PRT
<213> ORGANISM: Homo sapiens

<400> SEQUENCE: 870

Cys Phe Phe Gly Ala Leu Leu Glu Phe Ile His Ser Leu Trp Glu Leu
1               5                   10                  15

Leu Leu Glu Ala
            20

<210> SEQ ID NO 871
<211> LENGTH: 21
<212> TYPE: PRT
<213> ORGANISM: Homo sapiens

<400> SEQUENCE: 871

Cys Gly Leu Phe Gly Ala Leu Leu Glu Phe Ile His Ser Leu Trp Glu
1               5                   10                  15

Leu Leu Leu Glu Ala
            20

<210> SEQ ID NO 872
<211> LENGTH: 21
<212> TYPE: PRT
<213> ORGANISM: Homo sapiens

<400> SEQUENCE: 872

Cys Gly Phe Phe Gly Ala Leu Leu Glu Phe Ile His Ser Leu Trp Glu
1               5                   10                  15

Leu Leu Leu Glu Ala
            20

<210> SEQ ID NO 873
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(15)
<223> OTHER INFORMATION: Lys is conjugated to stearyl

<400> SEQUENCE: 873

Cys Ile Phe Gly Ala Ile Ala Gly Phe Ile Lys Asn Ile Trp Lys
1               5                   10                  15

<210> SEQ ID NO 874
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Ile is conjugated to stearyl

<400> SEQUENCE: 874

Ile Phe Gly Ala Ile Ala Gly Phe Ile Lys Asn Ile Trp Cys
1               5                   10

```
<210> SEQ ID NO 875
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(15)
<223> OTHER INFORMATION: Lys is conjugated to stearyl

<400> SEQUENCE: 875

Cys Phe Phe Gly Ala Ile Trp Glu Phe Ile Lys Ser Ile Leu Lys
1               5                   10                  15

<210> SEQ ID NO 876
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Phe is conjugated to stearyl

<400> SEQUENCE: 876

Phe Phe Gly Ala Ile Trp Glu Phe Ile Lys Ser Ile Leu Cys
1               5                   10

<210> SEQ ID NO 877
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(15)
<223> OTHER INFORMATION: Lys is conjugated to stearyl

<400> SEQUENCE: 877

Cys Phe Phe Gly Ala Ile Trp Glu Phe Ile His Ser Ile Leu Lys
1               5                   10                  15

<210> SEQ ID NO 878
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Phe is conjugated to stearyl

<400> SEQUENCE: 878

Phe Phe Gly Ala Ile Trp Glu Phe Ile His Ser Ile Leu Cys
1               5                   10

<210> SEQ ID NO 879
<211> LENGTH: 19
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (19)..(19)
<223> OTHER INFORMATION: Lys is conjugated to stearyl
```

-continued

<400> SEQUENCE: 879

Cys Ile Phe Gly Ala Ile Ala Gly Phe Ile Lys Asn Ile Trp Glu Gly
1               5                   10                  15

Leu Ile Lys

<210> SEQ ID NO 880
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Ile is conjugated to stearyl

<400> SEQUENCE: 880

Ile Phe Gly Ala Ile Ala Gly Phe Ile Lys Asn Ile Trp Glu Gly Leu
1               5                   10                  15

Ile Cys

<210> SEQ ID NO 881
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Ile is conjugated to stearyl

<400> SEQUENCE: 881

Ile Phe Gly Ala Ile Ala Gly Phe Ile Lys Asn Ile Leu Lys Gly Leu
1               5                   10                  15

Cys

<210> SEQ ID NO 882
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Gly is conjugated to stearyl

<400> SEQUENCE: 882

Gly Ile Phe Gly Ala Ile Ala Gly Phe Ile Lys Asn Ile Leu Lys Gly
1               5                   10                  15

Leu Cys

<210> SEQ ID NO 883
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (18)..(18)
<223> OTHER INFORMATION: Lys is conjugated to stearyl

<400> SEQUENCE: 883

Cys Ile Phe Gly Ala Ile Ala Gly Phe Ile Lys Asn Ile Leu Lys Gly

Leu Lys

<210> SEQ ID NO 884
<211> LENGTH: 21
<212> TYPE: PRT
<213> ORGANISM: Homo sapiens

<400> SEQUENCE: 884

Cys Gly Leu Phe Gly Ala Ile Ala Gly Phe Ile Val Asn Gly Trp Val
1               5                   10                  15

Gly Met Ile Asp Gly
            20

<210> SEQ ID NO 885
<211> LENGTH: 24
<212> TYPE: PRT
<213> ORGANISM: Homo sapiens

<400> SEQUENCE: 885

Cys Gly Leu Phe Gly Ala Ile Ala Gly Phe Ile Val Asn Gly Trp Val
1               5                   10                  15

Gly Met Ile Asp Gly Trp Tyr Gly
            20

<210> SEQ ID NO 886
<211> LENGTH: 24
<212> TYPE: PRT
<213> ORGANISM: Homo sapiens

<400> SEQUENCE: 886

Cys Gly Leu Phe Glu Ala Ile Glu Gly Phe Ile Val Asn Gly Trp Val
1               5                   10                  15

Gly Met Ile Asp Gly Trp Tyr Gly
            20

<210> SEQ ID NO 887
<211> LENGTH: 25
<212> TYPE: PRT
<213> ORGANISM: Homo sapiens

<400> SEQUENCE: 887

Cys Gly Leu Phe Gly Ala Ile Ala Gly Phe Ile Val Asn Gly Trp Val
1               5                   10                  15

Gly Met Ile Asp Gly Trp Tyr Gly Phe
            20                  25

<210> SEQ ID NO 888
<211> LENGTH: 26
<212> TYPE: PRT
<213> ORGANISM: Homo sapiens

<400> SEQUENCE: 888

Cys Gly Leu Phe Glu Ala Ile Glu Ala Gly Phe Ile Val Asn Gly Trp
1               5                   10                  15

Val Gly Met Ile Asp Gly Trp Tyr Gly Phe
            20                  25

<210> SEQ ID NO 889
<211> LENGTH: 25
<212> TYPE: PRT
<213> ORGANISM: Artificial Sequence

```
<220> FEATURE:
<223> OTHER INFORMATION: Synthetically Generated Peptide
<220> FEATURE:
<221> NAME/KEY: MISC_FEATURE
<222> LOCATION: (25)..(25)
<223> OTHER INFORMATION: Lys is conjugated to stearyl

<400> SEQUENCE: 889

Cys Gly Leu Phe Gly Ala Ile Ala Gly Phe Ile Val Asn Gly Trp Val
1               5                   10                  15

Gly Met Ile Asp Gly Trp Tyr Gly Lys
            20                  25

<210> SEQ ID NO 890
<211> LENGTH: 25
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (25)..(25)
<223> OTHER INFORMATION: Lys is conjugated to stearyl

<400> SEQUENCE: 890

Cys Gly Leu Phe Glu Ala Ile Glu Gly Phe Ile Val Asn Gly Trp Val
1               5                   10                  15

Gly Met Ile Asp Gly Trp Tyr Gly Lys
            20                  25

<210> SEQ ID NO 891
<211> LENGTH: 24
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (1)..(1)
<223> OTHER INFORMATION: Gly is conjugated to stearyl

<400> SEQUENCE: 891

Gly Leu Phe Gly Ala Ile Ala Gly Phe Ile Val Asn Gly Trp Val Gly
1               5                   10                  15

Met Ile Asp Gly Trp Tyr Gly Cys
            20

<210> SEQ ID NO 892
<211> LENGTH: 24
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Gly is conjugated to stearyl

<400> SEQUENCE: 892

Gly Leu Phe Glu Ala Ile Glu Gly Phe Ile Val Asn Gly Trp Val Gly
1               5                   10                  15

Met Ile Asp Gly Trp Tyr Gly Cys
            20

<210> SEQ ID NO 893
<211> LENGTH: 25
<212> TYPE: PRT
```

```
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Gly is conjugated to stearyl

<400> SEQUENCE: 893

Gly Leu Phe Gly Ala Ile Ala Gly Phe Ile Val Asn Gly Trp Val Gly
1               5                   10                  15

Met Ile Asp Gly Trp Tyr Gly Phe Cys
            20                  25

<210> SEQ ID NO 894
<211> LENGTH: 26
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (1)..(1)
<223> OTHER INFORMATION: Gly is conjugated to stearyl

<400> SEQUENCE: 894

Gly Leu Phe Glu Ala Ile Glu Ala Gly Phe Ile Val Asn Gly Trp Val
1               5                   10                  15

Gly Met Ile Asp Gly Trp Tyr Gly Phe Cys
            20                  25

<210> SEQ ID NO 895
<211> LENGTH: 15
<212> TYPE: PRT
<213> ORGANISM: Homo sapiens

<400> SEQUENCE: 895

Cys Phe Phe Gly Ala Ile Trp Gly Leu Leu His Ser Ile Leu His
1               5                   10                  15

<210> SEQ ID NO 896
<211> LENGTH: 14
<212> TYPE: PRT
<213> ORGANISM: Homo sapiens

<400> SEQUENCE: 896

Cys Phe Phe Gly Ala Ile Trp Glu Leu Leu His Ser Ile Leu
1               5                   10

<210> SEQ ID NO 897
<211> LENGTH: 15
<212> TYPE: PRT
<213> ORGANISM: Homo sapiens

<400> SEQUENCE: 897

Cys Phe Phe Gly Ala Ile Trp Glu Leu Leu His Ser Ile Leu His
1               5                   10                  15

<210> SEQ ID NO 898
<211> LENGTH: 15
<212> TYPE: PRT
<213> ORGANISM: Homo sapiens

<400> SEQUENCE: 898

Cys Phe Phe Gly Ala Ile Trp Gly Leu Leu His Ser Ile Leu Lys
1               5                   10                  15
```

```
<210> SEQ ID NO 899
<211> LENGTH: 15
<212> TYPE: PRT
<213> ORGANISM: Homo sapiens

<400> SEQUENCE: 899

Cys Phe Phe Gly Ala Ile Trp Glu Leu Leu His Ser Ile Leu Lys
1               5                   10                  15

<210> SEQ ID NO 900
<211> LENGTH: 21
<212> TYPE: PRT
<213> ORGANISM: Homo sapiens

<400> SEQUENCE: 900

Cys Gly Leu Phe Gly Ala Leu Leu His Leu Leu His Ser Leu Trp Glu
1               5                   10                  15

Leu Leu Leu Glu Ala
            20

<210> SEQ ID NO 901
<211> LENGTH: 21
<212> TYPE: PRT
<213> ORGANISM: Homo sapiens

<400> SEQUENCE: 901

Cys Gly Leu Phe Gly Ala Leu Leu Glu Leu Leu His Ser Leu Trp Glu
1               5                   10                  15

Leu Leu Leu Glu Ala
            20

<210> SEQ ID NO 902
<211> LENGTH: 20
<212> TYPE: PRT
<213> ORGANISM: Homo sapiens

<400> SEQUENCE: 902

Cys Phe Phe Gly Ala Ile Trp Glu Phe Ile His Ser Ile Leu Glu Leu
1               5                   10                  15

Leu Leu Glu Ala
        20

<210> SEQ ID NO 903
<211> LENGTH: 20
<212> TYPE: PRT
<213> ORGANISM: Homo sapiens

<400> SEQUENCE: 903

Cys Phe Phe Gly Ala Ile Trp Glu Phe Ile His Ser Ile Leu His Gly
1               5                   10                  15

Leu Leu Glu Ala
        20

<210> SEQ ID NO 904
<211> LENGTH: 20
<212> TYPE: PRT
<213> ORGANISM: Homo sapiens

<400> SEQUENCE: 904

Cys Phe Phe Gly Ala Ile Trp Glu Phe Ile His Ser Ile Leu Glu Gly
1               5                   10                  15
```

Leu Leu Glu Ala
        20

<210> SEQ ID NO 905
<211> LENGTH: 21
<212> TYPE: PRT
<213> ORGANISM: Homo sapiens

<400> SEQUENCE: 905

Cys Gly Phe Phe Gly Ala Ile Trp Glu Phe Ile His Ser Ile Leu His
1               5                   10                  15

Leu Leu Leu Glu Ala
            20

<210> SEQ ID NO 906
<211> LENGTH: 21
<212> TYPE: PRT
<213> ORGANISM: Homo sapiens

<400> SEQUENCE: 906

Cys Gly Phe Phe Gly Ala Ile Trp Glu Phe Ile His Ser Ile Leu Glu
1               5                   10                  15

Leu Leu Leu Glu Ala
            20

<210> SEQ ID NO 907
<211> LENGTH: 21
<212> TYPE: PRT
<213> ORGANISM: Homo sapiens

<400> SEQUENCE: 907

Cys Gly Phe Phe Gly Ala Ile Trp Glu Phe Ile His Ser Ile Leu His
1               5                   10                  15

Gly Leu Leu Glu Ala
            20

<210> SEQ ID NO 908
<211> LENGTH: 21
<212> TYPE: PRT
<213> ORGANISM: Homo sapiens

<400> SEQUENCE: 908

Cys Gly Phe Phe Gly Ala Ile Trp Glu Phe Ile His Ser Ile Leu Glu
1               5                   10                  15

Gly Leu Leu Glu Ala
            20

<210> SEQ ID NO 909
<211> LENGTH: 15
<212> TYPE: PRT
<213> ORGANISM: Homo sapiens

<400> SEQUENCE: 909

Cys Gly Phe Phe Gly Ala Ile Ala Gly Leu Leu His Ser Ile Leu
1               5                   10                  15

<210> SEQ ID NO 910
<211> LENGTH: 15
<212> TYPE: PRT
<213> ORGANISM: Homo sapiens

<400> SEQUENCE: 910

Cys Gly Phe Phe Gly Ala Ile Trp Gly Leu Leu His Ser Ile Leu

```
<210> SEQ ID NO 911
<211> LENGTH: 15
<212> TYPE: PRT
<213> ORGANISM: Homo sapiens

<400> SEQUENCE: 911

Cys Gly Phe Phe Gly Ala Leu Leu Gly Leu Leu His Ser Ile Leu
1               5                   10                  15

<210> SEQ ID NO 912
<211> LENGTH: 14
<212> TYPE: PRT
<213> ORGANISM: Homo sapiens

<400> SEQUENCE: 912

Cys Phe Phe Gly Ala Ile Trp Glu Phe Ala Lys Ser Ala Leu
1               5                   10

<210> SEQ ID NO 913
<211> LENGTH: 17
<212> TYPE: PRT
<213> ORGANISM: Homo sapiens

<400> SEQUENCE: 913

Cys Ile Phe Gly Ala Ile Ala Gly Phe Ile His Asn Ile Leu Lys Gly
1               5                   10                  15

Leu

<210> SEQ ID NO 914
<211> LENGTH: 17
<212> TYPE: PRT
<213> ORGANISM: Homo sapiens

<400> SEQUENCE: 914

Cys Phe Phe Gly Ala Ile Ala Gly Phe Ile Lys Asn Ile Leu Lys Gly
1               5                   10                  15

Leu

<210> SEQ ID NO 915
<211> LENGTH: 17
<212> TYPE: PRT
<213> ORGANISM: Homo sapiens

<400> SEQUENCE: 915

Cys Ile Phe Gly Ala Ile Trp Gly Phe Ile Lys Asn Ile Leu Lys Gly
1               5                   10                  15

Leu

<210> SEQ ID NO 916
<211> LENGTH: 17
<212> TYPE: PRT
<213> ORGANISM: Homo sapiens

<400> SEQUENCE: 916

Cys Ile Phe Gly Ala Ile Trp Gly Phe Ile His Asn Ile Leu Lys Gly
1               5                   10                  15

Leu

<210> SEQ ID NO 917
<211> LENGTH: 17
```

```
<212> TYPE: PRT
<213> ORGANISM: Homo sapiens

<400> SEQUENCE: 917

Cys Ile Phe Gly Ala Ile Ala Gly Leu Leu Lys Asn Ile Leu Lys Gly
1               5                   10                  15

Leu

<210> SEQ ID NO 918
<211> LENGTH: 17
<212> TYPE: PRT
<213> ORGANISM: Homo sapiens

<400> SEQUENCE: 918

Cys Ile Phe Gly Ala Ile Ala Gly Leu Leu His Asn Ile Leu Lys Gly
1               5                   10                  15

Leu

<210> SEQ ID NO 919
<211> LENGTH: 17
<212> TYPE: PRT
<213> ORGANISM: Homo sapiens

<400> SEQUENCE: 919

Cys Ile Phe Glu Ala Ile Ala Gly Phe Ile Lys Asn Ile Leu Lys Gly
1               5                   10                  15

Leu

<210> SEQ ID NO 920
<211> LENGTH: 17
<212> TYPE: PRT
<213> ORGANISM: Homo sapiens

<400> SEQUENCE: 920

Cys Ile Phe Glu Ala Ile Ala Gly Phe Ile His Asn Ile Leu Lys Gly
1               5                   10                  15

Leu

<210> SEQ ID NO 921
<211> LENGTH: 24
<212> TYPE: PRT
<213> ORGANISM: Homo sapiens

<400> SEQUENCE: 921

Cys Gly Asn Phe Gly Glu Ile Ala Glu Leu Ile Glu Glu Gly Leu Lys
1               5                   10                  15

Asn Leu Ile Asp Trp Trp Asn Gly
            20

<210> SEQ ID NO 922
<211> LENGTH: 24
<212> TYPE: PRT
<213> ORGANISM: Homo sapiens

<400> SEQUENCE: 922

Cys Gly Phe Phe Gly Glu Ile Ala Glu Leu Ile Glu Glu Gly Leu Glu
1               5                   10                  15

Asn Leu Ile Asp Trp Trp Asn Gly
            20

<210> SEQ ID NO 923
```

```
<211> LENGTH: 24
<212> TYPE: PRT
<213> ORGANISM: Homo sapiens

<400> SEQUENCE: 923

Cys Gly Asn Phe Gly Glu Ile Glu Glu Leu Ile Glu Glu Gly Leu Lys
1               5                   10                  15

Asn Leu Ile Asp Trp Trp Asn Gly
            20

<210> SEQ ID NO 924
<211> LENGTH: 24
<212> TYPE: PRT
<213> ORGANISM: Homo sapiens

<400> SEQUENCE: 924

Cys Gly Asn Phe Gly Glu Ile Ala Glu Leu Ile Glu Glu Gly Leu Glu
1               5                   10                  15

Asn Leu Ile Asp Trp Trp Asn Gly
            20

<210> SEQ ID NO 925
<211> LENGTH: 24
<212> TYPE: PRT
<213> ORGANISM: Homo sapiens

<400> SEQUENCE: 925

Cys Gly Phe Phe Gly Glu Ile Glu Glu Leu Ile Glu Glu Asn Gly Glu
1               5                   10                  15

Asn Leu Ile Asp Trp Trp Asn Gly
            20

<210> SEQ ID NO 926
<211> LENGTH: 24
<212> TYPE: PRT
<213> ORGANISM: Homo sapiens

<400> SEQUENCE: 926

Cys Gly Phe Phe Gly Ala Ile Glu Glu Leu Ile Glu Glu Gly Leu Lys
1               5                   10                  15

Asn Leu Ile Asp Trp Trp Asn Gly
            20

<210> SEQ ID NO 927
<211> LENGTH: 24
<212> TYPE: PRT
<213> ORGANISM: Homo sapiens

<400> SEQUENCE: 927

Cys Gly Phe Phe Gly Ala Ile Ala Glu Leu Ile Glu Glu Gly Leu Lys
1               5                   10                  15

Asn Leu Ile Asp Trp Trp Asn Gly
            20

<210> SEQ ID NO 928
<211> LENGTH: 25
<212> TYPE: PRT
<213> ORGANISM: Homo sapiens

<400> SEQUENCE: 928

Cys Gly Phe Phe Gly Glu Ile Ala Glu Leu Ile Glu Glu Gly Leu Lys
1               5                   10                  15
```

Asn Leu Ile Asp Trp Trp Asn Gly Phe
            20                  25

<210> SEQ ID NO 929
<211> LENGTH: 24
<212> TYPE: PRT
<213> ORGANISM: Homo sapiens

<400> SEQUENCE: 929

Gly Phe Phe Gly Glu Ile Ala Glu Leu Ile Glu Glu Gly Leu Lys Asn
1               5                   10                  15

Leu Ile Asp Trp Trp Asn Gly Cys
            20

<210> SEQ ID NO 930
<211> LENGTH: 24
<212> TYPE: PRT
<213> ORGANISM: Homo sapiens

<400> SEQUENCE: 930

Gly Asn Trp Trp Asp Ile Leu Asn Lys Leu Gly Glu Glu Ile Leu Glu
1               5                   10                  15

Ala Ile Glu Gly Phe Phe Gly Cys
            20

<210> SEQ ID NO 931
<211> LENGTH: 24
<212> TYPE: PRT
<213> ORGANISM: Homo sapiens

<400> SEQUENCE: 931

Cys Gly Asn Trp Trp Asp Ile Leu Asn Lys Leu Gly Glu Glu Ile Leu
1               5                   10                  15

Glu Ala Ile Glu Gly Phe Phe Gly
            20

<210> SEQ ID NO 932
<211> LENGTH: 24
<212> TYPE: PRT
<213> ORGANISM: Homo sapiens

<400> SEQUENCE: 932

Cys Gly Phe Leu Gly Glu Ile Ala Glu Leu Ile Glu Glu Gly Leu Lys
1               5                   10                  15

Asn Leu Ile Asp Trp Trp Asn Gly
            20

<210> SEQ ID NO 933
<211> LENGTH: 24
<212> TYPE: PRT
<213> ORGANISM: Homo sapiens

<400> SEQUENCE: 933

Cys Gly Phe Phe Gly Glu Ile Trp Glu Leu Ile Glu Glu Gly Leu Lys
1               5                   10                  15

Asn Leu Ile Asp Trp Trp Asn Gly
            20

<210> SEQ ID NO 934
<211> LENGTH: 24
<212> TYPE: PRT
<213> ORGANISM: Homo sapiens

```
<400> SEQUENCE: 934

Cys Gly Phe Phe Gly Glu Ile Ala Glu Leu Trp Glu Gly Leu Lys
1               5                   10                  15

Asn Leu Ile Asp Trp Trp Asn Gly
            20

<210> SEQ ID NO 935
<211> LENGTH: 24
<212> TYPE: PRT
<213> ORGANISM: Homo sapiens

<400> SEQUENCE: 935

Cys Gly Phe Phe Gly Glu Ile Ala Glu Leu Ile Trp Glu Gly Leu Lys
1               5                   10                  15

Asn Leu Ile Asp Trp Trp Asn Gly
            20

<210> SEQ ID NO 936
<211> LENGTH: 24
<212> TYPE: PRT
<213> ORGANISM: Homo sapiens

<400> SEQUENCE: 936

Cys Gly Phe Phe Gly Glu Ile Ala Glu Leu Ile Glu Trp Gly Leu Lys
1               5                   10                  15

Asn Leu Ile Asp Trp Trp Asn Gly
            20

<210> SEQ ID NO 937
<211> LENGTH: 24
<212> TYPE: PRT
<213> ORGANISM: Homo sapiens

<400> SEQUENCE: 937

Cys Gly Phe Phe Gly Glu Ile Ala Glu Leu Ile Glu Glu Gly Leu Arg
1               5                   10                  15

Asn Leu Ile Asp Trp Trp Asn Gly
            20

<210> SEQ ID NO 938
<211> LENGTH: 24
<212> TYPE: PRT
<213> ORGANISM: Homo sapiens

<400> SEQUENCE: 938

Cys Gly Phe Phe Gly Glu Ile Ala Glu Leu Ile Glu Glu Gly Leu Asp
1               5                   10                  15

Asn Leu Ile Asp Trp Trp Asn Gly
            20

<210> SEQ ID NO 939
<211> LENGTH: 24
<212> TYPE: PRT
<213> ORGANISM: Homo sapiens

<400> SEQUENCE: 939

Cys Gly Phe Phe Gly Glu Ile Ala Glu Leu Ile Glu Glu Gly Leu Lys
1               5                   10                  15

Asn Leu Asn Asp Trp Trp Asn Gly
            20
```

```
<210> SEQ ID NO 940
<211> LENGTH: 24
<212> TYPE: PRT
<213> ORGANISM: Homo sapiens

<400> SEQUENCE: 940

Cys Gly Phe Phe Gly Glu Ile Ala Glu Leu Ile Glu Glu Gly Leu Lys
1               5                   10                  15

Asn Leu Asn Asp Trp Trp Asn Gly
            20

<210> SEQ ID NO 941
<211> LENGTH: 24
<212> TYPE: PRT
<213> ORGANISM: Homo sapiens

<400> SEQUENCE: 941

Cys Gly Phe Leu Gly Glu Ile Glu Glu Leu Ile Glu Glu Gly Leu Lys
1               5                   10                  15

Asn Leu Ile Asp Trp Trp Asn Gly
            20

<210> SEQ ID NO 942
<211> LENGTH: 24
<212> TYPE: PRT
<213> ORGANISM: Homo sapiens

<400> SEQUENCE: 942

Cys Gly Phe Phe Gly Leu Ile Glu Glu Leu Ile Glu Glu Gly Leu Lys
1               5                   10                  15

Asn Leu Ile Asp Trp Trp Asn Gly
            20

<210> SEQ ID NO 943
<211> LENGTH: 25
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (25)..(25)
<223> OTHER INFORMATION: Lys is conjugated to stearyl

<400> SEQUENCE: 943

Cys Gly Phe Phe Gly Glu Ile Ala Glu Leu Ile Glu Glu Gly Leu Lys
1               5                   10                  15

Asn Leu Ile Asp Trp Trp Asn Gly Lys
            20                  25

<210> SEQ ID NO 944
<211> LENGTH: 24
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (1)..(1)
<223> OTHER INFORMATION: Gly is conjugated to stearyl

<400> SEQUENCE: 944

Gly Phe Phe Gly Glu Ile Ala Glu Leu Ile Glu Glu Gly Leu Lys Asn
1               5                   10                  15

Leu Ile Asp Trp Trp Asn Gly Cys
            20
```

-continued

```
<210> SEQ ID NO 945
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(15)
<223> OTHER INFORMATION: Lys is conjugated to stearyl

<400> SEQUENCE: 945

Cys Phe Phe Gly Ala Ile Trp Glu Phe Ala Lys Ser Ile Leu Lys
1               5                   10                  15

<210> SEQ ID NO 946
<211> LENGTH: 15
<212> TYPE: PRT
<213> ORGANISM: Homo sapiens

<400> SEQUENCE: 946

Cys Gly Phe Phe Gly Ala Ile Trp Glu Phe Ala Lys Ser Ile Leu
1               5                   10                  15

<210> SEQ ID NO 947
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(15)
<223> OTHER INFORMATION: Lys is conjugated to stearyl

<400> SEQUENCE: 947

Cys Phe Phe Gly Lys Ile Trp Glu Phe Ile Lys Ser Ile Leu Lys
1               5                   10                  15

<210> SEQ ID NO 948
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Phe is conjugated to stearyl

<400> SEQUENCE: 948

Phe Phe Gly Lys Ile Trp Glu Phe Ile Lys Ser Ile Leu Cys
1               5                   10

<210> SEQ ID NO 949
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(15)
<223> OTHER INFORMATION: Lys is conjugated to stearyl

<400> SEQUENCE: 949

Cys Phe Phe Gly Ala Ile Trp Glu Phe Ile Lys Ser Ile Ala Lys
```

```
1               5               10              15
```

<210> SEQ ID NO 950
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Phe is conjugated to stearyl

<400> SEQUENCE: 950

```
Phe Phe Gly Ala Ile Trp Glu Phe Ile Lys Ser Ile Ala Cys
1               5                   10
```

<210> SEQ ID NO 951
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Phe is conjugated to stearyl

<400> SEQUENCE: 951

```
Phe Phe Gly Ala Ile Trp Glu Phe Ala Lys Ser Ile Leu Cys
1               5                   10
```

<210> SEQ ID NO 952
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(15)
<223> OTHER INFORMATION: Lys is conjugated to stearyl

<400> SEQUENCE: 952

```
Cys Phe Phe Gly Gly Ile Trp Glu Phe Ile Lys Ser Ile Leu Lys
1               5                   10                  15
```

<210> SEQ ID NO 953
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Phe is conjugated to stearyl

<400> SEQUENCE: 953

```
Phe Phe Gly Gly Ile Trp Glu Phe Ile Lys Ser Ile Leu Cys
1               5                   10
```

<210> SEQ ID NO 954
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE

```
<222> LOCATION: (15)..(15)
<223> OTHER INFORMATION: Lys is conjugated to stearyl

<400> SEQUENCE: 954

Cys Phe Phe Lys Ala Ile Trp Glu Phe Ile Lys Ser Ile Leu Lys
1               5                   10                  15

<210> SEQ ID NO 955
<211> LENGTH: 14
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (1)..(1)
<223> OTHER INFORMATION: Phe is conjugated to stearyl

<400> SEQUENCE: 955

Phe Phe Lys Ala Ile Trp Glu Phe Ile Lys Ser Ile Leu Cys
1               5                   10

<210> SEQ ID NO 956
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(15)
<223> OTHER INFORMATION: Lys is conjugated to stearyl

<400> SEQUENCE: 956

Cys Phe Phe Gly Ala Ile Trp Glu Ala Ile Lys Ser Ile Leu Lys
1               5                   10                  15

<210> SEQ ID NO 957
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Phe is conjugated to stearyl

<400> SEQUENCE: 957

Phe Phe Gly Ala Ile Trp Glu Ala Ile Lys Ser Ile Leu Cys
1               5                   10

<210> SEQ ID NO 958
<211> LENGTH: 14
<212> TYPE: PRT
<213> ORGANISM: Homo sapiens

<400> SEQUENCE: 958

Cys Phe Phe Lys Ala Ile Trp Glu Phe Ala Lys Ser Ile Leu
1               5                   10

<210> SEQ ID NO 959
<211> LENGTH: 14
<212> TYPE: PRT
<213> ORGANISM: Homo sapiens

<400> SEQUENCE: 959

Cys Phe Phe Lys Ala Ile Trp Glu Phe Ala His Ser Ile Leu
```

-continued

```
1               5                   10

<210> SEQ ID NO 960
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(15)
<223> OTHER INFORMATION: Lys is conjugated to stearyl

<400> SEQUENCE: 960

Cys Phe Phe Lys Ala Ile Trp Glu Phe Ala Lys Ser Ile Leu Lys
1               5                   10                  15

<210> SEQ ID NO 961
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Phe is conjugated to stearyl

<400> SEQUENCE: 961

Phe Phe Lys Ala Ile Trp Glu Phe Ala Lys Ser Ile Leu Cys
1               5                   10

<210> SEQ ID NO 962
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(15)
<223> OTHER INFORMATION: Lys is conjugated to stearyl

<400> SEQUENCE: 962

Cys Phe Phe Lys Ala Ile Trp Glu Phe Ala His Ser Ile Leu Lys
1               5                   10                  15

<210> SEQ ID NO 963
<211> LENGTH: 24
<212> TYPE: PRT
<213> ORGANISM: Homo sapiens

<400> SEQUENCE: 963

Cys Gly Leu Phe Gly Glu Ile Ala Glu Leu Ile Glu Glu Gly Leu Glu
1               5                   10                  15

Asn Leu Ile Asp Trp Trp Asn Gly
            20

<210> SEQ ID NO 964
<211> LENGTH: 24
<212> TYPE: PRT
<213> ORGANISM: Homo sapiens

<400> SEQUENCE: 964

Cys Gly Leu Phe Gly Glu Ile Glu Glu Leu Ile Glu Glu Gly Leu Lys
1               5                   10                  15

Asn Leu Ile Asp Trp Trp Asn Gly
```

20

<210> SEQ ID NO 965
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(15)
<223> OTHER INFORMATION: Lys is conjugated to stearyl

<400> SEQUENCE: 965

Cys Phe Phe Gly Ala Ile Trp Glu Phe Ala Lys Ser Ile Leu Lys
1               5                   10                  15

<210> SEQ ID NO 966
<211> LENGTH: 24
<212> TYPE: PRT
<213> ORGANISM: Homo sapiens

<400> SEQUENCE: 966

Cys Gly Leu Phe Gly Glu Ile Glu Glu Leu Ile Glu Glu Gly Leu Lys
1               5                   10                  15

Gly Leu Ile Asp Trp Trp Asn Gly
            20

<210> SEQ ID NO 967
<211> LENGTH: 24
<212> TYPE: PRT
<213> ORGANISM: Homo sapiens

<400> SEQUENCE: 967

Cys Gly Leu Phe Gly Glu Ile Ala Glu Leu Ile Glu Glu Gly Leu Lys
1               5                   10                  15

Asn Leu Ile Asp Trp Trp Asn Gly
            20

<210> SEQ ID NO 968
<211> LENGTH: 24
<212> TYPE: PRT
<213> ORGANISM: Homo sapiens

<400> SEQUENCE: 968

Cys Gly Leu Phe Gly Glu Ile Ala Glu Leu Ile Glu Glu Gly Leu Glu
1               5                   10                  15

Gly Leu Ile Asp Trp Trp Asn Gly
            20

<210> SEQ ID NO 969
<211> LENGTH: 24
<212> TYPE: PRT
<213> ORGANISM: Homo sapiens

<400> SEQUENCE: 969

Gly Leu Phe Gly Glu Ile Glu Glu Leu Ile Glu Glu Gly Leu Glu Asn
1               5                   10                  15

Leu Ile Asp Trp Trp Asn Gly Cys
            20

<210> SEQ ID NO 970
<211> LENGTH: 24
<212> TYPE: PRT

<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Gly is conjugated to stearyl

<400> SEQUENCE: 970

Gly Leu Phe Gly Glu Ile Glu Glu Leu Ile Glu Glu Gly Leu Glu Asn
1               5                   10                  15
Leu Ile Asp Trp Trp Asn Gly Cys
            20

<210> SEQ ID NO 971
<211> LENGTH: 25
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (25)..(25)
<223> OTHER INFORMATION: Lys is conjugated to stearyl

<400> SEQUENCE: 971

Cys Gly Leu Phe Gly Glu Ile Glu Glu Leu Ile Glu Glu Gly Leu Glu
1               5                   10                  15
Asn Leu Ile Asp Trp Trp Asn Gly Lys
            20                  25

<210> SEQ ID NO 972
<211> LENGTH: 24
<212> TYPE: PRT
<213> ORGANISM: Homo sapiens

<400> SEQUENCE: 972

Cys Gly Asn Trp Trp Asp Ile Leu Asn Glu Leu Gly Glu Glu Ile Leu
1               5                   10                  15
Glu Glu Ile Glu Gly Phe Leu Gly
            20

<210> SEQ ID NO 973
<211> LENGTH: 24
<212> TYPE: PRT
<213> ORGANISM: Homo sapiens

<400> SEQUENCE: 973

Cys Ala Leu Phe Gly Glu Ile Glu Glu Leu Ile Glu Glu Gly Leu Glu
1               5                   10                  15
Asn Leu Ile Asp Trp Trp Asn Gly
            20

<210> SEQ ID NO 974
<211> LENGTH: 24
<212> TYPE: PRT
<213> ORGANISM: Homo sapiens

<400> SEQUENCE: 974

Cys Glu Leu Phe Gly Glu Ile Glu Glu Leu Ile Glu Glu Gly Leu Glu
1               5                   10                  15
Asn Leu Ile Asp Trp Trp Asn Gly
            20

```
<210> SEQ ID NO 975
<211> LENGTH: 24
<212> TYPE: PRT
<213> ORGANISM: Homo sapiens

<400> SEQUENCE: 975

Cys Ser Leu Phe Gly Glu Ile Glu Glu Leu Ile Glu Glu Gly Leu Glu
1               5                   10                  15

Asn Leu Ile Asp Trp Trp Asn Gly
            20

<210> SEQ ID NO 976
<211> LENGTH: 24
<212> TYPE: PRT
<213> ORGANISM: Homo sapiens

<400> SEQUENCE: 976

Cys Asn Leu Phe Gly Glu Ile Glu Glu Leu Ile Glu Glu Gly Leu Glu
1               5                   10                  15

Asn Leu Ile Asp Trp Trp Asn Gly
            20

<210> SEQ ID NO 977
<211> LENGTH: 24
<212> TYPE: PRT
<213> ORGANISM: Homo sapiens

<400> SEQUENCE: 977

Cys Val Leu Phe Gly Glu Ile Glu Glu Leu Ile Glu Glu Gly Leu Glu
1               5                   10                  15

Asn Leu Ile Asp Trp Trp Asn Gly
            20

<210> SEQ ID NO 978
<211> LENGTH: 24
<212> TYPE: PRT
<213> ORGANISM: Homo sapiens

<400> SEQUENCE: 978

Cys Gly Phe Phe Gly Glu Ile Glu Glu Leu Ile Glu Glu Gly Leu Glu
1               5                   10                  15

Asn Leu Ile Asp Trp Trp Asn Gly
            20

<210> SEQ ID NO 979
<211> LENGTH: 24
<212> TYPE: PRT
<213> ORGANISM: Homo sapiens

<400> SEQUENCE: 979

Cys Gly Val Phe Gly Glu Ile Glu Glu Leu Ile Glu Glu Gly Leu Glu
1               5                   10                  15

Asn Leu Ile Asp Trp Trp Asn Gly
            20

<210> SEQ ID NO 980
<211> LENGTH: 24
<212> TYPE: PRT
<213> ORGANISM: Homo sapiens

<400> SEQUENCE: 980

Cys Gly Ile Phe Gly Glu Ile Glu Glu Leu Ile Glu Glu Gly Leu Glu
1               5                   10                  15
```

Asn Leu Ile Asp Trp Trp Asn Gly
            20

<210> SEQ ID NO 981
<211> LENGTH: 24
<212> TYPE: PRT
<213> ORGANISM: Homo sapiens

<400> SEQUENCE: 981

Cys Gly Trp Phe Gly Glu Ile Glu Glu Leu Ile Glu Glu Gly Leu Glu
1               5                   10                  15

Asn Leu Ile Asp Trp Trp Asn Gly
            20

<210> SEQ ID NO 982
<211> LENGTH: 24
<212> TYPE: PRT
<213> ORGANISM: Homo sapiens

<400> SEQUENCE: 982

Cys Gly Tyr Phe Gly Glu Ile Glu Glu Leu Ile Glu Glu Gly Leu Glu
1               5                   10                  15

Asn Leu Ile Asp Trp Trp Asn Gly
            20

<210> SEQ ID NO 983
<211> LENGTH: 24
<212> TYPE: PRT
<213> ORGANISM: Homo sapiens

<400> SEQUENCE: 983

Cys Gly Leu Leu Gly Glu Ile Glu Glu Leu Ile Glu Glu Gly Leu Glu
1               5                   10                  15

Asn Leu Ile Asp Trp Trp Asn Gly
            20

<210> SEQ ID NO 984
<211> LENGTH: 24
<212> TYPE: PRT
<213> ORGANISM: Homo sapiens

<400> SEQUENCE: 984

Cys Gly Leu Val Gly Glu Ile Glu Glu Leu Ile Glu Glu Gly Leu Glu
1               5                   10                  15

Asn Leu Ile Asp Trp Trp Asn Gly
            20

<210> SEQ ID NO 985
<211> LENGTH: 24
<212> TYPE: PRT
<213> ORGANISM: Homo sapiens

<400> SEQUENCE: 985

Cys Gly Leu Ile Gly Glu Ile Glu Glu Leu Ile Glu Glu Gly Leu Glu
1               5                   10                  15

Asn Leu Ile Asp Trp Trp Asn Gly
            20

<210> SEQ ID NO 986
<211> LENGTH: 24
<212> TYPE: PRT
<213> ORGANISM: Homo sapiens

<400> SEQUENCE: 986

Cys Gly Leu Trp Gly Glu Ile Glu Glu Leu Ile Glu Glu Gly Leu Glu
1               5                   10                  15

Asn Leu Ile Asp Trp Trp Asn Gly
            20

<210> SEQ ID NO 987
<211> LENGTH: 24
<212> TYPE: PRT
<213> ORGANISM: Homo sapiens

<400> SEQUENCE: 987

Cys Gly Leu Tyr Gly Glu Ile Glu Glu Leu Ile Glu Glu Gly Leu Glu
1               5                   10                  15

Asn Leu Ile Asp Trp Trp Asn Gly
            20

<210> SEQ ID NO 988
<211> LENGTH: 24
<212> TYPE: PRT
<213> ORGANISM: Homo sapiens

<400> SEQUENCE: 988

Cys Gly Leu Phe Glu Glu Ile Glu Glu Leu Ile Glu Glu Gly Leu Glu
1               5                   10                  15

Asn Leu Ile Asp Trp Trp Asn Gly
            20

<210> SEQ ID NO 989
<211> LENGTH: 24
<212> TYPE: PRT
<213> ORGANISM: Homo sapiens

<400> SEQUENCE: 989

Cys Gly Leu Phe Ala Glu Ile Glu Glu Leu Ile Glu Glu Gly Leu Glu
1               5                   10                  15

Asn Leu Ile Asp Trp Trp Asn Gly
            20

<210> SEQ ID NO 990
<211> LENGTH: 24
<212> TYPE: PRT
<213> ORGANISM: Homo sapiens

<400> SEQUENCE: 990

Cys Gly Leu Phe Asn Glu Ile Glu Glu Leu Ile Glu Glu Gly Leu Glu
1               5                   10                  15

Asn Leu Ile Asp Trp Trp Asn Gly
            20

<210> SEQ ID NO 991
<211> LENGTH: 24
<212> TYPE: PRT
<213> ORGANISM: Homo sapiens

<400> SEQUENCE: 991

Cys Gly Leu Phe Ser Glu Ile Glu Glu Leu Ile Glu Glu Gly Leu Glu
1               5                   10                  15

Asn Leu Ile Asp Trp Trp Asn Gly
            20

<210> SEQ ID NO 992
<211> LENGTH: 24
<212> TYPE: PRT
<213> ORGANISM: Homo sapiens

<400> SEQUENCE: 992

Cys Gly Leu Phe Gly Ala Ile Glu Glu Leu Ile Glu Glu Gly Leu Glu
1               5                   10                  15

Asn Leu Ile Asp Trp Trp Asn Gly
            20

<210> SEQ ID NO 993
<211> LENGTH: 24
<212> TYPE: PRT
<213> ORGANISM: Homo sapiens

<400> SEQUENCE: 993

Cys Gly Leu Phe Gly Asp Ile Glu Glu Leu Ile Glu Glu Gly Leu Glu
1               5                   10                  15

Asn Leu Ile Asp Trp Trp Asn Gly
            20

<210> SEQ ID NO 994
<211> LENGTH: 24
<212> TYPE: PRT
<213> ORGANISM: Homo sapiens

<400> SEQUENCE: 994

Cys Gly Leu Phe Gly Asn Ile Glu Glu Leu Ile Glu Glu Gly Leu Glu
1               5                   10                  15

Asn Leu Ile Asp Trp Trp Asn Gly
            20

<210> SEQ ID NO 995
<211> LENGTH: 24
<212> TYPE: PRT
<213> ORGANISM: Homo sapiens

<400> SEQUENCE: 995

Cys Gly Leu Phe Gly Ser Ile Glu Glu Leu Ile Glu Glu Gly Leu Glu
1               5                   10                  15

Asn Leu Ile Asp Trp Trp Asn Gly
            20

<210> SEQ ID NO 996
<211> LENGTH: 24
<212> TYPE: PRT
<213> ORGANISM: Homo sapiens

<400> SEQUENCE: 996

Cys Gly Leu Phe Gly Glu Leu Glu Glu Leu Ile Glu Glu Gly Leu Glu
1               5                   10                  15

Asn Leu Ile Asp Trp Trp Asn Gly
            20

<210> SEQ ID NO 997
<211> LENGTH: 24
<212> TYPE: PRT
<213> ORGANISM: Homo sapiens

<400> SEQUENCE: 997

Cys Gly Leu Phe Gly Glu Val Glu Glu Leu Ile Glu Glu Gly Leu Glu

-continued

```
1               5                   10                  15
```

Asn Leu Ile Asp Trp Trp Asn Gly
            20

<210> SEQ ID NO 998
<211> LENGTH: 24
<212> TYPE: PRT
<213> ORGANISM: Homo sapiens

<400> SEQUENCE: 998

Cys Gly Leu Phe Gly Glu Phe Glu Glu Leu Ile Glu Glu Gly Leu Glu
1               5                   10                  15

Asn Leu Ile Asp Trp Trp Asn Gly
            20

<210> SEQ ID NO 999
<211> LENGTH: 24
<212> TYPE: PRT
<213> ORGANISM: Homo sapiens

<400> SEQUENCE: 999

Cys Gly Leu Phe Gly Glu Trp Glu Glu Leu Ile Glu Glu Gly Leu Glu
1               5                   10                  15

Asn Leu Ile Asp Trp Trp Asn Gly
            20

<210> SEQ ID NO 1000
<211> LENGTH: 24
<212> TYPE: PRT
<213> ORGANISM: Homo sapiens

<400> SEQUENCE: 1000

Cys Gly Leu Phe Gly Glu Tyr Glu Glu Leu Ile Glu Glu Gly Leu Glu
1               5                   10                  15

Asn Leu Ile Asp Trp Trp Asn Gly
            20

<210> SEQ ID NO 1001
<211> LENGTH: 24
<212> TYPE: PRT
<213> ORGANISM: Homo sapiens

<400> SEQUENCE: 1001

Cys Gly Leu Phe Gly Glu Ile Ala Glu Leu Ile Glu Glu Gly Leu Glu
1               5                   10                  15

Asn Leu Ile Asp Trp Trp Asn Gly
            20

<210> SEQ ID NO 1002
<211> LENGTH: 24
<212> TYPE: PRT
<213> ORGANISM: Homo sapiens

<400> SEQUENCE: 1002

Cys Gly Leu Phe Gly Glu Ile Gly Glu Leu Ile Glu Glu Gly Leu Glu
1               5                   10                  15

Asn Leu Ile Asp Trp Trp Asn Gly
            20

<210> SEQ ID NO 1003
<211> LENGTH: 24
<212> TYPE: PRT

<213> ORGANISM: Homo sapiens

<400> SEQUENCE: 1003

Cys Gly Leu Phe Gly Glu Ile Leu Glu Leu Ile Glu Glu Gly Leu Glu
1               5                   10                  15

Asn Leu Ile Asp Trp Trp Asn Gly
            20

<210> SEQ ID NO 1004
<211> LENGTH: 24
<212> TYPE: PRT
<213> ORGANISM: Homo sapiens

<400> SEQUENCE: 1004

Cys Gly Leu Phe Gly Glu Ile Val Glu Leu Ile Glu Glu Gly Leu Glu
1               5                   10                  15

Asn Leu Ile Asp Trp Trp Asn Gly
            20

<210> SEQ ID NO 1005
<211> LENGTH: 24
<212> TYPE: PRT
<213> ORGANISM: Homo sapiens

<400> SEQUENCE: 1005

Cys Gly Leu Phe Gly Glu Ile Ser Glu Leu Ile Glu Glu Gly Leu Glu
1               5                   10                  15

Asn Leu Ile Asp Trp Trp Asn Gly
            20

<210> SEQ ID NO 1006
<211> LENGTH: 24
<212> TYPE: PRT
<213> ORGANISM: Homo sapiens

<400> SEQUENCE: 1006

Cys Gly Leu Phe Gly Glu Ile Glu Asp Leu Ile Glu Glu Gly Leu Glu
1               5                   10                  15

Asn Leu Ile Asp Trp Trp Asn Gly
            20

<210> SEQ ID NO 1007
<211> LENGTH: 24
<212> TYPE: PRT
<213> ORGANISM: Homo sapiens

<400> SEQUENCE: 1007

Cys Gly Leu Phe Gly Glu Ile Glu Asn Leu Ile Glu Glu Gly Leu Glu
1               5                   10                  15

Asn Leu Ile Asp Trp Trp Asn Gly
            20

<210> SEQ ID NO 1008
<211> LENGTH: 24
<212> TYPE: PRT
<213> ORGANISM: Homo sapiens

<400> SEQUENCE: 1008

Cys Gly Leu Phe Gly Glu Ile Glu Ser Leu Ile Glu Glu Gly Leu Glu
1               5                   10                  15

Asn Leu Ile Asp Trp Trp Asn Gly
            20

<210> SEQ ID NO 1009
<211> LENGTH: 24
<212> TYPE: PRT
<213> ORGANISM: Homo sapiens

<400> SEQUENCE: 1009

Cys Gly Leu Phe Gly Glu Ile Glu Ala Leu Ile Glu Glu Gly Leu Glu
1               5                   10                  15

Asn Leu Ile Asp Trp Trp Asn Gly
            20

<210> SEQ ID NO 1010
<211> LENGTH: 24
<212> TYPE: PRT
<213> ORGANISM: Homo sapiens

<400> SEQUENCE: 1010

Cys Gly Leu Phe Gly Glu Ile Glu Gly Leu Ile Glu Glu Gly Leu Glu
1               5                   10                  15

Asn Leu Ile Asp Trp Trp Asn Gly
            20

<210> SEQ ID NO 1011
<211> LENGTH: 24
<212> TYPE: PRT
<213> ORGANISM: Homo sapiens

<400> SEQUENCE: 1011

Cys Gly Leu Phe Gly Glu Ile Glu Glu Val Ile Glu Glu Gly Leu Glu
1               5                   10                  15

Asn Leu Ile Asp Trp Trp Asn Gly
            20

<210> SEQ ID NO 1012
<211> LENGTH: 24
<212> TYPE: PRT
<213> ORGANISM: Homo sapiens

<400> SEQUENCE: 1012

Cys Gly Leu Phe Gly Glu Ile Glu Glu Ile Ile Glu Glu Gly Leu Glu
1               5                   10                  15

Asn Leu Ile Asp Trp Trp Asn Gly
            20

<210> SEQ ID NO 1013
<211> LENGTH: 24
<212> TYPE: PRT
<213> ORGANISM: Homo sapiens

<400> SEQUENCE: 1013

Cys Gly Leu Phe Gly Glu Ile Glu Glu Phe Ile Glu Glu Gly Leu Glu
1               5                   10                  15

Asn Leu Ile Asp Trp Trp Asn Gly
            20

<210> SEQ ID NO 1014
<211> LENGTH: 24
<212> TYPE: PRT
<213> ORGANISM: Homo sapiens

<400> SEQUENCE: 1014

-continued

```
Cys Gly Leu Phe Gly Glu Ile Glu Glu Ala Ile Glu Glu Gly Leu Glu
1               5                   10                  15

Asn Leu Ile Asp Trp Trp Asn Gly
            20

<210> SEQ ID NO 1015
<211> LENGTH: 24
<212> TYPE: PRT
<213> ORGANISM: Homo sapiens

<400> SEQUENCE: 1015

Cys Gly Leu Phe Gly Glu Ile Glu Glu Tyr Ile Glu Glu Gly Leu Glu
1               5                   10                  15

Asn Leu Ile Asp Trp Trp Asn Gly
            20

<210> SEQ ID NO 1016
<211> LENGTH: 24
<212> TYPE: PRT
<213> ORGANISM: Homo sapiens

<400> SEQUENCE: 1016

Cys Gly Leu Phe Gly Glu Ile Glu Glu Trp Ile Glu Glu Gly Leu Glu
1               5                   10                  15

Asn Leu Ile Asp Trp Trp Asn Gly
            20

<210> SEQ ID NO 1017
<211> LENGTH: 24
<212> TYPE: PRT
<213> ORGANISM: Homo sapiens

<400> SEQUENCE: 1017

Cys Gly Leu Phe Gly Glu Ile Glu Glu Leu Val Glu Glu Gly Leu Glu
1               5                   10                  15

Asn Leu Ile Asp Trp Trp Asn Gly
            20

<210> SEQ ID NO 1018
<211> LENGTH: 24
<212> TYPE: PRT
<213> ORGANISM: Homo sapiens

<400> SEQUENCE: 1018

Cys Gly Leu Phe Gly Glu Ile Glu Glu Leu Leu Glu Glu Gly Leu Glu
1               5                   10                  15

Asn Leu Ile Asp Trp Trp Asn Gly
            20

<210> SEQ ID NO 1019
<211> LENGTH: 24
<212> TYPE: PRT
<213> ORGANISM: Homo sapiens

<400> SEQUENCE: 1019

Cys Gly Leu Phe Gly Glu Ile Glu Glu Leu Phe Glu Glu Gly Leu Glu
1               5                   10                  15

Asn Leu Ile Asp Trp Trp Asn Gly
            20

<210> SEQ ID NO 1020
<211> LENGTH: 24
```

```
<212> TYPE: PRT
<213> ORGANISM: Homo sapiens

<400> SEQUENCE: 1020

Cys Gly Leu Phe Gly Glu Ile Glu Glu Leu Ala Glu Gly Leu Glu
1               5                   10                  15

Asn Leu Ile Asp Trp Trp Asn Gly
            20

<210> SEQ ID NO 1021
<211> LENGTH: 24
<212> TYPE: PRT
<213> ORGANISM: Homo sapiens

<400> SEQUENCE: 1021

Cys Gly Leu Phe Gly Glu Ile Glu Glu Leu Tyr Glu Gly Leu Glu
1               5                   10                  15

Asn Leu Ile Asp Trp Trp Asn Gly
            20

<210> SEQ ID NO 1022
<211> LENGTH: 24
<212> TYPE: PRT
<213> ORGANISM: Homo sapiens

<400> SEQUENCE: 1022

Cys Gly Leu Phe Gly Glu Ile Glu Glu Leu Trp Glu Gly Leu Glu
1               5                   10                  15

Asn Leu Ile Asp Trp Trp Asn Gly
            20

<210> SEQ ID NO 1023
<211> LENGTH: 24
<212> TYPE: PRT
<213> ORGANISM: Homo sapiens

<400> SEQUENCE: 1023

Cys Gly Leu Phe Gly Glu Ile Glu Glu Leu Ile Asp Glu Gly Leu Glu
1               5                   10                  15

Asn Leu Ile Asp Trp Trp Asn Gly
            20

<210> SEQ ID NO 1024
<211> LENGTH: 24
<212> TYPE: PRT
<213> ORGANISM: Homo sapiens

<400> SEQUENCE: 1024

Cys Gly Leu Phe Gly Glu Ile Glu Glu Leu Ile Asn Glu Gly Leu Glu
1               5                   10                  15

Asn Leu Ile Asp Trp Trp Asn Gly
            20

<210> SEQ ID NO 1025
<211> LENGTH: 24
<212> TYPE: PRT
<213> ORGANISM: Homo sapiens

<400> SEQUENCE: 1025

Cys Gly Leu Phe Gly Glu Ile Glu Glu Leu Ile Ser Glu Gly Leu Glu
1               5                   10                  15

Asn Leu Ile Asp Trp Trp Asn Gly
```

```
                    20

<210> SEQ ID NO 1026
<211> LENGTH: 24
<212> TYPE: PRT
<213> ORGANISM: Homo sapiens

<400> SEQUENCE: 1026

Cys Gly Leu Phe Gly Glu Ile Glu Glu Leu Ile Glu Asp Gly Leu Glu
1               5                   10                  15

Asn Leu Ile Asp Trp Trp Asn Gly
            20

<210> SEQ ID NO 1027
<211> LENGTH: 24
<212> TYPE: PRT
<213> ORGANISM: Homo sapiens

<400> SEQUENCE: 1027

Cys Gly Leu Phe Gly Glu Ile Glu Glu Leu Ile Glu Tyr Gly Leu Glu
1               5                   10                  15

Asn Leu Ile Asp Trp Trp Asn Gly
            20

<210> SEQ ID NO 1028
<211> LENGTH: 24
<212> TYPE: PRT
<213> ORGANISM: Homo sapiens

<400> SEQUENCE: 1028

Cys Gly Leu Phe Gly Glu Ile Glu Glu Leu Ile Glu Ser Gly Leu Glu
1               5                   10                  15

Asn Leu Ile Asp Trp Trp Asn Gly
            20

<210> SEQ ID NO 1029
<211> LENGTH: 24
<212> TYPE: PRT
<213> ORGANISM: Homo sapiens

<400> SEQUENCE: 1029

Cys Gly Leu Phe Gly Glu Ile Glu Glu Leu Ile Glu Gln Gly Leu Glu
1               5                   10                  15

Asn Leu Ile Asp Trp Trp Asn Gly
            20

<210> SEQ ID NO 1030
<211> LENGTH: 24
<212> TYPE: PRT
<213> ORGANISM: Homo sapiens

<400> SEQUENCE: 1030

Cys Gly Leu Phe Gly Glu Ile Glu Glu Leu Ile Glu Asn Gly Leu Glu
1               5                   10                  15

Asn Leu Ile Asp Trp Trp Asn Gly
            20

<210> SEQ ID NO 1031
<211> LENGTH: 24
<212> TYPE: PRT
<213> ORGANISM: Homo sapiens

<400> SEQUENCE: 1031
```

```
Cys Gly Leu Phe Gly Glu Ile Glu Glu Leu Ile Glu Glu Ala Leu Glu
1               5                   10                  15

Asn Leu Ile Asp Trp Trp Asn Gly
            20

<210> SEQ ID NO 1032
<211> LENGTH: 24
<212> TYPE: PRT
<213> ORGANISM: Homo sapiens

<400> SEQUENCE: 1032

Cys Gly Leu Phe Gly Glu Ile Glu Glu Leu Ile Glu Glu Asn Leu Glu
1               5                   10                  15

Asn Leu Ile Asp Trp Trp Asn Gly
            20

<210> SEQ ID NO 1033
<211> LENGTH: 24
<212> TYPE: PRT
<213> ORGANISM: Homo sapiens

<400> SEQUENCE: 1033

Cys Gly Leu Phe Gly Glu Ile Glu Glu Leu Ile Glu Glu Ser Leu Glu
1               5                   10                  15

Asn Leu Ile Asp Trp Trp Asn Gly
            20

<210> SEQ ID NO 1034
<211> LENGTH: 24
<212> TYPE: PRT
<213> ORGANISM: Homo sapiens

<400> SEQUENCE: 1034

Cys Gly Leu Phe Gly Glu Ile Glu Glu Leu Ile Glu Glu Gln Leu Glu
1               5                   10                  15

Asn Leu Ile Asp Trp Trp Asn Gly
            20

<210> SEQ ID NO 1035
<211> LENGTH: 24
<212> TYPE: PRT
<213> ORGANISM: Homo sapiens

<400> SEQUENCE: 1035

Cys Gly Leu Phe Gly Glu Ile Glu Glu Leu Ile Glu Glu Gly Trp Glu
1               5                   10                  15

Asn Leu Ile Asp Trp Trp Asn Gly
            20

<210> SEQ ID NO 1036
<211> LENGTH: 24
<212> TYPE: PRT
<213> ORGANISM: Homo sapiens

<400> SEQUENCE: 1036

Cys Gly Leu Phe Gly Glu Ile Glu Glu Leu Ile Glu Glu Gly Val Glu
1               5                   10                  15

Asn Leu Ile Asp Trp Trp Asn Gly
            20

<210> SEQ ID NO 1037
```

```
<211> LENGTH: 24
<212> TYPE: PRT
<213> ORGANISM: Homo sapiens

<400> SEQUENCE: 1037

Cys Gly Leu Phe Gly Glu Ile Glu Glu Leu Ile Glu Glu Gly Ile Glu
1               5                   10                  15

Asn Leu Ile Asp Trp Trp Asn Gly
            20

<210> SEQ ID NO 1038
<211> LENGTH: 24
<212> TYPE: PRT
<213> ORGANISM: Homo sapiens

<400> SEQUENCE: 1038

Cys Gly Leu Phe Gly Glu Ile Glu Glu Leu Ile Glu Glu Gly Phe Glu
1               5                   10                  15

Asn Leu Ile Asp Trp Trp Asn Gly
            20

<210> SEQ ID NO 1039
<211> LENGTH: 24
<212> TYPE: PRT
<213> ORGANISM: Homo sapiens

<400> SEQUENCE: 1039

Cys Gly Leu Phe Gly Glu Ile Glu Glu Leu Ile Glu Glu Gly Ala Glu
1               5                   10                  15

Asn Leu Ile Asp Trp Trp Asn Gly
            20

<210> SEQ ID NO 1040
<211> LENGTH: 24
<212> TYPE: PRT
<213> ORGANISM: Homo sapiens

<400> SEQUENCE: 1040

Cys Gly Leu Phe Gly Glu Ile Glu Glu Leu Ile Glu Glu Gly Tyr Glu
1               5                   10                  15

Asn Leu Ile Asp Trp Trp Asn Gly
            20

<210> SEQ ID NO 1041
<211> LENGTH: 24
<212> TYPE: PRT
<213> ORGANISM: Homo sapiens

<400> SEQUENCE: 1041

Cys Gly Leu Phe Gly Glu Ile Glu Glu Leu Ile Glu Glu Gly Leu Arg
1               5                   10                  15

Asn Leu Ile Asp Trp Trp Asn Gly
            20

<210> SEQ ID NO 1042
<211> LENGTH: 24
<212> TYPE: PRT
<213> ORGANISM: Homo sapiens

<400> SEQUENCE: 1042

Cys Gly Leu Phe Gly Glu Ile Glu Glu Leu Ile Glu Glu Gly Leu His
1               5                   10                  15
```

Asn Leu Ile Asp Trp Trp Asn Gly
            20

<210> SEQ ID NO 1043
<211> LENGTH: 23
<212> TYPE: PRT
<213> ORGANISM: Homo sapiens

<400> SEQUENCE: 1043

Cys Gly Leu Phe Gly Glu Ile Glu Glu Leu Ile Glu Glu Gly Leu Asn
1               5                   10                  15

Leu Ile Asp Trp Trp Asn Gly
            20

<210> SEQ ID NO 1044
<211> LENGTH: 24
<212> TYPE: PRT
<213> ORGANISM: Homo sapiens

<400> SEQUENCE: 1044

Cys Gly Leu Phe Gly Glu Ile Glu Glu Leu Ile Glu Glu Gly Leu Asp
1               5                   10                  15

Asn Leu Ile Asp Trp Trp Asn Gly
            20

<210> SEQ ID NO 1045
<211> LENGTH: 24
<212> TYPE: PRT
<213> ORGANISM: Homo sapiens

<400> SEQUENCE: 1045

Cys Gly Leu Phe Gly Glu Ile Glu Glu Leu Ile Glu Glu Gly Leu Lys
1               5                   10                  15

Asn Leu Ile Asp Trp Trp Asn Gly
            20

<210> SEQ ID NO 1046
<211> LENGTH: 24
<212> TYPE: PRT
<213> ORGANISM: Homo sapiens

<400> SEQUENCE: 1046

Cys Gly Leu Phe Gly Glu Ile Glu Glu Leu Ile Glu Glu Gly Leu Glu
1               5                   10                  15

Gly Leu Ile Asp Trp Trp Asn Gly
            20

<210> SEQ ID NO 1047
<211> LENGTH: 24
<212> TYPE: PRT
<213> ORGANISM: Homo sapiens

<400> SEQUENCE: 1047

Cys Gly Leu Phe Gly Glu Ile Glu Glu Leu Ile Glu Glu Gly Leu Glu
1               5                   10                  15

Tyr Leu Ile Asp Trp Trp Asn Gly
            20

<210> SEQ ID NO 1048
<211> LENGTH: 24
<212> TYPE: PRT
<213> ORGANISM: Homo sapiens

```
<400> SEQUENCE: 1048

Cys Gly Leu Phe Gly Glu Ile Glu Glu Leu Ile Glu Glu Gly Leu Glu
1               5                   10                  15

Gln Leu Ile Asp Trp Trp Asn Gly
            20

<210> SEQ ID NO 1049
<211> LENGTH: 24
<212> TYPE: PRT
<213> ORGANISM: Homo sapiens

<400> SEQUENCE: 1049

Cys Gly Leu Phe Gly Glu Ile Glu Glu Leu Ile Glu Glu Gly Leu Glu
1               5                   10                  15

Ser Leu Ile Asp Trp Trp Asn Gly
            20

<210> SEQ ID NO 1050
<211> LENGTH: 24
<212> TYPE: PRT
<213> ORGANISM: Homo sapiens

<400> SEQUENCE: 1050

Cys Gly Leu Phe Gly Glu Ile Glu Glu Leu Ile Glu Glu Gly Leu Glu
1               5                   10                  15

Ala Leu Ile Asp Trp Trp Asn Gly
            20

<210> SEQ ID NO 1051
<211> LENGTH: 23
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (16)..(16)
<223> OTHER INFORMATION: Glu is conjugated to Cit

<400> SEQUENCE: 1051

Cys Gly Leu Phe Gly Glu Ile Glu Glu Leu Ile Glu Glu Gly Leu Glu
1               5                   10                  15

Leu Ile Asp Trp Trp Asn Gly
            20

<210> SEQ ID NO 1052
<211> LENGTH: 24
<212> TYPE: PRT
<213> ORGANISM: Homo sapiens

<400> SEQUENCE: 1052

Cys Gly Leu Phe Gly Glu Ile Glu Glu Leu Ile Glu Glu Gly Leu Glu
1               5                   10                  15

Asn Met Ile Asp Trp Trp Asn Gly
            20

<210> SEQ ID NO 1053
<211> LENGTH: 24
<212> TYPE: PRT
<213> ORGANISM: Homo sapiens

<400> SEQUENCE: 1053

Cys Gly Leu Phe Gly Glu Ile Glu Glu Leu Ile Glu Glu Gly Leu Glu
```

```
1               5                   10                  15
Asn Phe Ile Asp Trp Trp Asn Gly
            20

<210> SEQ ID NO 1054
<211> LENGTH: 24
<212> TYPE: PRT
<213> ORGANISM: Homo sapiens

<400> SEQUENCE: 1054

Cys Gly Leu Phe Gly Glu Ile Glu Glu Leu Ile Glu Glu Gly Leu Glu
1               5                   10                  15

Asn Ile Ile Asp Trp Trp Asn Gly
            20

<210> SEQ ID NO 1055
<211> LENGTH: 24
<212> TYPE: PRT
<213> ORGANISM: Homo sapiens

<400> SEQUENCE: 1055

Cys Gly Leu Phe Gly Glu Ile Glu Glu Leu Ile Glu Glu Gly Leu Glu
1               5                   10                  15

Asn Trp Ile Asp Trp Trp Asn Gly
            20

<210> SEQ ID NO 1056
<211> LENGTH: 24
<212> TYPE: PRT
<213> ORGANISM: Homo sapiens

<400> SEQUENCE: 1056

Cys Gly Leu Phe Gly Glu Ile Glu Glu Leu Ile Glu Glu Gly Leu Glu
1               5                   10                  15

Asn Val Ile Asp Trp Trp Asn Gly
            20

<210> SEQ ID NO 1057
<211> LENGTH: 24
<212> TYPE: PRT
<213> ORGANISM: Homo sapiens

<400> SEQUENCE: 1057

Cys Gly Leu Phe Gly Glu Ile Glu Glu Leu Ile Glu Glu Gly Leu Glu
1               5                   10                  15

Asn Tyr Ile Asp Trp Trp Asn Gly
            20

<210> SEQ ID NO 1058
<211> LENGTH: 23
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (17)..(17)
<223> OTHER INFORMATION: Asn is conjugated to Nle

<400> SEQUENCE: 1058

Cys Gly Leu Phe Gly Glu Ile Glu Glu Leu Ile Glu Glu Gly Leu Glu
1               5                   10                  15

Asn Ile Asp Trp Trp Asn Gly
```

```
                20

<210> SEQ ID NO 1059
<211> LENGTH: 24
<212> TYPE: PRT
<213> ORGANISM: Homo sapiens

<400> SEQUENCE: 1059

Cys Gly Leu Phe Gly Glu Ile Glu Glu Leu Ile Glu Glu Gly Leu Glu
1               5                   10                  15

Asn Leu Leu Asp Trp Trp Asn Gly
            20

<210> SEQ ID NO 1060
<211> LENGTH: 24
<212> TYPE: PRT
<213> ORGANISM: Homo sapiens

<400> SEQUENCE: 1060

Cys Gly Leu Phe Gly Glu Ile Glu Glu Leu Ile Glu Glu Gly Leu Glu
1               5                   10                  15

Asn Leu Val Asp Trp Trp Asn Gly
            20

<210> SEQ ID NO 1061
<211> LENGTH: 24
<212> TYPE: PRT
<213> ORGANISM: Homo sapiens

<400> SEQUENCE: 1061

Cys Gly Leu Phe Gly Glu Ile Glu Glu Leu Ile Glu Glu Gly Leu Glu
1               5                   10                  15

Asn Leu Phe Asp Trp Trp Asn Gly
            20

<210> SEQ ID NO 1062
<211> LENGTH: 24
<212> TYPE: PRT
<213> ORGANISM: Homo sapiens

<400> SEQUENCE: 1062

Cys Gly Leu Phe Gly Glu Ile Glu Glu Leu Ile Glu Glu Gly Leu Glu
1               5                   10                  15

Asn Leu Trp Asp Trp Trp Asn Gly
            20

<210> SEQ ID NO 1063
<211> LENGTH: 24
<212> TYPE: PRT
<213> ORGANISM: Homo sapiens

<400> SEQUENCE: 1063

Cys Gly Leu Phe Gly Glu Ile Glu Glu Leu Ile Glu Glu Gly Leu Glu
1               5                   10                  15

Asn Leu Tyr Asp Trp Trp Asn Gly
            20

<210> SEQ ID NO 1064
<211> LENGTH: 24
<212> TYPE: PRT
<213> ORGANISM: Homo sapiens

<400> SEQUENCE: 1064
```

Cys Gly Leu Phe Gly Glu Ile Glu Glu Leu Ile Glu Glu Gly Leu Glu
1               5                   10                  15

Asn Leu Ile Glu Trp Trp Asn Gly
            20

<210> SEQ ID NO 1065
<211> LENGTH: 24
<212> TYPE: PRT
<213> ORGANISM: Homo sapiens

<400> SEQUENCE: 1065

Cys Gly Leu Phe Gly Glu Ile Glu Glu Leu Ile Glu Glu Gly Leu Glu
1               5                   10                  15

Asn Leu Ile Asn Trp Trp Asn Gly
            20

<210> SEQ ID NO 1066
<211> LENGTH: 24
<212> TYPE: PRT
<213> ORGANISM: Homo sapiens

<400> SEQUENCE: 1066

Cys Gly Leu Phe Gly Glu Ile Glu Glu Leu Ile Glu Glu Gly Leu Glu
1               5                   10                  15

Asn Leu Ile Ser Trp Trp Asn Gly
            20

<210> SEQ ID NO 1067
<211> LENGTH: 24
<212> TYPE: PRT
<213> ORGANISM: Homo sapiens

<400> SEQUENCE: 1067

Cys Gly Leu Phe Gly Glu Ile Glu Glu Leu Ile Glu Glu Gly Leu Glu
1               5                   10                  15

Asn Leu Ile Gln Trp Trp Asn Gly
            20

<210> SEQ ID NO 1068
<211> LENGTH: 24
<212> TYPE: PRT
<213> ORGANISM: Homo sapiens

<400> SEQUENCE: 1068

Cys Gly Leu Phe Gly Glu Ile Glu Glu Leu Ile Glu Glu Gly Leu Glu
1               5                   10                  15

Asn Leu Ile Asp Gly Trp Asn Gly
            20

<210> SEQ ID NO 1069
<211> LENGTH: 24
<212> TYPE: PRT
<213> ORGANISM: Homo sapiens

<400> SEQUENCE: 1069

Cys Gly Leu Phe Gly Glu Ile Glu Glu Leu Ile Glu Glu Gly Leu Glu
1               5                   10                  15

Asn Leu Ile Asp Ala Trp Asn Gly
            20

<210> SEQ ID NO 1070

```
<211> LENGTH: 24
<212> TYPE: PRT
<213> ORGANISM: Homo sapiens

<400> SEQUENCE: 1070

Cys Gly Leu Phe Gly Glu Ile Glu Glu Leu Ile Glu Glu Gly Leu Glu
1               5                   10                  15

Asn Leu Ile Asp Phe Trp Asn Gly
            20

<210> SEQ ID NO 1071
<211> LENGTH: 24
<212> TYPE: PRT
<213> ORGANISM: Homo sapiens

<400> SEQUENCE: 1071

Cys Gly Leu Phe Gly Glu Ile Glu Glu Leu Ile Glu Glu Gly Leu Glu
1               5                   10                  15

Asn Leu Ile Asp Leu Trp Asn Gly
            20

<210> SEQ ID NO 1072
<211> LENGTH: 24
<212> TYPE: PRT
<213> ORGANISM: Homo sapiens

<400> SEQUENCE: 1072

Cys Gly Leu Phe Gly Glu Ile Glu Glu Leu Ile Glu Glu Gly Leu Glu
1               5                   10                  15

Asn Leu Ile Asp Ile Trp Asn Gly
            20

<210> SEQ ID NO 1073
<211> LENGTH: 24
<212> TYPE: PRT
<213> ORGANISM: Homo sapiens

<400> SEQUENCE: 1073

Cys Gly Leu Phe Gly Glu Ile Glu Glu Leu Ile Glu Glu Gly Leu Glu
1               5                   10                  15

Asn Leu Ile Asp Val Trp Asn Gly
            20

<210> SEQ ID NO 1074
<211> LENGTH: 24
<212> TYPE: PRT
<213> ORGANISM: Homo sapiens

<400> SEQUENCE: 1074

Cys Gly Leu Phe Gly Glu Ile Glu Glu Leu Ile Glu Glu Gly Leu Glu
1               5                   10                  15

Asn Leu Ile Asp Trp Gly Asn Gly
            20

<210> SEQ ID NO 1075
<211> LENGTH: 24
<212> TYPE: PRT
<213> ORGANISM: Homo sapiens

<400> SEQUENCE: 1075

Cys Gly Leu Phe Gly Glu Ile Glu Glu Leu Ile Glu Glu Gly Leu Glu
1               5                   10                  15
```

Asn Leu Ile Asp Trp Ala Asn Gly
            20

<210> SEQ ID NO 1076
<211> LENGTH: 24
<212> TYPE: PRT
<213> ORGANISM: Homo sapiens

<400> SEQUENCE: 1076

Cys Gly Leu Phe Gly Glu Ile Glu Glu Leu Ile Glu Glu Gly Leu Glu
1               5                   10                  15

Asn Leu Ile Asp Trp Phe Asn Gly
            20

<210> SEQ ID NO 1077
<211> LENGTH: 24
<212> TYPE: PRT
<213> ORGANISM: Homo sapiens

<400> SEQUENCE: 1077

Cys Gly Leu Phe Gly Glu Ile Glu Glu Leu Ile Glu Glu Gly Leu Glu
1               5                   10                  15

Asn Leu Ile Asp Trp Ile Asn Gly
            20

<210> SEQ ID NO 1078
<211> LENGTH: 24
<212> TYPE: PRT
<213> ORGANISM: Homo sapiens

<400> SEQUENCE: 1078

Cys Gly Leu Phe Gly Glu Ile Glu Glu Leu Ile Glu Glu Gly Leu Glu
1               5                   10                  15

Asn Leu Ile Asp Trp Val Asn Gly
            20

<210> SEQ ID NO 1079
<211> LENGTH: 24
<212> TYPE: PRT
<213> ORGANISM: Homo sapiens

<400> SEQUENCE: 1079

Cys Gly Leu Phe Gly Glu Ile Glu Glu Leu Ile Glu Glu Gly Leu Glu
1               5                   10                  15

Asn Leu Ile Asp Trp Val Asn Gly
            20

<210> SEQ ID NO 1080
<211> LENGTH: 24
<212> TYPE: PRT
<213> ORGANISM: Homo sapiens

<400> SEQUENCE: 1080

Cys Gly Leu Phe Gly Glu Ile Glu Glu Leu Ile Glu Glu Gly Leu Glu
1               5                   10                  15

Asn Leu Ile Asp Trp Tyr Asn Gly
            20

<210> SEQ ID NO 1081
<211> LENGTH: 24
<212> TYPE: PRT
<213> ORGANISM: Homo sapiens -continued

```
<400> SEQUENCE: 1081

Cys Gly Leu Phe Gly Glu Ile Glu Glu Leu Ile Glu Glu Gly Leu Glu
1               5                   10                  15

Asn Leu Ile Asp Trp Trp Gln Gly
            20

<210> SEQ ID NO 1082
<211> LENGTH: 24
<212> TYPE: PRT
<213> ORGANISM: Homo sapiens

<400> SEQUENCE: 1082

Cys Gly Leu Phe Gly Glu Ile Glu Glu Leu Ile Glu Glu Gly Leu Glu
1               5                   10                  15

Asn Leu Ile Asp Trp Trp Ser Gly
            20

<210> SEQ ID NO 1083
<211> LENGTH: 24
<212> TYPE: PRT
<213> ORGANISM: Homo sapiens

<400> SEQUENCE: 1083

Cys Gly Leu Phe Gly Glu Ile Glu Glu Leu Ile Glu Glu Gly Leu Glu
1               5                   10                  15

Asn Leu Ile Asp Trp Trp Glu Gly
            20

<210> SEQ ID NO 1084
<211> LENGTH: 23
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (22)..(22)
<223> OTHER INFORMATION: Trp is conjugated to Cit

<400> SEQUENCE: 1084

Cys Gly Leu Phe Gly Glu Ile Glu Glu Leu Ile Glu Glu Gly Leu Glu
1               5                   10                  15

Asn Leu Ile Asp Trp Trp Gly
            20

<210> SEQ ID NO 1085
<211> LENGTH: 24
<212> TYPE: PRT
<213> ORGANISM: Homo sapiens

<400> SEQUENCE: 1085

Cys Gly Leu Phe Gly Glu Ile Glu Glu Leu Ile Glu Glu Gly Leu Glu
1               5                   10                  15

Asn Leu Ile Asp Trp Trp Asn Ala
            20

<210> SEQ ID NO 1086
<211> LENGTH: 24
<212> TYPE: PRT
<213> ORGANISM: Homo sapiens

<400> SEQUENCE: 1086

Cys Gly Leu Phe Gly Glu Ile Glu Glu Leu Ile Glu Glu Gly Leu Glu
```

-continued

```
                1               5                  10                 15

Asn Leu Ile Asp Trp Trp Asn Asn
            20

<210> SEQ ID NO 1087
<211> LENGTH: 24
<212> TYPE: PRT
<213> ORGANISM: Homo sapiens

<400> SEQUENCE: 1087

Cys Gly Leu Phe Gly Glu Ile Glu Glu Leu Ile Glu Glu Gly Leu Glu
1               5                   10                  15

Asn Leu Ile Asp Trp Trp Asn Ser
            20

<210> SEQ ID NO 1088
<211> LENGTH: 24
<212> TYPE: PRT
<213> ORGANISM: Homo sapiens

<400> SEQUENCE: 1088

Cys Gly Leu Phe Gly Glu Ile Glu Glu Leu Ile Glu Glu Gly Leu Glu
1               5                   10                  15

Asn Leu Ile Asp Trp Trp Asn Tyr
            20

<210> SEQ ID NO 1089
<211> LENGTH: 24
<212> TYPE: PRT
<213> ORGANISM: Homo sapiens

<400> SEQUENCE: 1089

Cys Gly Leu Phe Gly Glu Ile Glu Glu Leu Ile Glu Glu Gly Leu Glu
1               5                   10                  15

Asn Leu Ile Asp Trp Trp Asn Trp
            20

<210> SEQ ID NO 1090
<211> LENGTH: 14
<212> TYPE: PRT
<213> ORGANISM: Homo sapiens

<400> SEQUENCE: 1090

Cys Phe Phe Gly Ala Ile Trp Gly Leu Leu His Ser Ile Leu
1               5                   10

<210> SEQ ID NO 1091
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (5)..(5)
<223> OTHER INFORMATION: Lys is conjugated to stearyl

<400> SEQUENCE: 1091

Cys Phe Phe Gly Lys Ile Trp Glu Phe Ile Lys Ser Ile Leu
1               5                   10

<210> SEQ ID NO 1092
<211> LENGTH: 14
<212> TYPE: PRT
```

```
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (5)..(5)
<223> OTHER INFORMATION: Lys is conjugated to stearyl

<400> SEQUENCE: 1092

Cys Phe Phe Gly Lys Ile Trp Glu Phe Ile His Ser Ile Leu
1               5                   10

<210> SEQ ID NO 1093
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (4)..(4)
<223> OTHER INFORMATION: Lys is conjugated to stearyl

<400> SEQUENCE: 1093

Cys Phe Phe Lys Ala Ile Trp Glu Phe Ile Lys Ser Ile Leu
1               5                   10

<210> SEQ ID NO 1094
<211> LENGTH: 16
<212> TYPE: PRT
<213> ORGANISM: Homo sapiens

<400> SEQUENCE: 1094

Cys Gly Phe Phe Gly Ala Ile Trp Gly Leu Leu His Ser Ile Leu Lys
1               5                   10                  15

<210> SEQ ID NO 1095
<211> LENGTH: 15
<212> TYPE: PRT
<213> ORGANISM: Homo sapiens

<400> SEQUENCE: 1095

Cys Gly Phe Phe Glu Ala Ile Trp Gly Leu Leu His Ser Ile Leu
1               5                   10                  15

<210> SEQ ID NO 1096
<211> LENGTH: 14
<212> TYPE: PRT
<213> ORGANISM: Homo sapiens

<400> SEQUENCE: 1096

Cys Phe Phe Gly Ala Ile Trp Gly Leu Leu Lys Ser Ile Leu
1               5                   10

<210> SEQ ID NO 1097
<211> LENGTH: 15
<212> TYPE: PRT
<213> ORGANISM: Homo sapiens

<400> SEQUENCE: 1097

Cys Gly Phe Phe Gly Ala Ile Trp Gly Leu Leu Lys Ser Ile Leu
1               5                   10                  15

<210> SEQ ID NO 1098
<211> LENGTH: 14
<212> TYPE: PRT
<213> ORGANISM: Homo sapiens
```

-continued

<400> SEQUENCE: 1098

Cys Phe Phe Glu Ala Ile Trp Gly Leu Leu Lys Ser Ile Leu
1               5                   10

<210> SEQ ID NO 1099
<211> LENGTH: 15
<212> TYPE: PRT
<213> ORGANISM: Homo sapiens

<400> SEQUENCE: 1099

Cys Gly Phe Phe Glu Ala Ile Trp Gly Leu Leu Lys Ser Ile Leu
1               5                   10                  15

<210> SEQ ID NO 1100
<211> LENGTH: 23
<212> TYPE: PRT
<213> ORGANISM: Homo sapiens

<400> SEQUENCE: 1100

Cys Phe Phe Gly Ala Ile Trp Gly Leu Leu His Ser Ile Leu Lys Gly
1               5                   10                  15

Leu Ile Asp Trp Trp Asn Gly
            20

<210> SEQ ID NO 1101
<211> LENGTH: 23
<212> TYPE: PRT
<213> ORGANISM: Homo sapiens

<400> SEQUENCE: 1101

Cys Phe Phe Gly Ala Ile Trp Gly Leu Leu His Ser Ile Leu Lys Gly
1               5                   10                  15

Leu Ile Asp Gly Trp Tyr Gly
            20

<210> SEQ ID NO 1102
<211> LENGTH: 17
<212> TYPE: PRT
<213> ORGANISM: Homo sapiens

<400> SEQUENCE: 1102

Cys Gly Ile Phe Gly Ala Ile Ala Gly Leu Leu Lys Asn Ile Phe Lys
1               5                   10                  15

Gly

<210> SEQ ID NO 1103
<211> LENGTH: 17
<212> TYPE: PRT
<213> ORGANISM: Homo sapiens

<400> SEQUENCE: 1103

Cys Gly Ile Phe Gly Ala Ile Ala Gly Leu Leu Lys Asn Ile Phe Lys
1               5                   10                  15

Ala

<210> SEQ ID NO 1104
<211> LENGTH: 17
<212> TYPE: PRT
<213> ORGANISM: Homo sapiens

<400> SEQUENCE: 1104

Cys Gly Ile Phe Gly Ala Ile Ala Gly Leu Leu Lys Asn Ile Phe Lys
1               5                   10                  15

Leu

<210> SEQ ID NO 1105
<211> LENGTH: 17
<212> TYPE: PRT
<213> ORGANISM: Homo sapiens

<400> SEQUENCE: 1105

Cys Gly Ile Phe Gly Ala Ile Ala Gly Leu Leu Lys Asn Ile Phe Lys
1               5                   10                  15

Trp

<210> SEQ ID NO 1106
<211> LENGTH: 17
<212> TYPE: PRT
<213> ORGANISM: Homo sapiens

<400> SEQUENCE: 1106

Cys Gly Ile Phe Gly Ala Ile Ala Gly Leu Leu Lys Asn Ile Phe Lys
1               5                   10                  15

Phe

<210> SEQ ID NO 1107
<211> LENGTH: 17
<212> TYPE: PRT
<213> ORGANISM: Homo sapiens

<400> SEQUENCE: 1107

Cys Gly Ile Phe Gly Ala Ile Ala Gly Leu Leu Lys Asn Ile Phe Lys
1               5                   10                  15

Asn

<210> SEQ ID NO 1108
<211> LENGTH: 17
<212> TYPE: PRT
<213> ORGANISM: Homo sapiens

<400> SEQUENCE: 1108

Cys Gly Ile Phe Gly Ala Ile Ala Gly Leu Leu Lys Asn Ile Phe Lys
1               5                   10                  15

Glu

<210> SEQ ID NO 1109
<211> LENGTH: 17
<212> TYPE: PRT
<213> ORGANISM: Homo sapiens

<400> SEQUENCE: 1109

Cys Gly Ile Phe Gly Ala Ile Ala Gly Leu Leu Lys Asn Ile Phe Lys
1               5                   10                  15

Ser

<210> SEQ ID NO 1110
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (16)..(16)
<223> OTHER INFORMATION: Lys is conjugated to stearyl

<400> SEQUENCE: 1110

Cys Gly Ile Phe Gly Ala Ile Ala Gly Leu Leu Lys Asn Ile Phe Lys
1               5                   10                  15

<210> SEQ ID NO 1111
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (17)..(17)
<223> OTHER INFORMATION: Lys is conjugated to stearyl

<400> SEQUENCE: 1111

Cys Gly Ile Phe Gly Ala Ile Ala Gly Leu Leu Lys Asn Ile Phe Lys
1               5                   10                  15

Lys

<210> SEQ ID NO 1112
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Gly is conjugated to stearyl

<400> SEQUENCE: 1112

Gly Ile Phe Gly Ala Ile Ala Gly Leu Leu Lys Asn Ile Phe Lys Cys
1               5                   10                  15

<210> SEQ ID NO 1113
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (16)..(16)
<223> OTHER INFORMATION: Lys is conjugated to lauryl

<400> SEQUENCE: 1113

Cys Gly Ile Phe Gly Ala Ile Ala Gly Leu Leu Lys Asn Ile Phe Lys
1               5                   10                  15

<210> SEQ ID NO 1114
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (16)..(16)
<223> OTHER INFORMATION: Lys is conjugated to lauryl

<400> SEQUENCE: 1114

Cys Gly Ile Phe Gly Ala Ile Ala Gly Leu Leu Lys Asn Ile Phe Lys
1               5                   10                  15

Lys

<210> SEQ ID NO 1115
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Gly is conjugated to lauryl

<400> SEQUENCE: 1115

Gly Ile Phe Gly Ala Ile Ala Gly Leu Leu Lys Asn Ile Phe Lys Cys
1               5                   10                  15

<210> SEQ ID NO 1116
<211> LENGTH: 16
<212> TYPE: PRT
<213> ORGANISM: Homo sapiens

<400> SEQUENCE: 1116

Cys Gly Ile Phe Gly Ala Ile Ala Gly Leu Leu His Asn Ile Phe Lys
1               5                   10                  15

<210> SEQ ID NO 1117
<211> LENGTH: 15
<212> TYPE: PRT
<213> ORGANISM: Homo sapiens

<400> SEQUENCE: 1117

Cys Gly Ile Phe Gly Ala Ile Ala Gly Leu Leu Asn Ile Phe Lys
1               5                   10                  15

<210> SEQ ID NO 1118
<211> LENGTH: 16
<212> TYPE: PRT
<213> ORGANISM: Homo sapiens

<400> SEQUENCE: 1118

Cys Gly Ile Phe Gly Ala Ile Ala Gly Leu Leu Arg Asn Ile Phe Lys
1               5                   10                  15

<210> SEQ ID NO 1119
<211> LENGTH: 16
<212> TYPE: PRT
<213> ORGANISM: Homo sapiens

<400> SEQUENCE: 1119

Cys Gly Ile Phe Gly Ala Ile Ala Gly Leu Leu Glu Asn Ile Phe Lys
1               5                   10                  15

<210> SEQ ID NO 1120
<211> LENGTH: 16
<212> TYPE: PRT
<213> ORGANISM: Homo sapiens

<400> SEQUENCE: 1120

Cys Gly Ile Phe Gly Ala Ile Ala Gly Leu Leu Asp Asn Ile Phe Lys
1               5                   10                  15

<210> SEQ ID NO 1121
<211> LENGTH: 16
<212> TYPE: PRT
<213> ORGANISM: Homo sapiens

```
<400> SEQUENCE: 1121

Cys Gly Ile Phe Gly Ala Ile Ala Gly Leu Leu Lys Asn Ile Phe His
1               5                   10                  15

<210> SEQ ID NO 1122
<211> LENGTH: 15
<212> TYPE: PRT
<213> ORGANISM: Homo sapiens

<400> SEQUENCE: 1122

Cys Gly Ile Phe Gly Ala Ile Ala Gly Leu Leu Lys Asn Ile Phe
1               5                   10                  15

<210> SEQ ID NO 1123
<211> LENGTH: 16
<212> TYPE: PRT
<213> ORGANISM: Homo sapiens

<400> SEQUENCE: 1123

Cys Gly Ile Phe Gly Ala Ile Ala Gly Leu Leu Lys Ile Asn Phe Glu
1               5                   10                  15

<210> SEQ ID NO 1124
<211> LENGTH: 16
<212> TYPE: PRT
<213> ORGANISM: Homo sapiens

<400> SEQUENCE: 1124

Cys Gly Ile Phe Gly Ala Ile Ala Gly Leu Leu Lys Asn Ile Phe Asp
1               5                   10                  15

<210> SEQ ID NO 1125
<211> LENGTH: 16
<212> TYPE: PRT
<213> ORGANISM: Homo sapiens

<400> SEQUENCE: 1125

Cys Gly Ile Phe Gly Ala Ile Ala Gly Leu Leu Lys Asn Ile Phe Asn
1               5                   10                  15

<210> SEQ ID NO 1126
<211> LENGTH: 16
<212> TYPE: PRT
<213> ORGANISM: Homo sapiens

<400> SEQUENCE: 1126

Cys Gly Ile Phe Gly Ala Ile Ala Gly Leu Leu Asn Asn Ile Phe Lys
1               5                   10                  15

<210> SEQ ID NO 1127
<211> LENGTH: 31
<212> TYPE: PRT
<213> ORGANISM: Homo sapiens

<400> SEQUENCE: 1127

Cys Gly Ile Phe Gly Ile Ala Ile Gly Leu Leu Lys Asn Ile Phe Lys
1               5                   10                  15

Gly Ile Phe Gly Ala Ile Ala Gly Leu Leu Lys Asn Ile Phe Lys
            20                  25                  30

<210> SEQ ID NO 1128
<211> LENGTH: 17
<212> TYPE: PRT
<213> ORGANISM: Homo sapiens
```

```
<400> SEQUENCE: 1128

Cys Gly Ile Phe Gly Ala Ile Trp Gly Leu Leu Lys Asn Ile Phe Lys
 1               5                  10                  15
Gly

<210> SEQ ID NO 1129
<211> LENGTH: 17
<212> TYPE: PRT
<213> ORGANISM: Homo sapiens

<400> SEQUENCE: 1129

Cys Gly Ile Phe Gly Ala Ile Trp Gly Leu Leu Lys Asn Ile Phe Lys
 1               5                  10                  15
Ala

<210> SEQ ID NO 1130
<211> LENGTH: 17
<212> TYPE: PRT
<213> ORGANISM: Homo sapiens

<400> SEQUENCE: 1130

Cys Gly Ile Phe Gly Ala Ile Trp Gly Leu Leu Lys Asn Ile Phe Lys
 1               5                  10                  15
Leu

<210> SEQ ID NO 1131
<211> LENGTH: 17
<212> TYPE: PRT
<213> ORGANISM: Homo sapiens

<400> SEQUENCE: 1131

Cys Gly Ile Phe Gly Ala Ile Trp Gly Leu Leu Lys Asn Ile Phe Lys
 1               5                  10                  15
Trp

<210> SEQ ID NO 1132
<211> LENGTH: 17
<212> TYPE: PRT
<213> ORGANISM: Homo sapiens

<400> SEQUENCE: 1132

Cys Gly Ile Phe Gly Ala Ile Trp Gly Leu Leu Lys Asn Ile Phe Lys
 1               5                  10                  15
Phe

<210> SEQ ID NO 1133
<211> LENGTH: 17
<212> TYPE: PRT
<213> ORGANISM: Homo sapiens

<400> SEQUENCE: 1133

Cys Gly Ile Phe Gly Ala Ile Trp Gly Leu Leu Lys Asn Ile Phe Lys
 1               5                  10                  15
Asn

<210> SEQ ID NO 1134
<211> LENGTH: 17
<212> TYPE: PRT
<213> ORGANISM: Homo sapiens
```

```
<400> SEQUENCE: 1134

Cys Gly Ile Phe Gly Ala Ile Trp Gly Leu Leu Lys Asn Ile Phe Lys
1               5                   10                  15

Glu

<210> SEQ ID NO 1135
<211> LENGTH: 17
<212> TYPE: PRT
<213> ORGANISM: Homo sapiens

<400> SEQUENCE: 1135

Cys Gly Ile Phe Gly Ala Ile Trp Gly Leu Leu Lys Asn Ile Phe Lys
1               5                   10                  15

Ser

<210> SEQ ID NO 1136
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (16)..(16)
<223> OTHER INFORMATION: Lys is conjugated to stearyl

<400> SEQUENCE: 1136

Cys Gly Ile Phe Gly Ala Ile Trp Gly Leu Leu Lys Asn Ile Phe Lys
1               5                   10                  15

<210> SEQ ID NO 1137
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (17)..(17)
<223> OTHER INFORMATION: Lys is conjugated to stearyl

<400> SEQUENCE: 1137

Cys Gly Ile Phe Gly Ala Ile Trp Gly Leu Leu Lys Asn Ile Phe Lys
1               5                   10                  15

Lys

<210> SEQ ID NO 1138
<211> LENGTH: 16
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: MISC_FEATURE
<222> LOCATION: (1)..(1)
<223> OTHER INFORMATION: Gly is conjugated to stearyl

<400> SEQUENCE: 1138

Gly Ile Phe Gly Ala Ile Trp Gly Leu Leu Lys Asn Ile Phe Lys Cys
1               5                   10                  15

<210> SEQ ID NO 1139
<211> LENGTH: 16
<212> TYPE: PRT
<213> ORGANISM: Artificial Sequence
<220> FEATURE:
```

-continued

```
<223> OTHER INFORMATION: Synthetically generated peptide
<220> FEATURE:
<221> NAME/KEY: MISC_FEATURE
<222> LOCATION: (16)..(16)
<223> OTHER INFORMATION: Lys is conjugated to lauryl

<400> SEQUENCE: 1139

Cys Gly Ile Phe Gly Ala Ile Trp Gly Leu Leu Lys Asn Ile Phe Lys
1               5                   10                  15

<210> SEQ ID NO 1140
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (17)..(17)
<223> OTHER INFORMATION: Lys is conjugated to lauryl

<400> SEQUENCE: 1140

Cys Gly Ile Phe Gly Ala Ile Trp Gly Leu Leu Lys Asn Ile Phe Lys
1               5                   10                  15

Lys

<210> SEQ ID NO 1141
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Gly is conjugated to lauryl

<400> SEQUENCE: 1141

Gly Ile Phe Gly Ala Ile Trp Gly Leu Leu Lys Asn Ile Phe Lys Cys
1               5                   10                  15

<210> SEQ ID NO 1142
<211> LENGTH: 16
<212> TYPE: PRT
<213> ORGANISM: Homo sapiens

<400> SEQUENCE: 1142

Cys Gly Ile Phe Gly Ala Ile Trp Gly Leu Leu His Asn Ile Phe Lys
1               5                   10                  15

<210> SEQ ID NO 1143
<211> LENGTH: 15
<212> TYPE: PRT
<213> ORGANISM: Homo sapiens

<400> SEQUENCE: 1143

Cys Gly Ile Phe Gly Ala Ile Trp Gly Leu Leu Asn Ile Phe Lys
1               5                   10              15

<210> SEQ ID NO 1144
<211> LENGTH: 16
<212> TYPE: PRT
<213> ORGANISM: Homo sapiens

<400> SEQUENCE: 1144

Cys Gly Ile Phe Gly Ala Ile Trp Gly Leu Leu Arg Asn Ile Phe Lys
1               5                   10                  15
```

<210> SEQ ID NO 1145
<211> LENGTH: 16
<212> TYPE: PRT
<213> ORGANISM: Homo sapiens

<400> SEQUENCE: 1145

Cys Gly Ile Phe Gly Ala Ile Trp Gly Leu Leu Glu Asn Ile Phe Lys
1               5                   10                  15

<210> SEQ ID NO 1146
<211> LENGTH: 16
<212> TYPE: PRT
<213> ORGANISM: Homo sapiens

<400> SEQUENCE: 1146

Cys Gly Ile Phe Gly Ala Ile Trp Gly Leu Leu Asp Asn Ile Phe Lys
1               5                   10                  15

<210> SEQ ID NO 1147
<211> LENGTH: 16
<212> TYPE: PRT
<213> ORGANISM: Homo sapiens

<400> SEQUENCE: 1147

Cys Gly Ile Phe Gly Ala Ile Trp Gly Leu Leu Lys Asn Ile Phe His
1               5                   10                  15

<210> SEQ ID NO 1148
<211> LENGTH: 15
<212> TYPE: PRT
<213> ORGANISM: Homo sapiens

<400> SEQUENCE: 1148

Cys Gly Ile Phe Gly Ala Ile Trp Gly Leu Leu Lys Asn Ile Phe
1               5                   10                  15

<210> SEQ ID NO 1149
<211> LENGTH: 16
<212> TYPE: PRT
<213> ORGANISM: Homo sapiens

<400> SEQUENCE: 1149

Cys Gly Ile Phe Gly Ala Ile Trp Gly Leu Leu Lys Ile Asn Phe Glu
1               5                   10                  15

<210> SEQ ID NO 1150
<211> LENGTH: 16
<212> TYPE: PRT
<213> ORGANISM: Homo sapiens

<400> SEQUENCE: 1150

Cys Gly Ile Phe Gly Ala Ile Trp Gly Leu Leu Lys Asn Ile Phe Asp
1               5                   10                  15

<210> SEQ ID NO 1151
<211> LENGTH: 16
<212> TYPE: PRT
<213> ORGANISM: Homo sapiens

<400> SEQUENCE: 1151

Cys Gly Ile Phe Gly Ala Ile Trp Gly Leu Leu Lys Asn Ile Phe Asn
1               5                   10                  15

<210> SEQ ID NO 1152
<211> LENGTH: 16
<212> TYPE: PRT
<213> ORGANISM: Homo sapiens

<400> SEQUENCE: 1152

Cys Gly Ile Phe Gly Ala Ile Trp Gly Leu Leu Asn Asn Ile Phe Lys
1               5                   10                  15

<210> SEQ ID NO 1153
<211> LENGTH: 16
<212> TYPE: PRT
<213> ORGANISM: Homo sapiens

<400> SEQUENCE: 1153

Cys Gly Ile Phe Gly Ala Ile Trp Gly Leu Leu Asn Asn Ile Phe Lys
1               5                   10                  15

<210> SEQ ID NO 1154
<211> LENGTH: 16
<212> TYPE: PRT
<213> ORGANISM: Homo sapiens

<400> SEQUENCE: 1154

Cys Gly Phe Phe Gly Ala Ile Trp Gly Leu Leu Lys Asn Ile Phe Lys
1               5                   10                  15

<210> SEQ ID NO 1155
<211> LENGTH: 15
<212> TYPE: PRT
<213> ORGANISM: Homo sapiens

<400> SEQUENCE: 1155

Cys Ile Phe Gly Ala Ile Trp Gly Leu Leu Lys Asn Ile Phe Lys
1               5                   10                  15

<210> SEQ ID NO 1156
<211> LENGTH: 32
<212> TYPE: PRT
<213> ORGANISM: Homo sapiens

<400> SEQUENCE: 1156

Cys Gly Ile Phe Gly Ala Ile Trp Ile Gly Leu Leu Lys Asn Ile Phe
1               5                   10                  15

Lys Gly Ile Phe Gly Ala Ile Trp Gly Leu Leu Lys Asn Ile Phe Lys
            20                  25                  30

<210> SEQ ID NO 1157
<211> LENGTH: 16
<212> TYPE: PRT
<213> ORGANISM: Homo sapiens

<400> SEQUENCE: 1157

Cys Gly Ile Phe Gly Ala Ile Trp Gly Leu Leu His Asn Ile Phe His
1               5                   10                  15

<210> SEQ ID NO 1158
<211> LENGTH: 14
<212> TYPE: PRT
<213> ORGANISM: Homo sapiens

<400> SEQUENCE: 1158

Cys Gly Ile Phe Gly Ala Ile Trp Gly Leu Leu Asn Ile Phe
1               5                   10

<210> SEQ ID NO 1159
<211> LENGTH: 16
<212> TYPE: PRT
<213> ORGANISM: Homo sapiens

<400> SEQUENCE: 1159

Cys Gly Ile Phe Gly Ala Ile Ala Gly Leu Leu His Ser Ile Leu Lys
1               5                   10                  15

<210> SEQ ID NO 1160
<211> LENGTH: 16
<212> TYPE: PRT
<213> ORGANISM: Homo sapiens

<400> SEQUENCE: 1160

Cys Gly Ile Phe Gly Ala Ile Trp Gly Leu Leu His Ser Ile Leu Lys
1               5                   10                  15

<210> SEQ ID NO 1161
<211> LENGTH: 15
<212> TYPE: PRT
<213> ORGANISM: Homo sapiens

<400> SEQUENCE: 1161

Cys Gly Ile Phe Gly Ala Ile Ala Gly Leu Leu His Ser Ile Leu
1               5                   10                  15

<210> SEQ ID NO 1162
<211> LENGTH: 15
<212> TYPE: PRT
<213> ORGANISM: Homo sapiens

<400> SEQUENCE: 1162

Cys Gly Ile Phe Gly Ala Ile Trp Gly Leu Leu His Ser Ile Leu
1               5                   10                  15

<210> SEQ ID NO 1163
<211> LENGTH: 16
<212> TYPE: PRT
<213> ORGANISM: Homo sapiens

<400> SEQUENCE: 1163

Cys Gly Ile Phe Gly Ala Ile Trp Glu Leu Leu Lys Asn Ile Phe Lys
1               5                   10                  15

<210> SEQ ID NO 1164
<211> LENGTH: 31
<212> TYPE: PRT
<213> ORGANISM: Homo sapiens

<400> SEQUENCE: 1164

Cys Gly Ile Phe Gly Ala Ile Trp Gly Leu Leu His Asn Ile Phe His
1               5                   10                  15
Gly Ile Phe Gly Ala Ile Trp Gly Leu Leu His Asn Ile Phe Lys
            20                  25                  30

<210> SEQ ID NO 1165
<211> LENGTH: 31
<212> TYPE: PRT
<213> ORGANISM: Homo sapiens

<400> SEQUENCE: 1165

Cys Gly Ile Phe Glu Ala Ile Trp Gly Leu Leu His Asn Ile Phe His
1               5                   10                  15

Gly Ile Phe Glu Ala Ile Trp Gly Leu Leu His Asn Ile Phe His
            20                  25                  30

<210> SEQ ID NO 1166
<211> LENGTH: 31
<212> TYPE: PRT
<213> ORGANISM: Homo sapiens

<400> SEQUENCE: 1166

Cys Gly Ile Phe Glu Ala Ile Trp Gly Leu Leu Lys Asn Ile Phe His
1               5                   10                  15

Gly Ile Phe Glu Ala Ile Trp Gly Leu Leu His Asn Ile Phe His
            20                  25                  30

<210> SEQ ID NO 1167
<211> LENGTH: 31
<212> TYPE: PRT
<213> ORGANISM: Homo sapiens

<400> SEQUENCE: 1167

Cys Gly Ile Phe Glu Ala Ile Trp Gly Leu Leu Lys Asn Ile Phe Lys
1               5                   10                  15

Gly Ile Phe Glu Ala Ile Trp Glu Leu Leu Lys Asn Ile Phe His
            20                  25                  30

<210> SEQ ID NO 1168
<211> LENGTH: 31
<212> TYPE: PRT
<213> ORGANISM: Homo sapiens

<400> SEQUENCE: 1168

Cys Gly Ile Phe Glu Ala Ile Trp Gly Leu Leu Lys Asn Ile Phe His
1               5                   10                  15

Gly Ile Phe Glu Ala Ile Trp Gly Leu Leu Lys Asn Ile Phe His
            20                  25                  30

<210> SEQ ID NO 1169
<211> LENGTH: 24
<212> TYPE: PRT
<213> ORGANISM: Homo sapiens

<400> SEQUENCE: 1169

Cys Gly Leu Phe Glu Ala Leu Leu Glu Leu Glu Ser Leu Trp Glu
1               5                   10                  15

Leu Leu Leu Glu Ala Trp Asn Gly
            20

<210> SEQ ID NO 1170
<211> LENGTH: 24
<212> TYPE: PRT
<213> ORGANISM: Homo sapiens

<400> SEQUENCE: 1170

Cys Gly Leu Phe Glu Ala Leu Leu Glu Leu Glu Ser Leu Trp Glu
1               5                   10                  15

Leu Leu Leu Glu Trp Trp Asn Gly
            20

<210> SEQ ID NO 1171
<211> LENGTH: 24
<212> TYPE: PRT
<213> ORGANISM: Homo sapiens

<400> SEQUENCE: 1171

Cys Gly Leu Phe Gly Glu Leu Glu Glu Leu Leu Glu Glu Gly Leu Glu
1               5                   10                  15

Asn Leu Leu Asp Trp Trp Asn Gly
            20

<210> SEQ ID NO 1172
<211> LENGTH: 24
<212> TYPE: PRT
<213> ORGANISM: Homo sapiens

<400> SEQUENCE: 1172

Cys Gly Leu Phe Gly Glu Leu Glu Glu Leu Leu Glu Glu Gly Leu Glu
1               5                   10                  15

Asn Leu Leu Glu Trp Trp Asn Gly
            20

<210> SEQ ID NO 1173
<211> LENGTH: 24
<212> TYPE: PRT
<213> ORGANISM: Homo sapiens

<400> SEQUENCE: 1173

Cys Gly Leu Phe Gly Glu Leu Glu Glu Leu Leu Glu Glu Gly Trp Glu
1               5                   10                  15

Leu Leu Leu Glu Ala Trp Asn Gly
            20

<210> SEQ ID NO 1174
<211> LENGTH: 24
<212> TYPE: PRT
<213> ORGANISM: Homo sapiens

<400> SEQUENCE: 1174

Cys Gly Leu Phe Gly Glu Leu Glu Glu Leu Leu Glu Glu Gly Trp Glu
1               5                   10                  15

Leu Leu Leu Glu Trp Trp Asn Gly
            20

<210> SEQ ID NO 1175
<211> LENGTH: 24
<212> TYPE: PRT
<213> ORGANISM: Homo sapiens

<400> SEQUENCE: 1175

Cys Gly Leu Phe Gly Glu Leu Glu Glu Leu Leu Glu Glu Gly Trp Glu
1               5                   10                  15

Leu Leu Leu Asp Trp Trp Asn Gly
            20

<210> SEQ ID NO 1176
<211> LENGTH: 24
<212> TYPE: PRT
<213> ORGANISM: Homo sapiens

<400> SEQUENCE: 1176

Cys Gly Leu Phe Gly Ala Leu Leu Glu Leu Leu Glu Glu Gly Leu Glu
1               5                   10                  15

Asn Leu Ile Asp Trp Trp Asn Gly
            20

<210> SEQ ID NO 1177
<211> LENGTH: 24
<212> TYPE: PRT
<213> ORGANISM: Homo sapiens

<400> SEQUENCE: 1177

Cys Gly Leu Phe Glu Ala Leu Leu Glu Leu Leu Glu Glu Gly Leu Glu
1               5                   10                  15

Asn Leu Ile Asp Trp Trp Asn Gly
            20

<210> SEQ ID NO 1178
<211> LENGTH: 24
<212> TYPE: PRT
<213> ORGANISM: Homo sapiens

<400> SEQUENCE: 1178

Cys Gly Leu Phe Glu Ala Leu Leu Glu Leu Leu Glu Ser Leu Leu Glu
1               5                   10                  15

Asn Leu Ile Asp Trp Trp Asn Gly
            20

<210> SEQ ID NO 1179
<211> LENGTH: 24
<212> TYPE: PRT
<213> ORGANISM: Homo sapiens

<400> SEQUENCE: 1179

Cys Gly Leu Phe Gly Glu Leu Ala Glu Leu Leu Glu Glu Gly Leu Glu
1               5                   10                  15

Asn Leu Leu Asp Trp Trp Asn Gly
            20

<210> SEQ ID NO 1180
<211> LENGTH: 23
<212> TYPE: PRT
<213> ORGANISM: Homo sapiens

<400> SEQUENCE: 1180

Gly Leu Phe Gly Glu Ile Glu Glu Leu Ile Glu Glu Gly Leu Glu Asn
1               5                   10                  15

Leu Ile Asp Trp Trp Asn Gly
            20

<210> SEQ ID NO 1181
<211> LENGTH: 14
<212> TYPE: PRT
<213> ORGANISM: Homo sapiens

<400> SEQUENCE: 1181

Cys Phe Phe Gly Asn Ile Trp Glu Phe Ile His Ser Ile Leu
1               5                   10

<210> SEQ ID NO 1182
<211> LENGTH: 14
<212> TYPE: PRT
<213> ORGANISM: Homo sapiens

<400> SEQUENCE: 1182

Cys Phe Phe Gly Ala Ile Trp Asn Phe Ile His Ser Ile Leu
1               5                   10

```
<210> SEQ ID NO 1183
<211> LENGTH: 14
<212> TYPE: PRT
<213> ORGANISM: Homo sapiens

<400> SEQUENCE: 1183

Cys Phe Phe Gly Asn Ile Trp Asn Phe Ile His Ser Ile Leu
1               5                   10

<210> SEQ ID NO 1184
<211> LENGTH: 16
<212> TYPE: PRT
<213> ORGANISM: Homo sapiens

<400> SEQUENCE: 1184

Cys Gly Ile Phe Gly Asn Ile Trp Asn Phe Ile Lys Asn Ile Phe Lys
1               5                   10                  15

<210> SEQ ID NO 1185
<211> LENGTH: 16
<212> TYPE: PRT
<213> ORGANISM: Homo sapiens

<400> SEQUENCE: 1185

Cys Gly Ile Phe Gly Asn Ile Trp Asn Leu Leu Lys Asn Ile Phe Lys
1               5                   10                  15

<210> SEQ ID NO 1186
<211> LENGTH: 16
<212> TYPE: PRT
<213> ORGANISM: Homo sapiens

<400> SEQUENCE: 1186

Cys Gly Ile Phe Gly Asn Ile Trp Gly Leu Leu Lys Asn Ile Phe Lys
1               5                   10                  15

<210> SEQ ID NO 1187
<211> LENGTH: 16
<212> TYPE: PRT
<213> ORGANISM: Homo sapiens

<400> SEQUENCE: 1187

Cys Gly Ile Phe Gly Asn Ile Trp Asn Phe Ile Lys Asn Ile Phe His
1               5                   10                  15

<210> SEQ ID NO 1188
<211> LENGTH: 16
<212> TYPE: PRT
<213> ORGANISM: Homo sapiens

<400> SEQUENCE: 1188

Cys Gly Ile Phe Gly Asn Ile Trp Asn Leu Leu Lys Asn Ile Phe His
1               5                   10                  15

<210> SEQ ID NO 1189
<211> LENGTH: 16
<212> TYPE: PRT
<213> ORGANISM: Homo sapiens

<400> SEQUENCE: 1189

Cys Gly Ile Phe Gly Asn Ile Trp Gly Leu Leu Lys Asn Ile Phe His
1               5                   10                  15

<210> SEQ ID NO 1190
<211> LENGTH: 16
```

```
<212> TYPE: PRT
<213> ORGANISM: Homo sapiens

<400> SEQUENCE: 1190

Cys Gly Ile Phe Glu Asn Ile Trp Asn Phe Ile Lys Asn Ile Phe Lys
1               5                   10                  15

<210> SEQ ID NO 1191
<211> LENGTH: 16
<212> TYPE: PRT
<213> ORGANISM: Homo sapiens

<400> SEQUENCE: 1191

Cys Gly Ile Phe Glu Asn Ile Trp Asn Phe Ile Lys Asn Ile Phe His
1               5                   10                  15

<210> SEQ ID NO 1192
<211> LENGTH: 16
<212> TYPE: PRT
<213> ORGANISM: Homo sapiens

<400> SEQUENCE: 1192

Cys Gly Ile Phe Glu Asn Ile Trp Gly Leu Leu Lys Asn Ile Phe Lys
1               5                   10                  15

<210> SEQ ID NO 1193
<211> LENGTH: 16
<212> TYPE: PRT
<213> ORGANISM: Homo sapiens

<400> SEQUENCE: 1193

Cys Gly Ile Phe Glu Asn Ile Trp Gly Leu Leu Lys Asn Ile Phe His
1               5                   10                  15

<210> SEQ ID NO 1194
<211> LENGTH: 16
<212> TYPE: PRT
<213> ORGANISM: Homo sapiens

<400> SEQUENCE: 1194

Cys Gly Ile Phe Glu Asn Ile Trp Asn Leu Leu Lys Asn Ile Phe Lys
1               5                   10                  15

<210> SEQ ID NO 1195
<211> LENGTH: 16
<212> TYPE: PRT
<213> ORGANISM: Homo sapiens

<400> SEQUENCE: 1195

Cys Gly Ile Phe Glu Asn Ile Trp Asn Leu Leu Lys Asn Ile Phe His
1               5                   10                  15

<210> SEQ ID NO 1196
<211> LENGTH: 24
<212> TYPE: PRT
<213> ORGANISM: Homo sapiens

<400> SEQUENCE: 1196

Cys Gly Leu Phe Gly Ala Ile Ala Gly Leu Leu Glu Asn Ile Phe Glu
1               5                   10                  15

Asn Leu Ile Asp Trp Trp Asn Gly
            20

<210> SEQ ID NO 1197
```

<211> LENGTH: 24
<212> TYPE: PRT
<213> ORGANISM: Homo sapiens

<400> SEQUENCE: 1197

Cys Gly Leu Phe Gly Ala Ile Ala Gly Leu Leu Asn Lys Ile Phe Lys
1               5                   10                  15

Asn Leu Ile Asp Trp Trp Asn Gly
            20

<210> SEQ ID NO 1198
<211> LENGTH: 24
<212> TYPE: PRT
<213> ORGANISM: Homo sapiens

<400> SEQUENCE: 1198

Cys Gly Leu Phe Gly Ala Ile Ala Gly Leu Leu Glu Asn Ile Phe Lys
1               5                   10                  15

Asn Leu Ile Asp Trp Trp Asn Gly
            20

<210> SEQ ID NO 1199
<211> LENGTH: 24
<212> TYPE: PRT
<213> ORGANISM: Homo sapiens

<400> SEQUENCE: 1199

Cys Gly Leu Phe Gly Ala Ile Ala Gly Leu Leu Lys Asn Ile Phe Glu
1               5                   10                  15

Asn Leu Ile Asp Trp Trp Asn Gly
            20

<210> SEQ ID NO 1200
<211> LENGTH: 24
<212> TYPE: PRT
<213> ORGANISM: Homo sapiens

<400> SEQUENCE: 1200

Cys Gly Leu Phe Gly Ala Ile Ala Gly Leu Leu Lys Asn Ile Phe His
1               5                   10                  15

Asn Leu Ile Asp Trp Trp Asn Gly
            20

<210> SEQ ID NO 1201
<211> LENGTH: 27
<212> TYPE: PRT
<213> ORGANISM: Homo sapiens

<400> SEQUENCE: 1201

Cys Leu Ile Gly Ala Ile Leu Lys Val Leu Ala Thr Gly Leu Pro Thr
1               5                   10                  15

Leu Ile Ser Trp Ile Lys Asn Lys Arg Lys Gln
            20                  25

<210> SEQ ID NO 1202
<211> LENGTH: 24
<212> TYPE: PRT
<213> ORGANISM: Homo sapiens

<400> SEQUENCE: 1202

Cys Gly Leu Leu Glu Glu Ile Glu Glu Leu Leu Glu Glu Gly Leu Glu
1               5                   10                  15

Asn Leu Ile Asp Trp Trp Asn Gly
            20

<210> SEQ ID NO 1203
<211> LENGTH: 24
<212> TYPE: PRT
<213> ORGANISM: Homo sapiens

<400> SEQUENCE: 1203

Cys Gly Leu Phe Glu Glu Leu Glu Glu Leu Leu Glu Glu Gly Leu Glu
1               5                   10                  15

Asn Leu Ile Asp Trp Trp Asn Gly
            20

<210> SEQ ID NO 1204
<211> LENGTH: 21
<212> TYPE: PRT
<213> ORGANISM: Homo sapiens

<400> SEQUENCE: 1204

Cys Gly Leu Phe Glu Glu Leu Glu Glu Leu Leu Glu Glu Gly Leu Glu
1               5                   10                  15

Asn Leu Ile Glu Ala
            20

<210> SEQ ID NO 1205
<211> LENGTH: 24
<212> TYPE: PRT
<213> ORGANISM: Homo sapiens

<400> SEQUENCE: 1205

Cys Gly Leu Phe Glu Glu Leu Glu Glu Leu Leu Glu Glu Gly Leu Glu
1               5                   10                  15

Asn Leu Ile Glu Ala Trp Asn Gly
            20

<210> SEQ ID NO 1206
<211> LENGTH: 21
<212> TYPE: PRT
<213> ORGANISM: Homo sapiens

<400> SEQUENCE: 1206

Cys Gly Leu Phe Glu Glu Leu Glu Glu Leu Leu Glu Glu Gly Leu Glu
1               5                   10                  15

Asn Leu Ile Glu Trp
            20

<210> SEQ ID NO 1207
<211> LENGTH: 24
<212> TYPE: PRT
<213> ORGANISM: Homo sapiens

<400> SEQUENCE: 1207

Cys Gly Leu Phe Glu Glu Leu Glu Glu Leu Leu Glu Glu Gly Leu Glu
1               5                   10                  15

Asn Leu Ile Glu Trp Trp Asn Gly
            20

<210> SEQ ID NO 1208
<211> LENGTH: 21
<212> TYPE: PRT
<213> ORGANISM: Homo sapiens

```
<400> SEQUENCE: 1208

Cys Gly Leu Phe Glu Glu Leu Glu Glu Leu Leu Glu Glu Gly Leu Glu
1               5                   10                  15

Asn Leu Ile Asp Ala
            20

<210> SEQ ID NO 1209
<211> LENGTH: 24
<212> TYPE: PRT
<213> ORGANISM: Homo sapiens

<400> SEQUENCE: 1209

Cys Gly Leu Phe Glu Glu Leu Glu Glu Leu Leu Glu Glu Gly Leu Glu
1               5                   10                  15

Asn Leu Ile Asp Ala Trp Asn Gly
            20

<210> SEQ ID NO 1210
<211> LENGTH: 21
<212> TYPE: PRT
<213> ORGANISM: Homo sapiens

<400> SEQUENCE: 1210

Cys Gly Leu Phe Glu Glu Leu Glu Glu Leu Leu Glu Glu Gly Leu Glu
1               5                   10                  15

Asn Leu Ile Asp Trp
            20

<210> SEQ ID NO 1211
<211> LENGTH: 14
<212> TYPE: PRT
<213> ORGANISM: Homo sapiens

<400> SEQUENCE: 1211

Cys Phe Leu Gly Ala Leu Lys Phe Ala Leu Lys Ser Leu Leu
1               5                   10

<210> SEQ ID NO 1212
<211> LENGTH: 14
<212> TYPE: PRT
<213> ORGANISM: Homo sapiens

<400> SEQUENCE: 1212

Cys Phe Leu Gly Ala Leu His Phe Ala Leu Lys Ser Leu Leu
1               5                   10

<210> SEQ ID NO 1213
<211> LENGTH: 14
<212> TYPE: PRT
<213> ORGANISM: Homo sapiens

<400> SEQUENCE: 1213

Cys Phe Leu Gly Ala Leu Lys Phe Ala Leu His Ser Leu Leu
1               5                   10

<210> SEQ ID NO 1214
<211> LENGTH: 14
<212> TYPE: PRT
<213> ORGANISM: Homo sapiens

<400> SEQUENCE: 1214

Cys Phe Leu Gly Ala Leu His Phe Ala Leu His Ser Leu Leu
1               5                   10
```

```
<210> SEQ ID NO 1215
<211> LENGTH: 14
<212> TYPE: PRT
<213> ORGANISM: Homo sapiens

<400> SEQUENCE: 1215

Phe Leu Gly Ala Leu Lys Phe Ala Leu Lys Ser Leu Leu Cys
1               5                   10

<210> SEQ ID NO 1216
<211> LENGTH: 15
<212> TYPE: PRT
<213> ORGANISM: Homo sapiens

<400> SEQUENCE: 1216

Gly Phe Leu Gly Ala Leu Lys Phe Ala Leu Lys Ser Leu Leu Cys
1               5                   10                  15

<210> SEQ ID NO 1217
<211> LENGTH: 24
<212> TYPE: PRT
<213> ORGANISM: Homo sapiens

<400> SEQUENCE: 1217

Cys Gly Leu Phe Gly Glu Leu Glu Glu Leu Ile Glu Glu Gly Leu Glu
1               5                   10                  15

Asn Leu Leu Asp Trp Trp Asn Gly
            20

<210> SEQ ID NO 1218
<211> LENGTH: 24
<212> TYPE: PRT
<213> ORGANISM: Homo sapiens

<400> SEQUENCE: 1218

Cys Gly Leu Phe Gly Glu Ile Glu Glu Leu Leu Glu Glu Gly Leu Glu
1               5                   10                  15

Asn Leu Leu Asp Trp Trp Asn Gly
            20

<210> SEQ ID NO 1219
<211> LENGTH: 24
<212> TYPE: PRT
<213> ORGANISM: Homo sapiens

<400> SEQUENCE: 1219

Cys Gly Leu Phe Gly Glu Leu Glu Glu Leu Leu Glu Glu Gly Leu Glu
1               5                   10                  15

Asn Leu Ile Asp Trp Trp Asn Gly
            20

<210> SEQ ID NO 1220
<211> LENGTH: 24
<212> TYPE: PRT
<213> ORGANISM: Homo sapiens

<400> SEQUENCE: 1220

Cys Gly Leu Phe Gly Glu Ile Glu Glu Leu Ile Glu Glu Gly Leu Glu
1               5                   10                  15

Asn Leu Met Asp Trp Trp Asn Gly
            20
```

<210> SEQ ID NO 1221
<211> LENGTH: 24
<212> TYPE: PRT
<213> ORGANISM: Homo sapiens

<400> SEQUENCE: 1221

Cys Gly Leu Phe Gly Glu Ile Glu Glu Leu Ile Glu Glu Gly Leu Glu
1               5                   10                  15

Asn Leu Glu Asp Trp Trp Asn Gly
            20

<210> SEQ ID NO 1222
<211> LENGTH: 24
<212> TYPE: PRT
<213> ORGANISM: Homo sapiens

<400> SEQUENCE: 1222

Cys Gly Leu Phe Gly Glu Ile Glu Glu Leu Ile Glu Glu Gly Leu Glu
1               5                   10                  15

Asn Leu Asp Asp Trp Trp Asn Gly
            20

<210> SEQ ID NO 1223
<211> LENGTH: 24
<212> TYPE: PRT
<213> ORGANISM: Homo sapiens

<400> SEQUENCE: 1223

Cys Gly Leu Phe Gly Glu Ile Glu Glu Leu Ile Glu Glu Gly Leu Glu
1               5                   10                  15

Asn Leu Asn Asp Trp Trp Asn Gly
            20

<210> SEQ ID NO 1224
<211> LENGTH: 24
<212> TYPE: PRT
<213> ORGANISM: Homo sapiens

<400> SEQUENCE: 1224

Cys Gly Leu Phe Gly Glu Ile Glu Glu Leu Ile Glu Glu Gly Leu Glu
1               5                   10                  15

Asn Leu Ser Asp Trp Trp Asn Gly
            20

<210> SEQ ID NO 1225
<211> LENGTH: 24
<212> TYPE: PRT
<213> ORGANISM: Homo sapiens

<400> SEQUENCE: 1225

Cys Gly Leu Phe Gly Glu Ile Glu Glu Leu Ile Glu Glu Gly Leu Glu
1               5                   10                  15

Asn Leu Gln Asp Trp Trp Asn Gly
            20

<210> SEQ ID NO 1226
<211> LENGTH: 26
<212> TYPE: PRT
<213> ORGANISM: Homo sapiens

<400> SEQUENCE: 1226

Cys Gly Leu Phe Gly Glu Ile Glu Glu Leu Ile Glu Glu Gly Leu Glu

-continued

```
                1               5                   10                  15
Asn Leu Cys Ile Thr Asp Trp Trp Asn Gly
                20                  25

<210> SEQ ID NO 1227
<211> LENGTH: 24
<212> TYPE: PRT
<213> ORGANISM: Homo sapiens

<400> SEQUENCE: 1227

Cys Gly Leu Phe Gly Glu Ile Glu Glu Leu Ile Glu Glu Leu Leu Glu
1               5                   10                  15

Asn Leu Ile Asp Trp Trp Asn Gly
                20

<210> SEQ ID NO 1228
<211> LENGTH: 24
<212> TYPE: PRT
<213> ORGANISM: Homo sapiens

<400> SEQUENCE: 1228

Cys Gly Leu Phe Gly Glu Ile Glu Glu Leu Ile Glu Glu Ile Leu Glu
1               5                   10                  15

Asn Leu Ile Asp Trp Trp Asn Gly
                20

<210> SEQ ID NO 1229
<211> LENGTH: 24
<212> TYPE: PRT
<213> ORGANISM: Homo sapiens

<400> SEQUENCE: 1229

Cys Gly Leu Phe Gly Glu Ile Glu Glu Leu Ile Glu Glu Val Leu Glu
1               5                   10                  15

Asn Leu Ile Asp Trp Trp Asn Gly
                20

<210> SEQ ID NO 1230
<211> LENGTH: 14
<212> TYPE: PRT
<213> ORGANISM: Homo sapiens

<400> SEQUENCE: 1230

Cys Phe Leu Gly Ala Leu Trp Lys Leu Leu Ser His Leu Leu
1               5                   10

<210> SEQ ID NO 1231
<211> LENGTH: 14
<212> TYPE: PRT
<213> ORGANISM: Homo sapiens

<400> SEQUENCE: 1231

Cys Phe Leu Gly Ala Leu Trp Lys Ile Leu Ser His Leu Leu
1               5                   10

<210> SEQ ID NO 1232
<211> LENGTH: 15
<212> TYPE: PRT
<213> ORGANISM: Homo sapiens

<400> SEQUENCE: 1232

Cys Phe Leu Gly Ala Leu Trp Val Lys Val Leu Ser His Leu Leu
1               5                   10                  15
```

```
<210> SEQ ID NO 1233
<211> LENGTH: 14
<212> TYPE: PRT
<213> ORGANISM: Homo sapiens

<400> SEQUENCE: 1233

Cys Phe Leu Gly Ala Leu Trp Lys Phe Leu Ser His Leu Leu
1               5                   10

<210> SEQ ID NO 1234
<211> LENGTH: 14
<212> TYPE: PRT
<213> ORGANISM: Homo sapiens

<400> SEQUENCE: 1234

Cys Phe Leu Glu Ala Leu Trp Lys Ala Leu Ser His Leu Leu
1               5                   10

<210> SEQ ID NO 1235
<211> LENGTH: 14
<212> TYPE: PRT
<213> ORGANISM: Homo sapiens

<400> SEQUENCE: 1235

Cys Phe Leu His Ala Leu Trp Lys Ala Leu Ser His Leu Leu
1               5                   10

<210> SEQ ID NO 1236
<211> LENGTH: 14
<212> TYPE: PRT
<213> ORGANISM: Homo sapiens

<400> SEQUENCE: 1236

Cys Phe Leu Lys Ala Leu Trp Lys Ala Leu Ser His Leu Leu
1               5                   10

<210> SEQ ID NO 1237
<211> LENGTH: 14
<212> TYPE: PRT
<213> ORGANISM: Homo sapiens

<400> SEQUENCE: 1237

Cys Phe Leu Asn Ala Leu Trp Lys Ala Leu Ser His Leu Leu
1               5                   10

<210> SEQ ID NO 1238
<211> LENGTH: 14
<212> TYPE: PRT
<213> ORGANISM: Homo sapiens

<400> SEQUENCE: 1238

Cys Phe Leu Ser Ala Leu Trp Lys Ala Leu Ser His Leu Leu
1               5                   10

<210> SEQ ID NO 1239
<211> LENGTH: 14
<212> TYPE: PRT
<213> ORGANISM: Homo sapiens

<400> SEQUENCE: 1239

Cys Phe Leu Gln Ala Leu Trp Lys Ala Leu Ser His Leu Leu
1               5                   10
```

```
<210> SEQ ID NO 1240
<211> LENGTH: 14
<212> TYPE: PRT
<213> ORGANISM: Homo sapiens

<400> SEQUENCE: 1240

Cys Phe Leu Glu Ala Leu Trp Glu Ala Leu Ser His Leu Leu
1               5                   10

<210> SEQ ID NO 1241
<211> LENGTH: 14
<212> TYPE: PRT
<213> ORGANISM: Homo sapiens

<400> SEQUENCE: 1241

Cys Phe Leu Gly Ala Leu Trp Glu Ala Leu Ser His Leu Leu
1               5                   10

<210> SEQ ID NO 1242
<211> LENGTH: 14
<212> TYPE: PRT
<213> ORGANISM: Homo sapiens

<400> SEQUENCE: 1242

Cys Phe Leu Glu Ala Leu Trp Lys Leu Leu Ser His Leu Leu
1               5                   10

<210> SEQ ID NO 1243
<211> LENGTH: 14
<212> TYPE: PRT
<213> ORGANISM: Homo sapiens

<400> SEQUENCE: 1243

Cys Phe Leu Glu Ala Leu Trp Glu Ala Leu Glu Glu Leu Leu
1               5                   10

<210> SEQ ID NO 1244
<211> LENGTH: 14
<212> TYPE: PRT
<213> ORGANISM: Homo sapiens

<400> SEQUENCE: 1244

Cys Phe Leu Glu Glu Leu Trp Glu Ala Leu Glu Glu Leu Leu
1               5                   10

<210> SEQ ID NO 1245
<211> LENGTH: 14
<212> TYPE: PRT
<213> ORGANISM: Homo sapiens

<400> SEQUENCE: 1245

Cys Phe Leu Glu Ala Leu Trp Glu Ala Leu Glu His Leu Leu
1               5                   10

<210> SEQ ID NO 1246
<211> LENGTH: 14
<212> TYPE: PRT
<213> ORGANISM: Homo sapiens

<400> SEQUENCE: 1246

Cys Phe Leu Glu Glu Leu Trp Glu Ala Leu Glu His Leu Leu
1               5                   10

<210> SEQ ID NO 1247
<211> LENGTH: 14
```

<212> TYPE: PRT
<213> ORGANISM: Homo sapiens

<400> SEQUENCE: 1247

Cys Phe Leu Glu Glu Leu Trp Glu Leu Leu Glu Leu Leu
1               5                   10

<210> SEQ ID NO 1248
<211> LENGTH: 14
<212> TYPE: PRT
<213> ORGANISM: Homo sapiens

<400> SEQUENCE: 1248

Cys Phe Leu Glu Glu Leu Trp Glu Leu Leu Glu His Leu Leu
1               5                   10

<210> SEQ ID NO 1249
<211> LENGTH: 26
<212> TYPE: PRT
<213> ORGANISM: Homo sapiens

<400> SEQUENCE: 1249

Cys Gly Leu Phe Gly Glu Ile Glu Glu Leu Leu Glu Glu Gly Leu Glu
1               5                   10                  15

Cys Ile Thr Leu Ile Asp Trp Trp Asn Gly
            20                  25

<210> SEQ ID NO 1250
<211> LENGTH: 26
<212> TYPE: PRT
<213> ORGANISM: Homo sapiens

<400> SEQUENCE: 1250

Cys Gly Leu Phe Glu Glu Ile Glu Glu Leu Leu Glu Glu Gly Leu Glu
1               5                   10                  15

Cys Ile Thr Leu Ile Asp Trp Trp Asn Gly
            20                  25

<210> SEQ ID NO 1251
<211> LENGTH: 26
<212> TYPE: PRT
<213> ORGANISM: Homo sapiens

<400> SEQUENCE: 1251

Cys Gly Leu Phe Gly Glu Ile Ala Glu Leu Leu Glu Glu Gly Leu Glu
1               5                   10                  15

Cys Ile Thr Leu Ile Asp Trp Trp Asn Gly
            20                  25

<210> SEQ ID NO 1252
<211> LENGTH: 26
<212> TYPE: PRT
<213> ORGANISM: Homo sapiens

<400> SEQUENCE: 1252

Cys Gly Leu Phe Glu Glu Ile Ala Glu Leu Leu Glu Glu Gly Leu Glu
1               5                   10                  15

Cys Ile Thr Leu Ile Asp Trp Trp Asn Gly
            20                  25

<210> SEQ ID NO 1253
<211> LENGTH: 26
<212> TYPE: PRT

<213> ORGANISM: Homo sapiens

<400> SEQUENCE: 1253

Cys Gly Leu Phe Gly Glu Ile Glu Glu Leu Glu Glu Gly Leu Glu
1               5                   10                  15

Cys Ile Thr Leu Val Asp Trp Trp Asn Gly
            20                  25

<210> SEQ ID NO 1254
<211> LENGTH: 26
<212> TYPE: PRT
<213> ORGANISM: Homo sapiens

<400> SEQUENCE: 1254

Cys Gly Leu Phe Glu Glu Ile Glu Glu Leu Glu Glu Gly Leu Glu
1               5                   10                  15

Cys Ile Thr Leu Val Asp Trp Trp Asn Gly
            20                  25

<210> SEQ ID NO 1255
<211> LENGTH: 26
<212> TYPE: PRT
<213> ORGANISM: Homo sapiens

<400> SEQUENCE: 1255

Cys Gly Leu Phe Gly Glu Ile Ala Glu Leu Glu Glu Gly Leu Glu
1               5                   10                  15

Cys Ile Thr Leu Val Asp Trp Trp Asn Gly
            20                  25

<210> SEQ ID NO 1256
<211> LENGTH: 26
<212> TYPE: PRT
<213> ORGANISM: Homo sapiens

<400> SEQUENCE: 1256

Cys Gly Leu Phe Glu Glu Ile Ala Glu Leu Glu Glu Gly Leu Glu
1               5                   10                  15

Cys Ile Thr Leu Val Asp Trp Trp Asn Gly
            20                  25

<210> SEQ ID NO 1257
<211> LENGTH: 26
<212> TYPE: PRT
<213> ORGANISM: Homo sapiens

<400> SEQUENCE: 1257

Cys Gly Leu Phe Gly Glu Ile Glu Glu Leu Glu Glu Gly Leu Glu
1               5                   10                  15

Cys Ile Thr Leu Ile Asp Trp Trp Asn Glu
            20                  25

<210> SEQ ID NO 1258
<211> LENGTH: 26
<212> TYPE: PRT
<213> ORGANISM: Homo sapiens

<400> SEQUENCE: 1258

Cys Gly Leu Phe Glu Glu Ile Glu Glu Leu Glu Glu Gly Leu Glu
1               5                   10                  15

Cys Ile Thr Leu Ile Asp Trp Trp Asn Glu
            20                  25

<210> SEQ ID NO 1259
<211> LENGTH: 26
<212> TYPE: PRT
<213> ORGANISM: Homo sapiens

<400> SEQUENCE: 1259

Cys Gly Leu Phe Gly Glu Ile Ala Glu Leu Leu Glu Glu Gly Leu Glu
1               5                   10                  15

Cys Ile Thr Leu Ile Asp Trp Trp Asn Glu
            20                  25

<210> SEQ ID NO 1260
<211> LENGTH: 26
<212> TYPE: PRT
<213> ORGANISM: Homo sapiens

<400> SEQUENCE: 1260

Cys Gly Leu Phe Glu Glu Ile Ala Glu Leu Leu Glu Glu Gly Leu Glu
1               5                   10                  15

Cys Ile Thr Leu Ile Asp Trp Trp Asn Glu
            20                  25

<210> SEQ ID NO 1261
<211> LENGTH: 26
<212> TYPE: PRT
<213> ORGANISM: Homo sapiens

<400> SEQUENCE: 1261

Cys Gly Leu Phe Gly Glu Ile Glu Glu Leu Leu Glu Glu Gly Leu His
1               5                   10                  15

Cys Ile Thr Leu Ile Asp Trp Trp Asn Gly
            20                  25

<210> SEQ ID NO 1262
<211> LENGTH: 26
<212> TYPE: PRT
<213> ORGANISM: Homo sapiens

<400> SEQUENCE: 1262

Cys Gly Leu Phe Glu Glu Ile Glu Glu Leu Leu Glu Glu Gly Leu His
1               5                   10                  15

Cys Ile Thr Leu Ile Asp Trp Trp Asn Gly
            20                  25

<210> SEQ ID NO 1263
<211> LENGTH: 26
<212> TYPE: PRT
<213> ORGANISM: Homo sapiens

<400> SEQUENCE: 1263

Cys Gly Leu Phe Gly Glu Ile Ala Glu Leu Leu Glu Glu Gly Leu His
1               5                   10                  15

Cys Ile Thr Leu Ile Asp Trp Trp Asn Gly
            20                  25

<210> SEQ ID NO 1264
<211> LENGTH: 26
<212> TYPE: PRT
<213> ORGANISM: Homo sapiens

<400> SEQUENCE: 1264

Cys Gly Leu Phe Glu Glu Ile Ala Glu Leu Glu Glu Gly Leu His
1               5                   10                  15

Cys Ile Thr Leu Ile Asp Trp Trp Asn Gly
            20                  25

<210> SEQ ID NO 1265
<211> LENGTH: 26
<212> TYPE: PRT
<213> ORGANISM: Homo sapiens

<400> SEQUENCE: 1265

Cys Gly Leu Phe Gly Glu Ile Glu Leu Leu Glu Glu Gly Leu Glu
1               5                   10                  15

Cys Ile Thr Leu Val Asp Trp Trp Asn Glu
            20                  25

<210> SEQ ID NO 1266
<211> LENGTH: 26
<212> TYPE: PRT
<213> ORGANISM: Homo sapiens

<400> SEQUENCE: 1266

Cys Gly Leu Phe Glu Glu Ile Glu Leu Leu Glu Glu Gly Leu Glu
1               5                   10                  15

Cys Ile Thr Leu Val Asp Trp Trp Asn Glu
            20                  25

<210> SEQ ID NO 1267
<211> LENGTH: 26
<212> TYPE: PRT
<213> ORGANISM: Homo sapiens

<400> SEQUENCE: 1267

Cys Gly Leu Phe Gly Glu Ile Ala Glu Leu Glu Glu Gly Leu Glu
1               5                   10                  15

Cys Ile Thr Leu Val Asp Trp Trp Asn Glu
            20                  25

<210> SEQ ID NO 1268
<211> LENGTH: 26
<212> TYPE: PRT
<213> ORGANISM: Homo sapiens

<400> SEQUENCE: 1268

Cys Gly Leu Phe Gly Glu Ile Ala Glu Leu Glu Glu Gly Leu Glu
1               5                   10                  15

Cys Ile Thr Leu Val Asp Trp Trp Asn Glu
            20                  25

<210> SEQ ID NO 1269
<211> LENGTH: 14
<212> TYPE: PRT
<213> ORGANISM: Homo sapiens

<400> SEQUENCE: 1269

Cys Phe Phe Lys Asn Ile Trp Glu Phe Ile Lys Ser Ile Leu
1               5                   10

<210> SEQ ID NO 1270
<211> LENGTH: 14
<212> TYPE: PRT
<213> ORGANISM: Homo sapiens

<400> SEQUENCE: 1270

Cys Phe Phe Lys Asn Ile Trp Asn Phe Ile Lys Ser Ile Leu
1               5                   10

<210> SEQ ID NO 1271
<211> LENGTH: 15
<212> TYPE: PRT
<213> ORGANISM: Homo sapiens

<400> SEQUENCE: 1271

Cys Phe Phe Lys Ala Ile Trp Glu Phe Ile Lys Ser Ile Leu Glu
1               5                   10                  15

<210> SEQ ID NO 1272
<211> LENGTH: 15
<212> TYPE: PRT
<213> ORGANISM: Homo sapiens

<400> SEQUENCE: 1272

Cys Phe Phe Lys Ala Ile Trp Glu Phe Ile Lys Asn Ile Phe Lys
1               5                   10                  15

<210> SEQ ID NO 1273
<211> LENGTH: 16
<212> TYPE: PRT
<213> ORGANISM: Homo sapiens

<400> SEQUENCE: 1273

Cys Phe Phe Lys Ala Ile Trp Glu Phe Ile Lys Asn Ile Phe Lys Glu
1               5                   10                  15

<210> SEQ ID NO 1274
<211> LENGTH: 14
<212> TYPE: PRT
<213> ORGANISM: Homo sapiens

<400> SEQUENCE: 1274

Cys Phe Phe Lys Ala Ile Trp Glu Leu Leu Lys Ser Ile Leu
1               5                   10

<210> SEQ ID NO 1275
<211> LENGTH: 14
<212> TYPE: PRT
<213> ORGANISM: Homo sapiens

<400> SEQUENCE: 1275

Cys Phe Phe Lys Ala Ile Trp Gly Leu Leu Lys Ser Ile Leu
1               5                   10

<210> SEQ ID NO 1276
<211> LENGTH: 15
<212> TYPE: PRT
<213> ORGANISM: Homo sapiens

<400> SEQUENCE: 1276

Cys Phe Phe Lys Ala Ile Trp Glu Phe Ile Lys Ser Ile Leu Lys
1               5                   10                  15

<210> SEQ ID NO 1277
<211> LENGTH: 14
<212> TYPE: PRT
<213> ORGANISM: Homo sapiens

<400> SEQUENCE: 1277

Cys Phe Phe Lys Asn Ile Trp Gly Leu Leu Lys Ser Ile Leu
1               5                   10

<210> SEQ ID NO 1278
<211> LENGTH: 15
<212> TYPE: PRT
<213> ORGANISM: Homo sapiens

<400> SEQUENCE: 1278

Cys Phe Phe Lys Ala Ile Trp Gly Leu Leu Lys Asn Ile Phe Lys
1               5                   10                  15

<210> SEQ ID NO 1279
<211> LENGTH: 15
<212> TYPE: PRT
<213> ORGANISM: Homo sapiens

<400> SEQUENCE: 1279

Cys Phe Phe Lys Ala Ile Trp Glu Leu Leu Lys Asn Ile Phe Lys
1               5                   10                  15

<210> SEQ ID NO 1280
<211> LENGTH: 15
<212> TYPE: PRT
<213> ORGANISM: Homo sapiens

<400> SEQUENCE: 1280

Cys Phe Phe Lys Asn Ile Trp Gly Leu Leu Lys Asn Ile Phe Lys
1               5                   10                  15

<210> SEQ ID NO 1281
<211> LENGTH: 15
<212> TYPE: PRT
<213> ORGANISM: Homo sapiens

<400> SEQUENCE: 1281

Cys Phe Phe Lys Asn Ile Trp Glu Leu Leu Lys Asn Ile Phe Lys
1               5                   10                  15

<210> SEQ ID NO 1282
<211> LENGTH: 14
<212> TYPE: PRT
<213> ORGANISM: Homo sapiens

<400> SEQUENCE: 1282

Cys Phe Phe Lys Ala Ile Trp Glu Phe Ile Arg Ser Ile Leu
1               5                   10

<210> SEQ ID NO 1283
<211> LENGTH: 14
<212> TYPE: PRT
<213> ORGANISM: Homo sapiens

<400> SEQUENCE: 1283

Cys Phe Phe Lys Ala Ile Trp Glu Phe Ile Lys Ser Leu Leu
1               5                   10

<210> SEQ ID NO 1284
<211> LENGTH: 14
<212> TYPE: PRT
<213> ORGANISM: Homo sapiens

<400> SEQUENCE: 1284

Cys Phe Phe Lys Ala Ile Trp Glu Phe Ile Lys Ser Ala Leu
1               5                   10

<210> SEQ ID NO 1285
<211> LENGTH: 14
<212> TYPE: PRT
<213> ORGANISM: Homo sapiens

<400> SEQUENCE: 1285

Cys Phe Phe Lys Ala Ile Trp Glu Phe Ile Lys Ser Ile Phe
1               5                   10

<210> SEQ ID NO 1286
<211> LENGTH: 14
<212> TYPE: PRT
<213> ORGANISM: Homo sapiens

<400> SEQUENCE: 1286

Cys Phe Phe Lys Ala Leu Trp Glu Phe Leu Lys Ser Leu Leu
1               5                   10

<210> SEQ ID NO 1287
<211> LENGTH: 14
<212> TYPE: PRT
<213> ORGANISM: Homo sapiens

<400> SEQUENCE: 1287

Cys Ile Phe Lys Ala Ile Trp Glu Phe Ile Lys Ser Ile Leu
1               5                   10

<210> SEQ ID NO 1288
<211> LENGTH: 14
<212> TYPE: PRT
<213> ORGANISM: Homo sapiens

<400> SEQUENCE: 1288

Cys Phe Phe Lys Ala Ile Trp Glu Phe Ile Lys Ser Ile Trp
1               5                   10

<210> SEQ ID NO 1289
<211> LENGTH: 14
<212> TYPE: PRT
<213> ORGANISM: Homo sapiens

<400> SEQUENCE: 1289

Cys Phe Phe His Ala Ile Trp Glu Phe Ile Lys Ser Ile Leu
1               5                   10

<210> SEQ ID NO 1290
<211> LENGTH: 14
<212> TYPE: PRT
<213> ORGANISM: Homo sapiens

<400> SEQUENCE: 1290

Cys Phe Phe Glu Ala Ile Trp Glu Phe Ile Lys Ser Ile Leu
1               5                   10

<210> SEQ ID NO 1291
<211> LENGTH: 14
<212> TYPE: PRT
<213> ORGANISM: Homo sapiens

<400> SEQUENCE: 1291

Cys Phe Phe Lys Ala Ile Ala Glu Phe Ile Lys Ser Ile Leu
1               5                   10

<210> SEQ ID NO 1292
<211> LENGTH: 14
<212> TYPE: PRT
<213> ORGANISM: Homo sapiens

<400> SEQUENCE: 1292

Cys Phe Phe Lys Ala Ile Glu Glu Phe Ile Lys Ser Ile Leu
1               5                   10

<210> SEQ ID NO 1293
<211> LENGTH: 14
<212> TYPE: PRT
<213> ORGANISM: Homo sapiens

<400> SEQUENCE: 1293

Cys Phe Phe Lys Ala Ile Leu Glu Phe Ile Lys Ser Ile Leu
1               5                   10

<210> SEQ ID NO 1294
<211> LENGTH: 14
<212> TYPE: PRT
<213> ORGANISM: Homo sapiens

<400> SEQUENCE: 1294

Cys Phe Phe Lys Ala Ile Phe Glu Phe Ile Lys Ser Ile Leu
1               5                   10

<210> SEQ ID NO 1295
<211> LENGTH: 14
<212> TYPE: PRT
<213> ORGANISM: Homo sapiens

<400> SEQUENCE: 1295

Cys Phe Phe Lys Ala Ile Trp Gly Phe Ile Lys Ser Ile Leu
1               5                   10

<210> SEQ ID NO 1296
<211> LENGTH: 14
<212> TYPE: PRT
<213> ORGANISM: Homo sapiens

<400> SEQUENCE: 1296

Cys Phe Phe Lys Ala Ile Trp His Phe Ile Lys Ser Ile Leu
1               5                   10

<210> SEQ ID NO 1297
<211> LENGTH: 14
<212> TYPE: PRT
<213> ORGANISM: Homo sapiens

<400> SEQUENCE: 1297

Cys Phe Phe Lys Ala Ile Trp Lys Phe Ile Lys Ser Ile Leu
1               5                   10

<210> SEQ ID NO 1298
<211> LENGTH: 14
<212> TYPE: PRT
<213> ORGANISM: Homo sapiens

<400> SEQUENCE: 1298

Cys Phe Phe Glu Ala Ile Trp Lys Phe Ile Lys Ser Ile Leu
1               5                   10

<210> SEQ ID NO 1299
<211> LENGTH: 14

```
<212> TYPE: PRT
<213> ORGANISM: Homo sapiens

<400> SEQUENCE: 1299

Cys Phe Phe Lys Ala Ile Trp Glu Leu Ile Lys Ser Ile Leu
1               5                   10

<210> SEQ ID NO 1300
<211> LENGTH: 14
<212> TYPE: PRT
<213> ORGANISM: Homo sapiens

<400> SEQUENCE: 1300

Cys Phe Phe Lys Ala Leu Trp Glu Leu Leu Lys Ser Leu Leu
1               5                   10

<210> SEQ ID NO 1301
<211> LENGTH: 14
<212> TYPE: PRT
<213> ORGANISM: Homo sapiens

<400> SEQUENCE: 1301

Cys Phe Phe Lys Ala Ile Trp Glu Ala Ile Lys Ser Ile Leu
1               5                   10

<210> SEQ ID NO 1302
<211> LENGTH: 14
<212> TYPE: PRT
<213> ORGANISM: Homo sapiens

<400> SEQUENCE: 1302

Cys Phe Phe Lys Ala Ile Trp Glu Phe Leu Lys Ser Ile Leu
1               5                   10

<210> SEQ ID NO 1303
<211> LENGTH: 14
<212> TYPE: PRT
<213> ORGANISM: Homo sapiens

<400> SEQUENCE: 1303

Cys Phe Phe Lys Ala Ile Trp Glu Phe Ile His Ser Ile Leu
1               5                   10

<210> SEQ ID NO 1304
<211> LENGTH: 14
<212> TYPE: PRT
<213> ORGANISM: Homo sapiens

<400> SEQUENCE: 1304

Cys Phe Phe Lys Ala Ile Trp Glu Phe Ile Glu Ser Ile Leu
1               5                   10

<210> SEQ ID NO 1305
<211> LENGTH: 14
<212> TYPE: PRT
<213> ORGANISM: Homo sapiens

<400> SEQUENCE: 1305

Cys Phe Phe Lys Ala Ile Trp Glu Phe Ile Lys Asn Ile Leu
1               5                   10

<210> SEQ ID NO 1306
<211> LENGTH: 14
<212> TYPE: PRT
<213> ORGANISM: Homo sapiens
```

```
<400> SEQUENCE: 1306

Cys Phe Phe Lys Ala Ile Trp Glu Phe Ile Lys Trp Ile Leu
1               5                   10

<210> SEQ ID NO 1307
<211> LENGTH: 14
<212> TYPE: PRT
<213> ORGANISM: Homo sapiens

<400> SEQUENCE: 1307

Cys Phe Phe Lys Ala Ile Trp Glu Phe Ile Lys Glu Ile Leu
1               5                   10

<210> SEQ ID NO 1308
<211> LENGTH: 14
<212> TYPE: PRT
<213> ORGANISM: Homo sapiens

<400> SEQUENCE: 1308

Cys Phe Phe Lys Ala Ile Trp Glu Phe Ile Lys Gly Ile Leu
1               5                   10

<210> SEQ ID NO 1309
<211> LENGTH: 14
<212> TYPE: PRT
<213> ORGANISM: Homo sapiens

<400> SEQUENCE: 1309

Cys Phe Phe Lys Ala Ile Trp Glu Phe Ile Lys Ser Gly Leu
1               5                   10

<210> SEQ ID NO 1310
<211> LENGTH: 14
<212> TYPE: PRT
<213> ORGANISM: Homo sapiens

<400> SEQUENCE: 1310

Cys Phe Phe Lys Ala Ile Trp Glu Phe Ile Lys Ser Ile Ile
1               5                   10

<210> SEQ ID NO 1311
<211> LENGTH: 16
<212> TYPE: PRT
<213> ORGANISM: Homo sapiens

<400> SEQUENCE: 1311

Cys Phe Phe Lys Ala Ile Trp Glu Phe Ile Lys Cys Ile Thr Ile Leu
1               5                   10                  15

<210> SEQ ID NO 1312
<211> LENGTH: 14
<212> TYPE: PRT
<213> ORGANISM: Homo sapiens

<400> SEQUENCE: 1312

Cys Phe Phe Lys Ala Ile Trp Glu Phe Ile Lys Ser Ile Ala
1               5                   10

<210> SEQ ID NO 1313
<211> LENGTH: 14
<212> TYPE: PRT
<213> ORGANISM: Homo sapiens

<400> SEQUENCE: 1313
```

Cys Phe Phe Lys Ala Ile Trp Glu Phe Ile Lys Gln Ile Leu
1               5                   10

<210> SEQ ID NO 1314
<211> LENGTH: 15
<212> TYPE: PRT
<213> ORGANISM: Homo sapiens

<400> SEQUENCE: 1314

Cys Gly Phe Phe Lys Ala Ile Trp Glu Phe Ile Lys Ser Ile Leu
1               5                   10                  15

<210> SEQ ID NO 1315
<211> LENGTH: 20
<212> TYPE: PRT
<213> ORGANISM: Homo sapiens

<400> SEQUENCE: 1315

Cys Phe Phe Lys Ala Ile Trp Glu Phe Ile Lys Ser Ile Leu Lys Gly
1               5                   10                  15

Leu Ile Asp Gly
            20

<210> SEQ ID NO 1316
<211> LENGTH: 23
<212> TYPE: PRT
<213> ORGANISM: Homo sapiens

<400> SEQUENCE: 1316

Cys Phe Phe Lys Ala Ile Trp Glu Phe Ile Lys Ser Ile Leu Lys Gly
1               5                   10                  15

Leu Ile Asp Gly Trp Tyr Gly
            20

<210> SEQ ID NO 1317
<211> LENGTH: 20
<212> TYPE: PRT
<213> ORGANISM: Homo sapiens

<400> SEQUENCE: 1317

Cys Phe Phe Lys Ala Ile Trp Glu Phe Ile Lys Ser Ile Leu Glu Gly
1               5                   10                  15

Leu Ile Asp Gly
            20

<210> SEQ ID NO 1318
<211> LENGTH: 23
<212> TYPE: PRT
<213> ORGANISM: Homo sapiens

<400> SEQUENCE: 1318

Cys Phe Phe Lys Ala Ile Trp Glu Phe Ile Lys Ser Ile Leu Glu Gly
1               5                   10                  15

Leu Ile Asp Gly Trp Tyr Gly
            20

<210> SEQ ID NO 1319
<211> LENGTH: 20
<212> TYPE: PRT
<213> ORGANISM: Homo sapiens

<400> SEQUENCE: 1319

-continued

Cys Phe Phe Lys Ala Ile Trp Glu Phe Ile Lys Asn Ile Phe Lys Gly
1               5                   10                  15

Leu Ile Asp Gly
            20

<210> SEQ ID NO 1320
<211> LENGTH: 23
<212> TYPE: PRT
<213> ORGANISM: Homo sapiens

<400> SEQUENCE: 1320

Cys Phe Phe Lys Ala Ile Trp Glu Phe Ile Lys Asn Ile Phe Lys Gly
1               5                   10                  15

Leu Ile Asp Gly Trp Tyr Gly
            20

<210> SEQ ID NO 1321
<211> LENGTH: 20
<212> TYPE: PRT
<213> ORGANISM: Homo sapiens

<400> SEQUENCE: 1321

Cys Phe Phe Gly Asn Ile Trp Glu Phe Ile Lys Ser Ile Leu Lys Gly
1               5                   10                  15

Leu Ile Asp Gly
            20

<210> SEQ ID NO 1322
<211> LENGTH: 23
<212> TYPE: PRT
<213> ORGANISM: Homo sapiens

<400> SEQUENCE: 1322

Cys Phe Phe Gly Asn Ile Trp Glu Phe Ile Lys Ser Ile Leu Lys Gly
1               5                   10                  15

Leu Ile Asp Gly Trp Tyr Gly
            20

<210> SEQ ID NO 1323
<211> LENGTH: 20
<212> TYPE: PRT
<213> ORGANISM: Homo sapiens

<400> SEQUENCE: 1323

Cys Phe Phe Gly Asn Ile Trp Glu Phe Ile Lys Ser Ile Leu Glu Gly
1               5                   10                  15

Leu Ile Asp Gly
            20

<210> SEQ ID NO 1324
<211> LENGTH: 23
<212> TYPE: PRT
<213> ORGANISM: Homo sapiens

<400> SEQUENCE: 1324

Cys Phe Phe Gly Asn Ile Trp Glu Phe Ile Lys Ser Ile Leu Glu Gly
1               5                   10                  15

Leu Ile Asp Gly Trp Tyr Gly
            20

<210> SEQ ID NO 1325
<211> LENGTH: 20

```
<212> TYPE: PRT
<213> ORGANISM: Homo sapiens

<400> SEQUENCE: 1325

Cys Phe Phe Gly Asn Ile Trp Glu Phe Ile Lys Asn Ile Phe Lys Gly
1               5                   10                  15

Leu Ile Asp Gly
            20

<210> SEQ ID NO 1326
<211> LENGTH: 23
<212> TYPE: PRT
<213> ORGANISM: Homo sapiens

<400> SEQUENCE: 1326

Cys Phe Phe Gly Asn Ile Trp Glu Phe Ile Lys Asn Ile Phe Lys Gly
1               5                   10                  15

Leu Ile Asp Gly Glu Tyr Gly
            20

<210> SEQ ID NO 1327
<211> LENGTH: 20
<212> TYPE: PRT
<213> ORGANISM: Homo sapiens

<400> SEQUENCE: 1327

Cys Phe Phe Lys Ala Ile Trp Gly Leu Leu Lys Ser Ile Leu Lys Gly
1               5                   10                  15

Leu Ile Asp Gly
            20

<210> SEQ ID NO 1328
<211> LENGTH: 23
<212> TYPE: PRT
<213> ORGANISM: Homo sapiens

<400> SEQUENCE: 1328

Cys Phe Phe Lys Ala Ile Trp Gly Leu Leu Lys Ser Ile Leu Lys Gly
1               5                   10                  15

Leu Ile Asp Gly Trp Tyr Gly
            20

<210> SEQ ID NO 1329
<211> LENGTH: 20
<212> TYPE: PRT
<213> ORGANISM: Homo sapiens

<400> SEQUENCE: 1329

Cys Phe Phe Lys Ala Ile Trp Gly Leu Leu Lys Ser Ile Leu Glu Gly
1               5                   10                  15

Leu Ile Asp Gly
            20

<210> SEQ ID NO 1330
<211> LENGTH: 23
<212> TYPE: PRT
<213> ORGANISM: Homo sapiens

<400> SEQUENCE: 1330

Cys Phe Phe Lys Ala Ile Trp Gly Leu Leu Lys Ser Ile Leu Glu Gly
1               5                   10                  15

Leu Ile Asp Gly Trp Tyr Gly
```

20

<210> SEQ ID NO 1331
<211> LENGTH: 20
<212> TYPE: PRT
<213> ORGANISM: Homo sapiens

<400> SEQUENCE: 1331

Cys Phe Phe Lys Ala Ile Trp Gly Leu Leu Lys Asn Ile Phe Lys Gly
1               5                   10                  15

Leu Ile Asp Gly
            20

<210> SEQ ID NO 1332
<211> LENGTH: 23
<212> TYPE: PRT
<213> ORGANISM: Homo sapiens

<400> SEQUENCE: 1332

Cys Phe Phe Lys Ala Ile Trp Gly Leu Leu Lys Asn Ile Phe Lys Gly
1               5                   10                  15

Leu Ile Asp Gly Trp Tyr Gly
            20

<210> SEQ ID NO 1333
<211> LENGTH: 20
<212> TYPE: PRT
<213> ORGANISM: Homo sapiens

<400> SEQUENCE: 1333

Cys Phe Phe Lys Ala Ile Trp Gly Leu Leu Lys Asn Ile Phe Glu Gly
1               5                   10                  15

Leu Ile Asp Gly
            20

<210> SEQ ID NO 1334
<211> LENGTH: 23
<212> TYPE: PRT
<213> ORGANISM: Homo sapiens

<400> SEQUENCE: 1334

Cys Phe Phe Lys Ala Ile Trp Gly Leu Leu Lys Asn Ile Phe Glu Gly
1               5                   10                  15

Leu Ile Asp Gly Trp Tyr Gly
            20

<210> SEQ ID NO 1335
<211> LENGTH: 23
<212> TYPE: PRT
<213> ORGANISM: Homo sapiens

<400> SEQUENCE: 1335

Cys Phe Phe Lys Ala Ile Trp Glu Phe Ile Lys Ser Ile Leu Lys Gly
1               5                   10                  15

Leu Ile Asp Gly Trp Asn Gly
            20

<210> SEQ ID NO 1336
<211> LENGTH: 23
<212> TYPE: PRT
<213> ORGANISM: Homo sapiens

<400> SEQUENCE: 1336

-continued

Cys Phe Phe Lys Ala Ile Trp Glu Phe Ile Lys Asn Ile Phe Lys Gly
1               5                   10                  15

Leu Ile Asp Gly Trp Asn Gly
            20

<210> SEQ ID NO 1337
<211> LENGTH: 20
<212> TYPE: PRT
<213> ORGANISM: Homo sapiens

<400> SEQUENCE: 1337

Cys Ile Phe Gly Ala Ile Ala Gly Leu Leu Lys Asn Ile Leu Lys Gly
1               5                   10                  15

Leu Ile Asp Gly
            20

<210> SEQ ID NO 1338
<211> LENGTH: 23
<212> TYPE: PRT
<213> ORGANISM: Homo sapiens

<400> SEQUENCE: 1338

Cys Ile Phe Gly Ala Ile Ala Gly Leu Leu Lys Asn Ile Leu Lys Gly
1               5                   10                  15

Leu Ile Asp Gly Trp Tyr Gly
            20

<210> SEQ ID NO 1339
<211> LENGTH: 14
<212> TYPE: PRT
<213> ORGANISM: Homo sapiens

<400> SEQUENCE: 1339

Cys Phe Leu Glu Ala Leu Trp Lys Ala Leu Glu His Leu Leu
1               5                   10

<210> SEQ ID NO 1340
<211> LENGTH: 14
<212> TYPE: PRT
<213> ORGANISM: Homo sapiens

<400> SEQUENCE: 1340

Cys Phe Leu Glu Ala Leu Trp Glu Ala Leu Ser Lys Leu Leu
1               5                   10

<210> SEQ ID NO 1341
<211> LENGTH: 14
<212> TYPE: PRT
<213> ORGANISM: Homo sapiens

<400> SEQUENCE: 1341

Cys Phe Leu Glu Ala Leu Trp Glu Ala Leu Glu Lys Leu Leu
1               5                   10

<210> SEQ ID NO 1342
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(15)
<223> OTHER INFORMATION: Lys is conjugated to stearyl

<400> SEQUENCE: 1342

Cys Phe Leu Glu Ala Leu Trp Glu Ala Leu Glu His Leu Leu Lys
1               5                   10                  15

<210> SEQ ID NO 1343
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Phe is conjugated to stearyl

<400> SEQUENCE: 1343

Phe Leu Glu Ala Leu Trp Glu Ala Leu Glu His Leu Leu Cys
1               5                   10

<210> SEQ ID NO 1344
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Gly is conjugated to stearyl

<400> SEQUENCE: 1344

Gly Phe Leu Glu Ala Leu Trp Glu Ala Leu Glu His Leu Leu Cys
1               5                   10                  15

<210> SEQ ID NO 1345
<211> LENGTH: 14
<212> TYPE: PRT
<213> ORGANISM: Homo sapiens

<400> SEQUENCE: 1345

Cys Phe Leu Glu Ala Leu Trp Lys Ala Leu Ser Lys Leu Leu
1               5                   10

<210> SEQ ID NO 1346
<211> LENGTH: 14
<212> TYPE: PRT
<213> ORGANISM: Homo sapiens

<400> SEQUENCE: 1346

Cys Phe Leu Glu Ala Leu Trp Glu Ala Leu Asp His Leu Leu
1               5                   10

<210> SEQ ID NO 1347
<211> LENGTH: 14
<212> TYPE: PRT
<213> ORGANISM: Homo sapiens

<400> SEQUENCE: 1347

Cys Phe Leu Glu Ala Leu Trp Glu Ala Leu Thr His Leu Leu
1               5                   10

<210> SEQ ID NO 1348
<211> LENGTH: 14
<212> TYPE: PRT
<213> ORGANISM: Homo sapiens

<400> SEQUENCE: 1348

Cys Phe Leu Glu Ala Leu Trp Glu Ala Leu Asn His Leu Leu
1               5                   10

<210> SEQ ID NO 1349
<211> LENGTH: 14
<212> TYPE: PRT
<213> ORGANISM: Homo sapiens

<400> SEQUENCE: 1349

Cys Phe Leu Glu Ala Leu Trp Glu Ala Leu Gln His Leu Leu
1               5                   10

<210> SEQ ID NO 1350
<211> LENGTH: 15
<212> TYPE: PRT
<213> ORGANISM: Homo sapiens

<400> SEQUENCE: 1350

Cys Phe Leu Glu Ala Leu Trp Glu Ala Leu Glu His Leu Leu His
1               5                   10                  15

<210> SEQ ID NO 1351
<211> LENGTH: 15
<212> TYPE: PRT
<213> ORGANISM: Homo sapiens

<400> SEQUENCE: 1351

Cys Phe Leu Glu Ala Leu Trp Glu Ala Leu Glu His Leu Leu Lys
1               5                   10                  15

<210> SEQ ID NO 1352
<211> LENGTH: 15
<212> TYPE: PRT
<213> ORGANISM: Homo sapiens

<400> SEQUENCE: 1352

Cys Phe Leu Glu Ala Leu Trp Glu Ala Leu Glu His Leu Leu Glu
1               5                   10                  15

<210> SEQ ID NO 1353
<211> LENGTH: 13
<212> TYPE: PRT
<213> ORGANISM: Homo sapiens

<400> SEQUENCE: 1353

Cys Trp Leu Glu Ala Leu Glu Ala Leu Glu His Leu Leu
1               5                   10

<210> SEQ ID NO 1354
<211> LENGTH: 14
<212> TYPE: PRT
<213> ORGANISM: Homo sapiens

<400> SEQUENCE: 1354

Cys Leu Leu Glu Ala Leu Trp Glu Ala Leu Glu His Leu Leu
1               5                   10

<210> SEQ ID NO 1355
<211> LENGTH: 14
<212> TYPE: PRT
<213> ORGANISM: Homo sapiens

<400> SEQUENCE: 1355

Cys Phe Phe Glu Ala Leu Trp Glu Ala Leu Glu His Leu Leu
1               5                   10

<210> SEQ ID NO 1356
<211> LENGTH: 14
<212> TYPE: PRT
<213> ORGANISM: Homo sapiens

<400> SEQUENCE: 1356

Cys Phe Leu Glu Ala Leu Glu Glu Ala Leu Glu His Leu Leu
1               5                   10

<210> SEQ ID NO 1357
<211> LENGTH: 14
<212> TYPE: PRT
<213> ORGANISM: Homo sapiens

<400> SEQUENCE: 1357

Cys Phe Leu Glu Ala Leu Ala Glu Ala Leu Glu His Leu Leu
1               5                   10

<210> SEQ ID NO 1358
<211> LENGTH: 14
<212> TYPE: PRT
<213> ORGANISM: Homo sapiens

<400> SEQUENCE: 1358

Cys Phe Leu Glu Ala Leu Phe Glu Ala Leu Glu His Leu Leu
1               5                   10

<210> SEQ ID NO 1359
<211> LENGTH: 14
<212> TYPE: PRT
<213> ORGANISM: Homo sapiens

<400> SEQUENCE: 1359

Cys Leu Phe Glu Ala Leu Trp Glu Ala Leu His His Leu Leu
1               5                   10

<210> SEQ ID NO 1360
<211> LENGTH: 14
<212> TYPE: PRT
<213> ORGANISM: Homo sapiens

<400> SEQUENCE: 1360

Cys Leu Phe Glu Ala Leu Trp Glu Ala Leu Lys His Leu Leu
1               5                   10

<210> SEQ ID NO 1361
<211> LENGTH: 14
<212> TYPE: PRT
<213> ORGANISM: Homo sapiens

<400> SEQUENCE: 1361

Cys Phe Leu Glu Ala Leu Trp Glu Ala Leu Glu His Gly Leu
1               5                   10

<210> SEQ ID NO 1362
<211> LENGTH: 14
<212> TYPE: PRT
<213> ORGANISM: Homo sapiens

<400> SEQUENCE: 1362

Cys Leu Phe Glu Ala Leu Trp Glu Ala Leu Glu His Leu Phe
1               5                   10

<210> SEQ ID NO 1363
<211> LENGTH: 14
<212> TYPE: PRT
<213> ORGANISM: Homo sapiens

<400> SEQUENCE: 1363

Cys Leu Phe Glu Ala Leu Trp Glu Ala Leu Glu His Phe Leu
1               5                   10

<210> SEQ ID NO 1364
<211> LENGTH: 23
<212> TYPE: PRT
<213> ORGANISM: Homo sapiens

<400> SEQUENCE: 1364

Cys Leu Phe Glu Ala Leu Trp Glu Ala Leu Glu His Leu Leu Glu Gly
1               5                   10                  15

Leu Ile Asp Trp Trp Tyr Gly
            20

<210> SEQ ID NO 1365
<211> LENGTH: 23
<212> TYPE: PRT
<213> ORGANISM: Homo sapiens

<400> SEQUENCE: 1365

Cys Leu Phe Glu Ala Leu Trp Glu Ala Leu Glu His Leu Leu Glu Gly
1               5                   10                  15

Leu Ile Asp Trp Trp Asn Gly
            20

<210> SEQ ID NO 1366
<211> LENGTH: 23
<212> TYPE: PRT
<213> ORGANISM: Homo sapiens

<400> SEQUENCE: 1366

Cys Leu Phe Glu Ala Leu Trp Glu Ala Leu Glu His Leu Leu Glu Asn
1               5                   10                  15

Leu Ile Asp Trp Trp Asn Gly
            20

<210> SEQ ID NO 1367
<211> LENGTH: 14
<212> TYPE: PRT
<213> ORGANISM: Homo sapiens

<400> SEQUENCE: 1367

Cys Phe Leu Glu Glu Leu Trp Glu Leu Leu Glu Lys Leu Leu
1               5                   10

<210> SEQ ID NO 1368
<211> LENGTH: 15
<212> TYPE: PRT
<213> ORGANISM: Homo sapiens

<400> SEQUENCE: 1368

Cys Phe Leu Glu Glu Leu Trp Glu Leu Leu Glu Glu Leu Leu Glu
1               5                   10                  15

<210> SEQ ID NO 1369
<211> LENGTH: 18

<212> TYPE: PRT
<213> ORGANISM: Homo sapiens

<400> SEQUENCE: 1369

Cys Phe Leu Glu Glu Leu Trp Glu Leu Leu Glu Glu Leu Leu Glu Leu
1               5                   10                  15

Leu Glu

<210> SEQ ID NO 1370
<211> LENGTH: 18
<212> TYPE: PRT
<213> ORGANISM: Homo sapiens

<400> SEQUENCE: 1370

Cys Phe Leu Glu Glu Leu Trp Glu Leu Leu Glu His Leu Leu Glu Leu
1               5                   10                  15

Leu Asp

<210> SEQ ID NO 1371
<211> LENGTH: 18
<212> TYPE: PRT
<213> ORGANISM: Homo sapiens

<400> SEQUENCE: 1371

Cys Phe Leu Glu Glu Leu Trp Glu Leu Leu Glu Glu Leu Leu Glu Leu
1               5                   10                  15

Ile Asp

<210> SEQ ID NO 1372
<211> LENGTH: 18
<212> TYPE: PRT
<213> ORGANISM: Homo sapiens

<400> SEQUENCE: 1372

Cys Phe Leu Glu Glu Leu Trp Glu Leu Leu Glu Glu Leu Leu Glu Leu
1               5                   10                  15

Leu Asp

<210> SEQ ID NO 1373
<211> LENGTH: 18
<212> TYPE: PRT
<213> ORGANISM: Homo sapiens

<400> SEQUENCE: 1373

Cys Phe Leu Glu Glu Leu Trp Glu Leu Leu Glu His Leu Leu Glu Gly
1               5                   10                  15

Leu Glu

<210> SEQ ID NO 1374
<211> LENGTH: 18
<212> TYPE: PRT
<213> ORGANISM: Homo sapiens

<400> SEQUENCE: 1374

Cys Phe Leu Glu Glu Leu Trp Glu Leu Leu Glu His Leu Leu Glu Gly
1               5                   10                  15

Leu Asp

<210> SEQ ID NO 1375
<211> LENGTH: 19
<212> TYPE: PRT

<213> ORGANISM: Homo sapiens

<400> SEQUENCE: 1375

Cys Phe Leu Glu Glu Leu Trp Glu Leu Leu Glu His Leu Leu Glu Glu
1               5                   10                  15

Gly Leu Ile

<210> SEQ ID NO 1376
<211> LENGTH: 23
<212> TYPE: PRT
<213> ORGANISM: Homo sapiens

<400> SEQUENCE: 1376

Cys Phe Leu Glu Glu Leu Trp Glu Leu Leu Glu His Leu Leu Glu Gly
1               5                   10                  15

Leu Ile Asp Trp Trp Tyr Gly
            20

<210> SEQ ID NO 1377
<211> LENGTH: 23
<212> TYPE: PRT
<213> ORGANISM: Homo sapiens

<400> SEQUENCE: 1377

Cys Phe Leu Glu Glu Leu Trp Glu Leu Leu Glu His Leu Leu Glu Asn
1               5                   10                  15

Leu Ile Asp Trp Trp Asn Gly
            20

<210> SEQ ID NO 1378
<211> LENGTH: 18
<212> TYPE: PRT
<213> ORGANISM: Homo sapiens

<400> SEQUENCE: 1378

Cys Phe Leu Glu Ala Leu Trp Glu Ala Leu Glu His Leu Leu Glu Leu
1               5                   10                  15

Leu Asp

<210> SEQ ID NO 1379
<211> LENGTH: 24
<212> TYPE: PRT
<213> ORGANISM: Homo sapiens

<400> SEQUENCE: 1379

Cys Gly Leu Phe Gly Glu Leu Glu Glu Leu Leu Glu Glu Gly Leu Glu
1               5                   10                  15

Asn Leu Thr Asp Trp Trp Asn Gly
            20

<210> SEQ ID NO 1380
<211> LENGTH: 23
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (18)..(18)
<223> OTHER INFORMATION: Leu is conjugated to ALLO-I

<400> SEQUENCE: 1380

Cys Gly Leu Phe Gly Glu Leu Glu Glu Leu Leu Glu Glu Gly Leu Glu

-continued

```
                1               5                  10                  15

Asn Leu Asp Trp Trp Asn Gly
            20

<210> SEQ ID NO 1381
<211> LENGTH: 18
<212> TYPE: PRT
<213> ORGANISM: Homo sapiens

<400> SEQUENCE: 1381

Cys Phe Leu Glu Ala Leu Trp Glu Ala Leu Glu His Leu Leu Glu Leu
1               5                  10                  15

Ile Asp

<210> SEQ ID NO 1382
<211> LENGTH: 24
<212> TYPE: PRT
<213> ORGANISM: Homo sapiens

<400> SEQUENCE: 1382

Cys Glu Leu Phe Glu Glu Leu Glu Glu Leu Leu Glu Glu Gly Leu Glu
1               5                  10                  15

Asn Leu Ile Asp Trp Trp Asn Gly
            20

<210> SEQ ID NO 1383
<211> LENGTH: 24
<212> TYPE: PRT
<213> ORGANISM: Homo sapiens

<400> SEQUENCE: 1383

Cys Gly Leu Phe Glu Glu Leu Glu Glu Leu Leu Glu Glu Gly Leu Glu
1               5                  10                  15

Leu Leu Ile Asp Trp Trp Asn Gly
            20

<210> SEQ ID NO 1384
<211> LENGTH: 24
<212> TYPE: PRT
<213> ORGANISM: Homo sapiens

<400> SEQUENCE: 1384

Cys Gly Leu Phe Glu Glu Leu Glu Glu Leu Leu Glu Glu Gly Leu Glu
1               5                  10                  15

Leu Leu Ile Asp Trp Trp Asn Lys
            20

<210> SEQ ID NO 1385
<211> LENGTH: 24
<212> TYPE: PRT
<213> ORGANISM: Homo sapiens

<400> SEQUENCE: 1385

Cys Gly Leu Phe Glu Glu Leu Glu Glu Leu Leu Glu Glu Gly Leu Glu
1               5                  10                  15

Asn Leu Ile Asp Trp Trp Asn Lys
            20

<210> SEQ ID NO 1386
<211> LENGTH: 24
<212> TYPE: PRT
<213> ORGANISM: Homo sapiens
```

<400> SEQUENCE: 1386

Cys Gly Leu Phe Gly Glu Leu Glu Glu Leu Glu Glu Gly Leu Glu
1               5                   10                  15

Asn Leu Ile Asp Trp Trp Asn Gln
            20

<210> SEQ ID NO 1387
<211> LENGTH: 24
<212> TYPE: PRT
<213> ORGANISM: Homo sapiens

<400> SEQUENCE: 1387

Cys Gly Leu Phe Gly Glu Leu Glu Glu Leu Leu Glu Glu Gly Leu Glu
1               5                   10                  15

Asn Leu Ile Asp Trp Trp Asn Glu
            20

<210> SEQ ID NO 1388
<211> LENGTH: 24
<212> TYPE: PRT
<213> ORGANISM: Homo sapiens

<400> SEQUENCE: 1388

Cys Gly Leu Phe Gly Glu Leu Glu Glu Leu Leu Glu Glu Gly Leu Glu
1               5                   10                  15

Asn Leu Ile Asp Trp Trp Asn Asn
            20

<210> SEQ ID NO 1389
<211> LENGTH: 24
<212> TYPE: PRT
<213> ORGANISM: Homo sapiens

<400> SEQUENCE: 1389

Cys Gly Leu Phe Gly Glu Leu Glu Glu Leu Leu Glu Glu Gly Leu Glu
1               5                   10                  15

Asn Leu Ile Asp Trp Trp Asn Ser
            20

<210> SEQ ID NO 1390
<211> LENGTH: 24
<212> TYPE: PRT
<213> ORGANISM: Homo sapiens

<400> SEQUENCE: 1390

Cys Gly Leu Phe Glu Glu Leu Glu Glu Leu Leu Glu Glu Gly Leu Glu
1               5                   10                  15

Asn Leu Ile Asp Trp Trp Asn Gln
            20

<210> SEQ ID NO 1391
<211> LENGTH: 16
<212> TYPE: PRT
<213> ORGANISM: Homo sapiens

<400> SEQUENCE: 1391

Ala Cys Cys Phe Leu Glu Glu Leu Trp Glu Leu Leu Glu His Leu Leu
1               5                   10                  15

<210> SEQ ID NO 1392
<211> LENGTH: 16

-continued

<212> TYPE: PRT
<213> ORGANISM: Homo sapiens

<400> SEQUENCE: 1392

Ala Cys Cys Phe Leu Glu Glu Leu Trp Glu Leu Leu Glu Glu Leu Leu
1               5                   10                  15

<210> SEQ ID NO 1393
<211> LENGTH: 24
<212> TYPE: PRT
<213> ORGANISM: Homo sapiens

<400> SEQUENCE: 1393

Cys Gly Leu Leu Gly Glu Ile Glu Glu Leu Leu Glu Glu Gly Leu Glu
1               5                   10                  15

Asn Leu Ile Asp Trp Trp Asn Gly
            20

<210> SEQ ID NO 1394
<211> LENGTH: 24
<212> TYPE: PRT
<213> ORGANISM: Homo sapiens

<400> SEQUENCE: 1394

Cys Gly Leu Leu Ala Glu Ile Glu Glu Leu Leu Glu Glu Gly Leu Glu
1               5                   10                  15

Asn Leu Ile Asp Trp Trp Asn Gly
            20

<210> SEQ ID NO 1395
<211> LENGTH: 24
<212> TYPE: PRT
<213> ORGANISM: Homo sapiens

<400> SEQUENCE: 1395

Cys Gly Leu Leu Gly Glu Ile Glu Glu Leu Leu Glu Glu Gly Leu Glu
1               5                   10                  15

Asn Leu Ile Asp Trp Trp Asn Gln
            20

<210> SEQ ID NO 1396
<211> LENGTH: 24
<212> TYPE: PRT
<213> ORGANISM: Homo sapiens

<400> SEQUENCE: 1396

Cys Gly Leu Leu Ala Glu Ile Glu Glu Leu Leu Glu Glu Gly Leu Glu
1               5                   10                  15

Asn Leu Ile Asp Trp Trp Asn Gln
            20

<210> SEQ ID NO 1397
<211> LENGTH: 24
<212> TYPE: PRT
<213> ORGANISM: Homo sapiens

<400> SEQUENCE: 1397

Cys Gly Leu Leu Glu Glu Ile Glu Glu Leu Leu Glu Glu Gly Leu Glu
1               5                   10                  15

Asn Leu Ile Asp Trp Trp Asn Gln
            20

<210> SEQ ID NO 1398
<211> LENGTH: 24
<212> TYPE: PRT
<213> ORGANISM: Homo sapiens

<400> SEQUENCE: 1398

Cys Gly Leu Leu Gly Glu Ile Glu Glu Leu Leu Glu Glu Gly Leu Glu
1               5                   10                  15

Asn Leu Ile Asp Trp Trp Asn Glu
            20

<210> SEQ ID NO 1399
<211> LENGTH: 24
<212> TYPE: PRT
<213> ORGANISM: Homo sapiens

<400> SEQUENCE: 1399

Cys Gly Leu Leu Ala Glu Ile Glu Glu Leu Leu Glu Glu Gly Leu Glu
1               5                   10                  15

Asn Leu Ile Asp Trp Trp Asn Glu
            20

<210> SEQ ID NO 1400
<211> LENGTH: 24
<212> TYPE: PRT
<213> ORGANISM: Homo sapiens

<400> SEQUENCE: 1400

Cys Gly Leu Leu Glu Glu Ile Glu Glu Leu Leu Glu Glu Gly Leu Glu
1               5                   10                  15

Asn Leu Ile Asp Trp Trp Asn Glu
            20

<210> SEQ ID NO 1401
<211> LENGTH: 24
<212> TYPE: PRT
<213> ORGANISM: Homo sapiens

<400> SEQUENCE: 1401

Cys Gly Leu Leu Gly Glu Ile Glu Glu Leu Leu Glu Glu Gly Leu Glu
1               5                   10                  15

Asn Leu Ile Asp Trp Trp Asn Ser
            20

<210> SEQ ID NO 1402
<211> LENGTH: 24
<212> TYPE: PRT
<213> ORGANISM: Homo sapiens

<400> SEQUENCE: 1402

Cys Gly Leu Leu Ala Glu Ile Glu Glu Leu Leu Glu Glu Gly Leu Glu
1               5                   10                  15

Asn Leu Ile Asp Trp Trp Asn Ser
            20

<210> SEQ ID NO 1403
<211> LENGTH: 24
<212> TYPE: PRT
<213> ORGANISM: Homo sapiens

<400> SEQUENCE: 1403

Cys Gly Leu Leu Glu Glu Ile Glu Glu Leu Leu Glu Glu Gly Leu Glu
1               5                   10                  15

Asn Leu Ile Asp Trp Trp Asn Ser
            20

<210> SEQ ID NO 1404
<211> LENGTH: 24
<212> TYPE: PRT
<213> ORGANISM: Homo sapiens

<400> SEQUENCE: 1404

Cys Gly Leu Phe Ala Glu Leu Glu Glu Leu Leu Glu Glu Gly Leu Glu
1               5                   10                  15

Asn Leu Leu Glu Trp Trp Asn Gly
            20

<210> SEQ ID NO 1405
<211> LENGTH: 24
<212> TYPE: PRT
<213> ORGANISM: Homo sapiens

<400> SEQUENCE: 1405

Cys Gly Leu Phe Glu Glu Leu Glu Glu Leu Leu Glu Glu Gly Leu Glu
1               5                   10                  15

Asn Leu Leu Glu Trp Trp Asn Gly
            20

<210> SEQ ID NO 1406
<211> LENGTH: 24
<212> TYPE: PRT
<213> ORGANISM: Homo sapiens

<400> SEQUENCE: 1406

Cys Gly Leu Phe Gly Glu Leu Glu Glu Leu Leu Glu Glu Gly Leu Glu
1               5                   10                  15

Asn Leu Leu Glu Trp Trp Asn Glu
            20

<210> SEQ ID NO 1407
<211> LENGTH: 24
<212> TYPE: PRT
<213> ORGANISM: Homo sapiens

<400> SEQUENCE: 1407

Cys Gly Leu Phe Ala Glu Leu Glu Glu Leu Leu Glu Glu Gly Leu Glu
1               5                   10                  15

Asn Leu Leu Glu Trp Trp Asn Glu
            20

<210> SEQ ID NO 1408
<211> LENGTH: 24
<212> TYPE: PRT
<213> ORGANISM: Homo sapiens

<400> SEQUENCE: 1408

Cys Gly Leu Phe Glu Glu Leu Glu Glu Leu Leu Glu Glu Gly Leu Glu
1               5                   10                  15

Asn Leu Leu Glu Trp Trp Asn Glu
            20

<210> SEQ ID NO 1409
<211> LENGTH: 24
<212> TYPE: PRT
<213> ORGANISM: Homo sapiens

<400> SEQUENCE: 1409

Cys Gly Leu Leu Gly Glu Leu Glu Glu Leu Leu Glu Glu Gly Leu Glu
1               5                   10                  15

Asn Leu Leu Glu Trp Trp Asn Gly
            20

<210> SEQ ID NO 1410
<211> LENGTH: 24
<212> TYPE: PRT
<213> ORGANISM: Homo sapiens

<400> SEQUENCE: 1410

Cys Gly Leu Leu Gly Glu Leu Glu Glu Leu Leu Glu Glu Gly Leu Glu
1               5                   10                  15

Asn Leu Leu Glu Trp Trp Asn Glu
            20

<210> SEQ ID NO 1411
<211> LENGTH: 24
<212> TYPE: PRT
<213> ORGANISM: Homo sapiens

<400> SEQUENCE: 1411

Cys Gly Ile Leu Gly Glu Ile Glu Glu Leu Leu Glu Glu Gly Leu Glu
1               5                   10                  15

Asn Leu Ile Asp Trp Trp Asn Gly
            20

<210> SEQ ID NO 1412
<211> LENGTH: 24
<212> TYPE: PRT
<213> ORGANISM: Homo sapiens

<400> SEQUENCE: 1412

Cys Gly Ile Leu Gly Glu Ile Glu Glu Leu Leu Glu Glu Gly Leu Glu
1               5                   10                  15

Asn Leu Ile Asp Trp Trp Asn Glu
            20

<210> SEQ ID NO 1413
<211> LENGTH: 24
<212> TYPE: PRT
<213> ORGANISM: Homo sapiens

<400> SEQUENCE: 1413

Cys Gly Ile Leu Gly Glu Ile Glu Glu Leu Leu Glu Glu Gly Leu Glu
1               5                   10                  15

Asn Leu Ile Asp Trp Trp Asn Ser
            20

<210> SEQ ID NO 1414
<211> LENGTH: 24
<212> TYPE: PRT
<213> ORGANISM: Homo sapiens

<400> SEQUENCE: 1414

Cys Gly Ile Leu Ala Glu Ile Glu Glu Leu Leu Glu Glu Gly Leu Glu
1               5                   10                  15

Asn Leu Ile Asp Trp Trp Asn Gly
            20

<210> SEQ ID NO 1415
<211> LENGTH: 24
<212> TYPE: PRT
<213> ORGANISM: Homo sapiens

<400> SEQUENCE: 1415

Cys Gly Ile Leu Glu Glu Ile Glu Glu Leu Leu Glu Glu Gly Leu Glu
1               5                   10                  15

Asn Leu Ile Asp Trp Trp Asn Gly
            20

<210> SEQ ID NO 1416
<211> LENGTH: 15
<212> TYPE: PRT
<213> ORGANISM: Homo sapiens

<400> SEQUENCE: 1416

Cys Ile Phe Gly Ala Ile Ala Glu Leu Leu Lys Asn Ile Phe Lys
1               5                   10                  15

<210> SEQ ID NO 1417
<211> LENGTH: 15
<212> TYPE: PRT
<213> ORGANISM: Homo sapiens

<400> SEQUENCE: 1417

Cys Ile Phe Gly Ala Ile Ala Glu Leu Leu Glu Asn Ile Phe Lys
1               5                   10                  15

<210> SEQ ID NO 1418
<211> LENGTH: 15
<212> TYPE: PRT
<213> ORGANISM: Homo sapiens

<400> SEQUENCE: 1418

Cys Ile Phe Gly Ala Ile Ala Gly Leu Leu Glu Asn Ile Phe Lys
1               5                   10                  15

<210> SEQ ID NO 1419
<211> LENGTH: 14
<212> TYPE: PRT
<213> ORGANISM: Homo sapiens

<400> SEQUENCE: 1419

Cys Phe Leu Glu Glu Leu Trp Gly Leu Leu Glu His Leu Leu
1               5                   10

<210> SEQ ID NO 1420
<211> LENGTH: 24
<212> TYPE: PRT
<213> ORGANISM: Homo sapiens

<400> SEQUENCE: 1420

Cys Gly Ile Leu Ala Glu Ile Glu Glu Leu Leu Glu Glu Gly Leu Glu
1               5                   10                  15

Asn Leu Ile Asp Trp Trp Asn Gln
            20

<210> SEQ ID NO 1421
<211> LENGTH: 24
<212> TYPE: PRT
<213> ORGANISM: Homo sapiens

<400> SEQUENCE: 1421

Cys Gly Ile Leu Ala Glu Ile Glu Glu Leu Glu Glu Gly Leu Glu
1               5                   10                  15

Asn Leu Ile Asp Trp Trp Asn Glu
            20

<210> SEQ ID NO 1422
<211> LENGTH: 24
<212> TYPE: PRT
<213> ORGANISM: Homo sapiens

<400> SEQUENCE: 1422

Cys Gly Leu Phe Ala Glu Ile Glu Glu Leu Glu Glu Gly Leu Glu
1               5                   10                  15

Asn Leu Ile Asp Trp Trp Asn Gln
            20

<210> SEQ ID NO 1423
<211> LENGTH: 24
<212> TYPE: PRT
<213> ORGANISM: Homo sapiens

<400> SEQUENCE: 1423

Cys Gly Leu Phe Ala Glu Ile Glu Glu Leu Glu Glu Gly Leu Glu
1               5                   10                  15

Asn Leu Ile Asp Trp Trp Asn Glu
            20

<210> SEQ ID NO 1424
<211> LENGTH: 24
<212> TYPE: PRT
<213> ORGANISM: Homo sapiens

<400> SEQUENCE: 1424

Cys Gly Leu Phe Gly Glu Leu Glu Glu Leu Glu Glu Gly Leu Glu
1               5                   10                  15

Asn Leu Leu Glu Trp Trp Asn Gln
            20

<210> SEQ ID NO 1425
<211> LENGTH: 26
<212> TYPE: PRT
<213> ORGANISM: Homo sapiens

<400> SEQUENCE: 1425

Cys Gly Leu Phe Ala Glu Ile Ala Glu Leu Glu Glu Gly Leu Glu
1               5                   10                  15

Cys Ile Thr Leu Ile Asp Trp Trp Asn Glu
            20                  25

<210> SEQ ID NO 1426
<211> LENGTH: 24
<212> TYPE: PRT
<213> ORGANISM: Homo sapiens

<400> SEQUENCE: 1426

Cys Gly Ile Leu Ala Glu Ile Glu Glu Leu Glu Glu Gly Leu Glu
1               5                   10                  15

Asn Leu Leu Glu Trp Trp Asn Gly
            20

<210> SEQ ID NO 1427

-continued

```
<211> LENGTH: 24
<212> TYPE: PRT
<213> ORGANISM: Homo sapiens

<400> SEQUENCE: 1427

Cys Gly Ile Leu Glu Glu Ile Glu Glu Leu Leu Glu Glu Gly Leu Glu
1               5                   10                  15

Asn Leu Ile Asp Trp Trp Asn Glu
            20

<210> SEQ ID NO 1428
<211> LENGTH: 24
<212> TYPE: PRT
<213> ORGANISM: Homo sapiens

<400> SEQUENCE: 1428

Cys Gly Ile Leu Glu Glu Ile Glu Glu Leu Leu Glu Glu Gly Leu Glu
1               5                   10                  15

Asn Leu Ile Asp Trp Trp Asn Gln
            20

<210> SEQ ID NO 1429
<211> LENGTH: 24
<212> TYPE: PRT
<213> ORGANISM: Homo sapiens

<400> SEQUENCE: 1429

Cys Gly Leu Phe Gly Glu Ile Glu Glu Leu Ile Trp Glu Gly Leu Glu
1               5                   10                  15

Asn Leu Ile Asp Trp Trp Asn Gly
            20

<210> SEQ ID NO 1430
<211> LENGTH: 24
<212> TYPE: PRT
<213> ORGANISM: Homo sapiens

<400> SEQUENCE: 1430

Cys Gly Leu Phe Gly Glu Ile Ala Glu Leu Ile Trp Glu Gly Leu Glu
1               5                   10                  15

Asn Leu Ile Asp Trp Trp Asn Gly
            20

<210> SEQ ID NO 1431
<211> LENGTH: 24
<212> TYPE: PRT
<213> ORGANISM: Homo sapiens

<400> SEQUENCE: 1431

Cys Gly Leu Phe Glu Glu Ile Ala Glu Leu Ile Glu Glu Gly Leu Glu
1               5                   10                  15

Asn Leu Ile Asp Trp Trp Asn Gly
            20

<210> SEQ ID NO 1432
<211> LENGTH: 24
<212> TYPE: PRT
<213> ORGANISM: Homo sapiens

<400> SEQUENCE: 1432

Cys Gly Leu Phe Glu Glu Ile Ala Glu Leu Ile Trp Glu Gly Leu Glu
1               5                   10                  15
```

Asn Leu Ile Asp Trp Trp Asn Gly
            20

<210> SEQ ID NO 1433
<211> LENGTH: 24
<212> TYPE: PRT
<213> ORGANISM: Homo sapiens

<400> SEQUENCE: 1433

Cys Glu Leu Phe Glu Glu Ile Ala Glu Leu Ile Trp Glu Gly Leu Glu
1               5                   10                  15

Asn Leu Ile Asp Trp Trp Asn Gly
            20

<210> SEQ ID NO 1434
<211> LENGTH: 24
<212> TYPE: PRT
<213> ORGANISM: Homo sapiens

<400> SEQUENCE: 1434

Cys Glu Leu Phe Glu Glu Ile Ala Glu Leu Leu Trp Glu Gly Leu Glu
1               5                   10                  15

Asn Leu Ile Asp Trp Trp Asn Gly
            20

<210> SEQ ID NO 1435
<211> LENGTH: 24
<212> TYPE: PRT
<213> ORGANISM: Homo sapiens

<400> SEQUENCE: 1435

Cys Gly Leu Phe Glu Glu Ile Ala Glu Leu Leu Trp Glu Gly Leu Glu
1               5                   10                  15

Asn Leu Ile Asp Trp Trp Asn Gly
            20

<210> SEQ ID NO 1436
<211> LENGTH: 24
<212> TYPE: PRT
<213> ORGANISM: Homo sapiens

<400> SEQUENCE: 1436

Cys Gly Leu Phe Glu Glu Leu Ala Glu Leu Leu Trp Glu Gly Leu Glu
1               5                   10                  15

Asn Leu Ile Asp Trp Trp Asn Gly
            20

<210> SEQ ID NO 1437
<211> LENGTH: 24
<212> TYPE: PRT
<213> ORGANISM: Homo sapiens

<400> SEQUENCE: 1437

Cys Glu Leu Phe Glu Glu Leu Ala Glu Leu Leu Trp Glu Gly Leu Glu
1               5                   10                  15

Asn Leu Ile Asp Trp Trp Asn Gly
            20

<210> SEQ ID NO 1438
<211> LENGTH: 24
<212> TYPE: PRT
<213> ORGANISM: Homo sapiens -continued

<400> SEQUENCE: 1438

Cys Glu Leu Phe Glu Glu Leu Ala Glu Leu Leu Trp Glu Gly Leu Glu
1               5                   10                  15

Asn Leu Ile Asp Trp Trp Asn Ser
            20

<210> SEQ ID NO 1439
<211> LENGTH: 24
<212> TYPE: PRT
<213> ORGANISM: Homo sapiens

<400> SEQUENCE: 1439

Cys Gly Leu Phe Glu Glu Leu Ala Glu Leu Leu Trp Glu Gly Leu Glu
1               5                   10                  15

Asn Leu Ile Asp Trp Trp Asn Ser
            20

<210> SEQ ID NO 1440
<211> LENGTH: 24
<212> TYPE: PRT
<213> ORGANISM: Homo sapiens

<400> SEQUENCE: 1440

Cys Gly Ile Phe Glu Glu Leu Ala Glu Leu Leu Trp Glu Gly Leu Glu
1               5                   10                  15

Asn Leu Ile Asp Trp Trp Asn Gly
            20

<210> SEQ ID NO 1441
<211> LENGTH: 24
<212> TYPE: PRT
<213> ORGANISM: Homo sapiens

<400> SEQUENCE: 1441

Cys Gly Ile Phe Glu Glu Leu Ala Glu Leu Leu Trp Glu Gly Leu Glu
1               5                   10                  15

Asn Leu Ile Asp Trp Trp Asn Ser
            20

<210> SEQ ID NO 1442
<211> LENGTH: 24
<212> TYPE: PRT
<213> ORGANISM: Homo sapiens

<400> SEQUENCE: 1442

Cys Gly Leu Phe Glu Glu Leu Glu Glu Leu Leu Glu Glu Leu Leu Glu
1               5                   10                  15

Asn Leu Ile Asp Trp Trp Asn Ser
            20

<210> SEQ ID NO 1443
<211> LENGTH: 24
<212> TYPE: PRT
<213> ORGANISM: Homo sapiens

<400> SEQUENCE: 1443

Cys Glu Leu Phe Glu Glu Leu Glu Glu Leu Leu Glu Glu Leu Leu Glu
1               5                   10                  15

Asn Leu Ile Asp Trp Trp Asn Ser
            20

```
<210> SEQ ID NO 1444
<211> LENGTH: 24
<212> TYPE: PRT
<213> ORGANISM: Homo sapiens

<400> SEQUENCE: 1444

Cys Glu Leu Phe Glu Glu Leu Glu Glu Leu Leu Glu Glu Leu Leu Glu
1               5                   10                  15

Leu Leu Ile Asp Trp Trp Asn Ser
            20

<210> SEQ ID NO 1445
<211> LENGTH: 24
<212> TYPE: PRT
<213> ORGANISM: Homo sapiens

<400> SEQUENCE: 1445

Cys Glu Phe Leu Glu Glu Leu Glu Glu Leu Leu Glu Glu Leu Leu Glu
1               5                   10                  15

Asn Leu Ile Asp Trp Trp Asn Ser
            20

<210> SEQ ID NO 1446
<211> LENGTH: 24
<212> TYPE: PRT
<213> ORGANISM: Homo sapiens

<400> SEQUENCE: 1446

Cys Glu Leu Phe Glu Glu Leu Glu Glu Leu Leu Glu His Leu Leu Glu
1               5                   10                  15

Asn Leu Ile Asp Trp Trp Asn Ser
            20

<210> SEQ ID NO 1447
<211> LENGTH: 24
<212> TYPE: PRT
<213> ORGANISM: Homo sapiens

<400> SEQUENCE: 1447

Cys Glu Leu Phe Glu Glu Leu Glu Glu Leu Leu His Glu Leu Leu Glu
1               5                   10                  15

Asn Leu Ile Asp Trp Trp Asn Ser
            20

<210> SEQ ID NO 1448
<211> LENGTH: 24
<212> TYPE: PRT
<213> ORGANISM: Homo sapiens

<400> SEQUENCE: 1448

Cys Gly Leu Phe Gly Glu Leu Glu Glu Leu Leu Trp Glu Gly Leu Glu
1               5                   10                  15

Asn Leu Ile Asp Trp Trp Asn Gly
            20

<210> SEQ ID NO 1449
<211> LENGTH: 24
<212> TYPE: PRT
<213> ORGANISM: Homo sapiens

<400> SEQUENCE: 1449

Cys Gly Leu Phe Gly Glu Leu Glu Glu Leu Leu Trp Glu Gly Leu His
1               5                   10                  15
```

Asn Leu Ile Asp Trp Trp Asn Gly
            20

<210> SEQ ID NO 1450
<211> LENGTH: 24
<212> TYPE: PRT
<213> ORGANISM: Homo sapiens

<400> SEQUENCE: 1450

Cys Gly Leu Phe Gly Glu Leu Trp Glu Leu Leu Glu His Gly Leu Glu
1               5                   10                  15

Asn Leu Ile Asp Trp Trp Asn Gly
            20

<210> SEQ ID NO 1451
<211> LENGTH: 26
<212> TYPE: PRT
<213> ORGANISM: Homo sapiens

<400> SEQUENCE: 1451

Cys Gly Leu Arg His Gly Glu Leu Glu Glu Leu Ser His Glu Glu Gly
1               5                   10                  15

Leu Glu Asn Leu Ile Asp Trp Trp Asn Gly
            20                  25

<210> SEQ ID NO 1452
<211> LENGTH: 24
<212> TYPE: PRT
<213> ORGANISM: Homo sapiens

<400> SEQUENCE: 1452

Cys Gly Leu Phe Glu Ala Ile Glu Gly Phe Ile Glu Asn Gly Trp Glu
1               5                   10                  15

Gly Met Ile Asp Gly Trp Asn Gly
            20

<210> SEQ ID NO 1453
<211> LENGTH: 24
<212> TYPE: PRT
<213> ORGANISM: Homo sapiens

<400> SEQUENCE: 1453

Cys Gly Leu Phe Glu Ala Ile Glu Gly Phe Ile Glu Asn Gly Trp Glu
1               5                   10                  15

Gly Met Ile Asp Trp Trp Asn Gly
            20

<210> SEQ ID NO 1454
<211> LENGTH: 24
<212> TYPE: PRT
<213> ORGANISM: Homo sapiens

<400> SEQUENCE: 1454

Cys Gly Leu Phe Gly Ala Ile Glu Gly Phe Ile Glu Asn Gly Trp Glu
1               5                   10                  15

Gly Met Ile Asp Trp Trp Asn Gly
            20

<210> SEQ ID NO 1455
<211> LENGTH: 24
<212> TYPE: PRT
<213> ORGANISM: Homo sapiens

```
<400> SEQUENCE: 1455

Cys Gly Leu Phe Ala Glu Ile Glu Glu Leu Leu Glu Glu Gly Leu Glu
1               5                   10                  15

Asn Leu Leu Glu Trp Trp Asn Gly
            20

<210> SEQ ID NO 1456
<211> LENGTH: 24
<212> TYPE: PRT
<213> ORGANISM: Homo sapiens

<400> SEQUENCE: 1456

Cys Gly Leu Phe Ala Glu Leu Glu Glu Leu Leu Glu Glu Gly Leu Glu
1               5                   10                  15

Asn Leu Ile Asp Trp Trp Asn Gly
            20

<210> SEQ ID NO 1457
<211> LENGTH: 24
<212> TYPE: PRT
<213> ORGANISM: Homo sapiens

<400> SEQUENCE: 1457

Cys Gly Ile Phe Ala Glu Ile Glu Glu Leu Leu Glu Glu Gly Leu Glu
1               5                   10                  15

Asn Leu Ile Asp Trp Trp Asn Gly
            20

<210> SEQ ID NO 1458
<211> LENGTH: 25
<212> TYPE: PRT
<213> ORGANISM: Homo sapiens

<400> SEQUENCE: 1458

Cys Gly Leu Phe Ala Glu Ile Glu Glu Leu Leu Glu Glu Gly Leu Glu
1               5                   10                  15

Asn Leu Ile Asp Trp Trp Asn Gly Phe
            20                  25

<210> SEQ ID NO 1459
<211> LENGTH: 24
<212> TYPE: PRT
<213> ORGANISM: Homo sapiens

<400> SEQUENCE: 1459

Cys Gly Leu Phe Ala Glu Ile Glu Glu Leu Leu Glu Glu Gly Leu Glu
1               5                   10                  15

Asn Leu Ile Asp Trp Trp Asn Ala
            20

<210> SEQ ID NO 1460
<211> LENGTH: 24
<212> TYPE: PRT
<213> ORGANISM: Homo sapiens

<400> SEQUENCE: 1460

Cys Gly Leu Phe Ala Glu Ile Glu Glu Leu Leu Glu Glu Gly Leu Glu
1               5                   10                  15

Asn Leu Ile Asp Trp Trp Asn Ser
            20
```

<210> SEQ ID NO 1461
<211> LENGTH: 26
<212> TYPE: PRT
<213> ORGANISM: Homo sapiens

<400> SEQUENCE: 1461

Cys Gly Leu Phe Ala Glu Ile Glu Glu Leu Glu Glu Gly Leu Glu
1               5                   10                  15

Asn Leu Ile Asp Trp Trp Asn Cys Ile Thr
            20                  25

<210> SEQ ID NO 1462
<211> LENGTH: 24
<212> TYPE: PRT
<213> ORGANISM: Homo sapiens

<400> SEQUENCE: 1462

Cys Gly Leu Phe Gly Glu Ile Ala Gly Leu Leu Glu Glu Gly Leu His
1               5                   10                  15

Asn Leu Ile Asp Trp Trp Asn Gly
            20

<210> SEQ ID NO 1463
<211> LENGTH: 24
<212> TYPE: PRT
<213> ORGANISM: Homo sapiens

<400> SEQUENCE: 1463

Cys Gly Leu Phe Gly Glu Ile Ala Gly Leu Leu Glu Gln Gly Leu His
1               5                   10                  15

Asn Leu Ile Asp Trp Trp Asn Gly
            20

<210> SEQ ID NO 1464
<211> LENGTH: 24
<212> TYPE: PRT
<213> ORGANISM: Homo sapiens

<400> SEQUENCE: 1464

Cys Gly Leu Phe Gly Glu Ile Ala Gly Leu Leu Glu Ser Gly Leu His
1               5                   10                  15

Asn Leu Ile Asp Trp Trp Asn Gly
            20

<210> SEQ ID NO 1465
<211> LENGTH: 24
<212> TYPE: PRT
<213> ORGANISM: Homo sapiens

<400> SEQUENCE: 1465

Cys Gly Leu Phe Ala Glu Ile Ala Gly Leu Leu Glu Gln Gly Leu His
1               5                   10                  15

Asn Leu Ile Asp Trp Trp Asn Gly
            20

<210> SEQ ID NO 1466
<211> LENGTH: 24
<212> TYPE: PRT
<213> ORGANISM: Homo sapiens

<400> SEQUENCE: 1466

Cys Gly Leu Phe Ala Glu Ile Ala Gly Leu Leu Glu Glu Gly Leu His

```
                1               5                   10                  15

Asn Leu Ile Asp Trp Trp Asn Gly
            20

<210> SEQ ID NO 1467
<211> LENGTH: 24
<212> TYPE: PRT
<213> ORGANISM: Homo sapiens

<400> SEQUENCE: 1467

Cys Gly Leu Phe Ala Glu Ile Ala Gly Leu Leu Glu Ser Gly Leu His
1               5                   10                  15

Asn Leu Ile Asp Trp Trp Asn Gly
            20

<210> SEQ ID NO 1468
<211> LENGTH: 24
<212> TYPE: PRT
<213> ORGANISM: Homo sapiens

<400> SEQUENCE: 1468

Cys Gly Ile Phe Glu Ala Ile Ala Gly Leu Leu Glu Gln Gly Leu His
1               5                   10                  15

Asn Leu Ile Asp Trp Trp Asn Gly
            20

<210> SEQ ID NO 1469
<211> LENGTH: 24
<212> TYPE: PRT
<213> ORGANISM: Homo sapiens

<400> SEQUENCE: 1469

Cys Gly Leu Phe Gly Ala Ile Ala Glu Leu Leu Glu Glu Gly Leu His
1               5                   10                  15

Asn Leu Ile Asp Trp Trp Asn Gly
            20

<210> SEQ ID NO 1470
<211> LENGTH: 24
<212> TYPE: PRT
<213> ORGANISM: Homo sapiens

<400> SEQUENCE: 1470

Cys Gly Leu Phe Ala Ala Ile Ala Glu Leu Leu Glu Glu Gly Leu His
1               5                   10                  15

Asn Leu Ile Asp Trp Trp Asn Gly
            20

<210> SEQ ID NO 1471
<211> LENGTH: 24
<212> TYPE: PRT
<213> ORGANISM: Homo sapiens

<400> SEQUENCE: 1471

Cys Gly Ile Phe Glu Ala Ile Ala Gly Leu Leu Lys Asn Ile Phe Lys
1               5                   10                  15

Asn Leu Ile Asp Trp Trp Asn Gly
            20

<210> SEQ ID NO 1472
<211> LENGTH: 24
<212> TYPE: PRT
```

<213> ORGANISM: Homo sapiens

<400> SEQUENCE: 1472

Cys Gly Ile Phe Gly Ala Ile Trp Glu Leu Leu Glu Gln Gly Leu His
1               5                   10                  15

Asn Leu Ile Asp Trp Trp Asn Gly
            20

<210> SEQ ID NO 1473
<211> LENGTH: 24
<212> TYPE: PRT
<213> ORGANISM: Homo sapiens

<400> SEQUENCE: 1473

Cys Gly Leu Phe Ala Glu Leu Ala Gly Leu Leu Glu Gln Gly Leu His
1               5                   10                  15

Asn Leu Ile Asp Trp Trp Asn Gly
            20

<210> SEQ ID NO 1474
<211> LENGTH: 24
<212> TYPE: PRT
<213> ORGANISM: Homo sapiens

<400> SEQUENCE: 1474

Cys Gly Ile Leu Ala Glu Leu Ala Gly Leu Leu Glu Gln Gly Leu His
1               5                   10                  15

Asn Leu Ile Asp Trp Trp Asn Gly
            20

<210> SEQ ID NO 1475
<211> LENGTH: 15
<212> TYPE: PRT
<213> ORGANISM: Homo sapiens

<400> SEQUENCE: 1475

Cys Gly Leu Phe Gly Glu Ile Glu Glu Leu Leu Glu His Leu Leu
1               5                   10                  15

<210> SEQ ID NO 1476
<211> LENGTH: 15
<212> TYPE: PRT
<213> ORGANISM: Homo sapiens

<400> SEQUENCE: 1476

Cys Gly Leu Phe Gly Glu Ile Glu Glu Leu Leu Glu Glu Leu Leu
1               5                   10                  15

<210> SEQ ID NO 1477
<211> LENGTH: 15
<212> TYPE: PRT
<213> ORGANISM: Homo sapiens

<400> SEQUENCE: 1477

Cys Gly Leu Phe Gly Glu Ile Glu Glu Leu Leu Glu Glu Gly Leu
1               5                   10                  15

<210> SEQ ID NO 1478
<211> LENGTH: 15
<212> TYPE: PRT
<213> ORGANISM: Homo sapiens

<400> SEQUENCE: 1478

Cys Gly Leu Phe Gly Glu Ile Glu Glu Leu Leu Glu His Gly Leu
1               5                   10                  15

<210> SEQ ID NO 1479
<211> LENGTH: 15
<212> TYPE: PRT
<213> ORGANISM: Homo sapiens

<400> SEQUENCE: 1479

Cys Gly Leu Phe His Glu Ile Glu Glu Leu Leu Glu His Leu Leu
1               5                   10                  15

<210> SEQ ID NO 1480
<211> LENGTH: 15
<212> TYPE: PRT
<213> ORGANISM: Homo sapiens

<400> SEQUENCE: 1480

Cys Phe Leu Gly Ala Leu Trp Lys Ala Leu Ser Glu Leu Leu Glu
1               5                   10                  15

<210> SEQ ID NO 1481
<211> LENGTH: 15
<212> TYPE: PRT
<213> ORGANISM: Homo sapiens

<400> SEQUENCE: 1481

Cys Gly Leu Phe Gly Glu Ile Trp Glu Leu Leu Glu Glu Gly Leu
1               5                   10                  15

<210> SEQ ID NO 1482
<211> LENGTH: 16
<212> TYPE: PRT
<213> ORGANISM: Homo sapiens

<400> SEQUENCE: 1482

Cys Gly Leu Phe Gly Glu Ile Trp Glu Leu Leu Glu Glu Gly Leu Ile
1               5                   10                  15

<210> SEQ ID NO 1483
<211> LENGTH: 15
<212> TYPE: PRT
<213> ORGANISM: Homo sapiens

<400> SEQUENCE: 1483

Cys Gly Leu Phe Gly Glu Ile Trp Glu Leu Leu Glu Glu Leu Leu
1               5                   10                  15

<210> SEQ ID NO 1484
<211> LENGTH: 16
<212> TYPE: PRT
<213> ORGANISM: Homo sapiens

<400> SEQUENCE: 1484

Cys Gly Leu Phe Glu Glu Ile Glu Glu Leu Leu Glu Glu Leu Leu Glu
1               5                   10                  15

<210> SEQ ID NO 1485
<211> LENGTH: 34
<212> TYPE: PRT
<213> ORGANISM: Homo sapiens

<400> SEQUENCE: 1485

Cys Gly Leu Phe Glu Leu Ile Glu Gly Phe Ile Glu Trp Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 1486
<211> LENGTH: 35
<212> TYPE: PRT
<213> ORGANISM: Homo sapiens

<400> SEQUENCE: 1486

Cys Ile Phe Gly Ala Ile Ala Gly Phe Ile Lys Asn Ile Trp Leu His
1               5                   10                  15

Leu Leu His His Leu Leu His His Leu His Leu Leu His His Leu
            20                  25                  30

Leu His Leu
        35

<210> SEQ ID NO 1487
<211> LENGTH: 16
<212> TYPE: PRT
<213> ORGANISM: Homo sapiens

<400> SEQUENCE: 1487

Cys Glu Ala Leu Phe Gly Lys Ile Asn Ala Ile Phe Ile Gly Lys Leu
1               5                   10                  15

<210> SEQ ID NO 1488
<211> LENGTH: 24
<212> TYPE: PRT
<213> ORGANISM: Homo sapiens

<400> SEQUENCE: 1488

Cys Glu Glu Asn Trp Ile Gly Leu Phe Gly Gly Asn Ile Trp Glu
1               5                   10                  15

Glu Glu Glu Ile Leu Asp Leu Leu
            20

<210> SEQ ID NO 1489
<211> LENGTH: 14
<212> TYPE: PRT
<213> ORGANISM: Homo sapiens

<400> SEQUENCE: 1489

Cys Leu Glu Leu Trp Leu Glu His Leu Phe Leu Glu Leu Glu
1               5                   10

<210> SEQ ID NO 1490
<211> LENGTH: 34
<212> TYPE: PRT
<213> ORGANISM: Homo sapiens

<400> SEQUENCE: 1490

Cys Gly Asn Phe Glu Glu Ile Glu Gly Phe Ile Glu Asn Gly Trp Glu
1               5                   10                  15

Gly Leu Ile Asp Gly Trp Tyr Gly Tyr Gly Arg Lys Lys Arg Arg Gln
            20                  25                  30

Arg Arg

<210> SEQ ID NO 1491
<211> LENGTH: 34
<212> TYPE: PRT

<213> ORGANISM: Homo sapiens

<400> SEQUENCE: 1491

Cys Arg Gly Lys Trp Tyr Met Gly Phe Gly Glu Ile Lys Arg Gln Gly
1               5                   10                  15

Glu Gly Arg Arg Tyr Gly Leu Phe Glu Asp Trp Ile Ala Glu Asn Arg
            20                  25                  30

Gly Ile

<210> SEQ ID NO 1492
<211> LENGTH: 33
<212> TYPE: PRT
<213> ORGANISM: Homo sapiens

<400> SEQUENCE: 1492

Gly Leu Phe Glu Ala Ile Glu Gly Phe Ile Glu Asn Gly Trp Glu Gly
1               5                   10                  15

Leu Ala Glu Leu Ala Glu Ala Leu Glu Ala Leu Ala Ala Gly Gly Ser
            20                  25                  30

Cys

<210> SEQ ID NO 1493
<211> LENGTH: 35
<212> TYPE: PRT
<213> ORGANISM: Homo sapiens

<400> SEQUENCE: 1493

Gly Leu Phe Gly Ala Leu Ala Glu Ala Leu Ala Glu Ala Leu Ala Glu
1               5                   10                  15

His Leu Ala Glu Ala Leu Ala Glu Ala Leu Glu Ala Leu Ala Ala Gly
            20                  25                  30

Gly Ser Cys
        35

<210> SEQ ID NO 1494
<211> LENGTH: 24
<212> TYPE: PRT
<213> ORGANISM: Homo sapiens

<400> SEQUENCE: 1494

Cys Gly Phe Phe Gly Glu Ile Ala Gly Leu Leu Glu Asn Gly Leu His
1               5                   10                  15

Asn Leu Ile Asp Trp Trp Asn Gly
            20

<210> SEQ ID NO 1495
<211> LENGTH: 24
<212> TYPE: PRT
<213> ORGANISM: Homo sapiens

<400> SEQUENCE: 1495

Cys Gly Phe Phe Gly Glu Ile Ala Ala Leu Leu Glu Asn Gly Leu Glu
1               5                   10                  15

Asn Leu Ile Asp Trp Trp Asn Gly
            20

<210> SEQ ID NO 1496
<211> LENGTH: 24
<212> TYPE: PRT
<213> ORGANISM: Homo sapiens -continued

<400> SEQUENCE: 1496

Cys Gly Phe Phe Gly Glu Ile Ala Glu Phe Ile His Ser Gly Leu Lys
1               5                   10                  15

Asn Leu Ile Asp Trp Trp Asn Gly
            20

<210> SEQ ID NO 1497
<211> LENGTH: 24
<212> TYPE: PRT
<213> ORGANISM: Homo sapiens

<400> SEQUENCE: 1497

Cys Gly Phe Phe Gly Glu Ile Ala Gly Leu Leu Lys Asn Gly Leu Lys
1               5                   10                  15

Asn Leu Ile Asp Trp Trp Asn Gly
            20

<210> SEQ ID NO 1498
<211> LENGTH: 24
<212> TYPE: PRT
<213> ORGANISM: Homo sapiens

<400> SEQUENCE: 1498

Cys Gly Phe Phe Gly Glu Ile Ala Gly Phe Ile Lys Asn Gly Leu Lys
1               5                   10                  15

Asn Leu Ile Asp Trp Trp Asn Gly
            20

<210> SEQ ID NO 1499
<211> LENGTH: 24
<212> TYPE: PRT
<213> ORGANISM: Homo sapiens

<400> SEQUENCE: 1499

Cys Gly Phe Phe Gly Glu Ile Ala Glu Phe Ile His Ser Ile Leu Lys
1               5                   10                  15

Asn Leu Ile Asp Trp Trp Asn Gly
            20

<210> SEQ ID NO 1500
<211> LENGTH: 24
<212> TYPE: PRT
<213> ORGANISM: Homo sapiens

<400> SEQUENCE: 1500

Cys Gly Phe Phe Gly Glu Ile Ala Gly Leu Leu Lys Asn Ile Leu Lys
1               5                   10                  15

Asn Leu Ile Asp Trp Trp Asn Gly
            20

<210> SEQ ID NO 1501
<211> LENGTH: 24
<212> TYPE: PRT
<213> ORGANISM: Homo sapiens

<400> SEQUENCE: 1501

Cys Gly Phe Phe Gly Glu Ile Ala Gly Phe Ile Lys Asn Ile Leu Lys
1               5                   10                  15

Asn Leu Ile Asp Trp Trp Asn Gly
            20

```
<210> SEQ ID NO 1502
<211> LENGTH: 14
<212> TYPE: PRT
<213> ORGANISM: Homo sapiens

<400> SEQUENCE: 1502

Cys Phe Leu Gly Ala Leu Phe His Ala Leu Ser Glu Leu Leu
1               5                   10

<210> SEQ ID NO 1503
<211> LENGTH: 14
<212> TYPE: PRT
<213> ORGANISM: Homo sapiens

<400> SEQUENCE: 1503

Cys Phe Leu Gly Ala Leu Trp His Ala Leu Ser Glu Leu Leu
1               5                   10

<210> SEQ ID NO 1504
<211> LENGTH: 14
<212> TYPE: PRT
<213> ORGANISM: Homo sapiens

<400> SEQUENCE: 1504

Cys Phe Leu Gly Ala Leu Trp His Ala Leu Ser His Leu Leu
1               5                   10

<210> SEQ ID NO 1505
<211> LENGTH: 14
<212> TYPE: PRT
<213> ORGANISM: Homo sapiens

<400> SEQUENCE: 1505

Cys Phe Leu Gly Ala Leu Trp Glu Leu Leu Ser His Leu Leu
1               5                   10

<210> SEQ ID NO 1506
<211> LENGTH: 14
<212> TYPE: PRT
<213> ORGANISM: Homo sapiens

<400> SEQUENCE: 1506

Cys Phe Leu Gly Ala Leu Trp Lys Ala Leu Ser His Leu Leu
1               5                   10

<210> SEQ ID NO 1507
<211> LENGTH: 14
<212> TYPE: PRT
<213> ORGANISM: Homo sapiens

<400> SEQUENCE: 1507

Cys Phe Leu Gly Ala Leu Trp His Ala Leu Ser Lys Leu Leu
1               5                   10

<210> SEQ ID NO 1508
<211> LENGTH: 14
<212> TYPE: PRT
<213> ORGANISM: Homo sapiens

<400> SEQUENCE: 1508

Cys Phe Leu Gly Ala Leu Phe His Leu Leu Ser His Leu Leu
1               5                   10

<210> SEQ ID NO 1509
<211> LENGTH: 14
```

<212> TYPE: PRT
<213> ORGANISM: Homo sapiens

<400> SEQUENCE: 1509

Cys Phe Leu Gly Ala Leu Phe His Leu Leu Ser Glu Leu Leu
1               5                   10

<210> SEQ ID NO 1510
<211> LENGTH: 14
<212> TYPE: PRT
<213> ORGANISM: Homo sapiens

<400> SEQUENCE: 1510

Cys Phe Leu Gly Ala Leu Trp His Leu Leu Ser His Leu Leu
1               5                   10

<210> SEQ ID NO 1511
<211> LENGTH: 14
<212> TYPE: PRT
<213> ORGANISM: Homo sapiens

<400> SEQUENCE: 1511

Cys Phe Leu Gly Ala Leu Trp His Leu Leu Ser Glu Leu Leu
1               5                   10

<210> SEQ ID NO 1512
<211> LENGTH: 15
<212> TYPE: PRT
<213> ORGANISM: Homo sapiens

<400> SEQUENCE: 1512

Cys Phe Leu Gly Ala Leu Phe His Ala Leu Ser His Leu Leu Glu
1               5                   10                  15

<210> SEQ ID NO 1513
<211> LENGTH: 15
<212> TYPE: PRT
<213> ORGANISM: Homo sapiens

<400> SEQUENCE: 1513

Cys Phe Leu Gly Ala Leu Phe His Leu Leu Ser His Leu Leu Glu
1               5                   10                  15

<210> SEQ ID NO 1514
<211> LENGTH: 16
<212> TYPE: PRT
<213> ORGANISM: Homo sapiens

<400> SEQUENCE: 1514

Cys Gly Leu Phe Gly Ala Leu Phe His Ala Leu Ser His Leu Leu Glu
1               5                   10                  15

<210> SEQ ID NO 1515
<211> LENGTH: 14
<212> TYPE: PRT
<213> ORGANISM: Homo sapiens

<400> SEQUENCE: 1515

Cys Phe Leu Gly Ala Leu Trp Lys Ala Leu Ser His Leu Leu
1               5                   10

<210> SEQ ID NO 1516
<211> LENGTH: 24
<212> TYPE: PRT
<213> ORGANISM: Homo sapiens

<400> SEQUENCE: 1516

Cys Gly Leu Phe Ala Glu Ile Glu Glu Leu Leu Glu Glu Gly Leu Glu
1               5                   10                  15

Asn Leu Ile Asp Trp Trp Asn Gly
            20

<210> SEQ ID NO 1517
<211> LENGTH: 26
<212> TYPE: PRT
<213> ORGANISM: Homo sapiens

<400> SEQUENCE: 1517

Cys Gly Leu Phe Gly Glu Ile Glu Glu Leu Ile Glu Glu Gly Leu Glu
1               5                   10                  15

Cys Ile Thr Leu Ile Asp Trp Trp Asn Gly
            20                  25

<210> SEQ ID NO 1518
<211> LENGTH: 24
<212> TYPE: PRT
<213> ORGANISM: Homo sapiens

<400> SEQUENCE: 1518

Cys Gly Leu Phe Gly Glu Ile Glu Glu Leu Ile Glu Glu Gly Leu Glu
1               5                   10                  15

Asn Leu Ile Asp Trp Trp Asn Glu
            20

<210> SEQ ID NO 1519
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(15)
<223> OTHER INFORMATION: Lys is conjugated to stearyl

<400> SEQUENCE: 1519

Cys Phe Phe Gly Ala Ile Trp Glu Phe Ile His Ser Ile Leu Lys
1               5                   10                  15

<210> SEQ ID NO 1520
<211> LENGTH: 19
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (19)..(19)
<223> OTHER INFORMATION: Lys is conjugated to stearyl

<400> SEQUENCE: 1520

Cys Ile Phe Gly Ala Ile Ala Gly Phe Ile Lys Asn Ile Trp Glu Gly
1               5                   10                  15

Leu Ile Lys

<210> SEQ ID NO 1521
<211> LENGTH: 16
<212> TYPE: PRT
<213> ORGANISM: Artificial Sequence
<220> FEATURE:

```
<223> OTHER INFORMATION: Synthetically generated peptide
<220> FEATURE:
<221> NAME/KEY: MISC_FEATURE
<222> LOCATION: (16)..(16)
<223> OTHER INFORMATION: Lys is conjugated to stearyl

<400> SEQUENCE: 1521

Cys Gly Ile Phe Glu Ala Ile Ala Gly Leu Leu Lys Asn Ile Phe Lys
1               5                   10                  15

<210> SEQ ID NO 1522
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (17)..(17)
<223> OTHER INFORMATION: Lys is conjugated to stearyl

<400> SEQUENCE: 1522

Cys Gly Ile Phe Glu Ala Ile Ala Gly Leu Leu Lys Asn Ile Phe Lys
1               5                   10                  15

Lys

<210> SEQ ID NO 1523
<211> LENGTH: 14
<212> TYPE: PRT
<213> ORGANISM: Homo sapiens

<400> SEQUENCE: 1523

Cys Phe Leu Gly Ala Leu Phe His Ala Leu Ser His Leu Leu
1               5                   10

<210> SEQ ID NO 1524
<211> LENGTH: 22
<212> TYPE: PRT
<213> ORGANISM: Homo sapiens

<400> SEQUENCE: 1524

Ala Cys Cys Ile Phe Gly Ala Ile Ala Gly Phe Ile Lys Asn Ile Leu
1               5                   10                  15

Lys Gly Leu Ile Asp Gly
            20

<210> SEQ ID NO 1525
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (18)..(18)
<223> OTHER INFORMATION: Lys is conjugated to stearyl

<400> SEQUENCE: 1525

Cys Ile Phe Gly Ala Ile Ala Gly Phe Ile Lys Asn Ile Leu Lys Gly
1               5                   10                  15

Leu Lys

<210> SEQ ID NO 1526
<211> LENGTH: 20
<212> TYPE: PRT
<213> ORGANISM: Artificial Sequence
```

```
<220> FEATURE:
<223> OTHER INFORMATION: Synthetically generated peptide
<220> FEATURE:
<221> NAME/KEY: MISC_FEATURE
<222> LOCATION: (20)..(20)
<223> OTHER INFORMATION: Lys is conjugated to stearyl

<400> SEQUENCE: 1526

Ala Cys Cys Ile Phe Gly Ala Ile Ala Gly Phe Ile Lys Asn Ile Leu
1               5                   10                  15

Lys Gly Leu Lys
            20

<210> SEQ ID NO 1527
<211> LENGTH: 24
<212> TYPE: PRT
<213> ORGANISM: Homo sapiens

<400> SEQUENCE: 1527

Cys Gly Leu Phe Gly Glu Ile Glu Glu Leu Ile Glu Glu Gly Leu Glu
1               5                   10                  15

Asn Leu Ile Asp Trp Trp Asn Gly
            20

<210> SEQ ID NO 1528
<211> LENGTH: 23
<212> TYPE: PRT
<213> ORGANISM: Homo sapiens

<400> SEQUENCE: 1528

Cys Phe Leu Gly Ala Leu Trp Lys Ala Leu Ser Glu Leu Leu Lys Asn
1               5                   10                  15

Leu Ile Asp Trp Trp Asn Gly
            20

<210> SEQ ID NO 1529
<211> LENGTH: 24
<212> TYPE: PRT
<213> ORGANISM: Homo sapiens

<400> SEQUENCE: 1529

Cys Gly Phe Leu Gly Ala Leu Trp Lys Ala Leu Ser Glu Leu Leu Lys
1               5                   10                  15

Asn Leu Ile Asp Trp Trp Asn Gly
            20

<210> SEQ ID NO 1530
<211> LENGTH: 23
<212> TYPE: PRT
<213> ORGANISM: Homo sapiens

<400> SEQUENCE: 1530

Cys Phe Leu Gly Ala Leu Phe His Ala Leu Ser His Leu Leu Glu Asn
1               5                   10                  15

Leu Ile Asp Trp Trp Asn Gly
            20

<210> SEQ ID NO 1531
<211> LENGTH: 24
<212> TYPE: PRT
<213> ORGANISM: Homo sapiens

<400> SEQUENCE: 1531
```

Cys Gly Phe Leu Gly Ala Leu Phe His Ala Leu Ser His Leu Leu Glu
1               5                   10                  15

Asn Leu Ile Asp Trp Trp Asn Gly
            20

<210> SEQ ID NO 1532
<211> LENGTH: 24
<212> TYPE: PRT
<213> ORGANISM: Homo sapiens

<400> SEQUENCE: 1532

Cys Gly Leu Phe Gly Glu Leu Glu Gly Phe Ile Glu Asn Gly Leu Lys
1               5                   10                  15

Asn Leu Ile Asp Trp Trp Asn Gly
            20

<210> SEQ ID NO 1533
<211> LENGTH: 24
<212> TYPE: PRT
<213> ORGANISM: Homo sapiens

<400> SEQUENCE: 1533

Cys Gly Leu Phe Gly Glu Leu Glu Gly Leu Leu Trp His Gly Leu Lys
1               5                   10                  15

Asn Leu Ile Asp Trp Trp Asn Gly
            20

<210> SEQ ID NO 1534
<211> LENGTH: 24
<212> TYPE: PRT
<213> ORGANISM: Homo sapiens

<400> SEQUENCE: 1534

Cys Gly Leu Phe Gly Glu Leu Ala Glu Leu Leu Trp His Gly Leu Lys
1               5                   10                  15

Asn Leu Ile Asp Trp Trp Asn Gly
            20

<210> SEQ ID NO 1535
<211> LENGTH: 24
<212> TYPE: PRT
<213> ORGANISM: Homo sapiens

<400> SEQUENCE: 1535

Cys Gly Leu Phe Gly Glu Leu Ala Glu Leu Leu Trp Gln Gly Leu Lys
1               5                   10                  15

Asn Leu Ile Asp Trp Trp Asn Gly
            20

<210> SEQ ID NO 1536
<211> LENGTH: 24
<212> TYPE: PRT
<213> ORGANISM: Homo sapiens

<400> SEQUENCE: 1536

Cys Gly Leu Phe Gly Glu Leu Trp Glu Leu Leu Trp His Gly Leu Lys
1               5                   10                  15

Asn Leu Ile Asp Trp Trp Asn Gly
            20

<210> SEQ ID NO 1537
<211> LENGTH: 24

```
<212> TYPE: PRT
<213> ORGANISM: Homo sapiens

<400> SEQUENCE: 1537

Cys Gly Leu Phe Gly Glu Leu Trp Glu Leu Trp Gln Gly Leu Lys
1               5                   10                  15

Asn Leu Ile Asp Trp Trp Asn Gly
            20

<210> SEQ ID NO 1538
<211> LENGTH: 24
<212> TYPE: PRT
<213> ORGANISM: Homo sapiens

<400> SEQUENCE: 1538

Cys Gly Leu Phe Glu Glu Leu Ala Gly Leu Leu Trp His Gly Leu Lys
1               5                   10                  15

Asn Leu Ile Asp Trp Trp Asn Gly
            20

<210> SEQ ID NO 1539
<211> LENGTH: 24
<212> TYPE: PRT
<213> ORGANISM: Homo sapiens

<400> SEQUENCE: 1539

Cys Gly Leu Phe Glu Glu Leu Trp Gly Leu Leu Trp His Gly Leu Lys
1               5                   10                  15

Asn Leu Ile Asp Trp Trp Asn Gly
            20

<210> SEQ ID NO 1540
<211> LENGTH: 24
<212> TYPE: PRT
<213> ORGANISM: Homo sapiens

<400> SEQUENCE: 1540

Cys Gly Leu Phe Glu Glu Leu Ala Gly Leu Leu Trp Gln Gly Leu Lys
1               5                   10                  15

Asn Leu Ile Asp Trp Trp Asn Gly
            20

<210> SEQ ID NO 1541
<211> LENGTH: 24
<212> TYPE: PRT
<213> ORGANISM: Homo sapiens

<400> SEQUENCE: 1541

Cys Gly Leu Phe Glu Glu Leu Trp Gly Leu Leu Trp Gln Gly Leu Lys
1               5                   10                  15

Asn Leu Ile Asp Trp Trp Asn Gly
            20

<210> SEQ ID NO 1542
<211> LENGTH: 24
<212> TYPE: PRT
<213> ORGANISM: Homo sapiens

<400> SEQUENCE: 1542

Cys Gly Leu Phe Gly Glu Leu Ala Glu Leu Leu Trp His Gly Leu Lys
1               5                   10                  15

Asn Leu Ile Asp Trp Trp Asn Lys
```

```
<210> SEQ ID NO 1543
<211> LENGTH: 24
<212> TYPE: PRT
<213> ORGANISM: Homo sapiens

<400> SEQUENCE: 1543

Cys Gly Leu Phe Glu Glu Leu Ala Glu Leu Leu Trp His Gly Leu Lys
1               5                   10                  15

Asn Leu Ile Asp Trp Trp Asn Lys
            20

<210> SEQ ID NO 1544
<211> LENGTH: 24
<212> TYPE: PRT
<213> ORGANISM: Homo sapiens

<400> SEQUENCE: 1544

Cys Gly Leu Phe Gly Glu Leu Ala Glu Leu Leu Trp His Gly Leu Lys
1               5                   10                  15

Asn Leu Ile Asp Trp Trp Asn His
            20

<210> SEQ ID NO 1545
<211> LENGTH: 24
<212> TYPE: PRT
<213> ORGANISM: Homo sapiens

<400> SEQUENCE: 1545

Cys Gly Leu Phe Glu Glu Leu Ala Glu Leu Leu Trp His Gly Leu Lys
1               5                   10                  15

Asn Leu Ile Asp Trp Trp Asn His
            20

<210> SEQ ID NO 1546
<211> LENGTH: 24
<212> TYPE: PRT
<213> ORGANISM: Homo sapiens

<400> SEQUENCE: 1546

Cys Gly Leu Phe Ala Glu Leu Trp Gly Leu Leu Trp Gln Gly Leu Lys
1               5                   10                  15

Asn Leu Ile Asp Trp Trp Asn Gly
            20

<210> SEQ ID NO 1547
<211> LENGTH: 24
<212> TYPE: PRT
<213> ORGANISM: Homo sapiens

<400> SEQUENCE: 1547

Cys Gly Leu Phe Ala Glu Leu Trp Gly Leu Leu Trp His Gly Leu Lys
1               5                   10                  15

Asn Leu Ile Asp Trp Trp Asn Gly
            20

<210> SEQ ID NO 1548
<211> LENGTH: 24
<212> TYPE: PRT
<213> ORGANISM: Homo sapiens

<400> SEQUENCE: 1548
```

```
Cys Gly Leu Phe Ala Glu Leu Trp Gly Leu Trp His Gly Leu His
1               5                   10                  15

Asn Leu Leu Asp Trp Trp Asn Gly
            20
```

<210> SEQ ID NO 1549
<211> LENGTH: 24
<212> TYPE: PRT
<213> ORGANISM: Homo sapiens

<400> SEQUENCE: 1549

```
Cys Gly Leu Phe Ala Glu Leu Ala Glu Leu Trp Glu Gly Leu Lys
1               5                   10                  15

Asn Leu Ile Asp Trp Trp Asn Gly
            20
```

<210> SEQ ID NO 1550
<211> LENGTH: 24
<212> TYPE: PRT
<213> ORGANISM: Homo sapiens

<400> SEQUENCE: 1550

```
Cys Gly Leu Phe Ala Glu Leu Ala Glu Leu Leu Trp His Gly Leu Lys
1               5                   10                  15

Asn Leu Ile Asp Trp Trp Asn Gly
            20
```

<210> SEQ ID NO 1551
<211> LENGTH: 23
<212> TYPE: PRT
<213> ORGANISM: Homo sapiens

<400> SEQUENCE: 1551

```
Cys Gly Leu Phe Ala Glu Leu Glu Leu Leu Trp Gln Gly Leu Lys Asn
1               5                   10                  15

Leu Ile Asp Trp Trp Asn Gly
            20
```

<210> SEQ ID NO 1552
<211> LENGTH: 24
<212> TYPE: PRT
<213> ORGANISM: Homo sapiens

<400> SEQUENCE: 1552

```
Cys Glu Leu Phe Gly Glu Leu Ala Gly Leu Leu Trp His Gly Leu Lys
1               5                   10                  15

Asn Leu Ile Asp Trp Trp Asn Gly
            20
```

<210> SEQ ID NO 1553
<211> LENGTH: 16
<212> TYPE: PRT
<213> ORGANISM: Homo sapiens

<400> SEQUENCE: 1553

```
Cys Leu Phe Glu Ala Leu Trp Glu Ala Ile Asx Leu Glu Lys Leu Phe
1               5                   10                  15
```

<210> SEQ ID NO 1554
<211> LENGTH: 14
<212> TYPE: PRT
<213> ORGANISM: Homo sapiens

<400> SEQUENCE: 1554

Cys Phe Leu Glu Ala Leu Trp Glu Leu Glu His Leu Leu
1               5                   10

<210> SEQ ID NO 1555
<211> LENGTH: 14
<212> TYPE: PRT
<213> ORGANISM: Homo sapiens

<400> SEQUENCE: 1555

Cys Phe Leu Glu Ala Leu Trp Lys Ala Leu Glu Lys Leu Leu
1               5                   10

<210> SEQ ID NO 1556
<211> LENGTH: 26
<212> TYPE: PRT
<213> ORGANISM: Homo sapiens

<400> SEQUENCE: 1556

Cys Gly Leu Phe Ala Ile Asx Glu Ile Ala Gly Leu Leu Glu Glu Gly
1               5                   10                  15

Leu His Asn Leu Ile Asp Trp Trp Asn Gly
            20                  25

<210> SEQ ID NO 1557
<211> LENGTH: 26
<212> TYPE: PRT
<213> ORGANISM: Homo sapiens

<400> SEQUENCE: 1557

Cys Gly Leu Phe Gly Glu Ile Ala Ile Asx Gly Leu Leu Glu Glu Gly
1               5                   10                  15

Leu His Asn Leu Ile Asp Trp Trp Asn Gly
            20                  25

<210> SEQ ID NO 1558
<211> LENGTH: 26
<212> TYPE: PRT
<213> ORGANISM: Homo sapiens

<400> SEQUENCE: 1558

Cys Gly Phe Phe Gly Glu Ile Ala Gly Leu Leu Glu Glu Ala Ile Asx
1               5                   10                  15

Leu His Asn Leu Ile Asp Trp Trp Asn Gly
            20                  25

<210> SEQ ID NO 1559
<211> LENGTH: 26
<212> TYPE: PRT
<213> ORGANISM: Homo sapiens

<400> SEQUENCE: 1559

Cys Gly Leu Phe Gly Glu Ile Ala Gly Leu Leu Glu Glu Gly Leu His
1               5                   10                  15

Asn Leu Ile Asp Trp Trp Asn Ala Ile Asx
            20                  25

<210> SEQ ID NO 1560
<211> LENGTH: 28
<212> TYPE: PRT
<213> ORGANISM: Homo sapiens

<400> SEQUENCE: 1560

Cys Gly Leu Phe Ala Ile Asx Glu Ile Ala Gly Leu Leu Glu Ala
1               5                   10                  15

Ile Asx Leu His Asn Leu Ile Asp Trp Trp Asn Gly
                20                  25

<210> SEQ ID NO 1561
<211> LENGTH: 28
<212> TYPE: PRT
<213> ORGANISM: Homo sapiens

<400> SEQUENCE: 1561

Cys Gly Phe Phe Gly Glu Ile Ala Ile Asx Gly Leu Leu Glu Glu Ala
1               5                   10                  15

Ile Asx Leu His Asn Leu Ile Asp Trp Trp Asn Gly
                20                  25

<210> SEQ ID NO 1562
<211> LENGTH: 26
<212> TYPE: PRT
<213> ORGANISM: Homo sapiens

<400> SEQUENCE: 1562

Cys Gly Phe Phe Gly Glu Ile Ala Ile Asx Glu Leu Ile Trp Glu Gly
1               5                   10                  15

Leu Lys Asn Leu Ile Asp Trp Trp Asn Gly
                20                  25

<210> SEQ ID NO 1563
<211> LENGTH: 25
<212> TYPE: PRT
<213> ORGANISM: Homo sapiens

<400> SEQUENCE: 1563

Cys Gly Phe Phe Gly Glu Ile Ala Glu Leu Ile Trp Glu Leu Lys Asn
1               5                   10                  15

Leu Ile Asp Trp Trp Asn Ala Ile Asx
                20                  25

<210> SEQ ID NO 1564
<211> LENGTH: 28
<212> TYPE: PRT
<213> ORGANISM: Homo sapiens

<400> SEQUENCE: 1564

Cys Gly Phe Phe Ala Ile Asx Glu Ile Ala Glu Leu Ile Trp Glu Ala
1               5                   10                  15

Ile Asx Leu Lys Asn Leu Ile Asp Trp Trp Asn Gly
                20                  25

<210> SEQ ID NO 1565
<211> LENGTH: 16
<212> TYPE: PRT
<213> ORGANISM: Homo sapiens

<400> SEQUENCE: 1565

Ala Cys Cys Phe Leu Gly Ala Leu Trp Lys Ala Leu Ser His Leu Leu
1               5                   10                  15

<210> SEQ ID NO 1566
<211> LENGTH: 17
<212> TYPE: PRT

```
<213> ORGANISM: Homo sapiens

<400> SEQUENCE: 1566

Ala Cys Cys Phe Leu Glu Glu Leu Trp Glu Leu Leu Glu Glu Leu Leu
1               5                   10                  15

Glu

<210> SEQ ID NO 1567
<211> LENGTH: 16
<212> TYPE: PRT
<213> ORGANISM: Homo sapiens

<400> SEQUENCE: 1567

Ala Cys Cys Leu Phe Gly Ala Leu Trp Lys Ala Leu Ser Glu Leu Leu
1               5                   10                  15

<210> SEQ ID NO 1568
<211> LENGTH: 29
<212> TYPE: PRT
<213> ORGANISM: Homo sapiens

<400> SEQUENCE: 1568

Ala Cys Cys Gly Ile Gly Ala Val Leu Lys Val Leu Thr Thr Gly Leu
1               5                   10                  15

Pro Ala Leu Ile Ser Trp Ile Lys Arg Lys Arg Gln Gln
            20                  25

<210> SEQ ID NO 1569
<211> LENGTH: 36
<212> TYPE: PRT
<213> ORGANISM: Homo sapiens

<400> SEQUENCE: 1569

Ala Cys Cys Gly Leu Phe Glu Ala Ile Glu Gly Phe Ile Glu Asn Gly
1               5                   10                  15

Trp Glu Gly Met Ile Asp Gly Trp Tyr Gly Tyr Gly Arg Lys Lys Arg
            20                  25                  30

Arg Gln Arg Arg
        35

<210> SEQ ID NO 1570
<211> LENGTH: 35
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (35)..(35)
<223> OTHER INFORMATION: Lys is conjugated to stearyl

<400> SEQUENCE: 1570

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg Lys
        35

<210> SEQ ID NO 1571
<211> LENGTH: 16
<212> TYPE: PRT
<213> ORGANISM: Homo sapiens
```

<400> SEQUENCE: 1571

Ala Cys Cys Phe Leu Gly Ala Leu Trp Lys Ala Leu Ser His Leu Leu
1               5                   10                  15

<210> SEQ ID NO 1572
<211> LENGTH: 16
<212> TYPE: PRT
<213> ORGANISM: Homo sapiens

<400> SEQUENCE: 1572

Ala Cys Cys Phe Leu Gly Ala Leu Trp Lys Ala Leu Ser Glu Leu Leu
1               5                   10                  15

<210> SEQ ID NO 1573
<211> LENGTH: 24
<212> TYPE: PRT
<213> ORGANISM: Homo sapiens

<400> SEQUENCE: 1573

Cys Glu Leu Phe Glu Glu Ile Ala Glu Leu Leu Trp Glu Gly Leu Glu
1               5                   10                  15

Asn Leu Ile Asp Trp Trp Asn Gly
            20

<210> SEQ ID NO 1574
<211> LENGTH: 24
<212> TYPE: PRT
<213> ORGANISM: Homo sapiens

<400> SEQUENCE: 1574

Cys Gly Leu Phe Gly Glu Ile Ala Glu Leu Ile Trp Glu Gly Leu Glu
1               5                   10                  15

Asn Leu Ile Asp Trp Trp Asn Gly
            20

<210> SEQ ID NO 1575
<211> LENGTH: 24
<212> TYPE: PRT
<213> ORGANISM: Homo sapiens

<400> SEQUENCE: 1575

Cys Gly Leu Phe Gly Glu Ile Glu Glu Leu Leu Glu Glu Gly Leu Glu
1               5                   10                  15

Asn Leu Ile Asp Trp Trp Asn Gly
            20

<210> SEQ ID NO 1576
<211> LENGTH: 24
<212> TYPE: PRT
<213> ORGANISM: Homo sapiens

<400> SEQUENCE: 1576

Cys Gly Leu Phe Ala Glu Leu Ala Glu Leu Leu Trp Glu Gly Leu Glu
1               5                   10                  15

Asn Leu Ile Asp Trp Trp Asn Gly
            20

<210> SEQ ID NO 1577
<211> LENGTH: 24
<212> TYPE: PRT
<213> ORGANISM: Homo sapiens

```
<400> SEQUENCE: 1577

Cys Gly Leu Phe Ala Glu Leu Ala Glu Leu Leu Glu Glu Gly Leu Glu
1               5                   10                  15

Asn Leu Ile Asp Trp Trp Asn Gly
            20

<210> SEQ ID NO 1578
<211> LENGTH: 24
<212> TYPE: PRT
<213> ORGANISM: Homo sapiens

<400> SEQUENCE: 1578

Cys Gly Leu Phe Ala Glu Leu Ala Glu Leu Leu Trp Glu Gly Leu Glu
1               5                   10                  15

Asn Leu Ile Asp Trp Trp Asn Ser
            20

<210> SEQ ID NO 1579
<211> LENGTH: 24
<212> TYPE: PRT
<213> ORGANISM: Homo sapiens

<400> SEQUENCE: 1579

Cys Gly Leu Phe Ala Glu Leu Ala Glu Leu Leu Glu Glu Gly Leu Glu
1               5                   10                  15

Asn Leu Ile Asp Trp Trp Asn Ser
            20

<210> SEQ ID NO 1580
<211> LENGTH: 24
<212> TYPE: PRT
<213> ORGANISM: Homo sapiens

<400> SEQUENCE: 1580

Cys Gly Leu Phe Ala Glu Leu Ala Glu Leu Leu Trp Glu Gly Leu Glu
1               5                   10                  15

Asn Leu Ile Asp Trp Trp Asn Gln
            20

<210> SEQ ID NO 1581
<211> LENGTH: 24
<212> TYPE: PRT
<213> ORGANISM: Homo sapiens

<400> SEQUENCE: 1581

Cys Gly Leu Phe Ala Glu Leu Ala Glu Leu Leu Glu Glu Gly Leu Glu
1               5                   10                  15

Asn Leu Ile Asp Trp Trp Asn Gln
            20

<210> SEQ ID NO 1582
<211> LENGTH: 24
<212> TYPE: PRT
<213> ORGANISM: Homo sapiens

<400> SEQUENCE: 1582

Cys Gly Leu Phe Ala Glu Leu Ala Glu Leu Leu Trp Glu Gly Leu Glu
1               5                   10                  15

Asn Leu Ile Asp Trp Trp Asn Glu
            20
```

```
<210> SEQ ID NO 1583
<211> LENGTH: 24
<212> TYPE: PRT
<213> ORGANISM: Homo sapiens

<400> SEQUENCE: 1583

Cys Gly Leu Phe Ala Glu Leu Ala Glu Leu Leu Glu Glu Gly Leu Glu
1               5                   10                  15

Asn Leu Ile Asp Trp Trp Asn Glu
            20

<210> SEQ ID NO 1584
<211> LENGTH: 24
<212> TYPE: PRT
<213> ORGANISM: Homo sapiens

<400> SEQUENCE: 1584

Cys Glu Leu Phe Glu Glu Leu Ala Glu Leu Leu Trp Glu Gly Leu Glu
1               5                   10                  15

Asn Leu Ile Asp Trp Trp Asn Gln
            20

<210> SEQ ID NO 1585
<211> LENGTH: 24
<212> TYPE: PRT
<213> ORGANISM: Homo sapiens

<400> SEQUENCE: 1585

Cys Glu Leu Phe Glu Glu Leu Ala Glu Leu Leu Trp Glu Gly Leu Glu
1               5                   10                  15

Asn Leu Ile Asp Trp Trp Asn Glu
            20

<210> SEQ ID NO 1586
<211> LENGTH: 24
<212> TYPE: PRT
<213> ORGANISM: Homo sapiens

<400> SEQUENCE: 1586

Cys Glu Leu Phe Glu Glu Leu Ala Glu Leu Leu Glu Glu Gly Leu Glu
1               5                   10                  15

Asn Leu Ile Asp Trp Trp Asn Gly
            20

<210> SEQ ID NO 1587
<211> LENGTH: 24
<212> TYPE: PRT
<213> ORGANISM: Homo sapiens

<400> SEQUENCE: 1587

Cys Glu Leu Phe Ala Glu Leu Ala Glu Leu Leu Trp Glu Gly Leu Glu
1               5                   10                  15

Asn Leu Ile Asp Trp Trp Asn Gly
            20

<210> SEQ ID NO 1588
<211> LENGTH: 24
<212> TYPE: PRT
<213> ORGANISM: Homo sapiens

<400> SEQUENCE: 1588

Cys Glu Leu Phe Ala Glu Leu Ala Glu Leu Leu Glu Glu Gly Leu Glu
1               5                   10                  15
```

```
Asn Leu Ile Asp Trp Trp Asn Gly
            20

<210> SEQ ID NO 1589
<211> LENGTH: 24
<212> TYPE: PRT
<213> ORGANISM: Homo sapiens

<400> SEQUENCE: 1589

Cys Glu Leu Phe Ala Glu Leu Ala Glu Leu Leu Glu Glu Gly Leu Glu
1               5                   10                  15

Asn Leu Ile Asp Trp Trp Asn Gly
            20

<210> SEQ ID NO 1590
<211> LENGTH: 24
<212> TYPE: PRT
<213> ORGANISM: Homo sapiens

<400> SEQUENCE: 1590

Cys Glu Leu Phe Ala Glu Leu Ala Glu Leu Leu Trp Glu Gly Leu Glu
1               5                   10                  15

Asn Leu Ile Asp Trp Trp Asn Ser
            20

<210> SEQ ID NO 1591
<211> LENGTH: 24
<212> TYPE: PRT
<213> ORGANISM: Homo sapiens

<400> SEQUENCE: 1591

Cys Glu Leu Phe Ala Glu Leu Ala Glu Leu Leu Glu Glu Gly Leu Glu
1               5                   10                  15

Asn Leu Ile Asp Trp Trp Asn Ser
            20

<210> SEQ ID NO 1592
<211> LENGTH: 24
<212> TYPE: PRT
<213> ORGANISM: Homo sapiens

<400> SEQUENCE: 1592

Cys Glu Leu Phe Ala Glu Leu Ala Glu Leu Leu Trp Glu Gly Leu Glu
1               5                   10                  15

Asn Leu Ile Asp Trp Trp Asn Gln
            20

<210> SEQ ID NO 1593
<211> LENGTH: 24
<212> TYPE: PRT
<213> ORGANISM: Homo sapiens

<400> SEQUENCE: 1593

Cys Glu Leu Phe Ala Glu Leu Ala Glu Leu Leu Glu Glu Gly Leu Glu
1               5                   10                  15

Asn Leu Ile Asp Trp Trp Asn Gln
            20

<210> SEQ ID NO 1594
<211> LENGTH: 24
<212> TYPE: PRT
<213> ORGANISM: Homo sapiens
```

<400> SEQUENCE: 1594

Cys Glu Leu Phe Ala Glu Leu Ala Glu Leu Leu Trp Glu Gly Leu Glu
1               5                   10                  15

Asn Leu Ile Asp Trp Trp Asn Glu
            20

<210> SEQ ID NO 1595
<211> LENGTH: 24
<212> TYPE: PRT
<213> ORGANISM: Homo sapiens

<400> SEQUENCE: 1595

Cys Glu Leu Phe Ala Glu Leu Ala Glu Leu Leu Glu Glu Gly Leu Glu
1               5                   10                  15

Asn Leu Ile Asp Trp Trp Asn Glu
            20

<210> SEQ ID NO 1596
<211> LENGTH: 24
<212> TYPE: PRT
<213> ORGANISM: Homo sapiens

<400> SEQUENCE: 1596

Cys Glu Leu Phe Glu Glu Leu Ala Glu Leu Leu Trp Glu Gly Leu His
1               5                   10                  15

Asn Leu Ile Asp Trp Trp Asn Ser
            20

<210> SEQ ID NO 1597
<211> LENGTH: 24
<212> TYPE: PRT
<213> ORGANISM: Homo sapiens

<400> SEQUENCE: 1597

Cys Glu Leu Phe Glu Glu Leu Ala Glu Leu Leu Trp Glu Gly Leu His
1               5                   10                  15

Asn Leu Ile Asp Trp Trp Asn Gly
            20

<210> SEQ ID NO 1598
<211> LENGTH: 24
<212> TYPE: PRT
<213> ORGANISM: Homo sapiens

<400> SEQUENCE: 1598

Cys Glu Leu Phe Glu Glu Leu Ala Glu Leu Leu Trp Glu Gly Leu His
1               5                   10                  15

Asn Leu Ile Asp Trp Trp Asn Ser
            20

<210> SEQ ID NO 1599
<211> LENGTH: 24
<212> TYPE: PRT
<213> ORGANISM: Homo sapiens

<400> SEQUENCE: 1599

Cys Glu Leu Phe Glu Glu Leu Ala Glu Leu Leu Trp Glu Gly Leu His
1               5                   10                  15

Asn Leu Ile Asp Trp Trp Asn Gln
            20

<210> SEQ ID NO 1600
<211> LENGTH: 24
<212> TYPE: PRT
<213> ORGANISM: Homo sapiens

<400> SEQUENCE: 1600

Cys Glu Leu Phe Glu Glu Leu Ala Glu Leu Leu Trp Glu Gly Leu His
1               5                   10                  15

Asn Leu Ile Asp Trp Trp Asn Glu
            20

<210> SEQ ID NO 1601
<211> LENGTH: 24
<212> TYPE: PRT
<213> ORGANISM: Homo sapiens

<400> SEQUENCE: 1601

Cys Glu Leu Phe Gly Glu Leu Glu Gly Phe Ile Glu Asn Gly Leu Glu
1               5                   10                  15

Asn Leu Ile Asp Trp Trp Asn Gly
            20

<210> SEQ ID NO 1602
<211> LENGTH: 24
<212> TYPE: PRT
<213> ORGANISM: Homo sapiens

<400> SEQUENCE: 1602

Cys Gly Leu Phe Glu Glu Leu Glu Gly Phe Ile Glu Asn Gly Leu Glu
1               5                   10                  15

Asn Leu Ile Asp Trp Trp Asn Gly
            20

<210> SEQ ID NO 1603
<211> LENGTH: 24
<212> TYPE: PRT
<213> ORGANISM: Homo sapiens

<400> SEQUENCE: 1603

Cys Gly Leu Phe Ala Glu Leu Ala Gly Phe Ile Glu Asn Gly Leu Glu
1               5                   10                  15

Asn Leu Ile Asp Trp Trp Asn Gly
            20

<210> SEQ ID NO 1604
<211> LENGTH: 24
<212> TYPE: PRT
<213> ORGANISM: Homo sapiens

<400> SEQUENCE: 1604

Cys Glu Leu Phe Glu Glu Leu Glu Gly Phe Ile Glu Asn Gly Leu Glu
1               5                   10                  15

Asn Leu Ile Asp Trp Trp Asn Gly
            20

<210> SEQ ID NO 1605
<211> LENGTH: 24
<212> TYPE: PRT
<213> ORGANISM: Homo sapiens

<400> SEQUENCE: 1605

Cys Glu Leu Phe Ala Glu Leu Ala Gly Phe Ile Glu Asn Gly Leu Glu

-continued

```
                1               5                  10                  15
Asn Leu Ile Asp Trp Trp Asn Gly
            20

<210> SEQ ID NO 1606
<211> LENGTH: 24
<212> TYPE: PRT
<213> ORGANISM: Homo sapiens

<400> SEQUENCE: 1606

Cys Gly Leu Phe Gly Glu Leu Glu Gly Phe Ile Trp Asn Gly Leu Glu
1               5                  10                  15

Asn Leu Ile Asp Trp Trp Asn Gly
            20

<210> SEQ ID NO 1607
<211> LENGTH: 24
<212> TYPE: PRT
<213> ORGANISM: Homo sapiens

<400> SEQUENCE: 1607

Cys Gly Leu Phe Gly Glu Leu Glu Gly Phe Ile Glu Asn Gly Leu Glu
1               5                  10                  15

Asn Leu Ile Asp Trp Trp Asn Gly
            20

<210> SEQ ID NO 1608
<211> LENGTH: 24
<212> TYPE: PRT
<213> ORGANISM: Homo sapiens

<400> SEQUENCE: 1608

Cys Gly Leu Phe Gly Glu Leu Glu Gly Phe Ile Glu Asn Gly Leu Glu
1               5                  10                  15

Asn Leu Ile Asp Trp Trp Asn Gln
            20

<210> SEQ ID NO 1609
<211> LENGTH: 24
<212> TYPE: PRT
<213> ORGANISM: Homo sapiens

<400> SEQUENCE: 1609

Cys Gly Leu Phe Gly Glu Leu Glu Gly Phe Ile Glu Asn Gly Leu Glu
1               5                  10                  15

Asn Leu Ile Asp Trp Trp Asn Glu
            20

<210> SEQ ID NO 1610
<211> LENGTH: 24
<212> TYPE: PRT
<213> ORGANISM: Homo sapiens

<400> SEQUENCE: 1610

Cys Glu Leu Phe Glu Glu Leu Glu Gly Phe Ile Glu Asn Gly Leu Glu
1               5                  10                  15

Asn Leu Ile Asp Trp Trp Asn Glu
            20

<210> SEQ ID NO 1611
<211> LENGTH: 24
<212> TYPE: PRT
```

<213> ORGANISM: Homo sapiens

<400> SEQUENCE: 1611

Cys Gly Leu Leu Glu Glu Ile Ala Glu Leu Glu Glu Gly Leu Glu
1               5                   10                  15

Asn Leu Ile Asp Trp Trp Asn Ser
            20

<210> SEQ ID NO 1612
<211> LENGTH: 24
<212> TYPE: PRT
<213> ORGANISM: Homo sapiens

<400> SEQUENCE: 1612

Cys Gly Leu Leu Glu Glu Ile Glu Glu Leu Leu Trp Glu Gly Leu Glu
1               5                   10                  15

Asn Leu Ile Asp Trp Trp Asn Ser
            20

<210> SEQ ID NO 1613
<211> LENGTH: 24
<212> TYPE: PRT
<213> ORGANISM: Homo sapiens

<400> SEQUENCE: 1613

Cys Gly Leu Leu Glu Glu Ile Glu Glu Leu Leu Trp Glu Gly Leu Glu
1               5                   10                  15

Asn Leu Ile Asp Trp Trp Asn Ser
            20

<210> SEQ ID NO 1614
<211> LENGTH: 24
<212> TYPE: PRT
<213> ORGANISM: Homo sapiens

<400> SEQUENCE: 1614

Cys Gly Leu Leu Glu Glu Ile Ala Glu Leu Leu Trp Glu Gly Leu Glu
1               5                   10                  15

Asn Leu Ile Asp Trp Trp Asn Ser
            20

<210> SEQ ID NO 1615
<211> LENGTH: 24
<212> TYPE: PRT
<213> ORGANISM: Homo sapiens

<400> SEQUENCE: 1615

Cys Glu Leu Leu Glu Glu Ile Ala Glu Leu Leu Trp Glu Gly Leu Glu
1               5                   10                  15

Asn Leu Ile Asp Trp Trp Asn Ser
            20

<210> SEQ ID NO 1616
<211> LENGTH: 24
<212> TYPE: PRT
<213> ORGANISM: Homo sapiens

<400> SEQUENCE: 1616

Cys Glu Leu Leu Glu Glu Ile Glu Glu Leu Leu Glu Glu Gly Leu Glu
1               5                   10                  15

Asn Leu Ile Asp Trp Trp Asn Glu
            20

<210> SEQ ID NO 1617
<211> LENGTH: 24
<212> TYPE: PRT
<213> ORGANISM: Homo sapiens

<400> SEQUENCE: 1617

Cys Gly Leu Leu Glu Glu Leu Glu Leu Leu Glu Glu Gly Leu Glu
1               5                   10                  15

Asn Leu Ile Asp Trp Trp Asn Ser
            20

<210> SEQ ID NO 1618
<211> LENGTH: 24
<212> TYPE: PRT
<213> ORGANISM: Homo sapiens

<400> SEQUENCE: 1618

Cys Gly Leu Leu Glu Glu Leu Glu Leu Leu Glu Glu Gly Leu Glu
1               5                   10                  15

Asn Leu Leu Glu Trp Trp Asn Ser
            20

<210> SEQ ID NO 1619
<211> LENGTH: 24
<212> TYPE: PRT
<213> ORGANISM: Homo sapiens

<400> SEQUENCE: 1619

Cys Gly Leu Leu Glu Glu Ile Ala Glu Leu Leu Glu Glu Gly Leu Glu
1               5                   10                  15

Asn Leu Ile Asp Trp Trp Asn Gly
            20

<210> SEQ ID NO 1620
<211> LENGTH: 24
<212> TYPE: PRT
<213> ORGANISM: Homo sapiens

<400> SEQUENCE: 1620

Cys Gly Leu Leu Ala Glu Ile Ala Glu Leu Leu Glu Glu Gly Leu Glu
1               5                   10                  15

Asn Leu Ile Asp Trp Trp Asn Ser
            20

<210> SEQ ID NO 1621
<211> LENGTH: 24
<212> TYPE: PRT
<213> ORGANISM: Homo sapiens

<400> SEQUENCE: 1621

Cys Gly Leu Leu Ala Glu Ile Ala Glu Leu Leu Trp Glu Gly Leu Glu
1               5                   10                  15

Asn Leu Ile Asp Trp Trp Asn Ser
            20

<210> SEQ ID NO 1622
<211> LENGTH: 24
<212> TYPE: PRT
<213> ORGANISM: Homo sapiens

<400> SEQUENCE: 1622

Cys Gly Leu Leu Glu Glu Ile Glu Gly Phe Ile Glu Asn Gly Leu Glu
1               5                   10                  15

Asn Leu Ile Asp Trp Trp Asn Ser
            20

<210> SEQ ID NO 1623
<211> LENGTH: 24
<212> TYPE: PRT
<213> ORGANISM: Homo sapiens

<400> SEQUENCE: 1623

Cys Gly Leu Leu Glu Glu Ile Glu Gly Phe Ile Glu Asn Gly Leu Glu
1               5                   10                  15

Asn Leu Ile Asp Trp Trp Asn Gly
            20

<210> SEQ ID NO 1624
<211> LENGTH: 26
<212> TYPE: PRT
<213> ORGANISM: Homo sapiens

<400> SEQUENCE: 1624

Cys Gly Leu Leu Glu Glu Ile Glu Glu Leu Leu Glu Glu Gly Leu Glu
1               5                   10                  15

Cys Ile Thr Leu Ile Asp Trp Trp Asn Ser
            20                  25

<210> SEQ ID NO 1625
<211> LENGTH: 24
<212> TYPE: PRT
<213> ORGANISM: Homo sapiens

<400> SEQUENCE: 1625

Cys Gly Leu Leu Glu Glu Ile Glu Glu Leu Leu Glu Gln Gly Leu Glu
1               5                   10                  15

Asn Leu Ile Asp Trp Trp Asn Ser
            20

<210> SEQ ID NO 1626
<211> LENGTH: 24
<212> TYPE: PRT
<213> ORGANISM: Homo sapiens

<400> SEQUENCE: 1626

Cys Gly Leu Leu Ala Glu Leu Ala Glu Leu Leu Glu Glu Gly Leu Glu
1               5                   10                  15

Asn Leu Ile Asp Trp Trp Asn Ser
            20

<210> SEQ ID NO 1627
<211> LENGTH: 24
<212> TYPE: PRT
<213> ORGANISM: Homo sapiens

<400> SEQUENCE: 1627

Cys Gly Leu Leu Glu Glu Ile Glu Glu Leu Leu Glu Glu Gly Leu Glu
1               5                   10                  15

Asn Leu Ile Asp Trp Trp Asn Ala
            20

<210> SEQ ID NO 1628
<211> LENGTH: 26

```
<212> TYPE: PRT
<213> ORGANISM: Homo sapiens

<400> SEQUENCE: 1628

Cys Gly Leu Leu Ala Ile Asx Glu Ile Glu Glu Leu Leu Glu Glu Gly
1               5                   10                  15

Leu Glu Asn Leu Ile Asp Trp Trp Asn Ser
            20                  25

<210> SEQ ID NO 1629
<211> LENGTH: 26
<212> TYPE: PRT
<213> ORGANISM: Homo sapiens

<400> SEQUENCE: 1629

Cys Gly Leu Leu Glu Glu Ile Glu Glu Leu Leu Glu Glu Gly Leu Glu
1               5                   10                  15

Asn Leu Ile Asp Trp Trp Asn Ala Ile Asx
            20                  25

<210> SEQ ID NO 1630
<211> LENGTH: 26
<212> TYPE: PRT
<213> ORGANISM: Homo sapiens

<400> SEQUENCE: 1630

Cys Gly Leu Leu Glu Glu Ile Glu Glu Leu Leu Glu Glu Ala Ile Asx
1               5                   10                  15

Leu Glu Asn Leu Ile Asp Trp Trp Asn Gly
            20                  25

<210> SEQ ID NO 1631
<211> LENGTH: 24
<212> TYPE: PRT
<213> ORGANISM: Homo sapiens

<400> SEQUENCE: 1631

Cys Gly Leu Phe Gly His Ile His His Leu Ile His His Gly Leu His
1               5                   10                  15

Asn Leu Ile Asp Trp Trp Asn Gly
            20

<210> SEQ ID NO 1632
<211> LENGTH: 24
<212> TYPE: PRT
<213> ORGANISM: Homo sapiens

<400> SEQUENCE: 1632

Cys Gly Leu Phe Gly Glu Ile His His Leu Ile His His Gly Leu His
1               5                   10                  15

Asn Leu Ile Asp Trp Trp Asn Gly
            20

<210> SEQ ID NO 1633
<211> LENGTH: 24
<212> TYPE: PRT
<213> ORGANISM: Homo sapiens

<400> SEQUENCE: 1633

Cys Gly Leu Phe Gly Glu Ile His His Leu Ile His His Gly Leu Glu
1               5                   10                  15

Asn Leu Ile Asp Trp Trp Asn Gly
```

```
                    20

<210> SEQ ID NO 1634
<211> LENGTH: 24
<212> TYPE: PRT
<213> ORGANISM: Homo sapiens

<400> SEQUENCE: 1634

Cys Gly Leu Phe Gly Glu Ile His Glu Leu Ile His His Gly Leu Glu
1               5                   10                  15

Asn Leu Ile Asp Trp Trp Asn Gly
            20

<210> SEQ ID NO 1635
<211> LENGTH: 24
<212> TYPE: PRT
<213> ORGANISM: Homo sapiens

<400> SEQUENCE: 1635

Cys Glu Leu Leu Glu Glu Ile Glu Glu Leu Leu Glu Glu Gly Leu Glu
1               5                   10                  15

Asn Leu Ile Asp Trp Trp Asn Ser
            20

<210> SEQ ID NO 1636
<211> LENGTH: 24
<212> TYPE: PRT
<213> ORGANISM: Homo sapiens

<400> SEQUENCE: 1636

Cys Gly Leu Phe Gly Glu Leu Glu Glu Leu Ile Glu Glu Gly Leu Glu
1               5                   10                  15

Asn Leu Ile Asp Trp Trp Asn Gly
            20

<210> SEQ ID NO 1637
<211> LENGTH: 24
<212> TYPE: PRT
<213> ORGANISM: Homo sapiens

<400> SEQUENCE: 1637

Cys Gly Leu Leu Ala Glu Ile Glu Glu Leu Leu Trp Glu Gly Leu Glu
1               5                   10                  15

Asn Leu Ile Asp Trp Trp Asn Ser
            20

<210> SEQ ID NO 1638
<211> LENGTH: 24
<212> TYPE: PRT
<213> ORGANISM: Homo sapiens

<400> SEQUENCE: 1638

Cys Gly Leu Leu Glu Glu Ile Glu Glu Leu Leu Glu Glu Gly Leu Glu
1               5                   10                  15

Asn Leu Leu Glu Trp Trp Asn Ser
            20

<210> SEQ ID NO 1639
<211> LENGTH: 23
<212> TYPE: PRT
<213> ORGANISM: Artificial Sequence
<220> FEATURE:
<223> OTHER INFORMATION: Synthetically generated peptide
```

<220> FEATURE:
<221> NAME/KEY: MISC_FEATURE
<222> LOCATION: (1)..(1)
<223> OTHER INFORMATION: Cys is conjugated to b-ALA

<400> SEQUENCE: 1639

Cys Leu Leu Glu Glu Ile Glu Glu Leu Glu Glu Gly Leu Glu Asn
1               5                   10                  15

Leu Ile Asp Trp Trp Asn Ser
            20

<210> SEQ ID NO 1640
<211> LENGTH: 24
<212> TYPE: PRT
<213> ORGANISM: Homo sapiens

<400> SEQUENCE: 1640

Cys Gly Leu Leu Glu Glu Ile Glu Glu Leu Glu Glu Gly Leu Glu
1               5                   10                  15

Asn Leu Ile Asp Leu Trp Asn Ser
            20

<210> SEQ ID NO 1641
<211> LENGTH: 24
<212> TYPE: PRT
<213> ORGANISM: Homo sapiens

<400> SEQUENCE: 1641

Cys Gly Leu Leu Glu Glu Ile Glu Glu Leu Leu Glu Trp Gly Leu Glu
1               5                   10                  15

Asn Leu Ile Asp Trp Trp Asn Ser
            20

<210> SEQ ID NO 1642
<211> LENGTH: 24
<212> TYPE: PRT
<213> ORGANISM: Homo sapiens

<400> SEQUENCE: 1642

Cys Gly Leu Phe Gly Glu Ile Glu Glu Leu Ile Glu Glu Gly Leu Glu
1               5                   10                  15

Asn Leu Ile Asp Trp Gly Asn Gly
            20

<210> SEQ ID NO 1643
<211> LENGTH: 24
<212> TYPE: PRT
<213> ORGANISM: Homo sapiens

<400> SEQUENCE: 1643

Cys Gly Phe Phe Gly Glu Ile Ala Glu Leu Ile Glu Glu Gly Leu Lys
1               5                   10                  15

Asn Leu Ile Asp Trp Gly Asn Gly
            20

<210> SEQ ID NO 1644
<211> LENGTH: 24
<212> TYPE: PRT
<213> ORGANISM: Homo sapiens

<400> SEQUENCE: 1644

Cys Gly Leu Phe Gly Glu Ile Glu Glu Leu Ile Glu Glu Gly Leu Glu
1               5                   10                  15

Asn Leu Ile Asp Trp Ala Asn Gly
            20

<210> SEQ ID NO 1645
<211> LENGTH: 24
<212> TYPE: PRT
<213> ORGANISM: Homo sapiens

<400> SEQUENCE: 1645

Cys Gly Leu Phe Gly Glu Ile Glu Glu Leu Ile Glu Glu Gly Leu Glu
1               5                   10                  15

Asn Leu Ile Asp Trp Ser Asn Gly
            20

<210> SEQ ID NO 1646
<211> LENGTH: 23
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (21)..(21)
<223> OTHER INFORMATION: Trp is conjugated to Aib

<400> SEQUENCE: 1646

Cys Gly Leu Phe Gly Glu Ile Glu Glu Leu Ile Glu Glu Gly Leu Glu
1               5                   10                  15

Asn Leu Ile Asp Trp Asn Gly
            20

<210> SEQ ID NO 1647
<211> LENGTH: 24
<212> TYPE: PRT
<213> ORGANISM: Homo sapiens

<400> SEQUENCE: 1647

Cys Gly Leu Phe Gly Glu Ile Glu Glu Leu Ile Glu Glu Gly Leu Glu
1               5                   10                  15

Asn Leu Ile Asp Trp Pro Asn Gly
            20

<210> SEQ ID NO 1648
<211> LENGTH: 24
<212> TYPE: PRT
<213> ORGANISM: Homo sapiens

<400> SEQUENCE: 1648

Cys Gly Leu Phe Gly Glu Ile Glu Glu Leu Ile Glu Glu Gly Leu Glu
1               5                   10                  15

Asn Leu Ile Asp Trp His Asn Gly
            20

<210> SEQ ID NO 1649
<211> LENGTH: 24
<212> TYPE: PRT
<213> ORGANISM: Homo sapiens

<400> SEQUENCE: 1649

Cys Gly Leu Phe Gly Glu Ile Glu Glu Leu Ile Glu Glu Gly Leu Glu
1               5                   10                  15

Asn Leu Ile Asp Trp Gln Asn Gly
            20

<210> SEQ ID NO 1650
<211> LENGTH: 24
<212> TYPE: PRT
<213> ORGANISM: Homo sapiens

<400> SEQUENCE: 1650

Cys Gly Leu Phe Gly Glu Ile Glu Glu Leu Ile Glu Glu Gly Leu Glu
1               5                   10                  15

Asn Leu Ile Asp Trp Glu Asn Gly
            20

<210> SEQ ID NO 1651
<211> LENGTH: 24
<212> TYPE: PRT
<213> ORGANISM: Homo sapiens

<400> SEQUENCE: 1651

Cys Gly Leu Phe Glu Glu Ile Ala Glu Leu Ile Glu Glu Gly Leu Glu
1               5                   10                  15

Asn Leu Ile Asp Trp Gly Asn Gly
            20

<210> SEQ ID NO 1652
<211> LENGTH: 24
<212> TYPE: PRT
<213> ORGANISM: Homo sapiens

<400> SEQUENCE: 1652

Cys Glu Leu Phe Glu Glu Leu Ala Glu Leu Leu Trp Glu Gly Leu Glu
1               5                   10                  15

Asn Leu Ile Asp Trp Gly Asn Ser
            20

<210> SEQ ID NO 1653
<211> LENGTH: 24
<212> TYPE: PRT
<213> ORGANISM: Homo sapiens

<400> SEQUENCE: 1653

Cys Gly Leu Phe Gly Glu Ile Ala Glu Leu Ile Trp Glu Gly Leu Glu
1               5                   10                  15

Asn Leu Ile Asp Trp Gly Asn Gly
            20

<210> SEQ ID NO 1654
<211> LENGTH: 24
<212> TYPE: PRT
<213> ORGANISM: Homo sapiens

<400> SEQUENCE: 1654

Cys Gly Leu Leu Glu Glu Ile Glu Glu Leu Leu Glu Glu Gly Leu Glu
1               5                   10                  15

Asn Leu Ile Asp Trp Gly Asn Ser
            20

<210> SEQ ID NO 1655
<211> LENGTH: 24
<212> TYPE: PRT
<213> ORGANISM: Homo sapiens

<400> SEQUENCE: 1655

Cys Gly Leu Phe Ala Glu Ile Glu Glu Leu Glu Glu Gly Leu Glu
1               5                   10                  15

Asn Leu Ile Asp Trp Gly Asn Gly
            20

<210> SEQ ID NO 1656
<211> LENGTH: 21
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (4)..(4)
<223> OTHER INFORMATION: Leu is conjugated to Aib

<400> SEQUENCE: 1656

Cys Gly Leu Phe Gly Glu Ile Glu Glu Leu Ile Glu Glu Gly Leu Glu
1               5                   10                  15

Asn Leu Ile Asp Trp
            20

<210> SEQ ID NO 1657
<211> LENGTH: 24
<212> TYPE: PRT
<213> ORGANISM: Homo sapiens

<400> SEQUENCE: 1657

Cys Gly Leu Phe Gly Glu Ile Glu Glu Leu Ile Glu Glu Gly Leu Glu
1               5                   10                  15

Asn Leu Ile Asp Trp Asn Asn Gly
            20

<210> SEQ ID NO 1658
<211> LENGTH: 24
<212> TYPE: PRT
<213> ORGANISM: Homo sapiens

<400> SEQUENCE: 1658

Cys Gly Leu Phe Gly Glu Ile Glu Glu Leu Ile Glu Glu Gly Leu Glu
1               5                   10                  15

Asn Leu Ile Asp Trp Asp Asn Gly
            20

<210> SEQ ID NO 1659
<211> LENGTH: 23
<212> TYPE: PRT
<213> ORGANISM: Homo sapiens

<400> SEQUENCE: 1659

Cys Gly Leu Phe Gly Glu Ile Glu Glu Leu Ile Glu Glu Gly Leu Glu
1               5                   10                  15

Asn Leu Ile Asp Trp Asn Gly
            20

<210> SEQ ID NO 1660
<211> LENGTH: 24
<212> TYPE: PRT
<213> ORGANISM: Homo sapiens

<400> SEQUENCE: 1660

Cys Gly Leu Phe Ala Glu Ile Glu Glu Leu Leu Glu Glu Gly Leu Glu
1               5                   10                  15

Asn Leu Ile Asp Trp Gly Asn Gly
            20

<210> SEQ ID NO 1661
<211> LENGTH: 26
<212> TYPE: PRT
<213> ORGANISM: Homo sapiens

<400> SEQUENCE: 1661

Cys Gly Leu Leu Ala Ile Asx Glu Ile Glu Glu Leu Leu Glu Glu Gly
1               5                   10                  15

Leu Glu Asn Leu Ile Asp Trp Gly Asn Ser
            20                  25

<210> SEQ ID NO 1662
<211> LENGTH: 24
<212> TYPE: PRT
<213> ORGANISM: Homo sapiens

<400> SEQUENCE: 1662

Cys Gly Leu Phe Gly Glu Ile Glu Glu Leu Ile Glu Glu Gly Leu Glu
1               5                   10                  15

Asn Leu Ile Asp Gly Trp Asn Gly
            20

<210> SEQ ID NO 1663
<211> LENGTH: 24
<212> TYPE: PRT
<213> ORGANISM: Homo sapiens

<400> SEQUENCE: 1663

Cys Gly Leu Phe Gly Glu Ile Glu Glu Leu Ile Glu Glu Gly Leu Glu
1               5                   10                  15

Asn Leu Ile Asp Leu Trp Asn Gly
            20

<210> SEQ ID NO 1664
<211> LENGTH: 24
<212> TYPE: PRT
<213> ORGANISM: Homo sapiens

<400> SEQUENCE: 1664

Cys Gly Trp Phe Gly Glu Ile Glu Glu Leu Ile Glu Glu Gly Leu Glu
1               5                   10                  15

Asn Leu Ile Asp Trp Trp Asn Gly
            20

<210> SEQ ID NO 1665
<211> LENGTH: 24
<212> TYPE: PRT
<213> ORGANISM: Homo sapiens

<400> SEQUENCE: 1665

Cys Gly Leu Phe Gly Glu Val Glu Glu Leu Ile Glu Glu Gly Leu Glu
1               5                   10                  15

Asn Leu Ile Asp Trp Trp Asn Gly
            20

<210> SEQ ID NO 1666
<211> LENGTH: 24
<212> TYPE: PRT
<213> ORGANISM: Homo sapiens

<400> SEQUENCE: 1666

Cys Gly Leu Phe Gly Glu Ile Glu Glu Val Ile Glu Glu Gly Leu Glu
1               5                   10                  15

Asn Leu Ile Asp Trp Trp Asn Gly
            20

<210> SEQ ID NO 1667
<211> LENGTH: 24
<212> TYPE: PRT
<213> ORGANISM: Homo sapiens

<400> SEQUENCE: 1667

Cys Gly Leu Phe Gly Glu Ile Glu Glu Leu Val Glu Glu Gly Leu Glu
1               5                   10                  15

Asn Leu Ile Asp Trp Trp Asn Gly
            20

<210> SEQ ID NO 1668
<211> LENGTH: 24
<212> TYPE: PRT
<213> ORGANISM: Homo sapiens

<400> SEQUENCE: 1668

Cys Gly Leu Phe Gly Glu Ile Glu Glu Leu Ala Glu Glu Gly Leu Glu
1               5                   10                  15

Asn Leu Ile Asp Trp Trp Asn Gly
            20

<210> SEQ ID NO 1669
<211> LENGTH: 24
<212> TYPE: PRT
<213> ORGANISM: Homo sapiens

<400> SEQUENCE: 1669

Cys Gly Leu Phe Gly Glu Ile Glu Glu Leu Ile Asp Glu Gly Leu Glu
1               5                   10                  15

Asn Leu Ile Asp Trp Trp Asn Gly
            20

<210> SEQ ID NO 1670
<211> LENGTH: 24
<212> TYPE: PRT
<213> ORGANISM: Homo sapiens

<400> SEQUENCE: 1670

Cys Gly Leu Phe Gly Glu Ile Glu Glu Leu Ile Glu Asp Gly Leu Glu
1               5                   10                  15

Asn Leu Ile Asp Trp Trp Asn Gly
            20

<210> SEQ ID NO 1671
<211> LENGTH: 24
<212> TYPE: PRT
<213> ORGANISM: Homo sapiens

<400> SEQUENCE: 1671

Cys Gly Leu Phe Gly Glu Ile Glu Glu Leu Ile Glu Glu Gly Leu Glu
1               5                   10                  15

Ala Leu Ile Asp Trp Trp Asn Gly
            20

```
<210> SEQ ID NO 1672
<211> LENGTH: 24
<212> TYPE: PRT
<213> ORGANISM: Homo sapiens

<400> SEQUENCE: 1672

Cys Gly Leu Phe Gly Glu Ile Glu Glu Leu Ile Glu Glu Gly Leu Glu
1               5                   10                  15

Asn Ile Ile Asp Trp Trp Asn Gly
            20

<210> SEQ ID NO 1673
<211> LENGTH: 23
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (17)..(17)
<223> OTHER INFORMATION: Asn is conjugated to Nle

<400> SEQUENCE: 1673

Cys Gly Leu Phe Gly Glu Ile Glu Glu Leu Ile Glu Glu Gly Leu Glu
1               5                   10                  15

Asn Ile Asp Trp Trp Asn Gly
            20

<210> SEQ ID NO 1674
<211> LENGTH: 24
<212> TYPE: PRT
<213> ORGANISM: Homo sapiens

<400> SEQUENCE: 1674

Cys Gly Leu Phe Gly Glu Ile Glu Glu Leu Ile Glu Glu Gly Leu Glu
1               5                   10                  15

Asn Leu Ile Gly Trp Trp Asn Gly
            20

<210> SEQ ID NO 1675
<211> LENGTH: 38
<212> TYPE: PRT
<213> ORGANISM: Homo sapiens

<400> SEQUENCE: 1675

Cys Gly Leu Phe Glu Leu Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg Ala Leu Leu Asp
        35

<210> SEQ ID NO 1676
<211> LENGTH: 24
<212> TYPE: PRT
<213> ORGANISM: Homo sapiens

<400> SEQUENCE: 1676

Cys Gly Leu Phe Glu Ala Ile Glu Gly Phe Ile Glu Asn Gly Trp Glu
1               5                   10                  15

Gly Met Ile Asp Gly Trp Tyr Gly
            20
```

```
<210> SEQ ID NO 1677
<211> LENGTH: 34
<212> TYPE: PRT
<213> ORGANISM: Homo sapiens

<400> SEQUENCE: 1677

Cys Gly Leu Phe Gly Glu Ile Glu Glu Leu Ile Glu Asn Gly Leu Lys
1               5                   10                  15

Asn Leu Ile Asp Trp Trp Tyr Gly Tyr Gly Arg Lys Lys Arg Arg Gln
            20                  25                  30

Arg Arg

<210> SEQ ID NO 1678
<211> LENGTH: 31
<212> TYPE: PRT
<213> ORGANISM: Homo sapiens

<400> SEQUENCE: 1678

Cys Gly Leu Phe Glu Ala Leu Leu Glu Leu Leu Glu Ser Leu Trp Glu
1               5                   10                  15

Leu Leu Leu Glu Ala Tyr Gly Arg Lys Lys Arg Arg Gln Arg Arg
            20                  25                  30

<210> SEQ ID NO 1679
<211> LENGTH: 34
<212> TYPE: PRT
<213> ORGANISM: Homo sapiens

<400> SEQUENCE: 1679

Cys Gly Leu Phe Glu Glu Ile Glu Gly Phe Ile Glu Asn Gly Trp Glu
1               5                   10                  15

Gly Leu Ile Asp Trp Trp Tyr Gly Tyr Gly His Lys Lys His His Gln
            20                  25                  30

His Arg

<210> SEQ ID NO 1680
<211> LENGTH: 24
<212> TYPE: PRT
<213> ORGANISM: Homo sapiens

<400> SEQUENCE: 1680

Cys Gly Leu Phe Gly Glu Ile Glu Glu Leu Ile Glu Glu Gly Leu Glu
1               5                   10                  15

Asn Leu Ile Asp Trp Trp Asn Glu
            20

<210> SEQ ID NO 1681
<211> LENGTH: 24
<212> TYPE: PRT
<213> ORGANISM: Homo sapiens

<400> SEQUENCE: 1681

Cys Gly Leu Phe Gly Glu Ile Glu Glu Leu Ile Glu Glu Gly Leu Glu
1               5                   10                  15

Asn Leu Ile Asp Trp Trp Asn Ser
            20

<210> SEQ ID NO 1682
<211> LENGTH: 24
<212> TYPE: PRT
<213> ORGANISM: Homo sapiens
```

<400> SEQUENCE: 1682

Cys Gly Leu Phe Gly Glu Ile Glu Glu Leu Ile Glu Glu Gly Leu Glu
1               5                   10                  15

Asn Leu Ile Asp Trp Trp Asn Gln
            20

<210> SEQ ID NO 1683
<211> LENGTH: 34
<212> TYPE: PRT
<213> ORGANISM: Homo sapiens

<400> SEQUENCE: 1683

Cys Tyr Gly Arg Lys Lys Arg Arg Gln Arg Arg Leu Ile Arg Leu Trp
1               5                   10                  15

Ser His Leu Ile His Ile Trp Phe Gln Asn Arg Arg Leu Lys Trp Lys
            20                  25                  30

Lys Lys

<210> SEQ ID NO 1684
<211> LENGTH: 34
<212> TYPE: PRT
<213> ORGANISM: Homo sapiens

<400> SEQUENCE: 1684

Cys Gly Leu Phe Glu Ala Ile Glu Glu Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 1685
<211> LENGTH: 34
<212> TYPE: PRT
<213> ORGANISM: Homo sapiens

<400> SEQUENCE: 1685

Cys Gly Leu Phe Phe Ala Ile Glu Gly Phe Ile Glu Asn Gly Trp Glu
1               5                   10                  15

Gly Met Ile Asp Trp Trp Tyr Gly Tyr Gly Arg Lys Lys Arg Arg Gln
            20                  25                  30

Arg Arg

<210> SEQ ID NO 1686
<211> LENGTH: 35
<212> TYPE: PRT
<213> ORGANISM: Homo sapiens

<400> SEQUENCE: 1686

Cys Gly Leu Phe Glu Leu Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg Lys
        35

<210> SEQ ID NO 1687
<211> LENGTH: 34
<212> TYPE: PRT
<213> ORGANISM: Artificial Sequence
<220> FEATURE:

```
<223> OTHER INFORMATION: Synthetically generated peptide
<220> FEATURE:
<221> NAME/KEY: MISC_FEATURE
<222> LOCATION: (1)..(1)
<223> OTHER INFORMATION: Gly is conjugated to Stearyl

<400> SEQUENCE: 1687

Gly Leu Phe Glu Leu Ile Glu Gly Phe Ile Glu Asn Gly Trp Glu Gly
1               5                   10                  15

Met Ile Asp Gly Trp Tyr Gly Tyr Gly Arg Lys Lys Arg Arg Gln Arg
            20                  25                  30

Arg Cys

<210> SEQ ID NO 1688
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(16)
<223> OTHER INFORMATION: Lys is conjugated to Stearyl

<400> SEQUENCE: 1688

Cys Phe Phe Gly Ala Ile Trp Glu Phe Ile Lys Ser Ile Leu Lys Lys
1               5                   10                  15

<210> SEQ ID NO 1689
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(16)
<223> OTHER INFORMATION: Lys is conjugated to stearyl

<400> SEQUENCE: 1689

Cys Phe Phe Gly Ala Ile Trp Glu Phe Ile Lys Ser Ile Leu Lys Lys
1               5                   10                  15

<210> SEQ ID NO 1690
<211> LENGTH: 19
<212> TYPE: PRT
<213> ORGANISM: Homo sapiens

<400> SEQUENCE: 1690

Leu Ala Arg Tyr Leu Phe Phe Gly Ala Ile Trp Glu Phe Ile Lys Ser
1               5                   10                  15

Ile Leu Cys

<210> SEQ ID NO 1691
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (15)..(15)
<223> OTHER INFORMATION: Lys is conjugated to STEARYL

<400> SEQUENCE: 1691

Cys Phe Phe Gly Ala Ile Trp Glu Phe Ile His Ser Ile Leu Lys
1               5                   10                  15
```

<210> SEQ ID NO 1692
<211> LENGTH: 24
<212> TYPE: PRT
<213> ORGANISM: Homo sapiens

<400> SEQUENCE: 1692

Cys Gly Phe Phe Gly Glu Ile Ala Glu Leu Ile Glu Glu Gly Leu Lys
1               5                   10                  15

Asn Leu Ile Asp Trp Trp Asn Gly
            20

<210> SEQ ID NO 1693
<211> LENGTH: 31
<212> TYPE: PRT
<213> ORGANISM: Homo sapiens

<400> SEQUENCE: 1693

Cys Gly Ile Phe Glu Ala Ile Ala Gly Leu Leu Lys Asn Ile Phe Lys
1               5                   10                  15

Gly Ile Phe Glu Ala Ile Ala Gly Leu Leu Lys Asn Ile Phe Lys
            20                  25                  30

<210> SEQ ID NO 1694
<211> LENGTH: 20
<212> TYPE: PRT
<213> ORGANISM: Homo sapiens

<400> SEQUENCE: 1694

Cys Ile Phe Gly Ala Ile Ala Gly Phe Ile Lys Asn Ile Leu Lys Gly
1               5                   10                  15

Leu Ile Asp Gly
            20

<210> SEQ ID NO 1695
<211> LENGTH: 35
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (35)..(35)
<223> OTHER INFORMATION: Lys is conjugated to stearyl

<400> SEQUENCE: 1695

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg Lys
        35

<210> SEQ ID NO 1696
<211> LENGTH: 19
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Phe is conjugated to LAURYL

<400> SEQUENCE: 1696

Leu Ala Arg Tyr Leu Phe Phe Gly Ala Ile Trp Glu Phe Ile Lys Ser
1               5                   10                  15

Ile Leu Cys

<210> SEQ ID NO 1697
<211> LENGTH: 23
<212> TYPE: PRT
<213> ORGANISM: Homo sapiens

<400> SEQUENCE: 1697

Gly Leu Phe Gly Glu Ile Glu Glu Leu Ile Glu Cys Gly Leu Glu Asn
1               5                   10                  15

Leu Ile Asp Trp Gly Asn Gly
            20

<210> SEQ ID NO 1698
<211> LENGTH: 23
<212> TYPE: PRT
<213> ORGANISM: Homo sapiens

<400> SEQUENCE: 1698

Gly Leu Phe Gly Glu Ile Glu Glu Leu Ile Glu Cys Leu Glu Asn
1               5                   10                  15

Leu Ile Asp Trp Gly Asn Gly
            20

<210> SEQ ID NO 1699
<211> LENGTH: 22
<212> TYPE: PRT
<213> ORGANISM: Homo sapiens

<400> SEQUENCE: 1699

Cys Gly Leu Phe Gly Glu Glu Leu Glu Glu Leu Leu Glu Glu Gly Leu
1               5                   10                  15

Glu Asn Leu Ile Asp Gly
            20

<210> SEQ ID NO 1700
<211> LENGTH: 22
<212> TYPE: PRT
<213> ORGANISM: Homo sapiens

<400> SEQUENCE: 1700

Cys Gly Leu Phe Gly Glu Glu Leu Glu Glu Leu Leu Glu Glu Gly Leu
1               5                   10                  15

Glu Asn Leu Ile Glu Gly
            20

<210> SEQ ID NO 1701
<211> LENGTH: 26
<212> TYPE: PRT
<213> ORGANISM: Homo sapiens

<400> SEQUENCE: 1701

Cys Gly Leu Phe Gly Glu Ile Glu Glu Leu Ile Glu Glu Gly Leu Glu
1               5                   10                  15

Asn Leu Ile Asp Trp Ala Ile Asx Asn Gly
            20                  25

<210> SEQ ID NO 1702
<211> LENGTH: 26

```
<212> TYPE: PRT
<213> ORGANISM: Homo sapiens

<400> SEQUENCE: 1702

Ala Cys Gly Leu Leu Glu Glu Ile Glu Glu Leu Leu Glu Glu Gly Leu
1               5                   10                  15

Glu Asn Leu Ile Asp Trp Trp Asn Ser Cys
            20                  25

<210> SEQ ID NO 1703
<211> LENGTH: 33
<212> TYPE: PRT
<213> ORGANISM: Homo sapiens

<400> SEQUENCE: 1703

Gly Leu Leu Glu Glu Ile Glu Glu Leu Leu Glu Glu Gly Leu Glu Asn
1               5                   10                  15

Leu Ala Glu Leu Ala Glu Ala Leu Glu Ala Leu Ala Ala Gly Gly Ser
            20                  25                  30

Cys

<210> SEQ ID NO 1704
<211> LENGTH: 21
<212> TYPE: PRT
<213> ORGANISM: Homo sapiens

<400> SEQUENCE: 1704

Cys Gly Leu Phe Gly Glu Ile Glu Glu Leu Ile Glu Glu Gly Leu Glu
1               5                   10                  15

Asn Leu Ile Asp Trp
            20

<210> SEQ ID NO 1705
<211> LENGTH: 20
<212> TYPE: PRT
<213> ORGANISM: Homo sapiens

<400> SEQUENCE: 1705

Cys Gly Leu Phe Gly Glu Ile Glu Glu Leu Ile Glu Glu Gly Leu Glu
1               5                   10                  15

Asn Leu Ile Asp
            20

<210> SEQ ID NO 1706
<211> LENGTH: 19
<212> TYPE: PRT
<213> ORGANISM: Homo sapiens

<400> SEQUENCE: 1706

Cys Gly Leu Phe Gly Glu Ile Glu Glu Leu Ile Glu Glu Gly Leu Glu
1               5                   10                  15

Asn Leu Ile

<210> SEQ ID NO 1707
<211> LENGTH: 22
<212> TYPE: PRT
<213> ORGANISM: Homo sapiens

<400> SEQUENCE: 1707

Cys Glu Leu Phe Glu Glu Ile Ala Glu Leu Ile Glu Glu Gly Leu Glu
1               5                   10                  15
```

```
Asn Leu Ile Asp Trp Gly
         20

<210> SEQ ID NO 1708
<211> LENGTH: 26
<212> TYPE: PRT
<213> ORGANISM: Homo sapiens

<400> SEQUENCE: 1708

Ala Cys Gly Leu Phe Gly Glu Ile Glu Glu Leu Ile Glu Glu Gly Leu
1               5                   10                  15

Glu Asn Leu Ile Asp Trp Gly Asn Gly Cys
            20                  25

<210> SEQ ID NO 1709
<211> LENGTH: 26
<212> TYPE: PRT
<213> ORGANISM: Homo sapiens

<400> SEQUENCE: 1709

Ala Cys Cys Gly Leu Phe Gly Glu Ile Glu Glu Leu Ile Glu Glu Gly
1               5                   10                  15

Leu Glu Asn Leu Ile Asp Trp Gly Asn Gly
            20                  25

<210> SEQ ID NO 1710
<211> LENGTH: 26
<212> TYPE: PRT
<213> ORGANISM: Homo sapiens

<400> SEQUENCE: 1710

Ala Cys Cys Gly Leu Phe Gly Glu Ile Glu Glu Leu Ile Glu Glu Gly
1               5                   10                  15

Leu Glu Asn Leu Ile Asp Trp Trp Asn Gly
            20                  25

<210> SEQ ID NO 1711
<211> LENGTH: 28
<212> TYPE: PRT
<213> ORGANISM: Homo sapiens

<400> SEQUENCE: 1711

Cys Gly Phe Phe Gly Glu Ile Ala Ile Asx Gly Leu Leu Glu Glu Ala
1               5                   10                  15

Ile Asx Leu His Asn Leu Ile Asp Trp Trp Asn Gly
            20                  25

<210> SEQ ID NO 1712
<211> LENGTH: 23
<212> TYPE: PRT
<213> ORGANISM: Homo sapiens

<400> SEQUENCE: 1712

Cys Phe Leu Gly Ala Leu Trp Lys Ala Leu Ser Glu Leu Leu Lys Asn
1               5                   10                  15

Leu Ile Asp Trp Trp Asn Gly
            20

<210> SEQ ID NO 1713
<211> LENGTH: 26
<212> TYPE: PRT
<213> ORGANISM: Homo sapiens
```

```
<400> SEQUENCE: 1713

Cys Gly Leu Arg His Gly Glu Leu Glu Glu Leu Ser His Glu Glu Gly
1               5                   10                  15

Leu Glu Asn Leu Ile Asp Trp Trp Asn Gly
            20                  25

<210> SEQ ID NO 1714
<211> LENGTH: 26
<212> TYPE: PRT
<213> ORGANISM: Homo sapiens

<400> SEQUENCE: 1714

Cys Gly Leu Arg His Gly Glu Leu Glu Glu Leu Ser His Glu Glu Gly
1               5                   10                  15

Leu Glu Asn Leu Ile Asp Trp Trp Asn Gly
            20                  25

<210> SEQ ID NO 1715
<211> LENGTH: 28
<212> TYPE: PRT
<213> ORGANISM: Homo sapiens

<400> SEQUENCE: 1715

Cys Gly Phe Phe Gly Glu Ile Ala Ile Asx Glu Leu Ile Trp Glu Ala
1               5                   10                  15

Ile Asx Leu Lys Asn Leu Ile Asp Trp Trp Asn Gly
            20                  25

<210> SEQ ID NO 1716
<211> LENGTH: 24
<212> TYPE: PRT
<213> ORGANISM: Homo sapiens

<400> SEQUENCE: 1716

Cys Gly Leu Phe Glu Glu Leu Ala Gly Leu Leu Trp His Gly Leu Lys
1               5                   10                  15

Asn Leu Ile Asp Trp Trp Asn Gly
            20

<210> SEQ ID NO 1717
<211> LENGTH: 23
<212> TYPE: PRT
<213> ORGANISM: Homo sapiens

<400> SEQUENCE: 1717

Cys Phe Leu Gly Ala Leu Phe His Ala Leu Ser His Leu Leu Glu Asn
1               5                   10                  15

Leu Ile Asp Trp Trp Asn Gly
            20

<210> SEQ ID NO 1718
<211> LENGTH: 28
<212> TYPE: PRT
<213> ORGANISM: Homo sapiens

<400> SEQUENCE: 1718

Cys Gly Phe Phe Ala Ile Asx Glu Ile Ala Glu Leu Ile Trp Glu Ala
1               5                   10                  15

Ile Asx Leu Lys Asn Leu Ile Asp Trp Trp Asn Gly
            20                  25
```

```
<210> SEQ ID NO 1719
<211> LENGTH: 24
<212> TYPE: PRT
<213> ORGANISM: Homo sapiens

<400> SEQUENCE: 1719

Cys Gly Leu Phe Ala Glu Ile Glu Glu Leu Ile Trp Glu Gly Leu Glu
1               5                   10                  15

Asn Leu Ile Asp Trp Trp Asn Gln
            20

<210> SEQ ID NO 1720
<211> LENGTH: 33
<212> TYPE: PRT
<213> ORGANISM: Homo sapiens

<400> SEQUENCE: 1720

Ser Thr Glu Ala Arg Tyr Leu Ala Gly Tyr Leu Leu Gly Lys Leu Leu
1               5                   10                  15

Arg Asn Arg Asn Leu Ala Ala Ala Ala Leu Arg Asn Arg Asn Leu Leu
            20                  25                  30

Cys

<210> SEQ ID NO 1721
<211> LENGTH: 32
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid

<400> SEQUENCE: 1721

Arg Ala His Xaa Arg Ala His Xaa Arg Ile Leu Phe Gln Tyr Arg Ala
1               5                   10                  15

His Xaa Asx Ala Leu Ala Arg Ala His Xaa Arg Asx Ala Leu Ala Cys
            20                  25                  30

<210> SEQ ID NO 1722
<211> LENGTH: 39
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (24)..(24)
```

```
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid

<400> SEQUENCE: 1722

Arg Ala His Xaa Arg Arg Asx Ala Leu Ala Arg Ala His Xaa Glu Ile
1               5                   10                  15

Phe Phe Gln Tyr Arg Ala His Xaa Arg Asx Ala Leu Ala Arg Ala His
                20                  25                  30

Xaa Arg Asx Ala Leu Ala Cys
        35

<210> SEQ ID NO 1723
<211> LENGTH: 40
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid

<400> SEQUENCE: 1723

Arg Ala His Xaa Arg Arg Asx Ala Leu Ala Arg Arg Ala His Xaa Arg
1               5                   10                  15

Ile Leu Phe Gln Tyr Arg Ala His Xaa Arg Asx Ala Leu Ala Arg Ala
                20                  25                  30

His Xaa Arg Asx Ala Leu Ala Cys
        35                  40

<210> SEQ ID NO 1724
<211> LENGTH: 34
<212> TYPE: PRT
<213> ORGANISM: Artificial Sequence
<220> FEATURE:
<223> OTHER INFORMATION: Synthetically Generated Peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 1724

Arg Ala His Xaa Arg Arg Ala His Xaa Arg Arg Ala His Xaa Arg Ile
1               5                   10                  15

His Ile Leu Phe Gln Asn Arg Arg Met Lys Trp His Lys Asx Ala Leu
                20                  25                  30
```

Ala Cys

<210> SEQ ID NO 1725
<211> LENGTH: 13
<212> TYPE: PRT
<213> ORGANISM: Homo sapiens

<400> SEQUENCE: 1725

Cys Ser Ser Ala Trp Trp Ser Tyr Trp Pro Pro Val Ala
1               5                   10

<210> SEQ ID NO 1726
<211> LENGTH: 17
<212> TYPE: PRT
<213> ORGANISM: Homo sapiens

<400> SEQUENCE: 1726

Cys Gly Leu Phe Ala Val Ile Lys Lys Val Ala Ser Val Ile Gly Gly
1               5                   10                  15

Leu

<210> SEQ ID NO 1727
<211> LENGTH: 17
<212> TYPE: PRT
<213> ORGANISM: Homo sapiens

<400> SEQUENCE: 1727

Cys Gly Leu Phe Ala Val Ile His His Val Ala Ser Val Ile Gly Gly
1               5                   10                  15

Leu

<210> SEQ ID NO 1728
<211> LENGTH: 17
<212> TYPE: PRT
<213> ORGANISM: Homo sapiens

<400> SEQUENCE: 1728

Cys Gly Leu Phe Ala Val Ile Glu Glu Val Ala Ser Val Ile Gly Gly
1               5                   10                  15

Leu

<210> SEQ ID NO 1729
<211> LENGTH: 37
<212> TYPE: PRT
<213> ORGANISM: Homo sapiens

<400> SEQUENCE: 1729

Cys Gly Pro Ser Gln Pro Thr Tyr Pro Gly Asp Asp Ala Pro Val Arg
1               5                   10                  15

Asp Leu Ile Arg Phe Tyr Arg Asp Leu Arg Arg Tyr Leu Asn Val Val
            20                  25                  30

Thr Arg His Arg Tyr
        35

<210> SEQ ID NO 1730
<211> LENGTH: 27
<212> TYPE: PRT
<213> ORGANISM: Homo sapiens

<400> SEQUENCE: 1730

Cys Gly Ile Gly Ala Val Leu His Val Leu Thr Thr Gly Leu Pro Ala

```
                1               5                  10                 15
Leu Ile Ser Trp Ile Lys Arg Lys Arg Gln Gln
            20                  25

<210> SEQ ID NO 1731
<211> LENGTH: 27
<212> TYPE: PRT
<213> ORGANISM: Homo sapiens

<400> SEQUENCE: 1731

Cys Gly Ile Gly Ala Val Leu His Val Leu Thr Thr Gly Leu Pro Ala
1               5                   10                  15

Leu Ile Ser Trp Ile His His His His Gln Gln
            20                  25

<210> SEQ ID NO 1732
<211> LENGTH: 18
<212> TYPE: PRT
<213> ORGANISM: Homo sapiens

<400> SEQUENCE: 1732

Ala Cys Gly Ile Phe Glu Ala Ile Ala Gly Leu Leu Lys Ile Asn Phe
1               5                   10                  15

Lys Cys

<210> SEQ ID NO 1733
<211> LENGTH: 37
<212> TYPE: PRT
<213> ORGANISM: Homo sapiens

<400> SEQUENCE: 1733

Ala Cys Gly Leu Phe Gly Ala Leu Ala Glu Ala Leu Ala Glu Ala Leu
1               5                   10                  15

Ala Glu His Leu Ala Glu Ala Leu Ala Glu Ala Leu Ala Glu Ala Leu Ala
            20                  25                  30

Ala Gly Gly Ser Cys
            35

<210> SEQ ID NO 1734
<211> LENGTH: 35
<212> TYPE: PRT
<213> ORGANISM: Homo sapiens

<400> SEQUENCE: 1734

Ala Cys Gly Leu Phe Glu Ala Ile Glu Gly Phe Ile Glu Asn Gly Trp
1               5                   10                  15

Glu Gly Leu Ala Glu Leu Ala Glu Ala Leu Glu Ala Leu Ala Ala Gly
            20                  25                  30

Gly Ser Cys
        35

<210> SEQ ID NO 1735
<211> LENGTH: 18
<212> TYPE: PRT
<213> ORGANISM: Homo sapiens

<400> SEQUENCE: 1735

Ala Cys Gly Ile Phe Glu Ala Ile Ala Gly Leu Leu Lys Ile Asn Phe
1               5                   10                  15

Lys Cys
```

<210> SEQ ID NO 1736
<211> LENGTH: 37
<212> TYPE: PRT
<213> ORGANISM: Homo sapiens

<400> SEQUENCE: 1736

Ala Cys Gly Leu Phe Gly Ala Leu Ala Glu Ala Leu Ala Glu Ala Leu
1               5                   10                  15

Ala Glu His Leu Ala Glu Ala Leu Ala Glu Ala Leu Glu Ala Leu Ala
            20                  25                  30

Ala Gly Gly Ser Cys
        35

<210> SEQ ID NO 1737
<211> LENGTH: 37
<212> TYPE: PRT
<213> ORGANISM: Homo sapiens

<400> SEQUENCE: 1737

Ala Cys Gly Leu Phe Gly Ala Leu Ala Glu Ala Leu Ala Glu Ala Leu
1               5                   10                  15

Ala Glu His Leu Ala Glu Ala Leu Ala Glu Ala Leu Glu Ala Leu Ala
            20                  25                  30

Ala Gly Gly Ser Cys
        35

<210> SEQ ID NO 1738
<211> LENGTH: 40
<212> TYPE: PRT
<213> ORGANISM: Homo sapiens

<400> SEQUENCE: 1738

Gly Leu Phe Gly Glu Ile Glu Glu Leu Ile Glu Gly Leu Glu Asn
1               5                   10                  15

Leu Ile Asp Trp Gly Asn Gly Leu Ala Glu Leu Ala Glu Ala Leu Glu
            20                  25                  30

Ala Leu Ala Ala Gly Gly Ser Cys
        35                  40

<210> SEQ ID NO 1739
<211> LENGTH: 40
<212> TYPE: PRT
<213> ORGANISM: Homo sapiens

<400> SEQUENCE: 1739

Gly Leu Phe Gly Glu Ile Glu Glu Leu Ile Glu Gly Leu Glu Asn
1               5                   10                  15

Leu Ile Asp Trp Gly Asn Gly Leu Ala Glu Leu Ala Glu Ala Leu Glu
            20                  25                  30

Ala Leu Ala Ala Gly Gly Ser Cys
        35                  40

<210> SEQ ID NO 1740
<211> LENGTH: 33
<212> TYPE: PRT
<213> ORGANISM: Homo sapiens

<400> SEQUENCE: 1740

Gly Leu Phe Glu Ala Ile Glu Gly Phe Ile Glu Asn Gly Trp Glu Gly
1               5                   10                  15

```
Leu Ala Glu Ala Glu Ala Leu Glu Ala Leu Ala Ala Gly Gly Ser
        20                  25                  30

Cys

<210> SEQ ID NO 1741
<211> LENGTH: 35
<212> TYPE: PRT
<213> ORGANISM: Homo sapiens

<400> SEQUENCE: 1741

Gly Leu Phe Gly Ala Leu Ala Glu Ala Leu Ala Glu Ala Leu Ala Glu
1               5                   10                  15

His Leu Ala Glu Ala Leu Ala Glu Ala Leu Glu Ala Leu Ala Ala Gly
            20                  25                  30

Gly Ser Cys
        35

<210> SEQ ID NO 1742
<211> LENGTH: 33
<212> TYPE: PRT
<213> ORGANISM: Homo sapiens

<400> SEQUENCE: 1742

Gly Leu Phe Glu Ala Ile Glu Gly Phe Ile Glu Asn Gly Trp Glu Gly
1               5                   10                  15

Leu Ala Glu Leu Ala Glu Ala Leu Glu Ala Leu Ala Ala Gly Gly Ser
            20                  25                  30

Cys

<210> SEQ ID NO 1743
<211> LENGTH: 33
<212> TYPE: PRT
<213> ORGANISM: Homo sapiens

<400> SEQUENCE: 1743

Gly Leu Phe Glu Ala Ile Glu Gly Phe Ile Glu Asn Gly Trp Glu Gly
1               5                   10                  15

Leu Ala Glu Leu Ala Glu Ala Leu Glu Ala Leu Ala Ala Gly Gly Ser
            20                  25                  30

Cys

<210> SEQ ID NO 1744
<211> LENGTH: 24
<212> TYPE: PRT
<213> ORGANISM: Homo sapiens

<400> SEQUENCE: 1744

Cys Glu Glu Asn Trp Ile Gly Leu Phe Gly Gly Asn Ile Trp Glu
1               5                   10                  15

Glu Glu Glu Ile Leu Asp Leu Leu
            20

<210> SEQ ID NO 1745
<211> LENGTH: 24
<212> TYPE: PRT
<213> ORGANISM: Homo sapiens

<400> SEQUENCE: 1745

Cys Gly Leu Phe Gly Glu Ile Glu Glu Leu Ile Glu Glu Gly Leu Glu
1               5                   10                  15
```

Asn Leu Ile Asp Trp Gly Asn Gly
            20

<210> SEQ ID NO 1746
<211> LENGTH: 16
<212> TYPE: PRT
<213> ORGANISM: Homo sapiens

<400> SEQUENCE: 1746

Cys Glu Ala Leu Phe Gly Lys Ile Asn Ala Ile Phe Ile Gly Lys Leu
1               5                   10                  15

<210> SEQ ID NO 1747
<211> LENGTH: 24
<212> TYPE: PRT
<213> ORGANISM: Homo sapiens

<400> SEQUENCE: 1747

Cys Gly Leu Phe Gly Glu Ile Glu Glu Leu Leu Glu Glu Gly Leu Glu
1               5                   10                  15

Asn Leu Ile Asp Trp Gly Asn Gly
            20

<210> SEQ ID NO 1748
<211> LENGTH: 24
<212> TYPE: PRT
<213> ORGANISM: Homo sapiens

<400> SEQUENCE: 1748

Cys Gly Leu Phe Gly Glu Ile Glu Glu Leu Ile Glu Glu Ala Leu Glu
1               5                   10                  15

Asn Leu Ile Asp Trp Gly Asn Gly
            20

<210> SEQ ID NO 1749
<211> LENGTH: 24
<212> TYPE: PRT
<213> ORGANISM: Homo sapiens

<400> SEQUENCE: 1749

Cys Gly Leu Phe Gly Glu Ile Glu Glu Leu Ile Glu Glu Gly Phe Glu
1               5                   10                  15

Asn Leu Ile Asp Trp Gly Asn Gly
            20

<210> SEQ ID NO 1750
<211> LENGTH: 24
<212> TYPE: PRT
<213> ORGANISM: Homo sapiens

<400> SEQUENCE: 1750

Cys Gly Leu Phe Gly Glu Ile Glu Glu Leu Ile Glu Glu Gly Phe Glu
1               5                   10                  15

Asn Leu Ile Asp Trp Gly Asn Gly
            20

<210> SEQ ID NO 1751
<211> LENGTH: 24
<212> TYPE: PRT
<213> ORGANISM: Homo sapiens

<400> SEQUENCE: 1751

Cys Gly Leu Phe Gly Glu Ile Glu Glu Leu Ile Glu Glu Gly Trp Glu

```
1               5                   10                  15

Asn Leu Ile Asp Trp Gly Asn Gly
            20

<210> SEQ ID NO 1752
<211> LENGTH: 24
<212> TYPE: PRT
<213> ORGANISM: Homo sapiens

<400> SEQUENCE: 1752

Cys Gly Leu Phe Gly Glu Ile Glu Glu Trp Ile Glu Glu Gly Leu Glu
1               5                   10                  15

Asn Leu Ile Asp Trp Gly Asn Gly
            20

<210> SEQ ID NO 1753
<211> LENGTH: 24
<212> TYPE: PRT
<213> ORGANISM: Homo sapiens

<400> SEQUENCE: 1753

Cys Gly Leu Phe Gly Glu Ile Glu Glu Phe Ile Glu Glu Gly Leu Glu
1               5                   10                  15

Asn Leu Ile Asp Trp Gly Asn Gly
            20

<210> SEQ ID NO 1754
<211> LENGTH: 24
<212> TYPE: PRT
<213> ORGANISM: Homo sapiens

<400> SEQUENCE: 1754

Cys Gly Leu Phe Gly Glu Ile Glu Glu Phe Ile Glu Glu Gly Leu Glu
1               5                   10                  15

Asn Leu Ile Asp Trp Gly Asn Gly
            20

<210> SEQ ID NO 1755
<211> LENGTH: 24
<212> TYPE: PRT
<213> ORGANISM: Homo sapiens

<400> SEQUENCE: 1755

Cys Gly Leu Phe Gly Glu Ile Glu Glu Leu Phe Glu Glu Gly Leu Glu
1               5                   10                  15

Asn Leu Ile Asp Trp Gly Asn Gly
            20

<210> SEQ ID NO 1756
<211> LENGTH: 24
<212> TYPE: PRT
<213> ORGANISM: Homo sapiens

<400> SEQUENCE: 1756

Cys Gly Leu Phe Gly Glu Ile Glu Glu Leu Ile Glu Glu Gly Leu Glu
1               5                   10                  15

Asn Leu Ile Asp Trp Gly Asn Glu
            20

<210> SEQ ID NO 1757
<211> LENGTH: 24
<212> TYPE: PRT
```

<213> ORGANISM: Homo sapiens

<400> SEQUENCE: 1757

Cys Gly Leu Phe Gly Glu Ile Glu Glu Leu Ile Glu Glu Gly Leu Glu
1               5                   10                  15

Asn Leu Ile Asp Trp Gly Asn Glu
            20

<210> SEQ ID NO 1758
<211> LENGTH: 24
<212> TYPE: PRT
<213> ORGANISM: Homo sapiens

<400> SEQUENCE: 1758

Cys Gly Leu Phe Gly Glu Ile Glu Glu Leu Ile Glu Glu Gly Leu Glu
1               5                   10                  15

Glu Leu Ile Asp Trp Gly Asn Gly
            20

<210> SEQ ID NO 1759
<211> LENGTH: 24
<212> TYPE: PRT
<213> ORGANISM: Homo sapiens

<400> SEQUENCE: 1759

Cys Gly Leu Phe Gly Glu Ile Glu Glu Leu Ile Glu Glu Gly Leu Glu
1               5                   10                  15

Ser Leu Ile Asp Trp Gly Asn Gly
            20

<210> SEQ ID NO 1760
<211> LENGTH: 24
<212> TYPE: PRT
<213> ORGANISM: Homo sapiens

<400> SEQUENCE: 1760

Cys Gly Leu Phe Gly Glu Ile Glu Glu Leu Ile Glu Glu Gly Leu Glu
1               5                   10                  15

Gln Leu Ile Asp Trp Gly Asn Gly
            20

<210> SEQ ID NO 1761
<211> LENGTH: 24
<212> TYPE: PRT
<213> ORGANISM: Homo sapiens

<400> SEQUENCE: 1761

Cys Gly Leu Phe Gly Glu Ile Glu Glu Leu Ile Glu Glu Gly Leu Glu
1               5                   10                  15

Asn Trp Ile Asp Trp Gly Asn Gly
            20

<210> SEQ ID NO 1762
<211> LENGTH: 24
<212> TYPE: PRT
<213> ORGANISM: Homo sapiens

<400> SEQUENCE: 1762

Cys Gly Leu Phe Gly Glu Ile Glu Glu Leu Ile Glu Glu Gly Leu Glu
1               5                   10                  15

Asn Phe Ile Asp Trp Gly Asn Gly
            20

<210> SEQ ID NO 1763
<211> LENGTH: 24
<212> TYPE: PRT
<213> ORGANISM: Homo sapiens

<400> SEQUENCE: 1763

Cys Gly Leu Phe Gly Glu Ile Glu Glu Leu Ile Glu Glu Gly Leu Glu
1               5                   10                  15

Asn Leu Trp Asp Trp Gly Asn Gly
            20

<210> SEQ ID NO 1764
<211> LENGTH: 24
<212> TYPE: PRT
<213> ORGANISM: Homo sapiens

<400> SEQUENCE: 1764

Cys Gly Leu Phe Gly Glu Ile Glu Glu Leu Ile Glu Glu Gly Leu Glu
1               5                   10                  15

Asn Leu Val Asp Trp Gly Asn Gly
            20

<210> SEQ ID NO 1765
<211> LENGTH: 24
<212> TYPE: PRT
<213> ORGANISM: Homo sapiens

<400> SEQUENCE: 1765

Cys Gly Leu Phe Gly Glu Ile Glu Glu Leu Ile Glu Glu Gly Leu Glu
1               5                   10                  15

Asn Leu Ile Glu Trp Gly Asn Gly
            20

<210> SEQ ID NO 1766
<211> LENGTH: 24
<212> TYPE: PRT
<213> ORGANISM: Homo sapiens

<400> SEQUENCE: 1766

Cys Gly Leu Phe Gly Glu Ile Glu Glu Leu Ile Glu Glu Gly Leu Glu
1               5                   10                  15

Asn Leu Ile Asp Phe Gly Asn Gly
            20

<210> SEQ ID NO 1767
<211> LENGTH: 24
<212> TYPE: PRT
<213> ORGANISM: Homo sapiens

<400> SEQUENCE: 1767

Cys Gly Leu Phe Gly Glu Ile Glu Glu Leu Ile Glu Glu Gly Leu Glu
1               5                   10                  15

Asn Leu Ile Asp Leu Gly Asn Gly
            20

<210> SEQ ID NO 1768
<211> LENGTH: 24
<212> TYPE: PRT
<213> ORGANISM: Homo sapiens

<400> SEQUENCE: 1768

Cys Gly Leu Phe Gly Glu Ile Glu Glu Leu Ile Glu Glu Gly Leu Glu
1               5                   10                  15

Asn Leu Ile Asp Trp Gly Tyr Gly
            20

<210> SEQ ID NO 1769
<211> LENGTH: 24
<212> TYPE: PRT
<213> ORGANISM: Homo sapiens

<400> SEQUENCE: 1769

Cys Gly Leu Phe Gly Glu Ile Glu Glu Leu Ile Glu Glu Gly Leu Glu
1               5                   10                  15

Asn Leu Ile Asp Trp Gly Ser Gly
            20

<210> SEQ ID NO 1770
<211> LENGTH: 24
<212> TYPE: PRT
<213> ORGANISM: Homo sapiens

<400> SEQUENCE: 1770

Cys Gly Leu Phe Gly Glu Ile Glu Glu Leu Ile Glu Glu Gly Leu Glu
1               5                   10                  15

Asn Leu Ile Asp Trp Gly Asn Gln
            20

<210> SEQ ID NO 1771
<211> LENGTH: 26
<212> TYPE: PRT
<213> ORGANISM: Homo sapiens

<400> SEQUENCE: 1771

Cys Gly Leu Phe Gly Glu Ile Glu Glu Leu Ile Glu Glu Gly Leu Glu
1               5                   10                  15

Asn Leu Ile Asp Trp Gly Asn Ala Ile Asx
            20                  25

<210> SEQ ID NO 1772
<211> LENGTH: 24
<212> TYPE: PRT
<213> ORGANISM: Homo sapiens

<400> SEQUENCE: 1772

Cys Gly Leu Phe Glu Ala Leu Leu Glu Leu Leu Glu Ser Leu Trp Glu
1               5                   10                  15

Leu Leu Leu Glu Ala Gly Tyr Gly
            20

<210> SEQ ID NO 1773
<211> LENGTH: 24
<212> TYPE: PRT
<213> ORGANISM: Homo sapiens

<400> SEQUENCE: 1773

Cys Gly Leu Phe Gly Glu Ile Glu Glu Leu Ile Glu Glu Gly Leu Glu
1               5                   10                  15

Asn Leu Ile Asp Trp Gly Asn Ser
            20

<210> SEQ ID NO 1774
<211> LENGTH: 24

```
<212> TYPE: PRT
<213> ORGANISM: Homo sapiens

<400> SEQUENCE: 1774

Cys Gly Leu Phe Glu Ala Ile Glu Gly Phe Ile Glu Asn Gly Trp Glu
1               5                   10                  15

Gly Met Ile Asp Trp Gly Asn Gly
            20

<210> SEQ ID NO 1775
<211> LENGTH: 21
<212> TYPE: PRT
<213> ORGANISM: Homo sapiens

<400> SEQUENCE: 1775

Cys Gly Leu Phe Glu Ala Leu Leu Glu Leu Leu Glu Ser Leu Trp Glu
1               5                   10                  15

Leu Leu Leu Glu Ala
            20

<210> SEQ ID NO 1776
<211> LENGTH: 25
<212> TYPE: PRT
<213> ORGANISM: Homo sapiens

<400> SEQUENCE: 1776

Cys Gly Leu Phe Gly Glu Ile Glu Glu Leu Ile Glu Glu Gly Leu Glu
1               5                   10                  15

Asn Leu Ile Asp Trp Gly Asn Gly Cys
            20                  25

<210> SEQ ID NO 1777
<211> LENGTH: 24
<212> TYPE: PRT
<213> ORGANISM: Homo sapiens

<400> SEQUENCE: 1777

Cys Gly Asn Phe Gly Glu Ile Glu Glu Leu Ile Glu Glu Gly Leu Glu
1               5                   10                  15

Asn Leu Ile Asp Trp Gly Asn Gly
            20

<210> SEQ ID NO 1778
<211> LENGTH: 24
<212> TYPE: PRT
<213> ORGANISM: Homo sapiens

<400> SEQUENCE: 1778

Cys Gly Leu Phe Ala Glu Ile Glu Glu Leu Ile Glu Glu Gly Leu Glu
1               5                   10                  15

Asn Leu Ile Asp Trp Gly Asn Gly
            20

<210> SEQ ID NO 1779
<211> LENGTH: 24
<212> TYPE: PRT
<213> ORGANISM: Homo sapiens

<400> SEQUENCE: 1779

Cys Gly Leu Phe Glu Glu Ile Glu Glu Leu Ile Glu Glu Gly Leu Glu
1               5                   10                  15

Asn Leu Ile Asp Trp Gly Asn Gly
```

<210> SEQ ID NO 1780
<211> LENGTH: 24
<212> TYPE: PRT
<213> ORGANISM: Homo sapiens

<400> SEQUENCE: 1780

Cys Gly Leu Phe Gly Glu Ile Ala Glu Leu Ile Glu Glu Gly Leu Glu
1               5                   10                  15

Asn Leu Ile Asp Trp Gly Asn Gly
            20

<210> SEQ ID NO 1781
<211> LENGTH: 24
<212> TYPE: PRT
<213> ORGANISM: Homo sapiens

<400> SEQUENCE: 1781

Cys Glu Leu Phe Gly Glu Ile Glu Glu Leu Ile Glu Glu Gly Leu Glu
1               5                   10                  15

Asn Leu Ile Asp Trp Gly Asn Gly
            20

<210> SEQ ID NO 1782
<211> LENGTH: 24
<212> TYPE: PRT
<213> ORGANISM: Homo sapiens

<400> SEQUENCE: 1782

Cys Ala Leu Phe Gly Glu Ile Glu Glu Leu Ile Glu Glu Gly Leu Glu
1               5                   10                  15

Asn Leu Ile Asp Trp Gly Asn Gly
            20

<210> SEQ ID NO 1783
<211> LENGTH: 26
<212> TYPE: PRT
<213> ORGANISM: Homo sapiens

<400> SEQUENCE: 1783

Cys Ala Ile Asx Leu Phe Gly Glu Ile Glu Glu Leu Ile Glu Glu Gly
1               5                   10                  15

Leu Glu Asn Leu Ile Asp Trp Gly Asn Gly
            20                  25

<210> SEQ ID NO 1784
<211> LENGTH: 24
<212> TYPE: PRT
<213> ORGANISM: Homo sapiens

<400> SEQUENCE: 1784

Cys Gly Trp Phe Gly Glu Ile Glu Glu Leu Ile Glu Glu Gly Leu Glu
1               5                   10                  15

Asn Leu Ile Asp Trp Gly Asn Gly
            20

<210> SEQ ID NO 1785
<211> LENGTH: 24
<212> TYPE: PRT
<213> ORGANISM: Homo sapiens

<400> SEQUENCE: 1785

```
Cys Gly Leu Phe Gly Glu Leu Glu Glu Leu Ile Glu Glu Gly Leu Glu
1               5                   10                  15

Asn Leu Ile Asp Trp Gly Asn Gly
            20
```

<210> SEQ ID NO 1786
<211> LENGTH: 24
<212> TYPE: PRT
<213> ORGANISM: Homo sapiens

<400> SEQUENCE: 1786

```
Cys Gly Leu Phe Gly Glu Ile Glu Glu Leu Trp Glu Glu Gly Leu Glu
1               5                   10                  15

Asn Leu Ile Asp Trp Gly Asn Gly
            20
```

<210> SEQ ID NO 1787
<211> LENGTH: 24
<212> TYPE: PRT
<213> ORGANISM: Homo sapiens

<400> SEQUENCE: 1787

```
Cys Gly Leu Phe Gly Glu Ile Glu Glu Leu Trp Glu Glu Gly Leu Glu
1               5                   10                  15

Asn Leu Ile Asp Trp Gly Asn Gly
            20
```

<210> SEQ ID NO 1788
<211> LENGTH: 26
<212> TYPE: PRT
<213> ORGANISM: Homo sapiens

<400> SEQUENCE: 1788

```
Cys Gly Leu Phe Gly Glu Ile Glu Glu Leu Ile Glu Glu Ala Ile Asx
1               5                   10                  15

Leu Glu Asn Leu Ile Asp Trp Gly Asn Gly
            20                  25
```

<210> SEQ ID NO 1789
<211> LENGTH: 26
<212> TYPE: PRT
<213> ORGANISM: Homo sapiens

<400> SEQUENCE: 1789

```
Cys Gly Leu Phe Gly Glu Ile Glu Glu Leu Ile Glu Glu Ala Ile Asx
1               5                   10                  15

Leu Glu Asn Leu Ile Asp Trp Gly Asn Gly
            20                  25
```

<210> SEQ ID NO 1790
<211> LENGTH: 26
<212> TYPE: PRT
<213> ORGANISM: Homo sapiens

<400> SEQUENCE: 1790

```
Cys Gly Leu Phe Gly Glu Ile Glu Glu Leu Ile Glu Glu Ala Ile Asx
1               5                   10                  15

Leu Glu Asn Leu Ile Asp Trp Gly Asn Gly
            20                  25
```

<210> SEQ ID NO 1791

```
<211> LENGTH: 26
<212> TYPE: PRT
<213> ORGANISM: Homo sapiens

<400> SEQUENCE: 1791

Cys Gly Leu Phe Gly Glu Ile Glu Glu Leu Ile Glu Glu Ala Ile Asx
1               5                   10                  15

Leu Glu Asn Leu Ile Asp Trp Gly Asn Gly
            20                  25

<210> SEQ ID NO 1792
<211> LENGTH: 26
<212> TYPE: PRT
<213> ORGANISM: Homo sapiens

<400> SEQUENCE: 1792

Cys Gly Leu Phe Gly Glu Ile Glu Glu Leu Ile Glu Glu Ala Ile Asx
1               5                   10                  15

Leu Glu Asn Leu Ile Asp Trp Gly Asn Gly
            20                  25

<210> SEQ ID NO 1793
<211> LENGTH: 24
<212> TYPE: PRT
<213> ORGANISM: Homo sapiens

<400> SEQUENCE: 1793

Cys Gly Leu Leu Gly Glu Ile Glu Glu Leu Ile Glu Glu Gly Leu Glu
1               5                   10                  15

Asn Leu Ile Asp Trp Gly Asn Gly
            20

<210> SEQ ID NO 1794
<211> LENGTH: 24
<212> TYPE: PRT
<213> ORGANISM: Homo sapiens

<400> SEQUENCE: 1794

Cys Gly Leu Phe Gly Ala Ile Glu Glu Leu Ile Glu Glu Gly Leu Glu
1               5                   10                  15

Asn Leu Ile Asp Trp Gly Asn Gly
            20

<210> SEQ ID NO 1795
<211> LENGTH: 24
<212> TYPE: PRT
<213> ORGANISM: Homo sapiens

<400> SEQUENCE: 1795

Cys Gly Phe Phe Gly Glu Ile Glu Glu Leu Ile Glu Glu Gly Leu Glu
1               5                   10                  15

Asn Leu Ile Asp Trp Gly Asn Gly
            20

<210> SEQ ID NO 1796
<211> LENGTH: 24
<212> TYPE: PRT
<213> ORGANISM: Homo sapiens

<400> SEQUENCE: 1796

Cys Gly Leu Trp Gly Glu Ile Glu Glu Leu Ile Glu Glu Gly Leu Glu
1               5                   10                  15
```

Asn Leu Ile Asp Trp Gly Asn Gly
            20

<210> SEQ ID NO 1797
<211> LENGTH: 24
<212> TYPE: PRT
<213> ORGANISM: Homo sapiens

<400> SEQUENCE: 1797

Cys Gly Leu Phe Gly Glu Trp Glu Glu Leu Ile Glu Glu Gly Leu Glu
1               5                   10                  15

Asn Leu Ile Asp Trp Gly Asn Gly
            20

<210> SEQ ID NO 1798
<211> LENGTH: 24
<212> TYPE: PRT
<213> ORGANISM: Homo sapiens

<400> SEQUENCE: 1798

Cys Gly Leu Phe Gly Glu Phe Glu Glu Leu Ile Glu Glu Gly Leu Glu
1               5                   10                  15

Asn Leu Ile Asp Trp Gly Asn Gly
            20

<210> SEQ ID NO 1799
<211> LENGTH: 24
<212> TYPE: PRT
<213> ORGANISM: Homo sapiens

<400> SEQUENCE: 1799

Cys Gly Leu Phe Gly Glu Ile Glu Glu Leu Ile Glu Glu Gly Leu Glu
1               5                   10                  15

Asn Leu Leu Asp Trp Gly Asn Gly
            20

<210> SEQ ID NO 1800
<211> LENGTH: 24
<212> TYPE: PRT
<213> ORGANISM: Homo sapiens

<400> SEQUENCE: 1800

Cys Gly Leu Phe Gly Glu Ile Glu Glu Leu Ile Glu Glu Gly Leu Glu
1               5                   10                  15

Asn Leu Ile Asp Trp Gly Gln Gly
            20

<210> SEQ ID NO 1801
<211> LENGTH: 23
<212> TYPE: PRT
<213> ORGANISM: Homo sapiens

<400> SEQUENCE: 1801

Gly Leu Phe Gly Glu Ile Glu Glu Leu Ile Glu Glu Gly Leu Glu Asn
1               5                   10                  15

Leu Ile Asp Trp Gly Asn Gly
            20

<210> SEQ ID NO 1802
<211> LENGTH: 14
<212> TYPE: PRT
<213> ORGANISM: Homo sapiens

<400> SEQUENCE: 1802

Gly Phe Phe Gly Ala Ile Trp Glu Phe Ile His Ser Ile Leu
1               5                   10

<210> SEQ ID NO 1803
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: aminohexyl phosphate inverted abasic cap
<220> FEATURE:
<221> NAME/KEY: misc_feature
<222> LOCATION: (1)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (4)..(5)
<223> OTHER INFORMATION: 2'-O-methyl
<220> FEATURE:
<221> NAME/KEY: misc_feature
<222> LOCATION: (6)..(8)
<223> OTHER INFORMATION: 2'-deoxy-2'-fluoro
<220> FEATURE:
<221> NAME/KEY: misc_feature
<222> LOCATION: (9)..(10)
<223> OTHER INFORMATION: 2'-O-methyl
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (13)..(15)
<223> OTHER INFORMATION: 2'-O-methyl
<220> FEATURE:
<221> NAME/KEY: misc_feature
<222> LOCATION: (16)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage
<220> FEATURE:
<221> NAME/KEY: misc_feature
<222> LOCATION: (21)..(21)
<223> OTHER INFORMATION: inverted abasic cap

<400> SEQUENCE: 1803
cuguuggauu gauucgaaau u                                    21

<210> SEQ ID NO 1804
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (1)..(2)

-continued

```
<223> OTHER INFORMATION: phosphorothioate internucleotide linkage
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (2)..(3)
<223> OTHER INFORMATION: phosphorothioate internucleotide linkage
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (3)..(4)
<223> OTHER INFORMATION: phosphorothioate internucleotide linkage
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
```

```
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 1804
uuucgaauca auccaacagu u                                              21

<210> SEQ ID NO 1805
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal vinyl phosphate
<220> FEATURE:
<221> NAME/KEY: misc_feature
<222> LOCATION: (1)..(1)
<223> OTHER INFORMATION: 3'-deoxy; 2'-internucleotide linkage
<220> FEATURE:
<221> NAME/KEY: misc_feature
<222> LOCATION: (1)..(2)
<223> OTHER INFORMATION: phosphorothioate internucleotide linkage
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
```

```
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 1805
tuucgaauca auccaacagu u                                                21

<210> SEQ ID NO 1806
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal vinyl phosphate
<220> FEATURE:
<221> NAME/KEY: misc_feature
<222> LOCATION: (1)..(1)
<223> OTHER INFORMATION: 2'-methoxyethoxy
<220> FEATURE:
<221> NAME/KEY: misc_feature
<222> LOCATION: (2)..(21)
<223> OTHER INFORMATION: ribonucleotide unmodified or modified as
     described for this sequence
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
```

```
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 1806
tuucgaauca auccaacagu u                                              21

<210> SEQ ID NO 1807
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: aminohexyl phosphate inverted abasic cap
<220> FEATURE:
<221> NAME/KEY: misc_feature
<222> LOCATION: (1)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-fluoro
<220> FEATURE:
```

```
<221> NAME/KEY: misc_feature
<222> LOCATION: (4)..(5)
<223> OTHER INFORMATION: 2'-O-methyl
<220> FEATURE:
<221> NAME/KEY: misc_feature
<222> LOCATION: (6)..(8)
<223> OTHER INFORMATION: 2'-deoxy-2'-fluoro
<220> FEATURE:
<221> NAME/KEY: misc_feature
<222> LOCATION: (9)..(10)
<223> OTHER INFORMATION: 2'-O-methyl
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (13)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2' propagyl
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage
<220> FEATURE:
<221> NAME/KEY: misc_feature
<222> LOCATION: (21)..(21)
<223> OTHER INFORMATION: inverted abasic cap

<400> SEQUENCE: 1807
cuguuggauu gauucgaaau u                                          21

<210> SEQ ID NO 1808
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
```

```
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 1808
uuucgaauca auccaacagu u                                              21

<210> SEQ ID NO 1809
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-O-methyl
```

```
<220> FEATURE:
<221> NAME/KEY: misc_feature
<222> LOCATION: (5)..(7)
<223> OTHER INFORMATION: 2'-deoxy-2'-fluoro
<220> FEATURE:
<221> NAME/KEY: misc_feature
<222> LOCATION: (8)..(9)
<223> OTHER INFORMATION: 2'-O-methyl
<220> FEATURE:
<221> NAME/KEY: misc_feature
<222> LOCATION: (10)..(11)
<223> OTHER INFORMATION: 2'-deoxy-2'-fluoro
<220> FEATURE:
<221> NAME/KEY: misc_feature
<222> LOCATION: (12)..(13)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 1809
uuucgaauca auccaacagu u                                              21

<210> SEQ ID NO 1810
<211> LENGTH: 21
<212> TYPE: RNA
<213> ORGANISM: Artificial Sequence
<220> FEATURE:
<223> OTHER INFORMATION: Synthetic

<400> SEQUENCE: 1810
uuucgaauca auccaacagu u                                              21

<210> SEQ ID NO 1811
<211> LENGTH: 52
<212> TYPE: DNA
<213> ORGANISM: Artificial Sequence
<220> FEATURE:
<223> OTHER INFORMATION: Synthetic

<400> SEQUENCE: 1811
gtcgtatcca gtgcagggtc cgaggtattc gcactggata cgacaactgt tg            52

<210> SEQ ID NO 1812
<211> LENGTH: 21
<212> TYPE: DNA
<213> ORGANISM: Artificial Sequence
<220> FEATURE:
<223> OTHER INFORMATION: Synthetic

<400> SEQUENCE: 1812
ggcggctttc gaatcaatcc a                                              21
```

```
<210> SEQ ID NO 1813
<211> LENGTH: 15
<212> TYPE: DNA
<213> ORGANISM: Artificial Sequence
<220> FEATURE:
<223> OTHER INFORMATION: Synthetic

<400> SEQUENCE: 1813
agtgcagggt ccgag                                                    15

<210> SEQ ID NO 1814
<211> LENGTH: 18
<212> TYPE: DNA
<213> ORGANISM: Artificial Sequence
<220> FEATURE:
<223> OTHER INFORMATION: Synthetic

<400> SEQUENCE: 1814
tggatacgac aactgttg                                                 18

<210> SEQ ID NO 1815
<211> LENGTH: 22
<212> TYPE: DNA
<213> ORGANISM: Artificial Sequence
<220> FEATURE:
<223> OTHER INFORMATION: Synthetic

<400> SEQUENCE: 1815
uagcagcacg uaaauauugg cg                                            22
```